(12) United States Patent
Zhuo et al.

(10) Patent No.: US 8,481,732 B2
(45) Date of Patent: Jul. 9, 2013

(54) SUBSTITUTED HETEROCYCLIC COMPOUNDS

(75) Inventors: Jincong Zhuo, Garnet Valley, PA (US); Thomas P. Maduskuie, Wilmington, DE (US); Ding-quan Qian, Newark, DE (US); Wenqing Yao, Kennett Square, PA (US)

(73) Assignee: Incyte Corporation, Wilmington, DE (US)

( * ) Notice: Subject to any disclaimer, the term of this patent is extended or adjusted under 35 U.S.C. 154(b) by 151 days.

(21) Appl. No.: 12/727,490

(22) Filed: Mar. 19, 2010

(65) Prior Publication Data
US 2010/0240671 A1 Sep. 23, 2010

Related U.S. Application Data

(60) Provisional application No. 61/161,939, filed on Mar. 20, 2009.

(51) Int. Cl.
*C07D 239/42* (2006.01)

(52) U.S. Cl.
USPC .......................................................... 544/330

(58) Field of Classification Search
USPC .......................................................... 544/330
See application file for complete search history.

(56) References Cited

U.S. PATENT DOCUMENTS

| 6,919,484 | B2 | 7/2005 | Dolbier, Jr. et al. |
| 2007/0185075 | A1 | 8/2007 | Bell et al. |

FOREIGN PATENT DOCUMENTS

| EP | 1505064 | 2/2005 |
| WO | 2002/000196 | 1/2002 |
| WO | 2005/014579 | 2/2005 |
| WO | 2005054239 | 6/2005 |
| WO | 2007/072163 | 6/2007 |
| WO | 2007/117401 | 10/2007 |
| WO | 2008/008359 | 1/2008 |
| WO | 2008031556 | 3/2008 |
| WO | 2008/060766 | 5/2008 |
| WO | 2008/100565 | 8/2008 |
| WO | 2009038673 | 3/2009 |

OTHER PUBLICATIONS

Bissyris et al., "2-Amino-4-(pyrrolidino)thieno[2,3-d] pyrimidine-6-carboxylic acid as an N-terminal surrogate in amino and peptide analogues," Synthesis (2005) 18:3159-3166.
Non-Final Office Action dated Mar. 7, 2012 received in copending U.S. Appl. No. 12/643,739.
Ash et al., "Receptors mediating some actions of histamine.," Br. J. Pharmac. Chemother., (1966) 27(2):427-439.
Arrang et al., "Auto-inhibition of brain histamine release mediated by a novel class (H3) of histamine receptor," Nature (1983) 302(5911):832-837.
Bell et al., "Involvement of histamine H4 and H1 receptors in scratching induced by histamine receptor agonists in Balb C mice.," Br. J. Pharmcol. (2004) 142(2):374-380.
Black et al., "Definition and antagonism of histamine H 2-receptors," Nature (1972) 236(5347):385-390.
Blom et al., "Preparative LC-MS purification: improved compound-specific method optimization," J Comb Chem (2004) 6(6):874-883.
Breunig et al., "Histamine excites neurones in the human submucous plexus through activation of H1, H2, H3 and H4 receptors.," J. Physiol. (2007) 583(Pt.2):731-742.
Buckland et al., "Histamine induces cytoskeletal changes in human eosinophils via the H(4) receptor," Br. J. Pharmacol. (2003) 140(6):1117-1127.
Cogé et al., "Structure and expression of the human histamine H4-receptor gene," Biochem. Biophy. Res. Commun. (2001) 284(2):301-309.
Coruzzi et al., "Antiinflammatory and antinociceptive effects of the selective histamine H4-receptor antagonists JNJ7777120 and VUF6002 in a rat model of carrageenan-induced acute inflammation," Eur. J. Pharmacol. (2007) 563 (1-3):240-244.
Dunford et al., "The histamine H4 receptor mediates allergic airway inflammation by regulating the activation of CD4+ T cells," J. Immunol. (2006) 176(11)7062-7070.
Dunford et al., "Histamine H4 receptor antagonists are superior to traditional antihistamines in the attenuation of experimental pruritus," J. Allergy Clin. Immunol. (2007) 119(1)176-183.

(Continued)

*Primary Examiner* — Brian McDowell
(74) *Attorney, Agent, or Firm* — Pepper Hamilton LLP

(57) ABSTRACT

The present invention relates to substituted heterocyclic compounds of Formula I or XI:

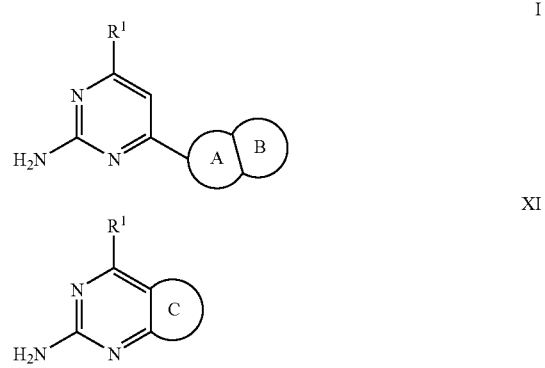

or pharmaceutically acceptable salts or N-oxides or quaternary ammonium salts thereof wherein constituent members are provided hereinwith, as well as their compositions and methods of use, which are histamine H4 receptor inhibitors useful in the treatment of histamine H4 receptor-associated conditions or diseases or disorders including, for example, inflammatory diseases or disorders, pruritus, and pain.

22 Claims, No Drawings

OTHER PUBLICATIONS

Hirasawa et al., "Modification of the picryl chloride-induced allergic dermatitis model in mouse ear lobes by 12-O-tetradecanoylphorbol 13-acetate, and analysis of the role of histamine in the modified model.," Int. Arch. Allergy Immunol. (2009) 148(4):279-288.

Hofstra et al., "Histamine H4 receptor mediates chemotaxis and calcium mobilization of mast cells," J. Pharmacol. Exp. Ther. (2003) 305(3)1212-1221.

Gutzmer et al., "Histamine H4 receptor stimulation suppresses IL-12p70 production and mediates chemotaxis in human monocyte-derived dendritic cells," J. Immunol. (2005) 174(9):5224-5232.

Ling et al., "Histamine H4 receptor mediates eosinophil chemotaxis with cell shape change and adhesion molecule upregulation," Br. J. Pharmcol. (2004) 142(1)161-171.

Liu et al., "Cloning and pharmacological characterization of a fourth histamine receptor (H(4)) expressed in bone marrow," Mol. Pharmacol. (2001) 59(3):420-426, 2001.

Morse et al., "Cloning and characterization of a novel human histamine receptor," J. Pharmacol. Exp. Ther. (2001) 296 (3):1058-1066.

Nguyen et al., "Discovery of a novel member of the histamine receptor family," Mol. Pharmacol. (2001) 59(3):427-433.

Oda et al., "Molecular Cloning and Characterization of a Novel Type of Histamine Receptor Preferentially Expressed in Leukocytes," J. Biol. Chem. (2000) 275(47):36781-36786.

O'Reilly et al., "Identification of a histamine H4 receptor on human eosinophils—role in eosinophil chemotaxis," J. Recept. Signal Transduct. (2002) 22(1-4):431-448.

Parsons et al., "Histamine and its receptors," Br. J. Pharm. (2006) 147(Suppl 1):S127-S135.

Takeshita et al., "Critical role of histamine H4 receptor in leukotriene B4 production and mast cell-dependent neutrophil recruitment induced by zymosan in vivo," J. Pharmacol. Exp.Ther., (2003) 307(3):1072-1078.

Thurmond et al., "The role of histamine H1 and H4 receptors in allergic inflammation: the search for new antihistamines," Nature Review Drug Discovery, (2008) 7(1):41-53.

Thurmond et al., "A potent and selective histamine H4 receptor antagonist with anti-inflammatory properties," J. Pharmacol. Exp. Ther. (2004) 309(1):404-413.

Wolfe, et. al. "Simple, Efficient Catalyst System for the Palladium-Catalyzed Amination of Aryl Chlorides, Bromides, and Triflates" J. Org. Chem. (2000) 65(4):1158-1174.

Varga et al., "Inhibitory effects of histamine H4 receptor antagonists on experimental colitis in the rat," Eur. J. Pharmacol., (2005) 522(1-3):130-138.

Zhu et al., "Cloning, expression, and pharmacological characterization of a novel human histamine receptor," Mol. Pharmcol. (2001) 59(3):434-441.

P. Chazot, Eur. Histamine Res. Soc.—37th Ann. Meeting, 2008.

Remington's Pharmaceutical Sciences, 17th ed., Mack Publishing Company, Easton, Pa., 1985, p. 1418.

Berge et al., "Pharmaceutical salts," Journal of Pharmaceutical Science, 66, pp. 1-19 (1977).

T. W. Greene and P. G. M. Wuts, Protective Groups in Organic Synthesis, 3rd Ed., Wiley & Sons, Inc., New York (1999).

International Search Report dated Jun. 28, 2010 for International Application No. PCT/US2010/027904.

Altenbach et al., "Structure-activity studies on a series of a 2-aminopyrimidine-containing histamine H4 receptor ligands," Journal of Medicinal Chemistry (2008) 51(20):6571-6580.

Hawthorne et al., "Amine reactivity changes in imide formation from heterocyclic bases," High Performance Polymers (1999) 11:315-329.

Notice of Allowance dated Sep. 17, 2012 received in related U.S. Appl. No. 12/643,739.

Blom "Two-pump at-column-dilution configuration for preparative liquid chromatography-mass spectrometry," J Comb Chem (2002) 4(4):295-301.

Blom "Optimizing preparative LC/MS configurations and methods for parallel synthesis purification," (2003) 5:670-683.

Notice of Allowance dated Jan. 10, 2013 received in copending U.S. Appl. No. 12/643,739.

SUBSTITUTED HETEROCYCLIC COMPOUNDS

This application claims benefit of priority to U.S. provisional patent application Ser. No. 61/161,939 filed on Mar. 20, 2009, which is hereby incorporated by reference in its entirety.

FIELD OF THE INVENTION

The present invention relates to substituted heterocyclic compounds, and compositions thereof as well as methods of use the same for treatment of histamine H4 receptor associated conditions or diseases or disorders such as inflammatory disorders, pruritus, and pain.

BACKGROUND OF THE INVENTION

Histamine is a biogenic amine that exerts its physiological and pathological functions through four G-protein coupled receptors, histamine receptors H1, H2, H3, and H4 (Parsons and Ganellin, Br. J. Pharm., 147:S127-S135, 2006). The roles of the first three receptors in mediating histamine functions have been well characterized: histamine mediates acute allergic responses via histamine H1 receptor (A. S. F. Ash and H. O. Schild, Br. J. Pharmac. Chemother., 27:427-439, 1966), gastric acid secretion via histamine H2 receptors (J. W. Black et al., Nature, 236:385-390, 1972), and controls neurotransmitter release in the central nervous system via histamine H3 receptor (J. M. Arrang et al., Nature, 302:832-837, 1983). Drugs based on histamine H1 or H2 receptors have achieved "block-bluster" status on the market and several therapeutic indications based on histamine H3 receptor inhibition are in different stages of clinical development for various neural disorders. Importantly, histamine has many additional functions in humans that cannot be explained by signaling pathways involving only histamine H1, H2 and/or H3 receptors. For examples, histamine is known to be involved in asthma and in the pruritus associated with atopic dermatitis and chronic idiopathic urticaria, but current anti-H1 and anti-H2 compounds (antagonists of H1 and/or H2 receptor), which are not active against H4 receptor (Thurmond et al., Nature Review Drug Discovery, 7:41-53, 2008), are ineffective in treating these conditions. With the human genome having been almost completely explored, histamine H4 receptor is the last and most likely the only histamine receptor left to account for these remaining functions of histamine.

Histamine has a relatively high affinity for histamine H4 receptor (Kd=10 nM), which was cloned based on sequence homology to histamine H3 receptor (Oda et al., J. Biol. Chem., 275:36781-36786, 2001; Liu et al., Mol. Pharmacol., 59:420-426, 2001; Morse et al., J. Pharmacol. Exp. Ther., 296:1058-1066, 2001; Nguyen et al., Mol. Pharmacol., 59:427-433, 2001; Zhu et al., Mol. Pharmcol., 59:434-441, 2001; O'Reilly et al., J. Recept. Signal Transduct., 22:431-448, 2002). Histamine H4 receptors are predominantly expressed in the cells of hematopoietic origins (Parsons and Ganellin, Br. J. Pharm., 147:S127-S135, 2006). Possible expression of H4 receptors was also reported in selective tissues within both rodent and human central nerve systems (P. Chazot, Eur. Histamine Res. Soc.-37th Ann. Meeting, 2008; Coge et al., Biochem. Biophy. Res. Commun., 284: 301-309, 2001) as well as submucous plexus (Breunig et al., J. Physiol., 583:731-742, 2007). In vitro studies indicated that histamine H4 receptor mediates histamine-induced migration of dendritic cells, mast cells and eosinophils (Hofstra et al., J. Pharmacol. Exp. Ther., 305:1212-1221, 2003; Buckland et al., Br. J. Pharmacol., 140:1117-1127, 2003; Ling et al., Br. J. Pharmcol., 142:161-171, 2004; Gutzmer et al., J. Immunol., 174:5224-5232, 2005). In addition, through histamine H4 receptor, histamine can synergize with other chemotactic agents to enhance migration of eosinophils (O'Reilly et al., supra; Buckland et al., supra; Ling et al., supra). These in vitro data clearly point to a role for histamine H4 receptor in inflammation, immune and possibly neurologic responses.

The predicted functions of histamine H4 receptor based on in vitro studies have been borne out in animal models. Using both H4 knockout animals as well as small molecule inhibitors, histamine H4 receptor has been shown to mediate mast cell migration in the trachea of mice after histamine inhalation (Thurmond et al., J. Pharmacol. Exp. Ther., 309:404-413, 204). Histamine H4 receptor has also been shown to play a critical role in a number of different acute and chronic inflammation models, including carrageenan-induced edema (Coruzzi et al., Eur. J. Pharmacol., 563:240-244, 2007), zymosan-induced pleurisy and peritonitis (Thurmond et al., J. Pharmacol. Exp. Ther., 309:404-413, 2004; Takeshita et al., J. Pharmacol. Exp. Ther., 307:1072-1078, 2003), trinitriobenzene sulphonic acid-induced colitis (Varga et al., Eur. J. Pharmacol., 522:130-138, 2005), picryl chloride-induced and 12-o-tetradecannoylphorbol 13-acetate-modified atopic dermatitis (Hirasawa et al., Int. Arch. Allergy Immunol., 148: 279-288, 2009), and allergic lung inflammation (Dunford et al., J. Immunol., 176:7062-7070, 2006). Consistent with its expression in the nervous system, histamine H4 receptor was demonstrated to mediate histamine or antigen-specific IgE-induced acute itch responses (Bell et al., Br. J. Pharmcol., 142:374-380; Dunford et al., J. Allergy Clin. Immunol., 119: 176-183, 2007) and inhibition of histamine H4 receptor had antinociceptive effects in various pain models (Coruzzi et al., supra; Altenbach et al., WO2008/060766 A2).

Taken together, histamine appears to mediate many immune, inflammatory, and/or neurologic responses through histamine H4 receptor. Accordingly, histamine H4 receptor is an attractive therapeutic target for inflammatory disorders, pruritus, and pain, including rhinitis, asthma, rheumatoid arthritis, atopic dermatitis, idiopathic chronic urticaria, inflammatory pain, and neuropathic pain.

Thus, new or improved agents that modulate (such as antagonizing/inhibiting) histamine H4 receptor are continually needed for developing new and more effective pharmaceuticals to treat histamine H4 receptor-associated conditions or diseases or disorders, such as inflammatory disorders, pruritus, and pain, including rhinitis, asthma, rheumatoid arthritis, atopic dermatitis, idiopathic chronic urticaria, inflammatory pain, and neuropathic pain, to name a few. The compounds, compositions and methods described herein are directed toward these needs and other ends.

SUMMARY OF THE INVENTION

The present invention provides, inter alia, compounds of Formula I or XI:

I

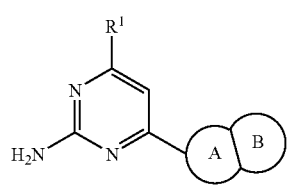

-continued

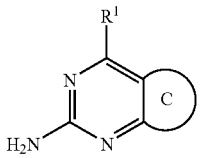

XI or pharmaceutically acceptable salts thereof or N-oxides thereof or quaternary ammonium salts thereof, wherein constituent members are provided below.

The present invention further provides pharmaceutical compositions comprising a compound of Formula I or XI, or pharmaceutically acceptable salt thereof, and at least one pharmaceutically acceptable carrier.

The present invention further provides methods of modulating an activity of histamine H4 receptor, comprising contacting the histamine H4 receptor with a compound of Formula I or XI, or pharmaceutically acceptable salt of the same.

The present invention further provides methods of inhibiting an activity of histamine H4 receptor with a compound of Formula I or XI, or pharmaceutically acceptable salt of the same.

The present invention further provides methods of treating one or more of the various histamine H4 receptor-associated conditions, diseases, and disorders named herein by administering to a patient a therapeutically effective amount of a compound of Formula I or XI, or pharmaceutically acceptable salt of the same.

The present invention further provides compounds of Formula I or XI, or pharmaceutically acceptable salts thereof, for use in therapy.

The present invention further provides use of the compounds of Formula I or XI, or pharmaceutically acceptable salts thereof, for the manufacture/preparation of a medicament for use in therapy.

DETAILED DESCRIPTION

The present invention provides, inter alia, compounds of Formula I or XI:

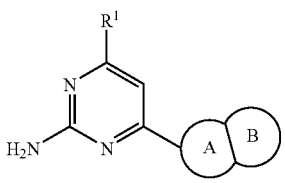

I

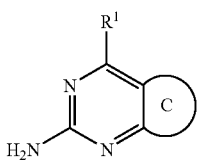

XI or pharmaceutically acceptable salts thereof or N-oxide thereofs or quaternary ammonium salts thereof, wherein:

ring A is an aryl or a 5- or 6-membered heteroaryl group wherein ring A is linked to the pyrimidine ring through a carbon atom of ring A, wherein each of the ring-forming atoms of the 5- or 6-membered heteroaryl group is independently selected from C, N, O, and S, and wherein ring A is substituted with 0, 1, 2, or 3 —$W^{1a}$—$X^{1a}$—$W^{1}$—$X^{1}$—$Y^{1}$—$Z^{1}$;

wherein —$W^{1a}$—$X^{1a}$—$W^{1}$—$X^{1}$—$Y^{1}$—$Z^{1}$ is other than H;

ring B is a 4-20 membered cycloalkyl or heterocycloalkyl group that is fused to ring A, wherein each of the ring-forming atoms of the 4-20 membered heterocycloalkyl group is independently selected from C, N, O, and S, wherein ring B is substituted with 0, 1, 2, 3, 4, 5, or 6 —$W^{2a}$—$X^{2a}$—$W^{2}$—$X^{2}$—$Y^{2}$—$Z^{2}$;

wherein —$W^{2a}$—$X^{2a}$—$W^{2}$—$X^{2}$—$Y^{2}$—$Z^{2}$ is other than H;

ring C is an aryl or a 5- or 6-membered heteroaryl group fused to the pyrimidine ring, wherein each of the ring-forming atoms of the 5- or 6-membered heteroaryl group is independently selected from C, N, O, and S, and wherein ring C is substituted with —C(O)$NR^{9}R^{10}$ and with 0, 1, 2, or 3 $R^{8}$;

$R^{1}$ is $NR^{2}R^{3}$, wherein $R^{2}$ and $R^{3}$ together with the N atom to which they are attached form a 4-10 membered heterocycloalkyl group wherein each of the ring-forming atoms of the 4-10 membered heterocycloalkyl group is independently selected from C, N, O, and S, and wherein the 4-10 membered heterocycloalkyl group is substituted with 0, 1, 2, 3, 4, 5, 6, 7, or 8 $R^{4}$;

each $R^{4}$ is independently selected from halo, CN, $C_{1-6}$ alkyl, $C_{1-6}$ haloalkyl, $C_{3-7}$ cycloalkyl, OH, oxo, $C_{1-6}$ alkoxy, $C_{1-6}$ haloalkoxy, $NH_{2}$, NH($C_{1-4}$ alkyl), NH($C_{3-7}$cycloalkyl), and N($C_{1-4}$ alkyl)$_{2}$, wherein each of the $C_{1-6}$ alkyl and $C_{3-7}$ cycloalkyl is substituted with 0, 1, 2, or 3 substituents each independently selected from halo, OH, CN, $NH_{2}$, NH($C_{1-4}$ alkyl), and N($C_{1-4}$ alkyl)$_{2}$;

each $R^{8}$ is independently selected from selected from halo, CN, $NO_{2}$, $OR^{a4}$, $SR^{a4}$, $SF_{5}$, $C(O)R^{b4}$, $C(O)NR^{c4}R^{d4}$, $C(O)OR^{a4}$, $OC(O)R^{b4}$, $OC(O)NR^{c4}R^{d4}$, $NR^{c4}R^{d4}$, $NR^{c4}C(O)R^{b4}$, $NR^{c4}C(O)NR^{c4}R^{d4}$, $NR^{c4}C(O)OR^{a4}$, $C(=NR^{g4})NR^{c4}R^{d4}$, $NR^{c4}C(=NR^{g4})NR^{c4}R^{d4}$, $NR^{c4}S(O)_{2}NR^{c4}R^{d4}$, $S(O)R^{b4}$, $S(O)NR^{c4}R^{d4}$, $S(O)_{2}R^{b4}$, $NR^{c4}S(O)_{2}R^{b4}$, $S(O)_{2}NR^{c4}R^{d4}$, $C_{1-6}$ alkyl, $C_{1-6}$ haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl, and heterocycloalkylalkyl, wherein each of the $C_{1-6}$ alkyl, $C_{1-6}$ haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl, and heterocycloalkylalkyl is substituted with 0, 1, 2, 3, 4, or 5 substituents each independently selected from $R^{8a}$, halo, CN, $NO_{2}$, oxo, $OR^{a4}$, $SR^{a4}$, $SF_{5}$, $C(O)R^{b4}$, $C(O)NR^{c4}R^{d4}$, $C(O)OR^{a4}$, $OC(O)R^{b4}$, $OC(O)NR^{c4}R^{d4}$, $NR^{c4}R^{d4}$, $NR^{c4}C(O)R^{d4}$, $NR^{c4}C(O)OR^{a4}$, $NR^{c4}S(O)_{2}R^{b4}$, $NR^{c4}S(O)_{2}NR^{c4}R^{d4}$, $S(O)R^{b4}$, $S(O)NR^{c4}R^{d4}$, $S(O)_{2}R^{b4}$, and $S(O)_{2}NR^{c4}R^{d4}$;

$R^{9}$ and $R^{10}$ are each, independently, selected from H, $C_{1-6}$ alkyl, $C_{1-6}$ haloalkyl, arylalkyl, heteroarylalkyl, cycloalkylalkyl, heterocycloalkylalkyl, $C_{2-6}$ alkenyl, $C_{2-6}$ alkynyl, aryl, heteroaryl, cycloalkyl, heterocycloalkyl, arylalkyl, heteroarylalkyl, cycloalkylalkyl and heterocycloalkylalkyl, wherein each of the $C_{1-6}$ alkyl, $C_{1-6}$ haloalkyl, arylalkyl, heteroarylalkyl, cycloalkylalkyl, heterocycloalkylalkyl, $C_{2-6}$ alkenyl, $C_{2-6}$ alkynyl, aryl, heteroaryl, cycloalkyl, heterocycloalkyl, arylalkyl, heteroarylalkyl, cycloalkylalkyl and heterocycloalkylalkyl is substituted with 0, 1, 2, 3, 4, or 5 substituents independently selected from $R^{10a}$, halo, CN, $NO_{2}$, oxo, $OR^{a5}$, $SR^{a5}$, $C(O)R^{b5}$, $C(O)NR^{c5}R^{d5}$, $C(O)OR^{a5}$, $OC(O)R^{b5}$, $OC(O)NR^{c5}R^{d5}$, $NR^{c5}R^{d5}$, $NR^{c5}C(O)R^{b5}$, $NR^{c5}C(O)NR^{c5}R^{d5}$, $NR^{c5}C(O)OR^{a5}$, $C(=NR^{g5})NR^{c5}R^{d5}$, $NR^{c5}C(=NR^{g5})NR^{c5}R^{d5}$, $NR^{c5}S(O)_{2}NR^{c5}R^{d5}$, $S(O)R^{b5}$, $S(O)NR^{c5}R^{d5}$, $S(O)_{2}R^{b5}$, $NR^{c5}S(O)_{2}R^{b5}$, and $S(O)_{2}NR^{c5}R^{d5}$;

or $R^9$ and $R^{10}$ together with the N atom to which they are attached form a 4-14 membered heterocycloalkyl group that is substituted with 0, 1, 2, 3, 4, or 5 substituents independently selected from $R^{10a}$, halo, CN, $NO_2$, oxo, $OR^{a5}$, $SR^{a5}$, $C(O)R^{b5}$, $C(O)NR^{c5}R^{d5}$, $C(O)OR^{a5}$, $OC(O)R^{b5}$, $OC(O)NR^{c5}R^{d5}$, $NR^{c5}R^{d5}$, $NR^{c5}C(O)R^{b5}$, $NR^{c5}C(O)NR^{c5}R^{d5}$, $NR^{c5}C(O)OR^{a5}$, $C(=NR^{g5})NR^{c5}R^{d5}$, $NR^{c5}C(=NR^{g5})NR^{c5}R^{d5}$, $NR^{c5}S(O)_2BR^{c5}R^{d5}$, $S(O)R^{b5}$, $S(O)NR^{c5}R^{d5}$, $S(O)_2R^{b5}$, $NR^{c5}S(O)_2R^{b5}$, and $S(O)_2NR^{c5}R^{d5}$;

$W^{1a}$, $W^{2a}$, $W^1$, and $W^2$ are each, independently, selected from absent, $C_{1-6}$ alkylenyl, $C_{2-6}$ alkenylenyl, $C_{2-6}$ alkynylenyl, $(CR^{11a}R^{11b})_{p1}O(CR^{11a}R^{11b})_{p2}$, $(CR^{11a}R^{11b})_{p1}S(CR^{11a}R^{11b})_{p2}$, $(CR^{11a}R^{11b})_{p1}NR^e(CR^{11a}R^{11b})_{p2}$, $(CR^{11a}R^{11b})_{p1}C(O)(CR^{11a}R^{11b})_{p2}$, $(CR^{11a}R^{11b})_{p1}C(S)(CR^{11a}R^{11b})_{p2}$, $(CR^{11a}R^{11b})_{p1}C(O)O(CR^{11a}R^{11b})_{p2}$, $(CR^{11a}R^{11b})_{p1}C(O)NR^e(CR^{11a}R^{11b})_{p2}$, $(CR^{11a}R^{11b})_{p1}C(S)NR^e(CR^{11a}R^{11b})_{p2}$, $(CR^{11a}R^{11b})_{p1}S(O)(CR^{11a}R^{11b})_{p2}$, $(CR^{11a}R^{11b})_{p1}S(O)_2(CR^{11a}R^{11b})_{p2}$, $(CR^{11a}R^{11b})_{p1}S(O)NR^c(CR^{11a}R^{11b})_{p2}$, $(CR^{11a}R^{11b})_{p1}S(O)_2NR^e(CR^{11a}R^{11b})_{p2}$, $(CR^{11a}R^{11b})_{p1}NR^eC(O)NR^f(CR^{11a}R^{11b})_{p2}$, $(CR^{11a}R^{11b})_{p1}NR^eC(S)NR^f(CR^{11a}R^{11b})_{p2}$, $(CR^{11a}R^{11b})_{p1}NR^eS(O)_2NR^f(CR^{11a}R^{11b})_{p2}$, $(CR^{11a}R^{11b})_{p1}C(=NR^g)NR^e(CR^{11a}R^{11b})_{p2}$, $(CR^{11a}R^{11b})_{p1}NR^eC(=NR^g)NR^f(CR^{11a}R^{11b})_{p2}$, $O(CR^{11a}R^{11b})_{q1}C(O)$, $S(CR^{11a}R^{11b})_{q1}C(O)$, $NR^e(CR^{11a}R^{11b})_{q1}C(O)$, $C(O)(CR^{11a}R^{11b})_{q1}C(O)$, $NR^e(CR^{11a}R^{11b})_{q1}NR^f$, $O(CR^{11a}R^{11b})_{q1}NR^f$, and $O(CR^{11a}R^{11b})_{q1}O$, wherein each of the $C_{1-6}$ alkylenyl, $C_{2-6}$ alkenylenyl and $C_{2-6}$ alkynylenyl is substituted with 0, 1, 2, 3, 4, 5, 6, 7, or 8 substituents each independently selected from halo, CN, $NO_2$, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cC(O)R^b$, $NR^cC(O)NR^cR^d$, $NR^cC(O)OR^a$, $C(=NR^g)NR^cR^d$, $NR^cC(=NR^g)NR^cR^d$, $NR^cS(O)_2NR^cR^d$, $S(O)R^b$, $S(O)NR^cR^d$, $S(O)_2R^b$, $NR^cS(O)_2R^b$, and $S(O)_2NR^cR^d$;

$X^{1a}$, $X^{2a}$, $X^1$, and $X^2$ are each, independently, selected from absent, $C_{1-6}$ alkylenyl, $C_{2-6}$ alkenylenyl, $C_{2-6}$ alkynylenyl, aryl, cycloalkyl, heteroaryl, heterocycloalkyl, arylalkyl, heteroarylalkyl, cycloalkylalkyl, and heterocycloalkylalkyl, wherein each of said $C_{1-6}$ alkylenyl, $C_{2-6}$ alkenylenyl, $C_{2-6}$ alkynylenyl, aryl, cycloalkyl, heteroaryl, heterocycloalkyl, arylalkyl, heteroarylalkyl, cycloalkylalkyl, and heterocycloalkylalkyl is substituted with 0, 1, 2, 3, 4, 5, 6, 7, or 8 substituents each independently selected from $R^{XX}$, halo, CN, $NO_2$, $OR^a$, $SR^a$, $SF_5$, $C(O)R^b$, $C(O)NR^cR^d$, $C(O)OR^a$, $OC(O)R^b$, $OC(O)NR^cR^d$, $NR^cR^d$, $NR^cC(O)R^b$, $NR^cC(O)NR^cR^d$, $NR^cC(O)OR^a$, $C(=NR^g)NR^cR^d$, $NR^cC(=NR^g)NR^cR^d$, $NR^cS(O)_2NR^cR^d$, $S(O)R^b$, $S(O)NR^cR^d$, $S(O)_2R^b$, $NR^cS(O)_2R^b$, and $S(O)_2NR^cR^d$;

$Y^1$ and $Y^2$ are each, independently, selected from absent, $C_{1-6}$ alkylenyl, $C_{2-6}$ alkenylenyl, $C_{2-6}$ alkynylenyl, $(CR^{12a}R^{12b})_{p3}O(CR^{12a}R^{12b})_{p4}$, $(CR^{12a}R^{12b})_{p3}S(CR^{12a}R^{12b})_{p4}$, $(CR^{12a}R^{12b})_{p3}NR^e(CR^{12a}R^{12b})_{p4}$, $(CR^{12a}R^{12b})_{p3}C(O)(CR^{12a}R^{12b})_{p4}$, $(CR^{12a}R^{12b})_{p3}C(S)(CR^{12a}R^{12b})_{p4}$, $(CR^{12a}R^{12b})_{p3}C(O)O(CR^{12a}R^{12b})_{p4}$, $(CR^{12a}R^{12b})_{p3}C(O)NR^e(CR^{12a}R^{12b})_{p4}$, $(CR^{12a}R^{12b})_{p3}C(S)NR^e(CR^{12a}R^{12b})_{p4}$, $(CR^{12a}R^{12b})_{p3}S(O)(CR^{12a}R^{12b})_{p4}$, $(CR^{12a}R^{12b})_{p3}S(O)_2(CR^{12a}R^{12b})_{p4}$, $(CR^{12a}R^{12b})_{p3}S(O)NR^e(CR^{12a}R^{12b})_{p4}$, $(CR^{12a}R^{12b})_{p3}S(O)_2NR^e(CR^{12a}R^{12b})_{p4}$, $(CR^{12a}R^{12b})_{p3}NR^eC(O)NR^f(CR^{12a}R^{12b})_{p4}$, $(CR^{12a}R^{12b})_{p3}NR^eC(S)NR^f(CR^{12a}R^{12b})_{p4}$, $(CR^{12a}R^{12b})_{p3}NR^eS(O)_2NR^f(CR^{12a}R^{12b})_{p4}$, $(CR^{12a}R^{12b})_{p3}C(=NR^g)NR^e(CR^{12a}R^{12b})_{p4}$, $(CR^{12a}R^{12b})_{p3}NR^eC(=NR^g)NR^f(CR^{12a}R^{12b})_{p4}$, $O(CR^{12a}R^{12b})_{q2}C(O)$, $S(CR^{12a}R^{12b})_{q2}C(O)$, $NR^e(CR^{12a}R^{12b})_{q2}C(O)$, $NR^e(CR^{12a}R^{12b})_{q2}NR^f$, $O(CR^{12a}R^{12b})_{q2}NR^f$, and $O(CR^{12a}R^{12b})_{q2}O$, wherein each of the $C_{1-6}$ alkylenyl, $C_{2-6}$ alkenylenyl, and $C_{2-6}$ alkynylenyl is substituted with 0, 1, 2, 3, 4, 5, 6, 7, or 8 substituents independently selected from $C_{1-6}$ alkyl, $C_{1-6}$ haloalkyl, $C_{2-6}$ alkenyl, $C_{2-6}$ alkynyl, halo, CN, $NO_2$, $OR^a$, $SR^a$, $SF_5$, $C(O)R^b$, $C(O)NR^cR^d$, $C(O)OR^a$, $OC(O)R^b$, $OC(O)NR^cR^d$, $NR^cR^d$, $NR^cC(O)R^b$, $NR^cC(O)NR^cR^d$, $NR^cC(O)OR^a$, $C(=NR^g)NR^cR^d$, $NR^cC(=NR^g)NR^cR^d$, $NR^cS(O)_2NR^cR^d$, $S(O)R^b$, $S(O)NR^cR^d$, $S(O)_2R^b$, $NR^cS(O)_2R^b$, and $S(O)_2NR^cR^d$;

$Z^1$ and $Z^2$ are each, independently, selected from H, halo, CN, $NO_2$, $OR^a$, $SR^a$, $SF_5$, $C(O)R^b$, $C(O)NR^cR^d$, $C(O)OR^a$, $OC(O)R^b$, $OC(O)NR^cR^d$, $NR^cR^d$, $NR^cC(O)R^b$, $NR^cC(O)NR^cR^d$, $NR^cC(O)OR^a$, $C(=NR^g)NR^cR^d$, $NR^cC(=NR^g)NR^cR^d$, $NR^cS(O)_2NR^cR^d$, $S(O)R^b$, $S(O)NR^cR^d$, $S(O)_2R^b$, $NR^cS(O)_2R^b$, $S(O)_2NR^cR^d$, $C_{1-6}$ alkyl, $C_{1-6}$ haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl, and heterocycloalkylalkyl, wherein each of the $C_{1-6}$ alkyl, $C_{1-6}$ haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl, and heterocycloalkylalkyl is substituted with 0, 1, 2, 3, 4, 5, 6, 7, or 8 substituents each independently selected from $R^{ZZ}$, halo, CN, $NO_2$, $OR^a$, $SR^a$, $SF_5$, $C(O)R^b$, $C(O)NR^cR^d$, $C(O)OR^a$, $OC(O)R^b$, $OC(O)NR^cR^d$, $NR^cR^d$, $NR^cC(O)R^d$, $NR^cC(O)OR^a$, $NR^cS(O)_2R^b$, $NR^cS(O)_2NR^cR^d$; $S(O)R^b$, $S(O)NR^cR^d$, $S(O)_2R^b$, and $S(O)_2NR^cR^d$;

$R^{11a}$, $R^{11b}$, $R^{12a}$, and $R^{12b}$ are each, independently, selected from H, halo, $C_{1-6}$ alkyl, $C_{2-6}$ alkenyl, $C_{2-6}$ alkynyl, $C_{1-6}$ haloalkyl, cycloalkyl, heterocycloalkyl, aryl, heteroaryl, arylalkyl, heteroarylalkyl, cycloalkylalkyl, heterocycloalkylalkyl, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{b1}$, $NR^{c1}C(O)NR^{c1}R^{d1}$, $NR^{c1}C(O)OR^{a1}$, $C(=NR^{g1})NR^{c1}R^{d1}$, $NR^{c1}C(=NR^{g1})NR^{c1}R^{d1}$, $NR^{c1}S(O)_2NR^{c1}R^{d1}$, $S(O)R^{b1}$, $S(O)NR^{c1}R^{d1}$, $S(O)_2R^{b1}$, $NR^{c1}S(O)_2R^{b1}$, and $S(O)_2NR^{c1}R^{d1}$, wherein each of said $C_{1-6}$ alkyl, $C_{2-6}$ alkenyl, $C_{2-6}$ alkynyl, $C_{1-6}$ haloalkyl, cycloalkyl, heterocycloalkyl, aryl, heteroaryl, arylalkyl, heteroarylalkyl, cycloalkylalkyl, and heterocycloalkylalkyl is substituted with 0, 1, 2, 3, 4, or 5 substituents each independently selected from halo, $C_{1-6}$ alkyl, $C_{2-6}$ alkenyl, $C_{2-6}$ alkynyl, $C_{1-6}$ haloalkyl, cycloalkyl, heterocycloalkyl, aryl, heteroaryl, arylalkyl, heteroarylalkyl, cycloalkylalkyl, heterocycloalkylalkyl, CN, $NO_2$, $OR^{a1}$, $SR^{a1}$, $SF_5$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{b1}$, $NR^{c1}C(O)NR^{c1}R^{d1}$, $NR^{c1}C(O)OR^{a1}$, $C(=NR^g)NR^{c1}R^{d1}$, $NR^{c1}C(=NR^g)NR^{c1}R^{d1}$, $NR^{c1}S(O)_2NR^{c1}R^{d1}$, $S(O)R^{b1}$, $S(O)NR^{c1}R^{d1}$, $S(O)_2R^{b1}$, $NR^{c1}S(O)_2R^{b1}$, and $S(O)_2NR^{c1}R^{d1}$;

each $R^{XX}$ is independently selected from $C_{1-6}$ alkyl, $C_{1-6}$ haloalkyl, arylalkyl, heteroarylalkyl, cycloalkylalkyl, heterocycloalkylalkyl, $C_{2-6}$ alkenyl, $C_{2-6}$ alkynyl, aryl, cycloalkyl, heteroaryl, and heterocycloalkyl, each substituted with 0, 1, 2, 3, 4, or 5 substituents each independently selected from $C_{1-6}$ alkyl, $C_{1-6}$ haloalkyl, arylalkyl, heteroarylalkyl, cycloalkylalkyl, heterocycloalkylalkyl, $C_{2-6}$ alkenyl, $C_{2-6}$ alkynyl, aryl, cycloalkyl, heteroaryl, heterocycloalkyl, halo, CN, $NO_2$, $OR^{a2}$, $SR^{a2}$, $SF_5$, $C(O)R^{b2}$, $C(O)NR^{c2}R^{d2}$, $C(O)OR^{a2}$, $OC(O)R^{b2}$, $OC(O)NR^{c2}R^{d2}$, $NR^{c2}R^{d2}$, $NR^{c2}C(O)R^{b2}$, $NR^{c2}C(O)NR^{c2}R^{d2}$, $NR^{c2}C(O)OR^{a2}$, $C(=NR^{g2})NR^{c2}R^{d2}$, $NR^{c2}C(=NR^{g2})NR^{c2}R^{d2}$, $NR^{c2}S(O)_2NR^{c2}R^{d2}$, $S(O)NR^{c2}R^{d2}$, $S(O)_2R^{b2}$, $NR^{c2}S(O)_2R^{b2}$, and $S(O)_2NR^{c2}R^{d2}$;

each $R^{ZZ}$ is independently selected from $C_{1-6}$ alkyl, $C_{1-6}$ haloalkyl, arylalkyl, heteroarylalkyl, cycloalkylalkyl, heterocycloalkylalkyl, $C_{2-6}$ alkenyl, $C_{2-6}$ alkynyl, aryl, cycloalkyl, heteroaryl, and heterocycloalkyl, each substituted with 0, 1, 2, 3, 4, or 5 substituents each independently selected from $C_{1-6}$ alkyl, $C_{1-6}$ haloalkyl, arylalkyl, heteroarylalkyl, cycloalkylalkyl, heterocycloalkylalkyl, $C_{2-6}$ alkenyl, $C_{2-6}$ alkynyl, aryl, cycloalkyl, heteroaryl, heterocycloalkyl, halo, CN, $NO_2$, $OR^{a3}$, $SR^{a3}$, $SF_5$, $C(O)R^{b3}$, $C(O)NR^{c3}R^{d3}$, $C(O)$ $OR^{a3}$, $OC(O)R^{b3}$, $OC(O)NR^{c3}R^{d3}$, $NR^{c3}R^{d3}$, $NR^{c3}C(O)R^{b3}$, $NR^{c3}C(O)NR^{c3}R^{d3}$, $NR^{c3}C(O)OR^{a3}$, $C(=NR^{g3})NR^{c3}R^{d3}$, $NR^{c3}C(=NR^{g3})NR^{c3}R^{d3}$, $NR^{c3}S(O)_2NR^{c3}R^{d3}$, $S(O)R^{b3}$, $S(O)NR^{c3}R^{d3}$, $S(O)_2R^{b3}$, $NR^{c3}S(O)_2R^{b3}$, and $S(O)_2NR^{c3}R^{d3}$;

each $R^{8a}$ is independently selected from $C_{1-6}$ alkyl, $C_{1-6}$ haloalkyl, arylalkyl, heteroarylalkyl, cycloalkylalkyl, heterocycloalkylalkyl, $C_{2-6}$ alkenyl, $C_{2-6}$ alkynyl, aryl, cycloalkyl, heteroaryl, and heterocycloalkyl, each substituted with 0, 1, 2, 3, 4, or 5 substituents each independently selected from $C_{1-6}$ alkyl, $C_{1-6}$ haloalkyl, arylalkyl, heteroarylalkyl, cycloalkylalkyl, heterocycloalkylalkyl, $C_{2-6}$ alkenyl, $C_{2-6}$ alkynyl, aryl, cycloalkyl, heteroaryl, heterocycloalkyl, halo, CN, $NO_2$, oxo, $OR^{a4}$, $SR^{a4}$, $SF_5$, $C(O)R^{b4}$, $C(O)NR^{c4}R^{d4}$, $C(O)OR^{a4}$, $OC(O)R^{b4}$, $OC(O)NR^{c4}R^{d4}$, $NR^{c4}R^{d4}$, $NR^{c4}C(O)R^{b4}$, $NR^{c4}C(O)NR^{c4}R^{d4}$, $NR^{c4}C(O)OR^{a4}$, $C(=NR^{g4})NR^{c4}R^{d4}$, $NR^{c4}C(=NR^{g4})NR^{c4}R^{d4}$, $NR^{c4}S(O)_2NR^{c4}R^{d4}$, $S(O)_2R^{b4}$, $S(O)NR^{c4}R^{d4}$, $S(O)_2R^{b4}$, $NR^{c4}S(O)_2R^{b4}$, and $S(O)_2NR^{c4}R^{d4}$;

each $R^{10a}$ is independently selected from $C_{1-6}$ alkyl, $C_{1-6}$ haloalkyl, arylalkyl, heteroarylalkyl, cycloalkylalkyl, heterocycloalkylalkyl, $C_{2-6}$ alkenyl, $C_{2-6}$ alkynyl, aryl, cycloalkyl, heteroaryl, and heterocycloalkyl, each substituted with 0, 1, 2, 3, 4, or 5 substituents each independently selected from $C_{1-6}$ alkyl, $C_{1-6}$ haloalkyl, arylalkyl, heteroarylalkyl, cycloalkylalkyl, heterocycloalkylalkyl, $C_{2-6}$ alkenyl, $C_{2-6}$ alkynyl, aryl, cycloalkyl, heteroaryl, heterocycloalkyl, halo, CN, $NO_2$, oxo, $OR^{a5}$, $SR^{a5}$, $SF_5$, $C(O)R^{b5}$, $C(O)NR^{c5}R^{d5}$, $C(O)OR^{a5}$, $OC(O)R^{b5}$, $OC(O)NR^{c5}R^{d5}$, $NR^{c5}R^{d5}$, $NR^{c5}C(O)R^{b5}$, $NR^{c5}C(O)NR^{c5}R^{d5}$, $NR^{c5}C(O)OR^{a5}$, $C(=NR^{g5})NR^{c5}R^{d5}$, $NR^{c5}C(=NR^{g5})NR^{c5}R^{d5}$, $NR^{c5}S(O)_2NR^{c5}R^{d5}$, $S(O)R^{b5}$, $S(O)NR^{c5}R^{d5}$, $S(O)_2R^{b5}$, $NR^{c5}S(O)_2R^{b5}$, and $S(O)_2NR^{c5}R^{d5}$;

$R^a$, $R^{a1}$, $R^{a2}$, $R^{a3}$, $R^{a4}$, and $R^{a5}$ are each, independently, selected from H, $C_{1-6}$ alkyl, $C_{1-6}$ haloalkyl, arylalkyl, heteroarylalkyl, cycloalkylalkyl, heterocycloalkylalkyl, $C_{2-6}$ alkenyl, $C_{2-6}$ alkynyl, aryl, cycloalkyl, heteroaryl and heterocycloalkyl, wherein each of the $C_{1-6}$ alkyl, $C_{1-6}$ haloalkyl, arylalkyl, heteroarylalkyl, cycloalkylalkyl, heterocycloalkylalkyl, $C_{2-6}$ alkenyl, $C_{2-6}$ alkynyl, aryl, cycloalkyl, heteroaryl and heterocycloalkyl is substituted with 0, 1, 2, 3, 4, or 5 substituents each independently selected from OH, CN, amino, $C_{1-6}$ alkylamino, $C_{2-8}$ dialkylamino, halo, $C_{1-6}$alkyl, $C_{1-6}$ haloalkyl, $C_{1-6}$ hydroxylalkyl, $C_{1-6}$ cyanoalkyl, $C_{1-6}$ alkoxy, $C_{1-6}$ haloalkoxy, $C_{2-8}$ alkoxyalkoxy, aryl, arylalkyl, heteroaryl, heteroarylalkyl, cycloalkyl, and heterocycloalkyl;

$R^b$, $R^{b1}$, $R^{b2}$, $R^{b3}$, $R^{b4}$, and $R^{b5}$ are each, independently, selected from H, $C_{1-6}$ alkyl, $C_{1-6}$ haloalkyl, arylalkyl, heteroarylalkyl, cycloalkylalkyl, heterocycloalkylalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl and heterocycloalkylalkyl, wherein each of the $C_{1-6}$ alkyl, $C_{1-6}$ haloalkyl, arylalkyl, heteroarylalkyl, cycloalkylalkyl, heterocycloalkylalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl and heterocycloalkylalkyl is substituted with 0, 1, 2, 3, 4, or 5 substituents each independently selected from OH, CN, amino, $C_{1-6}$ alkylamino, $C_{2-8}$ dialkylamino, halo, $C_{1-6}$ alkyl, $C_{1-6}$ haloalkyl, $C_{1-6}$ hydroxylalkyl, $C_{1-6}$ cyanoalkyl, $C_{1-6}$ alkoxy, $C_{1-6}$ haloalkoxy, $C_{2-8}$ alkoxyalkoxy, aryl, arylalkyl, heteroaryl, heteroarylalkyl, cycloalkyl, and heterocycloalkyl;

$R^c$ and $R^d$ are independently selected from H, $C_{1-6}$ alkyl, $C_{1-6}$ haloalkyl, arylalkyl, heteroarylalkyl, cycloalkylalkyl, heterocycloalkylalkyl, $C_{2-6}$ alkenyl, $C_{2-6}$ alkynyl, aryl, heteroaryl, cycloalkyl, heterocycloalkyl, arylalkyl, heteroarylalkyl, cycloalkylalkyl and heterocycloalkylalkyl, wherein each of the $C_{1-6}$ alkyl, $C_{1-6}$ haloalkyl, arylalkyl, heteroarylalkyl, cycloalkylalkyl, heterocycloalkylalkyl, $C_{2-6}$ alkenyl, $C_{2-6}$ alkynyl, aryl, heteroaryl, cycloalkyl, heterocycloalkyl, arylalkyl, heteroarylalkyl, cycloalkylalkyl and heterocycloalkylalkyl is substituted with 0, 1, 2, 3, 4, or 5 substituents each independently selected from OH, amino, $C_{1-6}$ alkylamino, $C_{2-8}$ dialkylamino, halo, CN, $C_{1-6}$ alkyl, $C_{1-6}$ haloalkyl, $C_{1-6}$ hydroxylalkyl, $C_{1-6}$ cyanoalkyl, $C_{1-6}$ alkoxy, $C_{1-6}$haloalkoxy, $C_{2-8}$ alkoxyalkoxy, aryl, arylalkyl, heteroaryl, heteroarylalkyl, cycloalkyl, and heterocycloalkyl;

or $R^c$ and $R^d$ together with the N atom to which they are attached form a 4-, 5-, 6- or 7-membered heterocycloalkyl group that is substituted with 0, 1, 2, 3, 4, or 5 substituents each independently selected from OH, amino, $C_{1-6}$ alkylamino, $C_{2-8}$ dialkylamino, halo, CN, $C_{1-6}$ alkyl, $C_{1-6}$ haloalkyl, $C_{1-6}$ hydroxylalkyl, $C_{1-6}$ cyanoalkyl, $C_{1-6}$ alkoxy, $C_{1-6}$haloalkoxy, $C_{2-8}$ alkoxyalkoxy, aryl, arylalkyl, heteroaryl, heteroarylalkyl, cycloalkyl, and heterocycloalkyl;

$R^{1c}$ and $R^{d1}$ are independently selected from H, $C_{1-6}$ alkyl, $C_{1-6}$ haloalkyl, arylalkyl, heteroarylalkyl, cycloalkylalkyl, heterocycloalkylalkyl, $C_{2-6}$ alkenyl, $C_{2-6}$ alkynyl, aryl, heteroaryl, cycloalkyl, heterocycloalkyl, arylalkyl, heteroarylalkyl, cycloalkylalkyl and heterocycloalkylalkyl, wherein each of the $C_{1-6}$ alkyl, $C_{1-6}$ haloalkyl, arylalkyl, heteroarylalkyl, cycloalkylalkyl, heterocycloalkylalkyl, $C_{2-6}$ alkenyl, $C_{2-6}$ alkynyl, aryl, heteroaryl, cycloalkyl, heterocycloalkyl, arylalkyl, heteroarylalkyl, cycloalkylalkyl and heterocycloalkylalkyl is substituted with 0, 1, 2, 3, 4, or 5 substituents each independently selected from OH, amino, $C_{1-6}$ alkylamino, $C_{2-8}$ dialkylamino, halo, CN, $C_{1-6}$ alkyl, $C_{1-6}$ haloalkyl, $C_{1-6}$ hydroxylalkyl, $C_{1-6}$ cyanoalkyl, $C_{1-6}$ alkoxy, $C_{1-6}$haloalkoxy, $C_{2-8}$ alkoxyalkoxy, aryl, arylalkyl, heteroaryl, heteroarylalkyl, cycloalkyl, and heterocycloalkyl;

or $R^{c1}$ and $R^{d1}$ together with the N atom to which they are attached form a 4-, 5-, 6- or 7-membered heterocycloalkyl group that is substituted with 0, 1, 2, 3, 4, or 5 substituents each independently selected from OH, amino, $C_{1-6}$ alkylamino, $C_{2-8}$ dialkylamino, halo, CN, $C_{1-6}$ alkyl, $C_{1-6}$ haloalkyl, $C_{1-6}$ hydroxylalkyl, $C_{1-6}$ cyanoalkyl, $C_{1-6}$ alkoxy, $C_{1-6}$haloalkoxy, $C_{2-8}$ alkoxyalkoxy, aryl, arylalkyl, heteroaryl, heteroarylalkyl, cycloalkyl, and heterocycloalkyl;

$R^{c2}$ and $R^{d2}$ are independently selected from H, $C_{1-6}$ alkyl, $C_{1-6}$ haloalkyl, arylalkyl, heteroarylalkyl, cycloalkylalkyl, heterocycloalkylalkyl, $C_{2-6}$ alkenyl, $C_{2-6}$ alkynyl, aryl, heteroaryl, cycloalkyl, heterocycloalkyl, arylalkyl, heteroarylalkyl, cycloalkylalkyl and heterocycloalkylalkyl, wherein each of the $C_{1-6}$ alkyl, $C_{1-6}$ haloalkyl, arylalkyl, heteroarylalkyl, cycloalkylalkyl, heterocycloalkylalkyl, $C_{2-6}$ alkenyl, $C_{2-6}$ alkynyl, aryl, heteroaryl, cycloalkyl, heterocycloalkyl, arylalkyl, heteroarylalkyl, cycloalkylalkyl and heterocycloalkylalkyl is substituted with 0, 1, 2, 3, 4, or 5 substituents each independently selected from OH, amino, $C_{1-6}$ alkylamino, $C_{2-8}$ dialkylamino, halo, CN, $C_{1-6}$ alkyl, $C_{1-6}$ haloalkyl, $C_{1-6}$ hydroxylalkyl, $C_{1-6}$ cyanoalkyl, $C_{1-6}$ alkoxy, $C_{1-6}$ haloalkoxy, $C_{2-8}$ alkoxyalkoxy, aryl, arylalkyl, heteroaryl, heteroarylalkyl, cycloalkyl, and heterocycloalkyl;

or $R^{c2}$ and $R^{d2}$ together with the N atom to which they are attached form a 4-, 5-, 6- or 7-membered heterocycloalkyl group that is substituted with 0, 1, 2, 3, 4, or 5 substituents each independently selected from OH, amino, $C_{1-6}$ alkylamino, $C_{2-8}$ dialkylamino, halo, CN, $C_{1-6}$ alkyl, $C_{1-6}$ haloalkyl, $C_{1-6}$ hydroxylalkyl, $C_{1-6}$ cyanoalkyl, $C_{1-6}$ alkoxy, $C_{1-6}$ haloalkoxy, $C_{2-8}$ alkoxyalkoxy, aryl, arylalkyl, heteroaryl, heteroarylalkyl, cycloalkyl, and heterocycloalkyl;

$R^{c3}$ and $R^{d3}$ are independently selected from H, $C_{1-6}$ alkyl, $C_{1-6}$ haloalkyl, arylalkyl, heteroarylalkyl, cycloalkylalkyl, heterocycloalkylalkyl, $C_{2-6}$ alkenyl, $C_{2-6}$ alkynyl, aryl, heteroaryl, cycloalkyl, heterocycloalkyl, arylalkyl, heteroarylalkyl, cycloalkylalkyl and heterocycloalkylalkyl, wherein each of the $C_{1-6}$ alkyl, $C_{1-6}$ haloalkyl, arylalkyl, heteroarylalkyl, cycloalkylalkyl, heterocycloalkylalkyl, $C_{2-6}$ alkenyl, $C_{2-6}$ alkynyl, aryl, heteroaryl, cycloalkyl, heterocycloalkyl, arylalkyl, heteroarylalkyl, cycloalkylalkyl and heterocycloalkylalkyl is substituted with 0, 1, 2, 3, 4, or 5 substituents each independently selected from OH, amino, $C_{1-6}$ alkylamino, $C_{2-8}$ dialkylamino, halo, CN, $C_{1-6}$ alkyl, $C_{1-6}$ haloalkyl, $C_{1-6}$ hydroxylalkyl, $C_{1-6}$ cyanoalkyl, $C_{1-6}$ alkoxy, $C_{1-6}$ haloalkoxy, $C_{2-8}$ alkoxyalkoxy, aryl, arylalkyl, heteroaryl, heteroarylalkyl, cycloalkyl, and heterocycloalkyl;

or $R^{c3}$ and $R^{d3}$ together with the N atom to which they are attached form a 4-, 5-, 6- or 7-membered heterocycloalkyl group that is substituted with 0, 1, 2, 3, 4, or 5 substituents each independently selected from OH, amino, $C_{1-6}$ alkylamino, $C_{2-8}$ dialkylamino, halo, CN, $C_{1-6}$ alkyl, $C_{1-6}$ haloalkyl, $C_{1-6}$ hydroxylalkyl, $C_{1-6}$ cyanoalkyl, $C_{1-6}$ alkoxy, $C_{1-6}$ haloalkoxy, $C_{2-8}$ alkoxyalkoxy, aryl, arylalkyl, heteroaryl, heteroarylalkyl, cycloalkyl, and heterocycloalkyl;

$R^{c4}$ and $R^{d4}$ are independently selected from H, $C_{1-6}$ alkyl, $C_{1-6}$ haloalkyl, arylalkyl, heteroarylalkyl, cycloalkylalkyl, heterocycloalkylalkyl, $C_{2-6}$ alkenyl, $C_{2-6}$ alkynyl, aryl, heteroaryl, cycloalkyl, heterocycloalkyl, arylalkyl, heteroarylalkyl, cycloalkylalkyl and heterocycloalkylalkyl, wherein each of the $C_{1-6}$ alkyl, $C_{1-6}$ haloalkyl, arylalkyl, heteroarylalkyl, cycloalkylalkyl, heterocycloalkylalkyl, $C_{2-6}$ alkenyl, $C_{2-6}$ alkynyl, aryl, heteroaryl, cycloalkyl, heterocycloalkyl, arylalkyl, heteroarylalkyl, cycloalkylalkyl and heterocycloalkylalkyl is substituted with 0, 1, 2, 3, 4, or 5 substituents each independently selected from OH, amino, $C_{1-6}$ alkylamino, $C_{2-8}$ dialkylamino, halo, CN, $C_{1-6}$ alkyl, $C_{1-6}$ haloalkyl, $C_{1-6}$ hydroxylalkyl, $C_{1-6}$ cyanoalkyl, $C_{1-6}$ alkoxy, $C_{1-6}$ haloalkoxy, $C_{2-8}$ alkoxyalkoxy, aryl, arylalkyl, heteroaryl, heteroarylalkyl, cycloalkyl, and heterocycloalkyl;

or $R^{c4}$ and $R^{d4}$ together with the N atom to which they are attached form a 4-, 5-, 6- or 7-membered heterocycloalkyl group that is substituted with 0, 1, 2, 3, 4, or 5 substituents each independently selected from OH, amino, $C_{1-6}$ alkylamino, $C_{2-8}$ dialkylamino, halo, CN, $C_{1-6}$ alkyl, $C_{1-6}$ haloalkyl, $C_{1-6}$ hydroxylalkyl, $C_{1-6}$ cyanoalkyl, $C_{1-6}$ alkoxy, $C_{1-6}$ haloalkoxy, $C_{2-8}$ alkoxyalkoxy, aryl, arylalkyl, heteroaryl, heteroarylalkyl, cycloalkyl, and heterocycloalkyl;

$R^{c5}$ and $R^{d5}$ are independently selected from H, $C_{1-6}$ alkyl, $C_{1-6}$ haloalkyl, arylalkyl, heteroarylalkyl, cycloalkylalkyl, heterocycloalkylalkyl, $C_{2-6}$ alkenyl, $C_{2-6}$ alkynyl, aryl, heteroaryl, cycloalkyl, heterocycloalkyl, arylalkyl, heteroarylalkyl, cycloalkylalkyl and heterocycloalkylalkyl, wherein each of the $C_{1-6}$ alkyl, $C_{1-6}$ haloalkyl, arylalkyl, heteroarylalkyl, cycloalkylalkyl, heterocycloalkylalkyl, $C_{2-6}$ alkenyl, $C_{2-6}$ alkynyl, aryl, heteroaryl, cycloalkyl, heterocycloalkyl, arylalkyl, heteroarylalkyl, cycloalkylalkyl and heterocycloalkylalkyl is substituted with 0, 1, 2, 3, 4, or 5 substituents each independently selected from OH, amino, $C_{1-6}$ alkylamino, $C_{2-8}$ dialkylamino, halo, CN, $C_{1-6}$ alkyl, $C_{1-6}$ haloalkyl, $C_{1-6}$ hydroxylalkyl, $C_{1-6}$ cyanoalkyl, $C_{1-6}$ alkoxy, $C_{1-6}$ haloalkoxy, $C_{2-8}$ alkoxyalkoxy, aryl, arylalkyl, heteroaryl, heteroarylalkyl, cycloalkyl, and heterocycloalkyl;

or $R^{c5}$ and $R^{d5}$ together with the N atom to which they are attached form a 4-, 5-, 6- or 7-membered heterocycloalkyl group that is substituted with 0, 1, 2, 3, 4, or 5 substituents each independently selected from OH, amino, $C_{1-6}$ alkylamino, $C_{2-8}$ dialkylamino, halo, CN, $C_{1-6}$ alkyl, $C_{1-6}$ haloalkyl, $C_{1-6}$ hydroxylalkyl, $C_{1-6}$ cyanoalkyl, $C_{1-6}$ alkoxy, $C_{1-6}$ haloalkoxy, $C_{2-8}$ alkoxyalkoxy, aryl, arylalkyl, heteroaryl, heteroarylalkyl, cycloalkyl, and heterocycloalkyl;

$R^e$, $R^{e1}$, $R^e$, $R^{e3}$, $R^{e4}$, and $R^{e5}$ are each, independently, selected from H, $C_{1-6}$ alkyl, $C_{1-6}$ haloalkyl, arylalkyl, heteroarylalkyl, cycloalkylalkyl, heterocycloalkylalkyl, $C_{2-6}$ alkenyl, $C_{2-6}$ alkynyl, aryl, heteroaryl, cycloalkyl, heterocycloalkyl, arylalkyl, heteroarylalkyl, cycloalkylalkyl and heterocycloalkylalkyl, wherein each of the $C_{1-6}$ alkyl, $C_{1-6}$ haloalkyl, arylalkyl, heteroarylalkyl, cycloalkylalkyl, heterocycloalkylalkyl, $C_{2-6}$ alkenyl, $C_{2-6}$ alkynyl, aryl, heteroaryl, cycloalkyl, heterocycloalkyl, arylalkyl, heteroarylalkyl, cycloalkylalkyl and heterocycloalkylalkyl is substituted with 0, 1, 2, 3, 4, or 5 substituents each independently selected from OH, amino, $C_{1-6}$ alkylamino, $C_{2-8}$ dialkylamino, halo, CN, $C_{1-6}$ alkyl, $C_{1-6}$ haloalkyl, $C_{1-6}$ hydroxylalkyl, $C_{1-6}$ cyanoalkyl, $C_{1-6}$ alkoxy, $C_{1-6}$ haloalkoxy, $C_{2-8}$ alkoxyalkoxy, aryl, arylalkyl, heteroaryl, heteroarylalkyl, cycloalkyl, and heterocycloalkyl;

$R^g$, $R^{g1}$, $R^{g2}$, $R^{g3}$, $R^{g4}$, and $R^{g5}$ are each, independently, selected from H, CN, and $NO_2$;

each p1 is, independently, 0, 1, or 2;
each p2 is, independently, 0, 1, or 2;
each p3 is, independently, 0, 1, or 2;
each p4 is, independently, 0, 1, or 2;
each q1 is, independently, 1 or 2; and
each q2 is, independently, 1 or 2.

In some embodiments, the present invention provides compounds of Formula I:

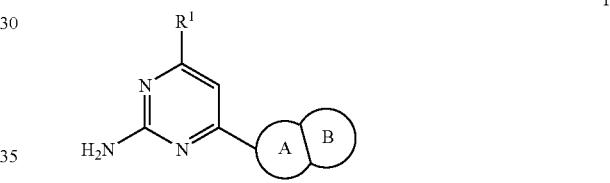

I or pharmaceutically acceptable salts thereof or N-oxide thereofs or quaternary ammonium salts thereof, wherein:

ring A is an aryl or a 5- or 6-membered heteroaryl group wherein ring A is linked to the pyrimidine ring through a carbon atom of ring A, wherein each of the ring-forming atoms of the 5- or 6-membered heteroaryl group is independently selected from C, N, O, and S, and wherein ring A is substituted with 0, 1, 2, or 3 —$W^{1a}$—$X^{1a}$—$W^1$—$X^1$—$Y^1$—$Z^1$;

wherein —$W^{1a}$—$X^{1a}$—$W^1$—$X^1$—$Y^1$—$Z^1$ is other than H;

ring B is a 4-20 membered cycloalkyl or heterocycloalkyl group that is fused to ring A, wherein each of the ring-forming atoms of the 4-20 membered heterocycloalkyl group is independently selected from C, N, O, and S, wherein ring B is substituted with 0, 1, 2, 3, 4, 5, or 6 —$W^{2a}$—$X^{2a}$—$W^2$—$X^2$—$Y^2$—$Z^2$;

wherein —$W^{2a}$—$X^{2a}$—$W^2$—$X^2$—$Y^2$—$Z^2$ is other than H;

$R^1$ is $NR^2R^3$, wherein $R^2$ and $R^3$ together with the N atom to which they are attached form a 4-10 membered heterocycloalkyl group wherein each of the ring-forming atoms of the 4-10 membered heterocycloalkyl group is independently selected from C, N, O, and S, and wherein the 4-10 membered heterocycloalkyl group is substituted with 0, 1, 2, 3, 4, 5, 6, 7, or 8 $R^4$;

each $R^4$ is, independently, selected from halo, CN, $C_{1-6}$ alkyl, $C_{1-6}$ haloalkyl, $C_{3-7}$ cycloalkyl, OH, oxo, $C_{1-6}$ alkoxy, $C_{1-6}$ haloalkoxy, $NH_2$, $NH(C_{1-4}$ alkyl), $NH(C_{3-7}$cycloalkyl), and $N(C_{1-4}$ alkyl)$_2$, wherein each of the $C_{1-6}$ alkyl and $C_{3-7}$ cycloalkyl is substituted with 0, 1, 2, or 3 substituents each independently selected from halo, OH, CN, $NH_2$, $NH(C_{1-4}$ alkyl), and $N(C_{1-4}$ alkyl$)_2$;

$W^{1a}$, $W^{3a}$, $W^1$, and $W^2$ are each, independently, selected from absent, $C_{1-6}$ alkylenyl, $C_{2-6}$ alkenylenyl, $C_{2-6}$ alkynylenyl, $(CR^{11a}R^{11b})_{p1}O(CR^{11a}R^{11b})_{p2}$, $(CR^{11a}R^{11b})_{p1}S(CR^{11a}R^{11b})_{p2}$, $(CR^{11a}R^{11b})_{p1}NR^e(CR^{11a}R^{11b})_{p2}$, $(CR^{11a}R^{11b})_{p1}C(O)(CR^{11a}R^{11b})_{p2}$, $(CR^{11a}R^{11b})_{p1}C(S)(CR^{11a}R^{11b})_{p2}$, $(CR^{11a}R^{11b})_{p1}C(O)O(CR^{11a}R^{11b})_{p2}$, $(CR^{11a}R^{11b})_{p1}C(O)NR^e(CR^{11a}R^{11b})_{p2}$, $(CR^{11a}R^{11b})_{p1}C(S)NR^e(CR^{11a}R^{11b})_{p2}$, $(CR^{11a}R^{11b})_{p1}S(O)CR^{11a}R^{11b})_{p2}$, $(CR^{11a}R^{11b})_{p1}S(O)_2(CR^{11a}R^{11b})_{p2}$, $(CR^{11a}R^{11b})_{p1}S(O)NR^3(CR^{11a}R^{11b})_{p2}$, $(CR^{11a}R^{11b})_{p1}S(O)_2NR^e(CR^{11a}R^{11b})_{p2}$, $(CR^{11a}R^{11b})_{p1}NR^e C(O)NR^f(CR^{11a}R^{11b})_{p2}$, $(CR^{11a}R^{11b})_{p1}NR^eC(S)NR^f(CR^{11a}R^{11b})_{p2}$, $(CR^{11a}R^{11b})_{p1}NR^e S(O)_2NR^f(CR^{11a}R^{11b})_{p2}$, $(CR^{11a}R^{11b})_{p1}C(=NR^g)NR^e(CR^{11a}R^{11b})_{p2}$, $(CR^{11a}R^{11b})_{p1}NR^e C(=NR^g)NR^f(CR^{11a}R^{11b})_{p2}$, $O(CR^{11a}R^{11b})_{q1}C(O)$, $S(CR^{11a}R^{11b})_{q1}C(O)$, $NR^e(CR^{11a}R^{11b})_{q1}C(O)$, $C(O)(CR^{11a}R^{11b})_{q1}C(O)$, $NR^e(CR^{11a}R^{11b})_{q1}NR^f$, $O(CR^{11a}R^{11b})_{q1}NR^f$, and $O(CR^{11a}R^{11b})_{q1}O$, wherein each of the $C_{1-6}$ alkylenyl, $C_{2-6}$ alkenylenyl and $C_{2-6}$ alkynylenyl is substituted with 0, 1, 2, 3, 4, 5, 6, 7, or 8 substituents each independently selected from halo, CN, $NO_2$, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cC(O)R^b$, $NR^cC(O)NR^cR^d$, $NR^cC(O)OR^a$, $C(=NR^g)NR^cR^d$, $NR^cC(=NR^g)NR^cR^d$, $NR^cS(O)_2NR^cR^d$, $S(O)R^b$, $S(O)NR^cR^d$, $S(O)_2R^b$, $NR^cS(O)_2R^b$, and $S(O)_2NR^cR^d$;

$X^{1a}$, $X^{2a}$, $X^1$, and $X^2$ are each, independently, selected from absent, $C_{1-6}$ alkylenyl, $C_{2-6}$ alkenylenyl, $C_{2-6}$ alkynylenyl, aryl, cycloalkyl, heteroaryl, heterocycloalkyl, arylalkyl, heteroarylalkyl, cycloalkylalkyl, and heterocycloalkylalkyl, wherein each of said $C_{1-6}$ alkylenyl, $C_{2-6}$ alkenylenyl, $C_{2-6}$ alkynylenyl, aryl, cycloalkyl, heteroaryl, heterocycloalkyl, arylalkyl, heteroarylalkyl, cycloalkylalkyl, and heterocycloalkylalkyl is substituted with 0, 1, 2, 3, 4, 5, 6, 7, or 8 substituents each independently selected from $R^{XX}$, halo, CN, $NO_2$, $OR^a$, $SR^a$, $SF_5$, $C(O)R^b$, $C(O)NR^cR^d$, $C(O)OR^a$, $OC(O)R^b$, $OC(O)NR^cR^d$, $NR^cR^d$, $NR^cC(O)R^b$, $NR^cC(O)NR^cR^d$, $NR^cC(O)OR^a$, $C(=NR^g)NR^cR^d$, $NR^cC(=NR^g)NR^cR^d$, $NR^cS(O)_2NR^cR^d$, $S(O)R^b$, $S(O)NR^cR^d$, $S(O)_2R^b$, $NR^cS(O)_2R^b$, and $S(O)_2NR^cR^d$;

$Y^1$ and $Y^2$ are each, independently, selected from absent, $C_{1-6}$ alkylenyl, $C_{2-6}$ alkenylenyl, $C_{2-6}$ alkynylenyl, $(CR^{12a}R^{12b})_{p3}O(CR^{12a}R^{12b})_{p4}$, $(CR^{12a}R^{12b})_{p3}S(CR^{12a}R^{12b})_{p4}$, $(CR^{12a}R^{12b})_{p3}NR^e(CR^{12a}R^{12b})_{p4}$, $(CR^{12a}R^{12b})_{p3}C(O)(CR^{12a}R^{12b})_{p4}$, $(CR^{12a}R^{12b})_{p3}C(S)(CR^{12a}R^{12b})_{p4}$, $(CR^{12a}R^{12b})_{p3}C(O)O(CR^{12a}R^{12b})_{p4}$, $(CR^{12a}R^{12b})_{p3}C(O)NR^e(CR^{12a}R^{12b})_{p4}$, $(CR^{12a}R^{12b})_{p3}C(S)NR^e(CR^{12a}R^{12b})_{p4}$, $(CR^{12a}R^{12b})_{p3}S(O)(CR^{12a}R^{12b})_{p4}$, $(CR^{12a}R^{12b})_{p3}S(O)_2(CR^{12a}R^{12b})_{p4}$, $(CR^{12a}R^{12b})_{p3}S(O)NR^e(CR^{12a}R^{12b})_{p4}$, $(CR^{12a}R^{12b})_{p3}S(O)_2NR^e(CR^{12a}R^{12b})_{p4}$, $(CR^{12a}R^{12b})_{p3}NR^eC(O)NR^f(CR^{12a}R^{12b})_{p4}$, $(CR^{12a}R^{12b})_{p3}NR^e C(S)NR^f(CR^{12a}R^{12b})_{p4}$, $(CR^{12a}R^{12b})_{p3}NR^eS(O)_2NR^f(CR^{12a}R^{12b})_{p4}$, $(CR^{12a}R^{12b})_{p3}C(=NR^g)NR^e(CR^{12a}R^{12b})_{p4}$, $(CR^{12a}R^{12b})_{p3}NR^eC(=NR^g)NR^f(CR^{12a}R^{12b})_{p4}$, $O(CR^{12a}R^{12b})_{q2}C(O)$, $S(CR^{12a}R^{12b})_{q2}C(O)$, $NR^e(CR^{12a}R^{12b})_{q2}C(O)$, $NR^e(CR^{12a}R^{12b})_{q2}NR^f$, $O(CR^{12a}R^{12b})_{q2} NR^f$, and $O(CR^{12a}R^{12b})_{q2}O$, wherein each of the $C_{1-6}$ alkylenyl, $C_{2-6}$ alkenylenyl, and $C_{2-6}$ alkynylenyl is substituted with 0, 1, 2, 3, 4, 5, 6, 7, or 8 substituents independently selected from $C_{1-6}$ alkyl, $C_{1-6}$haloalkyl, $C_{2-6}$ alkenyl, $C_{2-6}$ alkynyl, halo, CN, $NO_2$, $OR^a$, $SR^a$, $SF_5$, $C(O)R^b$, $C(O)NR^cR^d$, $C(O)OR^a$, $OC(O)R^b$, $OC(O)NR^cR^d$, $NR^cR^d$, $NR^cC(O)R^b$, $NR^cC(O)NR^cR^d$, $NR^cC(O)OR^a$, $C(=NR^g)NR^cR^d$, $NR^cC(=NR^g)NR^cR^d$, $NR^cS(O)_2NR^cR^d$, $S(O)R^b$, $S(O)NR^cR^d$, $S(O)_2R^b$, $NR^cS(O)_2R^b$, and $S(O)_2NR^cR^d$;

$Z^1$ and $Z^2$ are each, independently, selected from H, halo, CN, $NO_2$, $OR^a$, $SR^a$, $SF_5$, $C(O)R^b$, $C(O)NR^cR^d$, $C(O)OR^a$, $OC(O)R^b$, $OC(O)NR^cR^d$, $NR^cR^d$, $NR^cC(O)R^b$, $NR^c C(O)NR^cR^d$, $NR^cC(O)OR^a$, $C(=NR^g)NR^cR^d$, $NR^cC(=NR^g)NR^cR^d$, $NR^cS(O)_2NR^cR^d$, $S(O)R^b$, $S(O)NR^cR^d$, $S(O)_2R^b$, $NR^cS(O)_2R^b$, $S(O)_2NR^cR^d$, $C_{1-6}$ alkyl, $C_{1-6}$haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl, and heterocycloalkylalkyl, wherein each of the $C_{1-6}$ alkyl, $C_{1-6}$ haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl, and heterocycloalkylalkyl is substituted with 0, 1, 2, 3, 4, 5, 6, 7, or 8 substituents each independently selected from $R^{ZZ}$, halo, CN, $NO_2$, $OR^a$, $SR^a$, $SF_5$, $C(O)R^b$, $C(O)NR^cR^d$, $C(O)OR^a$, $OC(O)R^b$, $OC(O)NR^cR^d$, $NR^cR^d$, $NR^cC(O)R^d$, $NR^c C(O)OR^a$, $NR^cS(O)_2R^b$, $NR^cS(O)_2NR^cR^d$; $S(O)R^b$, $S(O)NR^cR^d$, $S(O)_2R^b$, and $S(O)_2NR^cR^d$;

or $-W^{2a}-X^{2a}-W^2-X^2-Y^2-Z^2$ is oxo;

$R^{11a}$, $R^{11b}$, $R^{12a}$, and $R^{12b}$ are each, independently, selected from H, halo, $C_{1-6}$ alkyl, $C_{2-6}$ alkenyl, $C_{2-6}$ alkynyl, $C_{1-6}$ haloalkyl, cycloalkyl, heterocycloalkyl, aryl, heteroaryl, arylalkyl, heteroarylalkyl, cycloalkylalkyl, heterocycloalkylalkyl, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{b1}$, $NR^{c1}C(O)NR^{c1}R^{d1}$, $NR^{c1}C(O)OR^{a1}$, $C(=NR^{g1})NR^{c1}R^{d1}$, $NR^{c1}C(=NR^{g1})NR^{c1}R^{d1}$, $NR^{c1}S(O)_2NR^{c1}R^{d1}$, $S(O)R^{b1}$, $S(O)NR^{c1}R^{d1}$, $S(O)_2R^{b1}$, $NR^{c1}S(O)_2R^{b1}$, and $S(O)_2 NR^{c1}R^{d1}$, wherein each of said $C_{1-6}$ alkyl, $C_{2-6}$ alkenyl, $C_{2-6}$ alkynyl, $C_{1-6}$ haloalkyl, cycloalkyl, heterocycloalkyl, aryl, heteroaryl, arylalkyl, heteroarylalkyl, cycloalkylalkyl, and heterocycloalkylalkyl is substituted with 0, 1, 2, 3, 4, or 5 substituents each independently selected from halo, $C_{1-6}$ alkyl, $C_{2-6}$ alkenyl, $C_{2-6}$ alkynyl, $C_{1-6}$ haloalkyl, cycloalkyl, heterocycloalkyl, aryl, heteroaryl, arylalkyl, heteroarylalkyl, cycloalkylalkyl, heterocycloalkylalkyl, CN, $NO_2$, $OR^{a1}$, $SR^{a1}$, $SF_5$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{b1}$, $NR^{c1}C(O)NR^{c1}R^{d1}$, $NR^{c1}C(O)OR^{a1}$, $C(=NR^g)NR^{c1}R^{d1}$, $NR^{c1}C(=NR^g)NR^{c1}R^{d1}$, $NR^{c1}S(O)_2NR^{c1}R^{d1}$, $S(O)R^{b1}$, $S(O)NR^{c1}R^{d1}$, $S(O)_2R^{b1}$, $NR^{c1}S(O)_2R^{b1}$, and $S(O)_2NR^{c1}R^{d1}$;

each $R^{XX}$ is independently selected from $C_{1-6}$ alkyl, $C_{1-6}$ haloalkyl, arylalkyl, heteroarylalkyl, cycloalkylalkyl, heterocycloalkylalkyl, $C_{2-6}$ alkenyl, $C_{2-6}$ alkynyl, aryl, cycloalkyl, heteroaryl, and heterocycloalkyl, each substituted with 0, 1, 2, 3, 4, or 5 substituents each independently selected from $C_{1-6}$ alkyl, $C_{1-6}$ haloalkyl, arylalkyl, heteroarylalkyl, cycloalkylalkyl, heterocycloalkylalkyl, $C_{2-6}$ alkenyl, $C_{2-6}$ alkynyl, aryl, cycloalkyl, heteroaryl, heterocycloalkyl, halo, CN, $NO_2$, $OR^{a2}$, $SR^{a2}$, $SF_5$, $C(O)R^{b2}$, $C(O)NR^{c2}R^{d2}$, $C(O)OR^{a2}$, $OC(O)R^{b2}$, $OC(O)NR^{c2}R^{d2}$, $NR^{c2}R^{d2}$, $NR^{c2}C(O)R^{b2}$, $NR^{c2}C(O)NR^{c2}R^{d2}$, $NR^{c2}C(O)OR^{a2}$, $C(=NR^{g2})NR^{c2}R^{d2}$, $NR^{c2}C(=NR^{g2})NR^{c2}R^{d2}$, $NR^{c2}S(O)_2NR^{c2}R^{d2}$, $S(O)R^{b2}$, $S(O)NR^{c2}R^{d2}$, $S(O)_2R^{b2}$, $NR^{c2}S(O)_2R^{b2}$, and $S(O)_2NR^{c2}R^{d2}$;

each $R^{ZZ}$ is independently selected from $C_{1-6}$ alkyl, $C_{1-6}$ haloalkyl, arylalkyl, heteroarylalkyl, cycloalkylalkyl, heterocycloalkylalkyl, $C_{2-6}$ alkenyl, $C_{2-6}$ alkynyl, aryl, cycloalkyl, heteroaryl, and heterocycloalkyl, each substituted with 0, 1, 2, 3, 4, or 5 substituents each independently selected from $C_{1-6}$ alkyl, $C_{1-6}$ haloalkyl, arylalkyl, heteroarylalkyl, cycloalkylalkyl, heterocycloalkylalkyl, $C_{2-6}$ alkenyl, $C_{2-6}$ alkynyl, aryl, cycloalkyl, heteroaryl, heterocycloalkyl, halo, CN, $NO_2$, $OR^{a3}$, $SR^{a3}$, $SF_5$, $C(O)R^{b3}$, $C(O)NR^{c3}R^{d3}$, $C(O)OR^{a3}$, $OC(O)R^{b3}$, $OC(O)NR^{c3}R^{d3}$, $NR^{c3}R^{d3}$, $NR^{c3}C(O)R^{b3}$, $NR^{c3}C(O)NR^{c3}R^{d3}$, $NR^{c3}C(O)OR^{a3}$, $C(=NR^{g3})NR^{c3}R^{d3}$, $NR^{c3}C(=NR^{g3})NR^{c3}R^{d3}$, $NR^{c3}S(O)_2NR^{c3}R^{d3}$, $S(O)R^{b3}$, $S(O)NR^{c3}R^{d3}$, $S(O)_2R^{b3}$, $NR^{c3}S(O)_2R^{b3}$, and $S(O)_2NR^{c3}R^{d3}$;

$R^a$, $R^{a1}$, $R^{a2}$, and $R^{a3}$ are each, independently, selected from H, $C_{1-6}$ alkyl, $C_{1-6}$ haloalkyl, arylalkyl, heteroarylalkyl, cycloalkylalkyl, heterocycloalkylalkyl, $C_{2-6}$ alkenyl, $C_{2-6}$ alkynyl, aryl, cycloalkyl, heteroaryl and heterocycloalkyl, wherein each of the $C_{1-6}$ alkyl, $C_{1-6}$ haloalkyl, arylalkyl, heteroarylalkyl, cycloalkylalkyl, heterocycloalkylalkyl, $C_{2-6}$ alkenyl, $C_{2-6}$ alkynyl, aryl, cycloalkyl, heteroaryl and heterocycloalkyl is substituted with 0, 1, 2, 3, 4, or 5 substituents each independently selected from OH, CN, amino, $C_{1-6}$ alkylamino, $C_{2-8}$ dialkylamino, halo, $C_{1-6}$ alkyl, $C_{1-6}$ haloalkyl, $C_{1-6}$ hydroxylalkyl, $C_{1-6}$ cyanoalkyl, $C_{1-6}$ alkoxy, $C_{1-6}$ haloalkoxy, $C_{2-8}$ alkoxyalkoxy, aryl, arylalkyl, heteroaryl, heteroarylalkyl, cycloalkyl, and heterocycloalkyl;

$R^b$, $R^{b1}$, $R^{b2}$, and $R^{b3}$ are each, independently, selected from H, $C_{1-6}$ alkyl, $C_{1-6}$ haloalkyl, arylalkyl, heteroarylalkyl, cycloalkylalkyl, heterocycloalkylalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl and heterocycloalkylalkyl, wherein each of the $C_{1-6}$ alkyl, $C_{1-6}$ haloalkyl, arylalkyl, heteroarylalkyl, cycloalkylalkyl, heterocycloalkylalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl and heterocycloalkylalkyl is substituted with 0, 1, 2, 3, 4, or 5 substituents each independently selected from OH, CN, amino, $C_{1-6}$ alkylamino, $C_{2-8}$ dialkylamino, halo, $C_{1-6}$ alkyl, $C_{1-6}$ haloalkyl, $C_{1-6}$ hydroxylalkyl, $C_{1-6}$ cyanoalkyl, $C_{1-6}$ alkoxy, $C_{1-6}$ haloalkoxy, $C_{2-8}$ alkoxyalkoxy, aryl, arylalkyl, heteroaryl, heteroarylalkyl, cycloalkyl, and heterocycloalkyl;

$R^c$ and $R^d$ are independently selected from H, $C_{1-6}$ alkyl, $C_{1-6}$ haloalkyl, arylalkyl, heteroarylalkyl, cycloalkylalkyl, heterocycloalkylalkyl, $C_{2-6}$ alkenyl, $C_{2-6}$ alkynyl, aryl, heteroaryl, cycloalkyl, heterocycloalkyl, arylalkyl, heteroarylalkyl, cycloalkylalkyl and heterocycloalkylalkyl, wherein each of the $C_{1-6}$ alkyl, $C_{1-6}$ haloalkyl, arylalkyl, heteroarylalkyl, cycloalkylalkyl, heterocycloalkylalkyl, $C_{2-6}$ alkenyl, $C_{2-6}$ alkynyl, aryl, heteroaryl, cycloalkyl, heterocycloalkyl, arylalkyl, heteroarylalkyl, cycloalkylalkyl and heterocycloalkylalkyl is substituted with 0, 1, 2, 3, 4, or 5 substituents each independently selected from OH, amino, $C_{1-6}$ alkylamino, $C_{2-8}$ dialkylamino, halo, CN, $C_{1-6}$ alkyl, $C_{1-6}$ haloalkyl, $C_{1-6}$ hydroxylalkyl, $C_{1-6}$ cyanoalkyl, $C_{1-6}$ alkoxy, $C_{1-6}$ haloalkoxy, $C_{2-8}$ alkoxyalkoxy, aryl, arylalkyl, heteroaryl, heteroarylalkyl, cycloalkyl, and heterocycloalkyl;

or $R^c$ and $R^d$ together with the N atom to which they are attached form a 4-, 5-, 6- or 7-membered heterocycloalkyl group that is substituted with 0, 1, 2, 3, 4, or 5 substituents each independently selected from OH, amino, $C_{1-6}$ alkylamino, $C_{2-8}$ dialkylamino, halo, CN, $C_{1-6}$ alkyl, $C_{1-6}$ haloalkyl, $C_{1-6}$ hydroxylalkyl, $C_{1-6}$ cyanoalkyl, $C_{1-6}$ alkoxy, $C_{1-6}$ haloalkoxy, $C_{2-8}$ alkoxyalkoxy, aryl, arylalkyl, heteroaryl, heteroarylalkyl, cycloalkyl, and heterocycloalkyl;

$R^{c1}$ and $R^{d1}$ are independently selected from H, $C_{1-6}$ alkyl, $C_{1-6}$ haloalkyl, arylalkyl, heteroarylalkyl, cycloalkylalkyl, heterocycloalkylalkyl, $C_{2-6}$ alkenyl, $C_{2-6}$ alkynyl, aryl, heteroaryl, cycloalkyl, heterocycloalkyl, arylalkyl, heteroarylalkyl, cycloalkylalkyl and heterocycloalkylalkyl, wherein each of the $C_{1-6}$ alkyl, $C_{1-6}$ haloalkyl, arylalkyl, heteroarylalkyl, cycloalkylalkyl, heterocycloalkylalkyl, $C_{2-6}$ alkenyl, $C_{2-6}$ alkynyl, aryl, heteroaryl, cycloalkyl, heterocycloalkyl, arylalkyl, heteroarylalkyl, cycloalkylalkyl and heterocycloalkylalkyl is substituted with 0, 1, 2, 3, 4, or 5 substituents each independently selected from OH, amino, $C_{1-6}$ alkylamino, $C_{2-8}$ dialkylamino, halo, CN, $C_{1-6}$ alkyl, $C_{1-6}$ haloalkyl, $C_{1-6}$ hydroxylalkyl, $C_{1-6}$ cyanoalkyl, $C_{1-6}$ alkoxy, $C_{1-6}$ haloalkoxy, $C_{2-8}$ alkoxyalkoxy, aryl, arylalkyl, heteroaryl, heteroarylalkyl, cycloalkyl, and heterocycloalkyl;

or $R^{c1}$ and $R^{d1}$ together with the N atom to which they are attached form a 4-, 5-, 6- or 7-membered heterocycloalkyl group that is substituted with 0, 1, 2, 3, 4, or 5 substituents each independently selected from OH, amino, $C_{1-6}$ alkylamino, $C_{2-8}$ dialkylamino, halo, CN, $C_{1-6}$ alkyl, $C_{1-6}$ haloalkyl, $C_{1-6}$ hydroxylalkyl, $C_{1-6}$ cyanoalkyl, $C_{1-6}$ alkoxy, $C_{1-6}$ haloalkoxy, $C_{2-8}$ alkoxyalkoxy, aryl, arylalkyl, heteroaryl, heteroarylalkyl, cycloalkyl, and heterocycloalkyl;

$R^{c2}$ and $R^{d2}$ are independently selected from H, $C_{1-6}$ alkyl, $C_{1-6}$ haloalkyl, arylalkyl, heteroarylalkyl, cycloalkylalkyl, heterocycloalkylalkyl, $C_{2-6}$ alkenyl, $C_{2-6}$ alkynyl, aryl, heteroaryl, cycloalkyl, heterocycloalkyl, arylalkyl, heteroarylalkyl, cycloalkylalkyl and heterocycloalkylalkyl, wherein each of the $C_{1-6}$ alkyl, $C_{1-6}$ haloalkyl, arylalkyl, heteroarylalkyl, cycloalkylalkyl, heterocycloalkylalkyl, $C_{2-6}$ alkenyl, $C_{2-6}$ alkynyl, aryl, heteroaryl, cycloalkyl, heterocycloalkyl, arylalkyl, heteroarylalkyl, cycloalkylalkyl and heterocycloalkylalkyl is substituted with 0, 1, 2, 3, 4, or 5 substituents each independently selected from OH, amino, $C_{1-6}$ alkylamino, $C_{2-8}$ dialkylamino, halo, CN, $C_{1-6}$ alkyl, $C_{1-6}$ haloalkyl, $C_{1-6}$ hydroxylalkyl, $C_{1-6}$ cyanoalkyl, $C_{1-6}$ alkoxy, $C_{1-6}$ haloalkoxy, $C_{2-8}$ alkoxyalkoxy, aryl, arylalkyl, heteroaryl, heteroarylalkyl, cycloalkyl, and heterocycloalkyl;

or $R^{c2}$ and $R^{d2}$ together with the N atom to which they are attached form a 4-, 5-, 6- or 7-membered heterocycloalkyl group that is substituted with 0, 1, 2, 3, 4, or 5 substituents each independently selected from OH, amino, $C_{1-6}$ alkylamino, $C_{2-8}$ dialkylamino, halo, CN, $C_{1-6}$ alkyl, $C_{1-6}$ haloalkyl, $C_{1-6}$ hydroxylalkyl, $C_{1-6}$ cyanoalkyl, $C_{1-6}$ alkoxy, $C_{1-6}$ haloalkoxy, $C_{2-8}$ alkoxyalkoxy, aryl, arylalkyl, heteroaryl, heteroarylalkyl, cycloalkyl, and heterocycloalkyl;

$R^{c3}$ and $R^{d3}$ are independently selected from H, $C_{1-6}$ alkyl, $C_{1-6}$ haloalkyl, arylalkyl, heteroarylalkyl, cycloalkylalkyl, heterocycloalkylalkyl, $C_{2-6}$ alkenyl, $C_{2-6}$ alkynyl, aryl, heteroaryl, cycloalkyl, heterocycloalkyl, arylalkyl, heteroarylalkyl, cycloalkylalkyl and heterocycloalkylalkyl, wherein each of the $C_{1-6}$ alkyl, $C_{1-6}$ haloalkyl, arylalkyl, heteroarylalkyl, cycloalkylalkyl, heterocycloalkylalkyl, $C_{2-6}$ alkenyl, $C_{2-6}$ alkynyl, aryl, heteroaryl, cycloalkyl, heterocycloalkyl, arylalkyl, heteroarylalkyl, cycloalkylalkyl and heterocycloalkylalkyl is substituted with 0, 1, 2, 3, 4, or 5 substituents each independently selected from OH, amino, $C_{1-6}$ alkylamino, $C_{2-8}$ dialkylamino, halo, CN, $C_{1-6}$ alkyl, $C_{1-6}$ haloalkyl, $C_{1-6}$ hydroxylalkyl, $C_{1-6}$ cyanoalkyl, $C_{1-6}$ alkoxy, $C_{1-6}$ haloalkoxy, $C_{2-8}$ alkoxyalkoxy, aryl, arylalkyl, heteroaryl, heteroarylalkyl, cycloalkyl, and heterocycloalkyl;

or $R^{c3}$ and $R^{d3}$ together with the N atom to which they are attached form a 4-, 5-, 6- or 7-membered heterocycloalkyl group that is substituted with 0, 1, 2, 3, 4, or 5 substituents each independently selected from OH, amino, $C_{1-6}$ alkylamino, $C_{2-8}$ dialkylamino, halo, CN, $C_{1-6}$ alkyl, $C_{1-6}$ haloalkyl, $C_{1-6}$ hydroxylalkyl, $C_{1-6}$ cyanoalkyl, $C_{1-6}$ alkoxy, $C_{1-6}$ haloalkoxy, $C_{2-8}$ alkoxyalkoxy, aryl, arylalkyl, heteroaryl, heteroarylalkyl, cycloalkyl, and heterocycloalkyl;

$R^e$, $R^{e1}$, $R^{e2}$, and $R^{e3}$ are each, independently, selected from H, $C_{1-6}$ alkyl, $C_{1-6}$ haloalkyl, arylalkyl, heteroarylalkyl, cycloalkylalkyl, heterocycloalkylalkyl, $C_{2-6}$ alkenyl, $C_{2-6}$ alkynyl, aryl, heteroaryl, cycloalkyl, heterocycloalkyl, arylalkyl, heteroarylalkyl, cycloalkylalkyl and heterocycloalkylalkyl, wherein each of the $C_{1-6}$ alkyl, $C_{1-6}$ haloalkyl, arylalkyl, heteroarylalkyl, cycloalkylalkyl, heterocycloalkylalkyl, $C_{2-6}$ alkenyl, $C_{2-6}$ alkynyl, aryl, heteroaryl, cycloalkyl, heterocycloalkyl, arylalkyl, heteroarylalkyl, cycloalkylalkyl and heterocycloalkylalkyl is substituted with 0, 1, 2, 3, 4, or 5 substituents each independently selected from OH, amino, $C_{1-6}$ alkylamino, $C_{2-8}$ dialkylamino, halo, CN, $C_{1-6}$ alkyl, $C_{1-6}$ haloalkyl, $C_{1-6}$ hydroxylalkyl, $C_{1-6}$ cyanoalkyl, $C_{1-6}$ alkoxy, $C_{1-6}$ haloalkoxy, $C_{2-8}$ alkoxyalkoxy, aryl, arylalkyl, heteroaryl, heteroarylalkyl, cycloalkyl, and heterocycloalkyl;

$R^g$, $R^{g1}$, $R^{g2}$, and $R^{g3}$ are each, independently, selected from H, CN, and $NO_2$;

each p1 is, independently, 0, 1, or 2;
each p2 is, independently, 0, 1, or 2;
each p3 is, independently, 0, 1, or 2;
each p4 is, independently, 0, 1, or 2;
each q1 is, independently, 1 or 2; and
each q2 is, independently, 1 or 2.

In some embodiments of the compounds of Formula I, the moiety having the structure of

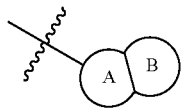

is other than a moiety of

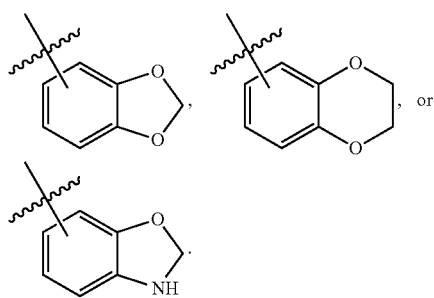

In some embodiments of the compounds of Formula I, the moiety having the structure of

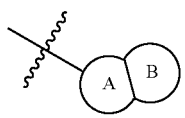

is other than a moiety of

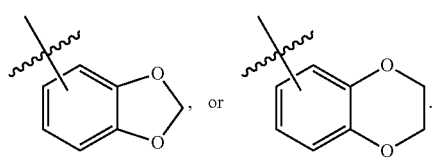

In some embodiments of the compounds of Formula I, the moiety having the structure of

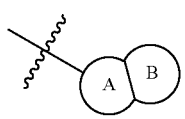

is other than a moiety of

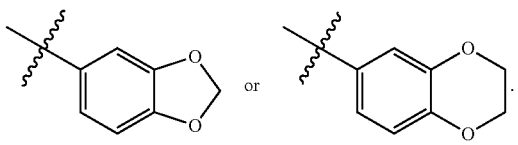 [SMILES: *c1ccc2c(c1)OCO2 ; *c1ccc2c(c1)OCCO2]

In some embodiments of the compounds of Formula I, both ring A and ring B are unsubstituted, or substituted with at least one substituent other than $C_{1-6}$ alkyl that is substituted with $NHR^d$ and with $COOR^a$.

In some embodiments of the compounds of Formula I, both ring A and ring B are unsubstituted, or substituted with at least one substituent other than $C_{1-6}$ alkyl that is substituted with $NH_2$ and with COOH.

In some embodiments of the compounds of Formula I, both ring A and ring B are unsubstituted.

In some embodiments of the compounds of Formula I, no substituent on either ring A or ring B is $C_{1-6}$ alkyl that is substituted with $NHR^d$ and with $COOR^a$.

In some embodiments of the compounds of Formula I, no substituent on either ring A or ring B is $C_{1-6}$ alkyl that is substituted with $NH_2$ and with COOH.

In some embodiments of the compounds of Formula I, at least one of the ring-forming atoms of ring A and ring B is selected from N, O, and S.

In some embodiments of the compounds of Formula I, at least one of the ring-forming atoms of ring A and ring B is N.

In some embodiments of the compounds of Formula I, at least one of the ring-forming atoms of ring B is N. In some embodiments of the compounds of Formula I, the ring formed by $R^2$ and $R^3$ together with the N atom to which they are attached is a 4-10 membered heterocycloalkyl group substituted with 0, 1, 2, 3, 4, or 5 $R^4$, and wherein each of the ring-forming atoms of the 4-10 membered heterocycloalkyl group is C, O, or N. In some further embodiments, the 4-10 membered heterocycloalkyl group is mono- or bi-cyclic. In some further embodiments, the 4-10 membered heterocycloalkyl group is saturated [i.e., it does not have any unsaturated ring bond (i.e. no double or triple bond as a ring bond for the 4-10 membered heterocycloalkyl group)].

In some embodiments of the compounds of Formula I, the ring formed by $R^2$ and $R^3$ together with the N atom to which they are attached is selected from:

(Q1)

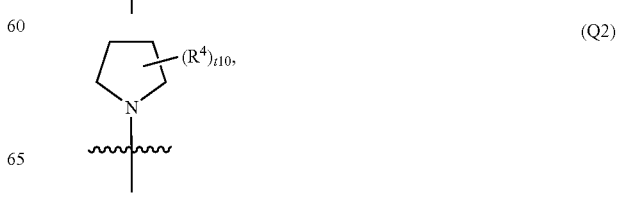
(Q2)

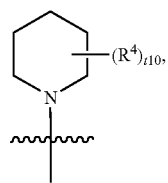 (Q3)
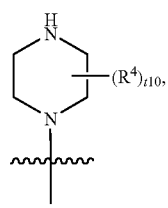 (Q4)
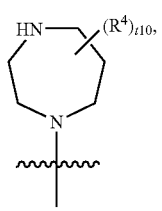 (Q5)
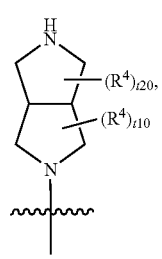 (Q6)
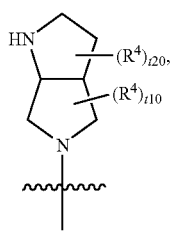 (Q7)
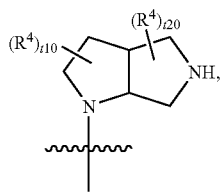 (Q8)
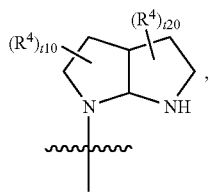 (Q9)
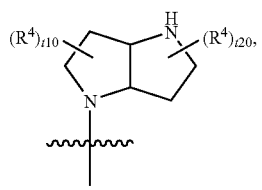 (Q10)
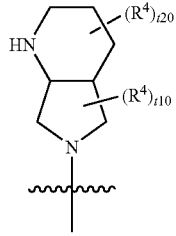 (Q11)
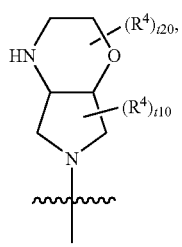 (Q12)
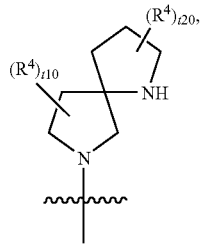 (Q13)
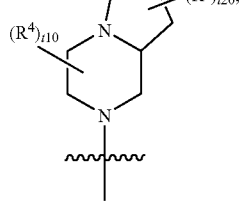 (Q14)
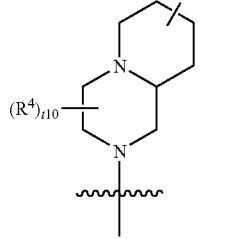 (Q15)
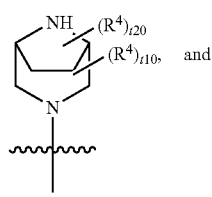 (Q16)
and

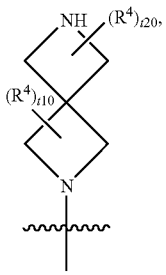
(Q17)

wherein t10 and t20 are each, independently, 0, 1, or 2. In some further embodiments, each $R^4$ is independently selected from $C_{1-6}$ alkyl, $C_{3-7}$ cycloalkyl, $NH_2$, $NH(C_{1-4}$ alkyl), $NH(C_{3-7}$ cycloalkyl), and $N(C_{1-4}$ alkyl)$_2$, wherein each of $C_{1-6}$ alkyl and $C_{3-7}$ cycloalkyl is substituted with 0 or 1 substituent selected from $NH_2$, $NH(C_{1-4}$ alkyl), and $N(C_{1-4}$ alkyl)$_2$. In some further embodiments, each $R^4$ is independently selected from $C_{1-6}$ alkyl, $C_{3-7}$ cycloalkyl, $NH_2$, $NH(C_{1-4}$ alkyl), $NH(C_{3-7}$ cycloalkyl), and $N(C_{1-4}$ alkyl)$_2$, wherein the $C_{1-6}$ alkyl is substituted with 0 or 1 substituent selected from $NH_2$, $NH(C_{1-4}$ alkyl), and $N(C_{1-4}$ alkyl)$_2$. In yet further embodiments, each $R^4$ is independently selected from methyl and $NH(CH_3)$.

In some embodiments of the compounds of Formula I, $R^2$ and $R^3$ together with the N atom to which they are attached form a 4-9 membered heterocycloalkyl group wherein each of the ring-forming atoms of the 4-9 membered heterocycloalkyl group is independently selected from C, N, and O, and wherein the 4-9 membered heterocycloalkyl group is substituted with 0, 1, 2, 3, 4, or 5 $R^4$. In some further embodiments, the 4-9 membered heterocycloalkyl group is substituted with 0, 1, or 2 $R^4$. In yet further embodiments, the 4-9 membered heterocycloalkyl group is substituted with 0 or 1 $R^4$.

In some embodiments of the compounds of Formula I, the ring formed by $R^2$ and $R^3$ together with the N atom to which they are attached is a pyrrolidine ring, a piperidine ring, or a piperazine ring, each substituted with 0, 1, 2, 3, 4, or 5 $R^4$.

In some embodiments of the compounds of Formula I, the ring formed by $R^2$ and $R^3$ together with the N atom to which they are attached is a pyrrolidine ring or a piperazine ring, each substituted with 0, 1, 2, 3, 4, or 5 $R^4$. In some further embodiments, the ring formed by $R^2$ and $R^3$ together with the N atom to which they are attached is a pyrrolidine ring or a piperazine ring, each substituted with 0, 1, or 2 $R^4$. In yet further embodiments, the ring formed by $R^2$ and $R^3$ together with the N atom to which they are attached is a pyrrolidine ring or a piperazine ring, each substituted with 0 or 1 $R^4$.

In some embodiments of the compounds of Formula I, the ring formed by $R^2$ and $R^3$ together with the N atom to which they are attached is a pyrrolidine ring substituted with 0, 1, 2, 3, 4, or 5 $R^4$. In some further embodiments, the ring formed by $R^2$ and $R^3$ together with the N atom to which they are attached is a pyrrolidine ring substituted with 0, 1, or 2 $R^4$. In yet further embodiments, the ring formed by $R^2$ and $R^3$ together with the N atom to which they are attached is a pyrrolidine ring substituted with 0 or 1 $R^4$.

In some embodiments of the compounds of Formula I, the ring formed by $R^2$ and $R^3$ together with the N atom to which they are attached is a piperazine ring substituted with 0, 1, 2, 3, 4, or 5 $R^4$. In some further embodiments, the ring formed by $R^2$ and $R^3$ together with the N atom to which they are attached is a piperazine ring substituted with 0, 1, or 2 $R^4$. In some further embodiments, the ring formed by $R^2$ and $R^3$ together with the N atom to which they are attached is a piperazine ring substituted with 0 or 1 $R^4$.

In some embodiments of the compounds of Formula I, the ring formed by $R^2$ and $R^3$ together with the N atom to which they are attached is substituted with 0, 1, 2, or 3 $R^4$; and each $R^4$ is independently selected from $C_{1-6}$ alkyl, $C_{1-6}$ haloalkyl, $C_{3-7}$ cycloalkyl, $NH_2$, $NH(C_{1-4}$ alkyl), $NH(C_{3-7}$ cycloalkyl), and $N(C_{1-4}$ alkyl)$_2$, wherein each of the $C_{1-6}$ alkyl, $C_{3-7}$ cycloalkyl, and $C_{1-6}$ haloalkyl is substituted with 0 or 1 substituent selected from halo, $NH_2$, $NH(C_{1-4}$ alkyl), and $N(C_{1-4}$ alkyl)$_2$.

In some embodiments of the compounds of Formula I, the ring formed by $R^2$ and $R^3$ together with the N atom to which they are attached is substituted with 0, 1, 2, or 3 $R^4$; and each $R^4$ is independently selected from $C_{1-6}$ alkyl, $C_{1-6}$ haloalkyl, $C_{3-7}$ cycloalkyl, $NH_2$, $NH(C_{1-4}$ alkyl), $NH(C_{3-7}$ cycloalkyl), and $N(C_{1-4}$ alkyl)$_2$, wherein each of the $C_{1-6}$ alkyl and $C_{3-7}$ cycloalkyl is substituted with 0 or 1 substituent selected from halo, $NH_2$, $NH(C_{1-4}$ alkyl), and $N(C_{1-4}$ alkyl)$_2$.

In some embodiments of the compounds of Formula I, the ring formed by $R^2$ and $R^3$ together with the N atom to which they are attached is substituted with 0, 1, 2, or 3 $R^4$; and each $R^4$ is independently selected from $C_{1-6}$ alkyl, $C_{1-6}$ haloalkyl, $C_{3-7}$ cycloalkyl, $NH_2$, $NH(C_{1-4}$ alkyl), $NH(C_{3-7}$ cycloalkyl), and $N(C_{1-4}$ alkyl)$_2$, wherein each of the $C_{1-6}$ alkyl and $C_{1-6}$ haloalkyl is substituted with 0 or 1 substituent selected from $NH_2$, $NH(C_{1-4}$ alkyl), and $N(C_{1-4}$ alkyl)$_2$.

In some embodiments, each $R^4$ is independently selected from $C_{1-6}$ alkyl, $NH_2$, $NH(C_{1-4}$ alkyl), and $N(C_{1-4}$ alkyl)$_2$, wherein the $C_{1-6}$ alkyl is substituted with 0 or 1 substituent selected from $NH_2$, $NH(C_{1-4}$ alkyl), and $N(C_{1-4}$ alkyl)$_2$.

In some embodiments of the compounds of Formula I, each $R^4$ is independently selected from $C_{1-6}$ alkyl and $NH(C_{1-4}$ alkyl), wherein the $C_{1-6}$ alkyl is substituted with 0 or 1 $NH(C_{1-4}$ alkyl). In some further embodiments, each $R^4$ is independently selected from methyl and $NH(CH_3)$.

In some embodiments of the compounds of Formula I, $R^1$ is selected from structures of formulas (A1), (B1), (C1), (D1), and (E1):

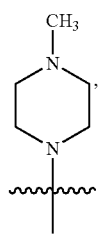
(A1)

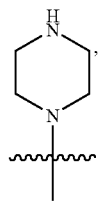
(B1)

-continued

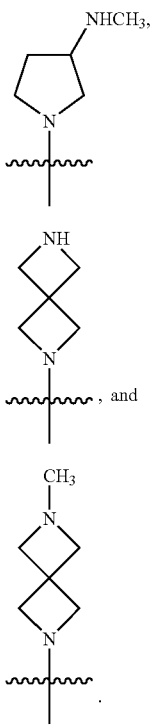

In some embodiments of the compounds of Formula I, $R^1$ is selected from structures of formulas (A1), (B1), and (C1):

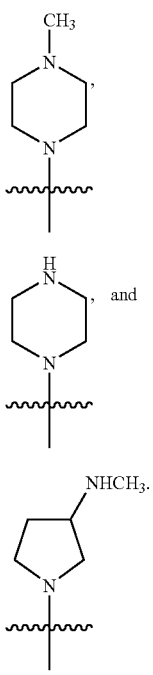

In some embodiments, ring A is aryl substituted with 0, 1, 2, or 3 —$W^{1a}$—$X^{1a}$—$W^1$—$X^1$—$Y^1$—$Z^1$.

In some embodiments, ring A is phenyl or naphthyl, each substituted with 0, 1, 2, or 3 —$W^{1a}$—$X^{1a}$—$W^1$—$X^1$—$Y^1$—$Z^1$.

In some embodiments, ring A is naphthyl substituted with 0, 1, 2, or 3 —$W^{1a}$—$X^{1a}$—$W^1$—$X^1$—$Y^1$—$Z^1$.

In some embodiments, ring A is naphthyl substituted with 0 or 1 —$W^{1a}$—$X^{1a}$—$W^1$—$X^1$—$Y^1$—$Z^1$.

In some embodiments, ring A is phenyl substituted with 0, 1, 2, or 3 —$W^{1a}$—$X^{1a}$—$W^1$—$X^1$—$Y^1$—$Z^1$.

In some embodiments, ring A is phenyl substituted with 0 or 1 —$W^{1a}$—$X^{1a}$—$W^1$—$X^1$—$Y^1$—$Z^1$.

In some embodiments, ring A is a 6-membered heteroaryl group substituted with 0, 1, 2, or 3 —$W^{1a}$—$X^{1a}$—$W^1$—$X^1$—$Y^1$—$Z^1$.

In some embodiments, ring A is a 6-membered heteroaryl group with 0 or 1 —$W^{1a}$—$X^{1a}$—$W^1$—$X^1$—$Y^1$—$Z^1$.

In some embodiments, the optionally substituted 6-membered heteroaryl group of ring A is an optionally substituted pyridine ring, an optionally substituted pyrimidine ring, an optionally substituted pyrazine ring, or an optionally substituted 1,2,4-triazine ring. In some embodiments, the optionally substituted 6-membered heteroaryl group of ring A is an optionally substituted pyridine ring.

In some embodiments, ring A is a 5-membered heteroaryl group substituted with 0, 1, or 2 —$W^{1a}$—$X^{1a}$—$W^1$—$X^1$—$Y^1$—$Z^1$.

In some embodiments, ring A is a 5-membered heteroaryl group with 0 or 1 —$W^{1a}$—$X^{1a}$—$W^1$—$X^1$—$Y^1$—$Z^1$. In some further embodiments, the optionally substituted 5-membered heteroaryl group of ring A is an optionally substituted ring selected from a thiophene ring, a furan ring, a thiazole ring, an oxazole ring, an isoxazole ring, a 1H-imidazole ring, a 1H-pyrazole ring, a 1H-1,2,4-triazole ring, and a 1H-pyrrole ring. In some further embodiments, the optionally substituted 5-membered heteroaryl group of ring A is an optionally substituted ring selected from a thiophene ring, a thiazole ring, an oxazole ring, a 1H-imidazole ring, a 1H-pyrazole ring, a 1H-1,2,4-triazole ring, and a 1H-pyrrole ring.

In some embodiments, each —$W^{1a}$—$X^{1a}$—$W^1$—$X^1$—$Y^1$—$Z^1$ is independently selected from halo, CN, $C_{1-6}$ alkyl, $C_{1-6}$ haloalkyl, $C_{3-7}$ cycloalkyl, $OR^a$, $SR^a$, $SF_5$, $C(O)R^b$, $C(O)NR^cR^d$, $C(O)OR^a$, $OC(O)R^b$, $OC(O)NR^cR^d$, $NR^cR^d$, $NR^cC(O)R^d$, $NR^eC(O)OR^a$, $NR^cS(O)_2NR^cR^d$; $S(O)R^b$, $S(O)NR^cR^d$, $S(O)_2R^b$, and $S(O)_2NR^cR^d$, wherein each of the $C_{1-6}$ alkyl, $C_{1-6}$ haloalkyl, and $C_{3-7}$ cycloalkyl is substituted with 0, 1, or 2 substituents independently selected from halo, CN, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cC(O)R^d$, $NR^cC(O)OR^a$, $NR^c S(O)_2R^b$, $NR^cS(O)_2NR^cR^d$; $S(O)R^b$, $S(O)NR^cR^d$, $S(O)_2R^b$, and $S(O)_2NR^cR^d$.

In some embodiments, each —$W^{1a}$—$X^{1a}$—$W^1$—$X^1$—$Y^1$—$Z^1$ is independently selected from halo, CN, $C_{1-6}$ alkyl, $C_{1-6}$ haloalkyl, $C_{1-6}$ hydroxylalkyl, $C_{1-6}$ cyanoalkyl, $C_{3-7}$ cycloalkyl, $NH_2$, $NH(C_{1-4}$ alkyl), $N(C_{1-4}$ alkyl$)_2$, —C(O)—$(C_{1-4}$ alkyl), $C(O)NR^cR^d$, OH, $C_{1-6}$ alkoxy, $C_{1-6}$ haloalkoxy, and $C_{2-8}$ alkoxyalkoxy, wherein each of the $C_{1-6}$ alkyl, $C_{1-6}$ haloalkyl, and $C_{3-7}$ cycloalkyl is substituted with 0, 1, or 2 substituents independently selected from halo, CN, and $C(O)NR^cR^d$.

In some embodiments, each —$W^{1a}$—$X^{1a}$—$W^1$—$X^1$—$Y^1$—$Z^1$ is independently selected from halo, CN, $C_{1-4}$ alkyl, $C_{1-4}$ haloalkyl, $C_{1-4}$ hydroxylalkyl, $C_{1-4}$ cyanoalkyl, $C_{3-7}$ cycloalkyl, OH, $C_{1-4}$ alkoxy, and $C_{1-4}$ haloalkoxy.

In some embodiments, each —$W^{1a}$—$X^{1a}$—$W^1$—$X^1$—$Y^1$—$Z^1$ is independently selected from halo, CN, $C_{1-6}$ alkyl, $C_{3-7}$ cycloalkyl, and $C(O)NR^cR^d$, wherein each of the $C_{1-6}$ alkyl and $C_{3-7}$ cycloalkyl is substituted with 0, 1, or 2 substituents independently selected from halo, CN, and $C(O)NR^cR^d$.

In some embodiments, one or more of ring-forming C atoms of the 4-20 membered cycloalkyl or heterocycloalkyl group of fused ring B are substituted with oxo [i.e. "=O"] or sulfido [i.e. =S; or thiono]. In some embodiments, one or more of ring-forming S atoms of the 4-20 membered heterocycloalkyl group of fused ring B are substituted with 1 or 2 oxo [forming S(O) and/or S(O)$_2$ moieties]. In such situations, the 4-20 membered cycloalkyl or heterocycloalkyl group of fused ring B are further substituted with 0, 1, 2, 3, 4, 5, or 6 —W$^{2a}$—X$^{2a}$—W$^2$—X$^2$—Y$^2$—Z$^2$.

In some embodiments, the 4-20 membered cycloalkyl or heterocycloalkyl group of fused ring B is monocyclic.

In some embodiments, the 4-20 membered cycloalkyl or heterocycloalkyl group of fused ring B are polycyclic: comprising fused rings, spiro rings, bridged ring, or any combination thereof.

In some embodiments, the fused ring B is a 4-14 membered cycloalkyl or heterocycloalkyl group substituted with 0, 1, 2, 3, 4, 5, or 6 —W$^{2a}$—X$^{3a}$—W$^2$—X$^2$—Y$^2$—Z$^2$.

In some embodiments, the fused ring B is a 5-10 membered cycloalkyl or heterocycloalkyl group substituted with 0, 1, 2, 3, 4, 5, or 6 —W$^{2a}$—X$^{2a}$—W$^2$—X$^2$—Y$^2$—Z$^2$.

In some embodiments, the fused ring B is a 5-10 membered heterocycloalkyl group substituted with 0, 1, 2, 3, 4, or 5 —W$^{2a}$—X$^{2a}$—W$^2$—X$^2$—Y$^2$—Z$^2$.

In some embodiments, the fused ring B is a 5-7 membered heterocycloalkyl group substituted with 0, 1, 2, 3, 4, or 5 —W$^{2a}$—X$^{2a}$—W$^2$—X$^2$—Y$^2$—Z$^2$.

In some embodiments, at least one of the ring-forming atoms of ring B is N.

In some embodiments, each of the ring-forming atoms of ring B is independently selected from C and N.

In some embodiments, the fused ring B is a 5-7 membered cycloalkyl group substituted with 0, 1, 2, 3, 4, or 5 —W$^{2a}$—X$^{2a}$—W$^2$—X$^3$—Y$^2$—Z$^2$.

In some embodiments, ring B is substituted with 1 or 2 —W$^{2a}$—X$^{3a}$—W$^2$—X$^2$—Y$^2$—Z$^2$.

In some embodiments, ring B is substituted with 1 —W$^{2a}$—X$^{2a}$—W$^2$—X$^2$—Y$^2$—Z$^2$.

In some embodiments, the moiety of

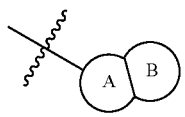

is a moiety of

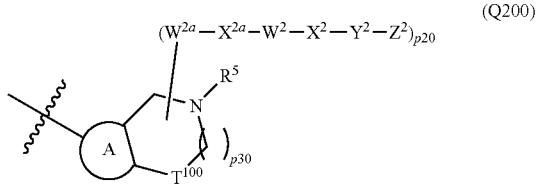

wherein:
R$^5$ is H or —W$^{2a}$—X$^{2a}$—W$^2$—X$^2$—Y$^2$—Z$^2$;
T$^{100}$ is CH$_2$, CH(—W$^{2a}$—X$^{2a}$—W$^2$—X$^2$—Y$^2$—Z$^2$), C(—W$^{2a}$—X$^{2a}$—W$^2$—X$^2$—Y$^2$—Z$^2$)$_2$, S, S(O) or —S(O)$_2$;
p20 is 0, 1, or 2; and
p30 is 0 or 1.

In some embodiments of moiety (Q200), R$^5$ is selected from H, Z$^2$, —C(O)Z$^2$, —C(S)Z$^2$, —C(O)NHZ$^2$, —C(O)N(C$_{1-6}$alkyl)Z$^2$, —C(S)NHZ$^2$, —C(S)N(C$_{1-6}$alkyl)Z$^2$, —C(O)OZ$^2$, —S(O)Z$^2$, —S(O)NHZ$^2$, —S(O)N(C$_{1-6}$alkyl)Z$^2$, —S(O)$_2$Z$^2$, —S(O)$_2$NHZ$^2$, and —S(O)$_2$N(C$_{1-6}$alkyl)Z$^2$; and each Z$^2$ is independently selected from C$_{1-6}$ alkyl, C$_{1-6}$haloalkyl, C$_{2-6}$ alkenyl, C$_{2-6}$ alkynyl, aryl, cycloalkyl, heteroaryl, heterocycloalkyl, arylalkyl, heteroarylalkyl, cycloalkylalkyl, and heterocycloalkylalkyl, each substituted with 0, 1, 2 or 3 substituents each independently selected from R$^{ZZ}$, halo, CN, NO$_2$, OR$^a$, SR$^a$, SF$_5$, C(O)R$^b$, C(O)NR$^c$R$^d$, C(O)OR$^a$, OC(O)R$^b$, OC(O)NR$^c$R$^d$, NR$^c$R$^d$, NR$^c$C(O)R$^d$, NR$^c$C(O)OR$^a$, NR$^c$S(O)$_2$R$^b$, NR$^c$S(O)$_2$NR$^c$R$^d$; S(O)R$^b$, S(O)NR$^c$R$^d$, S(O)$_2$R$^b$, and S(O)$_2$NR$^c$R$^d$. In some further embodiments, R$^5$ is selected from Z$^2$, —C(O)Z$^2$, —C(S)Z$^2$, —C(O)NHZ$^2$, —C(O)N(C$_{1-6}$alkyl)Z$^2$, —C(S)NHZ$^2$, —C(S)N(C$_{1-6}$alkyl)Z$^2$, —C(O)OZ$^2$, —S(O)Z$^2$, —S(O)NHZ$^2$, —S(O)N(C$_{1-6}$alkyl)Z$^2$, —S(O)$_2$Z$^2$, —S(O)$_2$NHZ$^2$, and —S(O)$_2$N(C$_{1-6}$alkyl)Z$^2$; and each Z$^2$ is independently selected from C$_{1-6}$ alkyl, C$_{1-6}$haloalkyl, C$_{2-6}$ alkenyl, C$_{2-6}$ alkynyl, aryl, cycloalkyl, heteroaryl, heterocycloalkyl, arylalkyl, heteroarylalkyl, cycloalkylalkyl, and heterocycloalkylalkyl, each substituted with 0, 1, 2 or 3 substituents each independently selected from R$^{ZZ}$, halo, CN, NO$_2$, OR$^a$, SR$^a$, SF$_5$, C(O)R$^b$, C(O)NR$^c$R$^d$, C(O)OR$^a$, OC(O)R$^b$, OC(O)NR$^c$R$^d$, NR$^c$R$^d$, NR$^c$C(O)R$^d$, NR$^c$C(O)OR$^a$, NR$^c$S(O)$_2$R$^b$, NR$^c$S(O)$_2$NR$^c$R$^d$; S(O)R$^b$, S(O)NR$^c$R$^d$, S(O)$_2$R$^b$, and S(O)$_2$NR$^c$R$^d$.

In some embodiments, the moiety of

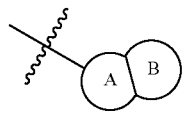

is a moiety selected from:

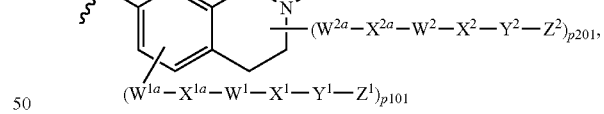

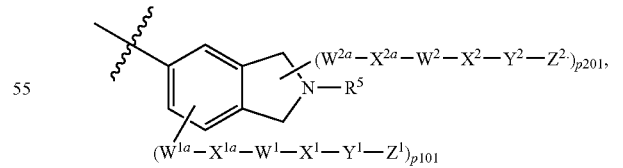

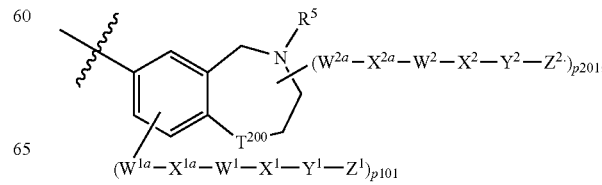

(Q204) 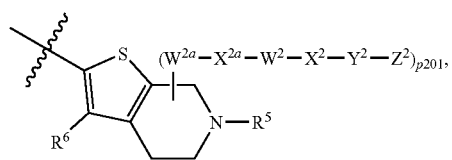
(Q205) 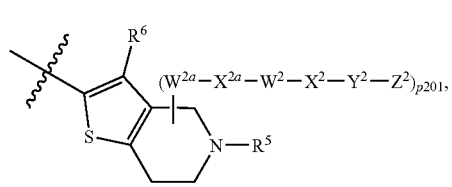
(Q206) 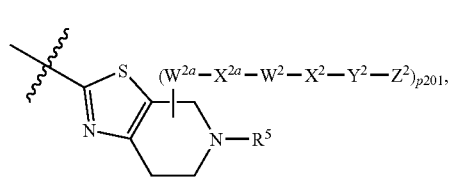
(Q207) 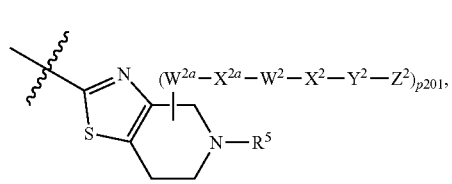
(Q208) 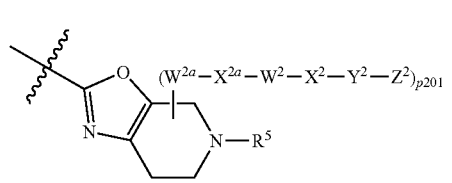
(Q209) 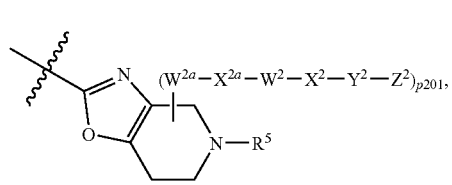
(Q210) 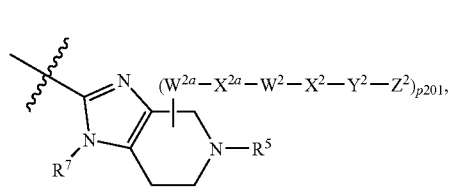
(Q211) 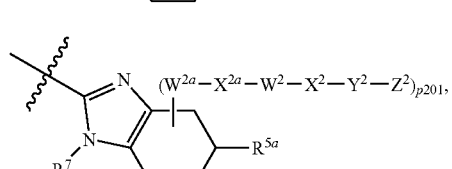
(Q212) 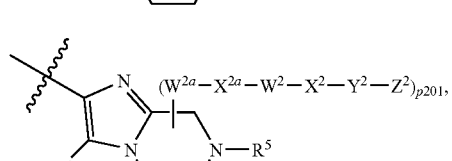
(Q213) 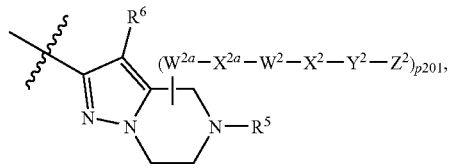
(Q214) 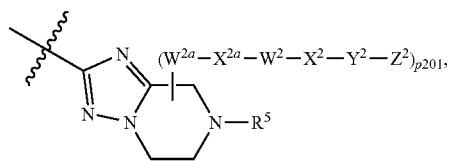
(Q215) 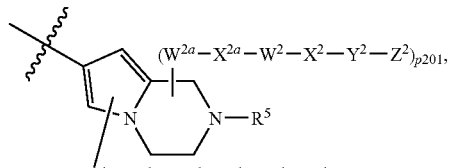
(Q216) 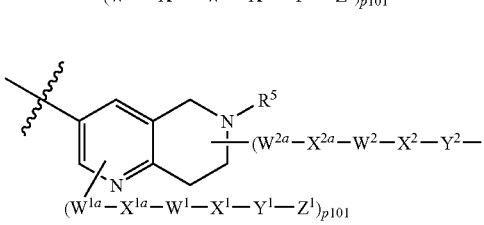
(Q217) 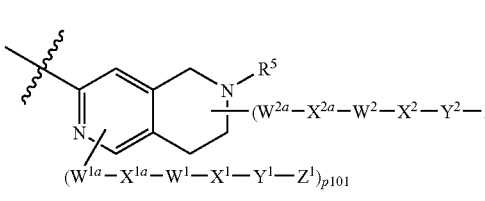
(Q218) 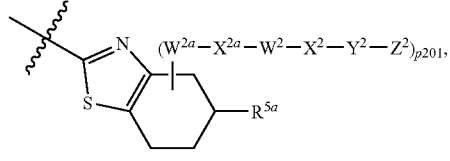
(Q219) 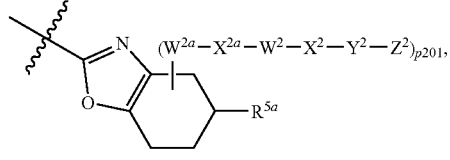
(Q220) 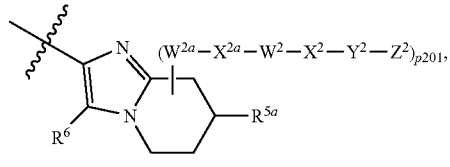
(Q221) 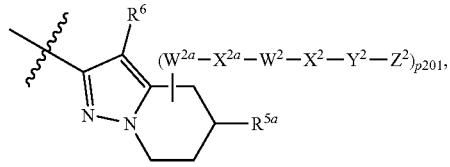

-continued

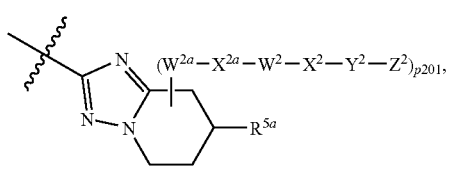
(Q222)

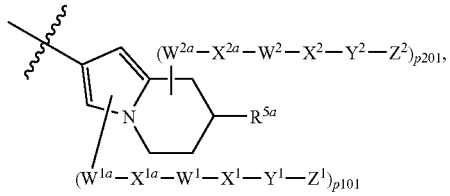
(Q223)

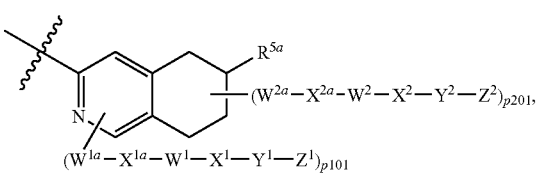
(Q224)

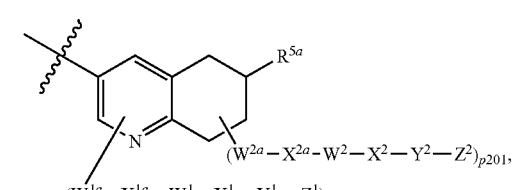
(Q225)

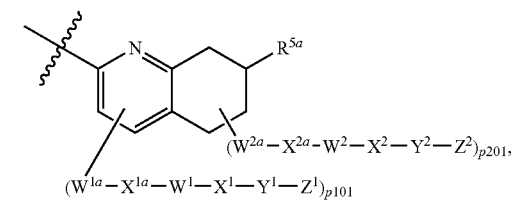
(Q226)

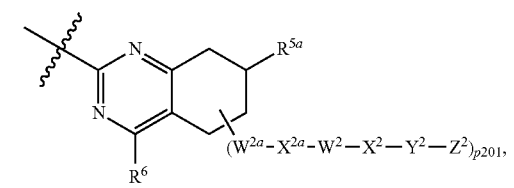
(Q227)

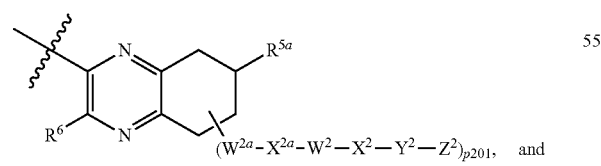
(Q228)

(Q229)

wherein:

each $R^5$ is independently H or $—W^{2a}—X^{2a}—W^2—X^2—Y^2—Z^2$;

each $R^6$ is independently H or $—W^{2a}—X^{2a}—W^2—X^2—Y^2—Z^2$;

each $R^7$ is independently H or $—W^{2a}—X^{2a}—W^2—X^2—Y^2—Z^2$;

each $R^{5a}$ is independently H or $—W^{2a}—X^{2a}—W^2—X^2—Y^2—Z^2$;

$T^{200}$ is $CH_2$, $CH(—W^{2a}—X^{2a}—W^2—X^2—Y^2—Z^2)$, $C(—W^{2a}—X^{2a}—W^2—X^2—Y^2—Z^2)_2$, S, S(O) or $S(O)_2$;

each p101 is 0, 1, or 2; and each p201 is 0, 1, or 2.

In some embodiments, the moiety of

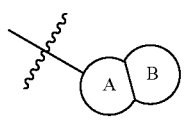

is a moiety selected from:

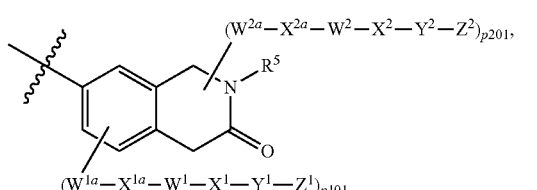
(Q301)

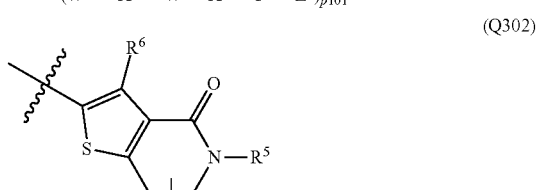
(Q302)

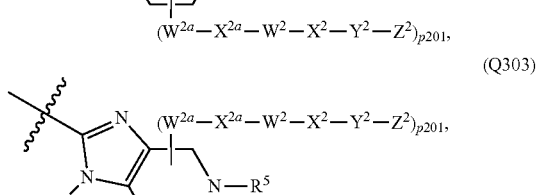
(Q303)

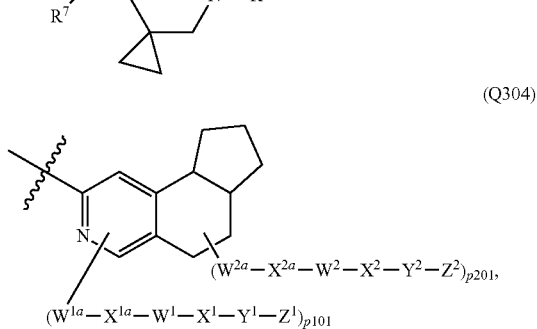
(Q304)

-continued (Q305)

(Q306)

(Q307)

(Q308)

wherein:
each $R^5$ is independently H or $-W^{2a}-X^{2a}-W^2-X^2-Y^2-Z^2$;
$R^6$ is H or $-W^{2a}-X^{2a}-W^2-X^2-Y^2-Z^2$;
$R^7$ is H or $-W^{2a}-X^{2a}-W^2-X^2-Y^2-Z^2$;
each p101 is 0, 1, or 2; and
each p201 is 0, 1, or 2.

In some embodiments of moieties (Q201)-(Q210), (212)-(Q217), (Q301-Q303), (Q305) and (Q307), each $R^5$ is independently selected from H, $Z^2$, $-C(O)Z^2$, $-C(S)Z^2$, $-C(O)NHZ^2$, $-C(O)N(C_{1-6}$ alkyl)$Z^2$, $-C(S)NHZ^2$, $-C(S)N(C_{1-6}$alkyl)$Z^2$, $-C(O)OZ^2$, $-S(O)Z^2$, $-S(O)NHZ^2$, $-S(O)N(C_{1-6}$ alkyl)$Z^2$, $-S(O)_2Z^2$, $-S(O)_2NHZ^2$, and $-S(O)_2N(C_{1-6}$ alkyl)$Z^2$; and each $Z^2$ is independently selected from $C_{1-6}$ alkyl, $C_{1-6}$ haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl, and heterocycloalkylalkyl, each substituted with 0, 1, 2 or 3 substituents each independently selected from $R^{zz}$, halo, CN, $NO_2$, $OR^a$, $SR^a$, $SF_5$, $C(O)R^b$, $C(O)NR^cR^d$, $C(O)OR^a$, $OC(O)R^b$, $OC(O)NR^cR^d$, $NR^cR^d$, $NR^cC(O)R^d$, $NR^cC(O)OR^a$, $NR^cS(O)_2R^b$, $NR^cS(O)_2NR^cR^d$; $S(O)R^b$, $S(O)NR^cR^d$, $S(O)_2R^b$, and $S(O)_2NR^cR^d$. In some further embodiments, each $R^5$ is independently selected from $Z^2$, $-C(O)Z^2$, $-C(S)Z^2$, $-C(O)NHZ^2$, $-C(O)N(C_{1-6}$alkyl)$Z^2$, $-C(S)NHZ^2$, $-C(S)N(C_{1-6}$ alkyl)$Z^2$, $-C(O)OZ^2$, $-S(O)Z^2$, $-S(O)NHZ^2$, $-S(O)N(C_{1-6}$ alkyl)$Z^2$, $-S(O)_2Z^2$, $-S(O)_2NHZ^2$, and $-S(O)_2N(C_{1-6}$ alkyl)$Z^2$; and each $Z^2$ is selected from $C_{1-6}$ alkyl, $C_{1-6}$ haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl, and heterocycloalkylalkyl, each substituted with 0, 1, 2 or 3 substituents each independently selected from $R^{zz}$, halo, CN, $NO_2$, $OR^a$, $SR^a$, $SF_5$, $C(O)R^b$, $C(O)NR^cR^d$, $C(O)OR^a$, $OC(O)R^b$, $OC(O)NR^cR^d$, $NR^cR^d$, $NR^cC(O)R^d$, $NR^cC(O)OR^a$, $NR^cS(O)_2R^b$, $NR^cS(O)_2NR^cR^d$; $S(O)R^b$, $S(O)NR^cR^d$, $S(O)_2R^b$, and $S(O)_2NR^cR^d$.

In some embodiments of moieties (Q210) and/or (Q210), $R^7$ is selected from H, $C_{1-6}$ alkyl, $C_{1-6}$ haloalkyl, $C_{2-6}$ alkenyl, $C_{2-6}$ alkynyl, aryl, $C_{3-7}$ cycloalkyl, heteroaryl, heterocycloalkyl, arylalkyl, heteroarylalkyl, cycloalkylalkyl, and heterocycloalkylalkyl. In some further embodiments, $R^7$ is selected from H and $C_{1-6}$ alkyl. In yet further embodiments, $R^7$ is H.

In some embodiments of moieties (Q201)-(Q210), (212)-(Q217), (Q301-Q303), (Q305) and (Q307), each $R^5$ is independently selected from the following 8 options:

(1) H;
(2) aryl (such as phenyl or naphthyl) substituted with 0, 1, 2, or 3 substituents each independently selected from $C_{1-6}$ alkyl, $C_{1-6}$ haloalkyl, halo, $C_{1-6}$ alkoxy, $C_{1-6}$ haloalkoxy, CN, $C(O)OR^a$, $C(O)R^b$, $OR^a$, $C(O)NR^cR^d$, $NR^cC(O)R^d$, $NR^cC(O)OR^a$, and $S(O)_2R^b$;
(3) heteroaryl (such as pyridinyl, pyrazinyl, quinoxalinyl, 2,1,3-benzothiadiazolyl, pyrazolyl, thienyl, 1,2,5-thiadiazolyl, isoquinolinyl, 1,3-thiazolyl, furanyl, benzofuranyl, 1,3-benzothiazolyl) substituted with 0, 1, 2, or 3 substituents each independently selected from $C_{1-6}$ alkyl, $C_{1-6}$ haloalkyl, halo, $C_{1-6}$ alkoxy, $C_{1-6}$ haloalkoxy, Ar, CN, $C(O)OR^a$, $C(O)R^b$, $OR^a$, $C(O)NR^cR^d$, $NR^cC(O)R^d$, $NR^cC(O)OR^a$, and $S(O)_2R^b$;
(4) $-C(O)Z^{21}$, wherein $Z^{21}$ is selected from $C_{1-6}$ alkyl, cycloalkyl, aryl, heterocycloalkyl (such as pyrrolidinyl, piperidinyl, tetrahydrofuranyl, or tetrahydropyranyl), heteroaryl, arylalkyl, heteroarylalkyl, cycloalkylalkyl, and heterocycloalkylalkyl, each substituted with 0, 1, 2, 3, 4, or 5 substituents each independently selected from halo, $C_{1-6}$ alkyl, $C_{1-6}$ haloalkyl, $C_{2-8}$ alkoxyalkyl, CN, $-OR^a$, $C(O)R^b$, $C(O)NR^cR^d$, $C(O)OR^a$, $S(O)_2R^b$, $NR^cR^d$, $NR^cC(O)R^b$, and $NR^cC(O)OR^a$;
(5) $-S(O)_2Z^{22}$, wherein $Z^{22}$ is selected from aryl and arylalkyl, each substituted with 0, 1, 2, 3, 4, or 5 substituents each independently selected from halo, $C_{1-6}$ alkyl, $C_{1-6}$ haloalkyl, $C_{2-8}$ alkoxyalkyl, CN, $-O-Ar$, $C(O)R^b$, $C(O)NR^cR^d$, $C(O)OR^a$, $S(O)_2R^b$, $NR^cR^d$, $NR^c(O)R^b$, and $NR^3C(O)OR^a$;
(6) $-C(O)OZ^{23}$; wherein $Z^{23}$ is selected from $C_{1-6}$ alkyl, cycloalkyl, aryl, heterocycloalkyl, heteroaryl, arylalkyl, heteroarylalkyl, cycloalkylalkyl, and heterocycloalkylalkyl, each substituted with 0, 1, 2, 3, 4, or 5 substituents each independently selected from halo, $C_{1-6}$ alkyl, $C_{1-6}$ haloalkyl, $C_{2-8}$ alkoxyalkyl, CN, $-OR^a$, $C(O)R^b$, $C(O)NR^cR^d$, $C(O)OR^a$, $S(O)_2R^b$, $NR^cR^d$, $NR^c C(O)R^b$, and $NR^cC(O)OR^a$;
(7) $-C(O)NZ^{24}Z^{25}$ wherein $Z^{24}$ and $Z^{25}$ together with the N atom to which they are attached form a 4-10 membered heterocycloalkyl group wherein each of the ring-forming atoms of the 4-10 membered heterocycloalkyl group is independently selected from C, N, O, and S, and wherein the 4-10 membered heterocycloalkyl group is substituted with 0, 1, 2 or 3 substituents each independently selected from $C_{1-6}$ alkyl, $C_{1-6}$ haloalkyl, halo, Ar, HetAr; and
(8) $-C(O)NZ^{26}Z^{27}$;
wherein:
$Z^{26}$ is selected from H and $C_{1-6}$ alkyl;
$Z^{27}$ is selected from $C_{1-6}$ alkyl, cycloalkyl, aryl, heterocycloalkyl, heteroaryl, arylalkyl, heteroarylalkyl, cycloalkylalkyl, and heterocycloalkylalkyl, each substituted with 0, 1, 2, 3, 4, or 5 substituents each independently selected from halo, $C_{1-6}$ alkyl, $C_{1-6}$ haloalkyl, $C_{2-8}$ alkoxyalkyl, CN, Ar, HetAr, —$OR^a$, $C(O)R^b$, $C(O)NR^cR^d$, $C(O)OR^a$, $S(O)_2R^b$, $NR^cR^d$, $NR^cC(O)R^b$, and $NR^cC(O)OR^a$;

each Ar is independently aryl (such as phenyl or naphthyl) substituted with 0, 1, 2, 3, 4, or 5 substituents each independently selected from halo (e.g. F or Cl), CN, $C_{1-6}$ alkyl (e.g. methyl or ethyl), $C_{1-6}$ haloalkyl (e.g. $CF_3$), $C_{2-8}$ alkoxyalkyl (e.g. methoxymethyl), $C_{1-6}$ alkoxy (e.g. —$OCH_3$), $C_{1-6}$ haloalkoxy (e.g. —$OCF_3$), and $C(O)OR^a$ [e.g. $C(O)O(C_{1-6}$ alkyl)], and each HetAr is independently heteroaryl (such as pyridinyl, pyrazinyl, quinoxalinyl, 2,1,3-benzothiadiazolyl, pyrazolyl, thienyl, 1,2,5-thiadiazolyl, isoquinolinyl, 1,3-thiazolyl, furanyl, benzofuranyl, 1,3-benzothiazolyl) substituted with 0, 1, 2, 3, 4, or 5 substituents each independently selected from halo (e.g. F or Cl), CN, $C_{1-6}$ alkyl (e.g. methyl or ethyl), $C_{1-6}$ haloalkyl (e.g. $CF_3$), $C_{2-8}$ alkoxyalkyl (e.g. methoxymethyl), $C_{1-6}$ alkoxy (e.g. —$OCH_3$), $C_{1-6}$ haloalkoxy (e.g. —$OCF_3$), and $C(O)OR^a$ [e.g. $C(O)O(C_{1-6}$ alkyl)].

In some embodiments of moieties (Q201)-(Q210), (212)-(Q217), (Q301-Q303), (Q305) and (Q307), each $R^5$ is independently selected from option 2. In some embodiments of moieties (Q201)-(Q210), (212)-(Q217), (Q301-Q303), (Q305) and (Q307), each $R^5$ is independently selected from option 3. In some embodiments of moieties (Q201)-(Q210), (212)-(Q217), (Q301-Q303), (Q305) and (Q307), each $R^5$ is independently selected from option 4. In some embodiments of moieties (Q201)-(Q210), (212)-(Q217), (Q301-Q303), (Q305) and (Q307), each $R^5$ is independently selected from option 5. In some embodiments of moieties (Q201)-(Q210), (212)-(Q217), (Q301-Q303), (Q305) and (Q307), each $R^5$ is independently selected from option 6. In some embodiments of moieties (Q201)-(Q210), (212)-(Q217), (Q301-Q303), (Q305) and (Q307), each $R^5$ is independently selected from option 7. In some embodiments of moieties (Q201)-(Q210), (212)-(Q217), (Q301-Q303), (Q305) and (Q307), each $R^5$ is independently selected from option 8.

In some embodiments of moieties (Q201)-(Q210), (212)-(Q217), (Q301-Q303), (Q305) and (Q307), each $R^5$ is independently selected from:

(1) H;
(2) phenyl or naphthyl, each substituted with 0, 1, 2, or 3 substituents each independently selected from $C_{1-6}$ alkyl, $C_{1-6}$ haloalkyl, halo, $C_{1-6}$ alkoxy, $C_{1-6}$ haloalkoxy, and CN;
(3) pyrdinyl, pyrazinyl, pyrazolyl, 1,3-thiazolyl, 1,3-benzothiazolyl, furanyl, benzofuranyl, thienyl, quinoxalinyl, and 2,1,3-benzothiadiazolyl, each substituted with 0, 1, 2, or 3 substituents each independently selected from $C_{1-6}$ alkyl, $C_{1-6}$ haloalkyl, halo, $C_{1-6}$ alkoxy, $C_{1-6}$ haloalkoxy, Ar, CN, and $C(O)NR^cR^d$;
(4) —$C(O)Z^{21}$, wherein $Z^{21}$ is selected from (a) $C_{1-6}$ alkyl substituted with 0, 1, 2, 3, or 4 substituents each independently selected from halo, CN, —OAr, and $NR^cC(O)OR^a$; (b) $C_{3-10}$ cycloalkyl substituted with 0, 1, 2, 3, or 4 substituents each independently selected from halo, CN, Ar, $C_{1-6}$ alkyl, and $C_{1-6}$ haloalkyl; (c) phenyl and naphthyl, each substituted with 0, 1, 2, 3, or 4 substituents each independently selected from $C_{1-6}$ alkyl, $C_{1-6}$ haloalkyl, halo, $C_{1-6}$ alkoxy, $C_{1-6}$ haloalkoxy, and CN;
(d) arylakyl substituted with 0, 1, 2, 3, or 4 substituents each independently selected from $C_{1-6}$ alkyl, $C_{1-6}$ haloalkyl, $C_{1-6}$ alkoxy, $C_{1-6}$ haloalkoxy, halo, and CN;
(e) cycloalkylalkyl substituted with 0, 1, 2, 3, or 4 substituents each independently selected from $C_{1-6}$ alkyl, $C_{1-6}$ haloalkyl, $C_{1-6}$ alkoxy, $C_{1-6}$ haloalkoxy, halo, $NR^cC(O)OR^a$, and CN; (f) heteroarylalkyl substituted with 0, 1, 2, 3, or 4 substituents each independently selected from $C_{1-6}$ alkyl, $C_{1-6}$ haloalkyl, $C_{1-6}$ alkoxy, $C_{1-6}$ haloalkoxy, $NR^cC(O)OR^a$, halo, $NR^c R^d$, and CN; and
(g) heterocycloalkylalkyl substituted with 0, 1, 2, 3, or 4 substituents each independently selected from $C_{1-6}$ alkyl, $C_{1-6}$ haloalkyl, $C_{1-6}$ alkoxy, $C_{1-6}$ haloalkoxy, $NR^cC(O)OR^a$, halo, $NR^cR^d$, CN, $C(O)R^b$, $C(O)OR^a$, and $S(O)_2R^b$;

(5) —$S(O)_2Z^{22}$, wherein $Z^{22}$ is selected from phenyl, naphthyl, benzyl, phenylethyl, and phenylpropyl, each substituted with 0, 1, 2, 3, 4, or 5 substituents each independently selected from halo, $C_{1-6}$ alkyl, $C_{1-6}$ haloalkyl, $C_{2-8}$ alkoxyalkyl, CN, —O—Ar, $C(O)R^b$, $C(O)NR^cR^d$, $C(O)OR^a$, $S(O)_2R^b$, $NR^cR^d$, $NR^cC(O)R^b$, and $NR^cC(O)OR^a$;

(6) —$C(O)OZ^{23}$; wherein $Z^{23}$ is selected from (a) $C_{1-6}$ alkyl substituted with 0, 1, 2, 3, or 4 substituents each independently selected from halo, CN, —OAr, and $NR^cC(O)OR^a$; (b) $C_{3-10}$ cycloalkyl substituted with 0, 1, 2, 3, or 4 substituents each independently selected from halo, CN, Ar, $C_{1-6}$ alkyl, and $C_{1-6}$ haloalkyl; (c) phenyl and naphthyl, each substituted with 0, 1, 2, 3, or 4 substituents each independently selected from $C_{1-6}$ alkyl, $C_{1-6}$ haloalkyl, halo, $C_{1-6}$ alkoxy, $C_{1-6}$ haloalkoxy, and CN;
(d) cycloalkylalkyl substituted with 0, 1, 2, 3, or 4 substituents each independently selected from $C_{1-6}$ alkyl, $C_{1-6}$ haloalkyl, $C_{1-6}$ alkoxy, $C_{1-6}$ haloalkoxy, halo, $NR^cC(O)OR^a$, and CN; and (e) heterocycloalkylalkyl substituted with 0, 1, 2, 3, or 4 substituents each independently selected from $C_{1-6}$ alkyl, $C_{1-6}$ haloalkyl, $C_{1-6}$ alkoxy, $C_{1-6}$ haloalkoxy, $NR^cC(O)OR^a$, halo, $NR^cR^d$, CN, $C(O)NR^cR^d$, $C(O)R^b$, $C(O)OR^a$, and $S(O)_2R^b$;

(7) —$C(O)NZ^{24}Z^{25}$ wherein $Z^{24}$ and $Z^{25}$ together with the N atom to which they are attached form a pyrrolidinyl or piperidinyl group, each substituted with 0, 1, 2 or 3 substituents each independently selected from $C_{1-6}$ alkyl, Ar, HetAr; and (8) —$C(O)NZ^{26}Z^{27}$;

wherein:
$Z^{26}$ is selected from H and $C_{1-3}$ alkyl;
$Z^{27}$ is selected from (a) $C_{1-6}$ alkyl substituted with 0, 1, 2, 3, or 4 substituents each independently selected from halo, and CN; (b) $C_{3-10}$ cycloalkyl substituted with 0, 1, 2, 3, or 4 substituents each independently selected from halo, CN, Ar, $C_{1-6}$ alkyl, $C_{1-6}$ haloalkyl, $C_{2-8}$ alkoxyalkyl, $OR^a$, $C(O)R^b$, $C(O)NR^cR^d$, and $C(O)OR^a$; (c) phenyl and naphthyl, each substituted with 0, 1, 2, 3, or 4 substituents each independently selected from $C_{1-6}$ alkyl, $C_{1-6}$ haloalkyl, halo, ORa, HetAr, and CN; (d) arylakyl substituted with 0, 1, 2, 3, or 4 substituents each independently selected from $C_{1-6}$ alkyl, $C_{1-6}$ haloalkyl, $C_{1-6}$ alkoxy, $C_{1-6}$ haloalkoxy, $C(O)NR^cR^d$, halo, and CN; (e) heteroaryl substituted with 0, 1, 2, 3, or 4 substituents each independently selected from $C_{1-6}$ alkyl, $C_{1-6}$ haloalkyl, $OR^a$, $C(O)OR^a$, halo, $NR^cR^d$, Ar, and CN; and (f) heterocycloalkyl substituted with 0, 1, 2, 3, or 4 substituents each independently selected from $C_{1-6}$ alkyl, $C_{1-6}$ haloalkyl, halo, CN, $C(O)R^b$, $C(O)OR^a$, Ar, and HetAr;

each Ar is independently aryl (such as phenyl or naphthyl) substituted with 0, 1, 2, 3, 4, or 5 substituents each independently selected from halo (e.g. F or Cl), CN, $C_{1-6}$ alkyl (e.g. methyl or ethyl), $C_{1-6}$ haloalkyl (e.g. $CF_3$), $C_{2-8}$ alkoxyalkyl (e.g. methoxymethyl), $C_{1-6}$ alkoxy (e.g. —$OCH_3$), $C_{1-6}$ haloalkoxy (e.g. —$OCF_3$), and $C(O)OR^a$ [e.g. $C(O)O(C_{1-6}$ alkyl)], and each HetAr is independently heteroaryl (such as pyridinyl, pyrazinyl, quinoxalinyl, 2,1,3-benzothiadiazolyl, pyrazolyl, thienyl, 1,2,5-thiadiazolyl, isoquinolinyl, 1,3-thiazolyl, furanyl, benzofuranyl, 1,3-benzothiazolyl) substituted with 0, 1, 2, 3, 4, or 5 substituents each independently selected from halo (e.g. F or Cl), CN, $C_{1-6}$ alkyl (e.g. methyl or ethyl), $C_{1-6}$ haloalkyl (e.g. $CF_3$), $C_{2-8}$ alkoxyalkyl (e.g. methoxymethyl), $C_{1-6}$ alkoxy (e.g. —$OCH_3$), $C_{1-6}$ haloalkoxy (e.g. —$OCF_3$), and $C(O)OR^a$ [e.g. $C(O)O(C_{1-6}$ alkyl)].

In some embodiments of moieties (Q201)-(Q210), (212)-(Q217), (Q301-Q303), (Q305) and (Q307), each $R^5$ is independently selected from:

(1) H;

(2) phenyl substituted with 0, 1, 2, or 3 substituents each independently selected from $C_{1-6}$ alkyl, $C_{1-6}$ haloalkyl, halo, $C_{1-6}$ alkoxy, $C_{1-6}$ haloalkoxy, and CN;

(3) pyrdinyl substituted with 0, 1, 2, or 3 substituents each independently selected from $C_{1-6}$ alkyl, $C_{1-6}$ haloalkyl, halo, $C_{1-6}$ alkoxy, $C_{1-6}$ haloalkoxy, Ar, CN, and $C(O)NR^cR^d$;

(4) —$C(O)Z^{21}$, wherein $Z^{21}$ is selected from (a) $C_{1-6}$ alkyl substituted with 0, 1, 2, 3, or 4 substituents each independently selected from halo, CN, —OAr, and $NR^cC(O)OR^a$; (b) $C_{3-10}$ cycloalkyl substituted with 0, 1, 2, 3, or 4 substituents each independently selected from halo, CN, Ar, $C_{1-6}$ alkyl, and $C_{1-6}$ haloalkyl; (c) phenyl substituted with 0, 1, 2, 3, or 4 substituents each independently selected from $C_{1-6}$ alkyl, $C_{1-6}$ haloalkyl, halo, $C_{1-6}$ alkoxy, $C_{1-6}$ haloalkoxy, and CN; (d) arylakyl substituted with 0, 1, 2, 3, or 4 substituents each independently selected from $C_{1-6}$ alkyl, $C_{1-6}$ haloalkyl, $C_{1-6}$ alkoxy, $C_{1-6}$ haloalkoxy, halo, and CN; (e) cycloalkylalkyl substituted with 0, 1, 2, 3, or 4 substituents each independently selected from $C_{1-6}$ alkyl, $C_{1-6}$ haloalkyl, $C_{1-6}$ alkoxy, $C_{1-6}$ haloalkoxy, halo, $NR^cC(O)OR^a$, and CN; (f) heteroarylalkyl substituted with 0, 1, 2, 3, or 4 substituents each independently selected from $C_{1-6}$ alkyl, $C_{1-6}$ haloalkyl, $C_{1-6}$ alkoxy, $C_{1-6}$ haloalkoxy, $NR^cC(O)OR^a$, halo, $NR^cR^d$, and CN; and (g) heterocycloalkylalkyl substituted with 0, 1, 2, 3, or 4 substituents each independently selected from $C_{1-6}$ alkyl, $C_{1-6}$ haloalkyl, $C_{1-6}$ alkoxy, $C_{1-6}$ haloalkoxy, $NR^cC(O)OR^a$, halo, $NR^cR^d$, CN, $C(O)R^b$, $C(O)OR^a$, and $S(O)_2R^b$;

(5) —$S(O)_2Z^{22}$, wherein $Z^{22}$ is selected from phenyl and benzyl, each substituted with 0, 1, 2, 3, 4, or 5 substituents each independently selected from halo, $C_{1-6}$ alkyl, $C_{1-6}$ haloalkyl, $C_{2-8}$ alkoxyalkyl, CN, —O—Ar, $C(O)R^b$, $C(O)NR^cR^d$, $C(O)OR^a$, $S(O)_2R^b$, $NR^cR^d$, $NR^cC(O)R^b$, and $NR^cC(O)OR^a$;

(6) —$C(O)OZ^{23}$; wherein $Z^{23}$ is selected from (a) $C_{1-6}$ alkyl substituted with 0, 1, 2, 3, or 4 substituents each independently selected from halo, CN, —OAr, and $NR^c$-$C(O)OR^a$; (b) $C_{3-10}$ cycloalkyl substituted with 0, 1, 2, 3, or 4 substituents each independently selected from halo, CN, Ar, $C_{1-6}$ alkyl, and $C_{1-6}$ haloalkyl; (c) phenyl substituted with 0, 1, 2, 3, or 4 substituents each independently selected from $C_{1-6}$ alkyl, $C_{1-6}$ haloalkyl, halo, $C_{1-6}$ alkoxy, $C_{1-6}$ haloalkoxy, and CN; (d) cycloalkylalkyl substituted with 0, 1, 2, 3, or 4 substituents each independently selected from $C_{1-6}$ alkyl, $C_{1-6}$ haloalkyl, $C_{1-6}$ alkoxy, $C_{1-6}$ haloalkoxy, halo, $NR^cC(O)OR^a$, and CN; and (e) heterocycloalkylalkyl substituted with 0, 1, 2, 3, or 4 substituents each independently selected from $C_{1-6}$ alkyl, $C_{1-6}$ haloalkyl, $C_{1-6}$ alkoxy, $C_{1-6}$ haloalkoxy, $NR^cC(O)OR^a$, halo, $NR^cR^d$, CN, $C(O)NR^cR^d$, $C(O)R^b$, $C(O)OR^a$, and $S(O)_2R^b$;

(7) —$C(O)NZ^{24}Z^{25}$ wherein $Z^{24}$ and $Z^{25}$ together with the N atom to which they are attached form a pyrrolidinyl or piperidinyl group, each substituted with 0, 1, 2 or 3 substituents each independently selected from $C_{1-6}$ alkyl, Ar, HetAr; and (8) —$C(O)NZ^{26}Z^{27}$;

wherein:

$Z^{26}$ is selected from H and $C_{1-3}$ alkyl;

$Z^{27}$ is selected from (a) $C_{1-6}$ alkyl substituted with 0, 1, 2, 3, or 4 substituents each independently selected from halo, and CN; (b) $C_{3-10}$ cycloalkyl substituted with 0, 1, 2, 3, or 4 substituents each independently selected from halo, CN, Ar, $C_{1-6}$ alkyl, $C_{1-6}$ haloalkyl, $C_{2-8}$ alkoxyalkyl, $OR^a$, $C(O)R^b$, $C(O)NR^cR^d$, and $C(O)OR^a$; (c) phenyl substituted with 0, 1, 2, 3, or 4 substituents each independently selected from $C_{1-6}$ alkyl, $C_{1-6}$ haloalkyl, halo, $OR^a$, HetAr, and CN; (d) arylakyl substituted with 0, 1, 2, 3, or 4 substituents each independently selected from $C_{1-6}$ alkyl, $C_{1-6}$ haloalkyl, $C_{1-6}$ alkoxy, $C_{1-6}$ haloalkoxy, $C(O)NR^cR^d$, halo, and CN; (e) heteroaryl substituted with 0, 1, 2, 3, or 4 substituents each independently selected from $C_{1-6}$ alkyl, $C_{1-6}$ haloalkyl, $OR^a$, $C(O)OR^a$, halo, $NR^cR^d$, Ar, and CN; and (f) heterocycloalkyl substituted with 0, 1, 2, 3, or 4 substituents each independently selected from $C_{1-6}$ alkyl, $C_{1-6}$ haloalkyl, halo, CN, $C(O)R^b$, $C(O)OR^a$, Ar, and HetAr;

each Ar is independently aryl substituted with 0, 1, 2, 3, 4, or 5 substituents each independently selected from halo, CN, $C_{1-6}$ alkyl, $C_{1-6}$ haloalkyl, $C_{2-8}$ alkoxyalkyl, $C_{1-6}$ alkoxy, $C_{1-6}$ haloalkoxy, and $C(O)OR^a$, and each HetAr is independently heteroaryl substituted with 0, 1, 2, 3, 4, or 5 substituents each independently selected from halo, CN, $C_{1-6}$ alkyl, $C_{1-6}$ haloalkyl, $C_{2-8}$ alkoxyalkyl, $C_{1-6}$ alkoxy, $C_{1-6}$ haloalkoxy, and $C(O)OR^a$.

In some embodiments of moieties (Q201)-(Q210), (212)-(Q217), (Q301-Q303), (Q305) and (Q307), each $R^5$ is other than H:

In some embodiments, the moiety of

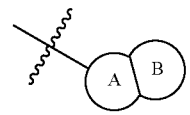

is selected from (Q200), (Q201)-(Q209), and (Q301)-(Q308); and $R^1$ is 4-methyl-piperazin-1-yl.

In some embodiments, the moiety of

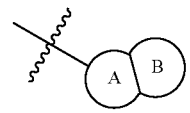

is selected from (Q200) and (Q201)-(Q209); and $R^1$ is 4-methyl-piperazin-1-yl.

In some embodiments, the moiety of

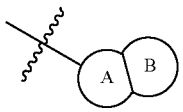

is selected from (Q201)-(Q209); and R¹ is 4-methyl-piperazin-1-yl.

In some embodiments, the compound of Formula I or pharmaceutically acceptable salt or N-oxide or quaternary ammonium salt thereof is a compound of Formula III-1, III-2, III-3, III-4, III-5, III-6, III-7, III-8, III-9, III-10, III-11, III-12, III-13, III-14, III-15, III-16, III-17, III-18, III-19, III-20, III-21, III-22, III-23, III-24, III-25, III-26, III-27, III-28, or III-29:

III-1
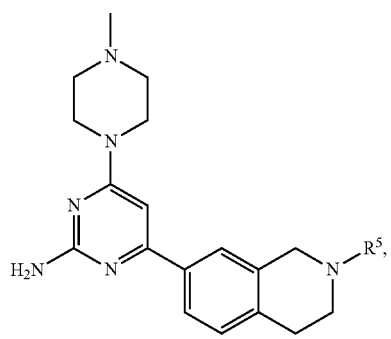

III-2
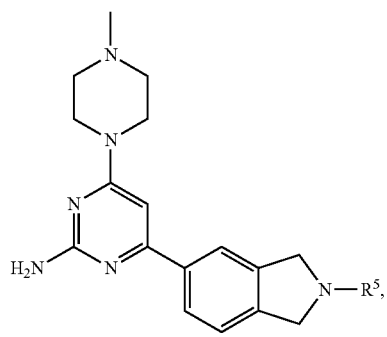

III-3
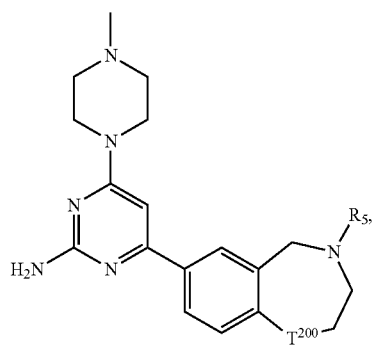

III-4
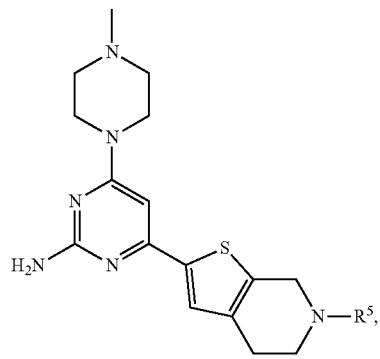

III-5
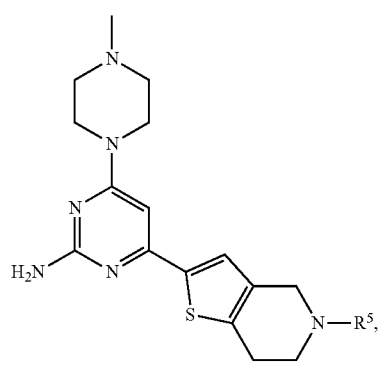

III-6
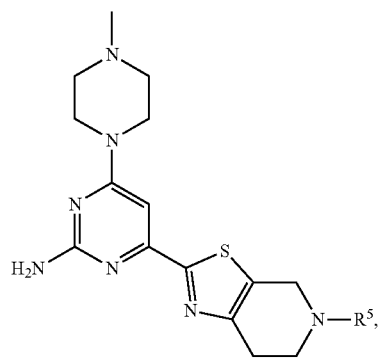

III-7
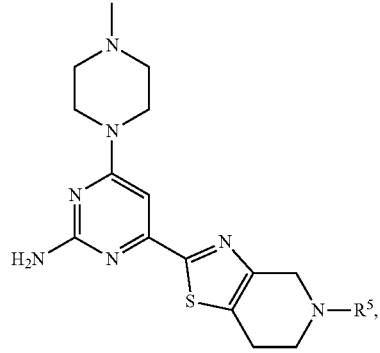

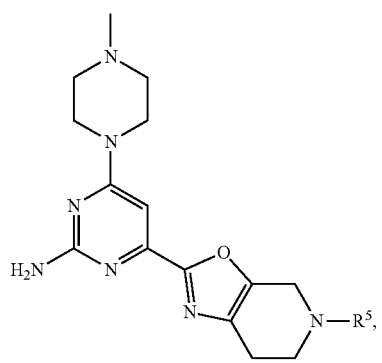
III-8
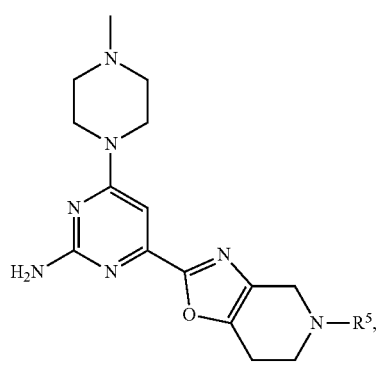
III-9
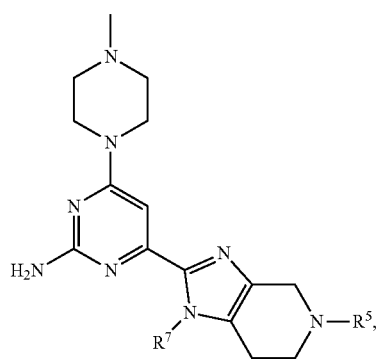
III-10
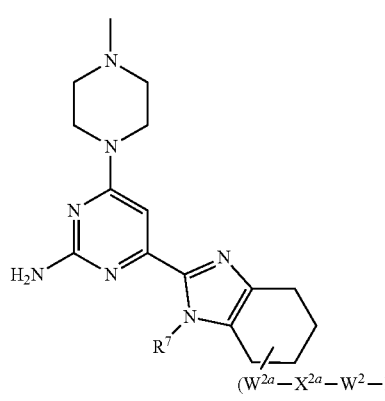
III-11
$(W^{2a}-X^{2a}-W^2-X^2-Y^2-Z^2)_{p201}$,
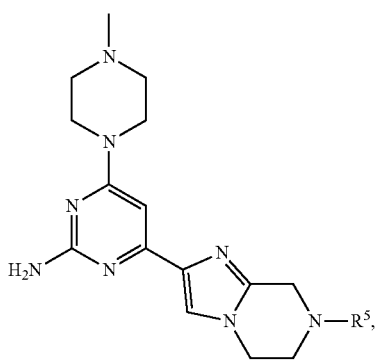
III-12
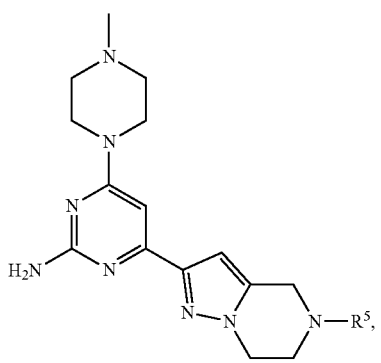
III-13
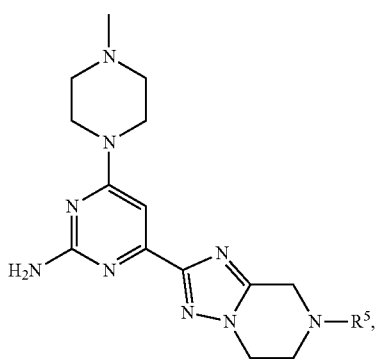
III-14
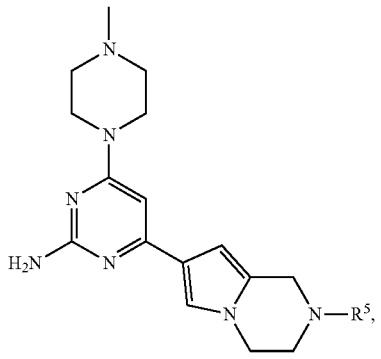
III-15

III-16
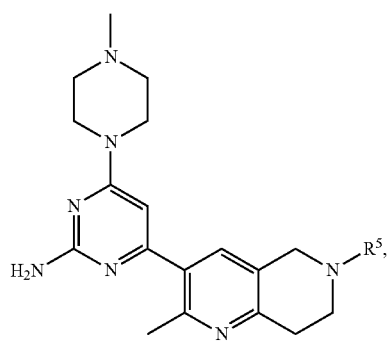
III-17
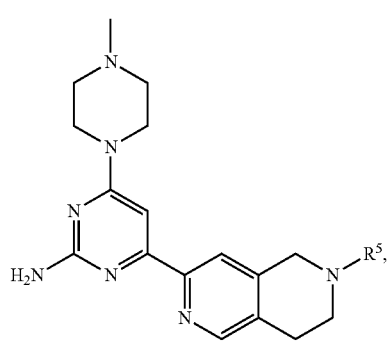
III-18
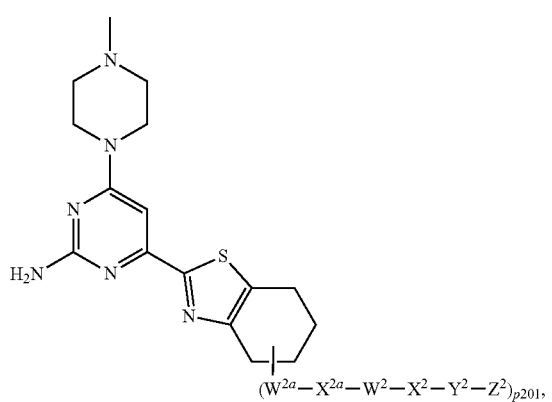
III-19
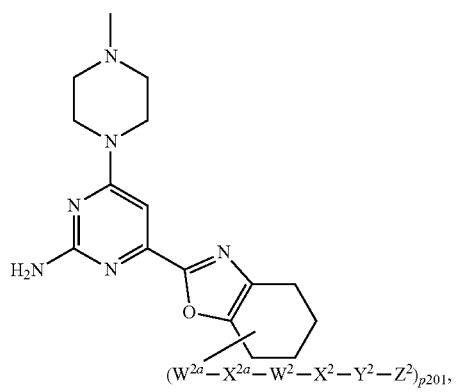
III-20
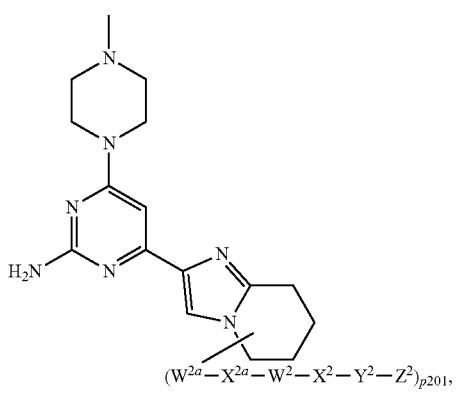
III-21
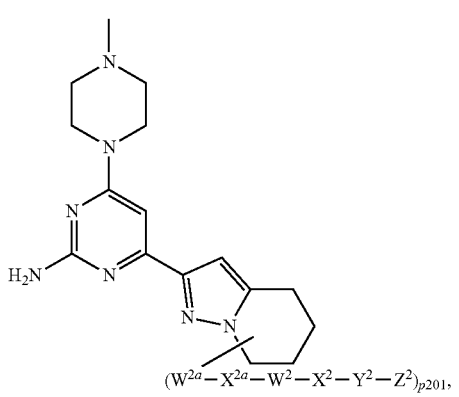
III-22
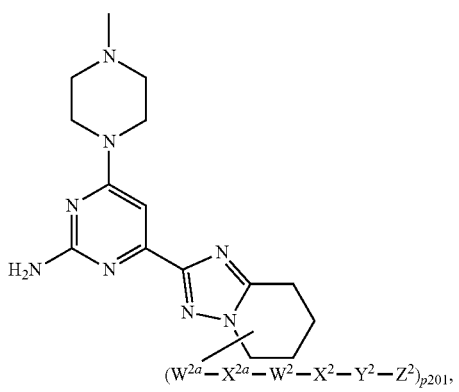
III-23
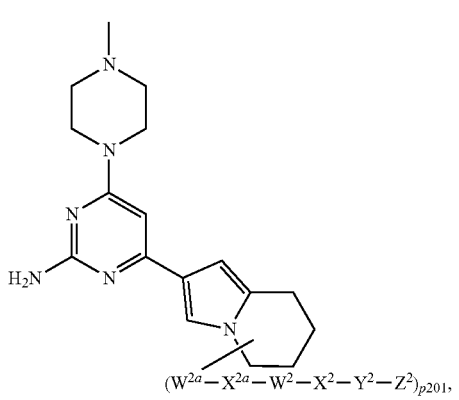

III-24

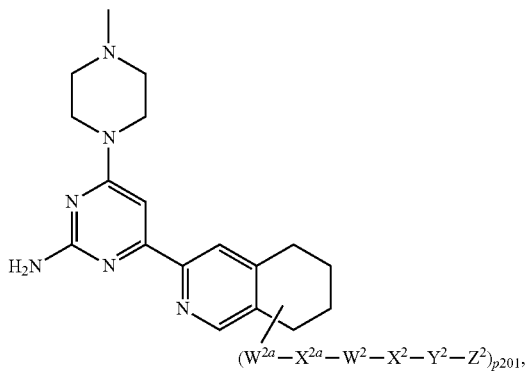

III-25

III-28

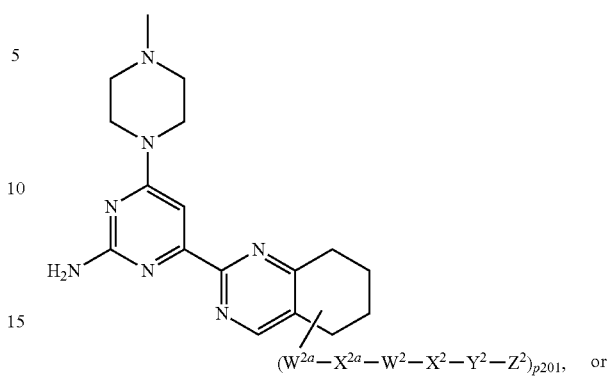

III-29

III-26

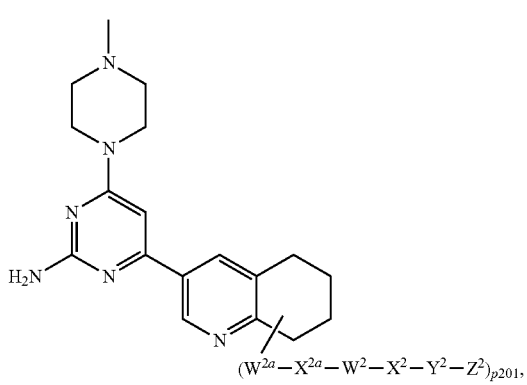

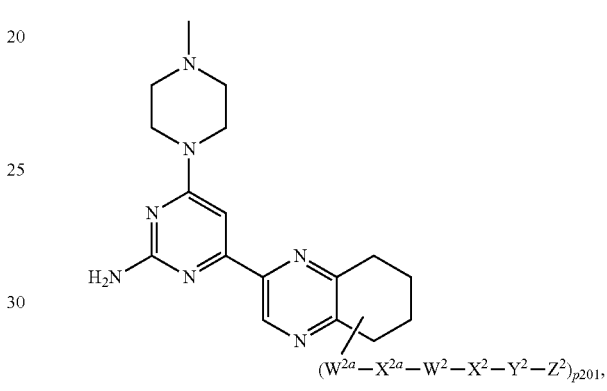

or pharmaceutically acceptable salt or N-oxide or quaternary ammonium salt thereof, wherein:

each $R^5$ is independently H or —$W^{2a}$—$X^{2a}$—$W^2$—$X^2$—$Y^2$—$Z^2$;

each $R^7$ is independently H or —$W^{2a}$—$X^{2a}$—$W^2$—$X^2$—$Y^2$—$Z^2$; and $T^{200}$ is $CH_2$, S, S(O) or $S(O)_2$.

In some embodiments, the compound of Formula I or pharmaceutically acceptable salt or N-oxide or quaternary ammonium salt thereof is a compound of Formula III-0-a, III-0-b, or III-1:

III-27

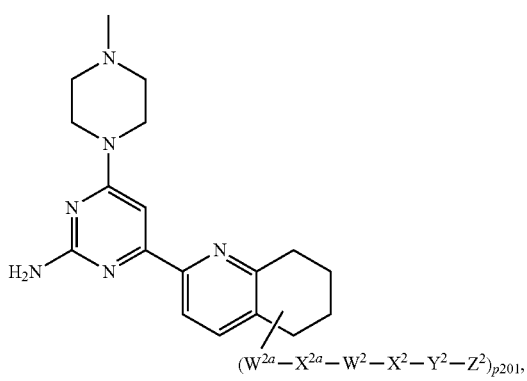

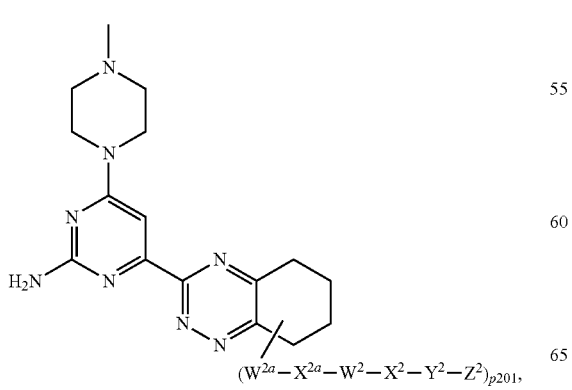

III-0-a

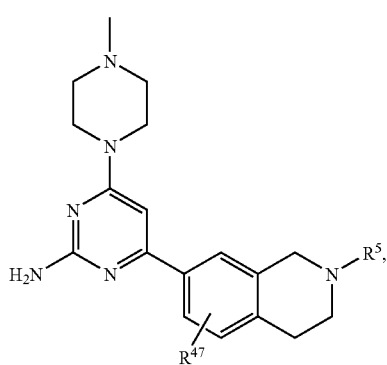

-continued

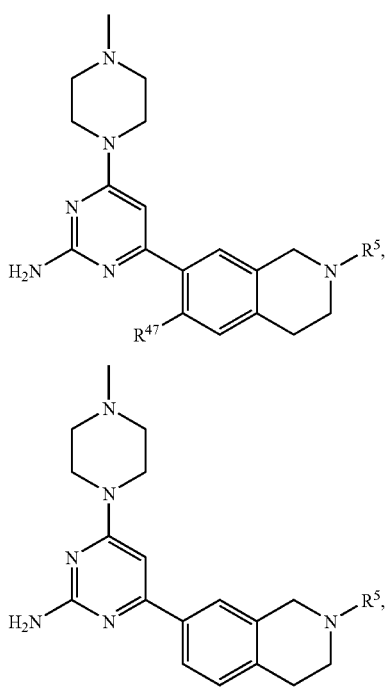

III-O-b

III-1 wherein $R^{47}$ is H, $C_{1-6}$ alkyl, $C_{1-6}$ haloalkyl, halo, $C_{1-6}$ alkoxy, $C_{1-6}$ haloalkoxy, or CN.

In some embodiments, the compound of Formula III-O-a or III-O-b or pharmaceutically acceptable salt or N-oxide or quaternary ammonium salt thereof, $R^{47}$ is H, $C_{1-6}$ alkyl (for example, methyl), $C_{1-6}$ haloalkyl (e.g. $CF_3$), and halo (for example, F or Cl). In some further embodiments, $R^{47}$ is H, $C_{1-6}$ alkyl (for example, methyl), and halo (for example, F). In yet further embodiments, $R^{47}$ is $C_{1-3}$ alkyl (for example, methyl), and halo (for example, F).

In some embodiments, the compound of Formula I is a compound of Formula III-1. In some other embodiments, the compound of Formula I is a compound of Formula III-O-a or III-O-b.

In some embodiments of compounds of any one of Formulas III-O-a, III-O-b, and III-1 to III-29, each $R^5$ is independently selected from H, $Z^2$, —C(O)$Z^2$, —C(S)$Z^2$, —C(O)NH$Z^2$, —C(O)N($C_{1-6}$ alkyl)$Z^2$, —C(S)NH$Z^2$, —C(S)N($C_{1-6}$ alkyl)$Z^2$, —C(O)O$Z^2$, —S(O)$Z^2$, —S(O)NH$Z^2$, —S(O)N($C_{1-6}$ alkyl)$Z^2$, —S(O)$_2Z^2$, —S(O)$_2$NH$Z^2$, and —S(O)$_2$N($C_{1-6}$ alkyl)$Z^2$; and each $Z^2$ is independently selected from $C_{1-6}$ alkyl, $C_{1-6}$ haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl, and heterocycloalkylalkyl, each substituted with 0, 1, 2 or 3 substituents each independently selected from $R^{zz}$, halo, CN, $NO_2$, $OR^a$, $SR^a$, $SF_5$, C(O)$R^b$, C(O)NR$^c$R$^d$, C(O)OR$^a$, OC(O)$R^b$, OC(O)NR$^c$R$^d$, NR$^c$R$^d$, NR$^c$C(O)R$^d$, NR$^c$C(O)OR$^a$, NR$^c$S(O)$_2$R$^b$, NR$^c$S(O)$_3$NR$^c$R$^d$; S(O)R$^b$, S(O)NR$^c$R$^d$, S(O)$_2$R$^b$, and S(O)$_2$NR$^c$R$^d$. In some further embodiments, each $R^5$ is independently selected from $Z^2$, —C(O)$Z^2$, —C(S)$Z^2$, —C(O)NH$Z^2$, —C(O)N($C_{1-6}$ alkyl)$Z^2$, —C(S)NH$Z^2$, —C(S)N($C_{1-6}$ alkyl)$Z^2$, —C(O)O$Z^2$, —S(O)$Z^2$, —S(O)NH$Z^2$, —S(O)N($C_{1-6}$ alkyl)$Z^2$, —S(O)$_2Z^2$, —S(O)$_2$NH$Z^2$, and —S(O)$_2$N($C_{1-6}$ alkyl)$Z^2$; and each $Z^2$ is independently selected from $C_{1-6}$ alkyl, $C_{1-6}$ haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl, and heterocycloalkylalkyl, each substituted with 0, 1, 2 or 3 substituents each independently selected from $R^{zz}$, halo, CN, $NO_2$, $OR^a$, $SR^a$, $SF_5$, C(O)$R^b$, C(O)NR$^c$R$^d$, C(O)OR$^a$, OC(O)$R^b$, OC(O)NR$^c$R$^d$, NR$^c$R$^d$, NR$^c$C(O)R$^d$, NR$^c$C(O)OR$^a$, NR$^c$S(O)$_2$R$^b$, NR$^c$S(O)$_2$NR$^c$R$^d$; S(O)R$^b$, S(O)NR$^c$R$^d$, S(O)$_2$R$^b$, and S(O)$_2$NR$^c$R$^d$.

In some embodiments of compounds of any one of Formulas III-O-a, III-O-b, and III-1 to III-29, each $R^5$ is independently selected from the following 8 options:

(1) H;
(2) aryl (such as phenyl or naphthyl) substituted with 0, 1, 2, or 3 substituents each independently selected from $C_{1-6}$ alkyl, $C_{1-6}$ haloalkyl, halo, $C_{1-6}$ alkoxy, $C_{1-6}$ haloalkoxy, CN, C(O)OR$^a$, C(O)R$^b$, OR$^a$, C(O)NR$^c$R$^d$, NR$^c$C(O)R$^d$, NR$^c$C(O)OR$^a$, and S(O)$_2$R$^b$;
(3) heteroaryl substituted with 0, 1, 2, or 3 substituents each independently selected from $C_{1-6}$ alkyl, $C_{1-6}$ haloalkyl, halo, $C_{1-6}$ alkoxy, $C_{1-6}$ haloalkoxy, Ar, CN, C(O)OR$^a$, C(O)R$^b$, OR$^a$, C(O)NR$^c$R$^d$, NR$^c$C(O)R$^d$, NR$^c$C(O)OR$^a$, and S(O)$_2$R$^b$;
(4) —C(O)$Z^{21}$, wherein $Z^{21}$ is selected from $C_{1-6}$ alkyl, cycloalkyl, aryl, heterocycloalkyl, heteroaryl, arylalkyl, heteroarylalkyl, cycloalkylalkyl, and heterocycloalkylalkyl, each substituted with 0, 1, 2, 3, 4, or 5 substituents each independently selected from halo, $C_{1-6}$ alkyl, $C_{1-6}$ haloalkyl, $C_{2-8}$ alkoxyalkyl, CN, —OR$^a$, C(O)R$^b$, C(O)NR$^c$R$^d$, C(O)OR$^a$, S(O)$_2$R$^b$, NR$^c$R$^d$, NR$^c$ C(O)R$^b$, and NR$^c$C(O)OR$^a$;
(5) —S(O)$_2Z^{22}$, wherein $Z^{22}$ is selected from aryl and arylalkyl, each substituted with 0, 1, 2, 3, 4, or 5 substituents each independently selected from halo, $C_{1-6}$ alkyl, $C_{1-6}$ haloalkyl, $C_{2-8}$ alkoxyalkyl, CN, —O—Ar, C(O)R$^b$, C(O)NR$^c$R$^d$, C(O)OR$^a$, S(O)$_2$R$^b$, NR$^c$R$^d$, NR$^c$C(O)R$^b$, and NR$^c$C(O)OR$^a$;
(6) —C(O)O$Z^{23}$; wherein $Z^{23}$ is selected from $C_{1-6}$ alkyl, cycloalkyl, aryl, heterocycloalkyl, heteroaryl, arylalkyl, heteroarylalkyl, cycloalkylalkyl, and heterocycloalkylalkyl, each substituted with 0, 1, 2, 3, 4, or 5 substituents each independently selected from halo, $C_{1-6}$ alkyl, $C_{1-6}$ haloalkyl, $C_{2-8}$ alkoxyalkyl, CN, —OR$^a$, C(O)R$^b$, C(O)NR$^c$R$^d$, C(O)OR$^a$, S(O)$_2$R$^b$, NR$^c$R$^d$, NR$^c$ C(O)R$^b$, and NR$^c$C(O)OR$^a$;
(7) —C(O)N$Z^{24}Z^{25}$ wherein $Z^{24}$ and $Z^{25}$ together with the N atom to which they are attached form a 4-10 membered heterocycloalkyl group wherein each of the ring-forming atoms of the 4-10 membered heterocycloalkyl group is independently selected from C, N, O, and S, and wherein the 4-10 membered heterocycloalkyl group is substituted with 0, 1, 2 or 3 substituents each independently selected from $C_{1-6}$ alkyl, $C_{1-6}$ haloalkyl, halo, Ar, HetAr; and
(8) —C(O)N$Z^{26}Z^{27}$;
wherein:
$Z^{26}$ is selected from H and $C_{1-6}$ alkyl;
$Z^{27}$ is selected from $C_{1-6}$ alkyl, cycloalkyl, aryl, heterocycloalkyl, heteroaryl, arylalkyl, heteroarylalkyl, cycloalkylalkyl, and heterocycloalkylalkyl, each substituted with 0, 1, 2, 3, 4, or 5 substituents each independently selected from halo, $C_{1-6}$ alkyl, $C_{1-6}$ haloalkyl, $C_{2-8}$ alkoxyalkyl, CN, Ar, HetAr, —OR$^a$, C(O)R$^b$, C(O)NR$^c$R$^d$, C(O)OR$^a$, S(O)$_2$R$^b$, NR$^c$R$^d$, NR$^c$C(O)R$^b$, and NR$^c$C(O)OR$^a$;
each Ar is independently aryl substituted with 0, 1, 2, 3, 4, or 5 substituents each independently selected from halo, CN, $C_{1-6}$ alkyl, $C_{1-6}$ haloalkyl, $C_{2-8}$ alkoxyalkyl, $C_{1-6}$ alkoxy, $C_{1-6}$ haloalkoxy, and C(O)OR$^a$, and
each HetAr is independently heteroaryl substituted with 0, 1, 2, 3, 4, or 5 substituents each independently selected from halo, CN, $C_{1-6}$ alkyl, $C_{1-6}$ haloalkyl, $C_{2-8}$ alkoxyalkyl, $C_{1-6}$ alkoxy, $C_{1-6}$ haloalkoxy, and $C(O)OR^a$.

In some such embodiments, each $R^5$ is independently selected from option (1). In some embodiments, each $R^5$ is independently selected from option (2). In some embodiments, each $R^5$ is independently selected from option (3). In some embodiments, each $R^5$ is independently selected from option (4). In some embodiments, each $R^5$ is independently selected from option (5). In some embodiments, each $R^5$ is independently selected from option (6). In some embodiments, each $R^5$ is independently selected from option (7). In some embodiments, each $R^5$ is independently selected from option (8).

In some embodiments of compounds of any one of Formulas III-0-a, III-0-b, and III-1 to III-29, each $R^5$ is independently selected from the following 8 options:
  (1) H;
  (2) phenyl or naphthyl, each substituted with 0, 1, 2, or 3 substituents each independently selected from $C_{1-6}$ alkyl, $C_{1-6}$ haloalkyl, halo, $C_{1-6}$ alkoxy, $C_{1-6}$ haloalkoxy, and CN;
  (3) pyrdinyl, pyrazinyl, pyrazolyl, 1,3-thiazolyl, 1,3-benzothiazolyl, furanyl, benzofuranyl, thienyl, quinoxalinyl, and 2,1,3-benzothiadiazolyl, each substituted with 0, 1, 2, or 3 substituents each independently selected from $C_{1-6}$ alkyl, $C_{1-6}$ haloalkyl, halo, $C_{1-6}$ alkoxy, $C_{1-6}$ haloalkoxy, Ar, CN, and $C(O)NR^cR^d$;
  (4) —$C(O)Z^{21}$, wherein $Z^{21}$ is selected from (a) $C_{1-6}$ alkyl substituted with 0, 1, 2, 3, or 4 substituents each independently selected from halo, CN, —OAr, and $NR^cC(O)OR^a$; (b) $C_{3-10}$ cycloalkyl substituted with 0, 1, 2, 3, or 4 substituents each independently selected from halo, CN, Ar, $C_{1-6}$ alkyl, and $C_{1-6}$ haloalkyl; (c) phenyl and naphthyl, each substituted with 0, 1, 2, 3, or 4 substituents each independently selected from $C_{1-6}$ alkyl, $C_{1-6}$ haloalkyl, halo, $C_{1-6}$ alkoxy, $C_{1-6}$ haloalkoxy, and CN;
  (d) arylakyl substituted with 0, 1, 2, 3, or 4 substituents each independently selected from $C_{1-6}$ alkyl, $C_{1-6}$ haloalkyl, $C_{1-6}$ alkoxy, $C_{1-6}$ haloalkoxy, halo, and CN;
  (e) cycloalkylalkyl substituted with 0, 1, 2, 3, or 4 substituents each independently selected from $C_{1-6}$ alkyl, $C_{1-6}$ haloalkyl, $C_{1-6}$ alkoxy, $C_{1-6}$ haloalkoxy, halo, $NR^cC(O)OR^a$, and CN; (f) heteroarylalkyl substituted with 0, 1, 2, 3, or 4 substituents each independently selected from $C_{1-6}$ alkyl, $C_{1-6}$ haloalkyl, $C_{1-6}$ alkoxy, $C_{1-6}$ haloalkoxy, $NR^cC(O)OR^a$, halo, $NR^cR^d$, and CN; and
  (g) heterocycloalkylalkyl substituted with 0, 1, 2, 3, or 4 substituents each independently selected from $C_{1-6}$ alkyl, $C_{1-6}$ haloalkyl, $C_{1-6}$ alkoxy, $C_{1-6}$ haloalkoxy, $NR^c$-$C(O)OR^a$, halo, $NR^cR^d$, CN, $C(O)R^b$, $C(O)OR^a$, and $S(O)_2R^b$;
  (5) —$S(O)_2Z^{22}$, wherein $Z^{22}$ is selected from phenyl, naphthyl, benzyl, phenylethyl, and phenylpropyl, each substituted with 0, 1, 2, 3, 4, or 5 substituents each independently selected from halo, $C_{1-6}$ alkyl, $C_{1-6}$ haloalkyl, $C_{2-8}$ alkoxyalkyl, CN, —O—Ar, $C(O)R^b$, $C(O)NR^cR^d$, $C(O)OR^a$, $S(O)_2R^b$, $NR^cR^d$, $NR^cC(O)R^b$, and $NR^cC(O)OR^a$;
  (6) —$C(O)OZ^{23}$; wherein $Z^{23}$ is selected from (a) $C_{1-6}$ alkyl substituted with 0, 1, 2, 3, or 4 substituents each independently selected from halo, CN, —OAr, and $NR^c$-$C(O)OR^a$; (b) $C_{3-10}$ cycloalkyl substituted with 0, 1, 2, 3, or 4 substituents each independently selected from halo, CN, Ar, $C_{1-6}$ alkyl, and $C_{1-6}$ haloalkyl; (c) phenyl and naphthyl, each substituted with 0, 1, 2, 3, or 4 substituents each independently selected from $C_{1-6}$ alkyl, $C_{1-6}$ haloalkyl, halo, $C_{1-6}$ alkoxy, $C_{1-6}$ haloalkoxy, and CN;
  (d) cycloalkylalkyl substituted with 0, 1, 2, 3, or 4 substituents each independently selected from $C_{1-6}$ alkyl, $C_{1-6}$ haloalkyl, $C_{1-6}$ alkoxy, $C_{1-6}$ haloalkoxy, halo, $NR^cC(O)OR^a$, and CN; and (e) heterocycloalkylalkyl substituted with 0, 1, 2, 3, or 4 substituents each independently selected from $C_{1-6}$ alkyl, $C_{1-6}$ haloalkyl, $C_{1-6}$ alkoxy, $C_{1-6}$ haloalkoxy, $NR^cC(O)OR^a$, halo, $NR^cR^d$, CN, $C(O)NR^cR^d$, $C(O)R^b$, $C(O)OR^a$, and $S(O)_2R^b$;
  (7) —$C(O)NZ^{24}Z^{25}$ wherein $Z^{24}$ and $Z^{25}$ together with the N atom to which they are attached form a pyrrolidinyl or piperidinyl group, each substituted with 0, 1, 2 or 3 substituents each independently selected from $C_{1-6}$ alkyl, Ar, HetAr; and
  (8) —$C(O)NZ^{26}Z^{27}$;
wherein:
  $Z^{26}$ is selected from H and $C_{1-3}$ alkyl;
  $Z^{27}$ is selected from (a) $C_{1-6}$ alkyl substituted with 0, 1, 2, 3, or 4 substituents each independently selected from halo, and CN; (b) $C_{3-10}$ cycloalkyl substituted with 0, 1, 2, 3, or 4 substituents each independently selected from halo, CN, Ar, $C_{1-6}$ alkyl, $C_{1-6}$ haloalkyl, $C_{2-8}$ alkoxyalkyl, $OR^a$, $C(O)R^b$, $C(O)NR^cR^d$, and $C(O)OR^a$; (c) phenyl and naphthyl, each substituted with 0, 1, 2, 3, or 4 substituents each independently selected from $C_{1-6}$ alkyl, $C_{1-6}$ haloalkyl, halo, $OR^a$, HetAr, and CN; (d) arylakyl substituted with 0, 1, 2, 3, or 4 substituents each independently selected from $C_{1-6}$ alkyl, $C_{1-6}$ haloalkyl, $C_{1-6}$ alkoxy, $C_{1-6}$ haloalkoxy, $C(O)NR^cR^d$, halo, and CN; (e) heteroaryl substituted with 0, 1, 2, 3, or 4 substituents each independently selected from $C_{1-6}$ alkyl, $C_{1-6}$ haloalkyl, $OR^a$, $C(O)OR^a$, halo, $NR^cR^d$, Ar, and CN; and (f) heterocycloalkyl substituted with 0, 1, 2, 3, or 4 substituents each independently selected from $C_{1-6}$ alkyl, $C_{1-6}$ haloalkyl, halo, CN, $C(O)R^b$, $C(O)OR^a$, Ar, and HetAr;

each Ar is independently aryl substituted with 0, 1, 2, 3, 4, or 5 substituents each independently selected from halo, CN, $C_{1-6}$ alkyl, $C_{1-6}$ haloalkyl, $C_{2-8}$ alkoxyalkyl, $C_{1-6}$ alkoxy, $C_{1-6}$ haloalkoxy, and $C(O)OR^a$, and each HetAr is independently heteroaryl substituted with 0, 1, 2, 3, 4, or 5 substituents each independently selected from halo, CN, $C_{1-6}$ alkyl, $C_{1-6}$ haloalkyl, $C_{2-8}$ alkoxyalkyl, $C_{1-6}$ alkoxy, $C_{1-6}$ haloalkoxy, and $C(O)OR^a$.

In some such embodiments, each $R^5$ is independently selected from option (1). In some embodiments, each $R^5$ is independently selected from option (2). In some embodiments, each $R^5$ is independently selected from option (3). In some embodiments, each $R^5$ is independently selected from option (4). In some embodiments, each $R^5$ is independently selected from option (5). In some embodiments, each $R^5$ is independently selected from option (6). In some embodiments, each $R^5$ is independently selected from option (7). In some embodiments, each $R^5$ is independently selected from option (8).

In some embodiments of compounds of any one of Formulas III-0-a, III-0-b, and III-1 to III-29, each $R^5$ is independently selected from the following options:
  (1) H;
  (2) phenyl substituted with 0, 1, 2, or 3 substituents each independently selected from $C_{1-6}$ alkyl, $C_{1-6}$ haloalkyl, halo, $C_{1-6}$ alkoxy, $C_{1-6}$ haloalkoxy, and CN;
  (3) pyrdinyl substituted with 0, 1, 2, or 3 substituents each independently selected from $C_{1-6}$ alkyl, $C_{1-6}$ haloalkyl, halo, $C_{1-6}$ alkoxy, $C_{1-6}$ haloalkoxy, Ar, CN, and $C(O)NR^cR^d$;
  (4) —$C(O)Z^{21}$, wherein $Z^{21}$ is selected from (a) $C_{1-6}$ alkyl substituted with 0, 1, 2, 3, or 4 substituents each independently selected from halo, CN, —OAr, and $NR^cC(O)OR^a$; (b) $C_{3-10}$ cycloalkyl substituted with 0, 1, 2, 3, or 4 substituents each independently selected from halo, CN, Ar, $C_{1-6}$ alkyl, and $C_{1-6}$ haloalkyl; (c) phenyl substituted with 0, 1, 2, 3, or 4 substituents each independently selected from $C_{1-6}$ alkyl, $C_{1-6}$ haloalkyl, halo, $C_{1-6}$ alkoxy, $C_{1-6}$ haloalkoxy, and CN; (d) arylakyl substituted with 0, 1, 2, 3, or 4 substituents each independently selected from $C_{1-6}$ alkyl, $C_{1-6}$ haloalkyl, $C_{1-6}$ alkoxy, $C_{1-6}$ haloalkoxy, halo, and CN; (e) cycloalkylalkyl substituted with 0, 1, 2, 3, or 4 substituents each independently selected from $C_{1-6}$ alkyl, $C_{1-6}$ haloalkyl, $C_{1-6}$ alkoxy, $C_{1-6}$ haloalkoxy, halo, $NR^cC(O)OR^a$, and CN; (f) heteroarylalkyl substituted with 0, 1, 2, 3, or 4 substituents each independently selected from $C_{1-6}$ alkyl, $C_{1-6}$ haloalkyl, $C_{1-6}$ alkoxy, $C_{1-6}$ haloalkoxy, $NR^cC(O)OR^a$, halo, $NR^cR^d$, and CN; and (g) heterocycloalkylalkyl substituted with 0, 1, 2, 3, or 4 substituents each independently selected from $C_{1-6}$ alkyl, $C_{1-6}$ haloalkyl, $C_{1-6}$ alkoxy, $C_{1-6}$ haloalkoxy, $NR^cC(O)OR^a$, halo, $NR^cR^d$, CN, $C(O)R^b$, $C(O)OR^a$, and $S(O)_2R^b$;

(5) —$S(O)_2Z^{22}$, wherein $Z^{22}$ is selected from phenyl and benzyl, each substituted with 0, 1, 2, 3, 4, or 5 substituents each independently selected from halo, $C_{1-6}$ alkyl, $C_{1-6}$ haloalkyl, $C_{2-8}$ alkoxyalkyl, CN, —O—Ar, $C(O)R^b$, $C(O)NR^cR^d$, $C(O)OR^a$, $S(O)_2R^b$, $NR^cR^d$, $NR^cC(O)R^b$, and $NR^cC(O)OR^a$;

(6) —$C(O)OZ^{23}$; wherein $Z^{23}$ is selected from (a) $C_{1-6}$ alkyl substituted with 0, 1, 2, 3, or 4 substituents each independently selected from halo, CN, —OAr, and $NR^c$-$C(O)OR^a$; (b) $C_{3-10}$ cycloalkyl substituted with 0, 1, 2, 3, or 4 substituents each independently selected from halo, CN, Ar, $C_{1-6}$ alkyl, and $C_{1-6}$ haloalkyl; (c) phenyl substituted with 0, 1, 2, 3, or 4 substituents each independently selected from $C_{1-6}$ alkyl, $C_{1-6}$ haloalkyl, halo, $C_{1-6}$ alkoxy, $C_{1-6}$ haloalkoxy, and CN; (d) cycloalkylalkyl substituted with 0, 1, 2, 3, or 4 substituents each independently selected from $C_{1-6}$ alkyl, $C_{1-6}$ haloalkyl, $C_{1-6}$ alkoxy, $C_{1-6}$ haloalkoxy, halo, $NR^cC(O)OR^a$, and CN; and (e) heterocycloalkylalkyl substituted with 0, 1, 2, 3, or 4 substituents each independently selected from $C_{1-6}$ alkyl, $C_{1-6}$ haloalkyl, $C_{1-6}$ alkoxy, $C_{1-6}$ haloalkoxy, $NR^c(O)OR^a$, halo, $NR^cR^d$, CN, $C(O)NR^cR^d$, $C(O)R^b$, $C(O)OR^a$, and $S(O)_2R^b$;

(7) —$C(O)NZ^{24}Z^{25}$ wherein $Z^{24}$ and $Z^{25}$ together with the N atom to which they are attached form a pyrrolidinyl or piperidinyl group, each substituted with 0, 1, 2 or 3 substituents each independently selected from $C_{1-6}$ alkyl, Ar, HetAr; and (8) —$C(O)NZ^{26}Z^{27}$;

wherein:

$Z^{26}$ is selected from H and $C_{1-3}$ alkyl;

$Z^{27}$ is selected from (a) $C_{1-6}$ alkyl substituted with 0, 1, 2, 3, or 4 substituents each independently selected from halo, and CN; (b) $C_{3-10}$ cycloalkyl substituted with 0, 1, 2, 3, or 4 substituents each independently selected from halo, CN, Ar, $C_{1-6}$ alkyl, $C_{1-6}$ haloalkyl, $C_{2-8}$ alkoxyalkyl, $OR^a$, $C(O)R^b$, $C(O)NR^cR^d$, and $C(O)OR^a$; (c) phenyl substituted with 0, 1, 2, 3, or 4 substituents each independently selected from $C_{1-6}$ alkyl, $C_{1-6}$ haloalkyl, halo, $OR^a$, HetAr, and CN; (d) arylakyl substituted with 0, 1, 2, 3, or 4 substituents each independently selected from $C_{1-6}$ alkyl, $C_{1-6}$ haloalkyl, $C_{1-6}$ alkoxy, $C_{1-6}$ haloalkoxy, $C(O)NR^cR^d$, halo, and CN; (e) heteroaryl substituted with 0, 1, 2, 3, or 4 substituents each independently selected from $C_{1-6}$ alkyl, $C_{1-6}$ haloalkyl, $OR^a$, $C(O)OR^a$, halo, $NR^cR^d$, Ar, and CN; and (f) heterocycloalkyl substituted with 0, 1, 2, 3, or 4 substituents each independently selected from $C_{1-6}$ alkyl, $C_{1-6}$ haloalkyl, halo, CN, $C(O)R^b$, $C(O)OR^a$, Ar, and HetAr;

each Ar is independently aryl substituted with 0, 1, 2, 3, 4, or 5 substituents each independently selected from halo, CN, $C_{1-6}$ alkyl, $C_{1-6}$ haloalkyl, $C_{2-8}$ alkoxyalkyl, $C_{1-6}$ alkoxy, $C_{1-6}$ haloalkoxy, and $C(O)OR^a$, and each HetAr is independently heteroaryl substituted with 0, 1, 2, 3, 4, or 5 substituents each independently selected from halo, CN, $C_{1-6}$ alkyl, $C_{1-6}$ haloalkyl, $C_{2-8}$ alkoxyalkyl, $C_{1-6}$ alkoxy, $C_{1-6}$ haloalkoxy, and $C(O)OR^a$.

In some such embodiments, each $R^5$ is other than H: In some other such embodiments, each $R^5$ is independently selected from option (2). In some embodiments, each $R^5$ is independently selected from option (3). In some embodiments, each $R^5$ is independently selected from option (4). In some embodiments, each $R^5$ is independently selected from option (5). In some embodiments, each $R^5$ is independently selected from option (6). In some embodiments, each $R^5$ is independently selected from option (7). In some embodiments, each $R^5$ is independently selected from option (8).

In some embodiments of compounds of Formula III-10 or Formula III-11, $R^7$ is selected from H, $C_{1-6}$ alkyl, $C_{1-6}$ haloalkyl, $C_{2-6}$ alkenyl, $C_{2-6}$ alkynyl, aryl, $C_{3-7}$ cycloalkyl, heteroaryl, heterocycloalkyl, arylalkyl, heteroarylalkyl, cycloalkylalkyl, and heterocycloalkylalkyl. In some further embodiments, $R^7$ is selected from H and $C_{1-6}$ alkyl. In yet further embodiments, $R^7$ is H.

In some embodiments of compounds disclosed herein, each $W^{2a}$ is independently absent, $C(O)$, $S(O)$, $S(O)_2$, $C(O)O$, $C(O)NH$, $S(O)_2NH$, $S(O)_2N(C_{1-6}$ alkyl), or $C(O)N(C_{1-6}$ alkyl); and each $X^{2a}$ is independently $C_{1-6}$ alkylenyl, aryl, arylalkyl, heteroarylalkyl, cycloalkylalkyl, heterocycloalkylalkyl, cycloalkyl, heteroaryl, or heterocycloalkyl, each substituted with 0, 1, 2, 3, 4, 5, or 6 substituents each independently selected from $R^{XX}$, halo, CN, $NO_2$, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cC(O)R^b$, $NR^cC(O)NR^cR^d$, $NR^cC(O)OR^a$, $C(=NR^g)NR^cR^d$, $NR^cC(=NR^g)NR^cR^d$, $NR^cS(O)_2NR^cR^d$, $S(O)R^b$, $S(O)NR^cR^d$, $S(O)_2R^b$, $NR^cS(O)_2R^b$, and $S(O)_2NR^cR^d$.

In some embodiments, each $W^{2a}$ is independently absent, $C(O)$, $S(O)_2$, $C(O)O$, $C(O)NH$, or $C(O)N(C_{1-6}$ alkyl); and each $X^{2a}$ is independently $C_{1-6}$ alkylenyl, aryl, arylalkyl, heteroarylalkyl, cycloalkylalkyl, heterocycloalkylalkyl, cycloalkyl, heteroaryl, or heterocycloalkyl, each substituted with 0, 1, 2, or 3 substituents each independently selected from $R^{XX}$, halo, CN, $NO_2$, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cC(O)R^b$, $NR^cC(O)NR^cR^d$, $NR^cC(O)OR^a$, $NR^cS(O)_2NR^cR^d$, $S(O)R^b$, $S(O)NR^cR^d$, $S(O)_2R^b$, $NR^cS(O)_2R^b$, and $S(O)_2NR^cR^d$.

In some embodiments, each $W^{2a}$ is independently absent, $C(O)$, $S(O)_2$, $C(O)O$, or $C(O)NH$; and each $X^{2a}$ is independently $C_{1-6}$ alkylenyl, aryl, arylalkyl, cycloalkyl, heteroaryl, or heterocycloalkyl, each substituted with 0, 1, 2, 3, 4, 5, or 6 substituents each independently selected from $R^{XX}$, halo, CN, $NO_2$, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cC(O)R^b$, $NR^cC(O)NR^cR^d$, $NR^c(O)OR^a$, $C(=NR^g)NR^cR^d$, $NR^cC(=NR^g)NR^cR^d$, $NR^cS(O)_2NR^cR^d$, $S(O)R^b$, $S(O)NR^cR^d$, $S(O)_2R^b$, $NR^cS(O)_2R^b$, and $S(O)_2NR^cR^d$.

In some embodiments, each $W^{2a}$ is independently absent, $C(O)$, $S(O)$, $S(O)_2$, $C(O)O$, $C(O)NH$, $S(O)_2NH$, $S(O)_2N(C_{1-6}$ alkyl), or $C(O)N(C_{1-6}$ alkyl); and each —$X^{2a}$—$W^2$—$X^2$—$Y^2$—$Z^2$ is independently $C_{1-6}$ alkyl, arylalkyl, heteroarylalkyl, cycloalkylalkyl, heterocycloalkylalkyl, aryl, cycloalkyl, heteroaryl, or heterocycloalkyl, each substituted with 0, 1, 2, 3, 4, 5, or 6 substituents each independently selected from $R^{XX}$, halo, CN, $C_{1-6}$ alkyl, $C_{1-6}$ hydroxylalkyl, $C_{1-6}$ cyanoalkyl, $C_{3-6}$ cycloalkyl, —$C(O)$—($C_{1-4}$ alkyl), —C(O)—NH($C_{1-4}$ alkyl), —C(O)—N($C_{1-4}$ alkyl)$_2$, OH, $C_{1-6}$ alkoxy, $C_{1-6}$ haloalkoxy, and $C_{2-8}$ alkoxyalkoxy.

In some embodiments, each $W^{2a}$ is independently absent, C(O), S(O)$_2$, C(O)O, or C(O)NH; and each —$X^{2a}$—$W^2$—$X^2$—$Y^2$—$Z^2$ is independently $C_{1-6}$ alkyl, arylalkyl, heteroarylalkyl, cycloalkylalkyl, heterocycloalkylalkyl, aryl, cycloalkyl, heteroaryl, or heterocycloalkyl, each substituted with 0, 1, 2, 3, 4, 5, or 6 substituents each independently selected from $R^{XX}$, halo, CN, $C_{1-6}$ alkyl, $C_{1-6}$ haloalkyl, $C_{1-6}$ hydroxylalkyl, $C_{1-6}$ cyanoalkyl, $C_{3-6}$ cycloalkyl, —C(O)—($C_{1-4}$ alkyl), —C(O)—NH($C_{1-4}$ alkyl), —C(O)—N($C_{1-4}$ alkyl)$_2$, OH, $C_{1-6}$ alkoxy, $C_{1-6}$ haloalkoxy, and $C_{2-8}$ alkoxyalkoxy.

In some embodiments, each $W^{2a}$ is independently absent, C(O), S(O), S(O)$_2$, C(O)O, C(O)NH, S(O)$_2$NH, S(O)$_2$N($C_{1-6}$ alkyl), or C(O)N($C_{1-6}$ alkyl); each —$X^{2a}$—$W^2$—$X^2$—$Y^2$—$Z^2$ is independently $C_{1-6}$ alkyl, arylalkyl, heteroarylalkyl, cycloalkylalkyl, heterocycloalkylalkyl, aryl, cycloalkyl, heteroaryl, or heterocycloalkyl, each substituted with 0, 1, 2, 3, 4, 5, or 6 substituents each independently selected from $R^{XX}$, halo, CN, $C_{1-6}$ alkyl, $C_{1-6}$ haloalkyl, $C_{1-6}$ hydroxylalkyl, $C_{1-6}$ cyanoalkyl, $C_{3-6}$ cycloalkyl, —C(O)—($C_{1-4}$ alkyl), —C(O)—NH($C_{1-4}$ alkyl), —C(O)—N($C_{1-4}$ alkyl)$_2$, OH, $C_{1-6}$ alkoxy, $C_{1-6}$ haloalkoxy, and $C_{2-8}$ alkoxyalkoxy; and each $R^{XX}$ is independently selected from arylalkyl, heteroarylalkyl, cycloalkylalkyl, heterocycloalkylalkyl, $C_{2-6}$ alkenyl, $C_{2-6}$ alkynyl, aryl, cycloalkyl, heteroaryl, and heterocycloalkyl, each substituted with 0, 1, 2, 3, 4, or 5 substituents each independently selected from halo, CN, $C_{1-6}$ alkyl, $C_{1-6}$ haloalkyl, $C_{1-6}$ hydroxylalkyl, $C_{1-6}$ cyanoalkyl, $C_{3-6}$ cycloalkyl, —C(O)—($C_{1-4}$ alkyl), —C(O)—NH($C_{1-4}$ alkyl), —C(O)—N($C_{1-4}$ alkyl)$_2$, OH, $C_{1-6}$ alkoxy, $C_{1-6}$ haloalkoxy, and $C_{2-8}$ alkoxyalkoxy.

In some embodiments, each $W^{2a}$ is independently absent, C(O), S(O)$_2$, C(O)O, or C(O)NH; each —$X^{2a}$—$W^2$—$X^2$—$Y^2$—$Z^2$ is independently $C_{1-6}$ alkyl, arylalkyl, heteroarylalkyl, cycloalkylalkyl, heterocycloalkylalkyl, aryl, cycloalkyl, heteroaryl, or heterocycloalkyl, each substituted with 0, 1, 2, 3, 4, 5, or 6 substituents each independently selected from $R^{XX}$, halo, CN, $C_{1-6}$ alkyl, $C_{1-6}$ haloalkyl, $C_{1-6}$ hydroxylalkyl, $C_{1-6}$ cyanoalkyl, $C_{3-6}$ cycloalkyl, —C(O)—($C_{1-4}$ alkyl), —C(O)—NH($C_{1-4}$ alkyl), —C(O)—N($C_{1-4}$ alkyl)$_2$, OH, $C_{1-6}$ alkoxy, $C_{1-6}$ haloalkoxy, and $C_{2-8}$ alkoxyalkoxy; and each $R^{XX}$ is independently selected from arylalkyl, heteroarylalkyl, cycloalkylalkyl, heterocycloalkylalkyl, $C_{2-6}$ alkenyl, $C_{2-6}$ alkynyl, aryl, cycloalkyl, heteroaryl, and heterocycloalkyl, each substituted with 0, 1, 2, 3, 4, or 5 substituents each independently selected from halo, CN, $C_{1-6}$ alkyl, $C_{1-6}$ haloalkyl, $C_{1-6}$ hydroxylalkyl, $C_{1-6}$ cyanoalkyl, $C_{3-6}$ cycloalkyl, —C(O)—($C_{1-4}$ alkyl), —C(O)—NH($C_{1-4}$ alkyl), —C(O)—N($C_{1-4}$ alkyl)$_2$, OH, $C_{1-6}$ alkoxy, $C_{1-6}$ haloalkoxy, and $C_{2-8}$ alkoxyalkoxy.

In some embodiments of —$W^{2a}$—$X^{2a}$—$W^2$—$X^2$—$Y^2$—$Z^2$, each $W^{2a}$ is absent, O, S, NH, N($C_{1-6}$ alkyl), C(O), C(S), C(O)NH, C(O)N($C_{1-6}$ alkyl), —C(S)NH—, —C(S)N($C_{1-6}$ alkyl)-, C(O)O, S(O), S(O)$_2$, S(O)NH, S(O)N($C_{1-6}$ alkyl), S(O)$_2$NH, S(O)$_2$N($C_{1-6}$ alkyl), OC(O)NH, OC(O)N($C_{1-6}$ alkyl), NHC(O)NH, NHC(O)N($C_{1-6}$ alkyl), N($C_{1-6}$ alkyl)C(O)N($C_{1-6}$ alkyl), NHC(S)NH, NHC(S)N($C_{1-6}$ alkyl), N($C_{1-6}$ alkyl)C(S)N($C_{1-6}$ alkyl), NHS(O)$_2$NH, NHS(O)$_2$N($C_{1-6}$ alkyl), or ($C_{1-6}$ alkyl)S(O)$_2$N($C_{1-6}$ alkyl); each of $X^{2a}$, $W^2$, $X^2$, and $Y^2$ is absent; and each $Z^2$ is independently selected from $C_{1-6}$ alkyl, $C_{1-6}$ haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl, and heterocycloalkylalkyl, each substituted with 0, 1, 2, 3, 4 or 5 substituents each independently selected from $R^{ZZ}$, halo, CN, NO$_2$, OR$^a$, SR$^a$, SF$_5$, C(O)R$^b$, C(O)NR$^c$R$^d$, C(O)OR$^a$, OC(O)R$^b$, OC(O)NR$^c$R$^d$, NR$^c$R$^d$, NR$^c$C(O)R$^d$, NR$^c$C(O)OR$^a$, NR$^c$S(O)$_2$R$^b$, NR$^c$S(O)$_2$NR$^c$R$^d$; S(O)R$^b$, S(O)NR$^c$R$^d$, S(O)$_2$R$^b$, and S(O)$_2$NR$^c$R$^d$.

In some embodiments of —$W^{2a}$—$X^{2a}$—$W^2$—$X^2$—$Y^2$—$Z^2$, each $W^{2a}$ is absent, O, S, NH, N($C_{1-6}$ alkyl), C(O), C(S), C(O)NH, C(O)N($C_{1-6}$ alkyl), —C(S)NH—, —C(S)N($C_{1-6}$ alkyl)-, C(O)O, S(O), S(O)$_2$, S(O)NH, S(O)N($C_{1-6}$ alkyl), S(O)$_2$NH, S(O)$_2$N($C_{1-6}$ alkyl), OC(O)NH, OC(O)N($C_{1-6}$ alkyl), NHC(O)NH, NHC(O)N($C_{1-6}$ alkyl), N($C_{1-6}$ alkyl)C(O)N($C_{1-6}$ alkyl), NHC(S)NH, NHC(S)N($C_{1-6}$ alkyl), N($C_{1-6}$ alkyl)C(S)N($C_{1-6}$ alkyl), NHS(O)$_2$NH, NHS(O)$_2$N($C_{1-6}$ alkyl), or ($C_{1-6}$ alkyl)S(O)$_2$N($C_{1-6}$ alkyl); each of $X^{2a}$, $W^2$, $X^2$, and $Y^2$ is absent; and each $Z^2$ is independently selected from $C_{1-6}$ alkyl, $C_{1-6}$ haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl, and heterocycloalkylalkyl, each substituted with 0, 1, 2, or 3 substituents each independently selected from $R^{ZZ}$, halo, CN, NO$_2$, OR$^a$, SR$^a$, SF$_5$, C(O)R$^b$, C(O)NR$^c$R$^d$, C(O)OR$^a$, OC(O)R$^b$, OC(O)NR$^c$R$^d$, NR$^c$R$^d$, NR$^c$C(O)R$^d$, NR$^c$C(O)OR$^a$, NR$^c$S(O)$_2$R$^b$, NR$^c$S(O)$_2$NR$^c$R$^d$; S(O)R$^b$, S(O)NR$^c$R$^d$, S(O)$_2$R$^b$, and S(O)$_2$NR$^c$R$^d$.

In some embodiments of —$W^{2a}$—$X^{2a}$—$W^2$—$X^2$—$Y^2$—$Z^2$, each $W^{2a}$ is absent, O, S, NH, N($C_{1-6}$ alkyl), C(O), C(S), C(O)NH, C(O)N($C_{1-6}$ alkyl), C(O)O, S(O), S(O)$_2$, S(O)$_2$NH, S(O)$_2$N($C_{1-6}$ alkyl), OC(O)NH, OC(O)N($C_{1-6}$ alkyl), NHC(O)NH, NHC(O)N($C_{1-6}$ alkyl), N($C_{1-6}$ alkyl)C(O)N($C_{1-6}$ alkyl), NHS(O)$_2$NH, NHS(O)$_2$N($C_{1-6}$ alkyl), or ($C_{1-6}$ alkyl)S(O)$_2$N($C_{1-6}$ alkyl); each of $X^{2a}$, $W^2$, $X^2$, and $Y^2$ is absent; and each $Z^2$ is independently selected from $C_{1-6}$ alkyl, $C_{1-6}$ haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl, and heterocycloalkylalkyl, each substituted with 0, 1, 2, 3, 4 or 5 substituents each independently selected from $R^{ZZ}$, halo, CN, NO$_2$, OR$^a$, SR$^a$, SF$_5$, C(O)R$^b$, C(O)NR$^c$R$^d$, C(O)OR$^a$, OC(O)R$^b$, OC(O)NR$^c$R$^d$, NR$^c$R$^d$, NR$^c$C(O)R$^d$, NR$^c$C(O)OR$^a$, NR$^c$S(O)$_2$R$^b$, NR$^c$S(O)$_2$NR$^c$R$^d$; S(O)R$^b$, S(O)NR$^c$R$^d$, S(O)$_2$R$^b$, and S(O)$_2$NR$^c$R$^d$.

In some embodiments of —$W^{2a}$—$X^{2a}$—$W^2$—$X^2$—$Y^2$—$Z^2$, each $W^{2a}$ is absent, O, S, NH, N($C_{1-6}$ alkyl), C(O), C(S), C(O)NH, C(O)N($C_{1-6}$ alkyl), C(O)O, S(O), S(O)$_2$, S(O)$_2$NH, S(O)$_2$N($C_{1-6}$ alkyl), OC(O)NH, OC(O)N($C_{1-6}$ alkyl), NHC(O)NH, NHC(O)N($C_{1-6}$ alkyl), N($C_{1-6}$ alkyl)C(O)N($C_{1-6}$ alkyl), NHS(O)$_2$NH, NHS(O)$_2$N($C_{1-6}$ alkyl), or ($C_{1-6}$ alkyl)S(O)$_2$N($C_{1-6}$ alkyl); each of $X^{2a}$, $W^2$, $X^2$, and $Y^2$ is absent; and each $Z^2$ is independently selected from $C_{1-6}$ alkyl, $C_{1-6}$ haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl, and heterocycloalkylalkyl, each substituted with 0, 1, 2, or 3 substituents each independently selected from $R^{ZZ}$, halo, CN, NO$_2$, OR$^a$, SR$^a$, SF$_5$, C(O)R$^b$, C(O)NR$^c$R$^d$, C(O)OR$^a$, OC(O)R$^b$, OC(O)NR$^c$R$^d$, NR$^c$R$^d$, NR$^c$C(O)R$^d$, NR$^c$C(O)OR$^a$, NR$^c$S(O)$_2$R$^b$, NR$^c$S(O)$_2$NR$^c$R$^d$; S(O)R$^b$, S(O)NR$^c$R$^d$, S(O)$_2$R$^b$, and S(O)$_2$NR$^c$R$^d$.

In some embodiments, $Z^1$ and $Z^2$ are each, independently, selected from H, halo, CN, NO$_2$, OH, $C_{1-6}$ alkoxy, $C_{1-6}$ haloalkoxy, amino, $C_{1-6}$ alkylamino, $C_{2-8}$ dialkylamino, $C_{1-6}$ alkyl, $C_{1-6}$ haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl, and heterocycloalkylalkyl, wherein each of the $C_{1-6}$ alkyl, $C_{1-6}$ haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl, and heterocycloalkylalkyl is substituted with 0, 1, 2, 3, 4, 5, 6, 7, or 8 substituents each independently selected from $R^{ZZ}$, halo, CN, NO$_2$, OR$^a$, SR$^a$, SF$_5$, C(O)R$^b$, C(O)NR$^c$R$^d$, C(O)OR$^a$, OC(O)R$^b$, OC(O)NR$^c$R$^d$, NR$^c$R$^d$, NR$^c$C(O)R$^d$, NR$^c$C(O)OR$^a$, NR$^c$S(O)$_2$R$^b$, NR$^c$S(O)$_2$NR$^c$R$^d$; S(O)R$^b$, S(O)NR$^c$R$^d$, S(O)$_2$R$^b$, and S(O)$_2$NR$^c$R$^d$.

In some embodiments, one or more —W$^{2a}$—X$^{2a}$—W$^2$—X$^2$—Y$^2$—Z$^2$ are oxo.

In some embodiments, the present invention provides compounds of Formula XI:

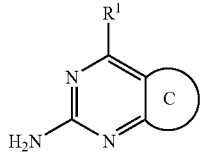

XI or pharmaceutically acceptable salts thereof or N-oxide thereofs or quaternary ammonium salts thereof, wherein:

ring C is an aryl or a 5- or 6-membered heteroaryl group fused to the pyrimidine ring, wherein each of the ring-forming atoms of the 5- or 6-membered heteroaryl group is independently selected from C, N, O, and S, and wherein ring C is substituted with —C(O)NR$^9$R$^{10}$ and with 0, 1, 2, or 3 R$^8$;

R$^1$ is NR$^2$R$^3$, wherein R$^2$ and R$^3$ together with the N atom to which they are attached form a 4-10 membered heterocycloalkyl group wherein each of the ring-forming atoms of the 4-10 membered heterocycloalkyl group is independently selected from C, N, O, and S, and wherein the 4-10 membered heterocycloalkyl group is substituted with 0, 1, 2, 3, 4, 5, 6, 7, or 8 R$^4$;

each R$^4$ is independently selected from halo, CN, C$_{1-6}$ alkyl, C$_{1-6}$ haloalkyl, C$_{3-7}$ cycloalkyl, OH, oxo, C$_{1-6}$ alkoxy, C$_{1-6}$ haloalkoxy, NH$_2$, NH(C$_{1-4}$ alkyl), NH(C$_{3-7}$cycloalkyl), and N(C$_{1-4}$ alkyl)$_2$, wherein each of the C$_{1-6}$ alkyl and C$_{3-7}$ cycloalkyl is substituted with 0, 1, 2, or 3 substituents each independently selected from halo, OH, CN, NH$_2$, NH(C$_{1-4}$ alkyl), and N(C$_{1-4}$ alkyl)$_2$;

each R$^8$ is independently selected from selected from halo, CN, NO$_2$, OR$^{a4}$, SR$^{a4}$, SF$_5$, C(O)R$^{b4}$, C(O)NR$^{c4}$R$^{d4}$, C(O)OR$^{a4}$, OC(O)R$^{b4}$, OC(O)NR$^{c4}$R$^{d4}$, NR$^{c4}$R$^{d4}$, NR$^{c4}$C(O)R$^{b4}$, NR$^{c4}$C(O)NR$^{c4}$R$^{d4}$, NR$^{c4}$C(O)OR$^{a4}$, C(=NR$^{g4}$)NR$^{c4}$R$^{d4}$, NR$^{c4}$C(=NR$^{g4}$)NR$^{c4}$R$^{d4}$, NR$^{c4}$S(O)$_2$NR$^{c4}$R$^{d4}$, S(O)R$^{b4}$, S(O)NR$^{c4}$R$^{d4}$, S(O)$_2$R$^{b4}$, NR$^{c4}$S(O)$_2$R$^{b4}$, S(O)$_2$NR$^{c4}$R$^{d4}$, C$_{1-6}$ alkyl, C$_{1-6}$ haloalkyl, C$_{2-6}$ alkenyl, C$_{2-6}$ alkynyl, aryl, cycloalkyl, heteroaryl, heterocycloalkyl, arylalkyl, heteroarylalkyl, cycloalkylalkyl, and heterocycloalkylalkyl, wherein each of the C$_{1-6}$ alkyl, C$_{1-6}$ haloalkyl, C$_{2-6}$ alkenyl, C$_{2-6}$ alkynyl, aryl, cycloalkyl, heteroaryl, heterocycloalkyl, arylalkyl, heteroarylalkyl, cycloalkylalkyl, and heterocycloalkylalkyl is substituted with 0, 1, 2, 3, 4, or 5 substituents each independently selected from R$^{8a}$, halo, CN, NO$_2$, oxo, OR$^{a4}$, SR$^{a4}$, SF$_5$, C(O)R$^{b4}$, C(O)NR$^{c4}$R$^{d4}$, C(O)OR$^{a4}$, OC(O)R$^{b4}$, OC(O)NR$^{c4}$R$^{d4}$, NR$^{c4}$R$^{d4}$, NR$^{c4}$C(O)R$^{b4}$, NR$^{c4}$C(O)OR$^{a4}$, NR$^{c4}$S(O)$_2$R$^{b4}$, NR$^{c4}$S(O)$_2$NR$^{c4}$R$^{d4}$, S(O)R$^{b4}$, S(O)NR$^{c4}$R$^{d4}$, S(O)$_2$R$^{b4}$, and S(O)$_2$NR$^{c4}$R$^{d4}$;

R$^9$ and R$^{10}$ are each, independently, selected from H, C$_{1-6}$ alkyl, C$_{1-6}$ haloalkyl, arylalkyl, heteroarylalkyl, cycloalkylalkyl, heterocycloalkylalkyl, C$_{2-6}$ alkenyl, C$_{2-6}$ alkynyl, aryl, heteroaryl, cycloalkyl, heterocycloalkyl, arylalkyl, heteroarylalkyl, cycloalkylalkyl and heterocycloalkylalkyl, wherein each of the C$_{1-6}$ alkyl, C$_{1-6}$ haloalkyl, arylalkyl, heteroarylalkyl, cycloalkylalkyl, heterocycloalkylalkyl, C$_{2-6}$ alkenyl, C$_{2-6}$ alkynyl, aryl, heteroaryl, cycloalkyl, heterocycloalkyl, arylalkyl, heteroarylalkyl, cycloalkylalkyl and heterocycloalkylalkyl is substituted with 0, 1, 2, 3, 4, or 5 substituents independently selected from R$^{10a}$, halo, CN, NO$_2$, oxo, OR$^{a5}$, SR$^{a5}$, C(O)R$^{b5}$, C(O)NR$^{c5}$R$^{d5}$, C(O)OR$^{a5}$, OC(O)R$^{b5}$, OC(O)NR$^{c5}$R$^{d5}$, NR$^{c5}$R$^{d5}$, NR$^{c5}$C(O)R$^{b5}$, NR$^{c5}$C(O)NR$^{c5}$R$^{d5}$, NR$^{c5}$C(O)OR$^{a5}$, C(=NR$^{g5}$)NR$^{c5}$R$^{d5}$, NR$^{c5}$C(=NR$^{g5}$)NR$^{c5}$R$^{d5}$, NR$^{c5}$S(O)$_2$NR$^{c5}$R$^{d5}$, S(O)R$^{b5}$, S(O)NR$^{c5}$R$^{d5}$, S(O)$_2$R$^{b5}$, NR$^{c5}$S(O)$_2$R$^{b5}$, and S(O)$_2$NR$^{c5}$R$^{d5}$;

or R$^9$ and R$^{10}$ together with the N atom to which they are attached form a 4-14 membered heterocycloalkyl group that is substituted with 0, 1, 2, 3, 4, or 5 substituents independently selected from R$^{10a}$, halo, CN, NO$_2$, oxo, OR$^{a5}$, SR$^{a5}$, C(O)R$^{b5}$, C(O)NR$^{c5}$R$^{d5}$, C(O)OR$^{a5}$, OC(O)R$^{b5}$, OC(O)NR$^{c5}$R$^{d5}$, NR$^{c5}$R$^{d5}$, NR$^{c5}$C(O)R$^{b5}$, NR$^{c5}$C(O)NR$^{c5}$R$^{d5}$, NR$^{c5}$C(O)OR$^{a5}$, C(=NR$^{g5}$)NR$^{c5}$R$^{d5}$, N$^{c5}$C(=NR$^{g5}$)NR$^{c5}$R$^{d5}$, NR$^{c5}$S(O)$_2$NR$^{c5}$R$^{d5}$, S(O)R$^{b5}$, S(O)NR$^{c5}$R$^{d5}$, S(O)$_2$R$^{b5}$, NR$^{c5}$S(O)$_2$R$^{b5}$, and S(O)$_2$NR$^{c5}$R$^{d5}$;

each R$^{8a}$ is independently selected from C$_{1-6}$ alkyl, C$_{1-6}$ haloalkyl, arylalkyl, heteroarylalkyl, cycloalkylalkyl, heterocycloalkylalkyl, C$_{2-6}$ alkenyl, C$_{2-6}$ alkynyl, aryl, cycloalkyl, heteroaryl, and heterocycloalkyl, each substituted with 0, 1, 2, 3, 4, or 5 substituents each independently selected from C$_{1-6}$ alkyl, C$_{1-6}$ haloalkyl, arylalkyl, heteroarylalkyl, cycloalkylalkyl, heterocycloalkylalkyl, C$_{2-6}$ alkenyl, C$_{2-6}$ alkynyl, aryl, cycloalkyl, heteroaryl, heterocycloalkyl, halo, CN, NO$_2$, oxo, OR$^{a4}$, SR$^{a4}$, SF$_5$, C(O)R$^{b4}$, C(O)NR$^{c4}$R$^{d4}$, C(O)OR$^{a4}$, OC(O)R$^{b4}$, OC(O)NR$^{c4}$R$^{d4}$, NR$^{c4}$R$^{d4}$, NR$^{c4}$C(O)R$^{b4}$, NR$^{c4}$C(O)NR$^{c4}$R$^{d4}$, NR$^{c4}$C(O)OR$^{a4}$, C(=NR$^{g4}$)NR$^{c4}$R$^{d4}$, NR$^{c4}$C(=NR$^{g4}$)NR$^{c4}$R$^{d4}$, NR$^{c4}$S(O)$_2$NR$^{c4}$R$^{d4}$, S(O)R$^{b4}$, S(O)NR$^{c4}$R$^{d4}$, S(O)$_2$R$^{b4}$, NR$^{c4}$S(O)$_2$R$^{b4}$, and S(O)$_2$NR$^{c4}$R$^{d4}$;

each R$^{10a}$ is independently selected from C$_{1-6}$ alkyl, C$_{1-6}$ haloalkyl, arylalkyl, heteroarylalkyl, cycloalkylalkyl, heterocycloalkylalkyl, C$_{2-6}$ alkenyl, C$_{2-6}$ alkynyl, aryl, cycloalkyl, heteroaryl, and heterocycloalkyl, each substituted with 0, 1, 2, 3, 4, or 5 substituents each independently selected from C$_{1-6}$ alkyl, C$_{1-6}$ haloalkyl, arylalkyl, heteroarylalkyl, cycloalkylalkyl, heterocycloalkylalkyl, C$_{2-6}$ alkenyl, C$_{2-6}$ alkynyl, aryl, cycloalkyl, heteroaryl, heterocycloalkyl, halo, CN, NO$_2$, oxo, OR$^{a5}$, SR$^{a5}$, SF$_5$, C(O)R$^{b5}$, C(O)NR$^{c5}$R$^{d5}$, C(O)OR$^{a5}$, OC(O)R$^{b5}$, OC(O)NR$^{c5}$R$^{d5}$, NR$^{c5}$R$^{d5}$, NR$^{c5}$C(O)R$^{b5}$, NR$^{c5}$C(O)NR$^{c5}$R$^{d5}$, NR$^{c5}$C(O)OR$^{a5}$, C(=NR$^{g5}$)NR$^{c5}$R$^{d5}$, NR$^{c5}$C(=NR$^{g5}$)NR$^{c5}$R$^{d5}$, NR$^{c5}$S(O)$_2$NR$^{c5}$R$^{d5}$, S(O)R$^{b5}$, S(O)NR$^{c5}$R$^{d5}$, S(O)$_2$R$^{b5}$, NR$^{c5}$S(O)$_2$R$^{b5}$, and S(O)$_2$NR$^{c5}$R$^{d5}$;

R$^{a4}$ and R$^{a5}$ are each, independently, selected from H, C$_{1-6}$ alkyl, C$_{1-6}$ haloalkyl, arylalkyl, heteroarylalkyl, cycloalkylalkyl, heterocycloalkylalkyl, C$_{2-6}$ alkenyl, C$_{2-6}$ alkynyl, aryl, cycloalkyl, heteroaryl and heterocycloalkyl, wherein each of the C$_{1-6}$ alkyl, C$_{1-6}$ haloalkyl, arylalkyl, heteroarylalkyl, cycloalkylalkyl, heterocycloalkylalkyl, C$_{2-6}$ alkenyl, C$_{2-6}$ alkynyl, aryl, cycloalkyl, heteroaryl and heterocycloalkyl is substituted with 0, 1, 2, 3, 4, or 5 substituents each independently selected from OH, CN, amino, C$_{1-6}$ alkylamino, C$_{2-8}$ dialkylamino, halo, C$_{1-6}$ alkyl, C$_{1-6}$ haloalkyl, C$_{1-6}$ hydroxylalkyl, C$_{1-6}$ cyanoalkyl, C$_{1-6}$ alkoxy, C$_{1-6}$haloalkoxy, C$_{2-8}$ alkoxyalkoxy, aryl, arylalkyl, heteroaryl, heteroarylalkyl, cycloalkyl, and heterocycloalkyl;

R$^{b4}$ and R$^{b5}$ are each, independently, selected from H, C$_{1-6}$ alkyl, C$_{1-6}$ haloalkyl, arylalkyl, heteroarylalkyl, cycloalkylalkyl, heterocycloalkylalkyl, C$_{2-6}$ alkenyl, C$_{2-6}$ alkynyl, aryl, cycloalkyl, heteroaryl, heterocycloalkyl, arylalkyl, heteroarylalkyl, cycloalkylalkyl and heterocycloalkylalkyl, wherein each of the C$_{1-6}$ alkyl, C$_{1-6}$ haloalkyl, arylalkyl, heteroarylalkyl, cycloalkylalkyl, heterocycloalkylalkyl, C$_{2-6}$ alkenyl, C$_{2-6}$ alkynyl, aryl, cycloalkyl, heteroaryl, heterocycloalkyl, arylalkyl, heteroarylalkyl, cycloalkylalkyl and heterocycloalkylalkyl is substituted with 0, 1, 2, 3, 4, or 5 substituents each independently selected from OH, CN, amino, $C_{1-6}$ alkylamino, $C_{2-8}$ dialkylamino, halo, $C_{1-6}$ alkyl, $C_{1-6}$ haloalkyl, $C_{1-6}$ hydroxylalkyl, $C_{1-6}$ cyanoalkyl, $C_{1-6}$ alkoxy, $C_{1-6}$ haloalkoxy, $C_{2-8}$ alkoxyalkoxy, aryl, arylalkyl, heteroaryl, heteroarylalkyl, cycloalkyl, and heterocycloalkyl;

$R^{c4}$ and $R^{d4}$ are independently selected from H, $C_{1-6}$ alkyl, $C_{1-6}$ haloalkyl, arylalkyl, heteroarylalkyl, cycloalkylalkyl, heterocycloalkylalkyl, $C_{2-6}$ alkenyl, $C_{2-6}$ alkynyl, aryl, heteroaryl, cycloalkyl, heterocycloalkyl, arylalkyl, heteroarylalkyl, cycloalkylalkyl and heterocycloalkylalkyl, wherein each of the $C_{1-6}$ alkyl, $C_{1-6}$ haloalkyl, arylalkyl, heteroarylalkyl, cycloalkylalkyl, heterocycloalkylalkyl, $C_{2-6}$ alkenyl, $C_{2-6}$ alkynyl, aryl, heteroaryl, cycloalkyl, heterocycloalkyl, arylalkyl, heteroarylalkyl, cycloalkylalkyl and heterocycloalkylalkyl is substituted with 0, 1, 2, 3, 4, or 5 substituents each independently selected from OH, amino, $C_{1-6}$ alkylamino, $C_{2-8}$ dialkylamino, halo, CN, $C_{1-6}$ alkyl, $C_{1-6}$ haloalkyl, $C_{1-6}$ hydroxylalkyl, $C_{1-6}$ cyanoalkyl, $C_{1-6}$ alkoxy, $C_{1-6}$ haloalkoxy, $C_{2-8}$ alkoxyalkoxy, aryl, arylalkyl, heteroaryl, heteroarylalkyl, cycloalkyl, and heterocycloalkyl;

or $R^{c4}$ and $R^{d4}$ together with the N atom to which they are attached form a 4-, 5-, 6- or 7-membered heterocycloalkyl group that is substituted with 0, 1, 2, 3, 4, or 5 substituents each independently selected from OH, amino, $C_{1-6}$ alkylamino, $C_{2-8}$ dialkylamino, halo, CN, $C_{1-6}$ alkyl, $C_{1-6}$ haloalkyl, $C_{1-6}$ hydroxylalkyl, $C_{1-6}$ cyanoalkyl, $C_{1-6}$ alkoxy, $C_{1-6}$ haloalkoxy, $C_{2-8}$ alkoxyalkoxy, aryl, arylalkyl, heteroaryl, heteroarylalkyl, cycloalkyl, and heterocycloalkyl;

$R^{c5}$ and $R^{d5}$ are independently selected from H, $C_{1-6}$ alkyl, $C_{1-6}$ haloalkyl, arylalkyl, heteroarylalkyl, cycloalkylalkyl, heterocycloalkylalkyl, $C_{2-6}$ alkenyl, $C_{2-6}$ alkynyl, aryl, heteroaryl, cycloalkyl, heterocycloalkyl, arylalkyl, heteroarylalkyl, cycloalkylalkyl and heterocycloalkylalkyl, wherein each of the $C_{1-6}$ alkyl, $C_{1-6}$ haloalkyl, arylalkyl, heteroarylalkyl, cycloalkylalkyl, heterocycloalkylalkyl, $C_{2-6}$ alkenyl, $C_{2-6}$ alkynyl, aryl, heteroaryl, cycloalkyl, heterocycloalkyl, arylalkyl, heteroarylalkyl, cycloalkylalkyl and heterocycloalkylalkyl is substituted with 0, 1, 2, 3, 4, or 5 substituents each independently selected from OH, amino, $C_{1-6}$ alkylamino, $C_{2-8}$ dialkylamino, halo, CN, $C_{1-6}$ alkyl, $C_{1-6}$ haloalkyl, $C_{1-6}$ hydroxylalkyl, $C_{1-6}$ cyanoalkyl, $C_{1-6}$ alkoxy, $C_{1-6}$ haloalkoxy, $C_{2-8}$ alkoxyalkoxy, aryl, arylalkyl, heteroaryl, heteroarylalkyl, cycloalkyl, and heterocycloalkyl;

or $R^{c5}$ and $R^{d5}$ together with the N atom to which they are attached form a 4-, 5-, 6- or 7-membered heterocycloalkyl group that is substituted with 0, 1, 2, 3, 4, or 5 substituents each independently selected from OH, amino, $C_{1-6}$ alkylamino, $C_{2-8}$ dialkylamino, halo, CN, $C_{1-6}$ alkyl, $C_{1-6}$ haloalkyl, $C_{1-6}$ hydroxylalkyl, $C_{1-6}$ cyanoalkyl, $C_{1-6}$ alkoxy, $C_{1-6}$ haloalkoxy, $C_{2-8}$ alkoxyalkoxy, aryl, arylalkyl, heteroaryl, heteroarylalkyl, cycloalkyl, and heterocycloalkyl;

$R^{e4}$ and $R^{e5}$ are each, independently, selected from H, $C_{1-6}$ alkyl, $C_{1-6}$ haloalkyl, arylalkyl, heteroarylalkyl, cycloalkylalkyl, heterocycloalkylalkyl, $C_{2-6}$ alkenyl, $C_{2-6}$ alkynyl, aryl, heteroaryl, cycloalkyl, heterocycloalkyl, arylalkyl, heteroarylalkyl, cycloalkylalkyl and heterocycloalkylalkyl, wherein each of the $C_{1-6}$ alkyl, $C_{1-6}$ haloalkyl, arylalkyl, heteroarylalkyl, cycloalkylalkyl, heterocycloalkylalkyl, $C_{2-6}$ alkenyl, $C_{2-6}$ alkynyl, aryl, heteroaryl, cycloalkyl, heterocycloalkyl, arylalkyl, heteroarylalkyl, cycloalkylalkyl and heterocycloalkylalkyl is substituted with 0, 1, 2, 3, 4, or 5 substituents each independently selected from OH, amino, $C_{1-6}$ alkylamino, $C_{2-8}$ dialkylamino, halo, CN, $C_{1-6}$ alkyl, $C_{1-6}$ haloalkyl, $C_{1-6}$ hydroxylalkyl, $C_{1-6}$ cyanoalkyl, $C_{1-6}$ alkoxy, $C_{1-6}$ haloalkoxy, $C_{2-8}$ alkoxyalkoxy, aryl, arylalkyl, heteroaryl, heteroarylalkyl, cycloalkyl, and heterocycloalkyl;

$R^{g4}$ and $R^{g5}$ are each, independently, selected from H, CN, and $NO_2$;

each p1 is, independently, 0, 1, or 2;

each p2 is, independently, 0, 1, or 2;

each p3 is, independently, 0, 1, or 2;

each p4 is, independently, 0, 1, or 2;

each q1 is, independently, 1 or 2; and each q2 is, independently, 1 or 2.

In some embodiments of the compounds of Formula XI, the ring formed by $R^2$ and $R^3$ together with the N atom to which they are attached is a 4-10 membered heterocycloalkyl group substituted with 0, 1, 2, 3, 4, or 5 $R^4$, and wherein each of the ring-forming atoms of the 4-10 membered heterocycloalkyl group is C, O, or N. In some further embodiments, the 4-10 membered heterocycloalkyl group is mono- or bicyclic. In some further embodiments, the 4-10 membered heterocycloalkyl group is saturated [i.e., it does not have any unsaturated ring bond (i.e. no double or triple bond as a ring bond for the 4-10 membered heterocycloalkyl group)].

In some embodiments of the compounds of Formula XI, the ring formed by $R^2$ and $R^3$ together with the N atom to which they are attached is selected from:

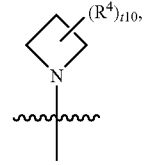

(Q1)

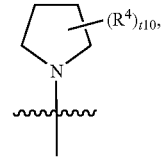

(Q2)

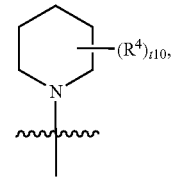

(Q3)

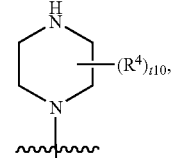

(Q4)

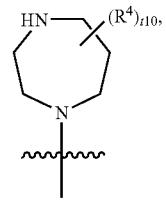

(Q5)

-continued

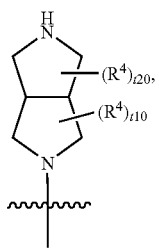
(Q6)

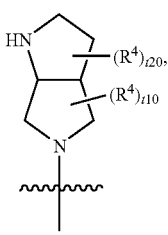
(Q7)

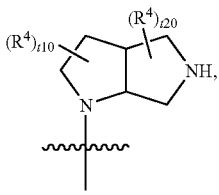
(Q8)

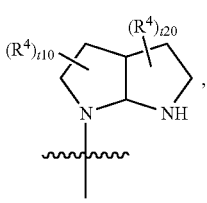
(Q9)

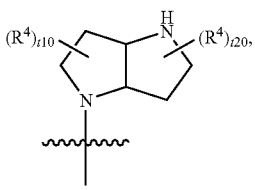
(Q10)

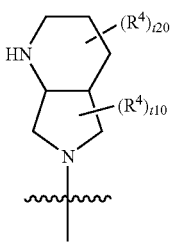
(Q11)

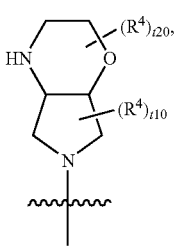
(Q12)

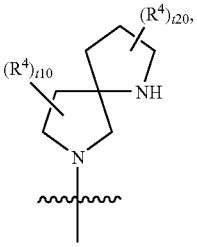
(Q13)

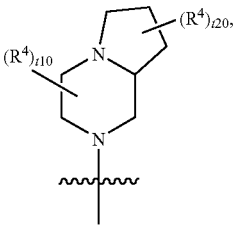
(Q14)

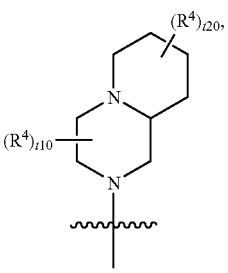
(Q15)

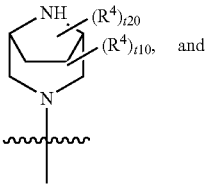
(Q16) and

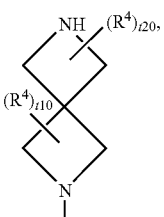
(Q17)

wherein t10 and t20 are each, independently, 0, 1, or 2. In some further embodiments, each $R^4$ is independently selected from $C_{1-6}$ alkyl, $C_{3-7}$ cycloalkyl, $NH_2$, $NH(C_{1-4}$ alkyl), $NH(C_{3-7}$ cycloalkyl), and $N(C_{1-4}$ alkyl)$_2$, wherein each of $C_{1-6}$ alkyl and $C_{3-7}$ cycloalkyl is substituted with 0 or 1 substituents from $NH_2$, $NH(C_{1-4}$ alkyl), and $N(C_{1-4}$ alkyl)$_2$. In some further embodiments, each $R^4$ is independently selected from $C_{1-6}$ alkyl, $C_{3-7}$ cycloalkyl, $NH_2$, $NH(C_{1-4}$ alkyl), $NH(C_{3-7}$ cycloalkyl), and $N(C_{1-4}$ alkyl)$_2$, wherein the $C_{1-6}$ alkyl is substituted with 0 or 1 substituent selected from $NH_2$, $NH(C_{1-4}$ alkyl), and $N(C_{1-4}$ alkyl)$_2$. In yet further embodiments, each $R^4$ is independently selected from methyl and $NH(CH_3)$.

In some embodiments of the compounds of Formula XI, $R^2$ and $R^3$ together with the N atom to which they are attached form a 4-9 membered heterocycloalkyl group wherein each of the ring-forming atoms of the 4-9 membered heterocycloalkyl group is independently selected from C, N, and O, and wherein the 4-9 membered heterocycloalkyl group is substituted with 0, 1, 2, 3, 4, or 5 $R^4$. In some further embodiments, the 4-9 membered heterocycloalkyl group is substituted with 0, 1, or 2 $R^4$. In yet further embodiments, the 4-9 membered heterocycloalkyl group is substituted with 0 or 1 $R^4$.

In some embodiments of the compounds of Formula XI, the ring formed by $R^2$ and $R^3$ together with the N atom to which they are attached is a pyrrolidine ring, a piperidine ring, or a piperazine ring, each substituted with 0, 1, 2, 3, 4, or 5 $R^4$.

In some embodiments of the compounds of Formula XI, the ring formed by $R^2$ and $R^3$ together with the N atom to which they are attached is a pyrrolidine ring or a piperazine ring, each substituted with 0, 1, 2, 3, 4, or 5 $R^4$. In some further embodiments, the ring formed by $R^2$ and $R^3$ together with the N atom to which they are attached is a pyrrolidine ring or a piperazine ring, each substituted with 0, 1, or 2 $R^4$. In yet further embodiments, the ring formed by $R^2$ and $R^3$ together with the N atom to which they are attached is a pyrrolidine ring or a piperazine ring, each substituted with 0 or 1 $R^4$.

In some embodiments of the compounds of Formula XI, the ring formed by $R^2$ and $R^3$ together with the N atom to which they are attached is a pyrrolidine ring substituted with 0, 1, 2, 3, 4, or 5 $R^4$. In some further embodiments, the ring formed by $R^2$ and $R^3$ together with the N atom to which they are attached is a pyrrolidine ring substituted with 0, 1, or 2 $R^4$. In yet further embodiments, the ring formed by $R^2$ and $R^3$ together with the N atom to which they are attached is a pyrrolidine ring substituted with 0 or 1 $R^4$.

In some embodiments of the compounds of Formula XI, the ring formed by $R^2$ and $R^3$ together with the N atom to which they are attached is a piperazine ring substituted with 0, 1, 2, 3, 4, or 5 $R^4$. In some further embodiments, the ring formed by $R^2$ and $R^3$ together with the N atom to which they are attached is a piperazine ring substituted with 0, 1, or 2 $R^4$. In some further embodiments, the ring formed by $R^2$ and $R^3$ together with the N atom to which they are attached is a piperazine ring substituted with 0 or 1 $R^4$.

In some embodiments of the compounds of Formula XI, the ring formed by $R^2$ and $R^3$ together with the N atom to which they are attached is substituted with 0, 1, 2, or 3 $R^4$; and each $R^4$ is independently selected from $C_{1-6}$ alkyl, $C_{1-6}$ haloalkyl, $C_{3-7}$ cycloalkyl, $NH_2$, $NH(C_{1-4}$ alkyl), $NH(C_{3-7}$ cycloalkyl), and $N(C_{1-4}$ alkyl)$_2$, wherein each of the $C_{1-6}$ alkyl, $C_{3-7}$ cycloalkyl, and $C_{1-6}$ haloalkyl is substituted with 0 or 1 substituent selected from halo, $NH_2$, $NH(C_{1-4}$ alkyl), and $N(C_{1-4}$ alkyl)$_2$.

In some embodiments of the compounds of Formula XI, the ring formed by $R^2$ and $R^3$ together with the N atom to which they are attached is substituted with 0, 1, 2, or 3 $R^4$; and each $R^4$ is independently selected from $C_{1-6}$ alkyl, $C_{1-6}$ haloalkyl, $C_{3-7}$ cycloalkyl, $NH_2$, $NH(C_{1-4}$ alkyl), $NH(C_{3-7}$ cycloalkyl), and $N(C_{1-4}$ alkyl)$_2$, wherein each of the $C_{1-6}$ alkyl and $C_{3-7}$ cycloalkyl is substituted with 0 or 1 substituent selected from halo, $NH_2$, $NH(C_{1-4}$ alkyl), and $N(C_{1-4}$ alkyl)$_2$.

In some embodiments of the compounds of Formula XI, the ring formed by $R^2$ and $R^3$ together with the N atom to which they are attached is substituted with 0, 1, 2, or 3 $R^4$; and each $R^4$ is independently selected from $C_{1-6}$ alkyl, $C_{1-6}$ haloalkyl, $C_{3-7}$ cycloalkyl, $NH_2$, $NH(C_{1-4}$ alkyl), $NH(C_{3-7}$ cycloalkyl), and $N(C_{1-4}$ alkyl)$_2$, wherein each of the $C_{1-6}$ alkyl and $C_{1-6}$ haloalkyl is substituted with 0 or 1 substituent selected from $NH_2$, $NH(C_{1-4}$ alkyl), and $N(C_{1-4}$ alkyl)$_2$.

In some embodiments, each $R^4$ is independently selected from $C_{1-6}$ alkyl, $NH_2$, $NH(C_{1-4}$ alkyl), and $N(C_{1-4}$ alkyl)$_2$, wherein the $C_{1-6}$ alkyl is substituted with 0 or 1 substituent selected from $NH_2$, $NH(C_{1-4}$ alkyl), and $N(C_{1-4}$ alkyl)$_2$.

In some embodiments of the compounds of Formula XI, each $R^4$ is independently selected from $C_{1-6}$ alkyl and $NH(C_{1-4}$ alkyl), wherein the $C_{1-6}$ alkyl is substituted with 0 or 1 $NH(C_{1-4}$ alkyl). In some further embodiments, each $R^4$ is independently selected from methyl and $NH(CH_3)$.

In some embodiments of the compounds of Formula XI, $R^1$ is selected from structures of formulas (A1), (B1), (C1), (D1), and (E1):

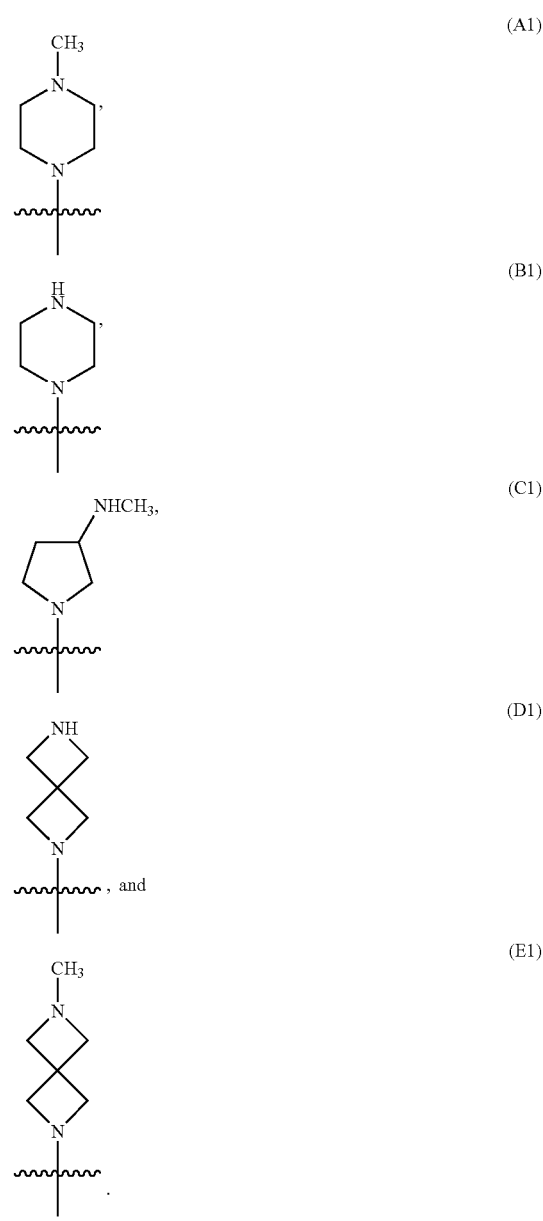

In some embodiments of the compounds of Formula XI, $R^1$ is selected from structures of formulas (A1), (B1), and (C1):

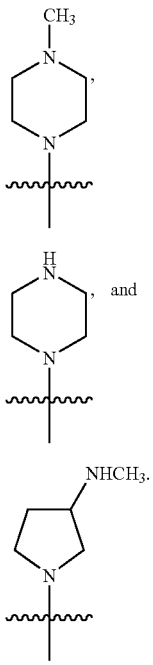

In some embodiments of the compounds of Formula XI, the fused ring C is an aryl group substituted with —C(O)NR$^9$R$^{10}$ and with 0, 1, 2, or 3 R$^8$.

In some embodiments of the compounds of Formula XI, the fused ring C is an aryl group substituted with —C(O)NR$^9$R$^{10}$ and with 0 or 1 R$^8$.

In some embodiments of the compounds of Formula XI, the fused ring C is a phenyl group (i.e. a benzene ring) substituted with —C(O)NR$^9$R$^{10}$ and with 0, 1, 2, or 3 R$^8$.

In some embodiments of the compounds of Formula XI, the fused ring C is a phenyl group substituted with —C(O)NR$^9$R$^{10}$ and with 0, or 1 R$^8$.

In some embodiments of the compounds of Formula XI, the fused ring C is 6-membered heteroaryl group substituted with —C(O)NR$^9$R$^{10}$ and with 0, 1, 2, or 3 R$^8$.

In some embodiments of the compounds of Formula XI, the fused ring C is 6-membered heteroaryl group substituted with —C(O)NR$^9$R$^{10}$ and with 0 or 1 R$^8$. IN some further embodiments, the optionally substituted 6-membered heteroaryl group of ring C is an optionally substituted pyridine ring, an optionally substituted pyrimidine ring, an optionally substituted pyrazine ring, or an optionally substituted 1,2,4-triazine ring. In yet further embodiments, the optionally substituted 6-membered heteroaryl group of ring C is an optionally substituted pyridine ring.

In some embodiments of the compounds of Formula XI, the fused ring C is 5-membered heteroaryl group substituted with —C(O)NR$^9$R$^{10}$ and with 0, 1, 2, or 3 R$^8$. In some further embodiment the fused ring C is 5-membered heteroaryl group substituted with —C(O)NR$^9$R$^{10}$ and with 0 or 1 R$^8$. In some further embodiments, the optionally substituted 5-membered heteroaryl group is an optionally substituted ring selected from a thiophene ring, a furan ring, a thiazole ring, an oxazole ring, an isoxazole ring, a 1H-imidazole ring, a 1H-pyrazole ring, and a 1H-pyrrole ring. In still further embodiments, the optionally substituted 5-membered heteroaryl group is an optionally substituted ring selected from a thiophene ring, a thiazole ring, an oxazole ring, an isoxazole ring, a 1H-imidazole ring, a 1H-pyrazole ring, and a 1H-pyrrole ring.

In some embodiments of the compounds of Formula XI, each R$^8$ is independently selected from halo, CN, C$_{1-6}$ alkyl, C$_{1-6}$ haloalkyl, C$_{3-7}$ cycloalkyl, OR$^{a4}$, SR$^{a4}$, SF$_5$, C(O)R$^{b4}$, C(O)NR$^{c4}$R$^{d4}$, C(O)OR$^{a4}$, OC(O)R$^{b4}$, OC(O)NR$^{c4}$R$^{d4}$, NR$^{c4}$R$^{d4}$, NR$^{c4}$C(O)R$^{d4}$, NR$^{c4}$C(O)OR$^{a4}$, NR$^{c4}$S(O)$_2$R$^{b4}$, NR$^{c4}$S(O)$_2$NR$^{c4}$R$^{d4}$, S(O)R$^{b4}$, S(O)NR$^{c4}$R$^{d4}$, S(O)$_2$R$^{b4}$, and S(O)$_2$NR$^{c4}$R$^{d4}$, wherein each of the C$_{1-6}$ haloalkyl, and C$_{3-7}$ cycloalkyl is substituted with 0, 1, or 2 substituents independently selected from halo, CN, OR$^{a4}$, SR$^{a4}$, C(O)R$^{b4}$, C(O)NR$^{c4}$R$^{d4}$, C(O)OR$^{a4}$, OC(O)R$^{b4}$, OC(O)NR$^{c4}$R$^{d4}$, NR$^{c4}$R$^{d4}$, NR$^{c4}$C(O)R$^{d4}$, NR$^{c4}$C(O)OR$^{a4}$, NR$^{c4}$S(O)$_2$R$^{b4}$, NR$^{c4}$S(O)$_2$NR$^{c4}$R$^{d4}$, S(O)R$^{b4}$, S(O)NR$^{c4}$R$^{d4}$, S(O)$_2$R$^{b4}$, and S(O)$_2$NR$^{c4}$R$^{d4}$.

In some embodiments of the compounds of Formula XI, each R$^8$ is independently selected from halo, CN, C$_{1-6}$ alkyl, C$_{1-6}$ haloalkyl, C$_{1-6}$ hydroxylalkyl, C$_{1-6}$ cyanoalkyl, C$_{3-7}$ cycloalkyl, NH$_2$, NH(C$_{1-4}$ alkyl), N(C$_{1-4}$ alkyl)$_2$, —C(O)—(C$_{1-4}$ alkyl), C(O)NR$^{c4}$R$^{d4}$, OH, C$_{1-6}$ alkoxy, C$_{1-6}$ haloalkoxy, and C$_{2-8}$ alkoxyalkoxy, wherein each of the C$_{1-6}$ alkyl, C$_{1-6}$ haloalkyl, and C$_{3-7}$ cycloalkyl is substituted with 0, 1, or 2 substituents independently selected from halo, CN, and C(O)NR$^{c4}$R$^{d4}$.

In some embodiments of the compounds of Formula XI, each R$^8$ is independently selected from halo, CN, C$_{1-4}$ alkyl, C$_{1-4}$ haloalkyl, C$_{1-4}$ hydroxylalkyl, C$_{1-4}$ cyanoalkyl, C$_{3-7}$ cycloalkyl, OH, C$_{1-4}$ alkoxy, and C$_{1-4}$ haloalkoxy.

In some embodiments of the compounds of Formula XI:
R$^9$ is selected from H and C$_{1-6}$ alkyl;
R$^{10}$ is selected from H, C$_{1-6}$ alkyl, C$_{1-6}$ haloalkyl, arylalkyl, heteroarylalkyl, cycloalkylalkyl, heterocycloalkylalkyl, C$_{2-6}$ alkenyl, C$_{2-6}$ alkynyl, aryl, heteroaryl, cycloalkyl, heterocycloalkyl, arylalkyl, heteroarylalkyl, cycloalkylalkyl and heterocycloalkylalkyl, wherein each of the C$_{1-6}$ alkyl, C$_{1-6}$ haloalkyl, arylalkyl, heteroarylalkyl, cycloalkylalkyl, heterocycloalkylalkyl, C$_{2-6}$ alkenyl, C$_{2-6}$ alkynyl, aryl, heteroaryl, cycloalkyl, heterocycloalkyl, arylalkyl, heteroarylalkyl, cycloalkylalkyl and heterocycloalkylalkyl is substituted with 0, 1, 2, 3, 4, or 5 substituents each independently selected from R$^{10a}$, halo, CN, OR$^{a5}$, SR$^{a5}$, C(O)R$^{b5}$, C(O)NR$^{c5}$R$^{d5}$, C(O)OR$^{a5}$, OC(O)R$^{b5}$, OC(O)NR$^{c5}$R$^{d5}$, NR$^{c5}$R$^{d5}$, NR$^{c5}$C(O)R$^{b5}$, NR$^{c5}$C(O)NR$^{c5}$R$^{d5}$, NR$^{c5}$C(O)OR$^{a5}$, C(=NR$^{g5}$)NR$^{c5}$R$^{d5}$, NR$^{c5}$C(=NR$^{g5}$)NR$^{c5}$R$^{d5}$, NR$^{c5}$S(O)$_2$NR$^{c5}$R$^{d5}$, S(O)R$^{b5}$, S(O)NR$^{c5}$R$^{d5}$, S(O)$_2$R$^{b5}$, NR$^{c5}$S(O)$_2$R$^{b5}$, and S(O)$_2$NR$^{c5}$R$^{d5}$; and In some embodiments of the compounds of Formula XI:
R$^9$ is selected from H and C$_{1-6}$ alkyl; and
R$^{10}$ is selected from C$_{1-6}$ alkyl, arylalkyl, heteroarylalkyl, cycloalkylalkyl, heterocycloalkylalkyl, C$_{2-6}$ alkenyl, C$_{2-6}$ alkynyl, aryl, heteroaryl, cycloalkyl, heterocycloalkyl, arylalkyl, heteroarylalkyl, cycloalkylalkyl and heterocycloalkylalkyl, each substituted with 0, 1, 2, 3, 4, or 5 substituents each independently selected from R$^{10a}$, halo, CN, OR$^{a5}$, C(O)R$^{b5}$, C(O)NR$^{c5}$R$^{d5}$, C(O)OR$^{a5}$, OC(O)R$^{b5}$, OC(O)NR$^{c5}$R$^{d5}$, NR$^{c5}$R$^{d5}$, NR$^{c5}$C(O)R$^{b5}$, NR$^{c5}$C(O)NR$^{c5}$R$^{d5}$, NR$^{c5}$C(O)OR$^{a5}$, C(=NR$^{g5}$)NR$^{c5}$R$^{d5}$, NR$^{c5}$C(=NR$^{g5}$)NR$^{c5}$R$^{d5}$, NR$^{c5}$S(O)$_2$NR$^{c5}$R$^{d5}$, S(O)R$^{b5}$, S(O)NR$^{c5}$R$^{d5}$, S(O)$_2$R$^{b5}$, NR$^{c5}$S(O)$_2$R$^{b5}$, and S(O)$_2$N$^{c5}$R$^{d5}$.

In some embodiments of the compounds of Formula XI:
R$^9$ is selected from H and C$_{1-6}$ alkyl; and
R$^{10}$ is selected from C$_{1-6}$ alkyl substituted with 0, 1, 2, 3, 4, or 5 substituents each independently selected from R$^{10a}$, halo, CN, OR$^{a5}$, SR$^{a5}$, C(O)R$^{b5}$, C(O)NR$^{c5}$R$^{d5}$, C(O)OR$^{a5}$, OC(O)R$^{b5}$, OC(O)NR$^{c5}$R$^{d5}$, NR$^{c5}$R$^{d5}$, NR$^{c5}$C(O)R$^{b5}$, NR$^{c5}$C(O)NR$^{c5}$R$^{d5}$, NR$^{c5}$C(O)OR$^{a5}$, C(=NR$^{g5}$)NR$^{c5}$R$^{d5}$, NR$^{c5}$C(=NR$^{g5}$)NR$^{c5}$R$^{d5}$, NR$^{c5}$S(O)$_2$NR$^{c5}$R$^{d5}$, S(O)R$^{b5}$, S(O)NR$^{c5}$R$^{d5}$, S(O)$_2$R$^{b5}$, NR$^{c5}$S(O)$_2$R$^{b5}$, and S(O)$_2$NR$^{c5}$R$^{d5}$.

In some embodiments of the compounds of Formula XI:
$R^9$ is selected from H and $C_{1-6}$ alkyl; and
$R^{10}$ is selected from $C_{1-6}$ alkyl substituted with 0, 1, 2, or 3 substituents each independently selected from halo, CN, $OR^{a5}$, $SR^{a5}$, $C(O)R^{b5}$, $C(O)NR^{c5}R^{d5}$, $C(O)OR^{a5}$, $OC(O)R^{b5}$, $OC(O)NR^{c5}R^{d5}$, $NR^{c5}R^{d5}$, $NR^{c5}C(O)R^{b5}$, $NR^{c5}C(O)NR^{c5}R^{d5}$, $NR^{c5}C(O)OR^{a5}$, $C(=NR^{g5})NR^{c5}R^{d5}$, $NR^{c5}C(=NR^{g5})NR^{c5}R^{d5}$, $NR^{c5}S(O)_2NR^{c5}R^{d5}$, $S(O)R^{b5}$, $S(O)NR^{c5}R^{d5}$, $S(O)_2R^{b5}$, $NR^{c5}S(O)_2R^{b5}$, and $S(O)_2NR^{c5}R^{d5}$.

In some embodiments of the compounds of Formula XI:
$R^9$ is selected from H and $C_{1-6}$ alkyl; and
$R^{10}$ is selected from $C_{1-6}$ alkyl.

In some embodiments of the compounds of Formula XI:
$R^9$ is selected from H and $C_{1-6}$ alkyl; and
$R^{10}$ is selected from arylalkyl, heteroarylalkyl, cycloalkylalkyl, and heterocycloalkylalkyl, each substituted with 0, 1, 2, 3, 4, or 5 substituents each independently selected from le$^a$, halo, CN, $OR^{a5}$, $SR^{a5}$, $C(O)R^{b5}$, $C(O)NR^{c5}R^{d5}$, $C(O)OR^{a5}$, $OC(O)R^{b5}$, $OC(O)NR^{c5}R^{d5}$, $NR^{c5}R^{d5}$, $NR^{c5}C(O)R^{b5}$, $NR^{c5}C(O)NR^{c5}R^{d5}$, $NR^{c5}C(O)OR^{a5}$, $C(=NR^{g5})NR^{c5}R^{d5}$, $NR^{c5}C(=NR^{g5})NR^{c5}R^{d5}$, $NR^{c5}S(O)_2NR^{c5}R^{d5}$, $S(O)R^{b5}$, $S(O)NR^{c5}R^{d5}$, $S(O)_2R^{b5}$, $NR^{c5}S(O)_2R^{b5}$, and $S(O)_2NR^{c5}R^{d5}$.

In some embodiments of the compounds of Formula XI:
$R^9$ is selected from H and $C_{1-6}$ alkyl; and
$R^{10}$ is selected from arylalkyl and cycloalkylalkyl, each substituted with 0, 1, 2, 3, 4, or 5 substituents each independently selected from $R^{10a}$, halo, CN, $OR^{a5}$, $SR^{a5}$, $C(O)R^{b5}$, $C(O)NR^{c5}R^{d5}$, $C(O)OR^{a5}$, $OC(O)R^{b5}$, $OC(O)NR^{c5}R^{d5}$, $NR^{c5}R^{d5}$, $NR^{c5}C(O)R^{b5}$, $NR^{c5}C(O)NR^{c5}R^{d5}$, $NR^{c5}C(O)OR^{a5}$, $C(=NR^{g5})NR^{c5}R^{d5}$, $NR^{c5}C(=NR^{g5})NR^{c5}R^{d5}$, $NR^{c5}S(O)_2NR^{c5}R^{d5}$, $S(O)^{b5}$, $S(O)NR^{c5}R^{d5}$, $S(O)_2R^{b5}$, $NR^{c5}S(O)_2R^{b5}$, and $S(O)_2NR^{c5}R^{d5}$.

In some embodiments of the compounds of Formula XI:
$R^9$ is H; and
$R^{10}$ is —$(CR^{10b}R^{10c})_{p33}R^{10d}$;
$R^{10b}$ and $R^{10c}$ are each, independently, H or $C_{1-3}$ alkyl;
$R^{10d}$ is aryl or cycloalkyl, each substituted with 0, 1, 2, 3, 4, or 5 substituents each independently selected from $R^{10a}$, halo, CN, $OR^{a5}$, $SR^{a5}$, $C(O)R^{b5}$, $C(O)NR^{c5}R^{d5}$, $C(O)OR^{a5}$, $OC(O)R^{b5}$, $OC(O)NR^{c5}R^{d5}$, $NR^{c5}R^{d5}$, $NR^{c5}C(O)R^{b5}$, $NR^{c5}C(O)NR^{c5}R^{d5}$, $NR^{c5}C(O)OR^{a5}$, $C(=NR^{g5})NR^{c5}R^{d5}$, $NR^{c5}C(=NR^{g5})NR^{c5}R^{d5}$, $NR^{c5}S(O)_2NR^{c5}R^{d5}$, $S(O)R^{b5}$, $S(O)NR^{c5}R^{d5}$, $S(O)_2R^{b5}$, $NR^{c5}S(O)_2R^{b5}$, and $S(O)_2NR^{c5}R^{d5}$; and
p33 is 0, 1, 2, 3, or 4.

In some embodiments of the compounds of Formula XI:
$R^9$ is H; and
$R^{10}$ is —$(CR^{10b}R^{10c})_{p33}R^{10d}$;
$R^{10b}$ and $R^{10c}$ are each, independently, H or methyl;
$R^{10d}$ is aryl or cycloalkyl, each substituted with 0, 1, 2, 3, 4, or 5 substituents each independently selected from $R^{10a}$, halo, CN, $OR^{a5}$, $SR^{a5}$, $C(O)R^{b5}$, $C(O)NR^{c5}R^{d5}$, $C(O)OR^{a5}$, $OC(O)R^{b5}$, $OC(O)NR^{c5}R^{d5}$, $NR^{c5}R^{d5}$, $NR^{c5}C(O)R^{b5}$, $NR^{c5}C(O)NR^{c5}R^{d5}$, $NR^{c5}C(O)OR^{a5}$, $C(=NR^{g5})NR^{c5}R^{d5}$, $NR^{c5}C(=NR^{g5})NR^{c5}R^{d5}$, $NR^{c5}S(O)_2NR^{c5}R^{d5}$, $S(O)R^{b5}$, $S(O)NR^{c5}R^{d5}$, $S(O)_2R^{b5}$, $NR^{c5}S(O)_2R^{b5}$, and $S(O)_2NR^{c5}R^{d5}$; and
p33 is 0, 1, 2, 3, or 4.

In some embodiments of the compounds of Formula XI:
$R^1$ is 4-methyl-piperazin-1-yl;
each $R^8$ is independently selected from halo, CN, $C_{1-4}$ alkyl, $C_{1-4}$ haloalkyl, $C_{1-4}$ hydroxylalkyl, $C_{1-4}$ cyanoalkyl, $C_{3-7}$ cycloalkyl, OH, $C_{1-4}$ alkoxy, and $C_{1-4}$ haloalkoxy;
$R^9$ is H or $C_{1-6}$ alkyl;
$R^{10}$ is —$(CR^{10b}R^{10c})_{p33}R^{10d}$;
$R^{10b}$ and $R^{10c}$ are each, independently, $HC_{1-3}$ alkyl, CN, —$C(O)N(C_{1-4}alkyl)_3$, —$C(O)O(C_{1-4}$ alkyl), Ar, or HetAr;
$R^{10d}$ is aryl or heteroaryl, each substituted with 0, 1, 2, 3, 4, or 5 substituents each independently selected from $C_{1-6}$ alkyl, $C_{1-6}$haloalkyl, Ar, HetAr, halo, CN, —$OR^a$, —$OC(O)NR^cR^d$, —$C(O)OR^a$, —$C(O)R^b$, —$C(O)NR^cR^d$, —O—Ar, —O-HetAr, —O-$L^d$-Ar, and —O-$L^d$-HetAr;
$L^d$ is selected from $C_{1-4}$ alkylenyl and —C(O)NH—, wherein the $C_{1-4}$ alkylenyl is substituted with 0, 1, 2, 3, 4, 5, 6, 7, or 8 substituents each independently selected from $C_{1-4}$ alkyl, $C_{1-4}$haloalkyl, halo, and CN;
each Ar is independently aryl substituted with 0, 1, 2, 3, 4, or 5 substituents each independently selected from halo, CN, $C_{1-6}$ alkyl, $C_{1-6}$ haloalkyl, $C_{2-8}$ alkoxyalkyl, $C_{1-6}$ alkoxy, $C_{1-6}$ haloalkoxy, and $C(O)OR^a$, and
each HetAr is independently heteroaryl substituted with 0, 1, 2, 3, 4, or 5 substituents each independently selected from halo, CN, $C_{1-6}$ alkyl, $C_{1-6}$ haloalkyl, $C_{2-8}$ alkoxyalkyl, $C_{1-6}$ alkoxy, $C_{1-6}$ haloalkoxy, and $C(O)OR^a$; and
p33 is 0, 1, 2, 3, or 4.

In some embodiments of the compounds of Formula XI:
$R^1$ is 4-methyl-piperazin-1-yl;
each $R^8$ is independently selected from halo, CN, $C_{1-4}$ alkyl, $C_{1-4}$ haloalkyl, $C_{1-4}$ hydroxylalkyl, $C_{1-4}$ cyanoalkyl, $C_{3-7}$ cycloalkyl, OH, $C_{1-4}$ alkoxy, and $C_{1-4}$ haloalkoxy;
$R^9$ is H;
$R^{10}$ is —$(CR^{10b}R^{10c})_{p33}R^{10d}$;
$R^{10b}$ and $R^{10c}$ are each, independently, $HC_{1-3}$ alkyl, CN, —$C(O)N(C_{1-4}alkyl)_3$, —$C(O)O(C_{1-4}$ alkyl), Ar, or HetAr;
$R^{10d}$ is aryl or heteroaryl, each substituted with 0, 1, 2, 3, 4, or 5 substituents each independently selected from $C_{1-6}$ alkyl, $C_{1-6}$ haloalkyl, Ar, HetAr, halo, CN, —$OR^a$, —$OC(O)NR^cR^d$, —$C(O)OR^a$, —$C(O)R^b$, —$C(O)NR^cR^d$, —O—Ar, —O-HetAr, —O-$L^d$-Ar, and —O-$L^d$-HetAr;
$L^d$ is selected from $C_{1-4}$ alkylenyl and —C(O)NH—, wherein the $C_{1-4}$ alkylenyl is substituted with 0, 1, 2, 3, 4, 5, 6, 7, or 8 substituents each independently selected from $C_{1-4}$ alkyl, $C_{1-4}$haloalkyl, halo, and CN;
each Ar is independently aryl substituted with 0, 1, 2, 3, 4, or 5 substituents each independently selected from halo, CN, $C_{1-6}$ alkyl, $C_{1-6}$ haloalkyl, $C_{2-8}$ alkoxyalkyl, $C_{1-6}$ alkoxy, $C_{1-6}$ haloalkoxy, and $C(O)OR^a$, and
each HetAr is independently heteroaryl substituted with 0, 1, 2, 3, 4, or 5 substituents each independently selected from halo, CN, $C_{1-6}$ alkyl, $C_{1-6}$ haloalkyl, $C_{2-8}$ alkoxyalkyl, $C_{1-6}$ alkoxy, $C_{1-6}$ haloalkoxy, and $C(O)OR^a$; and
p33 is 1, 2, or 3.

In some embodiments of the compounds of Formula XI:
$R^1$ is 4-methyl-piperazin-1-yl;
each $R^8$ is independently selected from halo, CN, $C_{1-4}$ alkyl, $C_{1-4}$ haloalkyl, $C_{1-4}$ hydroxylalkyl, $C_{1-4}$ cyanoalkyl, $C_{3-7}$ cycloalkyl, OH, $C_{1-4}$ alkoxy, and $C_{1-4}$ haloalkoxy;
$R^9$ is H or $C_{1-6}$ alkyl;
$R^{10}$ is —$(CR^{10b}R^{10c})_{p33}R^{10d}$;
$R^{10b}$ and $R^{10c}$ are each, independently, $HC_{1-3}$ alkyl, CN, —$C(O)N(C_{1-4}alkyl)_3$, —$C(O)O(C_{1-4}$ alkyl), Ar, or HetAr;
$R^{10d}$ is $C_{3-10}$ cycloalkyl (such as cyclopropyl, cyclobutyl, cyclopentyl, cyclohexyl, adamantyl, indenyl, or 1,2,3,4-tetrahydronaphthalenyl) or heterocycloalkyl (such as pyrrolidinyl, piperidinyl, tetrahydrofuranyl, or tetrahydropyranyl), each substituted with 0, 1, 2, 3, 4, or 5 substituents each independently selected from $C_{1-6}$ alkyl, $C_{1-6}$ haloalkyl, Ar, HetAr, halo, CN, —$OR^a$, —$OC(O)NR^cR^d$, —$C(O)OR^a$, —$C(O)R^b$, —$C(O)NR^cR^d$, —O—Ar, —O-HetAr, —O-$L^d$-Ar, and —O-$L^d$-HetAr;

$L^d$ is selected from $C_{1-4}$ alkylenyl and —C(O)NH—, wherein the $C_{1-4}$ alkylenyl is substituted with 0, 1, 2, 3, 4, 5, 6, 7, or 8 substituents each independently selected from $C_{1-4}$ alkyl, $C_{1-4}$ haloalkyl, halo, and CN;

each Ar is independently aryl substituted with 0, 1, 2, 3, 4, or 5 substituents each independently selected from halo, CN, $C_{1-6}$ alkyl, $C_{1-6}$ haloalkyl, $C_{2-8}$ alkoxyalkyl, $C_{1-6}$ alkoxy, $C_{1-6}$ haloalkoxy, and $C(O)OR^a$, and each HetAr is independently heteroaryl substituted with 0, 1, 2, 3, 4, or 5 substituents each independently selected from halo, CN, $C_{1-6}$ alkyl, $C_{1-6}$ haloalkyl, $C_{2-8}$ alkoxyalkyl, $C_{1-6}$ alkoxy, $C_{1-6}$ haloalkoxy, and $C(O)OR^a$; and p33 is 0, 1, 2, 3, or 4.

In some embodiments of the compounds of Formula XI:

$R^1$ is 4-methyl-piperazin-1-yl;

each $R^8$ is independently selected from halo, CN, $C_{1-4}$ alkyl, $C_{1-4}$ haloalkyl, $C_{1-4}$ hydroxylalkyl, $C_{1-4}$ cyanoalkyl, $C_{3-7}$ cycloalkyl, OH, $C_{1-4}$ alkoxy, and $C_{1-4}$ haloalkoxy;

$R^9$ is H;

$R^{10}$ is —$(CR^{10b}R^{10c})_{p33}R^{10}d$;

$R^{10b}$ and $R^{10c}$ are each, independently, $HC_{1-3}$ alkyl, CN, —C(O)N($C_{1-4}$alkyl)$_3$, —C(O)O($C_{1-4}$ alkyl), Ar, or HetAr;

$R^{10d}$ is aryl or heteroaryl, each substituted with 0, 1, 2, 3, 4, or 5 substituents each independently selected from $C_{1-6}$ alkyl, $C_{1-6}$ haloalkyl, Ar, HetAr, halo, CN, —$OR^a$, —OC(O)$NR^cR^d$, —C(O)$OR^a$, —C(O)$R^b$, —C(O)$NR^cR^d$, —O—Ar, —O-HetAr, —O-$L^d$-Ar, and —O-$L^d$-HetAr;

$L^d$ is selected from $C_{1-4}$ alkylenyl and —C(O)NH—, wherein the $C_{1-4}$ alkylenyl is substituted with 0, 1, 2, 3, 4, 5, 6, 7, or 8 substituents each independently selected from $C_{1-4}$ alkyl, $C_{1-4}$ haloalkyl, halo, and CN;

each Ar is independently aryl substituted with 0, 1, 2, 3, 4, or 5 substituents each independently selected from halo, CN, $C_{1-6}$ alkyl, $C_{1-6}$ haloalkyl, $C_{2-8}$ alkoxyalkyl, $C_{1-6}$ alkoxy, $C_{1-6}$ haloalkoxy, and $C(O)OR^a$, and each HetAr is independently heteroaryl substituted with 0, 1, 2, 3, 4, or 5 substituents each independently selected from halo, CN, $C_{1-6}$ alkyl, $C_{1-6}$ haloalkyl, $C_{2-8}$ alkoxyalkyl, $C_{1-6}$ alkoxy, $C_{1-6}$ haloalkoxy, and $C(O)OR^a$; and p33 is 1, 2, or 3.

In some embodiments of the compounds of Formula XI, $R^9$ and $R^{10}$ together with the N atom to which they are attached form a 4-14 membered heterocycloalkyl group substituted with 0, 1, 2, 3, 4, or 5 substituents independently selected from $R^{10a}$, halo, CN, NO$_2$, oxo, $OR^{a5}$, $SR^{a5}$, $C(O)R^{b5}$, $C(O)NR^{c5}R^{d5}$, $C(O)OR^{a5}$, $OC(O)R^{b5}$, $OC(O)NR^{c5}R^{d5}$, $NR^{c5}R^{d5}$, $NR^{c5}C(O)R^{b5}$, $NR^{c5}C(O)N^{c5}R^{d5}$, $NR^{c5}C(O)OR^{a5}$, $C(=NR^{g5})NR^{c5}R^{d5}$, $NR^{c5}C(=NR^{g5})NR^{c5}R^{d5}$, $NR^{c5}S(O)_2NR^{c5}R^{d5}$, $S(O)R^{b5}$, $S(O)NR^{c5}R^{d5}$, $S(O)_2R^{b5}$, $NR^{c5}S(O)_2R^{b5}$, and $S(O)_2NR^{c5}R^{d5}$.

In some embodiments of the compounds of Formula XI, each $R^{10a}$ is independently selected from $C_{1-6}$ alkyl, $C_{1-6}$ haloalkyl, arylalkyl, heteroarylalkyl, cycloalkylalkyl, heterocycloalkylalkyl, $C_{2-6}$ alkenyl, $C_{2-6}$ alkynyl, aryl, cycloalkyl, heteroaryl, and heterocycloalkyl, each substituted with 0, 1, 2, 3, 4, or 5 substituents each independently selected from $C_{1-6}$ alkyl, $C_{1-6}$ haloalkyl, arylalkyl, heteroarylalkyl, cycloalkylalkyl, heterocycloalkylalkyl, $C_{2-6}$ alkenyl, $C_{2-6}$ alkynyl, aryl, cycloalkyl, heteroaryl, heterocycloalkyl, halo, CN, NO$_2$, $OR^{a5}$, $SR^{a5}$, SF$_5$, $C(O)R^{b5}$, $C(O)NR^{c5}R^{d5}$, $C(O)OR^{a5}$, $OC(O)R^{b5}$, $OC(O)NR^{c5}R^{d5}$, $NR^{c5}R^{d5}$, $NR^{c5}C(O)R^{b5}$, $NR^{c5}C(O)NR^{c5}R^{d5}$, $NR^{c5}C(O)OR^{a5}$, $C(=NR^{g5})NR^{c5}R^{d5}$, $NR^{c5}C(=NR^{g5})NR^{c5}R^{d5}$, $NR^{c5}S(O)_2NR^{c5}R^{d5}$, $S(O)R^{b5}$, $S(O)NR^{c5}R^{d5}$, $S(O)_2R^{b5}$, $NR^{c5}S(O)_2R^{b5}$, and $S(O)_2NR^{c5}R^{d5}$.

In some embodiments of the compounds of Formula XI, each $R^{10a}$ is independently selected from $C_{1-6}$ alkyl, $C_{1-6}$ haloalkyl, arylalkyl, heteroarylalkyl, cycloalkylalkyl, heterocycloalkylalkyl, $C_{2-6}$ alkenyl, $C_{2-6}$ alkynyl, aryl, cycloalkyl, heteroaryl, and heterocycloalkyl, each substituted with 0, 1, 2, 3, 4, or 5 substituents each independently selected from halo, CN, NO$_2$, $OR^{a5}$, $SR^{a5}$, SF$_5$, $C(O)R^{b5}$, $C(O)NR^{c5}R^{d5}$, $C(O)OR^{a5}$, $OC(O)R^{b5}$, $OC(O)NR^{c5}R^{d5}$, $NR^{c5}R^{d5}$, $NR^{c5}C(O)R^{b5}$, $NR^{c5}C(O)NR^{c5}R^{d5}$, $NR^{c5}C(O)OR^{a5}$, $C(=NR^{g5})NR^{c5}R^{d5}$, $NR^{c5}C(=NR^{g5})NR^{c5}R^{d5}$, $NR^{c5}S(O)_2NR^{c5}R^{d5}$, $S(O)R^{b5}$, $S(O)NR^{c5}R^{d5}$, $S(O)_2R^{b5}$, $NR^{c5}S(O)_2R^{b5}$, and $S(O)_2NR^{c5}R^{d5}$.

In some embodiments of the compounds of Formula XI, the compound of Formula XI is a compound of Formula XI-1:

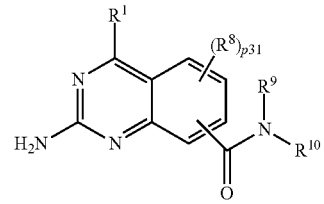

XI-1 wherein:

$R^1$ is selected from formulas (A1), (B1), (C1), (D1), and (E1):

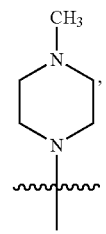

(A1)

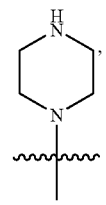

(B1)

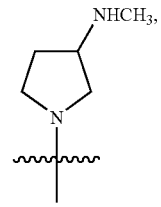

(C1)

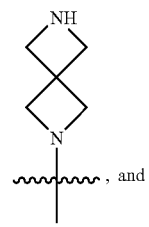

(D1)

, and

-continued

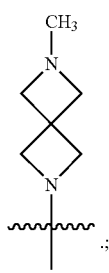
(E1)

R[8] is selected from halo, CN, $C_{1-4}$ alkyl, $C_{1-4}$ haloalkyl, $C_{1-4}$ hydroxylalkyl, $C_{1-4}$ cyanoalkyl, $C_{3-7}$ cycloalkyl, OH, $C_{1-4}$ alkoxy, and $C_{1-4}$ haloalkoxy;

R[9] is selected from H and $C_{1-6}$ alkyl;

R[10] is selected from arylalkyl and cycloalkylalkyl, each substituted with 0, 1, 2, 3, 4, or 5 substituents each independently selected from R[10a], halo, CN, OR[a5], SR[a5], C(O)R[b5], C(O)NR[c5]R[d5], C(O)OR[a5], OC(O)R[b5], OC(O)NR[c5]R[d5], NR[c5]R[d5], NR[c5]C(O)R[b5], NR[c5]C(O)NR[c5]R[d5], NR[c5]C(O)OR[a5], C(=NR[g5])NR[c5]R[d5], NR[c5]C(=NR[g5])NR[c5]R[d5], NR[c5]S(O)$_2$NR[c5]R[d5], S(O)R[b5], S(O)NR[c5]R[d5], S(O)$_2$R[b5], NR[c5]S(O)$_2$R[b5], and S(O)$_2$NR[c5]R[d5];

each R[10a] is independently selected from $C_{1-6}$ alkyl, $C_{1-6}$ haloalkyl, arylalkyl, heteroarylalkyl, cycloalkylalkyl, heterocycloalkylalkyl, $C_{2-6}$ alkenyl, $C_{2-6}$ alkynyl, aryl, cycloalkyl, heteroaryl, and heterocycloalkyl, each substituted with 0, 1, 2, 3, 4, or 5 substituents each independently selected from $C_{1-6}$ alkyl, $C_{1-6}$ haloalkyl, arylalkyl, heteroarylalkyl, cycloalkylalkyl, heterocycloalkylalkyl, $C_{2-6}$ alkenyl, $C_{2-6}$ alkynyl, aryl, cycloalkyl, heteroaryl, heterocycloalkyl, halo, CN, NO$_2$, OR[5], SR[a5], SF$_5$, C(O)R[b5], C(O)NR[c5]R[d5], C(O)OR[a5], OC(O)R[b5], OC(O)NR[c5]R[d5], NR[c5]R[d5], NR[c5]C(O)R[b5], NR[c5]C(O)NR[c5]R[d5], NR[c5]C(O)OR[a5], C(=NR[g5])NR[c5]R[d5], NR[c5]C(=NR[g5])NR[c5]R[d5], NR[c5]S(O)$_2$NR[c5]R[d5], S(O)R[b5], S(O)NR[c5]R[d5], S(O)$_2$R[b5], NR[c5]S(O)$_2$R[b5], and S(O)$_2$NR[c5]R[d5]; and p31 is 0 or 1.

In some embodiments of the compounds of Formula XI, the compound of Formula XI is a compound of Formula XI-1:

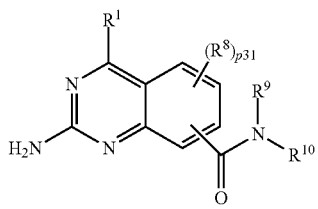
XI-1 wherein:

R[1] is selected from formulas (A1), (B1), (C1), (D1), and (E1):

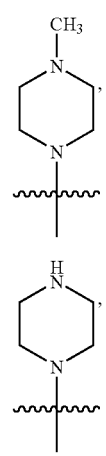
(A1)

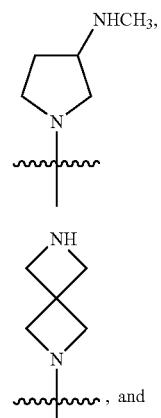
(B1)

(C1)

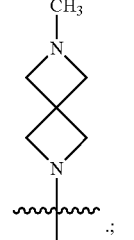
(D1)
, and

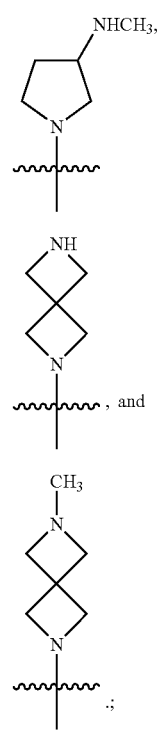
(E1)

R[8] is selected from halo, CN, $C_{1-4}$ alkyl, $C_{1-4}$ haloalkyl, $C_{1-4}$ hydroxylalkyl, $C_{1-4}$ cyanoalkyl, $C_{3-7}$ cycloalkyl, OH, $C_{1-4}$ alkoxy, and $C_{1-4}$ haloalkoxy;

R[9] is H; and

R[10] is —(CR[10b]R[10c])$_{p33}$R[10d];

R[10d] and R[10c] are each, independently, H or methyl;

R[10d] is aryl or cycloalkyl, each substituted with 0, 1, 2, 3, 4, or 5 substituents each independently selected from R[10a], halo, CN, OR[a5], SR[a5], C(O)R[a5], C(O)NR[c5]R[d5], C(O)OR[a5], OC(O)R[b5], OC(O)NR[c5]R[d5], NR[c5]R[d5], NR[c5]C(O)R[b5], NR[c5]C(O)NR[c5]R[d5], NR[c5]C(O)OR[a5], C(=NR[g5])NR[c5]R[d5], NR[c5]C(=NR[g5])NR[c5]R[d5], NeS(O)$_2$NR[c5]R[d5], S(O)R[b5], S(O)NR[c5]R[d5], S(O)$_2$R[b5], NR[c5]S(O)$_2$R[b5], and S(O)$_2$NR[c5]R[d5];

p33 is 0, 1, 2, 3, or 4;

each R[10a] is independently selected from $C_{1-6}$ alkyl, $C_{1-6}$ haloalkyl, arylalkyl, heteroarylalkyl, cycloalkylalkyl, heterocycloalkylalkyl, $C_{2-6}$ alkenyl, $C_{2-6}$ alkynyl, aryl, cycloalkyl, heteroaryl, and heterocycloalkyl, each substituted with 0, 1, 2, 3, 4, or 5 substituents each independently selected from $C_{1-6}$ alkyl, $C_{1-6}$ haloalkyl, arylalkyl, heteroarylalkyl, cycloalkylalkyl, heterocycloalkylalkyl, $C_{2-6}$ alkenyl, $C_{2-6}$ alkynyl, aryl, cycloalkyl, heteroaryl, heterocycloalkyl, halo, CN, $NO_2$, $OR^{a5}$, $SR^{a5}$, $SF_5$, $C(O)R^{b5}$, $C(O)NR^{c5}R^{d5}$, $C(O)OR^{a5}$, $OC(O)R^{b5}$, $OC(O)NR^{c5}R^{d5}$, $NR^{c5}R^{d5}$, $NR^{c5}C(O)R^{b5}$, $NR^{c5}C(O)NR^{c5}R^{d5}$, $NR^{c5}C(O)OR^{a5}$, $C(=NR^{g5})NR^{c5}R^{d5}$, $NR^{c5}C(=NR^{g5})NR^{c5}R^{d5}$, $NR^{c5}S(O)_2NR^{c5}R^{d5}$, $S(O)R^{b5}$, $S(O)NR^{c5}R^{d5}$, $S(O)_2R^{b5}$, $NR^{c5}S(O)_2R^{b5}$, and $S(O)_2NR^{c5}R^{d5}$; and p31 is 0 or 1.

In some embodiments of the compounds of Formula XI, the compound of Formula XI is a compound of Formula XI-1:

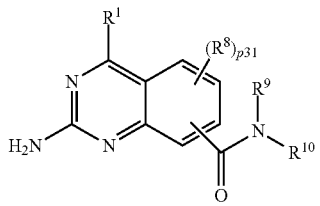

(XI-1)

wherein:

$R^1$ is selected from formulas (A1), (B1), (C1), (D1), and (E1):

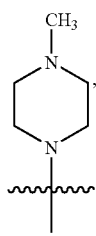

(A1)

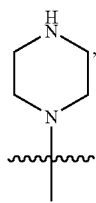

(B1)

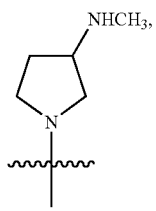

(C1)

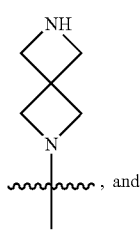

(D1)

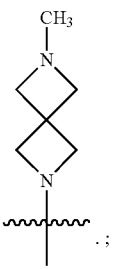

(E1)

$R^8$ is selected from halo, CN, $C_{1-4}$ alkyl, $C_{1-4}$ haloalkyl, $C_{1-4}$ hydroxyalkyl, $C_{1-4}$ cyanoalkyl, $C_{3-7}$ cycloalkyl, OH, $C_{1-4}$ alkoxy, and $C_{1-4}$ haloalkoxy;

$R^9$ is H or $C_{1-6}$ alkyl;

$R^{10}$ is $-(CR^{10b}R^{10c})_{p33}R^{10d}$;

$R^{10b}$ and $R^{10c}$ are each, independently, $HC_{1-3}$ alkyl, CN, $-C(O)N(C_{1-4}alkyl)_3$, $-C(O)O(C_{1-4}$ alkyl), Ar, or HetAr;

$R^{10d}$ is aryl or heteroaryl, each substituted with 0, 1, 2, 3, 4, or 5 substituents each independently selected from $C_{1-6}$ alkyl, $C_{1-6}$ haloalkyl, Ar, HetAr, halo, CN, $-OR^a$, $-OC(O)NR^cR^d$, $-C(O)OR^a$, $-C(O)R^b$, $-C(O)NR^cR^d$, $-O-Ar$, $-O$-HetAr, $-O-L^d$-Ar, and $-O-L^d$-HetAr;

$L^d$ is selected from $C_{1-4}$ alkylenyl and $-C(O)NH-$, wherein the $C_{1-4}$ alkylenyl is substituted with 0, 1, 2, 3, 4, 5, 6, 7, or 8 substituents each independently selected from $C_{1-4}$ alkyl, $C_{1-4}$haloalkyl, halo, and CN;

each Ar is independently aryl substituted with 0, 1, 2, 3, 4, or 5 substituents each independently selected from halo, CN, $C_{1-6}$ alkyl, $C_{1-6}$ haloalkyl, $C_{2-8}$ alkoxyalkyl, $C_{1-6}$ alkoxy, $C_{1-6}$ haloalkoxy, and $C(O)OR^a$, and each HetAr is independently heteroaryl substituted with 0, 1, 2, 3, 4, or 5 substituents each independently selected from halo, CN, $C_{1-6}$ alkyl, $C_{1-6}$ haloalkyl, $C_{2-8}$ alkoxyalkyl, $C_{1-6}$ alkoxy, $C_{1-6}$ haloalkoxy, and $C(O)OR^a$; and p33 is 0, 1, 2, 3, or 4.

In some embodiments of the compounds of Formula XI-1, $R^1$ is 4-methyl-piperazin-1-yl.

In some embodiments of the compounds of Formula XI-1:

$R^1$ is 4-methyl-piperazin-1-yl;

$R^8$ is selected from halo, CN, $C_{1-4}$ alkyl, $C_{1-4}$ haloalkyl, $C_{1-4}$ hydroxylalkyl, $C_{1-4}$ cyanoalkyl, $C_{3-7}$ cycloalkyl, OH, $C_{1-4}$ alkoxy, and $C_{1-4}$ haloalkoxy;

$R^9$ is H or $C_{1-3}$ alkyl;

$R^{10}$ is $-(CR^{10b}R^{10c})_{p33}R^{10d}$;

$R^{10b}$ and $R^{10c}$ are each, independently, $HC_{1-3}$ alkyl, CN, $-C(O)N(C_{1-4}alkyl)_3$, $-C(O)O(C_{1-4}$ alkyl), Ar, or HetAr;

$R^{10d}$ is cycloalkyl or heterocycloalkyl, each substituted with 0, 1, 2, 3, 4, or 5 substituents each independently selected from $C_{1-6}$ alkyl, $C_{1-6}$ haloalkyl, Ar, HetAr, halo, CN, $-OR^a$, $-OC(O)NR^cR^d$, $-C(O)OR^a$, $-C(O)R^b$, $-C(O)NR^cR^d$, $-O-Ar$, $-O$-HetAr, $-O-L^d$-Ar, and $-O-L$-HetAr;

$L^d$ is selected from $C_{1-4}$ alkylenyl and $-C(O)NH-$, wherein the $C_{1-4}$ alkylenyl is substituted with 0, 1, 2, 3, 4, 5, 6, 7, or 8 substituents each independently selected from $C_{1-4}$ alkyl, $C_{1-4}$ haloalkyl, halo, and CN;

each Ar is independently aryl substituted with 0, 1, 2, 3, 4, or 5 substituents each independently selected from halo, CN, $C_{1-6}$ alkyl, $C_{1-6}$ haloalkyl, $C_{2-8}$ alkoxyalkyl, $C_{1-6}$ alkoxy, $C_{1-6}$ haloalkoxy, and $C(O)OR^a$, and each HetAr is independently heteroaryl substituted with 0, 1, 2, 3, 4, or 5 substituents each independently selected from halo, CN, $C_{1-6}$ alkyl, $C_{1-6}$ haloalkyl, $C_{2-8}$ alkoxyalkyl, $C_{1-6}$ alkoxy, $C_{1-6}$ haloalkoxy, and $C(O)OR^a$; and p33 is 1, 2, or 3.

In some embodiments of the compounds of Formula XI-1:

R$^1$ is 4-methyl-piperazin-1-yl;

R$^8$ is selected from halo, CN, C$_{1-4}$ alkyl, C$_{1-4}$ haloalkyl, C$_{1-4}$ hydroxylalkyl, C$_{1-4}$ cyanoalkyl, C$_{3-7}$ cycloalkyl, OH, C$_{1-4}$ alkoxy, and C$_{1-4}$ haloalkoxy;

R$^9$ is H or C$_{1-3}$ alkyl;

R$^{10}$ is —(CR$^{10b}$R$^{10c}$)$_{p33}$R$^{10d}$;

R$^{10d}$ and R$^{10c}$ are each, independently, HC$_{1-3}$ alkyl, CN, —C(O)N(C$_{1-4}$alkyl)$_3$, —C(O)O(C$_{1-4}$ alkyl), Ar, or HetAr;

R$^{10d}$ is aryl or heteroaryl, each substituted with 0, 1, 2, 3, 4, or 5 substituents each independently selected from C$_{1-6}$ alkyl, C$_{1-6}$ haloalkyl, Ar, HetAr, halo, CN, —OR$^a$, —OC(O)NR$^c$R$^d$, —C(O)OR$^a$, —C(O)R$^b$, —C(O)NR$^c$R$^d$, —O—Ar, —O-HetAr, —O-L$^d$-Ar, and —O-L$^d$-HetAr;

L$^d$ is selected from C$_{1-4}$ alkylenyl and —C(O)NH—, wherein the C$_{1-4}$ alkylenyl is substituted with 0, 1, 2, 3, 4, 5, 6, 7, or 8 substituents each independently selected from C$_{1-4}$ alkyl, C$_{1-4}$ haloalkyl, halo, and CN;

each Ar is independently aryl substituted with 0, 1, 2, 3, 4, or 5 substituents each independently selected from halo, CN, C$_{1-6}$ alkyl, C$_{1-6}$ haloalkyl, C$_{2-8}$ alkoxyalkyl, C$_{1-6}$ alkoxy, C$_{1-6}$ haloalkoxy, and C(O)OR$^a$; and each HetAr is independently heteroaryl substituted with 0, 1, 2, 3, 4, or 5 substituents each independently selected from halo, CN, C$_{1-6}$ alkyl, C$_{1-6}$ haloalkyl, C$_{2-8}$ alkoxyalkyl, C$_{1-6}$ alkoxy, C$_{1-6}$ haloalkoxy, and C(O)OR$^a$; and p33 is 1, 2, or 3.

In some embodiments of the compounds of Formula XI-1, the compound of Formula XI-1 is a compound of Formula XI-1a:

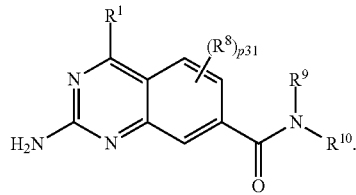

XI-1a

In some embodiments of the compounds of Formula XI, the compound of Formula XI is a compound of Formula XI-2 or XI-2a:

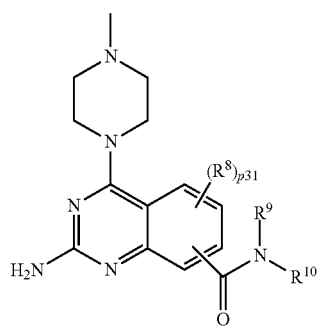

XI-2

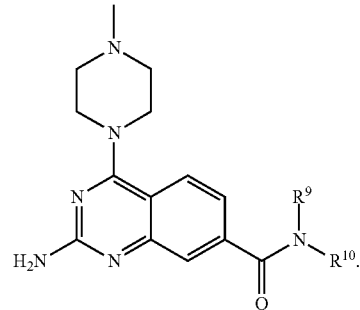

XI-2a wherein:

R$^8$ is selected from halo, CN, C$_{1-4}$ alkyl, C$_{1-4}$ haloalkyl, C$_{1-4}$ hydroxylalkyl, C$_{1-4}$ cyanoalkyl, C$_{3-7}$ cycloalkyl, OH, C$_{1-4}$ alkoxy, and C$_{1-4}$ haloalkoxy;

R$^9$ is H or C$_{1-4}$ alkyl; and

R$^{10}$ is selected from (a) C$_{1-6}$ alkyl substituted with 0, 1, 2, 3, or 4 substituents each independently selected from halo, CN, C(O)OR$^a$, —OAr, and NR$^c$C(O)OR$^a$; (b) C$_{3-10}$ cycloalkyl (such as cyclopropyl, cyclobutyl, cyclopentyl, cyclohexyl, adamantyl, indenyl, or 1,2,3,4-tetrahydronaphthalenyl) substituted with 0, 1, 2, 3, or 4 substituents each independently selected from halo, CN, Ar, HetAr, —O—Ar, —O-HetAr, —O-L$^d$-Ar, —O-L$^d$-HetAr, C$_{1-6}$ alkyl, and C$_{1-6}$ haloalkyl; (c) aryl (such as phenyl or naphthyl) substituted with 0, 1, 2, 3, or 4 substituents each independently selected from C$_{1-6}$ alkyl, C$_{1-6}$ haloalkyl, C$_{1-6}$ alkoxy, C$_{1-6}$ haloalkoxy, halo, and CN; (d) arylakyl (such as naphthalenylmethyl, benzyl, phenylethyl, or phenylpropyl) substituted with 0, 1, 2, 3, or 4 substituents each independently selected from C$_{1-6}$ alkyl, C$_{1-6}$ haloalkyl, Ar, HetAr, halo, CN, —OR$^a$, —OC(O)NR$^c$R$^d$, —C(O)OR$^a$, —C(O)NR$^c$R$^d$, —O—Ar, —O-HetAr, —O-L$^d$-Ar, and —O-L$^d$-HetAr; (e) cycloalkylalkyl (such as cyclopropylmethyl) substituted with 0, 1, 2, 3, or 4 substituents each independently selected from C$_{1-6}$ alkyl, C$_{1-6}$ haloalkyl, C$_{1-6}$ alkoxy, C$_{1-6}$ haloalkoxy, halo, NR$^c$C(O)OR$^a$, and CN; and (f) heteroarylalkyl (such as benzofuranylethyl, 1,3-benzothiazolylmethyl, 1,3-benzothiazolylethyl, or thienylmethyl) substituted with 0, 1, 2, 3, or 4 substituents each independently selected from C$_{1-6}$ alkyl, C$_{1-6}$ haloalkyl, C$_{1-6}$ alkoxy, C$_{1-6}$ haloalkoxy, —C(O)NR$^c$R$^d$, Ar, NR$^c$C(O)OR$^a$, halo, NR$^c$R$^d$, and CN; and (g) heterocycloalkylalkyl [such as (1,3,-benzodioxol-5-yl)ethyl] substituted with 0, 1, 2, 3, or 4 substituents each independently selected from C$_{1-6}$ alkyl, C$_{1-6}$ haloalkyl, C$_{1-6}$ alkoxy, C$_{1-6}$ haloalkoxy, NR$^c$C(O)OR$^a$, halo, Ar, NR$^c$R$^d$, CN, —C(O)NR$^c$R$^d$, (O)R$^b$, C(O)OR$^a$, and S(O)$_2$R$^b$;

or R$^9$ and R$^{10}$ together with the N atom to which they are attached form a 4-14 membered heterocycloalkyl group that is substituted with 0, 1, 2, 3, 4, or 5 substituents independently selected from C$_{1-6}$ alkyl, C$_{1-6}$ haloalkyl, Ar, HetAr, halo, CN, —OR$^a$, —OC(O)NR$^c$R$^d$, —C(O)OR$^a$, —C(O)NR$^c$R$^d$, —O—Ar, —O-HetAr, —O-L$^d$-Ar, and —O-L$^d$-HetAr;

L$^d$ is selected from C$_{1-4}$ alkylenyl and —C(O)NH—, wherein the C$_{1-4}$ alkylenyl is substituted with 0, 1, 2, 3, 4, 5, 6, 7, or 8 substituents each independently selected from C$_{1-4}$ alkyl, C$_{1-4}$haloalkyl, halo, and CN;

p31 is 0 or 1;

each Ar is independently aryl (such as phenyl or naphthyl) substituted with 0, 1, 2, 3, 4, or 5 substituents each independently selected from halo (e.g. F or Cl), CN, C$_{1-6}$ alkyl (e.g. methyl or ethyl), C$_{1-6}$ haloalkyl (e.g. CF$_3$), C$_{2-8}$ alkoxyalkyl (e.g. methoxymethyl), $C_{1-6}$ alkoxy (e.g. —OCH$_3$), $C_{1-6}$ haloalkoxy (e.g. —OCF$_3$), and C(O)OR$^a$ [e.g. C(O)O(C$_{1-6}$ alkyl)], and each HetAr is independently heteroaryl (such as pyridinyl, pyrazinyl, quinoxalinyl, 2,1,3-benzothiadiazolyl, pyrazolyl, thienyl, 1,2,5-thiadiazolyl, isoquinolinyl, 1,3-thiazolyl, furanyl, benzofuranyl, 1,3-benzothiazolyl) substituted with 0, 1, 2, 3, 4, or 5 substituents each independently selected from halo (e.g. F or Cl), CN, $C_{1-6}$ alkyl (e.g. methyl or ethyl), $C_{1-6}$ haloalkyl (e.g. CF$_3$), $C_{2-8}$ alkoxyalkyl (e.g. methoxymethyl), $C_{1-6}$ alkoxy (e.g. —OCH$_3$), $C_{1-6}$ haloalkoxy (e.g. —OCF$_3$), and C(O)OR$^a$ [e.g. C(O)O(C$_{1-6}$ alkyl)].

In some embodiments of the compounds of Formula XI, the compound of Formula XI is a compound of Formula XI-2 or XI-2a:

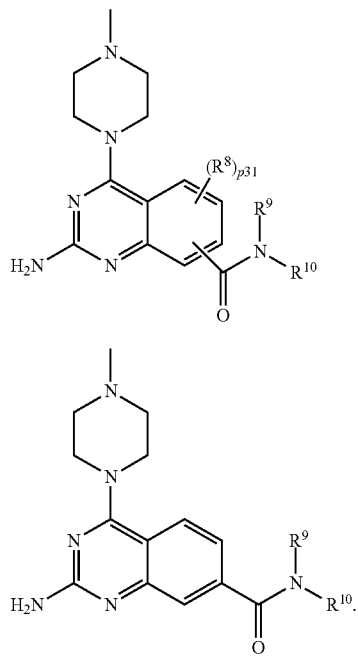

XI-2

XI-2a wherein:

$R^8$ is selected from halo, CN, $C_{1-4}$ alkyl, $C_{1-4}$ haloalkyl, $C_{1-4}$ hydroxylalkyl, $C_{1-4}$ cyanoalkyl, $C_{3-7}$ cycloalkyl, OH, $C_{1-4}$ alkoxy, and $C_{1-4}$ haloalkoxy;

the moiety of

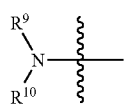

is a moiety of M1, M2, M3, M4, M5, M6, M7, or M8:

(M1)

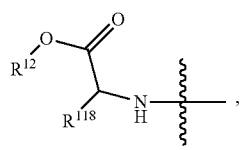

(M2)

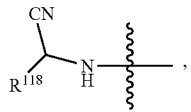

(M3)

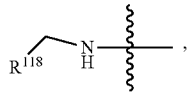

M4

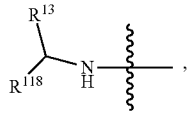

(M5)

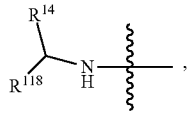

(M6)

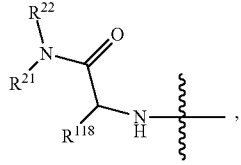

(M7)

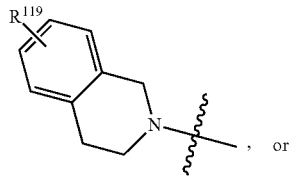

, or (M8)

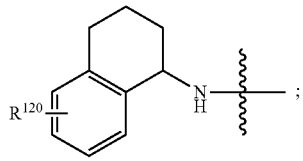

;

$R^{12}$ is $C_{1-4}$ alkyl (such as methyl, ethy, 1-propyl, or 2-propyl);

$R^{13}$ is $C_{1-4}$ alkyl (such as methyl or ethyl);

$R^{14}$ is Ar (such as phenyl) or HetAr (such as 1,3-thiazolyl or 1,3-thiazol-2-yl);

$R^{21}$ is $C_{1-4}$ alkyl (such as methyl);

$R^{22}$ is $C_{1-4}$ alkyl (such as methyl);

$R^{118}$ is selected from $C_{3-10}$ cycloalkyl (such as cyclopropyl, cyclobutyl, cyclopentyl, cyclohexyl, adamantyl, indenyl, or 1,2,3,4-tetrahydronaphthalenyl), aryl (such as phenyl or naphthyl), heteroaryl, heterocycloalkyl, cycloalkylalkyl, arylalkyl, heteroarylalkyl, and heterocycloalkylalkyl, each substituted with substituted with 0, 1, 2, 3, or 4 substituents each independently selected from $C_{1-6}$ alkyl, $C_{1-6}$ haloalkyl, $C_{2-8}$ alkoxyalkyl, Ar, HetAr, halo, CN, NR$^c$C(O)OR$^a$, NR$^c$R$^d$, C(O)R$^b$, S(O)$_2$R$^b$, —OR$^a$, —OC(O)NR$^c$R$^d$, —C(O)OR$^a$, —C(O)NR$^c$R$^d$, —O—Ar, —O-HetAr, —O-L$^d$-Ar, and —O-L$^d$-HetAr;

$R^{119}$ is selected from Ar, HetAr, —OR$^a$, —OC(O)NR$^c$R$^d$, —C(O)OR$^a$, —C(O)NR$^c$R$^d$, —O—Ar, —O-HetAr, —O-L$^d$-Ar, and —O-L$^d$-HetAr;

$R^{120}$ is selected from Ar, HetAr, —OR$^a$, —OC(O)NR$^c$R$^d$, —C(O)OR$^a$, —C(O)NR$^c$R$^d$, —O—Ar, —O-HetAr, —O-L$^d$-Ar, and —O-L$^d$-HetAr;

$L^d$ is selected from $C_{1-4}$ alkylenyl and —C(O)NH—, wherein the $C_{1-4}$ alkylenyl is substituted with 0, 1, 2, 3, 4, 5, 6, 7, or 8 substituents each independently selected from $C_{1-4}$ alkyl, $C_{1-4}$ haloalkyl, halo, and CN;

p31 is 0 or 1;

each Ar is independently aryl substituted with 0, 1, 2, 3, 4, or 5 substituents each independently selected from halo, CN, $C_{1-6}$ alkyl, $C_{1-6}$ haloalkyl, $C_{2-8}$ alkoxyalkyl, $C_{1-6}$ alkoxy, $C_{1-6}$ haloalkoxy, and $C(O)OR^a$, and each HetAr is independently heteroaryl substituted with 0, 1, 2, 3, 4, or 5 substituents each independently selected from halo, CN, $C_{1-6}$ alkyl, $C_{1-6}$ haloalkyl, $C_{2-8}$ alkoxyalkyl, $C_{1-6}$ alkoxy, $C_{1-6}$ haloalkoxy, and $C(O)OR^a$.

In some embodiments of the compounds of Formula XI, the compound of Formula XI is a compound of Formula XI-2 or XI-2a:

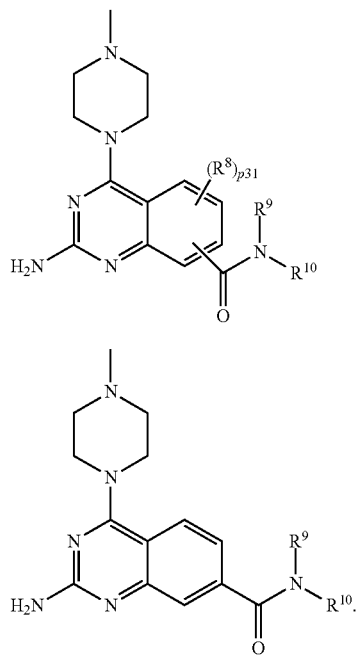

wherein:

$R^8$ is selected from halo, $C_{1-4}$ alkyl, $C_{1-4}$ haloalkyl, $C_{1-4}$ alkoxy, and $C_{1-4}$ haloalkoxy;

is a moiety of

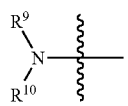

is a moiety of M1, M2, M3, M4, M5, M6, M7, or M8:

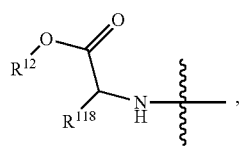

(M1)

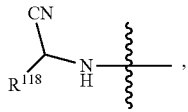

(M2)

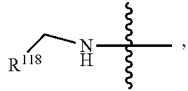

(M3)

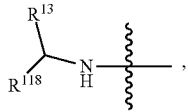

M4

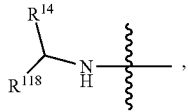

(M5)

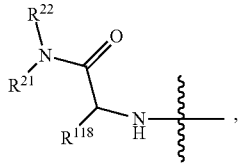

(M6)

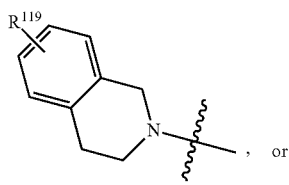

(M7)

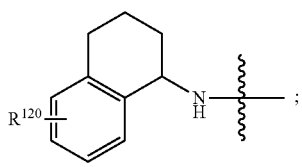

(M8), or $R^{12}$ is $C_{1-4}$ alkyl;

$R^{13}$ is $C_{1-4}$ alkyl;

$R^{14}$ is Ar or HetAr;

$R^{21}$ is $C_{1-4}$ alkyl;

$R^{22}$ is $C_{1-4}$ alkyl;

$R^{118}$ is selected from aryl (such as phenyl or naphthyl), heteroaryl (such as pyridinyl, pyrazinyl, benzofuranyl, 1,3-benzothiazolyl, thienyl), arylalkyl (such as benzyl or phenylethyl), and heteroarylalkyl (such as 1,3-benzothiazolylmethyl, thienylmethyl, pyrazolylmethyl, benzofuranylmethyl, or benzofuranylethyl), each substituted with substituted with 0, 1, 2, 3, or 4 substituents each independently selected from $C_{1-6}$ alkyl, $C_{1-6}$ haloalkyl, $C_{2-8}$ alkoxyalkyl, Ar, HetAr, halo, CN, $NR^cC(O)OR^a$, $NR^cR^d$, $C(O)R^b$, $S(O)_2R^b$, —$OR^a$, —OC(O)$NR^cR^d$, —$C(O)OR^a$, —$C(O)NR^cR^d$, —O—Ar, —O-HetAr, —O-$L^d$-Ar, and —O-$L^d$-HetAr;

$R^{119}$ is selected from —O—Ar, —O-HetAr, —O-$L^d$-Ar, and —O-$L^d$-HetAr;

$R^{129}$ is selected from —O—Ar, —O-HetAr, —O-$L^d$-Ar, and —O-$L^d$-HetAr;

p31 is 0 or 1;

$L^d$ is selected from $C_{1-4}$ alkylenyl and —C(O)NH—, wherein the $C_{1-4}$ alkylenyl is substituted with 0, 1, 2, 3, 4, 5, 6, 7, or 8 substituents each independently selected from $C_{1-4}$ alkyl and halo;

each Ar is independently aryl substituted with 0, 1, 2, 3, 4, or 5 substituents each independently selected from halo, CN, $C_{1-6}$ alkyl, $C_{1-6}$ haloalkyl, $C_{2-8}$ alkoxyalkyl, $C_{1-6}$ alkoxy, $C_{1-6}$ haloalkoxy, and $C(O)OR^a$, and each HetAr is independently heteroaryl substituted with 0, 1, 2, 3, 4, or 5 substituents each independently selected from halo, CN, $C_{1-6}$ alkyl, $C_{1-6}$ haloalkyl, $C_{2-8}$ alkoxyalkyl, $C_{1-6}$ alkoxy, $C_{1-6}$ haloalkoxy, and $C(O)OR^a$.

In some embodiments of the compounds of Formula XI-2 or XI-2a, the moiety of

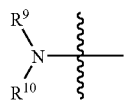

("the moiety M100") is a moiety of M1.

In some embodiments of the compounds of Formula XI-2 or XI-2a, the moiety M100 is a moiety of M2. In some embodiments of the compounds of Formula XI-2 or XI-2a, the moiety M100 is a moiety of M3. In some embodiments of the compounds of Formula XI-2 or XI-2a, the moiety M100 is a moiety of M4. In some embodiments of the compounds of Formula XI-2 or XI-2a, the moiety M100 is a moiety of M5. In some embodiments of the compounds of Formula XI-2 or XI-2a, the moiety M100 is a moiety of M6. In some embodiments of the compounds of Formula XI-2 or XI-2a, the moiety M100 is a moiety of M7. In some embodiments of the compounds of Formula XI-2 or XI-2a, the moiety M100 is a moiety of M8.

As used herein, unless otherwise indicated (e.g., indicated specifically or dictated by stability of the molecule), a linkage—a moiety that links two other moieties—can be attached to the other two moieties in either direction, if the linkage is asymmetric. For example, when $W^{2a}$ in —$W^{2a}$—$X^{2a}$—$W^2$—$X^2$—$Y^2$—$Z^2$ is $O(CR^{11a}R^{11b})_{q1}NR^f$, $W^{2a}$ can be linked to $X^{2a}$ either via the O or the N atom. For another example, when $W^{2a}$ in —$W^{2a}$—$X^{2a}$—$W^2$—$X^2$—$Y^2$—$Z^2$ is C(O)NH, $W^{2a}$ can be linked to $X^{2a}$ either via the C or the N atom.

At various places in the present specification, substituents of compounds of the invention are disclosed in groups or in ranges. It is specifically intended that the invention include each and every individual subcombination of the members of such groups and ranges. For example, the term "$C_{1-6}$ alkyl" is specifically intended to individually disclose methyl, ethyl, $C_3$ alkyl, $C_4$ alkyl, $C_5$ alkyl, and $C_6$ alkyl.

For compounds of the invention in which a variable appears more than once, each variable can be a different moiety selected from the Markush group defining the variable. For example, each of $R^4$, —$W^{1a}$—$X^{1a}$—$W^1$—$X^1$—$Y^1$—$Z^1$, and —$W^{2a}$—$X^{2a}$—$W^2$—$X^2$—$Y^2$—$Z^2$ can be a different moiety selected group defining the variable. For example, where a structure is described having two R groups that are simultaneously present on the same compound; the two R groups can represent different moieties selected from the Markush group defined for R. In another example, when an optionally multiple substituent is designated in the form:

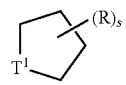

then it is understood that substituent R can occur s number of times on the ring, and R can be a different moiety at each occurrence. Further, in the above example, should the variable $T^1$ be defined to include hydrogens, such as when $T^1$ is said to be $CH_2$, NH, etc., any floating substituent such as R in the above example, can replace a hydrogen of the $T^1$ variable as well as a hydrogen in any other non-variable component of the ring.

It is further appreciated that certain features of the invention, which are, for clarity, described in the context of separate embodiments, can also be provided in combination in a single embodiment. Conversely, various features of the invention which are, for brevity, described in the context of a single embodiment, can also be provided separately or in any suitable subcombination.

The term "n-membered" where n is an integer typically describes the number of ring-forming atoms in a moiety where the number of ring-forming atoms is n. For example, pyridine is an example of a 6-membered heteroaryl ring and thiophene is an example of a 5-membered heteroaryl group.

As used herein, the term "alkyl" is meant to refer to a saturated hydrocarbon group which is straight-chained or branched. Example alkyl groups include, but are not limited to, methyl (Me), ethyl (Et), propyl (e.g., n-propyl and isopropyl), butyl (e.g., n-butyl, isobutyl, t-butyl), pentyl (e.g., n-pentyl, isopentyl, neopentyl), and the like. An alkyl group can contain from 1 to about 20, from 2 to about 20, from 1 to about 10, from 1 to about 8, from 1 to about 6, from 1 to about 4, or from 1 to about 3 carbon atoms. The term "alkylene" refers to a divalent alkyl linking group. An example of alkylene is methylene ($CH_2$).

As used herein, "alkenyl" refers to an alkyl group having one or more double carbon-carbon bonds. Example alkenyl groups include, but are not limited to, ethenyl, propenyl, cyclohexenyl, and the like. The term "alkenylenyl" refers to a divalent linking alkenyl group.

As used herein, "alkynyl" refers to an alkyl group having one or more triple carbon-carbon bonds. Example alkynyl groups include, but are not limited to, ethynyl, propynyl, and the like. The term "alkynylenyl" refers to a divalent linking alkynyl group.

As used herein, "haloalkyl" refers to an alkyl group having one or more halogen substituents Example haloalkyl groups include, but are not limited to, $CF_3$, $C_2F_5$, $CHF_2$, $CCl_3$, $CHCl_2$, $C_2Cl_5$, $CH_2CF_3$, and the like.

As used herein, "aryl" refers to monocyclic or polycyclic (e.g., having 2, 3, or 4 fused rings) aromatic hydrocarbons such as, for example, phenyl, napthyl, anthracenyl, phenanthrenyl, indanyl, indenyl, and the like. In some embodiments, aryl groups have from 6 to about 20 carbon atoms. In some embodiments, aryl groups have from 6 to about 10 carbon atoms.

As used herein, "cycloalkyl" refers to non-aromatic cyclic hydrocarbons including cyclized alkyl, alkenyl, and alkynyl groups that contain up to 20 ring-forming carbon atoms. Cycloalkyl groups can include mono- or polycyclic ring systems such as fused ring systems, bridged ring systems, spiro ring systems, and any combination thereof. In some embodiments, examples of polycyclic ring systems include 2, 3, or 4 fused rings. In some other embodiments, examples of polycyclic ring systems include 2 fused rings and 1 sprio ring. A cycloalkyl group can contain from 3 to about 15, from 3 to about 10, from 3 to about 8, from 3 to about 6, from 4 to about 6, from 3 to about 5, or from 5 to about 6 ring-forming carbon atoms. Example cycloalkyl groups include, but are not limited to, cyclopropyl, cyclobutyl, cyclopentyl, cyclohexyl, cycloheptyl, cyclopentenyl, cyclohexenyl, cyclohexadienyl, cycloheptatrienyl, norbornyl, norpinyl, norcarnyl, adamantyl, and the like. Ring-forming carbon atoms of a cycloalkyl group can be optionally substituted by oxo [i.e. =O] or sulfido [i.e. =S; or thiono]. Also included in the definition of cycloalkyl are moieties that have one or more oxo and/or sulfido on the ring forming carbon atoms, for example, 2-oxo-cyclopent-1-yl or 3-sulfido-cyclohexan-1-yl. Also included in the definition of cycloalkyl are moieties that have one or more aromatic rings fused (i.e., having a bond in common with) to the cycloalkyl ring, for example, benzo or thienyl derivatives of pentane, pentene, hexane, and the like (e.g., 2,3-dihydro-1H-inden-1-yl, or 1H-inden-2(3H)-one-1-yl).

As used herein, "heteroaryl" groups refer to an aromatic heterocycle having up to 20 ring-forming atoms and having at least one heteroatom ring member (ring-forming atom) such as sulfur, oxygen, or nitrogen. In some embodiments, the heteroaryl group has at least one or more heteroatom ring-forming atoms each independently selected from sulfur, oxygen, and nitrogen. Heteroaryl groups include monocyclic and polycyclic (e.g., having 2, 3 or 4 fused rings) systems. Examples of heteroaryl groups include without limitation, pyridyl, pyrimidinyl, pyrazinyl, pyridazinyl, triazinyl, furyl, quinolyl, isoquinolyl, thienyl, imidazolyl, thiazolyl, indolyl, pyrryl, oxazolyl, benzofuryl, benzothienyl, benzthiazolyl, isoxazolyl, pyrazolyl, triazolyl, tetrazolyl, indazolyl, 1,2,4-thiadiazolyl, isothiazolyl, benzothienyl, purinyl, carbazolyl, benzimidazolyl, indolinyl, and the like. In some embodiments, the heteroaryl group has from 1 to about 20 carbon atoms, and in further embodiments from about 1 to about 5, from about 1 to about 4, from about 1 to about 3, from about 1 to about 2, carbon atoms as ring-forming atoms. In some embodiments, the heteroaryl group contains 3 to about 14, 3 to about 7, or 5 to 6 ring-forming atoms. In some embodiments, the heteroaryl group has 1 to about 4, 1 to about 3, or 1 to 2 heteroatoms.

As used herein, "heterocycloalkyl" refers to non-aromatic heterocycles having up to 20 ring-forming atoms including cyclized alkyl, alkenyl, and alkynyl groups where one or more of the ring-forming carbon atoms is replaced by a heteroatom such as an O, N, or S atom. Hetercycloalkyl groups can be mono or polycyclic (e.g., fused, bridged, or spiro systems). Ring-forming carbon atoms and heteroatoms of a heterocycloalkyl group can be optionally substituted by oxo [i.e., =O] or sulfido [i.e. =S; or thiono]. For example, a ring-forming S atom can be substituted by 1 or 2 oxo [i.e., forming S(O) or S(O)$_2$]. For another example, a ring-forming C atom can be substituted by oxo (i.e., forming carbonyl) or sulfido [i.e., forming a C=S moiety]. Example "heterocycloalkyl" groups include morpholino, thiomorpholino, piperazinyl, tetrahydrofuranyl, tetrahydrothienyl, 2,3-dihydrobenzofuryl, 1,3-benzodioxole, benzo-1,4-dioxane, piperidinyl, pyrrolidinyl, isoxazolidinyl, isothiazolidinyl, pyrazolidinyl, oxazolidinyl, thiazolidinyl, imidazolidinyl, pyrrolidin-2-one-3-yl, 1,1-dioxo-isothiazolidin-5-yl, and the like. Also included in the definition of heterocycloalkyl are moieties that have one or more aromatic rings fused (i.e., having a bond in common with) to the nonaromatic heterocyclic ring, for example pyridinyl, thiophenyl, phthalimidyl, naphthalimidyl, and benzo derivatives of heterocycles such as indolene, isoindolene, isoindolin-1-one-3-yl, 4,5,6,7-tetrahydrothieno[2,3-c]pyridine-5-yl, 5,6-dihydrothieno[2,3-c]pyridin-7(4H)-one-5-yl, and 3,4-dihydroisoquinolin-1(2H)-one-3yl groups. In some embodiment heterocycloalkyl group has from 1 to about 20 carbon atoms, and in further embodiments from about 3 to about 20 carbon atoms. In some embodiments, the heterocycloalkyl group contains 3 to about 14, 3 to about 7, or 5 to 6 ring-forming atoms. In some embodiments, the heterocycloalkyl group has 1 to about 4, 1 to about 3, or 1 to 2 heteroatoms. In some embodiments, the heterocycloalkyl group contains 0 to 3 double bonds. In some embodiments, the heterocycloalkyl group contains 0 to 2 triple bonds.

As used herein, "halo" or "halogen" includes fluoro, chloro, bromo, and iodo.

As used herein, "alkoxy" refers to an —O-alkyl group. Example alkoxy groups include methoxy, ethoxy, propoxy (e.g., n-propoxy and isopropoxy), t-butoxy, and the like.

As used herein, "haloalkoxy" refers to an —O-haloalkyl group. An example haloalkoxy group is OCF$_3$.

As used herein, "cyanoalkyl" refers to an alkyl group substituted by a cyano group (CN). One example of cyanoalkyl is —CH$_2$—CN.

As used herein, "alkoxyalkoxy" refers to an alkoxy group substituted by an alkoxy group. One example of alkoxyalkoxy is —OCH$_2$CH$_2$—OCH$_3$.

As used herein, "arylalkyl" refers to a C$_{1-6}$ alkyl substituted by aryl and "cycloalkylalkyl" refers to C$_{1-6}$ alkyl substituted by cycloalkyl.

As used herein, "heteroarylalkyl" refers to a C$_{1-6}$ alkyl group substituted by a heteroaryl group, and "heterocycloalkylalkyl" refers to a C$_{1-6}$ alkyl substituted by heterocycloalkyl.

As used herein, "amino" refers to NH$_2$.

As used herein, "alkylamino" refers to an amino group substituted by an alkyl group.

As used herein, "dialkylamino" refers to an amino group substituted by two alkyl groups.

As used herein, "hydroxylalkyl" or "hydroxylalkyl" refers to an alkyl group substituted by a hydroxyl group. An example is —CH$_2$OH or —CH$_2$CH$_2$OH.

As used herein, "alkoxyalkyl" refers to an alkyl group substituted by an alkoxy group. One example of alkoxyalkyl is —CH$_2$—OCH$_3$.

As used here, C(O) refers to C(=O).

As used here, C(S) refers to C(=S).

As used here, S(O) refers to S(=O).

As used here, S(O)$_2$ refers to S(=O)$_2$.

As used used herein, the term "optionally substituted" means that substitution is optional and therefore includes both unsubstituted and substituted atoms and moieties. A "substituted" atom or moiety indicates that any hydrogen on the designated atom or moiety can be replaced with a selection from the indicated substituent group, provided that the normal valency of the designated atom or moiety is not exceeded, and that the substitution results in a stable compound. For example, if a methyl group (i.e., CH$_3$) is optionally substituted, then 3 hydrogen atoms on the carbon atom can be replaced with substituent groups. For another example, a substituent for an arylakyl can be on the aryl portion or the alkyl portion of the arylalkyl.

The compounds described herein can be asymmetric (e.g., having one or more stereocenters). All stereoisomers, such as enantiomers and diastereomers, are intended unless otherwise indicated. Compounds of the present invention that contain asymmetrically substituted carbon atoms can be isolated in optically active or racemic forms. Methods on how to prepare optically active forms from optically active starting materials are known in the art, such as by resolution of racemic mixtures or by stereoselective synthesis. Many geometric isomers of olefins, C=N double bonds, and the like can also be present in the compounds described herein, and all such stable isomers are contemplated in the present invention. Cis and trans geometric isomers of the compounds of the present invention are described and may be isolated as a mixture of isomers or as separated isomeric forms. Where a compound capable of stereoisomerism or geometric isomerism is designated in its structure or name without reference to specific R/S or cis/trans configurations, it is intended that all such isomers are contemplated.

Resolution of racemic mixtures of compounds can be carried out by any of numerous methods known in the art. An example method includes fractional recrystallization using a chiral resolving acid which is an optically active, salt-forming organic acid. Suitable resolving agents for fractional recrystallization methods are, for example, optically active acids, such as the D and L forms of tartaric acid, diacetyltartaric acid, dibenzoyltartaric acid, mandelic acid, malic acid, lactic acid or the various optically active camphorsulfonic acids such as β-camphorsulfonic acid. Other resolving agents suitable for fractional crystallization methods include stereoisomerically pure forms of α-methylbenzylamine (e.g., S and R forms, or diastereomerically pure forms), 2-phenylglycinol, norephedrine, ephedrine, N-methylephedrine, cyclohexylethylamine, 1,2-diaminocyclohexane, and the like.

Resolution of racemic mixtures can also be carried out by elution on a column packed with an optically active resolving agent (e.g., dinitrobenzoylphenylglycine). Suitable elution solvent composition can be determined by one skilled in the art.

Compounds of the invention also include tautomeric forms. Tautomeric forms result from the swapping of a single bond with an adjacent double bond together with the concomitant migration of a proton. Tautomeric forms include prototropic tautomers which are isomeric protonation states having the same empirical formula and total charge. Example prototropic tautomers include ketone—enol pairs, amide—imidic acid pairs, lactam—lactim pairs, enamine—imine pairs, and annular forms where a proton can occupy two or more positions of a heterocyclic system, for example, 1H- and 3H-imidazole, 1H-, 2H- and 4H-1,2,4-triazole, 1H- and 2H-isoindole, and 1H- and 2H-pyrazole. Tautomeric forms can be in equilibrium or sterically locked into one form by appropriate substitution.

Compounds of the invention further include hydrates and solvates, as well as anhydrous and non-solvated forms.

The term, "compound," as used herein is meant to include all stereoisomers, geometric iosomers, tautomers, and isotopes of the structures depicted.

All compounds and pharmaceutically acceptable salts thereof, can be prepared or present together with other substances such as water and solvents (e.g. hydrates and solvates) or can be isolated.

Compounds of the invention can also include all isotopes of atoms occurring in the intermediates or final compounds. Isotopes include those atoms having the same atomic number but different mass numbers. For example, isotopes of hydrogen include tritium and deuterium.

In some embodiments, the compounds of the invention, or salts thereof, are substantially isolated. By "substantially isolated" is meant that the compound is at least partially or substantially separated from the environment in which is formed or detected. Partial separation can include, for example, a composition enriched in the compound of the invention. Substantial separation can include compositions containing at least about 50%, at least about 60%, at least about 70%, at least about 80%, at least about 90%, at least about 95%, at least about 97%, or at least about 99% by weight of the compound of the invention, or salt thereof. Methods for isolating compounds and their salts are routine in the art.

Compounds of the invention are intended to include compounds with stable structures. As used herein, "stable compound" and "stable structure" are meant to indicate a compound that is sufficiently robust to survive isolation to a useful degree of purity from a reaction mixture, and formulation into an efficacious therapeutic agent.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The expressions, "ambient temperature" and "room temperature," as used herein, are understood in the art, and refer generally to a temperature, e.g. a reaction temperature, that is about the temperature of the room in which the reaction is carried out, for example, a temperature from about 20° C. to about 30° C.

The present invention also includes pharmaceutically acceptable salts of the compounds described herein. As used herein, "pharmaceutically acceptable salts" refers to derivatives of the disclosed compounds wherein the parent compound is modified by converting an existing acid or base moiety to its salt form. Examples of pharmaceutically acceptable salts include, but are not limited to, mineral or organic acid salts of basic residues such as amines; alkali or organic salts of acidic residues such as carboxylic acids; and the like. The pharmaceutically acceptable salts of the present invention include the conventional non-toxic salts of the parent compound formed, for example, from non-toxic inorganic or organic acids. The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile (ACN) are preferred. Lists of suitable salts are found in *Remington's Pharmaceutical Sciences,* 17th ed., Mack Publishing Company, Easton, Pa., 1985, p. 1418 and *Journal of Pharmaceutical Science,* 66, 2 (1977), each of which is incorporated herein by reference in its entirety.

The present invention also includes quaternary ammonium salts of the compounds described herein, where the compounds have one or more tertiary amine moiety. As used herein, "quaternary ammonium salts" refers to derivatives of the disclosed compounds with one or more tertiary amine moieties wherein at least one of the tertiary amine moieties in the parent compound is modified by converting the tertiary amine moiety to a quaternary ammonium cation via alkylation (and the cations are balanced by anions such as $Cl^-$, $CH_3COO^-$, or $CF_3COO^-$), for example methylation or ethylation.

The present invention also includes N-oxides of the compounds described herein. An N-oxide of a compound can be formed where the nitrogen atom of a tertiary amine moiety (including nitrogen-containing aromatic moiety) of the parent compound is oxidized to form the N-oxide.

Synthesis

Compounds of the invention, including salts thereof and N-oxides thereof and quaternary ammonium salts thereof, can be prepared using known organic synthesis techniques and can be synthesized according to any of numerous possible synthetic routes.

The reactions for preparing compounds of the invention can be carried out in suitable solvents which can be readily selected by one of skill in the art of organic synthesis. Suitable solvents can be substantially non-reactive with the starting materials (reactants), the intermediates, or products at the temperatures at which the reactions are carried out, e.g., temperatures which can range from the solvent's freezing temperature to the solvent's boiling temperature. A given reaction can be carried out in one solvent or a mixture of more than one solvent. Depending on the particular reaction step, suitable solvents for a particular reaction step can be selected by the skilled artisan.

Preparation of compounds of the invention can involve the protection and deprotection of various chemical groups. The need for protection and deprotection, and the selection of appropriate protecting groups, can be readily determined by one skilled in the art. The chemistry of protecting groups can be found, for example, in T. W. Greene and P. G. M. Wuts, *Protective Groups in Organic Synthesis*, 3$^{rd}$ Ed., Wiley & Sons, Inc., New York (1999), which is incorporated herein by reference in its entirety.

Reactions can be monitored according to any suitable method known in the art. For example, product formation can be monitored by spectroscopic means, such as nuclear magnetic resonance spectroscopy (e.g., $^1$H or $^{13}$C), infrared spectroscopy, spectrophotometry (e.g., UV-visible), mass spectrometry, or by chromatographic methods such as high performance liquid chromatography (HPLC) or thin layer chromatography (TLC).

The compounds of invention can be prepared, for example, according to the reaction pathways, synthetic procedures, and techniques described below.

A series of pyrimidin-2-amine derivatives 1-8 [wherein $R^2$ and $R^3$ together with the N atom to which they are attached form an optionally substituted 4-20 membered heterocycloalkyl group such as pyrrolidin-1-yl, 3-(methylamino)-pyrrolidin-1-yl, piperidin-1-yl, piperizin-1-yl, or 4-methyl-piperazin-1-yl; and $R^{50}$ can be an aryl or heteroaryl group, each optionally substituted with 1, 2, 3, 4, or 5 independently selected substituents such as halo, $C_{1-6}$ alkyl, $C_{1-6}$haloalkyl, OH, amino, $C_{1-6}$ cyanoalkyl, $C_{1-6}$ alkoxy, $C_{1-6}$haloalkoxy, $C_{1-6}$ alkylamino, $C_{2-8}$ dialkylamino, halo, $C_{1-6}$ alkyl, $C_{1-6}$haloalkyl, $C_{1-6}$ hydroxylalkyl, and the like] can be prepared by the method outlined in Scheme 1. A carboxylic acid 1-1 [wherein $PG^1$ is an amino protecting group such as tert-butyloxycarbonyl (Boc) or carbobenzyloxy (Cbz)] can be converted to its corresponding anhydride 1-2 by treatment with an alkyl chloroform ClC(O)OR (wherein R is alkyl such as isopropyl, isobutyl, or the like) in the presence of an organic base such as triethylamine (TEA), diisopropylethylamine (DIPEA), 4-methylmorpholine, pyridine, or the like. Anhydride 1-2 can be converted to beta-keto ester 1-3 by reacting it with alkyl acetate CH$_3$C(O)OR' [wherein R can be, for example, alkyl (e.g. methyl, ethyl, 1-propyl, isopropyl or isobutyl)] in the present of a base [such as a strong base for example, lithium bis(trimethylsilyl)amide (LiHMDS), sodium hexamethyldisilazane (NaHMDS), and lithium diisopropylamide (LDA)]. Reaction of keto-ester 1-3 with guanidine or a guanidine-producing reagent (a reagent that produces guanidine by adding an acid or a base or by heating) such as a guanidine salt (e.g. guanidine carbonate, guanidine nitrate, or guanidine HCl salt) can afford pyrimidine 1-4. The OH group of pyrimidine 1-4 can be converted to a leaving group such as —OTs (or mesylate), —OTf (triflate), or Cl by reacting pyrimidine 1-4 with TsCl (p-toluenesulfonyl chloride), or triflyl chloride, or phosphoryl chloride in the presence of a base such as a tertiary amine [e.g., triethylamine (TEA)]. Pyrimidine 1-5 with the leaving group (such as the —OTs, —OTf, or Cl) can be reacted with a suitable amine HNR$^2$R$^3$ to provides pyrimidine amine 1-6. Removal of the protecting group PG$^1$ from pyrimidine amine 1-6 affords the corresponding amine 1-7, which can be converted to pyrimidine derivative 1-8 by reaction with compound 1-7a [wherein R$^{50}$ can be, for example, an optionally substituted aryl or a substituted heteroaryl; and X$^{10}$ can be a leaving group such as triflate group (—OTf) or halo (e.g. Cl or Br)] under a suitable condition such as at an elevated temperature or in the presence of a Pd catalyst.

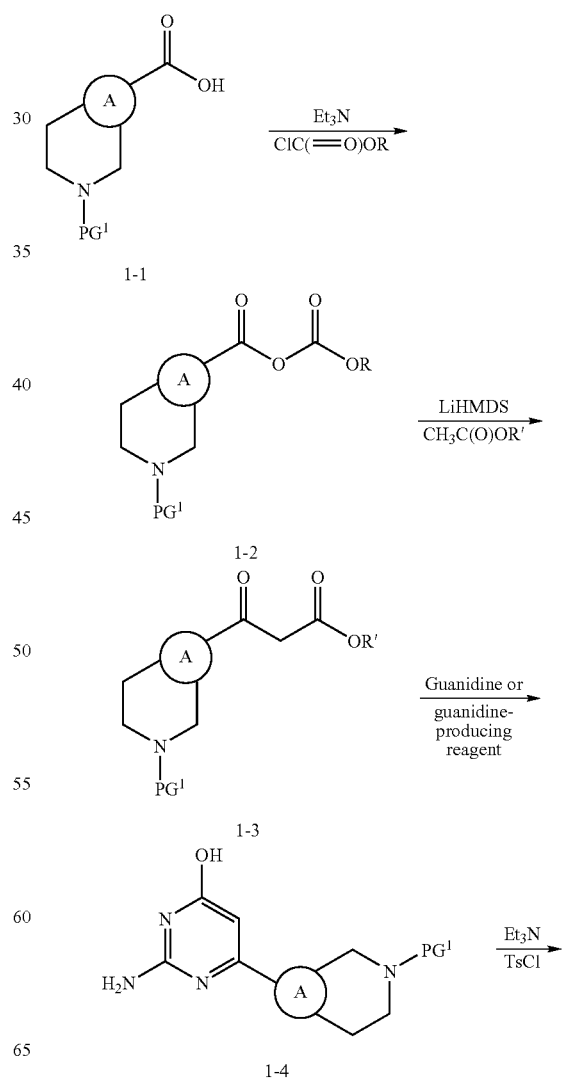

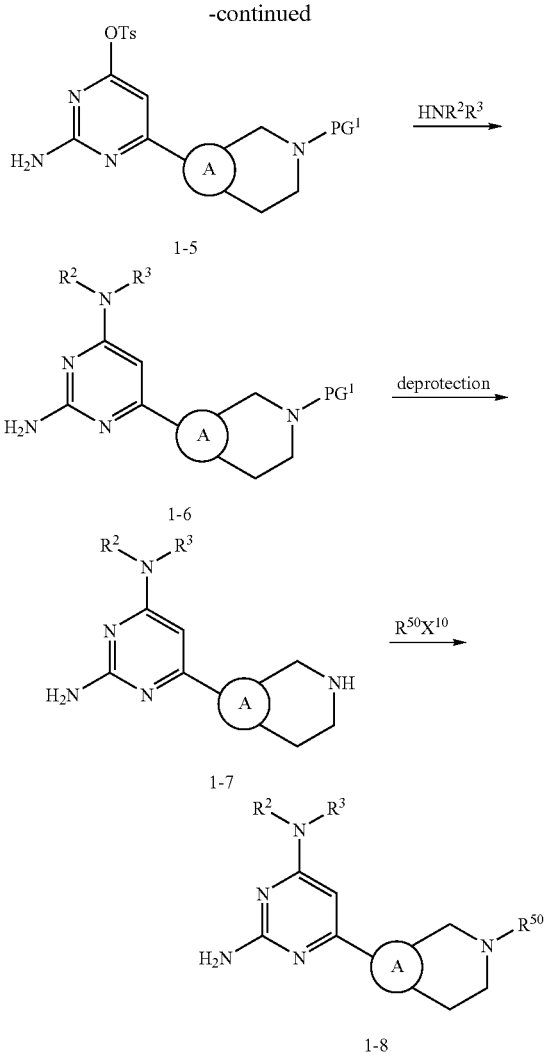

A series of pyrimidine amine derivatives 2-3, 2-5, 2-7, 2-9, 2-11, and/or 2-13 can be prepared by the methods outlined in Scheme 2. For example, compound 2-1 can be reacted with an acid of formula $R^{51}$—COOH or an activated species of the acid such as an acid halide for example acid chloride 2-2 (wherein $R^{51}$ can be —$X^2$—$Y^2$—$Z^2$, for example, optionally substituted alkyl (e.g. methyl, 2-cyanoethyl, pentafluoroethyl, isopropyl, and the like), optionally substituted cycloalkyl (e.g. cyclopropyl, 2-methyl-cyclopropyl, cyclobutyl, cyclopentyl, and the like), optionally substituted arylalkyl (e.g. benzyl, 2-phenyl-ethyl, and the like), optionally substituted heterocycloalkyl (e.g. pyrrolidin-1-yl, 3-methyl-pyrrolidin-1-yl, piperidin-1-yl, and the like), optionally substituted arylalkyl (e.g. benzyl, 2-phenyl-ethyl, and the like), optionally substituted heteroarylalkyl (e.g. pyridine-3-yl-methyl and the like), optionally substituted aryl (e.g. phenyl, 2-methylphenyl, and the like), or optionally substituted heteroaryl (e.g., pyridin-3-yl, 5-methyl-pyridin-3-yl, and the like) to afford compound 2-3. If the acid of formula $R^{51}$—COOH is reacted with amine 2-2 to provide amide 2-3, standard coupling reactions conditions can be employed, for example, in the presence of an amide coupling reagent such as benzotriazol-1-yloxytris(dimethylamino)phosphonium hexafluorophosphate (BOP), 2-(1H-benzotriazol-1-yl)-1,1,3,3-tetramethyluronium hexafluorophosphate (HBTU), O-(7-azabenzotriazol1-yl)-N,N,N',N'-tetramethyluronium hexafluorophosphate (HATU), 1-ethyl-3-(3-dimethylaminopropyl)carbodiimide (EDC), or dicyclohexylcarbodimide (DCC), and in the presence of a suitable base such as triethylamine, diisopropylethylamine, N-methylmorpholine, or N—N-dimethylaminopyridine.

Compound 2-1 can also be reacted with a haloformate such as chloroformate 2-4 [wherein $R^{52}$ can be —$X^2$—$Y^2$—$Z^2$, for example, optionally substituted alkyl (e.g. methyl, 2-cyanoethyl, pentafluoroethyl, isopropyl, and the like), optionally substituted cycloalkyl (e.g. cyclopropyl, 2-methyl-cyclopropyl, cyclobutyl, cyclopentyl, and the like), optionally substituted arylalkyl (e.g. benzyl, 2-phenyl-ethyl, and the like), optionally substituted heteroarylalkyl (e.g. pyridine-3-yl-methyl and the like), optionally substituted aryl (e.g. phenyl, 2-methylphenyl, and the like), or optionally substituted heteroaryl (e.g., pyridin-3-yl, 5-methyl-pyridin-3-yl, and the like)] to afford compound 2-5. Compound 2-1 can also be reacted with a sulfonyl halide such as sulfonyl chloride 2-6 [wherein $R^{53}$ can be —$X^2$—$Y^2$—$Z^2$, for example, optionally substituted alkyl (e.g. methyl, 2-cyanoethyl, pentafluoroethyl, isopropyl, and the like), optionally substituted cycloalkyl (e.g. cyclopropyl, 2-methyl-cyclopropyl, cyclobutyl, cyclopentyl, and the like), optionally substituted arylalkyl (e.g. benzyl, 2-phenyl-ethyl, and the like), optionally substituted heteroarylalkyl (e.g. pyridine-3-yl-methyl and the like), optionally substituted aryl (e.g. phenyl, 2-methylphenyl, and the like), or optionally substituted heteroaryl (e.g., pyridin-3-yl, 5-methyl-pyridin-3-yl, and the like)] to afford compound 2-7.

Compound 2-1 can also be reacted with a carbamic halide such as carbamic chloride 2-8 [wherein $R^{54}$ can be $R^e$, for example, H, optionally substituted $C_{1-10}$ alkyl (e.g. methyl, 2-cyanoethyl, and the like), $C_{1-6}$ haloalkyl (trifluoromethyl, difluoromethyl, pentafluoroethyl, and the like), optionally substituted cycloalkyl (e.g. cyclopropyl, 2-methyl-cyclopropyl, cyclobutyl, cyclopentyl, and the like), optionally substituted arylalkyl (e.g. benzyl, 2-phenyl-ethyl, and the like), optionally substituted heteroarylalkyl (e.g. pyridine-3-yl-methyl and the like), optionally substituted $C_{2-6}$ alkenyl(ethen-1-yl or the like), optionally substituted aryl (e.g. phenyl, 2-methylphenyl, and the like), or optionally substituted heteroaryl (e.g., pyridin-3-yl, 5-methyl-pyridin-3-yl, and the like); $R^{55}$ can be H or —$X^2$—$Y^2$—$Z^2$, for example, optionally substituted cycloalkyl (e.g. cyclopropyl, 2-methyl-cyclopropyl, cyclobutyl, cyclopentyl, and the like), optionally substituted arylalkyl (e.g. benzyl, 2-phenyl-ethyl, and the like), optionally substituted heteroarylalkyl (e.g. pyridine-3-yl-methyl and the like), optionally substituted aryl (e.g. phenyl, 2-methylphenyl, and the like), or optionally substituted heteroaryl (e.g., pyridin-3-yl, 5-methyl-pyridin-3-yl, and the like); or $R^{54}$ and $R^{55}$ together with the N atom to which they are attached form an optionally substituted heterocycloalkyl group (e.g., piperidin-1-yl, 3-methyl-piperidin-1-yl, and the like) or an optionally substituted heteroaryl group (e.g., M-pyrrol-1-yl, 3-methyl-M-pyrrol-1-yl, and the like)] to afford compound 2-9. Compound 2-1 can also be reacted with an isocyanide 2-10 (wherein $R^{56}$ can be —$X^2$—$Y^2$—$Z^2$, for example, optionally substituted alkyl (e.g. methyl, 2-cyanoethyl, pentafluoroethyl, isopropyl, and the like), optionally substituted cycloalkyl (e.g. cyclopropyl, 2-methyl-cyclopropyl, cyclobutyl, cyclopentyl, and the like), optionally substituted arylalkyl (e.g. benzyl, 2-phenyl-ethyl, and the like), optionally substituted heteroarylalkyl (e.g. pyridine-3-yl-methyl and the like), optionally substituted aryl (e.g. phenyl, 2-methylphenyl, and the like), or optionally substituted heteroaryl (e.g., pyridin-3-yl, 5-methyl-pyridin-3-yl, and the like) to afford compound 2-11 under suitable conditions.

Compound 2-1 can also be reacted with an aryl or heteroaryl compound 2-12 [wherein $R^{57}$ can be optionally substituted aryl (e.g. phenyl, 2-methylphenyl, 4-cyanophenyl, and the like) or optionally substituted hetero aryl (e.g., pyridin-3-yl, 5-methyl-pyridin-3-yl, 4-cyano-pyridin-3-yl, 5-(4-cyanophenyl)pyridin-2-yl, and the like); and and $X^{30}$ can be a leaving group such as halo (e.g. F, Cl or Br) or triflate group (—OTf)] to afford compound 2-12 under suitable conditions such as in the presence of an organic base (e.g. TEA DIPEA, or 4-methylmorpholine) or those for palladium catalyzed amination reactions [See e.g. J. P. Wolfe, et. al.; "Simple, Efficient Catalyst System for the Palladium-Catalyzed Amination of Aryl Chlorides, Bromides, and Triflates"; J. Org. Chem., 2000, 65 (4), pp 1158-1174.].

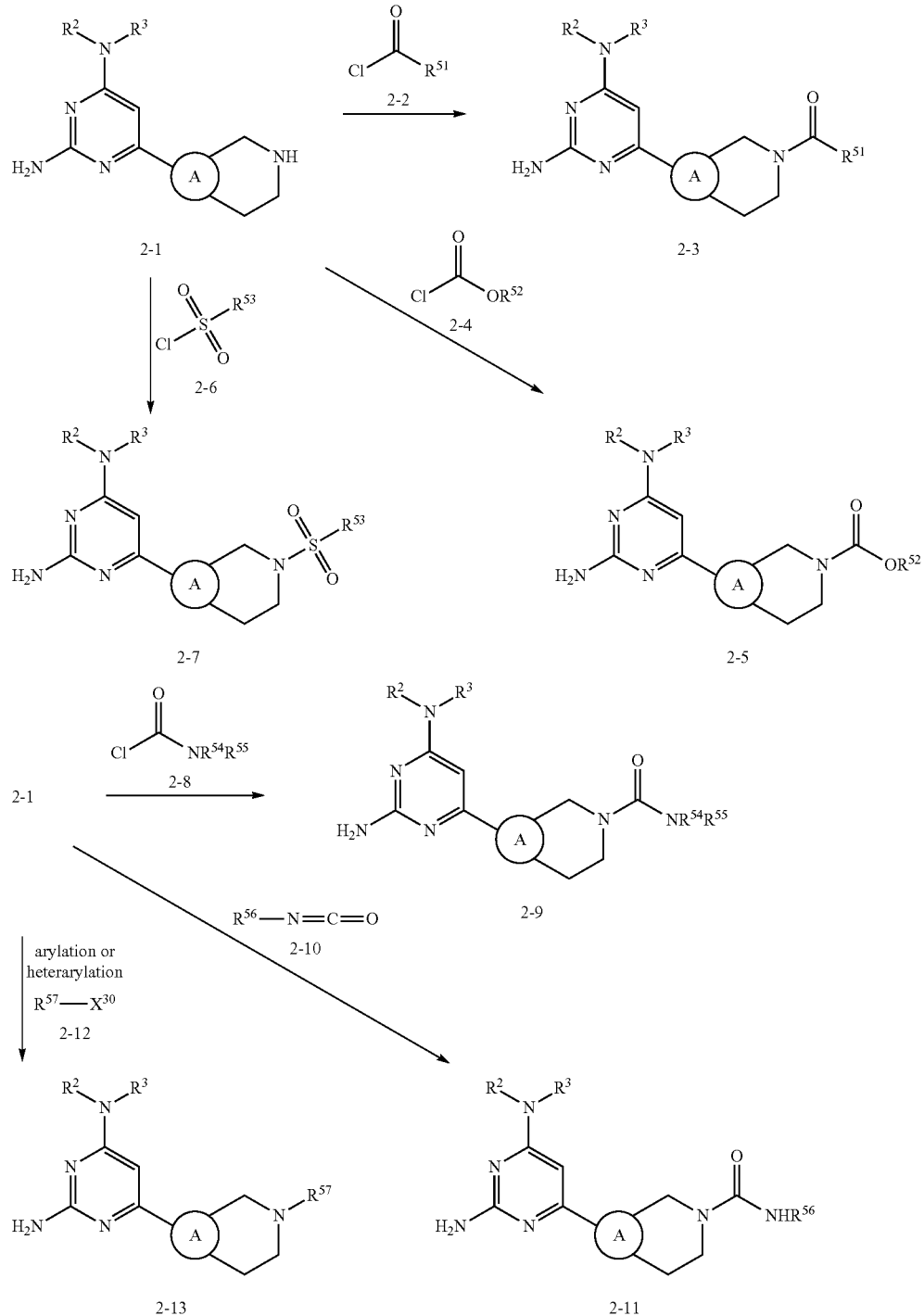

Scheme 2

Alternatively, pyrimidine amines 3-6 (same as compounds 1-7 or 2-1) can be prepared by the method outlined in Scheme 3. Chloropyrimidine amine 3-2 can be obtained by reacting commercially available 4,6-dichloropyrimidin-2-amine 3-1 with amine $HNR^2R^3$. Compound 3-3 [wherein $PG^2$ is an amino protecting group such as tert-butyloxycarbonyl (Boc) or carbobenzyloxy (Cbz); and $X^{21}$ can be a leaving group such as triflate group (—OTf) or halo (e.g. Cl or Br)] can be reacted with a suitable boron reagent such as $(R^{61}O)(R^{62}O)$B—B$(OR^{61})(OR^{62})$ [wherein $R^{61}$ and $R^{62}$ are each, independently, H or $C_{1-6}$ alkyl; or B$(OR^{61})(OR^{62})$ together form a 4-9 membered heterocycloalkyl optionally substituted with one or more $C_{1-6}$ alkyl] to afford the boronic acid or ester 3-4. Suzuki coupling of chloropyrimidine amine 3-2 with the boronic acid or ester 3-4 affords compound 3-5. Removal of the protecting group $PG^2$ from the compound 3-5 under suitable conditions can afford amine 3-6, which can undergo similar chemical transformation to those shown in Scheme 2.

Scheme 4

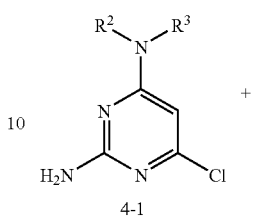

4-1

Scheme 3

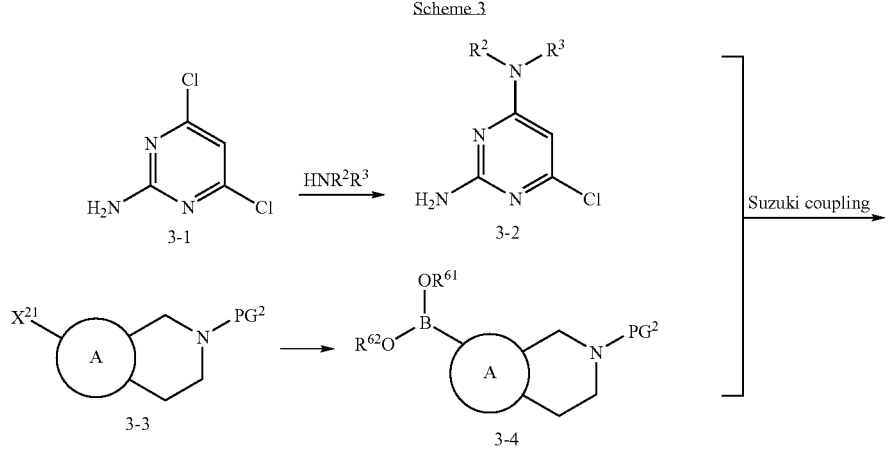

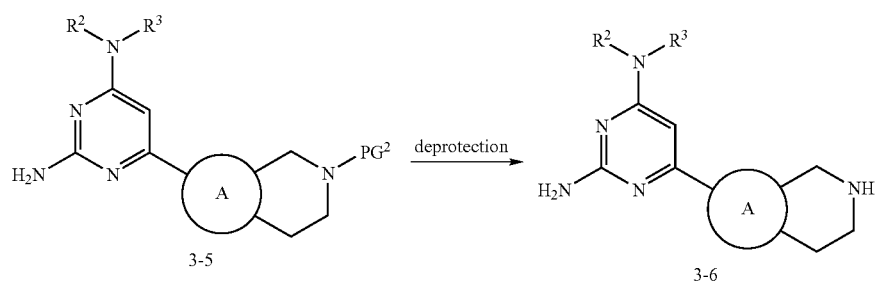

Alternatively, pyrimidine amines 4-4 (same as compounds 1-7, 2-1, or 3-6) can be prepared by the method outlined in Scheme 4. Suzuki coupling of chloropyrimidine amine 4-1 with the boronic acid or ester 4-2 [wherein $R^{61}$ and $R^{62}$ are each, independently, H or $C_{1-6}$ alkyl; or B$(OR^{61})(OR^{62})$ together form a 4-9 membered heterocycloalkyl optionally substituted with one or more $C_{1-6}$ alkyl] affords compound 4-3. Hydrogenation of compound 4-3 under suitable conditions (such as in the presence of Pd/C catalyst) can afford pyrimidine amine 4-4.

-continued

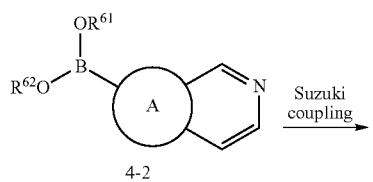

4-2

-continued

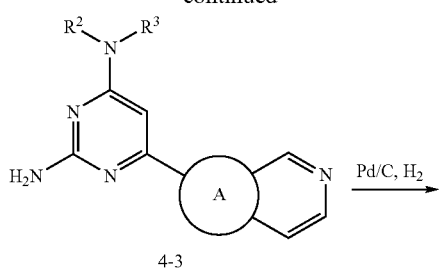

4-3

Pd/C, H₂

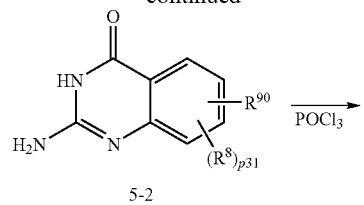

5-2

POCl₃

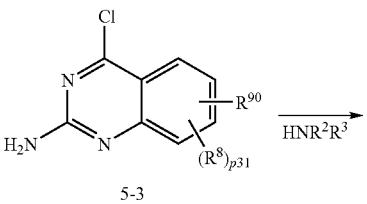

5-3

HNR²R³

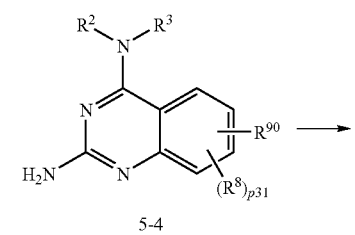

5-4

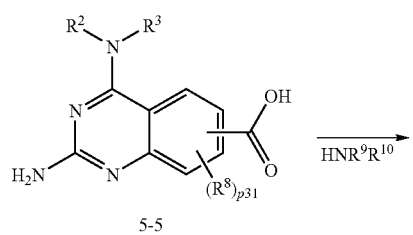

5-5

HNR⁹R¹⁰

4-4

Compounds of Formula XI wherein ring C is an optionally substituted benzene ring can be prepared by the method outlined in Scheme 5. Compound 5-1 [wherein $R^{91}$ can be H, alkyl, or the like; each $R^8$ can be halo, alkyl, haloalkyl, alkoxy, haloalkoxy, or the like; $R^{90}$ can be CN, —COOH, —COO-(alkyl), —COO-(aralkyl), —CONR⁹R¹⁰, or another functional group that can be converted to COOH; and p31 can be, for example, 0, 1, 2, or 3] can be reacted with cyanamide (H₂NCN) in a solvent such as acetonitrile in the presence of an acid (such as hydrochloric acid) at an elevated temperature to afford pyrimidone 5-2. Pyrimidone 5-2 can be treated with phosphoryl chloride at an elevated temperature to afford chloro compound 5-3, which can further be reacted with amine HNR²R³ to form compound 5-4. Where $R^{90}$ is other than —CONR⁹R¹⁰, for example, where $R^{90}$ is CN, —COO-(alkyl), or —COO-(aralkyl), it can be converted to COOH (as in compound 5-5) by suitable methods such as hydrolysis (for example, saponification methods well known in the literature, i.e., hydrolysis of an ester under basic condition; or CN can be hydrolyzed to form COOH under acidic conditions). Reaction of acid 5-5 with amine HNR⁹R¹⁰ [R⁹ and R¹⁰ are each, independently, selected from, for example, H or $C_{1-6}$ alkyl; or R⁹ and R¹⁰ together with the N atom to which they are attached form a 4-14 membered heterocycloalkyl group such as piperidinyl or pyrrolidinyl] under standard coupling reaction conditions, for example, in the presence of an amide coupling reagent such as benzotriazol-1-yloxytris(dimethylamino)phosphonium hexafluorophosphate (BOP), and in the presence of a suitable base such as triethylamine, affords compound 5-6.

Scheme 5

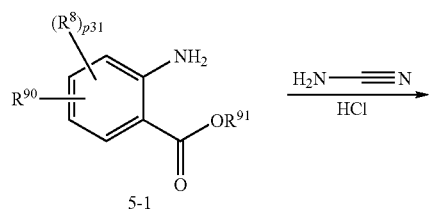

5-1

H₂N—C≡N
HCl

A series of tyrosine derivatives 6-4 can be prepared by the method outlined in Scheme 6. An appropriately protected tyrosine compound 6-1 [wherein $R^{12}$ is an alkyl (e.g. methyl or ethyl); and Pr is an amine protecting group such as tert-butyloxycarbonyl (Boc) or carbobenzyloxy (Cbz)] may be reacted with a compound of formula R-Lg [wherein R is, for example, alkyl, arylmethyl, or heteroarylmethyl; and Lg is halide, tosylate or a similar leaving group] in a solvent such as DMF, actonitrile or THF using a base such as potassium carbonate or sodium hydride to give compound 6-2 [wherein R is an alkyl, arylmethyl, or heteroarylmethyl]. The protecting group Pr of compound 6-2 can be removed under suitable conditions known to those in the art of organic synthesis. For example, where Pr on compound 6-2 is Boc, it can be removed in the presence of trifluoroacetic acid in methylene chloride or HCl in dioxane to give the amine compound 6-3. Amine compound 6-3 can be coupled to the carboxylic acid 5-5 as previously described in Scheme 5 to give the substituted compound 6-4.

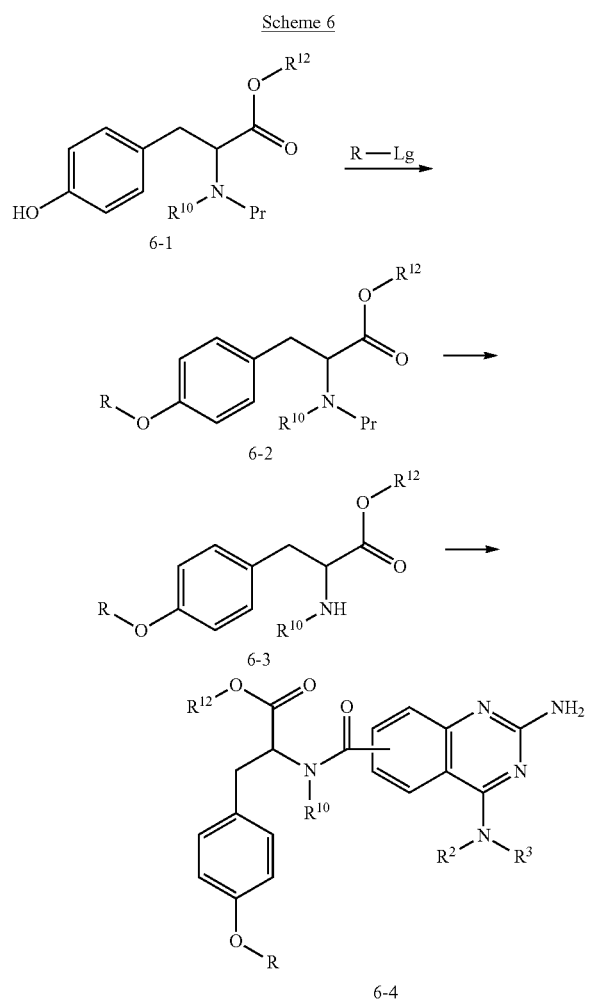

Amide compound 7-5 can be prepared as outlined in Scheme 7. An optionally substituted compound 7-1 [wherein $R^{10}$ can be, for example, H or alkyl (e.g. methyl or ethyl); and Pr is an amine protecting group such as tert-butyloxycarbonyl (Boc) or carbobenzyloxy (Cbz)] can be reacted with an alkali base (for example, lithium, sodium or potassium hydroxide) in methanol and water to give the carboxylic acid compound 7-2. The amide compound 7-3 can be prepared from the carboxylic acid 7-2 and optionally substituted amine $R^{21}R^{22}NH[R^{21}$ and $R^{22}$ are each, independently, selected from, for example, H, methyl, ethyl, benzyl or the like; or $R^{21}$ and $R^{22}$ together with the N atom to which they are attached form a 4-14 membered heterocycloalkyl group such as piperidinyl or pyrrolidinyl] using standard coupling reactions conditions known in the literature such as benzotriazol-1-yloxytris(dimethylamino)phosphonium hexafluorophosphate (BOP), 2-(1H-benzotriazol-1-yl)-1,1,3,3-tetramethyluronium hexafluorophosphate (HBTU), O-(7-azabenzotriazoll-yl)-N,N,N',N'-tetramethyluronium hexafluorophosphate (HATU), 1-ethyl-3-(3-dimethylaminopropyl)carbodiimide (EDC), or dicyclohexylcarbodiimide (DCC), and in the presence of a suitable base such as triethylamine, diisopropylethylamine, N-methylmorpholine, or N—N-dimethylaminopyridine in a solvent like DMF, methylene chloride or THF. The protecting group Pr of compound 7-3 can be removed under suitable conditions known to those in the art of organic synthesis. For example, where Pr on compound 7-3 is Boc, it can be removed in the presence of trifluoroacetic acid in methylene chloride or HCl in dioxane to give the corresponding amine, which can be coupled to the carboxylic acid 5-5 as previously described in Scheme 5 to give the compound 7-4.

Alternatively compound 7-5 can be prepared by treating compound 7-3 (wherein $R^{21}$ and $R^{22}$ are both H) with a reagent such as trichloroacetic anhydride in methylene chloride and a base such as triethylamine Compound 7-6 can be prepared by the method similar to that for making compound 7-4.

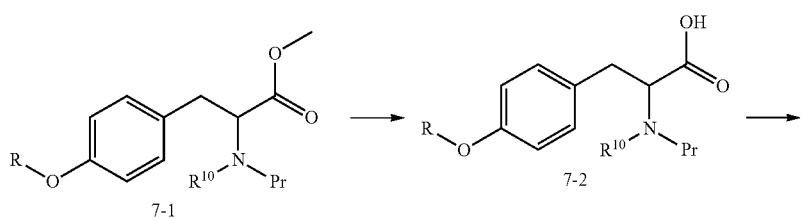

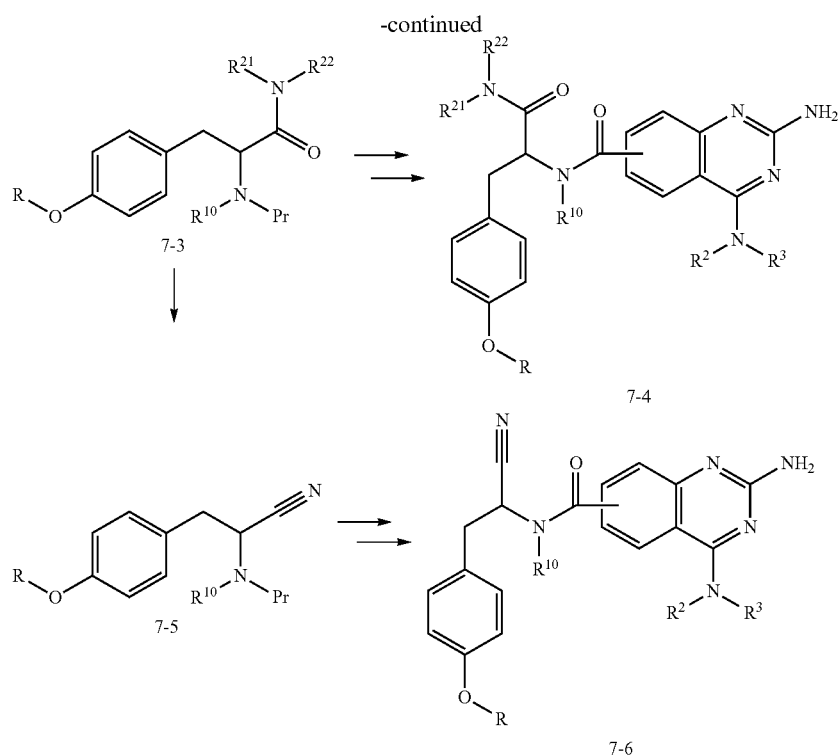

7-3

7-4

7-5

7-6

Amine compounds 8-3 and 8-5 (wherein ring B is aryl or heteroaryl) can be prepared as outlined in Scheme 8. Compound 8-1 can be prepared from an optionally substituted tyrosine compound 8-0 [wherein $R^{10}$ can be, for example, H or alkyl (e.g. methyl or ethyl); and Pr is an amine protecting group such as tert-butyloxycarbonyl (Boc) or carbobenzyloxy (Cbz)] by treating it with trifluoromethanesulfonic acid anhydride in a solvent like methylene chloride with a base such as N,N-diisopropylethylamine. Compound 8-2 (wherein ring B1 is an optionally substituted aryl or heteroaryl) can be prepared by Suzuki methods which are well known in the literature by reacting Compound 8-1 with an optionally substituted boronic acid (i.e. wherein ring B1 is optionally substituted by 1, 2, 3, 4, or 5 substituents such as alkyl, alkoxy, haloalkyl, haloalkoxy, or the like) or ester in a solvent such as dioxane or THF and water with sodium or potassium carbonate and a palladium catalyst such as tetrakis(triphenylphosphine)palladium at an elevated temperature. The protecting group Pr of compound 8-2 can be removed under suitable conditions known to those in the art of organic synthesis. For example, where Pr on compound 8-2 is Boc, it can be removed in the presence of trifluoroacetic acid in methylene chloride or HCl in dioxane to give the corresponding amine, which can be coupled to the carboxylic acid 5-5 as previously described in Scheme 5 to afford amide 8-4.

Carboxylic acid compound 8-5 can be prepared by treating Compound 8-3 with an alkali base such as lithium, sodium, or potassium hydroxide in methanol and water. Amide compound 8-6 can be prepared from the carboxylic acid 8-5 and an optionally substituted amine $R^{21}R^{22}NH$ [$R^{21}$ and $R^{22}$ are each, independently, selected from, for example, H, methyl, ethyl, benzyl or the like; or $R^{21}$ and $R^{22}$ together with the N atom to which they are attached form a 4-14 membered heterocycloalkyl group such as piperidinyl or pyrrolidinyl], using standard coupling reactions conditions known in the literature and previously described. The protecting group Pr of compound 8-6 can be removed under suitable conditions known to those in the art of organic synthesis to afford the corresponding amine, which can be coupled to the carboxylic acid 5-5 as previously described in Scheme 5.

Scheme 8

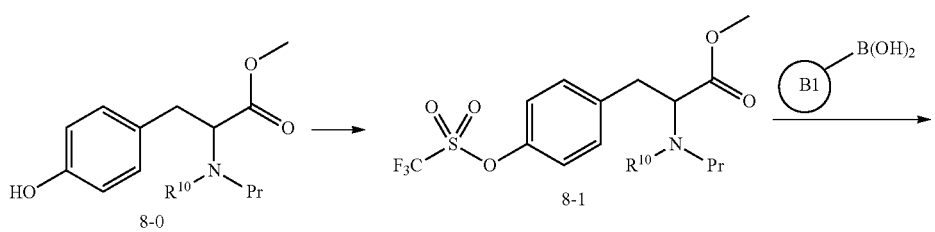

8-0

8-1

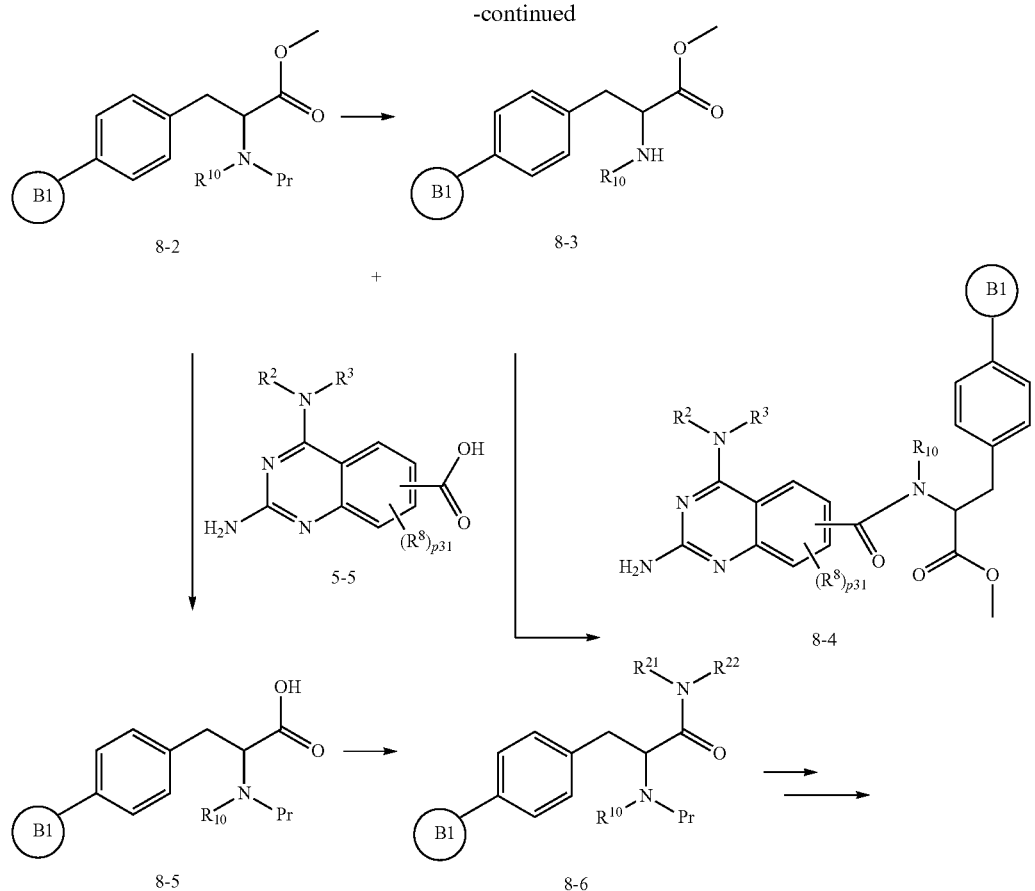

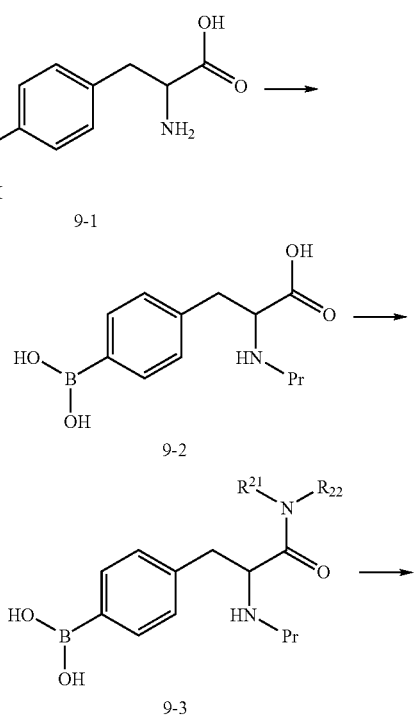

Scheme 9

Compound 9-4 wherein ring B1 is aryl or heteroaryl may be prepared as outlined in Scheme 9. The amino group of Compound 9-1 can be protected by an appropriate amine protecting group. For example, N-Boc protected boronic acid compound 9-2 can be prepared by reacting a commercially available boronic acid carboxylic acid compound 9-1 with di-tert-butyldicarbonate in a mixture of solvents such as THF and water at ambient temperature. The amide compound 9-3 can be prepared by reacting carboxylic acid boronic acid compound 9-2 with an optionally substituted amine $R^{21}R^{22}NH$ [$R^{21}$ and $R^{22}$ are each, independently, selected from, for example, H, methyl, ethyl, benzyl or the like; or $R^{21}$ and $R^{22}$ together with the N atom to which they are attached form a 4-14 membered heterocycloalkyl group such as piperidinyl or pyrrolidinyl], using standard coupling reactions conditions known in the literature.

Compound 9-4 (wherein ring B1 is an optionally substituted aryl or heteroaryl) can be prepared using Suzuki methods well known in the literature by reacting boronic acid 9-3 with an optionally substituted aryl or heteroaryl bromide, iodide or tosylate in a solvent such as dioxane, and water with sodium or potassium carbonate and a palladium catalyst like tetrakis(triphenylphosphine)palladium at elevated temperature. The protecting group Pr can be removed and the resulting amine compound can be coupled to carboxylic acid 5-5 as previously described in Scheme 5.

-continued

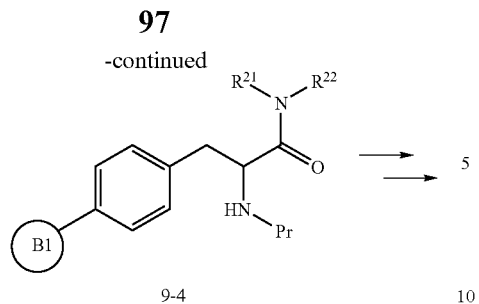

9-4

A series of amine derivatives 10-6 wherein ring B1 is an optionally substituted cycloalkyl, cycloheteroalkyl, aryl or heteroaryl group (wherein each R is independently, for example, alkyl, halo, haloakyl, alkoxy, haloalkoxy, and the like; n11 is, for example, 0, 1, 2, 3, 4, or 5; and R" is, for example, H, alkyl, and the like) can be prepared by the method outlined in Scheme 10. The α,β-unsaturated compound 10-2 can be prepared through a Wittig-Horner reaction by treatment of an optionally substituted cycloalkyl, cycloheteroalkyl, aryl or heteroaryl aldehyde or ketone compound 10-1 with Boc-α-phosphonoglycine trimethyl ester or other triphenylphosphine or phosphonate reagents in a solvent such as methylene chloride using a base such as 1,8-Diazabicyclo [5.4.0]undec-7-ene (DBU). Hydrogenation of the α,β-unsaturated compound 10-2 in the presence of a catalyst such as palladium on carbon or platinum oxide can afford the corresponding amino ester derivative 10-3, the ester group of which can be hydrolyzed to afford acid 10-4. The amide compound 10-5 can be prepared by reacting carboxylic acid compound 10-4 with an optionally substituted amine $R^{21}R^{22}NH[R^{21}$ and $R^{22}$ are each, independently, selected from, for example, H, methyl, ethyl, benzyl or the like; or $R^{21}$ and $R^{22}$ together with the N atom to which they are attached form a 4-14 membered heterocycloalkyl group such as piperidinyl or pyrrolidinyl], using standard coupling reactions conditions known in the literature. The protecting group BOC of compound 10-5 can be removed under acidic condition (for example, by TFA in methylene chloride or HCl in dioxane) and the resulting amine compound 10-6 can be coupled to carboxylic acid 5-5 as previously described in Scheme 5.

Scheme 10

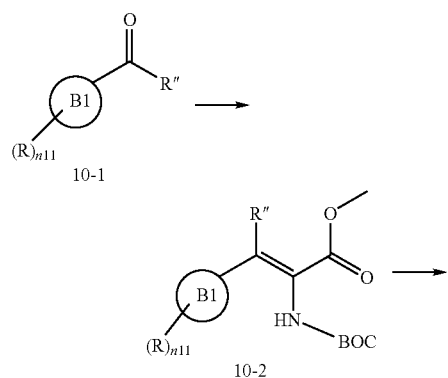

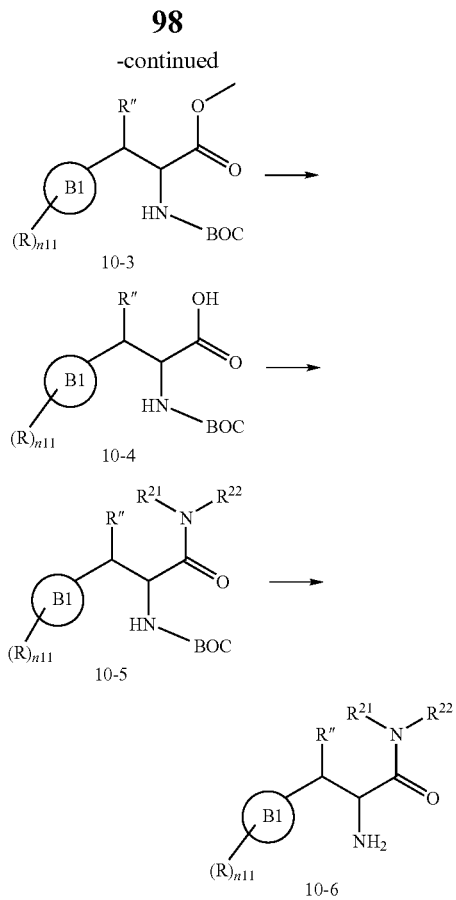

A series of amine derivatives 11-4 wherein ring B1 is an optionally substituted cycloalkyl, cycloheteroalkyl, aryl or heteroaryl group (wherein each R is independently, for example, alkyl, halo, haloalkyl, alkoxy, haloalkoxy, and the like; and n11 is, for example, 0, 1, 2, 3, 4, or 5) can be prepared by the method outlined in Scheme 11. α,β-Unsaturated nitro derivatives 11-3 can be prepared by condensation of an optionally substituted cycloalkyl, cycloheteroalkyl, aryl or heteroaryl, aldehyde or ketone 11-1 (wherein R" is, for example, H, alkyl, haloalkyl, arylalkyl, or the like) with the alkyl nitro compound 11-2 (wherein $R^a$ is, for example, H, alkyl, haloalkyl, arylalkyl, or the like) in a solvent like acetic acid and a base like cyclohexylamine, at elevated temperature. Reduction of the nitro group and the double bond in 11-3 to the corresponding amine derivative 11-4 can be achieved by hydrogenation in the presence of a suitable catalyst or by reaction with a reductive agent such as lithium aluminium hydride. The amine 11-4 can be coupled to carboxylic acid 5-5 as previously described in Scheme 5.

Scheme 11

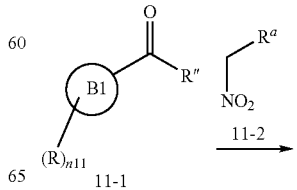

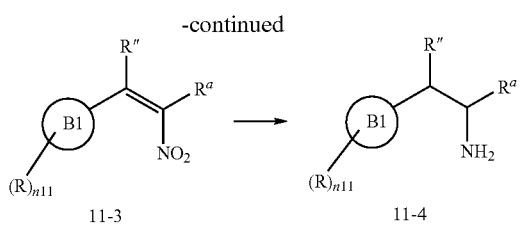

A series of amine 12-5 wherein ring B1 is an optionally substituted cycloalkyl, cycloheteroalkyl, aryl, or heteroaryl group (wherein each R is independently, for example, alkyl, halo, haloalkyl, alkoxy, haloalkoxy, and the like; and n11 is, for example, 0, 1, 2, 3, 4, or 5) and wherein ring C1 is an optionally substituted aryl or heteroaryl group (wherein each R is independently, for example, alkyl, halo, haloalkyl, alkoxy, haloalkoxy, and the like; and n12 is, for example, 0, 1, 2, 3, 4, or 5) can be prepared by the methods outlined in Scheme 12. The compound 12-2 can be prepared from the carboxylic acid 12-1 and N,O-dimethylhydroxylamine by methods previously described for amide forming reactions. Ketone 12-3 can be produced by reaction of the compound 12-2 with a magnesium or lithium heteroaryl such as thiazole or oxazole or phenyl magnesium or lithium reagent, generated at low temperatures with isopropyl magnesium chloride, n-butyl lithium, t-butyl lithium or LDA and an aryl or heteroaryl halide compound (such as a bromide compound) in a solvent such as THF. Reaction of ketone 12-3 with hydroxylamine or its salt (such as hydroxylamine hydrochloride) in a solvent such as ethanol and in the presence of a base such as sodium acetate at elevated temperatures can yield the corresponding oxime compound 12-4, which can be transformed to the corresponding amine derivative 12-5 (wherein $R^{10}$ is H) by reduction of the oxime group of compound 12-4 in acetic acid with zinc metal at room temperature or elevated temperatures. Alternatively, amine compound 12-5 (wherein $R^{10}$ can be, for example, H, alkyl, or the like) can be prepared by reductive amination of the carbonyl compound 12-3 with an appropriately substituted amine $R^{10}$—$NH_2$ in a solvent such as dioxane, toluene, or acetic acid with a reducing agent such as triacetoxyborohydride or sodium borohydride at ambient temperature to elevated temperature.

A series of amine derivatives 13-7 can be prepared by methods outlined in Scheme 13 Amine 13-3 can be prepared by reaction of ketone 13-1 (wherein n is, for example, 0, 1, 2, or 3) with hydroxylamine or its salt (such as hydroxylamine hydrochloride) followed by reduction of the oxime group of compound 13-2 as previously described. Protecting the amino group of 13-3 can afford the corresponding compound 13-4 [wherein the protecting group Pr is an amine protecting group such as tert-butyloxycarbonyl (Boc) or carbobenzyloxy (Cbz)]. The ether derivative 13-5 [where $R^x$ is, for example, an optionally substituted alkyl, cycloalkyl, aryl, heteroaryl, arylalkyl, or heteroarylalkyl] can be prepared by treatment of the phenol 13-4 with an optionally substituted alkyl/cycloalkyl/aryl/heteroaryl bromide or mesylate, activated aryl fluoride, heteroaryl bromide or chloride in the presents of a base such as potassium carbonate, cesium carbonate or sodium hydride in a solvent such as DMF or acetonitrile at elevated temperature. Removal of the protecting group Pr in 13-5 can afford the amine 13-6, which can be coupled to carboxylic acid 5-5 as previously described.

Scheme 13

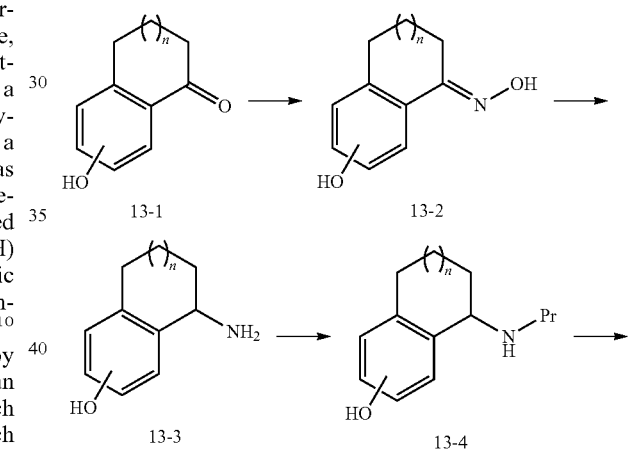

Scheme 12

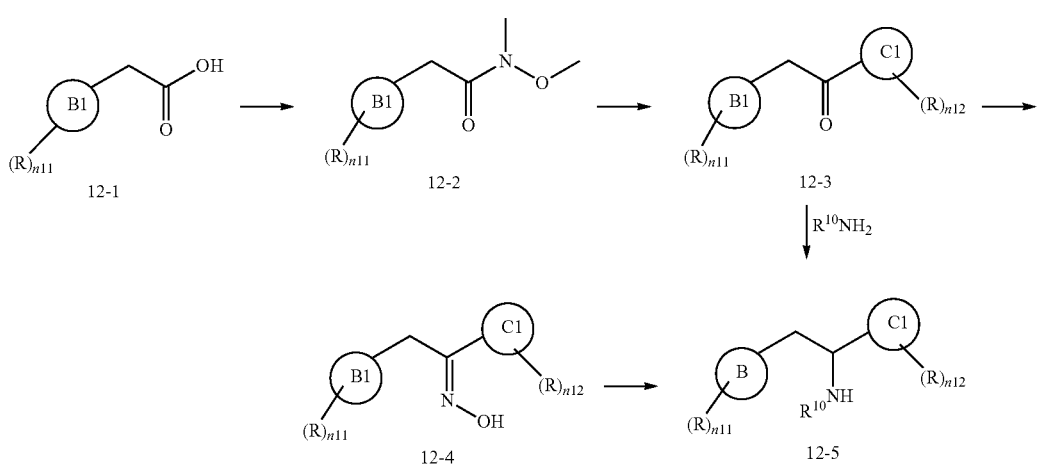

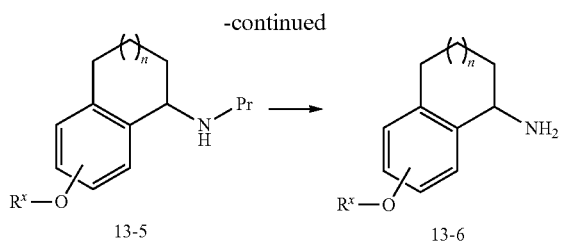

13-5    13-6

A series of tetrahydroisoquinoline derivatives 14-2 (wherein each R is independently, for example, alkyl, halo, haloalkyl, alkoxy, haloalkoxy, and the like; and n11 is, for example, 0, 1, 2, 3, 4, or 5) can be prepared by the methods outlined in Scheme 14. Hydrogenation of isoquinoline 14-1 in the presence of a catalyst such as platinum dioxide in acetic acid at elevated hydrogen pressure can afford tetrahydroisoquinoline 14-2, which can be coupled to carboxylic acid 5-5 as previously described.

Scheme 14

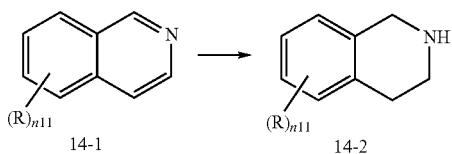

14-1    14-2

Additional starting materials and intermediates useful for making the compounds of the present invention can be obtained from chemical vendors such as Sigma-Aldrich or can be made according to methods described in the chemical art. For example, introducing pentafluorosulfanyl ($SF_5$) group to aromatic rings can be achieved according to the methods disclosed in U.S. Pat. No. 6,919,484 and/or the references cited therein.

Those skilled in the art can recognize that in all of the schemes described herein, if there are functional (reactive) groups present on a substituent group such as $X^2, Y^2, Z^2, R^{51}$, $R^{52}, R^{53}, R^{54}, R^{55}, R^{56}, R^{57}$, etc., further modification can be made if appropriate and/or desired. For example, a CN group can be hydrolyzed to afford an amide group or a carboxylic acid group; a carboxylic acid can be converted to an amide [for example, by standard coupling reactions with another amine (such as in the presence of an amide coupling reagent such BOP, HBTU, HATU, EDC, or DCC), and in the presence of a suitable base such as triethylamine, diisopropylethylamine, N-methylmorpholine, or N—N-dimethylaminopyridine]; a carboxylic acid can be converted to an ester, which in turn can be reduced to an alcohol, which in turn can be further modified. For another example, an OH group can be converted into a better leaving group such as mesylate, which in turn is suitable for nucleophilic substitution, such as by CN. For another example, an —S— can be oxidized to —S(O)— and/or —S(O)$_2$—. For yet another example, unsaturated bond such as C=C or C≡C can be reduced to saturated bond by hydrogenation. In some embodiments, a primary amine or a secondary amine moiety (present on a part of the compound of invention such as on ring B) can be converted to amide, sulfonamide, urea, or thiourea moiety by reacting it with an appropriate reagent such as an acid chloride, a sulfonyl chloride, an isocyanate, or a thioisocyanate compound. In some embodiments, a primary amine, a secondary amine, or a tertiary amine moiety (such as those present on part of the compound of invention such as on ring B) can be alkylated to form a quaternary ammonium salt. One skilled in the art will recognize further such modifications. Thus, a compound of Formula I (such as compound 2-3, 2-5, 2-7, 2-9, 2-11, or 2-13 of Scheme 2) or a compound of Formula XI (such as compound 5-6 of Scheme 5) having a substituent which contains a functional group can be converted to another compound of Formula I or XI having a different substituent group.

As used herein, the term "reacting" refers to the bringing together of designated chemical reactants such that a chemical transformation takes place generating a compound different from any initially introduced into the system. Reacting can take place in the presence or absence of solvent.

Methods

Compounds of the invention (including pharmaceutically acceptable salts thereof or N-oxides thereof or quaternary ammonium salts thereof) and/or compositions thereof, can modulate activity of histamine H4 receptor. The term "modulate" is meant to refer to an ability to increase or decrease activity of a histamine H4 receptor. Accordingly, compounds of the invention can be used in methods of modulating a histamine H4 receptor by contacting the histamine H4 receptor with any one or more of the compounds (or pharmaceutically acceptable salts thereof or N-oxides thereof or quaternary ammonium salts thereof) or compositions described herein. In some embodiments, compounds of the present invention can act as inhibitors (or antagonists) of histamine H4 receptor. In further embodiments, the compounds of the invention can be used to modulate activity of a histamine H4 receptor in an individual in need of modulation of the receptor by administering a modulating amount of a compound of the invention.

In some embodiments, one or more of the compounds of the invention can be used in treating a condition or disease or disorder in a patient, wherein the condition or disease or disorder is associated with histamine H4 receptor (for example, associated with expression of histamine H4 receptor or mediated by activity of histamine H4 receptor). In some embodiments, the condition or disease or disorder associated with expression of histamine H4 receptor or mediated by activity of histamine H4 receptor is selected from an inflammatory disease or disorder, pruritus/pruritis, and pain. In some embodiments, the condition or disease or disorder associated with expression of histamine H4 receptor or mediated by activity of histamine H4 receptor is selected from rhinitis, asthma, rheumatoid arthritis, atopic dermatitis, idiopathic chronic urticaria, inflammatory pain, and neuropathic pain.

In some embodiments, examples of the condition or disease or disorder histamine H4 receptor include inflammatory disorders (inflammation), allergic disorders (allergy), dermatological disorders, rheumatoid arthritis, asthma, pruritis, autoimmune diseases, lymphatic disorders, and immunodeficiency disorders. See e.g. WO 2008008359 and WO 2008100565. In some embodiments, examples condition or disease or disorder associated with histamine H4 receptor include allergy, asthma, chronic obstructed pulmonary disease (COPD), atherosclerosis, rheumatoid arthritis, multiple sclerosis, inflammatory bowel diseases, colitis, Crohn's disease, ulcerative colitis, psoriasis, pruritis, itchy skin, atopic dermatitis, urticaria, hives, ocular inflammation, conjunctivitis, dry eye, nasal polyps, allergic rhinitis, nasal itch, scleroderma, autoimmune thyroid diseases, immune-mediated diabetes mellitus, lupus, Myasthenia gravis, autoimmune neuropathies, Guillain-Barre, autoimmune uveitis, autoimmune hemolytic anemia, pernicious anemia, autoimmune thrombocytopenia, temporal arteritis, anti-phospholipid syndrome, vasculitides, Wegener's granulomatosis, Behcet's disease, dermatitis herpetiformis, pemphigus vulgaris, vitiligio, primary biliary cirrhosis, autoimmune hepatitis, autoimmune oophoritis, autoimmune orchitis, autoimmune disease of the adrenal gland, polymyositis, dermatomyositis, spondyloarthropathies, ankylosing spondylitis, and Sjogren's syndrome. See WO 2008008359.

In some embodiments, examples condition or disease or disorder associated with histamine H4 receptor include allergy, rheumatoid arthritis, asthma, autoimmune diseases, and pruritis. See WO 2008100565. In some embodiments, examples condition or disease or disorder associated with histamine H4 receptor include inflammatory diseases, respiratory diseases (e.g. adult respiratory distress syndrome, acute respiratory distress syndrome, bronchitis, chronic bronchitis, chronic obstructive pulmonary disease, cystic fibrosis, asthma, emphysema, rhinitis, chronic sinusitis), allergy; allergy-induced airway responses, allergic rhinitis, viral rhinitis, non-allergic rhinitis, perennial and seasonal rhinitis, nasal congestion, allergic congestion, female and male sexual dysfunction, skin diseases such as dermatitis and psoriasis, cardiac dysfunctions such as myocardial ischaemia and arrythmia, diseases of the gastrointestinal tract such as inflammatory bowel disease, Crohn's disease and colitis ulcerosa, cancer, rheumatoid arthritis, hypotension, pain and overactive bladder conditions. See WO2007072163. Additional examples of condition or disease or disorder associated with histamine H4 receptor can be found, for example, in WO 2007117401 and WO 2005014579.

In some embodiments, one or more of the compounds of the invention can be used in combination with one or more other histamine H1, H2, H3, and/or H4 receptor inhibitors/antagonists (in particular one or more other histamine H4 receptor inhibitors/antagonists).

In some embodiments, one or more H4 receptor inhibitors/antagonists of the invention can be used in combination with one or more other therapeutics used in the treatment of histamine H4 receptor-mediated/associated conditions/diseases/disorders, and may improve the treatment response as compared to the response to the other therapeutics alone, without exacerbation of its toxic effects. Examples of the other therapeutical agents suitable for combination include, for example, H4 receptor inhibitors/antagonists such as N-Cyclohexyl-4-(1H-imidazol-4-yl)piperidine-1-carbothioamide (Thioperamide), 5-chloro-2-[(4-methylpiperazin-1-yl)carbonyl]-1H-indole (JNJ-7777120), and 5-Chloro-2-[(4-methylpiperazin-1-yl)carbonyl]-1H-benzimidazole (VUF-6002 or JNJ 10191584). Additive or synergistic effects are desirable outcomes of combining an H4 receptor inhibitors/antagonists of the present invention with one or more additional agent. The additional agents can be combined with the present compounds in a single or continuous dosage form, or the agents can be administered simultaneously or sequentially as separate dosage forms. In some embodiments, one or more additional agents can be administered to a patient in combination with at least one H4 receptor inhibitor/antagonist described herein where the additional agents are administered intermittently as opposed to continuously.

Pharmaceutical Formulations and Dosage Forms

When employed as pharmaceuticals, the compounds of the invention can be administered in the form of pharmaceutical compositions. These compositions can be prepared in a manner well known in the pharmaceutical art, and can be administered by a variety of routes, depending upon whether local or systemic treatment is desired and upon the area to be treated. Administration may be topical (including transdermal, epidermal, ophthalmic and to mucous membranes including intranasal, vaginal and rectal delivery), pulmonary (e.g., by inhalation or insufflation of powders or aerosols, including by nebulizer; intratracheal or intranasal), oral or parenteral. Parenteral administration includes intravenous, intraarterial, subcutaneous, intraperitoneal or intramuscular injection or infusion; or intracranial, e.g., intrathecal or intraventricular, administration. Parenteral administration can be in the form of a single bolus dose, or may be, for example, by a continuous perfusion pump. Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable. Coated condoms, gloves and the like may also be useful.

This invention also includes pharmaceutical compositions which contain, as the active ingredient, one or more of the compounds of the invention above in combination with one or more pharmaceutically acceptable carriers (excipients). In making the compositions of the invention, the active ingredient is typically mixed with an excipient, diluted by an excipient or enclosed within such a carrier in the form of, for example, a capsule, sachet, paper, or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders.

In preparing a formulation, the active compound can be milled to provide the appropriate particle size prior to combining with the other ingredients. If the active compound is substantially insoluble, it can be milled to a particle size of less than 200 mesh. If the active compound is substantially water soluble, the particle size can be adjusted by milling to provide a substantially uniform distribution in the formulation, e.g. about 40 mesh.

The compounds of the invention may be milled using known milling procedures such as wet milling to obtain a particle size appropriate for tablet formation and for other formulation types. Finely divided (nano particulate) preparations of the compounds of the invention can be prepared by processes known in the art, for example see International Patent Application No. WO 2002/000196.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include: lubricating agents such as talc, magnesium stearate, and mineral oil; wetting agents;

emulsifying and suspending agents; preserving agents such as methyl- and propylhydroxy-benzoates; sweetening agents; and flavoring agents. The compositions of the invention can be formulated so as to provide quick, sustained or delayed release of the active ingredient after administration to the patient by employing procedures known in the art.

The compositions can be formulated in a unit dosage form, each dosage containing from about 5 to about 1000 mg (1 g), more usually about 100 to about 500 mg, of the active ingredient. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient.

The active compound can be effective over a wide dosage range and can be generally administered in a pharmaceutically effective amount. For example, the dosage of the active compounds of the invention as employed for the treatment of a patient in need thereof (such as an adult human) may range from 0.1 to 3000 mg per day, depending on the route and frequency of administration. Such a dosage corresponds to 0.001 to 50 mg/kg per day. In some embodiments, the dosage of the active compounds of the invention as employed for the treatment of a patient in need thereof (such as an adult human) may range from 1 to 2000 mg per day, from 1 to 1000 mg per day, from 10 to 1000 mg per day, or from 10 to 500 mg per day. It will be understood, however, that the amount of the compound actually administered will usually be determined by a physician, according to the relevant circumstances, including the condition to be treated, the chosen route of administration, the actual compound administered, the age, weight, and response of the individual patient, the severity of the patient's symptoms, and the like.

For preparing solid compositions such as tablets, the principal active ingredient can be mixed with a pharmaceutical excipient to form a solid pre-formulation composition containing a homogeneous mixture of a compound of the present invention. When referring to these pre-formulation compositions as homogeneous, the active ingredient is typically dispersed evenly throughout the composition so that the composition can be readily subdivided into equally effective unit dosage forms such as tablets, pills and capsules. This solid pre-formulation is then subdivided into unit dosage forms of the type described above containing from, for example, about 0.1 to about 1000 mg of the active ingredient of the present invention.

The tablets or pills of the present invention can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid forms in which the compounds and compositions of the present invention can be incorporated for administration orally or by injection include aqueous solutions, suitably flavored syrups, aqueous or oil suspensions, and flavored emulsions with edible oils such as cottonseed oil, sesame oil, coconut oil, or peanut oil, as well as elixirs and similar pharmaceutical vehicles.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. In some embodiments, the compositions are administered by the oral or nasal respiratory route for local or systemic effect. Compositions in can be nebulized by use of inert gases. Nebulized solutions may be breathed directly from the nebulizing device or the nebulizing device can be attached to a face masks tent, or intermittent positive pressure breathing machine. Solution, suspension, or powder compositions can be administered orally or nasally from devices which deliver the formulation in an appropriate manner.

The amount of compound or composition administered to a patient will vary depending upon what is being administered, the purpose of the administration, such as prophylaxis or therapy, the state of the patient, the manner of administration, and the like. In therapeutic applications, compositions can be administered to a patient already suffering from a disease in an amount sufficient to cure or at least partially arrest the symptoms of the disease and its complications. Effective doses will depend on the disease condition being treated as well as by the judgment of the attending clinician depending upon factors such as the severity of the disease, the age, weight and general condition of the patient, and the like.

The compositions administered to a patient can be in the form of pharmaceutical compositions described above. These compositions can be sterilized by conventional sterilization techniques, or may be sterile filtered. Aqueous solutions can be packaged for use as is, or lyophilized, the lyophilized preparation being combined with a sterile aqueous carrier prior to administration. The pH of the compound preparations typically will be between 3 and 11, more preferably from 5 to 9 and most preferably from 7 to 8. It will be understood that use of certain of the foregoing excipients, carriers, or stabilizers will result in the formation of pharmaceutical salts.

The therapeutic dosage of the compounds of the present invention can vary according to, for example, the particular use for which the treatment is made, the manner of administration of the compound, the health and condition of the patient, and the judgment of the prescribing physician. The proportion or concentration of a compound of the invention in a pharmaceutical composition can vary depending upon a number of factors including dosage, chemical characteristics (e.g., hydrophobicity), and the route of administration. For example, the compounds of the invention can be provided in an aqueous physiological buffer solution containing about 0.1 to about 10% w/v of the compound for parenteral administration. Some typical dose ranges are from about 1 μg/kg to about 1 g/kg of body weight per day. In some embodiments, the dose range is from about 0.01 mg/kg to about 100 mg/kg of body weight per day. The dosage is likely to depend on such variables as the type and extent of progression of the disease or disorder, the overall health status of the particular patient, the relative biological efficacy of the compound selected, formulation of the excipient, and its route of administration. Effective doses can be extrapolated from dose-response curves derived from in vitro or animal model test systems.

The compositions of the invention can further include one or more additional pharmaceutical agents such as a chemotherapeutic, steroid, anti-inflammatory compound, or immunosuppressant, examples of which are listed hereinabove.

Labeled Compounds and Assay Methods

Another aspect of the present invention relates to labeled compounds of the invention (radio-labeled, fluorescent-labeled, etc.) that would be useful not only in radio-imaging but also in assays, both in vitro and in vivo, for localizing and quantitating the enzyme in tissue samples, including human, and for identifying ligands by inhibition binding of a labeled compound. Accordingly, the present invention includes enzyme assays that contain such labeled compounds.

The present invention further includes isotopically-labeled compounds of the invention. An "isotopically" or "radio-labeled" compound is a compound of the invention where one or more atoms are replaced or substituted by an atom having an atomic mass or mass number different from the atomic mass or mass number typically found in nature (i.e., naturally occurring). Suitable radionuclides that may be incorporated in compounds of the present invention include but are not limited to $^2$H (also written as D for deuterium), $^3$H (also written as T for tritium), $^{11}$C, $^{13}$C, $^{14}$C, $^{13}$N, $^{15}$N, $^{15}$O, $^{17}$O, $^{18}$O, $^{18}$F, $^{35}$S, $^{36}$Cl, $^{82}$Br, $^{75}$Br, $^{76}$Br, $^{77}$Br, $^{123}$I, $^{124}$I, $^{125}$I and $^{131}$I. The radionuclide that is incorporated in the radio-labeled compounds will depend on the specific application of that radio-labeled compound. For example, for in vitro receptor labeling and competition assays, compounds that incorporate $^3$H, $^{14}$C, $^{82}$Br, $^{125}$I, $^{131}$I, or $^{35}$S will generally be most useful. For radio-imaging applications $^{11}$C, $^{18}$F, $^{125}$I, $^{123}$I, $^{124}$I, $^{131}$I, $^{75}$Br, $^{76}$Br or $^{77}$Br will generally be most useful.

It is understood that a "radio-labeled compound" is a compound that has incorporated at least one radionuclide. In some embodiments the radionuclide is selected from $^3$H, $^{14}$C, $^{125}$I, $^{35}$S and $^{82}$Br.

In some embodiments, the labeled compounds of the present invention contain a fluorescent label.

Synthetic methods for incorporating radio-isotopes and fluorescent labels into organic compounds are well known in the art.

A labeled compound of the invention (radio-labeled, fluorescent-labeled, etc.) can be used in a screening assay to identify/evaluate compounds. For example, a newly synthesized or identified compound (i.e., test compound) which is labeled can be evaluated for its ability to bind a histamine H4 receptor by monitoring its concentration variation when contacting with the histamine H4 receptor, through tracking the labeling. For another example, a test compound (labeled) can be evaluated for its ability to reduce binding of another compound which is known to bind to histamine H4 receptor (i.e., standard compound). Accordingly, the ability of a test compound to compete with the standard compound for binding to the histamine H4 receptor directly correlates to its binding affinity. Conversely, in some other screening assays, the standard compound is labeled and test compounds are unlabeled. Accordingly, the concentration of the labeled standard compound is monitored in order to evaluate the competition between the standard compound and the test compound, and the relative binding affinity of the test compound is thus ascertained.

Kits

The present invention also includes pharmaceutical kits useful, for example, in the treatment or prevention of histamine H4 receptor-mediated conditions/diseases/disorders such as inflammatory disorders, pruritus, and pain (including rhinitis, asthma, rheumatoid arthritis, atopic dermatitis, idiopathic chronic urticaria, inflammatory pain, and other diseases referred to herein), which include one or more containers containing a pharmaceutical composition comprising a therapeutically effective amount of a compound of the invention. Such kits can further include, if desired, one or more of various conventional pharmaceutical kit components, for example, containers with one or more pharmaceutically acceptable carriers, additional containers, etc., as will be readily apparent to those skilled in the art. Instructions, either as inserts or as labels, indicating quantities of the components to be administered, guidelines for administration, and/or guidelines for mixing the components, can also be included in the kit.

The invention will be described in greater detail by way of specific examples. The following examples are offered for illustrative purposes, and are not intended to limit the invention in any manner. Those of skill in the art will readily recognize a variety of non-critical parameters which can be changed or modified to yield essentially the same results. In some instances where the compounds of the examples were isolated by preparative HPLC in the presence of trifluoroacetic acid (TFA) or other acid, the compound may have been obtained as the corresponding salt. Certain compounds of the Examples were found to be inhibitors of histamine H4 receptor according to one or more of the assays provided herein. In some embodiments, the $IC_{50}$ value for the compound of invention with respect to histamine H4 receptor is less than about 100, 80, 50, 20, 10, 8, 5, 2, or 1 µM. In some embodiments, the $IC_{50}$ value for the compound of invention with respect to histamine H4 receptor is less than about 1000, 800, 500, 200, 100, 80, 50, 20, or 10 nM. Certain compounds described in Tables A1 and in the Example section were tested for inhibitory activity of histamine H4 receptor targets according to assays such as those described herein or those known in the art [e.g., histamine H4 binding assays described in WO 2008100565]. For instance, Examples 1-38 were found to have $IC_{50}$ values less than 1000 nM, 800 nM, 500 nM, 200 nM, or 100 nM for histamine H4 receptor.

EXAMPLES

Experimental procedures for compounds of the invention are provided below. Typically, the compounds prepared were separated on a preparative scale by reverse-phase high performance liquid chromatography (RP-HPLC) with MS detector or flash chromatography (silica gel) as indicated in the Examples. Typical preparative reverse-phase high performance liquid chromatography (RP-HPLC) column conditions are as follows:

pH=2 purifications: Waters Sunfire™ $C_{18}$ 5 Tm, 19×100 mm column, eluting with mobile phase A: 0.1% TFA (trifluoroacetic acid) in water and mobile phase B: 0.1% TFA in acetonitrile; the flow rate was 30 mL/minute, the separating gradient was optimized for each compound using the Compound Specific Method Optimization protocol as described in the literature [see "Preparative LCMS Purification: Improved Compound Specific Method Optimization", K. Blom, B. Glass, R. Sparks, A. Combs, *J. Comb. Chem.*, 6, 874-883 (2004)].

pH=10 purifications: Waters XBridge $C_{18}$ 5 Tm, 19×100 mm column, eluting with mobile phase A: 0.15% $NH_4OH$ in water and mobile phase B: 0.15% $NH_4OH$ in acetonitrile; the flow rate was 30 mL/minute, the separating gradient was optimized for each compound using the Compound Specific Method Optimization protocol as described in the literature [See "Preparative LCMS Purification: Improved Compound Specific Method Optimization", K. Blom, B. Glass, R. Sparks, A. Combs, *J. Comb. Chem.*, 6, 874-883 (2004)].

The compounds separated were typically subjected to analytical liquid chromatography mass spectrometry (LCMS) for purity under the following conditions: Instrument; Agilent 1100 series, LC/MSD, Column: Waters Sunfire™ $C_{18}$ 5 Tm, 2.1×5.0 mm, Buffers: mobile phase A: 0.025% TFA in water and mobile phase B: 0.025% TFA in acetonitrile; gradient 2% to 80% of B in 3 minutes with flow rate 1.5 mL/minute.

Example 1

4-(4-Methylpiperazin-1-yl)-6-(1,2,3,4-tetrahydroisoquinolin-7-yl)pyrimidin-2-amine

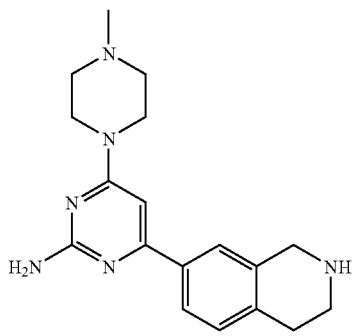 [SMILES: CN1CCN(c2cc(-c3ccc4c(c3)CNCC4)nc(N)n2)CC1]

Step 1: tert-butyl 7-bromo-3,4-dihydroisoquinoline-2(1H)-carboxylate

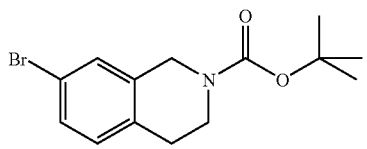

Di-tert-butyldicarbonate (0.34 g, 1.6 mmol) was added to a mixture of 7-bromo-1,2,3,4-tetrahydroisoquinoline (0.30 g, 1.4 mmol, Alfa Aesar, Cat. #: B25712) and triethylamine (0.29 g, 2.8 mmol) in THF (4.0 mL). The mixture was stirred at room temperature (r.t.) for 1 hour (1 h.), quenched with aqueous $Na_2CO_3$, and extracted with ethyl acetate (3×20 mL). The combined organic layers were washed with brine, dried over $MgSO_4$, filtered, and concentrated under reduced pressure to afford the desired product (0.43 g, yield: 97%) which was directly used in next step reaction without further purification. Analytic LCMS $(M+Na)^+$: m/z=334.2/336.2; $(M-Bu^t+H)^+$=256.1/258.1.

Step 2: tert-butyl 7-(4,4,5,5-tetramethyl-1,3,2-dioxaborolan-2-yl)-3,4-dihydroisoquinoline-2(1H)-carboxylate

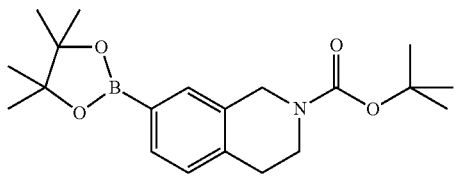 [SMILES: CC(C)(C)OC(=O)N1CCc2ccc(B3OC(C)(C)C(C)(C)O3)cc2C1]

To a solution of tert-butyl 7-bromo-3,4-dihydroisoquinoline-2(1H)-carboxylate (0.43 g, 1.4 mmol) and 4,4,5,5,4',4',5',5'-octamethyl-[2,2']bi[[1,3,2]dioxaborolanyl] (0.37 g, 1.5 mmol) in 1,4-dioxane (3.9 mL) were added [1,1'-bis(diphenylphosphino)ferrocene]dichloropalladium(II)dichloromethane (1:1) complex (0.056 g, 0.069 mmol), potassium acetate (0.40 g, 4.1 mmol), and 1,1'-bis(diphenylphosphino)ferrocene (0.04 g, 0.07 mmol) under an atmosphere of nitrogen. The reaction mixture was stirred at 100° C. overnight. After cooled to room temperature, the mixture was filtered, washed with dichloromethane, and concentrated under reduced pressure. The residue was purified by flash chromatography on a silica gel column with 30% ethyl acetate in hexanes to afford the desired product (0.54 g, purity: 90%, yield: 98%). Analytic LCMS $(M+Na)^+$: m/z=382.3; $(M-Bu^t+H)^+$=304.3.

Step 3: tert-butyl 7-[2-amino-6-(4-methylpiperazin-1-yl)pyrimidin-4-yl]-3,4-dihydroisoquinoline-2(1H)-carboxylate

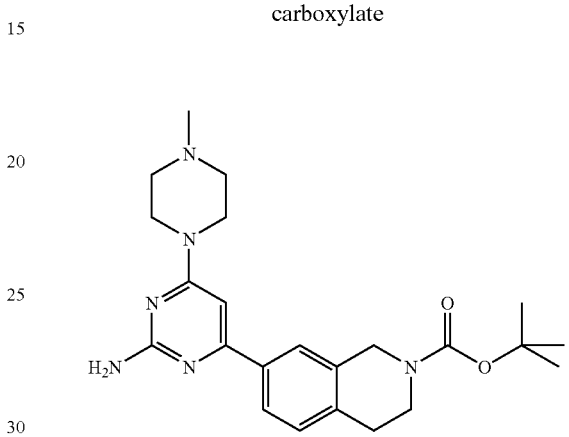

A mixture of 4-chloro-6-(4-methylpiperazin-1-yl)pyrimidin-2-amine (0.10 g, 0.44 mmol), tert-butyl 7-(4,4,5,5-tetramethyl-1,3,2-dioxaborolan-2-yl)-3,4-dihydroisoquinoline-2(1H)-carboxylate (0.16 g, 0.44 mmol), [1,1'-bis(diphenylphosphino)ferrocene]dichloropalladium(II) dichloromethane (1:1) complex (0.02 g, 0.02 mmol) and potassium carbonate (0.18 g, 1.3 mmol) in 1,4-dioxane (3 mL), and water (1 mL) was heated at 110° C. overnight. After cooled to r.t., the mixture was diluted with MeOH, filtered, and concentrated under reduced pressure. The residue was purified by flash chromatography on a silica gel column eluting with 10% MeOH in dichloromethane (DCM) to afford the desired product (0.14 g, yield: 75%). Analytic LCMS $(M+H)^+$: m/z=425.4.

Step 4: 4-(4-methylpiperazin-1-yl)-6-(1,2,3,4-tetrahydroisoquinolin-7-yl)pyrimidin-2-amine

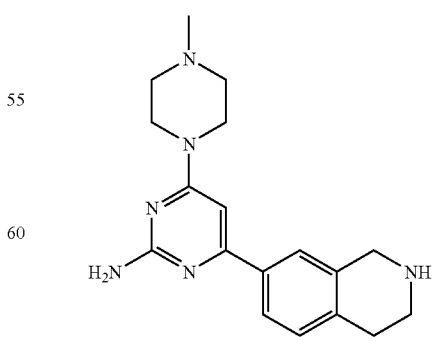

6 mL of 4N HCl in dioxane was added to a solution of tert-butyl 7-[2-amino-6-(4-methylpiperazin-1-yl)pyrimidin- 4-yl]-3,4-dihydroisoquinoline-2(1H)-carboxylate (0.90 g, 2.1 mmol) in methanol (5 mL). The mixture was stirred at r.t. for 2 h. The mixture was concentrated under reduced pressure. The residue was washed with ether and dried under vacuum to afford the desired product as an HCl salt (0.83 g). Analytic LCMS (M+H)⁺: m/z=325.4.

Example 2

4-[2-(4-Chlorobenzoyl)-1,2,3,4-tetrahydroisoquinolin-7-yl]-6-(4-methylpiperazin-1-yl)pyrimidin-2-amine

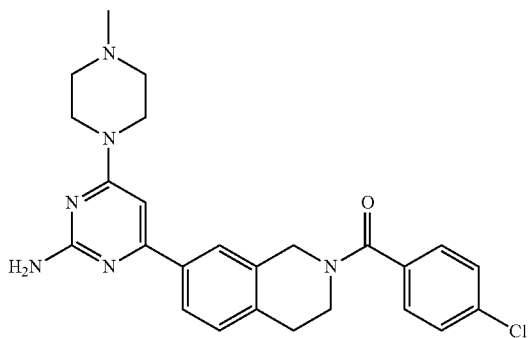 [SMILES: CN1CCN(c2cc(-c3ccc4c(c3)CN(C(=O)c3ccc(Cl)cc3)CC4)nc(N)n2)CC1]

4-Chlorobenzoic acid chloride (4.4 µL, 0.034 mmol) was added to a mixture of 4-(4-methylpiperazin-1-yl)-6-(1,2,3,4-tetrahydroisoquinolin-7-yl)pyrimidin-2-amine HCl salt (10 mg, 0.02 mmol) and triethylamine (16 µL, 0.12 mmol) in tetrahydrofuran (0.3 mL). After 30 min, the mixture was purified by RP-LCMS (pH=10) to afford the desired products. Analytic LCMS (M+H)⁺: m/z=463.3/465.3

Example 3

4-[2-(Cyclobutylcarbonyl)-1,2,3,4-tetrahydroisoquinolin-7-yl]-6-(4-methylpiperazin-1-yl)pyrimidin-2-amine

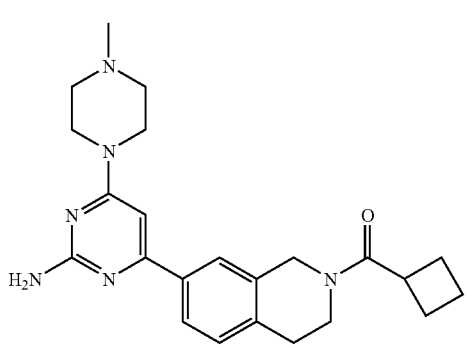 [SMILES: CN1CCN(c2cc(-c3ccc4c(c3)CN(C(=O)C3CCC3)CC4)nc(N)n2)CC1]

This compound was prepared from cyclobutanecarboxylic acid chloride and 4-(4-methylpiperazin-1-yl)-6-(1,2,3,4-tetrahydroisoquinolin-7-yl)pyrimidin-2-amine HCl salt using procedures analogous to those for Example 2. Analytic LCMS (M+H)⁺: m/z=407.4.

Example 4

4-(4-Methylpiperazin-1-yl)-6-[2-(phenylsulfonyl)-1,2,3,4-tetrahydroisoquinolin-7-yl]pyrimidin-2-amine

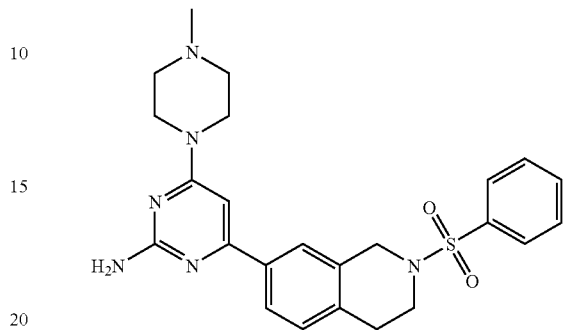

This compound was prepared from benzenesulfonyl chloride and 4-(4-methylpiperazin-1-yl)-6-(1,2,3,4-tetrahydroisoquinolin-7-yl)pyrimidin-2-amine HCl salt using procedures analogous to those for Example 2. Analytic LCMS (M+H)⁺: m/z=465.3.

Example 5

7-[2-Amino-6-(4-methylpiperazin-1-yl)pyrimidin-4-yl]-N-cyclopentyl-3,4-dihydroisoquinoline-2(1H)-carboxamide

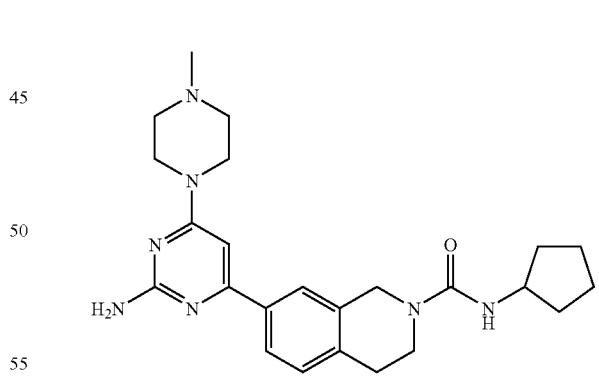

Isocyanatocyclopentane (0.030 mmol) was added to a mixture of 4-(4-methylpiperazin-1-yl)-6-(1,2,3,4-tetrahydroisoquinolin-7-yl)pyrimidin-2-amine HCl salt (10 mg, 0.02 mmol) and triethylamine (16 µL, 0.12 mmol) in tetrahydrofuran (0.3 mL). After 30 minutes, the mixture was purified by RP-LCMS (pH=10) to afford the desired products. Analytic LCMS (M+H)⁺: m/z=436.5.

Example 6

4-(4-Methylpiperazin-1-yl)-6-[2-(phenylacetyl)-1,2,3,4-tetrahydroisoquinolin-7-yl]pyrimidin-2-amine

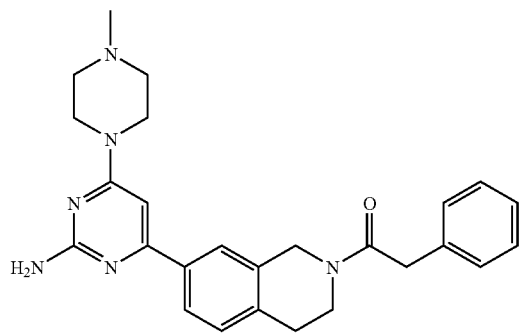 [SMILES: CN1CCN(c2cc(-c3ccc4c(c3)CN(C(=O)Cc3ccccc3)CC4)nc(N)n2)CC1]

This compound was prepared from benzeneacetyl chloride and 4-(4-methylpiperazin-1-yl)-6-(1,2,3,4-tetrahydroisoquinolin-7-yl)pyrimidin-2-amine HCl salt using procedures analogous to those for Example 2. Analytic LCMS (M+H)$^+$: m/z=443.4.

Example 7

Cyclopentyl 7-[2-amino-6-(4-methylpiperazin-1-yl)pyrimidin-4-yl]-3,4-dihydroisoquinoline-2(1H)-carboxylate

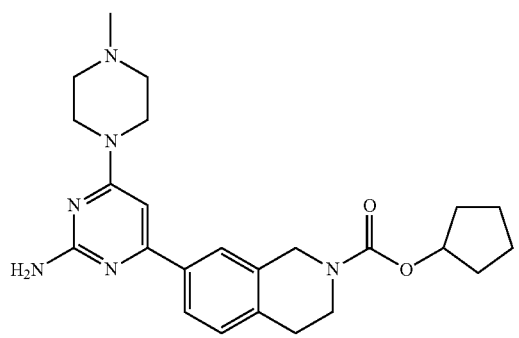 [SMILES: CN1CCN(c2cc(-c3ccc4c(c3)CN(C(=O)OC3CCCC3)CC4)nc(N)n2)CC1]

Step 1: cyclopentyl 4-nitrophenyl carbonate

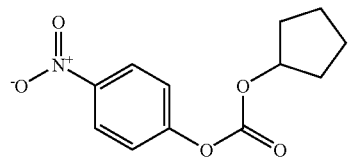

To a mixture of cyclopentanol (0.5 g, 6 mol), p-nitrophenyl chloroformate (1.3 g, 6.4 mmol) in methylene chloride (10 mL) was added triethylamine (1.2 mL, 8.7 mmol). The mixture was stirred at r.t. for 2 h. After removal of solvent, the crude residue was purified by flash chromatography on a silica gel column eluted with 20% EtOAc in hexane to yield the desired product (0.86 g, 59%).

Step 2: cyclopentyl 7-[2-amino-6-(4-methylpiperazin-1-yl)pyrimidin-4-yl]-3,4-dihydroisoquinoline-2(1H)-carboxylate This compound was prepared from cyclopentyl 4-nitrophenyl carbonate and 4-(4-methylpiperazin-1-yl)-6-(1,2,3,4-tetrahydroisoquinolin-7-yl)pyrimidin-2-amine HCl salt using procedures analogous to those for Example 2. Analytic LCMS (M+H)$^+$: m/z=437.4.

Example 8

7-[2-Amino-6-(4-methylpiperazin-1-yl)pyrimidin-4-yl]-N-(4-chlorophenyl)-3,4-dihydroisoquinoline-2(1H)-carboxamide

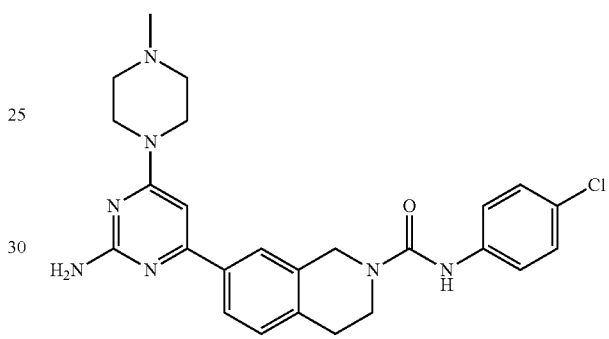

This compound was prepared from 4-chlorophenyl isocyanate and 4-(4-methylpiperazin-1-yl)-6-(1,2,3,4-tetrahydroisoquinolin-7-yl)pyrimidin-2-amine HCl salt using procedures analogous to those for Example 5. Analytic LCMS (M+H)$^+$: m/z=478.3/480.3.

Example 9

4-(4-Methylpiperazin-1-yl)-6-[2-(pyrrolidin-1-ylcarbonyl)-1,2,3,4-tetrahydroisoquinolin-7-yl]pyrimidin-2-amine

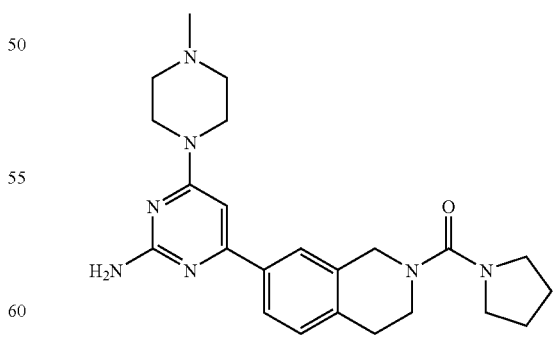

This compound was prepared from 1-pyrrolidinecarbonyl chloride and 4-(4-methylpiperazin-1-yl)-6-(1,2,3,4-tetrahydroisoquinolin-7-yl)pyrimidin-2-amine HCl salt using procedures analogous to those for Example 2. Analytic LCMS (M+H)$^+$: m/z=422.4.

Example 10

Isobutyl 7-[2-amino-6-(4-methylpiperazin-1-yl)pyrimidin-4-yl]-3,4-dihydroisoquinoline-2(1H)-carboxylate

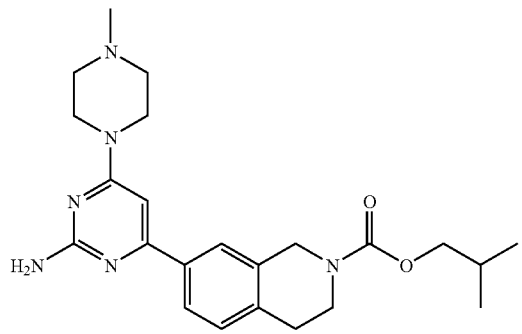 [SMILES: CC(C)COC(=O)N1CCc2ccc(-c3cc(N4CCN(C)CC4)nc(N)n3)cc2C1]

This compound was prepared from isobutyl chloroformate and 4-(4-methylpiperazin-1-yl)-6-(1,2,3,4-tetrahydroisoquinolin-7-yl)pyrimidin-2-amine HCl salt using procedures analogous to those for Example 2. Analytic LCMS (M+H)$^+$: m/z=425.4.

Example 11

Isopropyl 7-[2-amino-6-(4-methylpiperazin-1-yl)pyrimidin-4-yl]-3,4-dihydroisoquinoline-2(1H)-carboxylate

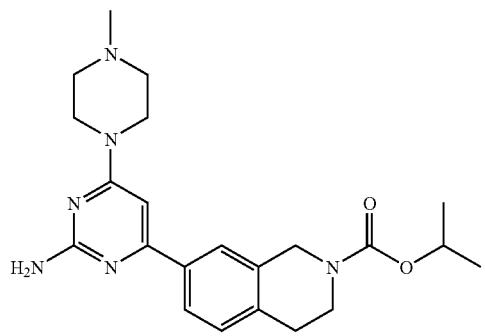 [SMILES: CC(C)OC(=O)N1CCc2ccc(-c3cc(N4CCN(C)CC4)nc(N)n3)cc2C1]

This compound was prepared from isopropyl chloroformate and 4-(4-methylpiperazin-1-yl)-6-(1,2,3,4-tetrahydroisoquinolin-7-yl)pyrimidin-2-amine HCl salt using procedures analogous to those for Example 2. Analytic LCMS (M+H)$^+$: m/z=411.4.

Example 12

7-[2-Amino-6-(4-methylpiperazin-1-yl)pyrimidin-4-yl]-N-phenyl-3,4-dihydroisoquinoline-2(1H)-carboxamide

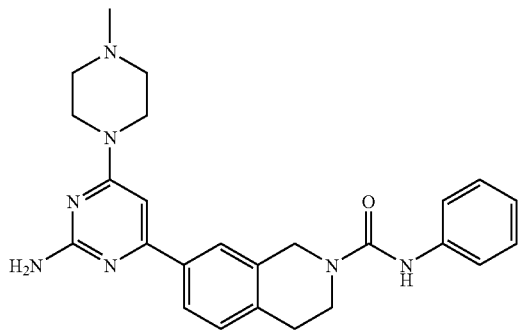

This compound was prepared from phenyl isocyanate and 4-(4-methylpiperazin-1-yl)-6-(1,2,3,4-tetrahydroisoquinolin-7-yl)pyrimidin-2-amine HCl salt using procedures analogous to those for Example 5. Analytic LCMS (M+H)$^+$: m/z=444.4.

Example 13

7-[2-Amino-6-(4-methylpiperazin-1-yl)pyrimidin-4-yl]-N-isopropyl-3,4-dihydroisoquinoline-2(1H)-carboxamide This compound was prepared from 2-isocyanatopropane and 4-(4-methylpiperazin-1-yl)-6-(1,2,3,4-tetrahydroisoquinolin-7-yl)pyrimidin-2-amine HCl salt using procedures analogous to those for Example 5. Analytic LCMS (M+H)$^+$: m/z=410.4.

Example 14

4-{7-[2-Amino-6-(4-methylpiperazin-1-yl)pyrimidin-4-yl]-3,4-dihydroisoquinolin-2(1H)-yl}benzonitrile

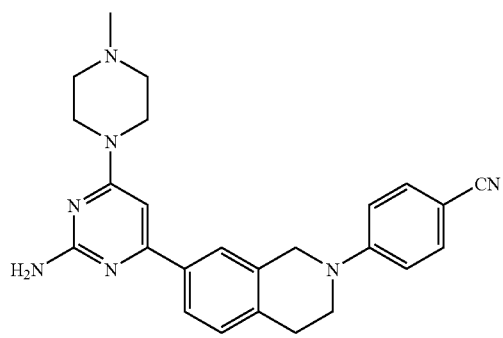 [SMILES: CN1CCN(c2cc(-c3ccc4c(c3)CN(c3ccc(C#N)cc3)CC4)nc(N)n2)CC1]

A mixture of 4-(4-methylpiperazin-1-yl)-6-(1,2,3,4-tetrahydroisoquinolin-7-yl)pyrimidin-2-amine HCl salt (17 mg, 0.039 mmol), 4-fluorobenzonitrile (7.1 mg, 0.058 mmol) and 4-methylmorpholine (13 µL, 0.12 mmol) in N-methylpyrrolidinone (0.4 mL) was heated at 180° C. overnight. After cooling, the mixture was filtered, diluted with methanol, and purified by RP-LCMS (pH=10) to afford the desired product. Analytic LCMS (M+H)$^+$: m/z=426.4.

Example 15

4-{7-[2-Amino-6-(4-methylpiperazin-1-yl)pyrimidin-4-yl]-3,4-dihydroisoquinolin-2(1H)-yl}-2-fluorobenzonitrile

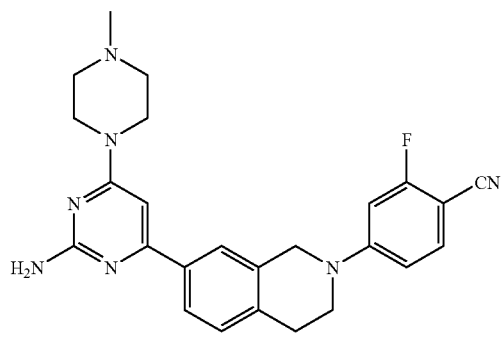 [SMILES: CN1CCN(c2cc(-c3ccc4c(c3)CN(c3ccc(C#N)c(F)c3)CC4)nc(N)n2)CC1]

This compound was prepared from 4-(4-methylpiperazin-1-yl)-6-(1,2,3,4-tetrahydroisoquinolin-7-yl)pyrimidin-2-amine HCl salt and 2,4-difluorobenzonitrile using procedures analogous to those for Example 14. Analytic LCMS (M+H)$^+$: m/z=444.4.

Example 16

6-{7-[2-Amino-6-(4-methylpiperazin-1-yl)pyrimidin-4-yl]-3,4-dihydroisoquinolin-2(1H)-yl}nicotinonitrile

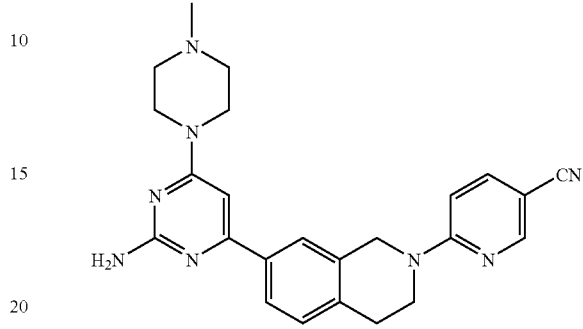

This compound was prepared from 4-(4-methylpiperazin-1-yl)-6-(1,2,3,4-tetrahydroisoquinolin-7-yl)pyrimidin-2-amine HCl salt and 6-bromonicotinonitrile using procedures analogous to those for Example 14. Analytic LCMS (M+H)$^+$: m/z=427.4.

Example 17

5-{7-[2-Amino-6-(4-methylpiperazin-1-yl)pyrimidin-4-yl]-3,4-dihydroisoquinolin-2(1H)-yl}-N-methylpyridine-2-carboxamide

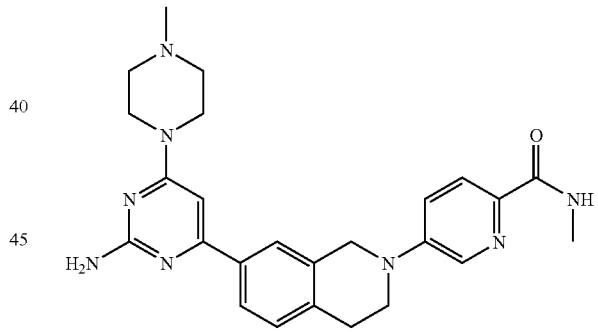

Step 1: 5-(7-bromo-3,4-dihydroisoquinolin-2(1H)-yl)pyridine-2-carbonitrile

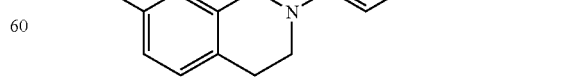

A mixture of 7-bromo-1,2,3,4-tetrahydroisoquinoline (0.30 g, 1.4 mmol), 5-bromopyridine-2-carbonitrile (0.28 g, 1.5 mmol) and potassium carbonate (0.39 g, 2.8 mmol) in dimethyl sulfoxide (2.0 mL) was heated at 160° C. for 2 h.

After cooled to r.t., the mixture was quenched with water (10 mL), and extracted with ethyl acetate (3×20 mL). The combined organic layers were washed with brine, dried over MgSO$_4$, filtered, and concentrated under reduced pressure. The residue was purified by flash chromatography on a silica gel column with 30% ethyl acetate in hexanes to afford the desired product (0.15 g, yield: 34%). Analytic LCMS (M+H)$^+$: m/z=314.2/316.2.

Step 2: 5-[7-(4,4,5,5-tetramethyl-1,3,2-dioxaborolan-2-yl)-3,4-dihydroisoquinolin-2(1H)-yl]pyridine-2-carbonitrile

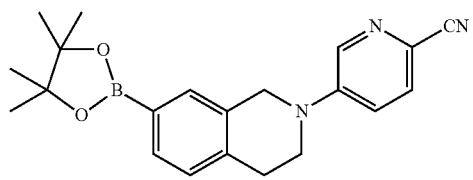 [SMILES: CC1(C)OB(c2ccc3c(c2)CN(c2ccc(C#N)nc2)CC3)OC1(C)C]

To a mixture of 5-(7-bromo-3,4-dihydroisoquinolin-2(1H)-yl)pyridine-2-carbonitrile (0.15 g, 0.48 mmol) and 4,4,5,5,4',4',5',5'-octamethyl-[2,2']bi[[1,3,2]dioxaborolanyl] (0.13 g, 0.51 mmol) in 1,4-dioxane (1.3 mL) were added [1,1'-bis(diphenylphosphino)ferrocene]dichloropalladium (II)dichloromethane (1:1) complex (0.019 g, 0.024 mmol), potassium acetate (0.14 g, 1.4 mmol), and 1,1'-bis(diphenylphosphino)ferrocene (0.01 g, 0.02 mmol) under an atmosphere of nitrogen. The reaction mixture was stirred at 90° C. overnight. After cooled to r.t., the mixture was filtered, washed with DCM, and concentrated under reduced pressure. The residue was purified by flash chromatography on a silica gel column with 30% ethyl acetate in hexane to afford the desired product (0.12 g, yield: 70%). Analytic LCMS (M+H)$^+$: m/z=362.3.

Step 3: 5-{7-[2-amino-6-(4-methylpiperazin-1-yl)pyrimidin-4-yl]-3,4-dihydroisoquinolin-2(1H)-yl}pyridine-2-carbonitrile

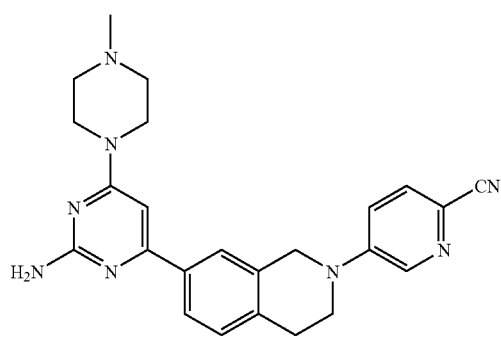 [SMILES: CN1CCN(c2cc(-c3ccc4c(c3)CN(c3ccc(C#N)nc3)CC4)nc(N)n2)CC1]

A mixture of 4-chloro-6-(4-methylpiperazin-1-yl)pyrimidin-2-amine (0.075 g, 0.33 mmol), 5-[7-(4,4,5,5-tetramethyl-1,3,2-dioxaborolan-2-yl)-3,4-dihydroisoquinolin-2(1H)-yl]pyridine-2-carbonitrile (0.12 g, 0.33 mmol), [1,1'-bis(diphenylphosphino)ferrocene]dichloropalladium(II) dichloromethane (1:1) complex (0.01 g, 0.02 mmol) and potassium carbonate (0.14 g, 0.99 mmol) in 1,4-dioxane (2 mL), and water (1 mL) was heated at 120° C. for 2 h. After cooled to r.t., the mixture was diluted with MeOH, filtered, concentrated under reduced pressure. The residue was purified by flash chromatography on a silica gel column eluting with 10% MeOH in DCM to give the desired product. The product was further purified by RP-LCMS (pH=10) to afford the desired product (0.10 g, yield: 71%). Analytic LCMS (M+H)$^+$: m/z=427.3.

Step 4: 5-{7-[2-amino-6-(4-methylpiperazin-1-yl)pyrimidin-4-yl]-3,4-dihydroisoquinolin-2(1H)-yl}pyridine-2-carboxylic acid

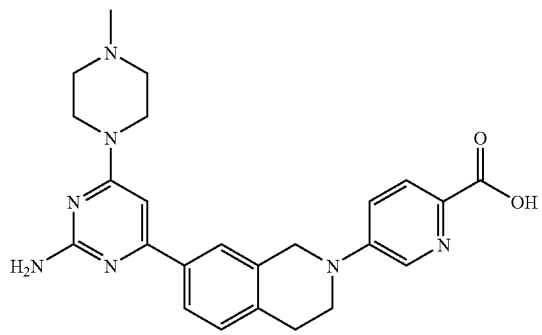

5-{7-[2-Amino-6-(4-methylpiperazin-1-yl)pyrimidin-4-yl]-3,4-dihydroisoquinolin-2(1H)-yl}pyridine-2-carbonitrile (0.10 g, 0.23 mmol) was dissolved in concentrated HCl aqueous solution. The reaction mixture was heated at 100° C. overnight. The mixture was concentrated under reduced pressure. The crude product was azeotroped with toluene (3×) to afford the desired product as an HCl salt in quantitative yield. Analytic LCMS (M+H)$^+$: m/z=446.4.

Step 5: 5-{7-[2-amino-6-(4-methylpiperazin-1-yl)pyrimidin-4-yl]-3,4-dihydroisoquinolin-2(1H)-yl}-N-methylpyridine-2-carboxamide A mixture of 5-{7-[2-amino-6-(4-methylpiperazin-1-yl)pyrimidin-4-yl]-3,4-dihydroisoquinolin-2(1H)-yl}pyridine-2-carboxylic acid HCl salt (16.4 mg, 0.0296 mmol), methylamine (0.018 ml, 0.036 mmol) (2.0 M solution in THF), benzotriazol-1-yloxytris(dimethylamino)phosphonium hexafluorophosphate (14.4 mg, 0.0326 mmol) and 4-methylmorpholine (16.3 uL, 0.148 mmol) in N,N-dimethylformamide (0.5 mL) was stirred at r.t. overnight. The mixture was purified by RP-LCMS (pH=10) to afford the desired product. Analytic LCMS (M+H)$^+$: m/z=459.4.

Example 18

4-{6-[7-[2-Amino-6-(4-methylpiperazin-1-yl)pyrimidin-4-yl]-3,4-dihydroisoquinolin-2(1H)-yl]pyridin-3-yl}benzonitrile

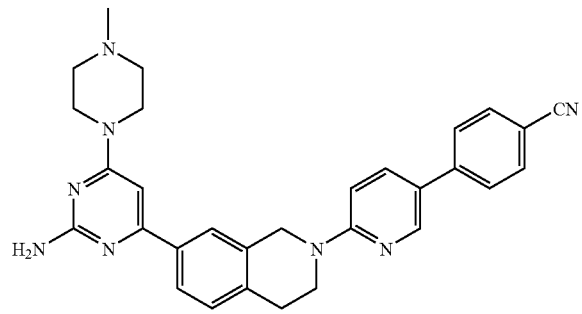 [SMILES: CN1CCN(c2cc(-c3ccc4c(c3)CN(c3ccc(-c5ccc(C#N)cc5)cn3)CC4)nc(N)n2)CC1]

Step 1: 4-(6-fluoropyridin-3-yl)benzonitrile

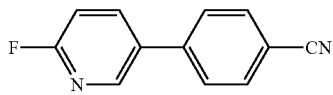 [SMILES: N#Cc1ccc(-c2ccc(F)nc2)cc1]

A mixture of 4-bromobenzonitrile (0.20 g, 1.1 mmol), (6-fluoropyridin-3-yl)boronic acid (0.15 g, 1.1 mmol), [1,1'-bis(diphenylphosphino)ferrocene]dichloropalladium(II) dichloromethane (1:1) complex (0.04 g, 0.05 mmol) and potassium carbonate (0.46 g, 3.3 mmol) in 1,4-dioxane (7 mL), and water (3 mL) was heated at 110° C. for 2 h. After cooled to r.t., the mixture was diluted with MeOH, filtered, concentrated under reduced pressure and purified by flash chromatography on a silica gel column eluting with 5% MeOH in DCM to afford the desired product (0.17 g, yield: 78%). Analytic LCMS (M+H)$^+$: m/z=199.2.

Step 2: 4-{6-[7-[2-amino-6-(4-methylpiperazin-1-yl)pyrimidin-4-yl]-3,4-dihydroisoquinolin-2(1H)-yl]pyridin-3-yl}benzonitrile This compound was prepared from 4-(4-methylpiperazin-1-yl)-6-(1,2,3,4-tetrahydroisoquinolin-7-yl)pyrimidin-2-amine HCl salt and 4-(6-fluoropyridin-3-yl)benzonitrile using procedures analogous to those for Example 14. Analytic LCMS (M+H)$^+$: m/z=503.4.

Example 19

4-{6-[7-[2-Amino-6-(4-methylpiperazin-1-yl)pyrimidin-4-yl]-3,4-dihydroisoquinolin-2(1H)-yl]pyridin-3-yl}-N-methylbenzamide

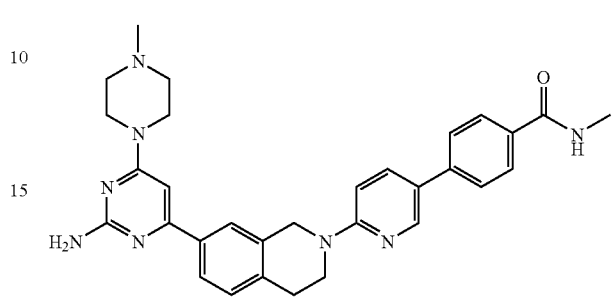

Step 1: 4-(6-fluoropyridin-3-yl)-N-methylbenzamide

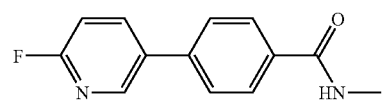 [SMILES: CNC(=O)c1ccc(-c2ccc(F)nc2)cc1]

This compound was prepared from 5-bromo-2-fluoropyridine and {4-[(methylamino)carbonyl]phenyl}boronic acid using procedures analogous to those for Example 18, step 1. Analytic LCMS (M+H)$^+$: m/z=231.1.

Step 2: 4-{6-[7-[2-amino-6-(4-methylpiperazin-1-yl)pyrimidin-4-yl]-3,4-dihydroisoquinolin-2(1H)-yl]pyridin-3-yl}-N-methylbenzamide This compound was prepared from 4-(4-methylpiperazin-1-yl)-6-(1,2,3,4-tetrahydroisoquinolin-7-yl)pyrimidin-2-amine HCl salt and 4-(6-fluoropyridin-3-yl)-N-methylbenzamide using procedures analogous to those for Example 14. Analytic LCMS (M+H)$^+$: m/z=535.5.

Example 20

7-[2-Amino-6-(4-methylpiperazin-1-yl)pyrimidin-4-yl]-N-(3-chlorophenyl)-3,4-dihydroisoquinoline-2(1H)-carboxamide

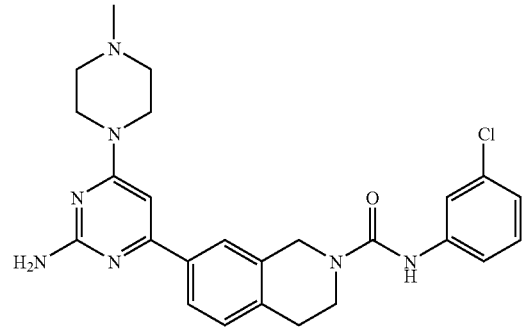 [SMILES: CN1CCN(c2cc(-c3ccc4c(c3)CN(C(=O)Nc3cccc(Cl)c3)CC4)nc(N)n2)CC1]

This compound was prepared from 3-chlorophenyl isocyanate and 4-(4-methylpiperazin-1-yl)-6-(1,2,3,4-tetrahydroisoquinolin-7-yl)pyrimidin-2-amine HCl salt using procedures analogous to those for Example 5. Analytic LCMS (M+H)+: m/z=478.3/480.3.

Example 21

(R)-2-Amino-4-(4-methylpiperazin-1-yl)-N-[1-(naphthalen-2-yl)ethyl]quinazoline-7-carboxamide

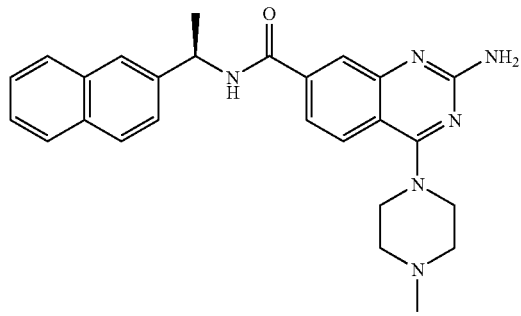 [SMILES: C[C@@H](NC(=O)c1ccc2c(N3CCN(C)CC3)nc(N)nc2c1)c1ccc2ccccc2c1]

Step 1: methyl 2-amino-4-oxo-4,4a-dihydroquinazoline-7-carboxylate

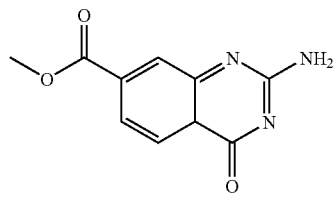 [SMILES: COC(=O)C1=CC2=NC(N)=NC(=O)C2C=C1]

Concentrated hydrogen chloride aqueous solution (800 µl, 26.1 mmol) was added to a solution of dimethyl 2-aminoterephthalate (1.82 g, 8.69 mmol), and cyanamide (658 mg, 15.6 mmol) in acetonitrile (20 mL). After the HCl addition, the reaction mixture became slurry and it was heated at 80° C. overnight. The reaction mixture was allowed to cool to room temperature and became thick slurry; then the solids were filtered, washed with ethyl ether, and dried to give the crude product (1.50 g, 78.7%) as a white solid. $^1$H NMR (300 MHz, DMSO): δ 3.9 (s, 3H), 7.84 (dd, 1H), 7.99 (d, 1H), 8.09 (d, 1H), 8.55 (b, 2H); Analytic LCMS (M+H)+: m/z=220.1.

Step 2: methyl 2-amino-4-chloroquinazoline-7-carboxylate

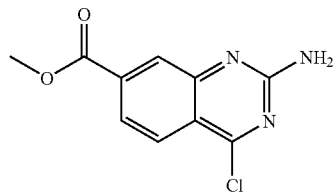 [SMILES: COC(=O)c1ccc2c(Cl)nc(N)nc2c1]

A solution of methyl 2-amino-4-oxo-3,4-dihydroquinazoline-7-carboxylate (500 mg, 2.28 mmol) and phosphoryl chloride (4 mL, 42.9 mmol) was stirred at 110° C. for 6 h. The starting material was consumed and the reaction mixture was concentrated to give the crude product (500 mg, 92.2%) as an oil. $^1$H NMR (300 MHz, DMSO) δ 3.9 (s, 3H), 7.79 (dd, 1H), 8.05 (d, 1H), 8.13 (d, 1H); Analytic LCMS (M+H)+: m/z=238.0.

Step 3: methyl 2-amino-4-(4-methylpiperazin-1-yl)quinazoline-7-carboxylate

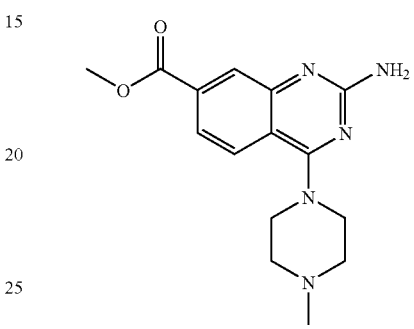

1-Methyl-piperazine (210 uL, 1.9 mmol) was added to a mixture of methyl 2-amino-4-chloroquinazoline-7-carboxylate (300 mg, 1 mmol) in ethanol (3 mL) and triethylamine (350 µL, 2.5 mmol). The mixture was heated in an oil bath at 110° C. for 1 h. The reaction mixture was concentrated to remove the ethanol and was partitioned between water and EtOAc. The organic phase was washed with saturated NaCl aqueous solution, dried over MgSO$_4$, filtered, and concentrated to give the crude product, (190 mg, 50%) as an off white amorphous solid. $^1$H NMR (300 MHz, DMSO) δ 2.23 (s, 3H), 3.56 (m, 4H), 3.86 (s, 3H), 3.90 (m, 4H), 6.53 (b, 2H), 7.50 (d, 1H), 7.80 (m, 2H); Analytic LCMS (M+H)+: m/z=302.1.

Step 4: 2-amino-4-(4-methylpiperazin-1-yl)quinazoline-7-carboxylic acid

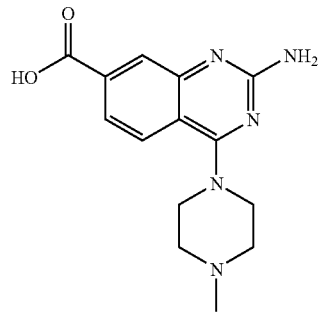 [SMILES: CN1CCN(c2nc(N)nc3cc(C(=O)O)ccc23)CC1]

Lithium hydroxide (29 mg, 1.2 mmol) in water (1 mL) was added to a solution of methyl 2-amino-4-(4-methylpiperazin-1-yl)quinazoline-7-carboxylate (180 mg, 0.60 mmol) in methanol (2 mL) at room temperature. The starting material was consumed after stirring for 5 h, and the reaction mixture was concentrated and dried on lyophilizer to obtain the crude product (190 mg) as an amorphous white solid. (quantitative yield). $^1$H NMR (300 MHz, DMSO): δ 2.22 (s, 3H), 2.48 (m, 4H), 3.49 (m, 4H), 6.23 (b, 2H), 7.55 (M, 2H), 7.75 (d, 1H); Analytic LCMS (M+H)+: m/z=288.1.

Step 5: (R)-2-amino-4-(4-methylpiperazin-1-yl)-N-[1-(naphthalen-2-yl)ethyl]quinazoline-7-carboxamide

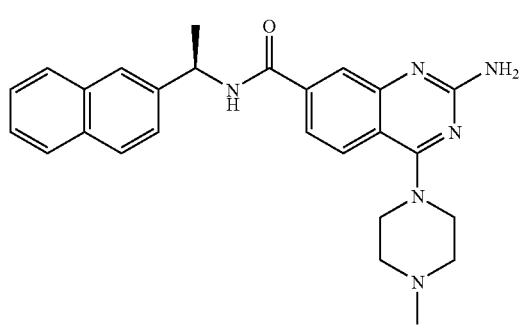 [SMILES: C[C@@H](NC(=O)c1ccc2c(N3CCN(C)CC3)nc(N)nc2c1)c1ccc2ccccc2c1]

N,N,N',N'-Tetramethyl-O-(7-azabenzotriazol-1-yl)uronium hexafluorophosphate (40 mg, 0.1 mmol) was added to a solution of 2-amino-4-(4-methylpiperazin-1-yl)quinazoline-7-carboxylic acid (20 mg, 0.07 mmol) in N,N-dimethylformamide (1 mL) and N,N-diisopropylethylamine (24 μL, 0.14 mmol). The reaction mixture was stirred for 10 minutes, and then (1R)-1-(2-naphthyl)ethanamine (24 mg, 0.14 mmol) was added. The crude reaction mixture stirred for 18 h. at r.t. and then was purified on RP-HPLC (pH=2) to afford the title product (15 mg, 27%) as a TFA salt as an off white amorphous solid. $^1$H NMR (300 MHz, DMSO): δ 1.52 (d, 3H), 2.82 (s, 3H), 3.22 (m, 2H), 3.65 (m, 4H), 4.65 (m, 2H), 5.32 (m, 1H), 7.44 (m, 2H), 7.54 (dd, 1H), 7.76-7.86 (m, 5H), 7.92 (d, 1H), 8.02 (d, 1H); Analytic LCMS (M+H)+: m/z=441.2.

Example 22

(S)-2-Amino-4-(4-methylpiperazin-1-yl)-N-(1-(naphthalen-2-yl)ethyl)quinazoline-7-carboxamide

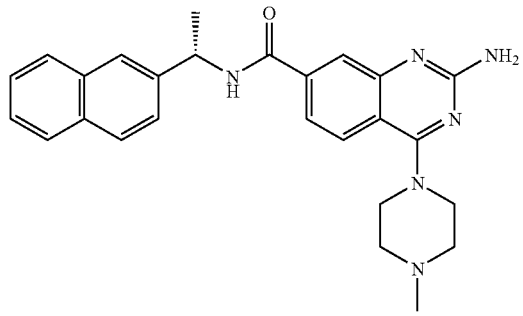 [SMILES: C[C@H](NC(=O)c1ccc2c(N3CCN(C)CC3)nc(N)nc2c1)c1ccc2ccccc2c1]

This compound was prepared as a TFA salt using procedures analogous to those for Example 21, but using (1S)-1-(2-naphthyl)ethanamine in Step 5. Analytic LCMS (M+H)+: m/z=441.2.

Example 23

2-Amino-N-(1-methyl-1-phenylethyl)-4-(4-methylpiperazin-1-yl)quinazoline-7-carboxamide

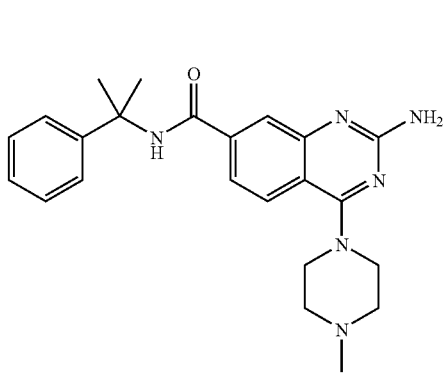 [SMILES: CN1CCN(c2nc(N)nc3cc(C(=O)NC(C)(C)c4ccccc4)ccc23)CC1]

This compound was prepared using procedures analogous to those for Example 21, but using cumylamine in Step 5. Analytic LCMS (M+H)+: m/z=405.2.

Example 24

2-Amino-4-(4-methylpiperazin-1-yl)-N-(1-phenylethyl)quinazoline-7-carboxamide

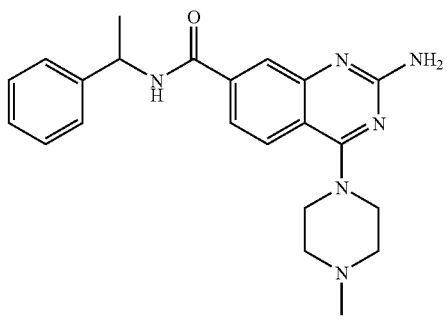 [SMILES: CC(NC(=O)c1ccc2c(N3CCN(C)CC3)nc(N)nc2c1)c1ccccc1]

This compound was prepared as a TFA salt using procedures analogous to those for Example 21, but using α-methylbenzenemethanamine in Step 5. Analytic LCMS (M+H)+: m/z=391.2.

Example 25

2-Amino-N-(cyclopropylmethyl)-4-(4-methylpiperazin-1-yl)quinazoline-7-carboxamide

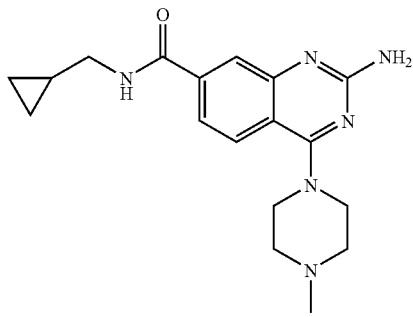 [SMILES: CN1CCN(c2nc(N)nc3cc(C(=O)NCC4CC4)ccc23)CC1]

This compound was prepared as a TFA salt using procedures analogous to those for Example 21, but using cyclopropylmethylamine in Step 5. Analytic LCMS (M+H)$^+$: m/z=341.2.

Example 26

2-Amino-N-methyl-4-(4-methylpiperazin-1-yl)quinazoline-7-carboxamide

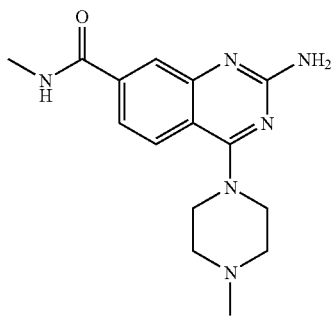 [SMILES: CNC(=O)c1ccc2c(N3CCN(C)CC3)nc(N)nc2c1]

This compound was prepared using procedures analogous to those for Example 21, but using methylamine in tetrahydrofuran (2.00 M) in Step 5. Analytic LCMS (M+H)$^+$: m/z=301.1.

Example 27

2-Amino-N-(3-chlorophenyl)-4-(4-methylpiperazin-1-yl)quinazoline-7-carboxamide

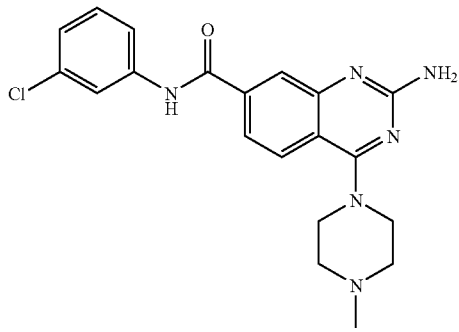 [SMILES: CN1CCN(c2nc(N)nc3cc(C(=O)Nc4cccc(Cl)c4)ccc23)CC1]

This compound was prepared using procedures analogous to those for Example 21, but using m-chloroaniline in Step 5. $^1$H NMR (300 MHz, DMSO): δ 2.23 (s, 3H), 2.50 (m, 4H), 3.54 (m, 4H), 6.48 (b, 2H), 7.11 (m, 1H), 7.32 (t, 1H), 7.45 (d, 1H), 7.66 (m, 1H), 7.76 (d, 1H), 7.83 (d, 1H), 7.93 (t, 1H); Analytic LCMS (M+H)$^+$: m/z=397.1.

Example 28

2-Amino-N-[1-(4-isobutylphenyl)ethyl]-4-(4-methylpiperazin-1-yl)quinazoline-7-carboxamide

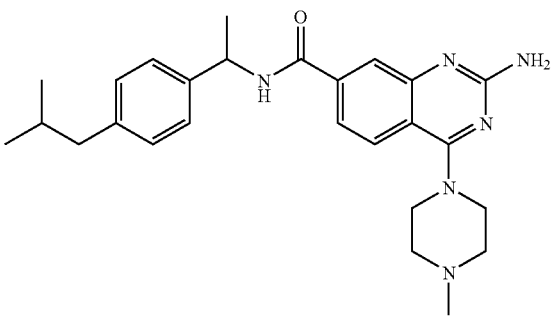 [SMILES: CC(C)Cc1ccc(C(C)NC(=O)c2ccc3c(N4CCN(C)CC4)nc(N)nc3c2)cc1]

This compound was prepared using procedures analogous to those for Example 21, but using 1-(4-isobutylphenyl)ethanamine in Step 5. Analytic LCMS (M+H)$^+$: m/z=447.3.

Example 29

2-Amino-4-(4-methylpiperazin-1-yl)-N-[1-(4-henoxyphenyl)ethyl]quinazoline-7-carboxamide

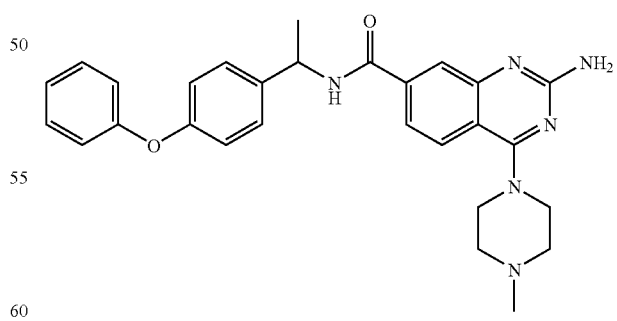

This compound was prepared using procedures analogous to those for Example 21, but 1-(4-phenoxyphenyl)ethanamine in Step 5. Analytic LCMS (M+H)$^+$: m/z=483.3.

Example 30

2-Amino-N-[(1R)-1-(4-methoxyphenyl)ethyl]-4-(4-methylpiperazin-1-yl)quinazoline-7-carboxamide

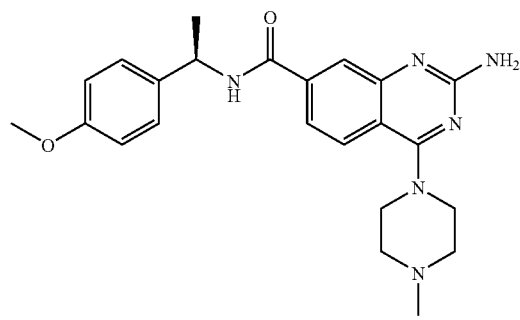 [SMILES: COc1ccc([C@@H](C)NC(=O)c2ccc3c(N4CCN(C)CC4)nc(N)nc3c2)cc1]

This compound was prepared using procedures analogous to those for Example 21, but using (1R)-1-(4-methoxyphenyl)ethanamine in Step 5. Analytic LCMS (M+H)$^+$: m/z=421.2.

Example 31

2-Amino-N-[1-(4-bromophenyl)ethyl]-4-(4-methylpiperazin-1-yl)quinazoline-7-carboxamide

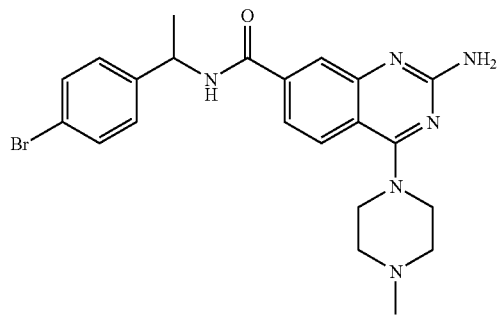 [SMILES: CC(NC(=O)c1ccc2c(N3CCN(C)CC3)nc(N)nc2c1)c1ccc(Br)cc1]

This compound was prepared using procedures analogous to those for Example 21, but using 1-(4-bromophenyl)ethanamine in Step 5. Analytic LCMS (M+H)$^+$: m/z=469.1, 471.1.

Example 32

2-Amino-N-[(1S)-1-(4-methylphenyl)ethyl]-4-(4-methylpiperazin-1-yl)quinazoline-7-carboxamide

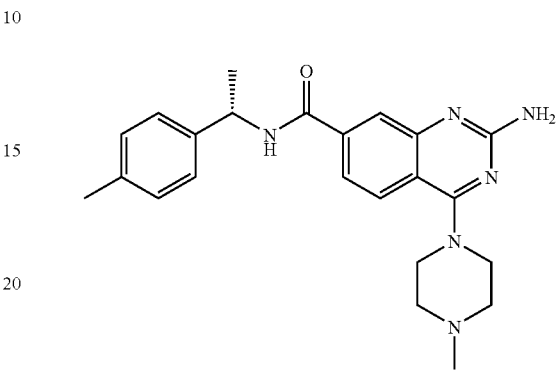

This compound was prepared as a TFA salt using procedures analogous to those for Example 21, but using (1S)-1-(4-methylphenyl)ethanamine in Step 5. Analytic LCMS (M+H)$^+$: m/z=405.2.

Example 33

2-Amino-4-(4-methylpiperazin-1-yl)-N-(4-phenoxyphenyl)quinazoline-7-carboxamide

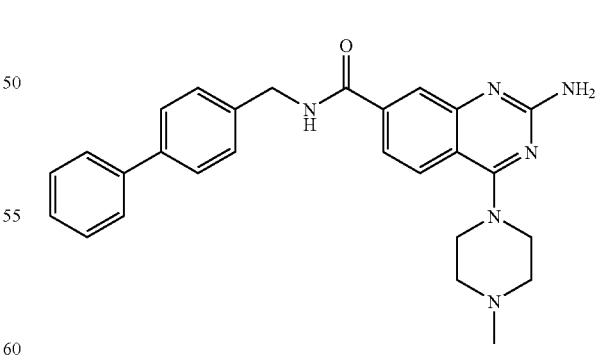

This compound was prepared using procedures analogous to those for Example 21, but using 1-biphenyl-4-ylmethanamine in Step 5. Analytic LCMS (M+H)$^+$: m/z=453.3.

Example 34

2-Amino-4-(4-methylpiperazin-1-yl)-N-(4-phenoxy-benzyl)quinazoline-7-carboxamide

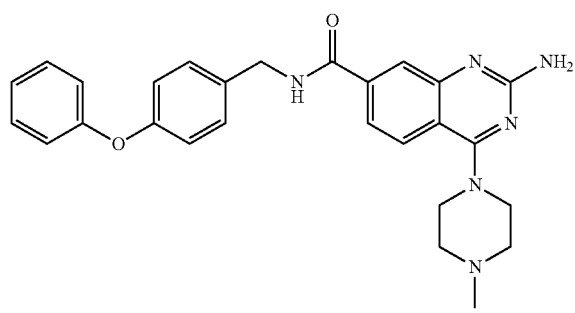 [SMILES: CN1CCN(c2nc(N)nc3cc(C(=O)NCc4ccc(Oc5ccccc5)cc4)ccc23)CC1]

This compound was prepared using procedures analogous to those for Example 21, but using 1-(4-phenoxyphenyl)methanamine in Step 5. Analytic LCMS (M+H)$^+$: m/z=469.2.

Example 35

2-Amino-4-(4-methylpiperazin-1-yl)-N-(4-phenoxyphenyl)quinazoline-7-carboxamide

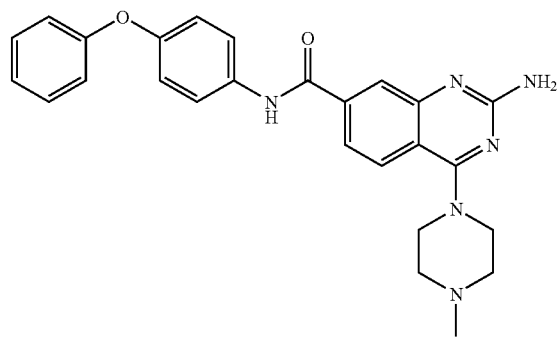 [SMILES: CN1CCN(c2nc(N)nc3cc(C(=O)Nc4ccc(Oc5ccccc5)cc4)ccc23)CC1]

This compound was prepared using procedures analogous to those for Example 21, but using 4-phenoxy-benzenamine in Step 5. Analytic LCMS (M+H)$^+$: m/z=455.1.

Example 36

2-Amino-N-(3-chloro-4-methylbenzyl)-4-(4-methylpiperazin-1-yl)quinazoline-7-carboxamide

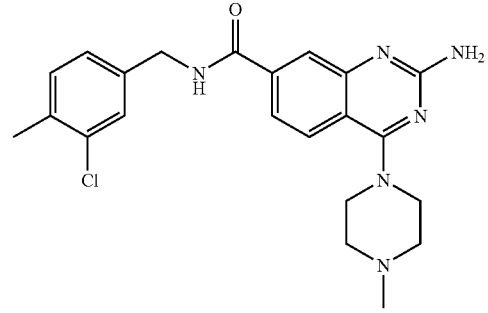 [SMILES: Cc1ccc(CNC(=O)c2ccc3c(N4CCN(C)CC4)nc(N)nc3c2)cc1Cl]

This compound was prepared using procedures analogous to those for Example 21, but using 1-(3-chloro-4-methylphenyl)methanamine in Step 5. Analytic LCMS (M+H)$^+$: m/z=425.2.

Example 37

2-Amino-4-(4-methylpiperazin-1-yl)-N-(2-phenylethyl)quinazoline-7-carboxamide

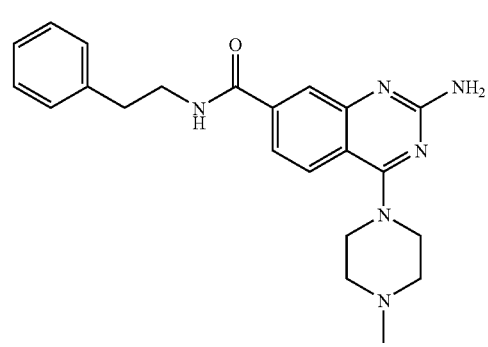 [SMILES: CN1CCN(c2nc(N)nc3cc(C(=O)NCCc4ccccc4)ccc23)CC1]

This compound was prepared using procedures analogous to those for Example 21, but using phenylethylamine in Step 5. Analytic LCMS (M+H)$^+$: m/z=391.2.

Example 38

2-Amino-4-(4-methylpiperazin-1-yl)-N-(3-phenyl-propyl)quinazoline-7-carboxamide

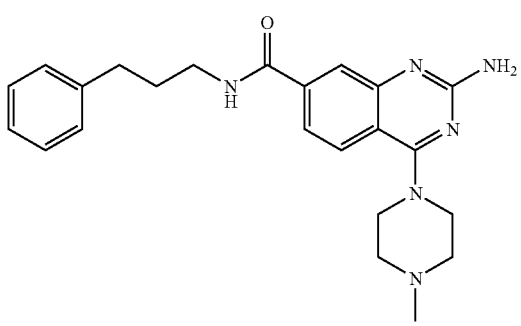 [SMILES: CN1CCN(c2nc(N)nc3cc(C(=O)NCCCc4ccccc4)ccc23)CC1]

This compound was prepared using procedures analogous to those for Example 21, but using benzenepropanamine in Step 5. Analytic LCMS (M+H)$^+$: m/z=405.2.

Example 39

4-[2-(3-Chlorobenzoyl)-1,2,3,4-tetrahydroisoquinolin-7-yl]-6-(4-methylpiperazin-1-yl)pyrimidin-2-amine

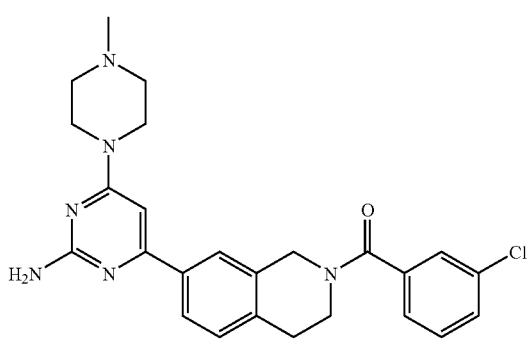 [SMILES: CN1CCN(c2cc(-c3ccc4c(c3)CN(C(=O)c3cccc(Cl)c3)CC4)nc(N)n2)CC1]

This compound was prepared by using procedures analogous to those described for the synthesis of Example 2 starting from 3-chlorobenzoyl chloride (Lancaster, Cat. #L01191) and 4-(4-methylpiperazin-1-yl)-6-(1,2,3,4-tetrahydroisoquinolin-7-yl)pyrimidin-2-amine HCl salt. Analytic LCMS (M+H)$^+$: m/z=463.3/465.3.

Example 40

7-[2-Amino-6-(4-methylpiperazin-1-yl)pyrimidin-4-yl]-N-(3-chloro-2-fluorophenyl)-3,4-dihydroisoquinoline-2(1H)-carboxamide

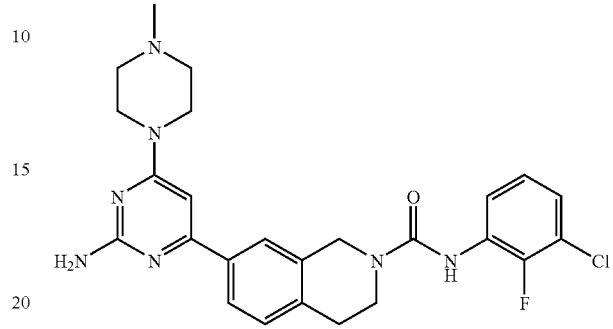

To a solution of 20% phosgene in toluene (phosgene:toluene=1:4, 54.9 uL, 0.104 mmol) was added a solution of 3-chloro-2-fluoroaniline (6.5 mg, 0.045 mmol) (Aldrich, Cat. #530174) and triethylamine (19.3 uL, 0.138 mmol) in THF (0.4 mL). The resulting mixture was stirred at r.t. for 2 h., and concentrated. To the residue was added a solution of 4-(4-methylpiperazin-1-yl)-6-(1,2,3,4-tetrahydroisoquinolin-7-yl)pyrimidin-2-amine HCl salt (15 mg, 0.034 mmol) and triethylamine (19.3 uL, 0.138 mmol) in acetonitrile (0.4 mL). The reaction mixture was stirred at r.t. for 30 min The mixture was purified by RP-LCMS (pH=10) to afford the desired product. Analytic LCMS (M+H)$^+$: m/z=496.1/498.1.

Example 41

4-[2-(Cyclopentylacetyl)-1,2,3,4-tetrahydroisoquinolin-7-yl]-6-(4-methylpiperazin-1-yl)pyrimidin-2-amine

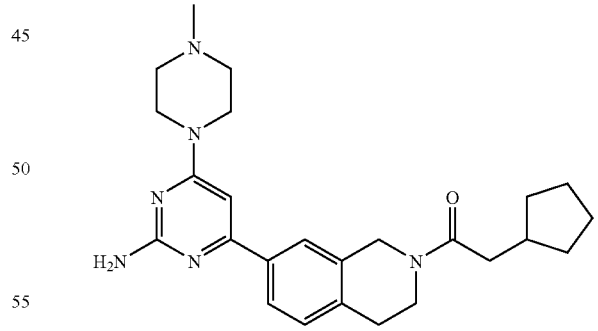

Triethylamine (24 uL, 0.17 mmol) was added to a mixture of 4-(4-methylpiperazin-1-yl)-6-(1,2,3,4-tetrahydroisoquinolin-7-yl)pyrimidin-2-amine HCl salt (15 mg, 0.034 mmol), cyclopentaneacetic acid (5.2 uL, 0.041 mmol) (Aldrich, Cat. #125490), and benzotriazol-1-yloxytris(dimethylamino)phosphonium hexafluorophosphate (17 mg, 0.038 mmol) (Chem-Impex, Cat. #00604) in N,N-dimethylformate (0.5 mL). The mixture was stirred at r.t. for 30 min., and then purified by RP-LCMS (pH=10) to afford the desired product. Analytic LCMS (M+H)$^+$: m/z=435.2.

Example 42

7-[2-Amino-6-(4-methylpiperazin-1-yl)pyrimidin-4-yl]-N-[1-(3-methylpyridin-2-yl)piperidin-4-yl]-3,4-dihydroisoquinoline-2(1H)-carboxamide

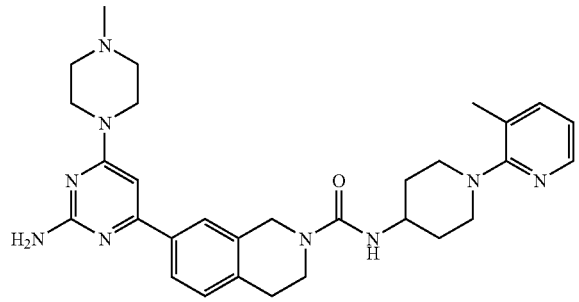 [SMILES: Cc1cccnc1N1CCC(NC(=O)N2CCc3ccc(-c4cc(N5CCN(C)CC5)nc(N)n4)cc3C2)CC1]

To a solution of 20% phosgene in toluene (Phosgene:Toluene=1:4, 20.1 uL, 0.0380 mmol) was added a solution of 4-(4-methylpiperazin-1-yl)-6-(1,2,3,4-tetrahydroisoquinolin-7-yl)pyrimidin-2-amine HCl salt (15 mg, 0.034 mmol) and triethylamine (14.4 uL, 0.104 mmol) in acetonitrile (0.5 mL). The resulting mixture was stirred for 10 min A mixture of 1-(3-methylpyridin-2-yl)piperidin-4-amine (9.8 mg, 0.051 mmol) (Alfa Aesar, Cat. #H50779) and triethylamine (14 uL, 0.10 mmol) in acetonitrile (0.3 mL) was added to above mixture. The reaction mixture was stirred at r.t. for 30 min., and then purified by RP-LCMS (pH=10) to afford the desired product. Analytic LCMS (M+H)$^+$: m/z=542.3.

Example 43

7-[2-Amino-6-(4-methylpiperazin-1-yl)pyrimidin-4-yl]-N-(5-cyanopyridin-2-yl)-3,4-dihydroisoquinoline-2(1H)-carboxamide

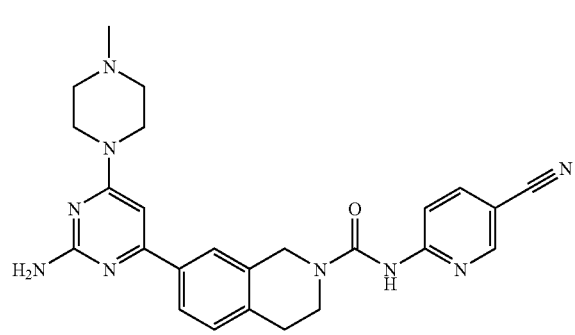 [SMILES: CN1CCN(c2cc(-c3ccc4c(c3)CN(C(=O)Nc3ccc(C#N)cn3)CC4)nc(N)n2)CC1]

This compound was prepared by using procedures analogous to those described for the synthesis of Example 40 starting from 6-aminonicotinonitrile (Aldrich, Cat. #637475), phosgene and 4-(4-methylpiperazin-1-yl)-6-(1,2,3,4-tetrahydroisoquinolin-7-yl)pyrimidin-2-amine HCl salt. Analytic LCMS (M+H)$^+$: m/z=470.2.

Example 44

7-[2-Amino-6-(4-methylpiperazin-1-yl)pyrimidin-4-yl]-N-(6-cyanopyridin-3-yl)-3,4-dihydroisoquinoline-2(1H)-carboxamide

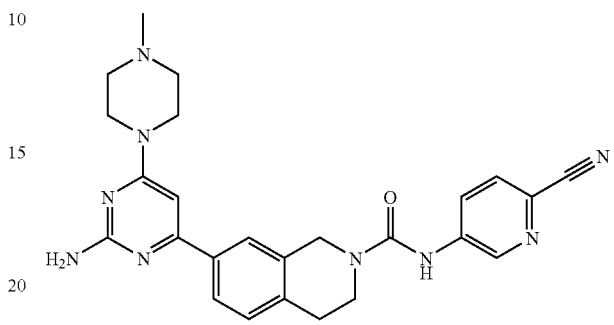

This compound was prepared by using procedures analogous to those described for the synthesis of Example 40 starting from 5-aminopyridine-2-carbonitrile (Aldrich, Cat. #538906), phosgene and 4-(4-methylpiperazin-1-yl)-6-(1,2,3,4-tetrahydroisoquinolin-7-yl)pyrimidin-2-amine HCl salt. Analytic LCMS (M+H)$^+$: m/z=470.2.

Example 45

Methyl 6-({[7-[2-amino-6-(4-methylpiperazin-1-yl)pyrimidin-4-yl]-3,4-dihydroisoquinolin-2(1H)-yl]carbonyl}amino)nicotinate

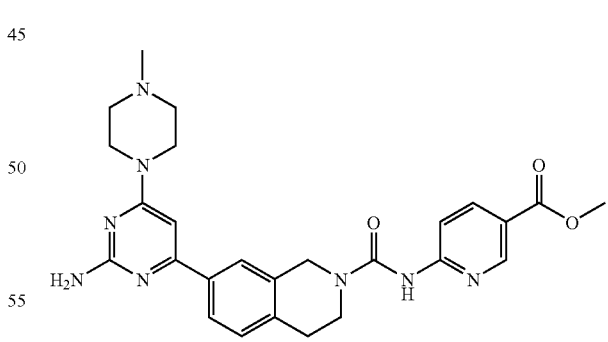

This compound was prepared by using procedures analogous to those described for the synthesis of Example 40 starting from methyl 6-aminonicotinate (Aldrich, Cat. #648736), phosgene and 4-(4-methylpiperazin-1-yl)-6-(1,2,3,4-tetrahydroisoquinolin-7-yl)pyrimidin-2-amine HCl salt. Analytic LCMS (M+H)$^+$: m/z=503.2.

Example 46

7-[2-Amino-6-(4-methylpiperazin-1-yl)pyrimidin-4-yl]-N-(6-methoxypyridin-3-yl)-3,4-dihydroisoquinoline-2(1H)-carboxamide

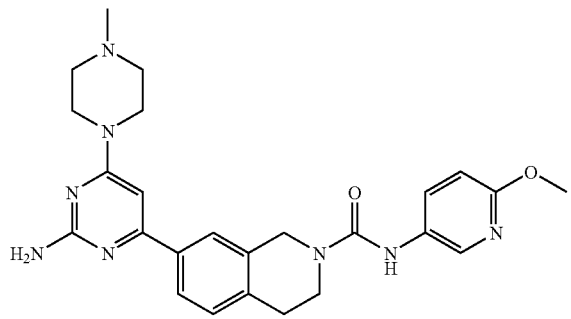 [SMILES: COc1ccc(NC(=O)N2CCc3ccc(-c4cc(N5CCN(C)CC5)nc(N)n4)cc3C2)cn1]

This compound was prepared by using procedures analogous to those described for the synthesis of Example 40 starting from 5-amino-2-methoxypyridine (Aldrich, Cat. #A61209), phosgene and 4-(4-methylpiperazin-1-yl)-6-(1,2,3,4-tetrahydroisoquinolin-7-yl)pyrimidin-2-amine HCl salt. Analytic LCMS (M+H)$^+$: m/z=475.2.

Example 47

7-[2-Amino-6-(4-methylpiperazin-1-yl)pyrimidin-4-yl]-N-(1-methylcyclohexyl)-3,4-dihydroisoquinoline-2(1H)-carboxamide

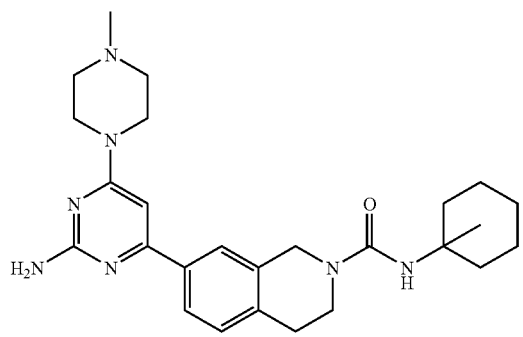

This compound was prepared by using procedures analogous to those described for the synthesis of Example 40 starting from 1-methylcyclohexanamine hydrochloride, phosgene and 4-(4-methylpiperazin-1-yl)-6-(1,2,3,4-tetrahydroisoquinolin-7-yl)pyrimidin-2-amine HCl salt. Analytic LCMS (M+H)$^+$: m/z=464.2.

Example 48

7-[2-Amino-6-(4-methylpiperazin-1-yl)pyrimidin-4-yl]-N-[4-(4-chlorophenyl)-1,3-thiazol-2-yl]-3,4-dihydroisoquinoline-2(1H)-carboxamide

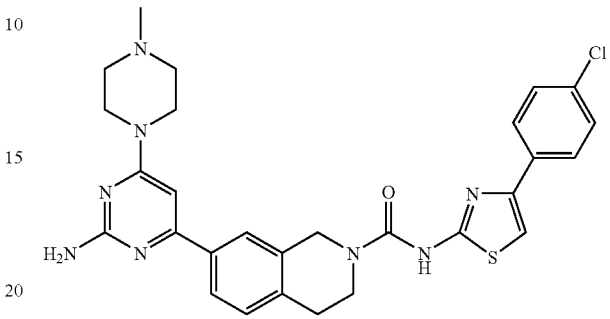

This compound was prepared by using procedures analogous to those described for the synthesis of Example 40 starting from 4-(4-chlorophenyl)-1,3-thiazol-2-amine (Aldrich, Cat. #339369), phosgene and 4-(4-methylpiperazin-1-yl)-6-(1,2,3,4-tetrahydroisoquinolin-7-yl)pyrimidin-2-amine HCl salt. Analytic LCMS (M+H)$^+$: m/z=561.2/563.2.

Example 49

7-[2-Amino-6-(4-methylpiperazin-1-yl)pyrimidin-4-yl]-N-(trans-2-phenylcyclopropyl)-3,4-dihydroisoquinoline-2(1H)-carboxamide

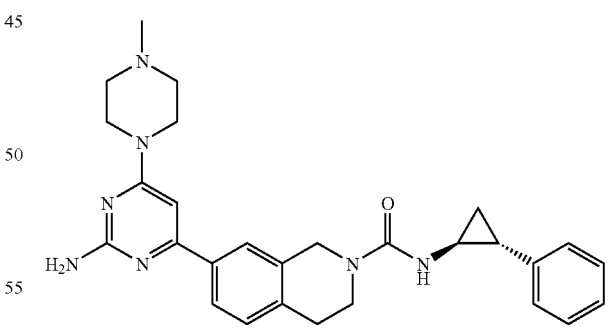

This compound was prepared by using procedures analogous to those described for the synthesis of Example 40 starting from trans-2-phenylcyclopropanamine hydrochloride (Aldrich, Cat. #P2237-0), phosgene and 4-(4-methylpiperazin-1-yl)-6-(1,2,3,4-tetrahydroisoquinolin-7-yl)pyrimidin-2-amine HCl salt. Analytic LCMS (M+H)$^+$: m/z=484.3.

Example 50

7-[2-Amino-6-(4-methylpiperazin-1-yl)pyrimidin-4-yl]-N-[4-(trifluoromethyl)-1,3-thiazol-2-yl]-3,4-dihydroisoquinoline-2(1H)-carboxamide

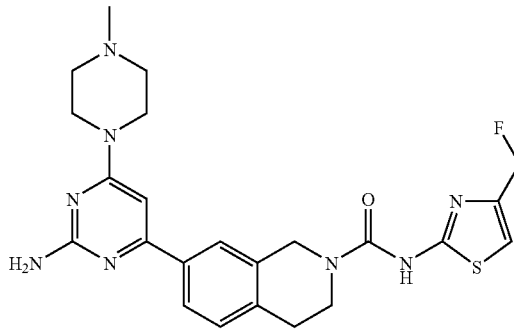

This compound was prepared by using procedures analogous to those described for the synthesis of Example 40 starting from 4-(trifluoromethyl)-1,3-thiazol-2-amine (Oakwood, Cat. #009875), phosgene and 4-(4-methylpiperazin-1-yl)-6-(1,2,3,4-tetrahydroisoquinolin-7-yl)pyrimidin-2-amine HCl salt. Analytic LCMS (M+H)$^+$: m/z=519.2.

Example 51

7-[2-Amino-6-(4-methylpiperazin-1-yl)pyrimidin-4-yl]-N-(1-phenylethyl)-3,4-dihydroisoquinoline-2(1H)-carboxamide

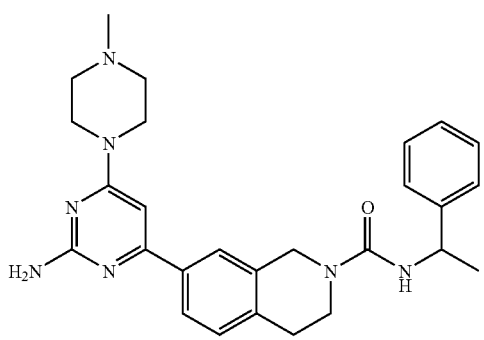 [SMILES: CC(NC(=O)N1CCc2ccc(-c3cc(N4CCN(C)CC4)nc(N)n3)cc2C1)c1ccccc1]

This compound was prepared by using procedures analogous to those described for the synthesis of Example 40 starting from a-methylbenzenemethanamine (Aldrich, Cat. #M31104), phosgene and 4-(4-methylpiperazin-1-yl)-6-(1,2,3,4-tetrahydroisoquinolin-7-yl)pyrimidin-2-amine HCl salt. Analytic LCMS (M+H)$^+$: m/z=472.3.

Example 52

Ethyl 4-({[7-[2-amino-6-(4-methylpiperazin-1-yl)pyrimidin-4-yl]-3,4-dihydroisoquinolin-2(1H)-yl]carbonyl}amino)piperidine-1-carboxylate

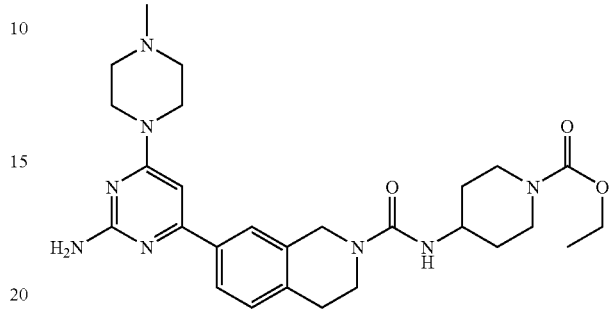

This compound was prepared by using procedures analogous to those described for the synthesis of Example 40 starting from ethyl 4-aminopiperidine-1-carboxylate (Aldrich, Cat. #198064), phosgene and 4-(4-methylpiperazin-1-yl)-6-(1,2,3,4-tetrahydroisoquinolin-7-yl)pyrimidin-2-amine HCl salt. Analytic LCMS (M+H)$^+$: m/z=523.3.

Example 53

Ethyl cis-2-({[7-[2-amino-6-(4-methylpiperazin-1-yl)pyrimidin-4-yl]-3,4-dihydroisoquinolin-2(1H)-yl]carbonyl}amino)cyclohexanecarboxylate

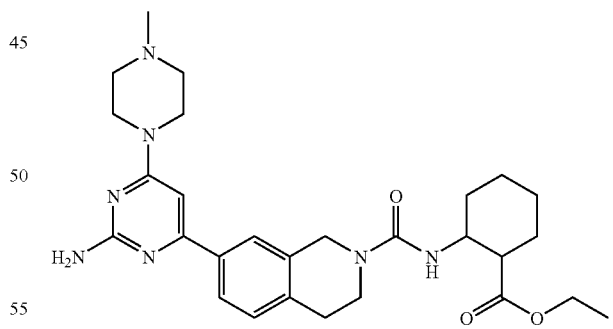

This compound was prepared by using procedures analogous to those described for the synthesis of Example 40 starting from ethyl cis-2-aminocyclohexanecarboxylate hydrochloride (Acros Organics, Cat. #26564), phosgene and 4-(4-methylpiperazin-1-yl)-6-(1,2,3,4-tetrahydroisoquinolin-7-yl)pyrimidin-2-amine HCl salt. Analytic LCMS (M+H)$^+$: m/z=522.3.

Example 54

7-[2-Amino-6-(4-methylpiperazin-1-yl)pyrimidin-4-yl]-N-{4-[(dimethylamino)carbonyl]cyclohexyl}-3,4-dihydroisoquinoline-2(1H)-carboxamide

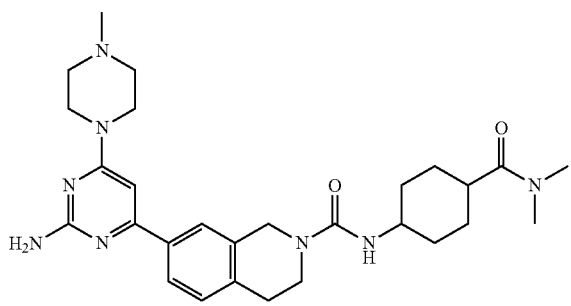 [SMILES: CN1CCN(c2cc(-c3ccc4c(c3)CN(C(=O)NC3CCC(C(=O)N(C)C)CC3)CC4)nc(N)n2)CC1]

Step 1: 4-[(tert-butoxycarbonyl)amino]cyclohexanecarboxylic acid

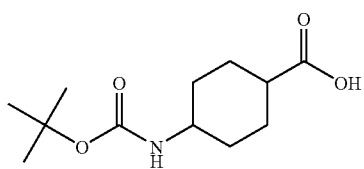 [SMILES: CC(C)(C)OC(=O)NC1CCC(C(=O)O)CC1]

Di-tert-butyldicarbonate (0.48 g, 2.2 mmol) was added to a mixture of cis-4-aminocyclohexanecarboxylic acid (0.30 g, 2.1 mmol) (Aldrich, Cat. #404853) and triethylamine (0.88 mL, 6.3 mmol) in methylene chloride (5.0 mL) at 0° C. The reaction mixture was stirred at r.t. for 30 min The mixture was directly used for next step reaction without further purification. Analytic LCMS (M+Na)$^+$: m/z=266.1; (M–Bu$^t$+H)$^+$: m/z=188.1.

Step 2: tert-butyl{4-[(dimethylamino)carbonyl]cyclohexyl}carbamate

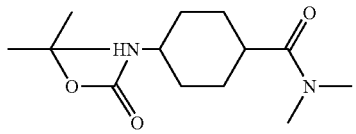

Triethylamine (0.42 mL, 3.0 mmol) was added to a mixture of 4-[(tert-butoxycarbonyl)amino]cyclohexanecarboxylic acid (1.0 mmol), dimethylamine (0.6 mL, 1.2 mmol) (2 N THF solution) and benzotriazol-1-yloxytris(dimethylamino)phosphonium hexafluorophosphate (0.46 g, 1.1 mmol) in methylene chloride (5.0 mL). The mixture was stirred at r.t. overnight. The mixture was diluted with water, and extracted with ethyl acetate (3×10 mL). The combined organic layers were dried over MgSO$_4$, filtered and concentrated. The residue was purified by flash chromatography on a silica gel column with ethyl acetate in hexanes (0-40%) to afford the desired product (0.20 g, 74%). Analytic LCMS (M+Na)$^+$: m/z=293.1; (M–Boc+H)$^+$: m/z=171.1.

Step 3: 4-amino-N,N-dimethylcyclohexanecarboxamide

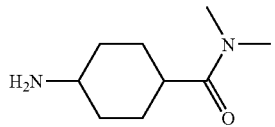

2 mL of 4 N HCl in 1,4-dioxane was added to a solution of tert-butyl{4-[(dimethylamino)carbonyl]cyclohexyl}carbamate (0.20 g, 0.74 mmol) in methanol (1.0 mL). The reaction mixture was stirred at r.t. for 2 h. The volatiles were removed under reduced pressure to afford the desired product as an HCl salt.

Step 4: 7-[2-amino-6-(4-methylpiperazin-1-yl)pyrimidin-4-yl]-N-{4-[(dimethylamino)carbonyl]cyclohexyl}-3,4-dihydroisoquinoline-2(1H)-carboxamide This compound was prepared by using procedures analogous to those described for the synthesis of Example 40 starting from 4-amino-N,N-dimethylcyclohexanecarboxamide hydrochloride, phosgene and 4-(4-methylpiperazin-1-yl)-6-(1,2,3,4-tetrahydroisoquinolin-7-yl)pyrimidin-2-amine HCl salt. Analytic LCMS (M+H)$^+$: m/z=521.3.

Example 55

7-[2-Amino-6-(4-methylpiperazin-1-yl)pyrimidin-4-yl]-N-(cis-2-methoxycyclohexyl)-3,4-dihydroisoquinoline-2(1H)-carboxamide

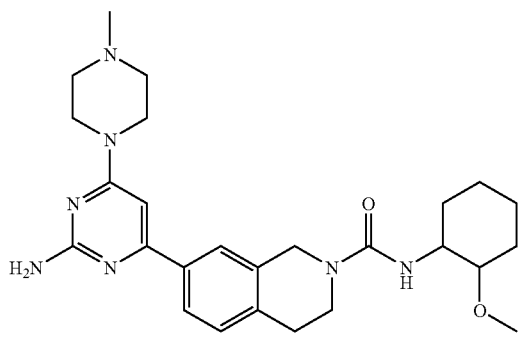 [SMILES: COC1CCCCC1NC(=O)N1CCc2ccc(-c3cc(N4CCN(C)CC4)nc(N)n3)cc2C1]

Step 1: tert-butyl(cis-2-methoxycyclohexyl)carbamate

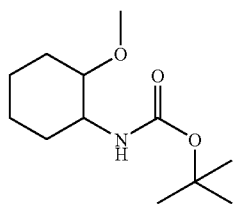 [SMILES: COC1CCCCC1NC(=O)OC(C)(C)C]

Di-tert-butyldicarbonate (0.48 g, 2.2 mmol) was added to a solution of cis-2-aminocyclohexanol hydrochloride (0.30 g, 2.0 mmol) (Acros Organics, Cat. #26585) and triethylamine (0.55 mL, 4.0 mmol) in THF (7.5 mL). After stirring at r.t. for 30 min, the mixture was quenched with aqueous $Na_2CO_3$, extracted with ethyl acetate (3×20 mL), the combined organic layers were washed with brine, dried over $MgSO_4$, filtered and concentrated under reduced pressure [LCMS (M+Na)$^+$: m/z=238.1]. The residue was dissolved in N,N-dimethylformate (4.0 mL). To the solution was added sodium hydride (0.095 g, 2.4 mmol, 60% dispersion in mineral oil) under $N_2$. The mixture was stirred at r.t. for 10 min, and methyl iodide (0.18 mL, 3.0 mmol) was added. The reaction mixture was stirred at r.t. overnight. The mixture was diluted with water, and extracted with ethyl acetate (3×10 mL). The combined organic layers were dried over $MgSO_4$, filtered and concentrated under reduced pressure. The residue was purified by flash chromatography on a silica gel column with ethyl acetate in hexanes (0-40%) to afford the desired product (0.17 g, 37%). Analytic LCMS (M+Na)$^+$: m/z=252.1.

Step 2: cis-2-methoxycyclohexanamine

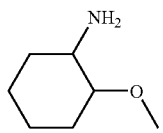

2 mL of 4 N HCl in 1,4-dioxane was added to a solution of tert-butyl(cis-2-methoxycyclohexyl)carbamate (0.17 g, 0.74 mmol) in methanol (0.5 mL). The reaction mixture was stirred at r.t. overnight. The volatiles were removed under reduced pressure to afford the desired product as HCl salt. Analytic LCMS (M+H)$^+$: m/z=130.1.

Step 3: 7-[2-amino-6-(4-methylpiperazin-1-yl)pyrimidin-4-yl]-N-(cis-2-methoxycyclohexyl)-3,4-dihydroisoquinoline-2(1H)-carboxamide To a solution of 20% phosgene in toluene [Phosgene:Toluene=1:4 v/v, 24.4 uL, 0.0461 mmol) was added a solution of (cis)-2-methoxycyclohexanamine hydrochloride (5.0 mg, 0.030 mmol) and triethylamine (9.6 uL, 0.069 mmol) in tetrahydrofuran (0.3 mL). The resulted mixture was stirred at r.t. for 2 h., and concentrated. To the residue was added a solution of 4-(4-methylpiperazin-1-yl)-6-(1,2,3,4-tetrahydroisoquinolin-7-yl)pyrimidin-2-amine HCl salt (10 mg, 0.02 mmol) and triethylamine (12.8 uL, 0.092 mmol) in acetonitrile (0.3 mL). The reaction mixture was stirred at room temperature for 30 min The mixture was purified by RP-LCMS (pH=10) to afford the desired product. Analytic LCMS (M+H)$^+$: m/z=480.2.

Example 56

7-[2-Amino-6-(4-methylpiperazin-1-yl)pyrimidin-4-yl]-N-(trans-4-methoxycyclohexyl)-3,4-dihydroisoquinoline-2(1H)-carboxamide

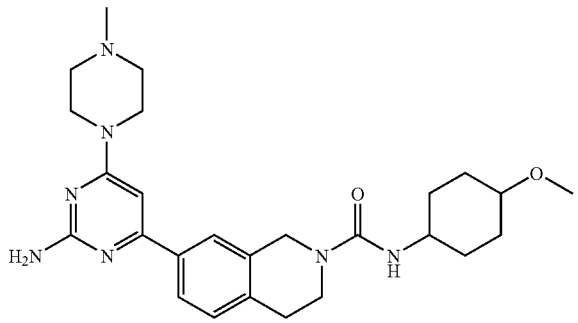 [SMILES: COC1CCC(NC(=O)N2CCc3ccc(-c4cc(N5CCN(C)CC5)nc(N)n4)cc3C2)CC1]

Step 1: 2-(trans-4-hydroxycyclohexyl)-1H-isoindole-1,3(2H)-dione

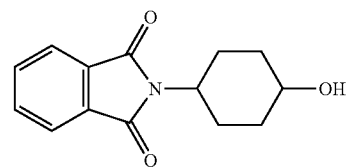 [SMILES: O=C1c2ccccc2C(=O)N1C1CCC(O)CC1]

A mixture of trans-4-aminocyclohexanol hydrochloride (1.0 g, 6.6 mmol) (Aldrich, Cat. #263761), N-carbethoxyphthalimide (1.4 g, 6.6 mmol) (Aldrich, Cat. #C5459), and triethylamine (2.0 mL, 14 mmol) in methylene chloride (10 mL) was stirred at r.t. overnight. The mixture was diluted with water, and extracted with ethyl acetate (3×20 mL). The combined organic layers were dried over $Na_2SO_4$, filtered and concentrated under reduced pressure. The residue was purified by flash chromatography on a silica gel column with ethyl acetate in hexanes to afford the desired product (1.2 g, 76%).

Step 2: 2-(trans-4-methoxycyclohexyl)-1H-isoindole-1,3(2H)-dione

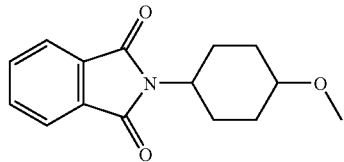 [SMILES: COC1CCC(N2C(=O)c3ccccc3C2=O)CC1]

At 0° C. to a suspension of sodium hydride (98 mg, 2.4 mmol) in N,N-dimethylformamide (4 mL) was added 2-(trans-4-hydroxycyclohexyl)-1H-isoindole-1,3(2H)-dione (0.5 g, 2 mmol) with stirring.

After stirring at r.t. for 30 min, to the mixture was added methyl iodide (190 uL, 3.0 mmol). The mixture was stirred at r.t. for 3 h. The mixture was diluted with water, and extracted with ethyl acetate (3×20 mL). The combined organic layers were dried over Na₂SO₄, filtered and concentrated under reduced pressure. The residue was purified by flash chromatography on a silica gel column with ethyl acetate in hexanes to afford the desired product (0.27 g, 50%)

Step 3: trans-4-methoxycyclohexanamine

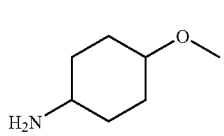

A mixture of 2-(trans-4-methoxycyclohexyl)-1H-isoindole-1,3(2H)-dione (0.27 g, 1.0 mmol), and hydrazine hydrate (63.3 uL, 0.00130 mol) in ethanol (2.0 mL) was heated at reflux for 1 h. After cooling, the solid was filtered off, and the filtrate was concentrated to yield the desired product (0.12 g, 89%).

Step 4: 7-[2-Amino-6-(4-methylpiperazin-1-yl)pyrimidin-4-yl]-N-(trans-4-methoxycyclohexyl)-3,4-dihydroisoquinoline-2(1H)-carboxamide This compound was prepared by using procedures analogous to those described for the synthesis of Example 55, Step 3 starting from trans-4-methoxycyclohexanamine and 4-(4-methylpiperazin-1-yl)-6-(1,2,3,4-tetrahydroisoquinolin-7-yl)pyrimidin-2-amine HCl salt. Analytic LCMS (M+H)⁺: m/z=480.2.

Example 57

7-[2-Amino-6-(4-methylpiperazin-1-yl)pyrimidin-4-yl]-N-[(1S,2R)-2-methoxy-2,3-dihydro-1H-inden-1-yl]-3,4-dihydroisoquinoline-2(1H)-carboxamide

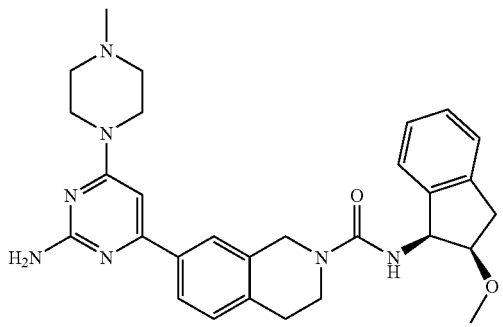 [SMILES: CO[C@@H]1Cc2ccccc2[C@@H]1NC(=O)N1CCc2ccc(-c3cc(N4CCN(C)CC4)nc(N)n3)cc2C1]

Step 1: tert-butyl[(1S,2R)-2-hydroxy-2,3-dihydro-1H-inden-1-yl]carbamate

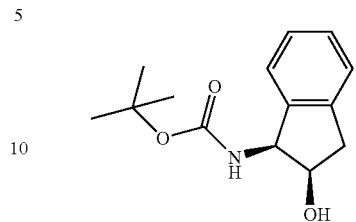

Di-tert-butyldicarbonate (0.80 g, 3.7 mmol) was added to a solution of (1S,2R)-1-aminoindan-2-ol (0.50 g, 3.4 mmol) (Aldrich, Cat. #440833) and triethylamine (0.70 mL, 5.0 mmol) in methylene chloride (7.0 mL) at r.t. The reaction mixture was stirred at r.t. for 30 min The mixture was quenched with aqueous Na₂CO₃, and extracted with ethyl acetate (3×10 mL). The combined organic layers were dried over MgSO₄, filtered and concentrated under reduced pressure. The residue was purified by flash chromatography on a silica gel column with MeOH in dichloromethane (0-10%) to afford the desired product (0.88 g, 100%). Analytic LCMS (M+Na)⁺: m/z=272.1.

Step 2: (1S,2R)-2-methoxyindan-1-amine

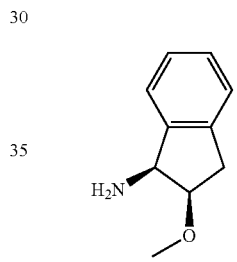

Sodium hydride (0.048 g, 1.2 mmol, 60% dispersion in mineral oil) was added to a mixture of the above intermediate in N,N-dimethylformate (2.3 mL) under N₂. The mixture was stirred at r.t. for 10 min., and methyl iodide (0.075 mL, 1.2 mmol) was added. The reaction mixture was stirred at r.t. overnight. The mixture was diluted with water, and extracted with ethyl acetate (3×10 mL). The combined organic layers were dried over MgSO₄, filtered and concentrated under reduced pressure. The residue was purified by flash chromatography on a silica gel column with ethyl acetate in hexanes (0-30%) to afford tert-butyl (1S,2R)-2-methoxy-2,3-dihydro-1H-inden-1-ylcarbamate [LCMS (M+Na)+: 286.1]. 2 mL of 4 N HCl in 1,4-dioxane was added to a solution of tert-butyl (1S,2R)-2-methoxy-2,3-dihydro-1H-inden-1-ylcarbamate in methanol (1 mL). The reaction mixture was stirred at r.t. overnight. The volatiles were removed under reduced pressure to afford the desired product as HCl salt.

Step 3: 7-[2-amino-6-(4-methylpiperazin-1-yl)pyrimidin-4-yl]-N-[(1S,2R)-2-methoxy-2,3-dihydro-1H-inden-1-yl]-3,4-dihydroisoquinoline-2(1H)-carboxamide To a solution of 20% phosgene in toluene (Phosgene:Toluene=1:4 v/v, 24.4 uL, 0.0461 mmol) was added a solution of (1S,2R)-2-methoxyindan-1-amine HCl salt (6.0 mg, 0.030 mmol) and triethylamine (9.6 uL, 0.069 mmol) in tetrahydrofuran (0.3 mL). The resulted mixture was stirred at r.t. for 2 h., and concentrated. To the residue was added a solution of 4-(4-methylpiperazin-1-yl)-6-(1,2,3,4-tetrahydroisoquinolin-7-yl)pyrimidin-2-amine HCl salt (10 mg, 0.02 mmol) and triethylamine (12.8 uL, 0.092 mmol) in acetonitrile (0.3 mL). The reaction mixture was stirred at room temperature for 30 min The mixture was purified by RP-LCMS (pH=10) to afford the desired product. Analytic LCMS (M+H)$^+$: m/z=514.2.

Example 58

7-[2-Amino-6-(4-methylpiperazin-1-yl)pyrimidin-4-yl]-N-[(1R,2S)-2-methoxy-2,3-dihydro-1H-inden-1-yl]-3,4-dihydroisoquinoline-2(1H)-carboxamide

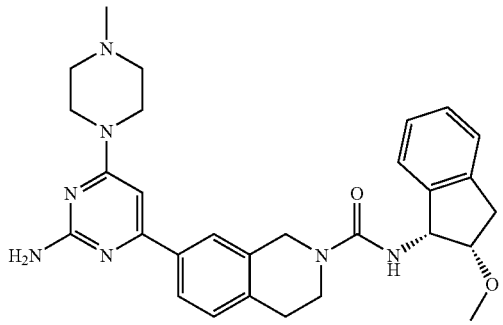 [SMILES: CO[C@H]1Cc2ccccc2[C@H]1NC(=O)N1CCc2ccc(-c3cc(N4CCN(C)CC4)nc(N)n3)cc2C1]

Step 1: tert-butyl[(1R,2S)-2-hydroxy-2,3-dihydro-1H-inden-1-yl]carbamate

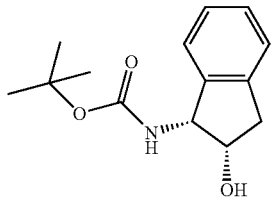 [SMILES: CC(C)(C)OC(=O)N[C@@H]1c2ccccc2C[C@@H]1O]

This compound was prepared by using procedures analogous to those described for the synthesis of Example 57, Step 1 starting from (1R,2S)-1-aminoindan-2-ol (Aldrich, Cat. #440841), and di-tert-butyldicarbonate. Analytic LCMS (M+Na)+: m/z=272.1.

Step 2: (1R,2S)-2-methoxyindan-1-amine

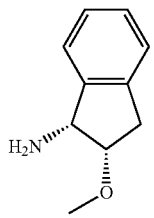

This compound was prepared by using procedures analogous to those described for the synthesis of Example 57, Step 2 starting from tert-butyl[(1R,2S)-2-hydroxy-2,3-dihydro-1H-inden-1-yl]carbamate, sodium hydride and methyl iodide.

Step 3: 7-[2-amino-6-(4-methylpiperazin-1-yl)pyrimidin-4-yl]-N-[(1R,2S)-2-methoxy-2,3-dihydro-1H-inden-1-yl]-3,4-dihydroisoquinoline-2(1H)-carboxamide This compound was prepared by using procedures analogous to those described for the synthesis of Example 57, Step 3 starting from (1R,2S)-2-methoxyindan-1-amine HCl salt and 4-(4-methylpiperazin-1-yl)-6-(1,2,3,4-tetrahydroisoquinolin-7-yl)pyrimidin-2-amine HCl salt. Analytic LCMS (M+H)+: m/z=514.2.

Example 59

N-1-Adamantyl-7-[2-amino-6-(4-methylpiperazin-1-yl)pyrimidin-4-yl]-3,4-dihydroisoquinoline-2(1H)-carboxamide

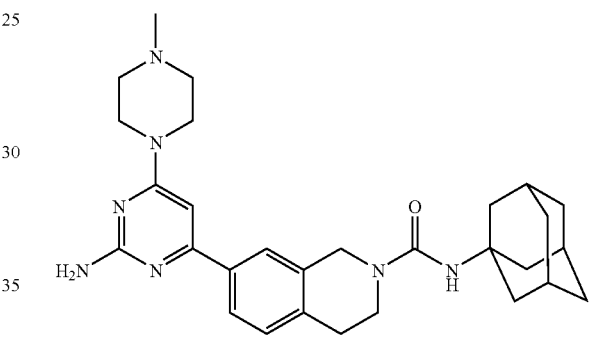

This compound was prepared by using procedures analogous to those described for the synthesis of Example 5 starting from 1-isocyanatoadamantane (Aldrich, Cat. #375073) and 4-(4-methylpiperazin-1-yl)-6-(1,2,3,4-tetrahydroisoquinolin-7-yl)pyrimidin-2-amine HCl salt. Analytic LCMS (M+H)$^+$: m/z=502.3.

Example 60

7-[2-Amino-6-(4-methylpiperazin-1-yl)pyrimidin-4-yl]-N-[(1R)-1-benzyl-2-(dimethylamino)-2-oxoethyl]-3,4-dihydroisoquinoline-2(1H)-carboxamide

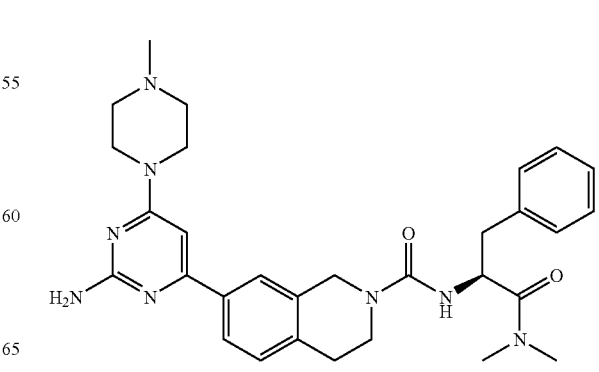

Step 1: methyl (2S)-2-({[7-[2-amino-6-(4-methylpiperazin-1-yl]pyrimidin-4-yl]-3,4-dihydroisoquinolin-2(1H)-yl]carbonyl}amino)-3-phenylpropanoate

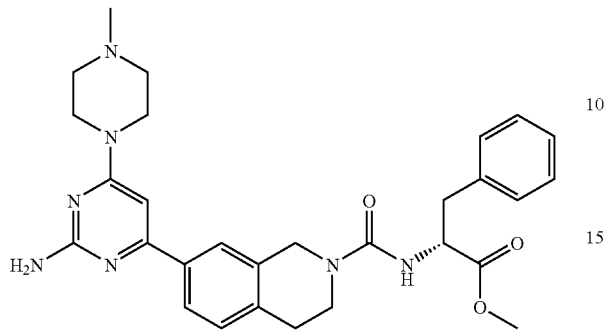

Methyl (2S)-2-isocyanato-3-phenylpropanoate (12.5 mg, 0.0609 mmol) (Aldrich, Cat. #409731) was added to a mixture of 4-(4-methylpiperazin-1-yl)-6-(1,2,3,4-tetrahydroisoquinolin-7-yl)pyrimidin-2-amine HCl salt (25.0 mg, 0.0576 mmol) and triethylamine (32 uL, 0.23 mmol) in acetonitrile (1.0 mL). After 30 min., the mixture was concentrated, and purified by flash chromatography on a silica gel column with MeOH in dichloromethylene (0-5%) to afford the desired product (30 mg, 98%). Analytic LCMS (M+H)$^+$: m/z=530.2.

Step 2: (S)-2-(7-(2-amino-6-(4-methylpiperazin-1-yl)pyrimidin-4-yl)-1,2,3,4-tetrahydroisoquinoline-2-carboxamido)-3-phenylpropanoic acid

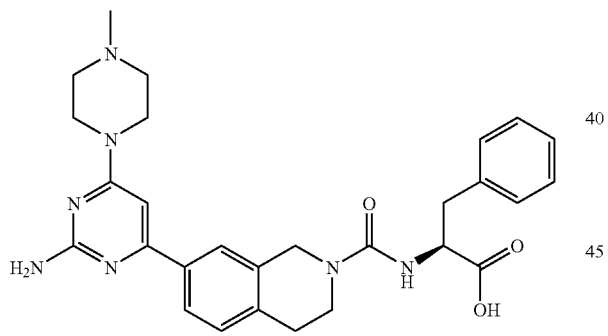

Lithium hydroxide monohydrate (7.1 mg, 0.17 mmol) was added to a mixture of methyl (2S)-2-({[7-[2-amino-6-(4-methylpiperazin-1-yl)pyrimidin-4-yl]-3,4-dihydroisoquinolin-2(1H)-yl]carbonyl}amino)-3-phenylpropanoate (30 mg, 0.057 mmol) in methanol (0.6 mL) and water (0.2 mL). The reaction mixture was stirred at r.t. overnight, and adjusted with 4N HCl in 1,4-dioxane to pH=5. The volatiles were removed under reduced pressure to afford the product which contaminated with LiCl and was directly used for next step reaction without further purification.

Step 3: 7-[2-amino-6-(4-methylpiperazin-1-yl)pyrimidin-4-yl]-N-[(1R)-1-benzyl-2-(dimethylamino)-2-oxoethyl]-3,4-dihydroisoquinoline-2(1H)-carboxamide This compound was prepared by using procedures analogous to those described for the synthesis of Example 41 starting from dimethylamine (2.0 M solution in THF), (S)-2-(7-(2-amino-6-(4-methylpiperazin-1-yl)pyrimidin-4-yl)-1,2,3,4-tetrahydroisoquinoline-2-carboxamido)-3-phenylpropanoic acid, triethylamine, and benzotriazol-1-yloxytris(dimethylamino)phosphonium hexafluorophosphate. Analytic LCMS (M+H)$^+$: m/z=543.2.

Example 61

4-{2-[Difluoro(phenyl)acetyl]-1,2,3,4-tetrahydroisoquinolin-7-yl}-6-(4-methylpiperazin-1-yl)pyrimidin-2-amine

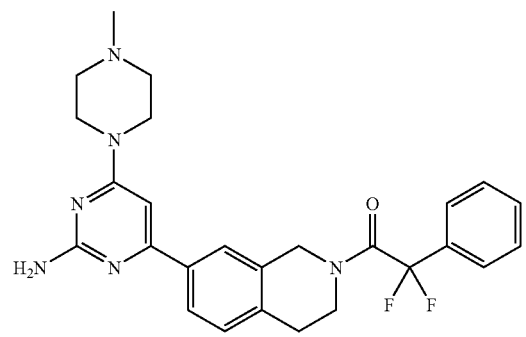 [SMILES: CN1CCN(c2cc(-c3ccc4c(c3)CN(C(=O)C(F)(F)c3ccccc3)CC4)nc(N)n2)CC1]

This compound was prepared by using procedures analogous to those described for the synthesis of Example 41 starting from difluoro(phenyl)acetic acid (Matrix Scientific, Cat. #018321) and 4-(4-methylpiperazin-1-yl)-6-(1,2,3,4-tetrahydroisoquinolin-7-yl)pyrimidin-2-amine HCl salt. Analytic LCMS (M+H)$^+$: m/z=479.2.

Example 62

4-(4-Methylpiperazin-1-yl)-6-[2-(4,4,4-trifluoro-3-methylbutanoyl)-1,2,3,4-tetrahydroisoquinolin-7-yl]pyrimidin-2-amine

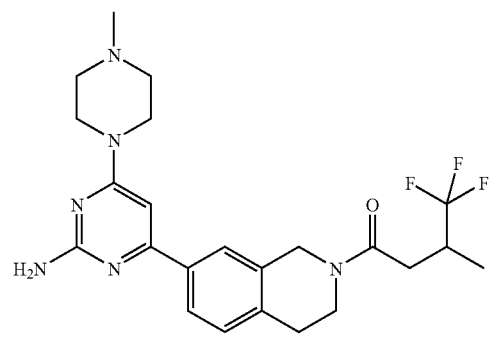 [SMILES: CC(CC(=O)N1CCc2ccc(-c3cc(N4CCN(C)CC4)nc(N)n3)cc2C1)C(F)(F)F]

This compound was prepared by using procedures analogous to those described for the synthesis of Example 41 starting from 4,4,4-trifluoro-3-methylbutanoic acid (Lancaster, Cat. #L12160) and 4-(4-methylpiperazin-1-yl)-6-(1,2,3,4-tetrahydroisoquinolin-7-yl)pyrimidin-2-amine HCl salt. Analytic LCMS (M+H)$^+$: m/z=463.2.

Example 63

7-[2-Amino-6-(4-methylpiperazin-1-yl)pyrimidin-4-yl]-N-(4,4-difluorocyclohexyl)-3,4-dihydroisoquinoline-2(1H)-carboxamide

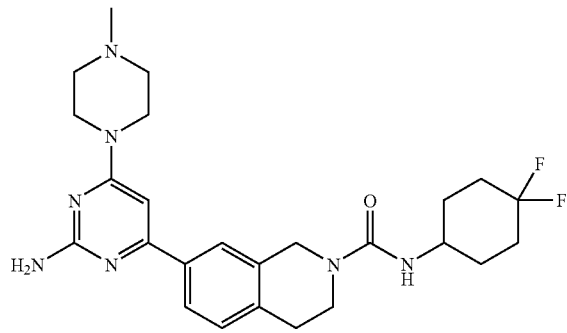 [SMILES: CN1CCN(c2cc(-c3ccc4c(c3)CN(C(=O)NC3CCC(F)(F)CC3)CC4)nc(N)n2)CC1]

Step 1: 1,1-difluoro-4-isocyanatocyclohexane

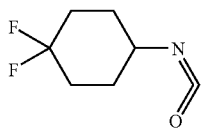

A mixture of 4,4-difluorocyclohexanecarboxylic acid (0.20 g, 1.2 mmol) (Matrix Scientific, Cat. #018320), diphenylphosphonic azide (0.67 g, 2.4 mmol) (Aldrich, Cat. #178756) and triethylamine (0.51 mL, 3.6 mmol) in toluene (10 mL) was refluxed overnight. The volatiles were removed under reduced pressure to afford the product which was directly used for next step reaction without further purification.

Step 2: 7-[2-amino-6-(4-methylpiperazin-1-yl)pyrimidin-4-yl]-N-(4,4-difluorocyclohexyl)-3,4-dihydroisoquinoline-2(1H)-carboxamide This compound was prepared by using procedures analogous to those described for the synthesis of Example 5 starting from 1,1-difluoro-4-isocyanatocyclohexane and 4-(4-methylpiperazin-1-yl)-6-(1,2,3,4-tetrahydroisoquinolin-7-yl)pyrimidin-2-amine HCl salt. Analytic LCMS (M+H)$^+$: m/z=486.2.

Example 64

7-[2-Amino-6-(4-methylpiperazin-1-yl)pyrimidin-4-yl]-N-[4-(trifluoromethyl)cyclohexyl]-3,4-dihydroisoquinoline-2(1H)-carboxamide

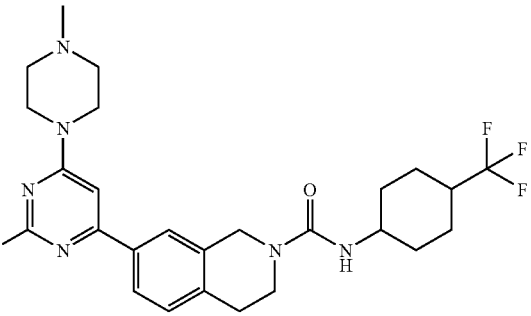

Step 1: 1-isocyanato-4-(trifluoromethyl)cyclohexane

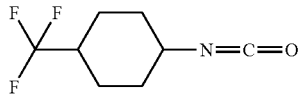

This compound was prepared by using procedures analogous to those described for the synthesis of Example 63, Step 1 starting from 4-(trifluoromethyl)cyclohexanecarboxylic acid (Aldrich, Cat. #579122) and diphenylphosphonic azide.

Step 2: 7-[2-Amino-6-(4-methylpiperazin-1-yl)pyrimidin-4-yl]-N-[4-(trifluoromethyl)cyclohexyl]-3,4-dihydroisoquinoline-2(1H)-carboxamide This compound was prepared by using procedures analogous to those described for the synthesis of Example 5 starting from 1-isocyanato-4-(trifluoromethyl)cyclohexane, and 4-(4-methylpiperazin-1-yl)-6-(1,2,3,4-tetrahydroisoquinolin-7-yl)pyrimidin-2-amine HCl salt. Analytic LCMS (M+H)$^+$: m/z=518.2.

Example 65

4-{2-[(4-Fluorophenyl)acetyl]-1,2,3,4-tetrahydroisoquinolin-7-yl}-6-(4-methylpiperazin-1-yl)pyrimidin-2-amine

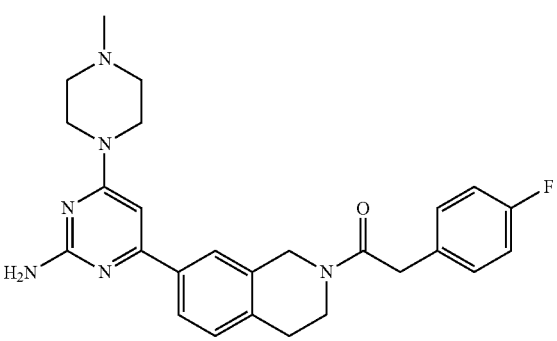 [SMILES: CN1CCN(c2cc(-c3ccc4c(c3)CN(C(=O)Cc3ccc(F)cc3)CC4)nc(N)n2)CC1]

This compound was prepared by using procedures analogous to those described for the synthesis of Example 2 starting from (4-fluorophenyl)acetyl chloride (Aldrich, Cat. #466956) and 4-(4-methylpiperazin-1-yl)-6-(1,2,3,4-tetrahydroisoquinolin-7-yl)pyrimidin-2-amine HCl salt. Analytic LCMS (M+H)+: m/z=461.2.

Example 66

4-{2-[(3-Chlorophenoxy)acetyl]-1,2,3,4-tetrahydroisoquinolin-7-yl}-6-(4-methylpiperazin-1-yl)pyrimidin-2-amine

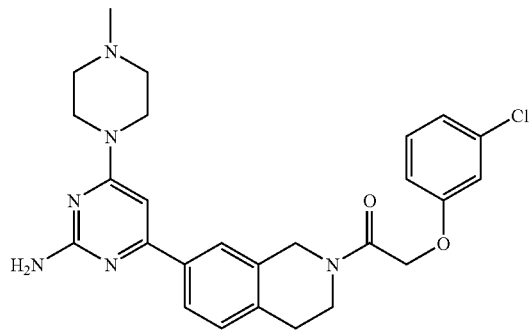 [SMILES: CN1CCN(c2cc(-c3ccc4c(c3)CN(C(=O)COc3cccc(Cl)c3)CC4)nc(N)n2)CC1]

This compound was prepared by using procedures analogous to those described for the synthesis of Example 2 starting from (3-chlorophenoxy)acetyl chloride (Lancaster, Cat. #L18427) and 4-(4-methylpiperazin-1-yl)-6-(1,2,3,4-tetrahydroisoquinolin-7-yl)pyrimidin-2-amine HCl salt. Analytic LCMS (M+H)+: m/z=493.2/495.1.

Example 67

1-(Cyclopentylcarbonyl)piperidin-4-yl 7-[2-amino-6-(4-methylpiperazin-1-yl)pyrimidin-4-yl]-3,4-dihydroisoquinoline-2(1H)-carboxylate

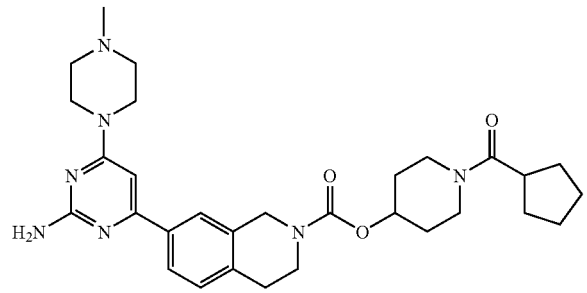 [SMILES: CN1CCN(c2cc(-c3ccc4c(c3)CN(C(=O)OC3CCN(C(=O)C5CCCC5)CC3)CC4)nc(N)n2)CC1]

Step 1: tert-butyl 4-{[(4-nitrophenoxy)carbonyl]oxy}piperidine-1-carboxylate

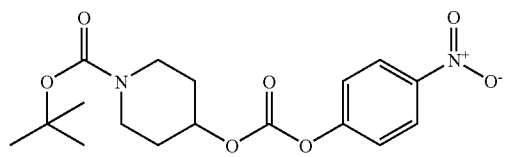 [SMILES: CC(C)(C)OC(=O)N1CCC(OC(=O)Oc2ccc([N+](=O)[O-])cc2)CC1]

To a mixture of tert-butyl 4-hydroxypiperidine-1-carboxylate (0.30 g, 0.0015 mol) (Aldrich Cat. #495484) and triethylamine (0.31 mL, 0.0022 mol) in methylene chloride (2 mL) was added p-nitrophenyl chloroformate (0.33 g, 0.0016 mol) (Acros Organics, Cat. #17080). The mixture was stirred at r.t. for 2 h. After removal of the solvent under reduced pressure, the residue was purified by flash chromatography on a silica gel with ethyl acetate in hexanes (0-20%) to afford the desired product (0.32 g, 58%). Analytic LCMS (M+Na)+: m/z=389.0.

Step 2: 1-(tert-butoxycarbonyl)piperidin-4-yl 7-[2-amino-6-(4-methylpiperazin-1-yl)pyrimidin-4-yl]-3,4-dihydroisoquinoline-2(1H)-carboxylate

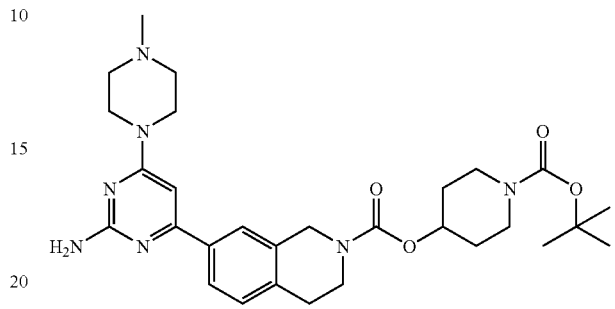

tert-Butyl 4-{[(4-nitrophenoxy)carbonyl]oxy}piperidine-1-carboxylate (0.093 g, 0.25 mmol) was added to a solution of 4-(4-methylpiperazin-1-yl)-6-(1,2,3,4-tetrahydroisoquinolin-7-yl)pyrimidin-2-amine HCl salt (0.10 g, 0.23 mmol) and triethylamine (0.13 mL, 0.92 mmol) in acetonitrile (5.0 mL). The reaction mixture was stirred at r.t. overnight. The mixture was diluted with water, and extracted with ethyl acetate (3×10 mL). The combined organic layers were dried over MgSO4, filtered and concentrated under reduced pressure. The residue was purified by flash chromatography on a silica gel column with MeOH in dichloromethane (0-10%) to afford the desired product (0.10 g, 79%). Analytic LCMS (M+H)+: m/z=552.3.

Step 3: piperidin-4-yl 7-[2-amino-6-(4-methylpiperazin-1-yl)pyrimidin-4-yl]-3,4-dihydroisoquinoline-2(1H)-carboxylate

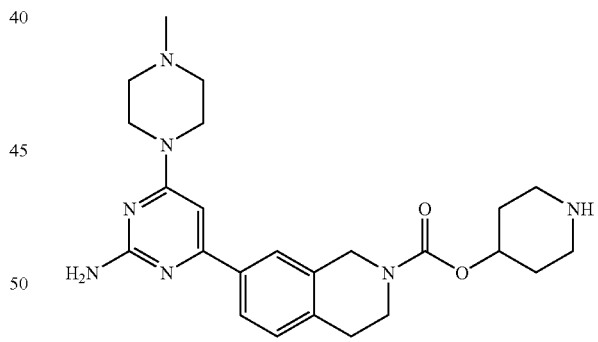

4 mL of 4 N HCl in 1,4-dioxane was added to a solution of 1-(tert-butoxycarbonyl)piperidin-4-yl 7-[2-amino-6-(4-methylpiperazin-1-yl)pyrimidin-4-yl]-3,4-dihydroisoquinoline-2(1H)-carboxylate (0.10 g, 0.18 mmol) in methanol (1.0 mL). The reaction mixture was stirred at r.t. for 2 h. The volatiles were removed under reduced pressure to afford the product as an HCl salt. Analytic LCMS (M+H)+: m/z=452.2.

Step 4: 1-(cyclopentylcarbonyl)piperidin-4-yl 7-[2-amino-6-(4-methylpiperazin-1-yl)pyrimidin-4-yl]-3,4-dihydroisoquinoline-2(1H)-carboxylate Cyclopentanecarbonyl chloride (2.0 uL, 0.016 mmol) was added to a mixture of piperidin-4-yl 7-[2-amino-6-(4-methylpiperazin-1-yl)pyrimidin-4-yl]-3,4-dihydroisoquinoline-2 (1H)-carboxylate HCl salt (6.0 mg, 0.011 mmol) and N,N-diisopropylethylamine (9.3 uL, 0.054 mmol) in acetonitrile (0.4 mL). The reaction mixture was stirred at r.t. for 30 min., purified by RP-LCMS (pH=10) to afford the desired product. Analytic LCMS (M+H)+: m/z=548.3.

Example 68

1-(Isopropoxycarbonyl)piperidin-4-yl 7-[2-amino-6-(4-methylpiperazin-1-yl)pyrimidin-4-yl]-3,4-dihydroisoquinoline-2(1H)-carboxylate

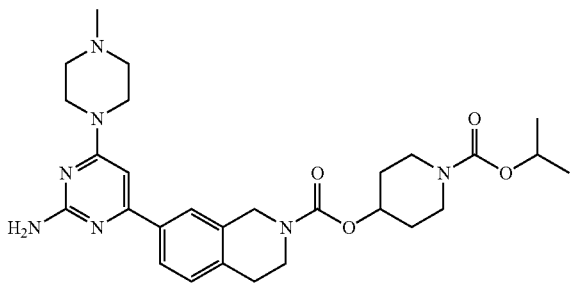

This compound was prepared by using procedures analogous to those described for the synthesis of Example 67, Step 4 starting from isopropyl chloroformate and piperidin-4-yl 7-[2-amino-6-(4-methylpiperazin-1-yl)pyrimidin-4-yl]-3,4-dihydroisoquinoline-2(1H)-carboxylate HCl salt. Analytic LCMS (M+H)+: m/z=538.3.

Example 69

1-[(Cyclopentyloxy)carbonyl]piperidin-4-yl 7-[2-amino-6-(4-methylpiperazin-1-yl)pyrimidin-4-yl]-3,4-dihydroisoquinoline-2(1H)-carboxylate

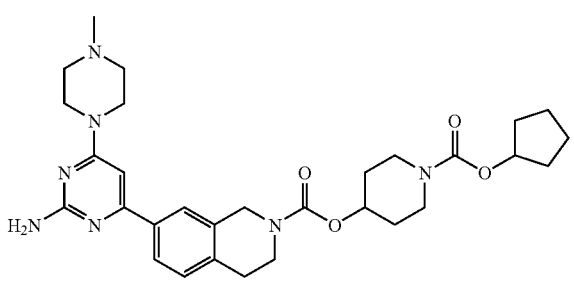

This compound was prepared by using procedures analogous to those described for the synthesis of Example 67, Step 4 starting from cyclopentyl 4-nitrophenyl carbonate and piperidin-4-yl 7-[2-amino-6-(4-methylpiperazin-1-yl)pyrimidin-4-yl]-3,4-dihydroisoquinoline-2(1H)-carboxylate HCl salt. Analytic LCMS (M+H)+: m/z=564.3.

Example 70

1-[(Cyclopentylamino)carbonyl]piperidin-4-yl 7-[2-amino-6-(4-methylpiperazin-1-yl)pyrimidin-4-yl]-3,4-dihydroisoquinoline-2(1H)-carboxylate

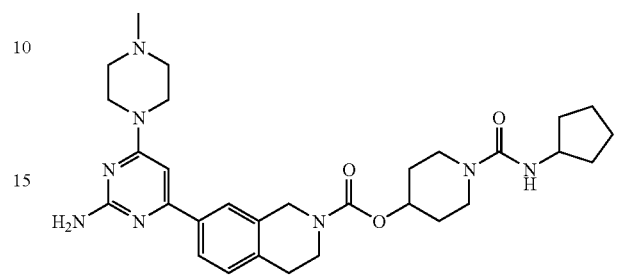

This compound was prepared by using procedures analogous to those described for the synthesis of Example 67, Step 4 starting from isocyanatocyclopentane and piperidin-4-yl 7-[2-amino-6-(4-methylpiperazin-1-yl)pyrimidin-4-yl]-3,4-dihydroisoquinoline-2(1H)-carboxylate HCl salt. Analytic LCMS (M+H)+: m/z=563.3.

Example 71

Isopropyl 4-{2-[7-[2-amino-6-(4-methylpiperazin-1-yl)pyrimidin-4-yl]-3,4-dihydroisoquinolin-2(1H)-yl]-2-oxoethyl}piperidine-1-carboxylate

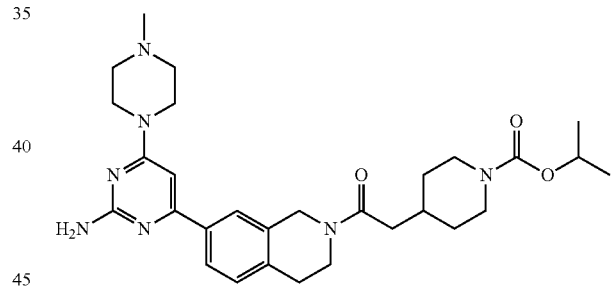

Step 1: tert-butyl 4-{2-[7-[2-amino-6-(4-methylpiperazin-1-yl)pyrimidin-4-yl]-3,4-dihydroisoquinolin-2(1H)-yl]-2-oxoethyl}piperidine-1-carboxylate

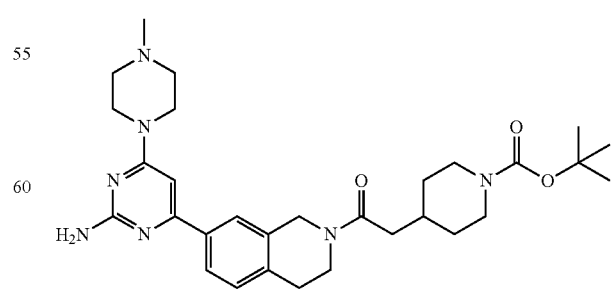

Triethylamine (40 uL, 0.29 mmol) was added to a mixture of 4-(4-methylpiperazin-1-yl)-6-(1,2,3,4-tetrahydroisoquinolin-7-yl)pyrimidin-2-amine HCl salt (25 mg, 0.058 mmol), [1-(tert-butoxycarbonyl)piperidin-4-yl]acetic acid (17 mg, 0.069 mmol) (AstaTech Cat. #66860), and benzotriazol-1-yloxytris(dimethylamino)phosphonium hexafluorophosphate (28 mg, 0.063 mmol) in N,N-dimethylformamide (0.8 mL). The mixture was stirred at r.t. overnight. The mixture was diluted with water, and extracted with ethyl acetate (3×10 mL). The combined organic layers were dried over MgSO$_4$, filtered and concentrated under reduced pressure. The residue was purified by flash chromatography on a silica gel column with MeOH in dichloromethane (0-10%) to afford the desired product (25 mg, 79%). Analytic LCMS (M+H)$^+$: m/z=550.3.

Step 2: 4-(4-methylpiperazin-1-yl)-6-[2-(piperidin-4-ylacetyl)-1,2,3,4-tetrahydroisoquinolin-7-yl]pyrimidin-2-amine

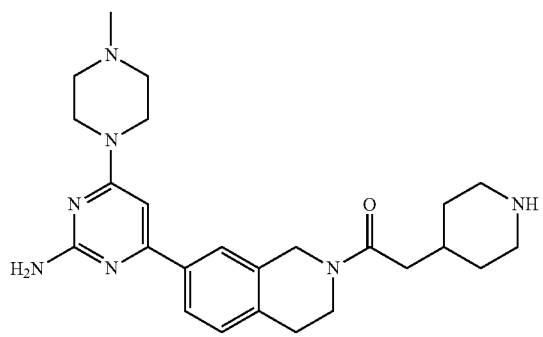 [SMILES: CN1CCN(c2cc(-c3ccc4c(c3)CN(C(=O)OC3CCNCC3)CC4)nc(N)n2)CC1]

2 mL of 4.0 N HCl in 1,4-dioxane was added to a solution of tert-butyl 4-{2-[7-[2-amino-6-(4-methylpiperazin-1-yl)pyrimidin-4-yl]-3,4-dihydroisoquinolin-2(1H)-yl]-2-oxoethyl}piperidine-1-carboxylate (25 mg, 0.045 mmol) in methanol (1.0 mL). The reaction mixture was stirred at r.t. for 2 h. The volatiles were removed under reduced pressure to afford the product as an HCl salt (25 mg, 98%). Analytic LCMS (M+H)$^+$: m/z=450.2.

Step 3: isopropyl 4-{2-[7-[2-amino-6-(4-methylpiperazin-1-yl)pyrimidin-4-yl]-3,4-dihydroisoquinolin-2(1H)-yl]-2-oxoethyl}piperidine-1-carboxylate Isopropyl chloroformate (16 ul, 0.016 mmol, 1.0M solution in toluene) was added to a mixture of 4-(4-methylpiperazin-1-yl)-6-[2-(piperidin-4-ylacetyl)-1,2,3,4-tetrahydroisoquinolin-7-yl]pyrimidin-2-amine HCl salt (6.0 mg, 0.011 mmol) and N,N-diisopropylethylamine (9.3 uL, 0.054 mmol) in acetonitrile (0.4 mL). The reaction mixture was stirred at r.t. for 30 min., and purified by RP-LCMS (pH=2) to afford the desired product as a TFA salt. Analytic LCMS (M+H)$^+$: m/z=536.3.

Example 72

4-(2-{[1-(Cyclopropylcarbonyl)piperidin-4-yl]acetyl}-1,2,3,4-tetrahydroisoquinolin-7-yl)-6-(4-methylpiperazin-1-yl)pyrimidin-2-amine

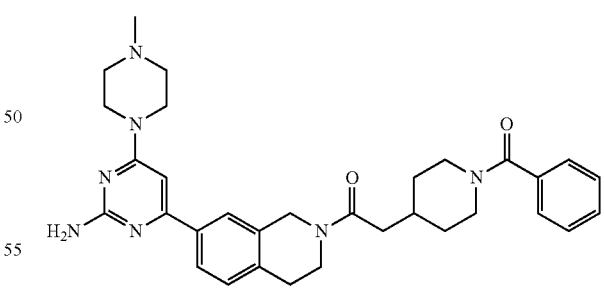

This compound was prepared by using procedures analogous to those described for the synthesis of Example 71, Step 4 starting from cyclopropanecarbonyl chloride (Aldrich, Cat. #C116807) and 4-(4-methylpiperazin-1-yl)-6-[2-(piperidin-4-ylacetyl)-1,2,3,4-tetrahydroisoquinolin-7-yl]pyrimidin-2-amine HCl salt. Analytic LCMS (M+H)$^+$: m/z=518.3.

Example 73

4-{2-[(1-Benzoylpiperidin-4-yl)acetyl]-1,2,3,4-tetrahydroisoquinolin-7-yl}-6-(4-methylpiperazin-1-yl)pyrimidin-2-amine This compound was prepared by using procedures analogous to those described for the synthesis of Example 71, Step 4 starting from benzoyl chloride (Alfa Aesar, Cat. #A14107) and 4-(4-methylpiperazin-1-yl)-6-[2-(piperidin-4-ylacetyl)-1,2,3,4-tetrahydroisoquinolin-7-yl]pyrimidin-2-amine HCl salt. Analytic LCMS (M+H)$^+$: m/z=554.3.

Example 74

4-(2-{[1-(Ethylsulfonyl)piperidin-4-yl]acetyl}-1,2,3,4-tetrahydroisoquinolin-7-yl)-6-(4-methylpiperazin-1-yl)pyrimidin-2-amine

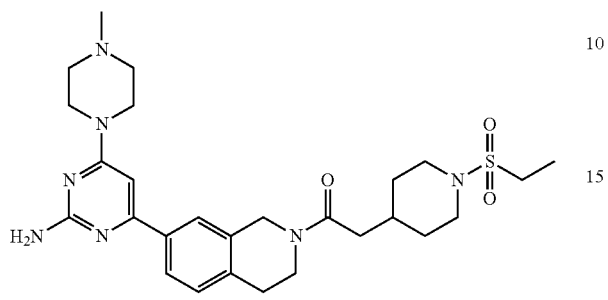

This compound was prepared by using procedures analogous to those described for the synthesis of Example 71, Step 4 starting from ethanesulfonyl chloride and 4-(4-methylpiperazin-1-yl)-6-[2-(piperidin-4-ylacetyl)-1,2,3,4-tetrahydroisoquinolin-7-yl]pyrimidin-2-amine HCl salt. Analytic LCMS (M+H)$^+$: m/z=542.3.

Example 75

7-[2-Amino-6-(4-methylpiperazin-1-yl)pyrimidin-4-yl]-N-(4-chlorophenyl)-6-fluoro-3,4-dihydroisoquinoline-2(1H)-carboxamide

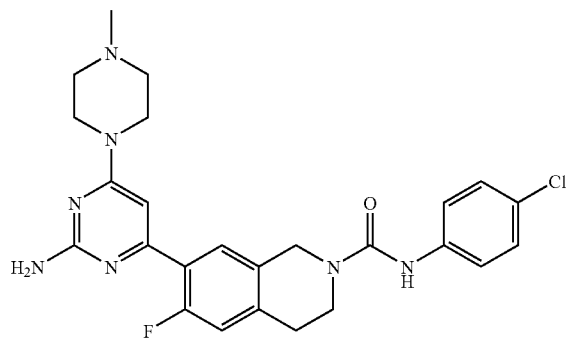 [SMILES: CN1CCN(c2cc(-c3cc4c(cc3F)CCN(C(=O)Nc3ccc(Cl)cc3)C4)nc(N)n2)CC1]

Step 1: 7-bromo-6-fluoroisoquinoline

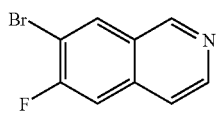

A reaction mixture of 3-bromo-4-fluorobenzaldehyde (1.70 g, 8.37 mmol) (Aldrich, Cat. #339547) and aminoacetaldehyde dimethyl acetal (0.917 mL, 8.37 mmol) (Aldrich, Cat. #121967) in toluene (17.0 mL) was stirred at r.t. overnight. The mixture was then added to sulfuric acid (10 mL) and phosphorus pentoxide (2.38 g, 8.37 mmol) at 160° C. The mixture was stirred at 160° C. for 1 h. After cooled to r.t., the mixture was poured onto crushed ice. The acidic mixture was adjusted to pH=8 by the careful addition of NaOH in water with stirring and external cooling. The basic mixture was extracted with ethyl acetate (3×200 mL). The combined organic layers were washed with brine, dried over MgSO$_4$, filtered, and concentrated under reduced pressure. The residue was purified by flash chromatography on a silica gel column with ethyl acetate in hexanes (0-40%) to afford the desired product. Analytic LCMS (M+H)$^+$: m/z=225.9/227.9.

Step 2: tert-butyl 7-bromo-6-fluoro-3,4-dihydroisoquinoline-2(1H)-carboxylate

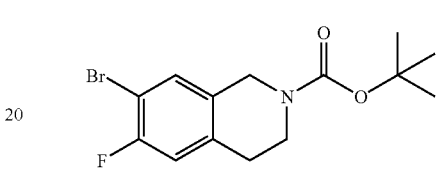

To a solution of 7-bromo-6-fluoroisoquinoline (0.50 g, 2.2 mmol) in THF (10 mL) was added dropwise 1.0 M of lithium triethylborohydride in THF (9.7 mL) under N$_2$ at r.t. The reaction mixture was stirred for 2 h., and adjusted to pH=2 with aqueous HCl, then adjusted to pH=10 with aqueous Na$_2$CO$_3$. Analytic LCMS (M+H)$^+$: m/z=229.9/232.0.

A solution of di-tert-butyldicarbonate (0.53 g, 2.4 mmol) in THF (4.0 mL) was added to the above mixture at r.t. The reaction mixture was stirred at r.t. for 30 min., and extracted with ethyl acetate (3×20 mL). The combined organic layers were dried over MgSO$_4$, filtered and concentrated under reduced pressure. The residue was purified by flash chromatography on a silica gel column with ethyl acetate in hexanes (0-20%) to afford the desired product. Analytic LCMS (M+H)$^+$: m/z=272.0/273.9.

Step 3: tert-butyl 6-fluoro-7-(4,4,5,5-tetramethyl-1,3,2-dioxaborolan-2-yl)-3,4-dihydroisoquinoline-2(1H)-carboxylate

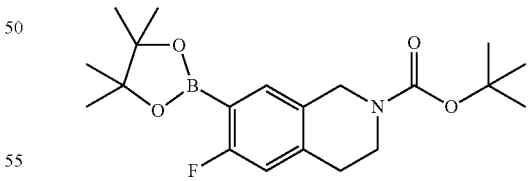

To a solution of tert-butyl 7-bromo-6-fluoro-3,4-dihydroisoquinoline-2(1H)-carboxylate (0.30 g, 0.91 mmol) and 4,4,5,5,4',4',5',5'-octamethyl-[2,2']bi[(1,3,2)dioxaborolanyl] (0.25 g, 0.97 mmol) (Aldrich, Cat. #473294) in 1,4-dioxane (3.0 mL) was added [1,1'-bis(diphenylphosphino)ferrocene]dichloropalladium(II) complex with dichloromethane (1:1) (0.037 g, 0.045 mmol) (Aldrich, Cat. #379670), potassium acetate (0.27 g, 2.7 mol), and 1,1'-bis(diphenylphosphino)ferrocene (0.02 g, 0.04 mmol) (Aldrich, Cat. #177261) under an atmosphere of nitrogen. The reaction mixture was stirred at 100° C. overnight. After cooled to r.t., the mixture was filtered, and concentrated under reduced pressure. The residue was purified by flash chromatography on a silica gel column with ethyl acetate in hexanes (0-20%) to afford the desired product. Analytic LCMS (M+Na)⁺: m/z=400.1.

Step 4: tert-butyl 7-[2-amino-6-(4-methylpiperazin-1-yl)pyrimidin-4-yl]-6-fluoro-3,4-dihydroisoquinoline-2(1H)-carboxylate

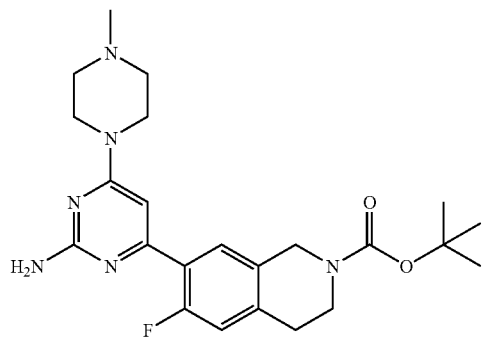 [SMILES: CN1CCN(c2cc(-c3cc4c(cc3F)CCN(C(=O)OC(C)(C)C)C4)nc(N)n2)CC1]

A mixture of 4-chloro-6-(4-methylpiperazin-1-yl)pyrimidin-2-amine (0.045 g, 0.20 mmol), tert-butyl 6-fluoro-7-(4,4,5,5-tetramethyl-1,3,2-dioxaborolan-2-yl)-3,4-dihydroisoquinoline-2(1H)-carboxylate (0.15 g, 0.20 mmol), [1,1'-bis(diphenylphosphino)ferrocene]dichloropalladium(II) complex with dichloromethane (1:1) (0.008 g, 0.01 mmol) and potassium carbonate (0.082 g, 0.60 mmol) in 1,4-dioxane (1 mL) and water (0.5 mL) was heated at 105° C. overnight. After cooled to r.t., the mixture was diluted with MeOH, filtered, and concentrated. The residue was purified by RP-LCMS (pH=10) to afford the desired product. Analytic LCMS (M+H)⁺: m/z=443.2.

Step 5: 4-(6-fluoro-1,2,3,4-tetrahydroisoquinolin-7-yl)-6-(4-methylpiperazin-1-yl)pyrimidin-2-amine

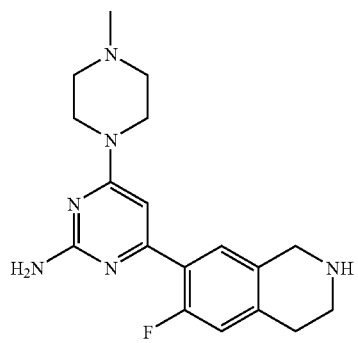 [SMILES: CN1CCN(c2cc(-c3cc4c(cc3F)CCNC4)nc(N)n2)CC1]

2.0 mL of 4 N HCl in 1,4-dioxane was added to a solution of tert-butyl 7-[2-amino-6-(4-methylpiperazin-1-yl)pyrimidin-4-yl]-6-fluoro-3,4-dihydroisoquinoline-2(1H)-carboxylate (0.050 g, 0.11 mmol) in methanol (1 mL). The reaction mixture was stirred at r.t. for 30 min The volatiles were removed under reduced pressure to afford the desired product as an HCl salt. Analytic LCMS (M+H)⁺: m/z=343.1.

Step 6: 7-[2-amino-6-(4-methylpiperazin-1-yl)pyrimidin-4-yl]-N-(4-chlorophenyl)-6-fluoro-3,4-dihydroisoquinoline-2(1H)-carboxamide

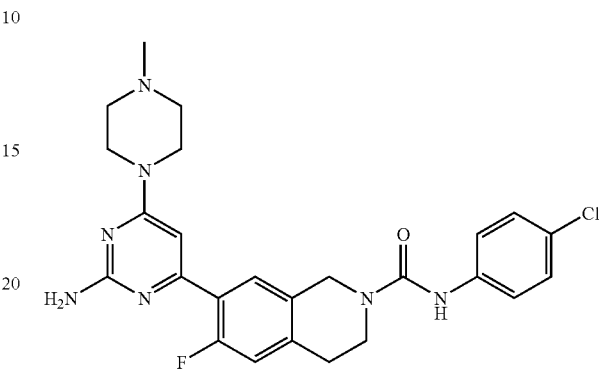

1-Chloro-4-isocyanatobenzene (4.1 mg, 0.026 mmol) was added to a mixture of 4-(6-fluoro-1,2,3,4-tetrahydroisoquinolin-7-yl)-6-(4-methylpiperazin-1-yl)pyrimidin-2-amine HCl salt (10 mg, 0.02 mmol) and triethylamine (15 uL, 0.11 mmol) in acetonitrile (0.3 mL). After 30 min., the mixture was purified by RP-LCMS (pH=10) to afford the desired products. Analytic LCMS (M+H)+: m/z=496.1/498.1.

Example 76

7-[2-Amino-6-(4-methylpiperazin-1-yl)pyrimidin-4-yl]-N-cyclohexyl-6-fluoro-3,4-dihydroisoquinoline-2(1H)-carboxamide

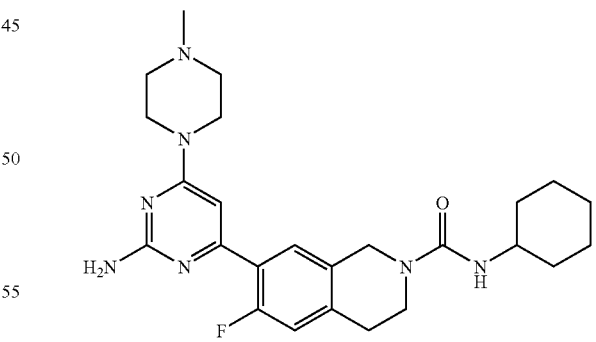

This compound was prepared by using procedures analogous to those described for the synthesis of Example 75, Step 6 starting from cyclohexylisocyanate (Aldrich, Cat. #C105198) and 4-(6-fluoro-1,2,3,4-tetrahydroisoquinolin-7-yl)-6-(4-methylpiperazin-1-yl)pyrimidin-2-amine HCl salt. Analytic LCMS (M+H)⁺: m/z=468.2.

Example 77

7-[2-Amino-6-(4-methylpiperazin-1-yl)pyrimidin-4-yl]-N-(4-chlorophenyl)-6-methyl-3,4-dihydroisoquinoline-2(1H)-carboxamide

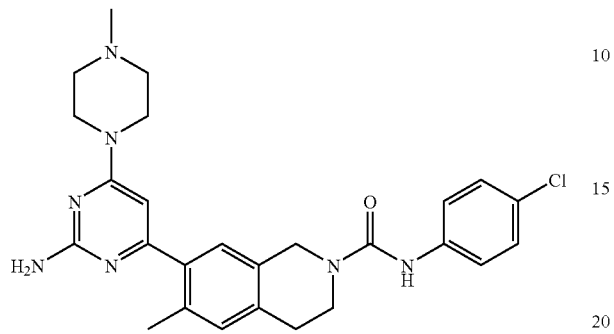

Step 1: 7-bromo-6-methylisoquinoline

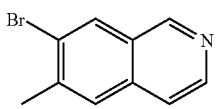

This compound was prepared by using procedures analogous to those described for the synthesis of Example 75, Step 1 starting from 3-bromo-4-methylbenzaldehyde (Aldrich, Cat. #4017458) and. aminoacetaldehyde dimethyl acetal. Analytic LCMS (M+H)$^+$: m/z=221.95/223.95.

Step 2: tert-butyl 7-bromo-6-methyl-3,4-dihydroisoquinoline-2(1H)-carboxylate

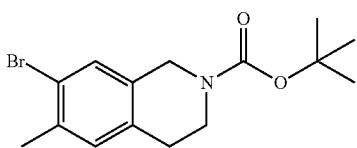 [SMILES: Cc1cc2c(cc1Br)CN(C(=O)OC(C)(C)C)CC2]

This compound was prepared by using procedures analogous to those described for the synthesis of Example 75, Step 2 starting from 7-bromo-6-methylisoquinoline, lithium triethylborohydride and di-tert-Butyldicarbonate. Analytic LCMS (M–Bu$^t$+H)$^+$: m/z=268.0/270.0.

Step 3: tert-butyl 6-methyl-7-(4,4,5,5-tetramethyl-1,3,2-dioxaborolan-2-yl)-3,4-dihydroisoquinoline-2(1H)-carboxylate

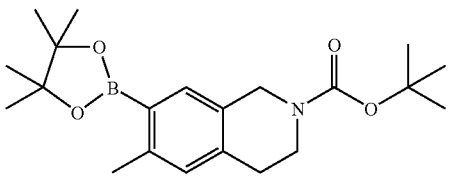 [SMILES: Cc1cc2c(cc1B1OC(C)(C)C(C)(C)O1)CN(C(=O)OC(C)(C)C)CC2]

This compound was prepared by using procedures analogous to those described for the synthesis of Example 75, Step 3 starting from tert-butyl 7-bromo-6-methyl-3,4-dihydroisoquinoline-2(1H)-carboxylate and 4,4,5,5,4',4',5',5'-octamethyl-[2,2']bi[[1,3,2]dioxaborolanyl]. Analytic LCMS (M–Boc+H)$^+$: m/z=274.1.

Step 4: tert-butyl 7-(2-amino-6-(4-methylpiperazin-1-yl)pyrimidin-4-yl)-6-methyl-3,4-dihydroisoquinoline-2(1H)-carboxylate

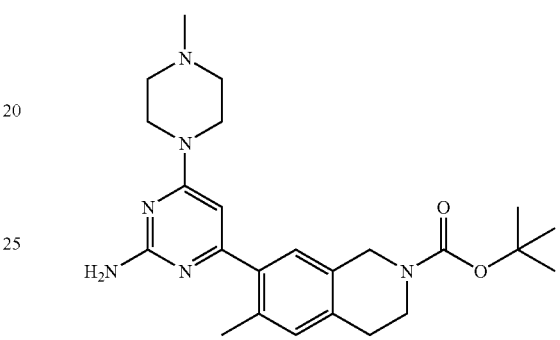

This compound was prepared by using procedures analogous to those described for the synthesis of Example 75, Step 4 starting from tert-butyl 6-methyl-7-(4,4,5,5-tetramethyl-1,3,2-dioxaborolan-2-yl)-3,4-dihydroisoquinoline-2(1H)-carboxylate and 4-chloro-6-(4-methylpiperazin-1-yl)pyrimidin-2-amine Analytic LCMS (M+H)$^+$: m/z=439.2.

Step 5: 4-(6-methyl-1,2,3,4-tetrahydroisoquinolin-7-yl)-6-(4-methylpiperazin-1-yl)pyrimidin-2-amine HCl salt

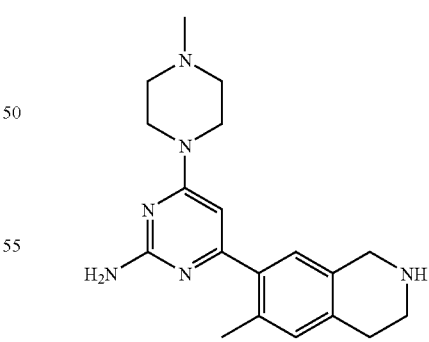

2.0 mL of 4 N HCl in 1,4-dioxane was added to a solution of tert-butyl 7-[2-amino-6-(4-methylpiperazin-1-yl)pyrimidin-4-yl]-6-methyl-3,4-dihydroisoquinoline-2(1H)-carboxylate (0.19 g, 0.43 mmol) in methanol (1 mL). The reaction mixture was stirred at r.t. for 30 min The volatiles were removed under reduced pressure to afford the desired product as an HCl salt. Analytic LCMS (M+H)$^+$: m/z=339.2.

Step 6: 7-[2-amino-6-(4-methylpiperazin-1-yl)pyrimidin-4-yl]-N-(4-chlorophenyl)-6-methyl-3,4-dihydroisoquinoline-2(1H)-carboxamide

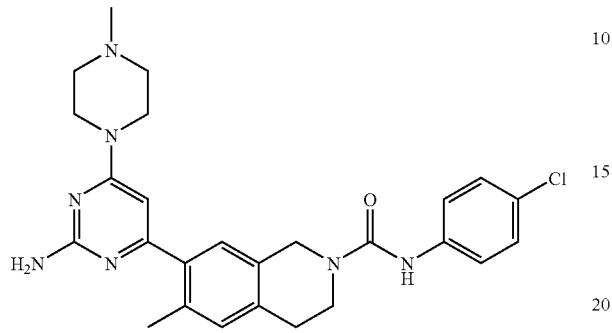

1-Chloro-4-isocyanatobenzene (4.1 mg, 0.026 mmol) was added to a mixture of 4-(6-methyl-1,2,3,4-tetrahydroisoquinolin-7-yl)-6-(4-methylpiperazin-1-yl)pyrimidin-2-amine HCl salt (10 mg, 0.02 mmol) and triethylamine (15 uL, 0.11 mmol) in acetonitrile (0.3 mL). After 30 min., the mixture was purified by RP-LCMS (pH=10) to afford the desired products. Analytic LCMS (M+H)$^+$: m/z=492.2/494.1.

Example 78

7-[2-Amino-6-(4-methylpiperazin-1-yl)pyrimidin-4-yl]-N-cyclohexyl-6-methyl-3,4-dihydroisoquinoline-2(1H)-carboxamide

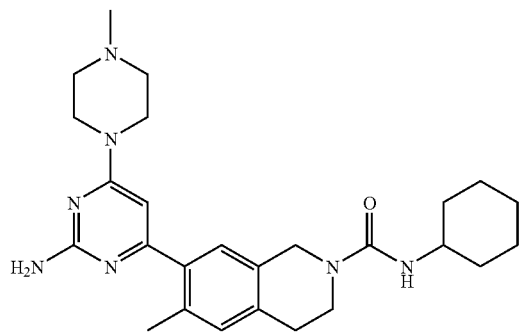 [SMILES: Cc1cc2c(cc1-c1cc(N3CCN(C)CC3)nc(N)n1)CN(C(=O)NC1CCCCC1)CC2]

This compound was prepared by using procedures analogous to those described for the synthesis of Example 77, Step 6 starting from 4-(6-methyl-1,2,3,4-tetrahydroisoquinolin-7-yl)-6-(4-methylpiperazin-1-yl)pyrimidin-2-amine HCl salt, and cyclohexylisocyanate. Analytic LCMS (M+H)$^+$: m/z=464.2.

Example 79

Tetrahydrofuran-3-yl 7-[2-amino-6-(4-methylpiperazin-1-yl)pyrimidin-4-yl]-3,4-dihydroisoquinoline-2(1H)-carboxylate

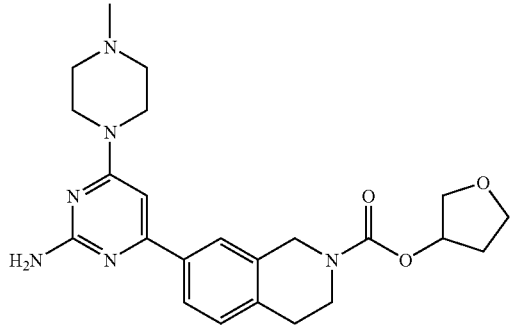 [SMILES: CN1CCN(c2cc(-c3ccc4c(c3)CN(C(=O)OC3CCOC3)CC4)nc(N)n2)CC1]

Step 1: 4-nitrophenyl tetrahydrofuran-3-yl carbonate

This compound was prepared by using procedures analogous to those described for the synthesis of Example 67, Step 1 starting from 3-hydroxytetrahydrofuran (Aldrich, Cat. #H59109) and p-nitrophenyl chloroformate.

Step 2: Tetrahydrofuran-3-yl 7-[2-amino-6-(4-methylpiperazin-1-yl)pyrimidin-4-yl]-3,4-dihydroisoquinoline-2(1H)-carboxylate This compound was prepared by using procedures analogous to those described for the synthesis of Example 67, Step 2 starting from 4-nitrophenyl tetrahydrofuran-3-yl carbonate and 4-(4-methylpiperazin-1-yl)-6-(1,2,3,4-tetrahydroisoquinolin-7-yl)pyrimidin-2-amine HCl salt. Analytic LCMS (M+H)$^+$: m/z=439.4.

Example 80

7-[2-Amino-6-(4-methylpiperazin-1-yl)pyrimidin-4-yl]-N-benzyl-3,4-dihydroisoquinoline-2(1H)-carboxamide

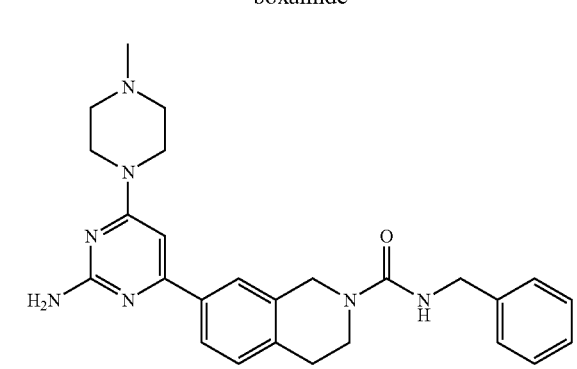

This compound was prepared by using procedures analogous to those described for the synthesis of Example 5 starting from benzyl isocyanate (Aldrich, Cat. #227969) and 4-(4-methylpiperazin-1-yl)-6-(1,2,3,4-tetrahydroisoquinolin-7-yl)pyrimidin-2-amine HCl salt. Analytic LCMS (M+H)+: m/z=458.4.

Example 81

7-[2-Amino-6-(4-methylpiperazin-1-yl)pyrimidin-4-yl]-N-cyclohexyl-N-methyl-3,4-dihydroisoquinoline-2(1H)-carboxamide

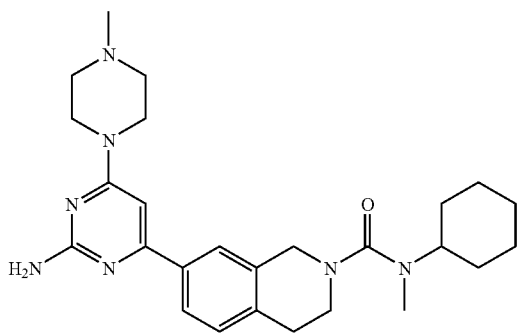

This compound was prepared by using procedures analogous to those described for the synthesis of Example 40 starting from N-methylcyclohexanamine (Aldrich, Cat. #103322), phosgene and 4-(4-methylpiperazin-1-yl)-6-(1,2,3,4-tetrahydroisoquinolin-7-yl)pyrimidin-2-amine HCl salt. Analytic LCMS (M+H)+: m/z=464.5.

Example 82

7-[2-Amino-6-(4-methylpiperazin-1-yl)pyrimidin-4-yl]-N-(2,3-dihydro-1H-inden-1-yl)-3,4-dihydroisoquinoline-2(1H)-carboxamide

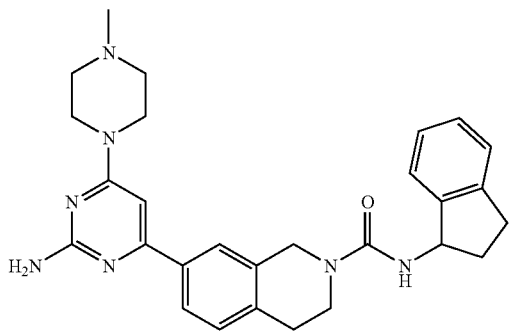 [SMILES: CN1CCN(c2cc(-c3ccc4c(c3)CN(C(=O)NC3CCc5ccccc53)CC4)nc(N)n2)CC1]

This compound was prepared by using procedures analogous to those described for the synthesis of Example 40 starting from 2,3-dihydro-1H-inden-1-amine (Aldrich, Cat. #A59506), phosgene and 4-(4-methylpiperazin-1-yl)-6-(1,2,3,4-tetrahydroisoquinolin-7-yl)pyrimidin-2-amine HCl salt. Analytic LCMS (M+H)+: m/z=484.2.

Example 83

7-[2-Amino-6-(4-methylpiperazin-1-yl)pyrimidin-4-yl]-N-(1,2,3,4-tetrahydronaphthalen-1-yl)-3,4-dihydroisoquinoline-2(1H)-carboxamide

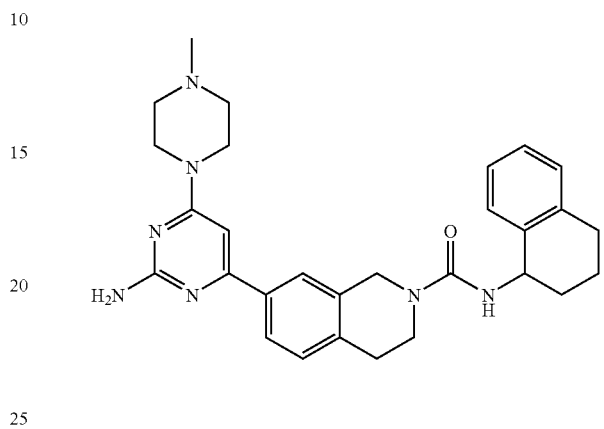

This compound was prepared by using procedures analogous to those described for the synthesis of Example 40 starting from 1,2,3,4-tetrahydronaphthalen-1-amine (Aldrich, Cat. #247820), phosgene and 4-(4-methylpiperazin-1-yl)-6-(1,2,3,4-tetrahydroisoquinolin-7-yl)pyrimidin-2-amine HCl salt. Analytic LCMS (M+H)+: m/z=498.3.

Example 84

7-[2-Amino-6-(4-methylpiperazin-1-yl)pyrimidin-4-yl]-N-[(3R)-tetrahydrofuran-3-yl]-3,4-dihydroisoquinoline-2(1H)-carboxamide

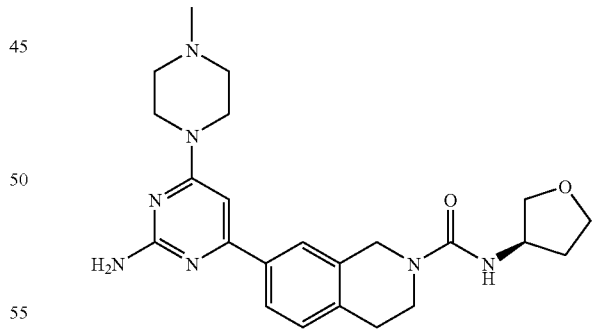

This compound was prepared by using procedures analogous to those described for the synthesis of Example 40 starting from (3R)-tetrahydrofuran-3-amine 4-methylbenzenesulfonate (Fluka, Cat. #09440), phosgene and 4-(4-methylpiperazin-1-yl)-6-(1,2,3,4-tetrahydroisoquinolin-7-yl)pyrimidin-2-amine HCl salt. Analytic LCMS (M+H)+: m/z=438.3.

Example 85

7-[2-Amino-6-(4-methylpiperazin-1-yl)pyrimidin-4-yl]-N-[(cis)-2-ethoxycyclohexyl]-3,4-dihydroisoquinoline-2(1H)-carboxamide

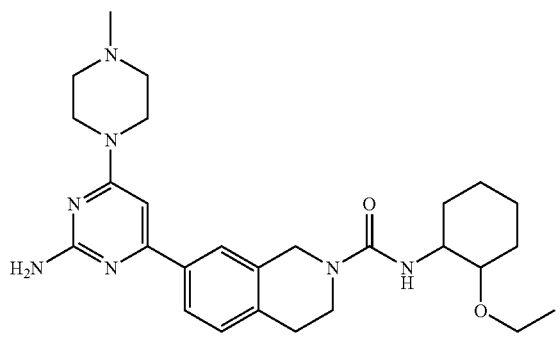 [SMILES: CCOC1CCCCC1NC(=O)N1CCc2ccc(-c3cc(N4CCN(C)CC4)nc(N)n3)cc2C1]

Step 1: tert-butyl(cis-2-ethoxycyclohexyl)carbamate

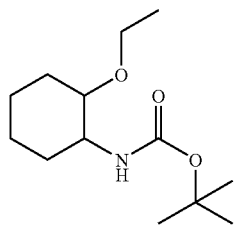 [SMILES: CCOC1CCCCC1NC(=O)OC(C)(C)C]

This compound was prepared by using procedures analogous to those described for the synthesis of Example 55, Step 1 starting from cis-2-aminocyclohexanol hydrochloride (Acros Organics, Cat. #26585), di-tert-butyldicarbonate, and iodoethane. Analytic LCMS (M-Boc+H)$^+$: m/z=144.1; (M+Na)$^+$: m/z=266.1.

Step 2: cis-2-ethoxycyclohexanamine

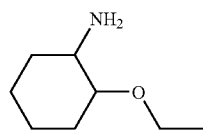

This compound was prepared as HCl salt by using procedures analogous to those described for the synthesis of Example 55, Step 2 starting from tert-butyl(cis-2-ethoxycyclohexyl)carbamate. Analytic LCMS (M+H)$^+$: m/z=144.1.

Step 3: 7-[2-Amino-6-(4-methylpiperazin-1-yl)pyrimidin-4-yl]-N-[(cis)-2-ethoxycyclohexyl]-3,4-dihydroisoquinoline-2(1H)-carboxamide This compound was prepared by using procedures analogous to those described for the synthesis of Example 55, Step 3 starting from cis-2-ethoxycyclohexanamine HCl salt, phosgene and 4-(4-methylpiperazin-1-yl)-6-(1,2,3,4-tetrahydroisoquinolin-7-yl)pyrimidin-2-amine HCl salt. Analytic LCMS (M+H)$^+$: m/z=494.3.

Example 86

7-[2-Amino-6-(4-methylpiperazin-1-yl)pyrimidin-4-yl]-N-[cis]-2-(cyclopropylmethoxy)cyclohexyl]-3,4-dihydroisoquinoline-2(1H)-carboxamide

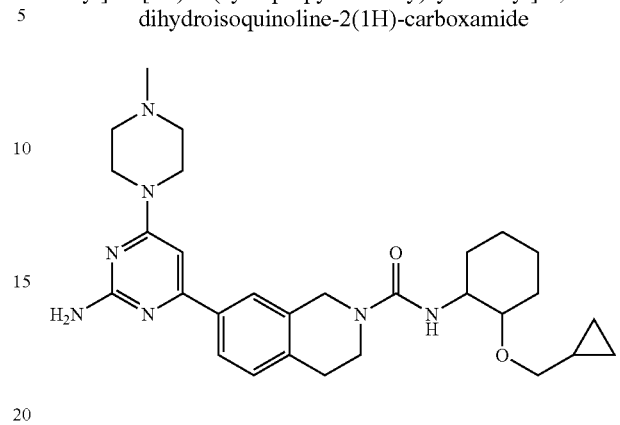

Step 1: tert-butyl cis-2-(cyclopropylmethoxy)cyclohexylcarbamate

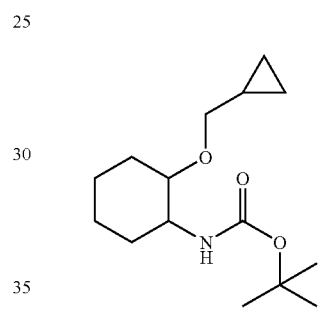

This compound was prepared by using procedures analogous to those described for the synthesis of Example 55, Step 1 starting from cis-2-aminocyclohexanol hydrochloride, di-tert-butyldicarbonate, and (bromomethyl)cyclopropane (Aldrich, Cat. #242403). Analytic LCMS (M-Boc+H)$^+$: m/z=170.1; (M+Na)$^+$: m/z=292.2.

Step 2: cis-2-(cyclopropylmethoxy)cyclohexanamine

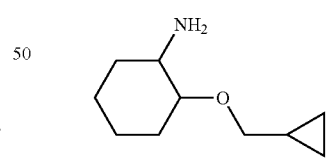

This compound was prepared as HCl salt by using procedures analogous to those described for the synthesis of Example 55, Step 2 starting from tert-butyl cis-2-(cyclopropylmethoxy)cyclohexylcarbamate. Analytic LCMS (M+H)$^+$: m/z=144.1.

Step 3: 7-[2-Amino-6-(4-methylpiperazin-1-yl)pyrimidin-4-yl]-N-[cis]-2-(cyclopropylmethoxy)cyclohexyl]-3,4-dihydroisoquinoline-2(1H)-carboxamide This compound was prepared by using procedures analogous to those described for the synthesis of Example 55, Step 3 starting from cis-2-(cyclopropylmethoxy)cyclohexanamine HCl salt, phosgene and 4-(4-methylpiperazin-1-yl)-6-(1,2,3,4-tetrahydroisoquinolin-7-yl)pyrimidin-2-amine HCl salt. Analytic LCMS (M+H)+: m/z=520.3.

Example 87

7-[2-Amino-6-(4-methylpiperazin-1-yl)pyrimidin-4-yl]-N-[(1R,2S)-2-hydroxy-2,3-dihydro-1H-inden-1-yl]-3,4-dihydroisoquinoline-2(1H)-carboxamide

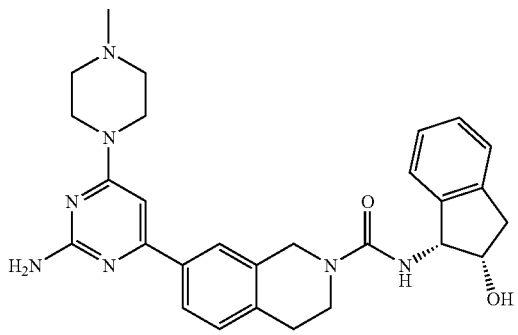 [SMILES: CN1CCN(c2cc(-c3ccc4c(c3)CN(C(=O)N[C@@H]3c5ccccc5C[C@@H]3O)CC4)nc(N)n2)CC1]

This compound was prepared by using procedures analogous to those described for the synthesis of Example 42 starting from phosgene, 4-(4-methylpiperazin-1-yl)-6-(1,2,3,4-tetrahydroisoquinolin-7-yl)pyrimidin-2-amine HCl salt and (1R,2S)-1-aminoindan-2-ol. Analytic LCMS (M+H)+: m/z=500.3.

Example 88

7-[2-Amino-6-(4-methylpiperazin-1-yl)pyrimidin-4-yl]-N-1,3-thiazol-2-yl-3,4-dihydroisoquinoline-2(1H)-carboxamide

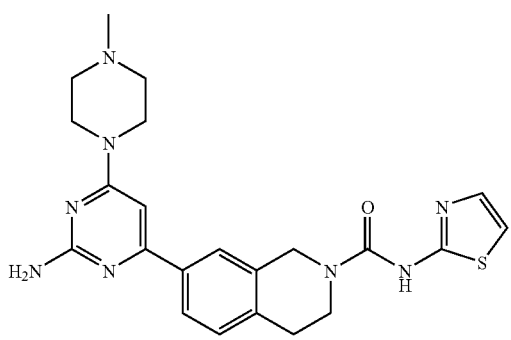 [SMILES: CN1CCN(c2cc(-c3ccc4c(c3)CN(C(=O)Nc3nccs3)CC4)nc(N)n2)CC1]

This compound was prepared by using procedures analogous to those described for the synthesis of Example 40 starting from 1,3-thiazol-2-amine (Aldrich, Cat. #123129), phosgene and 4-(4-methylpiperazin-1-yl)-6-(1,2,3,4-tetrahydroisoquinolin-7-yl)pyrimidin-2-amine HCl salt. Analytic LCMS (M+H)+: m/z=451.1.

Example 89

1-(Cyclopentylsulfonyl)piperidin-4-yl 7-[2-amino-6-(4-methylpiperazin-1-yl)pyrimidin-4-yl]-3,4-dihydroisoquinoline-2(1H)-carboxylate

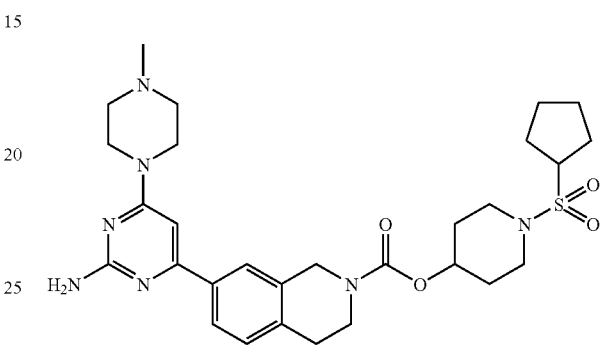

This compound was prepared by using procedures analogous to those described for the synthesis of Example 67, Step 4 starting from cyclopentanesulfonyl chloride (Aldrich, Cat. #656607) and piperidin-4-yl 7-[2-amino-6-(4-methylpiperazin-1-yl)pyrimidin-4-yl]-3,4-dihydroisoquinoline-2(1H)-carboxylate HCl salt. Analytic LCMS (M+H)+: m/z=584.2.

Example 90

7-[2-Amino-6-(4-methylpiperazin-1-yl)pyrimidin-4-yl]-N-1,3-benzothiazol-2-yl-3,4-dihydroisoquinoline-2(1H)-carboxamide

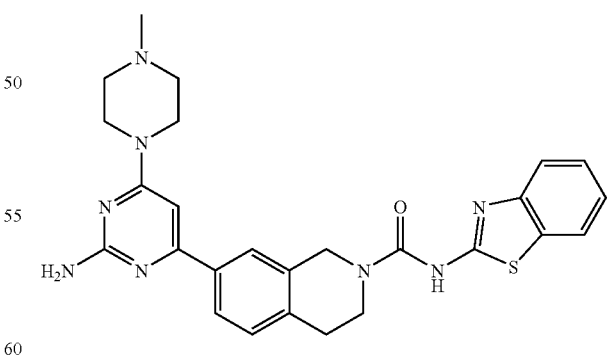

This compound was prepared by using procedures analogous to those described for the synthesis of Example 40 starting from 1,3-benzothiazol-2-amine (Aldrich, Cat. #108812), phosgene and 4-(4-methylpiperazin-1-yl)-6-(1,2,3,4-tetrahydroisoquinolin-7-yl)pyrimidin-2-amine HCl salt. Analytic LCMS (M+H)+: m/z=501.2.

Example 91

7-[2-Amino-6-(4-methylpiperazin-1-yl)pyrimidin-4-yl]-N-(5-phenylpyridin-2-yl)-3,4-dihydroisoquinoline-2(1H)-carboxamide

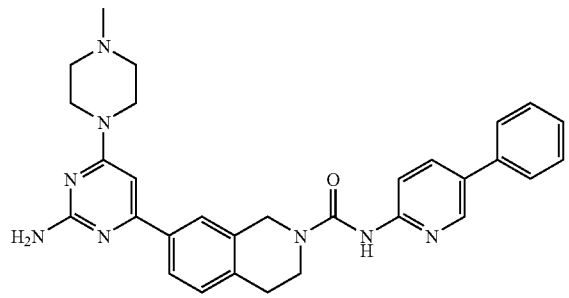 [SMILES: CN1CCN(c2cc(-c3ccc4c(c3)CN(C(=O)Nc3ccc(-c5ccccc5)cn3)CC4)nc(N)n2)CC1]

This compound was prepared by using procedures analogous to those described for the synthesis of Example 40 starting from 5-phenylpyridin-2-amine (Matrix Scientific, Cat. #007056), phosgene and 4-(4-methylpiperazin-1-yl)-6-(1,2,3,4-tetrahydroisoquinolin-7-yl)pyrimidin-2-amine HCl salt. Analytic LCMS (M+H)$^+$: m/z=521.2.

Example 92

7-[2-Amino-6-(4-methylpiperazin-1-yl)pyrimidin-4-yl]-N-(4-isopropoxyphenyl)-3,4-dihydroisoquinoline-2(1H)-carboxamide

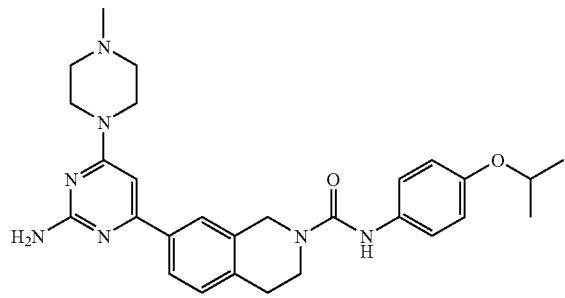 [SMILES: CC(C)Oc1ccc(NC(=O)N2CCc3ccc(-c4cc(N5CCN(C)CC5)nc(N)n4)cc3C2)cc1]

This compound was prepared by using procedures analogous to those described for the synthesis of Example 40 starting from 4-isopropoxyaniline (TCI, Cat. #10399), phosgene and 4-(4-methylpiperazin-1-yl)-6-(1,2,3,4-tetrahydroisoquinolin-7-yl)pyrimidin-2-amine HCl salt. Analytic LCMS (M+H)$^+$: m/z=502.2.

Example 93

7-[2-Amino-6-(4-methylpiperazin-1-yl)pyrimidin-4-yl]-N-[4-(1H-pyrazol-1-yl)phenyl]-3,4-dihydroisoquinoline-2(1H)-carboxamide

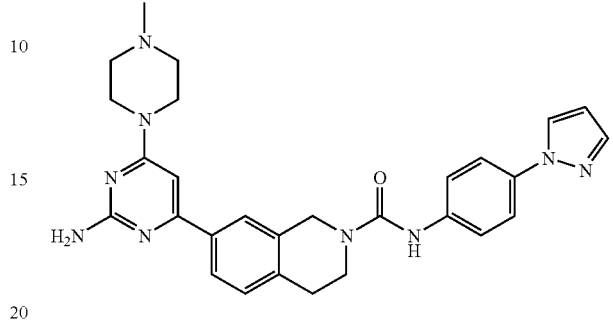

This compound was prepared by using procedures analogous to those described for the synthesis of Example 40 starting from 4-(1H-pyrazol-1-yl)aniline (Maybridge, Cat. #CC 18414), phosgene and 4-(4-methylpiperazin-1-yl)-6-(1,2,3,4-tetrahydroisoquinolin-7-yl)pyrimidin-2-amine HCl salt. Analytic LCMS (M+H)$^+$: m/z=510.2.

Example 94

7-[2-Amino-6-(4-methylpiperazin-1-yl)pyrimidin-4-yl]-N-[1-(methoxymethyl)cyclopentyl]-3,4-dihydroisoquinoline-2(1H)-carboxamide

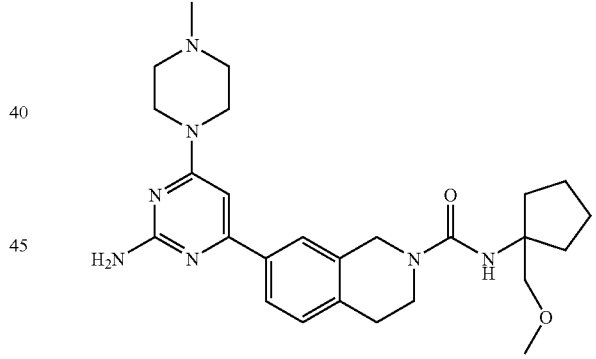

Step 1: tert-butyl 1-(methoxymethyl)cyclopentylcarbamate

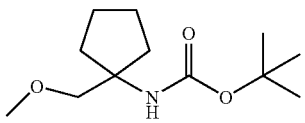 [SMILES: COCC1(NC(=O)OC(C)(C)C)CCCC1]

This compound was prepared by using procedures analogous to those described for the synthesis of Example 55, Step 1 starting from (1-aminocyclopentyl)methanol (Aldrich, Cat. #192279), di-tert-butyldicarbonate, and iodomethane. Analytic LCMS (M-Boc+H)$^+$: m/z=130.1; (M+Na)$^+$: m/z=252.1.

Step 2: 1-(methoxymethyl)cyclopentanamine

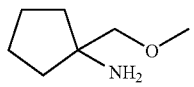

This compound was prepared as HCl salt by using procedures analogous to those described for the synthesis of Example 55, Step 2 starting from tert-butyl 1-(methoxymethyl)cyclopentylcarbamate. Analytic LCMS (M+H)$^+$: m/z=144.1.

Step 3: 7-[2-Amino-6-(4-methylpiperazin-1-yl)pyrimidin-4-yl]-N-[(cis)-2-ethoxycyclohexyl]-3,4-dihydroisoquinoline-2(1H)-carboxamide This compound was prepared by using procedures analogous to those described for the synthesis of Example 55, Step 3 starting from 1-(methoxymethyl)cyclopentanamine HCl salt, phosgene and 4-(4-methylpiperazin-1-yl)-6-(1,2,3,4-tetrahydroisoquinolin-7-yl)pyrimidin-2-amine HCl salt. Analytic LCMS (M+H)$^+$: m/z=480.3.

Example 95

7-[2-Amino-6-(4-methylpiperazin-1-yl)pyrimidin-4-yl]-N-cyclohexyl-3,4-dihydroisoquinoline-2(1H)-carboxamide

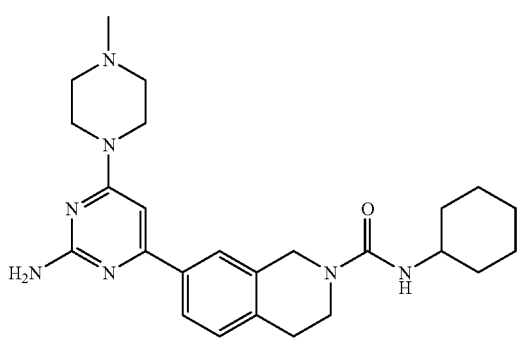 [SMILES: CN1CCN(c2cc(-c3ccc4c(c3)CN(C(=O)NC3CCCCC3)CC4)nc(N)n2)CC1]

This compound was prepared by using procedures analogous to those described for the synthesis of Example 5 starting from cyclohexylisocyanate and 4-(4-methylpiperazin-1-yl)-6-(1,2,3,4-tetrahydroisoquinolin-7-yl)pyrimidin-2-amine HCl salt. Analytic LCMS (M+H)$^+$: m/z=450.2.

Example 96

7-[2-Amino-6-(4-methylpiperazin-1-yl)pyrimidin-4-yl]-N-(4-phenoxyphenyl)-3,4-dihydroisoquinoline-2(1H)-carboxamide

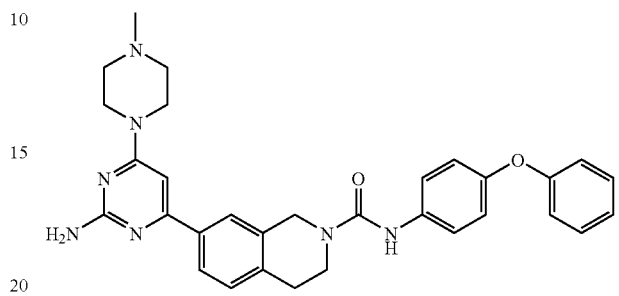

This compound was prepared by using procedures analogous to those described for the synthesis of Example 5 starting from 4-phenoxyphenyl isocyanate (Aldrich, Cat. #478970) and 4-(4-methylpiperazin-1-yl)-6-(1,2,3,4-tetrahydroisoquinolin-7-yl)pyrimidin-2-amine HCl salt. Analytic LCMS (M+H)$^+$: m/z=536.2.

Example 97

7-[2-Amino-6-(4-methylpiperazin-1-yl)pyrimidin-4-yl]-N-[(1S)-1,2-dimethylpropyl]-3,4-dihydroisoquinoline-2(1H)-carboxamide

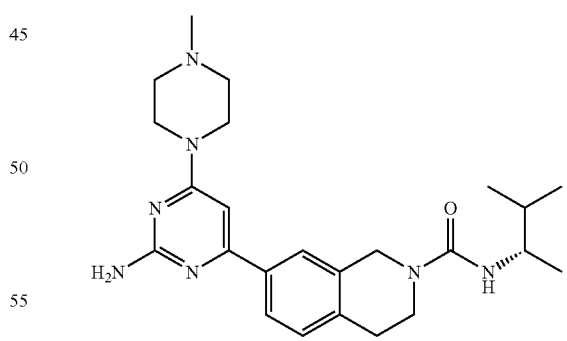

This compound was prepared by using procedures analogous to those described for the synthesis of Example 5 starting from (2S)-2-isocyanato-3-methylbutane (Alfa Aesar, Cat. #L20354) and 4-(4-methylpiperazin-1-yl)-6-(1,2,3,4-tetrahydroisoquinolin-7-yl)pyrimidin-2-amine HCl salt. Analytic LCMS (M+H)$^+$: m/z=438.3.

Example 98

7-[2-Amino-6-(4-methylpiperazin-1-yl)pyrimidin-4-yl]-N-[(1R)-1,2-dimethylpropyl]-3,4-dihydroisoquinoline-2(1H)-carboxamide

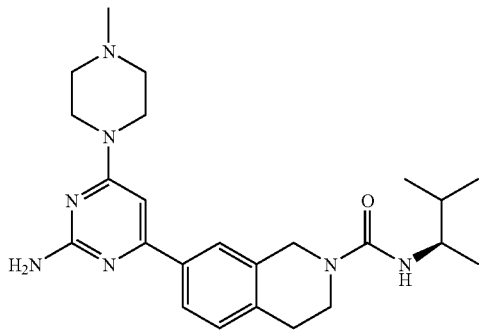 [SMILES: CC(C)[C@@H](C)NC(=O)N1CCc2ccc(-c3cc(N4CCN(C)CC4)nc(N)n3)cc2C1]

This compound was prepared by using procedures analogous to those described for the synthesis of Example 5 starting from (2R)-2-isocyanato-3-methylbutane (Alfa Aesar, Cat. #L20241) and 4-(4-methylpiperazin-1-yl)-6-(1,2,3,4-tetrahydroisoquinolin-7-yl)pyrimidin-2-amine HCl salt. Analytic LCMS (M+H)$^+$: m/z=438.3.

Example 99

7-[2-Amino-6-(4-methylpiperazin-1-yl)pyrimidin-4-yl]-N-(2-fluorophenyl)-3,4-dihydroisoquinoline-2(1H)-carboxamide

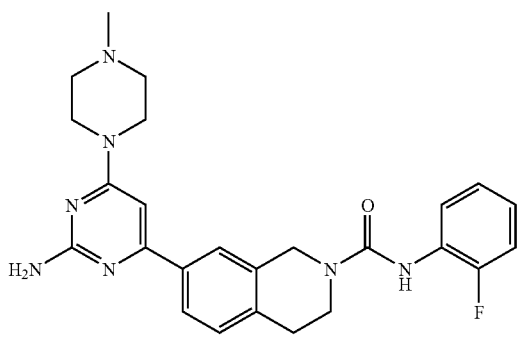 [SMILES: CN1CCN(c2cc(-c3ccc4c(c3)CN(C(=O)Nc3ccccc3F)CC4)nc(N)n2)CC1]

This compound was prepared by using procedures analogous to those described for the synthesis of Example 5 starting from 1-fluoro-2-isocyanatobenzene (Aldrich, Cat. #159352) and 4-(4-methylpiperazin-1-yl)-6-(1,2,3,4-tetrahydroisoquinolin-7-yl)pyrimidin-2-amine HCl salt. Analytic LCMS (M+H)$^+$: m/z=462.2.

Example 100

4-[2-(3-Methylbutanoyl)-1,2,3,4-tetrahydroisoquinolin-7-yl]-6-(4-methylpiperazin-1-yl)pyrimidin-2-amine

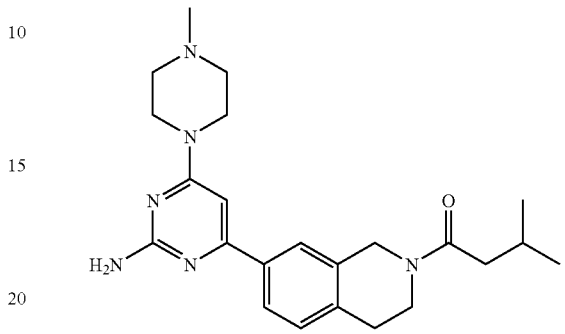

This compound was prepared by using procedures analogous to those described for the synthesis of Example 2 starting from 3-methylbutanoyl chloride (Aldrich, Cat. #157422) and 4-(4-methylpiperazin-1-yl)-6-(1,2,3,4-tetrahydroisoquinolin-7-yl)pyrimidin-2-amine HCl salt. Analytic LCMS (M+H)$^+$: m/z=409.2.

Example 101

4-(4-Methylpiperazin-1-yl)-6-[2-(3-phenylpropanoyl)-1,2,3,4-tetrahydroisoquinolin-7-yl]pyrimidin-2-amine

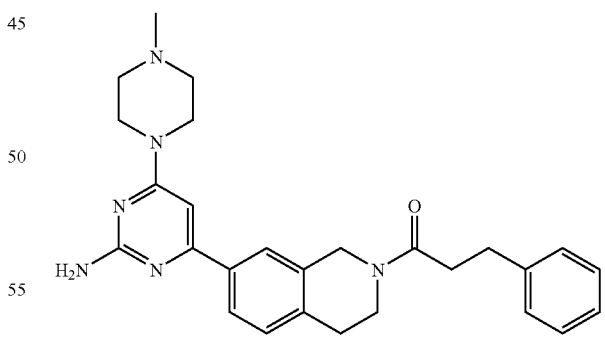

This compound was prepared by using procedures analogous to those described for the synthesis of Example 2 starting from benzenepropanoyl chloride (Aldrich, Cat. #249440) and 4-(4-methylpiperazin-1-yl)-6-(1,2,3,4-tetrahydroisoquinolin-7-yl)pyrimidin-2-amine HCl salt. Analytic LCMS (M+H)$^+$: m/z=457.2.

Example 102

4-[2-(2-Cyclohexylpropanoyl)-1,2,3,4-tetrahydroisoquinolin-7-yl]-6-(4-methylpiperazin-1-yl)pyrimidin-2-amine

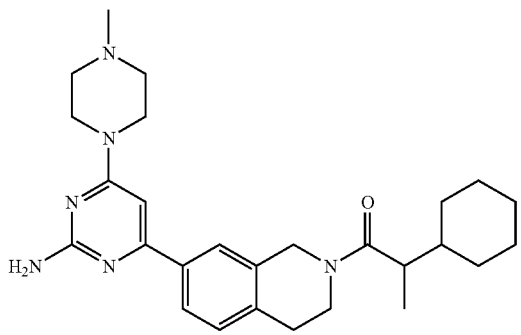 [SMILES: CC(C(=O)N1CCc2ccc(-c3cc(N4CCN(C)CC4)nc(N)n3)cc2C1)C1CCCCC1]

Step 1: methyl 2-cyclohexylpropanoate

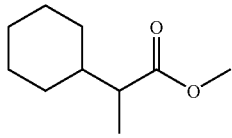

1.0 M of Lithium hexamethyldisilazide in tetrahydrofuran (2.2 mL, 2.2 mmol) was added to a solution of methylcyclohexylacetate (0.30 g, 1.9 mmol) (Aldrich, Cat. #209600) in tetrahydrofuran (7.0 mL) at −78° C. The mixture was stirred at −78° C. for 1 h., then methyl iodide (0.14 mL, 2.3 mmol) was added. The mixture was allowed to warm slowly to r.t., and stirred at r.t. overnight. The mixture was diluted with water, and extracted with ethyl acetate (3×10 mL). The combined organic layers were dried over MgSO$_4$, filtered and concentrated under reduced pressure. The residue was purified by flash chromatography on a silica gel column with ethyl acetate in hexanes (0-10%) to afford the desired product (0.30 g, 92%).

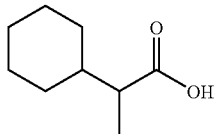

Step 2: 2-cyclohexylpropanoic acid

A reaction mixture of methyl 2-cyclohexylpropanoate (0.30 g, 1.8 mmol) and lithium hydroxide monohydrate (0.12 g, 2.8 mmol) in methanol (3.0 mL) and water (1.0 mL) was stirred at 60° C. for 2 h. The mixture was concentrated to remove methanol, washed with ether to remove some impurity, then adjusted to pH=2 with 1 N HCl (aqueous). The mixture was extracted with ethyl acetate (3×20 mL). The combined organic layers were dried over MgSO$_4$, filtered and concentrated to afford the crude product which was directly used for next step without further purification.

Step 3: 4-[2-(2-cyclohexylpropanoyl)-1,2,3,4-tetrahydroisoquinolin-7-yl]-6-(4-methylpiperazin-1-yl)pyrimidin-2-amine This compound was prepared by using procedures analogous to those described for the synthesis of Example 41 starting from 2-cyclohexylpropanoic acid and 4-(4-methylpiperazin-1-yl)-6-(1,2,3,4-tetrahydroisoquinolin-7-yl)pyrimidin-2-amine HCl salt. Analytic LCMS (M+H)$^+$: m/z=463.3.

Example 103

4-(4-Methylpiperazin-1-yl)-6-{2-[(4-phenylpiperidin-1-yl)carbonyl]-1,2,3,4-tetrahydroisoquinolin-7-yl}pyrimidin-2-amine

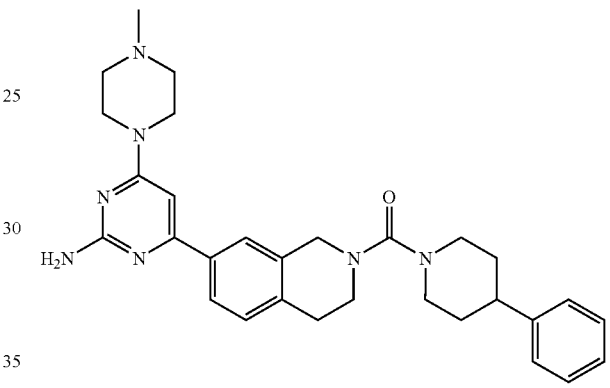

Step 1: 4-nitrophenyl 7-[2-amino-6-(4-methylpiperazin-1-yl)pyrimidin-4-yl]-3,4-dihydroisoquinoline-2(1H)-carboxylate

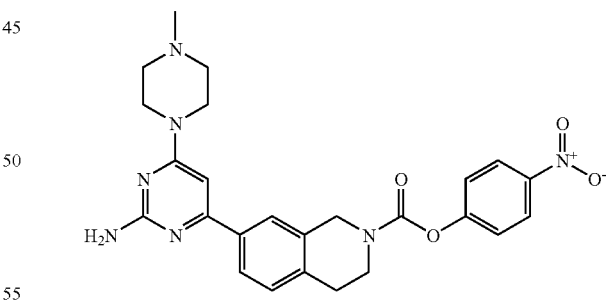

4-Nitrophenyl carbonochloridate (0.14 g, 0.69 mmol) was added to 4-(4-methylpiperazin-1-yl)-6-(1,2,3,4-tetrahydroisoquinolin-7-yl)pyrimidin-2-amine HCl salt (0.30 g, 0.69 mmol) and triethylamine (0.38 mL, 2.8 mmol) in acetonitrile (8.0 mL, 150 mmol) at 0° C. After 1 h., the mixture was diluted with water, and extracted with ethyl acetate (3×10 mL). The combined organic layers were dried over MgSO$_4$, filtered and concentrated under reduced pressure. The residue was purified by flash chromatography on a silica gel column with MeOH in dicloromethane (0-10%) to afford the desired product (0.32 g, 94%). Analytic LCMS (M+H)$^+$: m/z=490.2.

Step 2: 4-(4-methylpiperazin-1-yl)-6-{2-[(4-phenylpiperidin-1-yl)carbonyl]-1,2,3,4-tetrahydroisoquinolin-7-yl}pyrimidin-2-amine 4-Nitrophenyl 7-[2-amino-6-(4-methylpiperazin-1-yl)pyrimidin-4-yl]-3,4-dihydroisoquinoline-2(1H)-carboxylate (10 mg, 0.02 mmol) was added to a mixture of 4-phenylpiperidine (4.9 mg, 0.031 mmol) (Aldrich, Cat. #639869) and N,N-diisopropylethylamine (11 uL, 0.061 mmol) in N-methylpyrrolidinone (0.5 mL). The reaction mixture was stirred at 110° C. for 5 h. The mixture was purified by RP-LCMS (pH=10) to afford the desired product. Analytic LCMS (M+H)$^+$: m/z=512.3.

Example 104

4-{2-[(4,4-Difluoropiperidin-1-yl)carbonyl]-1,2,3,4-tetrahydroisoquinolin-7-yl}-6-(4-methylpiperazin-1-yl)pyrimidin-2-amine

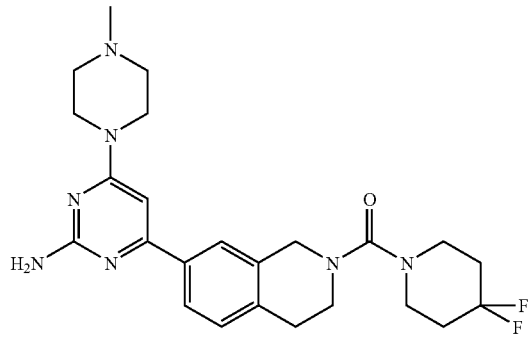 [SMILES: CN1CCN(c2cc(-c3ccc4c(c3)CN(C(=O)N3CCC(F)(F)CC3)CC4)nc(N)n2)CC1]

This compound was prepared by using procedures analogous to those described for the synthesis of Example 103, Step 2 starting from 4,4-difluoropiperidine (Ryan Scientific, Cat. #1006) and 4-nitrophenyl 7-[2-amino-6-(4-methylpiperazin-1-yl)pyrimidin-4-yl]-3,4-dihydroisoquinoline-2(1H)-carboxylate. Analytic LCMS (M+H)$^+$: m/z=472.2.

Example 105

4-[2-(Cyclohexylcarbonyl)-1,2,3,4-tetrahydroisoquinolin-7-yl]-6-(4-methylpiperazin-1-yl)pyrimidin-2-amine

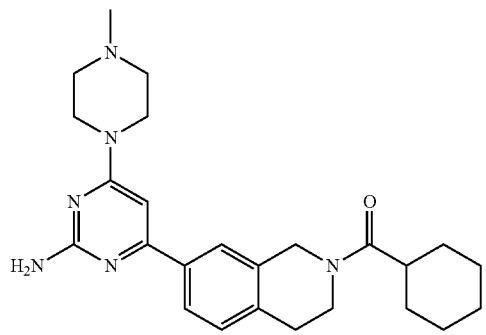 [SMILES: CN1CCN(c2cc(-c3ccc4c(c3)CN(C(=O)C3CCCCC3)CC4)nc(N)n2)CC1]

This compound was prepared by using procedures analogous to those described for the synthesis of Example 41 starting from cyclohexanecarboxylic acid (Aldrich, Cat. #101834) and 4-(4-methylpiperazin-1-yl)-6-(1,2,3,4-tetrahydroisoquinolin-7-yl)pyrimidin-2-amine HCl salt. Analytic LCMS (M+H)$^+$: m/z=435.2.

Example 106

4-[2-(Cyclopropylacetyl)-1,2,3,4-tetrahydroisoquinolin-7-yl]-6-(4-methylpiperazin-1-yl)pyrimidin-2-amine

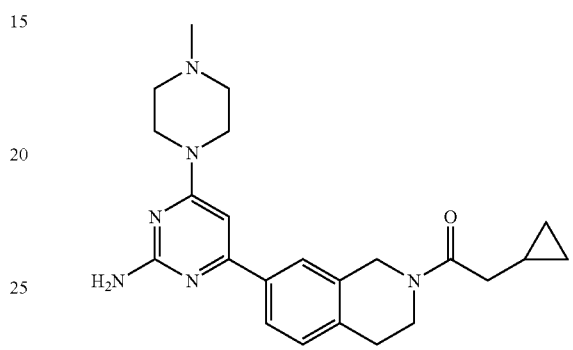

This compound was prepared by using procedures analogous to those described for the synthesis of Example 41 starting from cyclopropylacetic acid (Oakwood, Cat. #003710) and 4-(4-methylpiperazin-1-yl)-6-(1,2,3,4-tetrahydroisoquinolin-7-yl)pyrimidin-2-amine HCl salt. Analytic LCMS (M+H)$^+$: m/z=407.2.

Example 107

4-{2-[7-[2-Amino-6-(4-methylpiperazin-1-yl)pyrimidin-4-yl]-3,4-dihydroisoquinolin-2(1H)-yl]-2-oxoethyl}benzonitrile

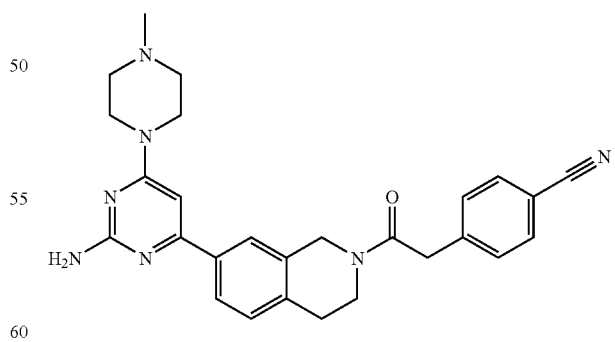

This compound was prepared by using procedures analogous to those described for the synthesis of Example 41 starting from (4-cyanophenyl)acetic acid (Aldrich, Cat. #633453) and 4-(4-methylpiperazin-1-yl)-6-(1,2,3,4-tetrahydroisoquinolin-7-yl)pyrimidin-2-amine HCl salt. Analytic LCMS (M+H)$^+$: m/z=468.1.

Example 108

4-{2-[(6-Chloropyridin-3-yl)acetyl]-1,2,3,4-tetrahydroisoquinolin-7-yl}-6-(4-methylpiperazin-1-yl)pyrimidin-2-amine

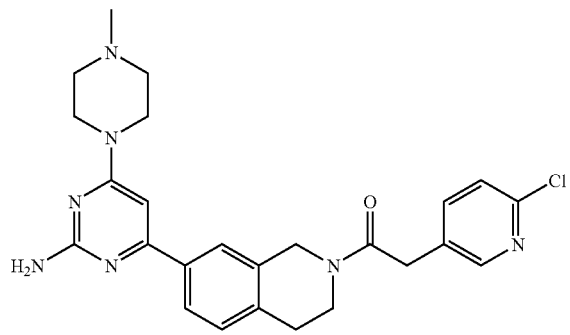 [SMILES: CN1CCN(c2cc(-c3ccc4c(c3)CN(C(=O)Cc3ccc(Cl)nc3)CC4)nc(N)n2)CC1]

This compound was prepared by using procedures analogous to those described for the synthesis of Example 41 starting from (6-chloropyridin-3-yl)acetic acid (Matrix Scientific, Cat. #023734) and 4-(4-methylpiperazin-1-yl)-6-(1,2,3,4-tetrahydroisoquinolin-7-yl)pyrimidin-2-amine HCl salt. Analytic LCMS (M+H)$^+$: m/z=478.2/480.1.

Example 109

4-[2-(Cyclobutylacetyl)-1,2,3,4-tetrahydroisoquinolin-7-yl]-6-(4-methylpiperazin-1-yl)pyrimidin-2-amine

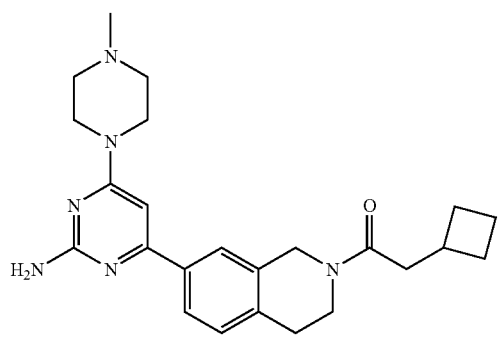 [SMILES: CN1CCN(c2cc(-c3ccc4c(c3)CN(C(=O)CC3CCC3)CC4)nc(N)n2)CC1]

This compound was prepared by using procedures analogous to those described for the synthesis of Example 41 starting from cyclobutylacetic acid and 4-(4-methylpiperazin-1-yl)-6-(1,2,3,4-tetrahydroisoquinolin-7-yl)pyrimidin-2-amine HCl salt. Analytic LCMS (M+H)$^+$: m/z=421.1.

Example 110

4-(4-Methylpiperazin-1-yl)-6-[2-(tetrahydro-2H-pyran-4-ylacetyl)-1,2,3,4-tetrahydroisoquinolin-7-yl]pyrimidin-2-amine

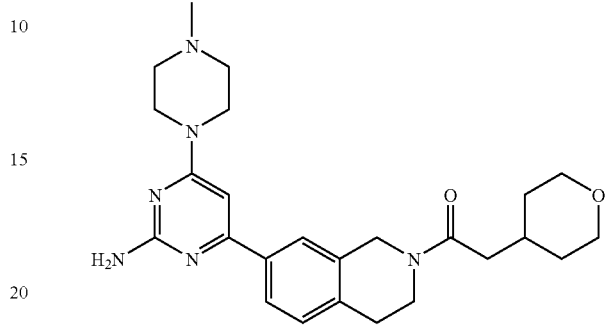

This compound was prepared by using procedures analogous to those described for the synthesis of Example 41 starting from tetrahydro-2H-pyran-4-ylacetic acid (Combi-Blocks, Cat. #AM-1005) and 4-(4-methylpiperazin-1-yl)-6-(1,2,3,4-tetrahydroisoquinolin-7-yl)pyrimidin-2-amine HCl salt. Analytic LCMS (M+H)$^+$: m/z=451.1.

Example 111

4-[2-(3-Methylpentanoyl)-1,2,3,4-tetrahydroisoquinolin-7-yl]-6-(4-methylpiperazin-1-yl)pyrimidin-2-amine

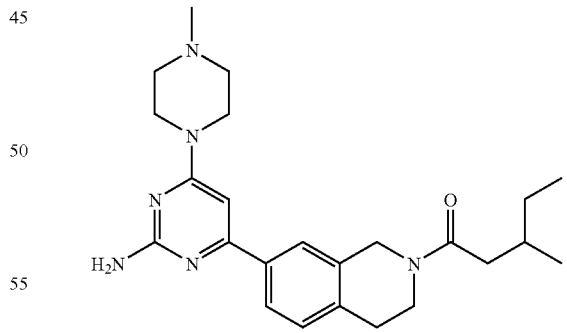

This compound was prepared by using procedures analogous to those described for the synthesis of Example 41 starting from 3-methylpentanoic acid (Aldrich, Cat. #223453) and 4-(4-methylpiperazin-1-yl)-6-(1,2,3,4-tetrahydroisoquinolin-7-yl)pyrimidin-2-amine HCl salt. Analytic LCMS (M+H)$^+$: m/z=423.2.

Example 112

4-(4-Methylpiperazin-1-yl)-6-[2-(1H-pyrazol-1-ylacetyl)-1,2,3,4-tetrahydroisoquinolin-7-yl]pyrimidin-2-amine

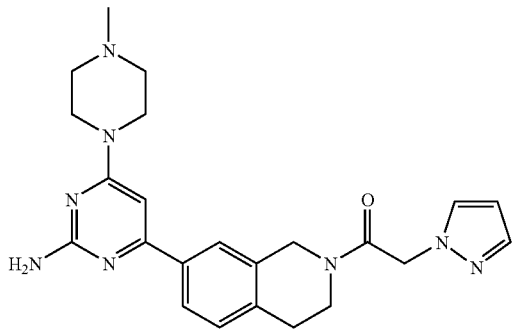 [SMILES: CN1CCN(c2cc(-c3ccc4c(c3)CN(C(=O)Cn3cccn3)CC4)nc(N)n2)CC1]

Lithium hydroxide monohydrate (4.4 mg, 0.10 mmol) was added to a solution of ethyl 1H-pyrazol-1-ylacetate (8.0 mg, 0.052 mmol) (Key Organics/Bionet, Cat. #4Y-0601) in methanol (1.0 mL) and water (0.3 mL). The reaction mixture was stirred at r.t. overnight. The mixture was adjusted to pH=4 with aqueous HCl, and concentrated. The residue was dissolved in N,N-dimethylformamide (0.5 mL). To the solution was added 4-(4-methylpiperazin-1-yl)-6-(1,2,3,4-tetrahydroisoquinolin-7-yl)pyrimidin-2-amine HCl salt (15 mg, 0.034 mmol), followed by benzotriazol-1-yloxytris(dimethylamino)phosphonium hexafluorophosphate (18 mg, 0.041 mmol) and triethylamine (19 uL, 0.14 mmol). The reaction mixture was stirred at r.t. for 2 h. The mixture was purified by RP-LCMS (pH=10) to afford the desired product. Analytic LCMS (M+H)$^+$: m/z=433.1.

Step 1: 3-[(methoxycarbonyl)amino]butanoic acid

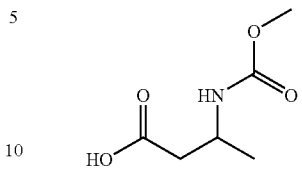

Methyl chloroformate (0.071 mL, 0.91 mmol) was added to a solution of ethyl 3-aminobutanoate (0.10 g, 0.76 mmol) (Aldrich, Cat. #E10556) and triethylamine (0.16 mL, 1.1 mmol) in tetrahydrofuran (2.0 mL) at r.t. After stirring at r.t. for 30 min, the mixture was diluted with water, and extracted with ethyl acetate (3×10 mL). The combined organic layers were dried over MgSO$_4$, filtered and concentrated under reduced pressure. The residue was dissolved in methanol (3.0 mL) and water (1.0 mL). To the solution was added lithium hydroxide monohydrate (0.049 g, 1.2 mmol). The reaction mixture was stirred at r.t. overnight. The mixture was adjusted to pH=2 with aqueous HCl, and extracted with ethyl acetate (3×10 mL). The combined organic layers were dried over MgSO$_4$, filtered and concentrated to afford the desired product.

Step 2: methyl{3-[7-[2-amino-6-(4-methylpiperazin-1-yl)pyrimidin-4-yl]-3,4-dihydroisoquinolin-2(1H)-yl]-1-methyl-3-oxopropyl}carbamate This compound was prepared by using procedures analogous to those described for the synthesis of Example 41 starting from 3-[(methoxycarbonyl)amino]butanoic acid and 4-(4-methylpiperazin-1-yl)-6-(1,2,3,4-tetrahydroisoquinolin-7-yl)pyrimidin-2-amine HCl salt. Analytic LCMS (M+H)$^+$: m/z=468.2.

Example 113

Methyl{3-[7-[2-amino-6-(4-methylpiperazin-1-yl)pyrimidin-4-yl]-3,4-dihydroisoquinolin-2(1H)-yl]-1-methyl-3-oxopropyl}carbamate

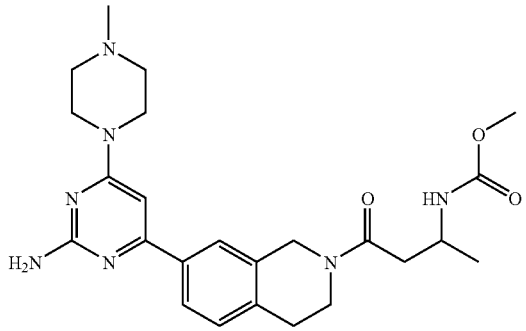 [SMILES: COC(=O)NC(C)CC(=O)N1CCc2ccc(-c3cc(N4CCN(C)CC4)nc(N)n3)cc2C1]

Example 114

Methyl{3-[7-[2-amino-6-(4-methylpiperazin-1-yl)pyrimidin-4-yl]-3,4-dihydroisoquinolin-2(1H)-yl]-1-cyclohexyl-3-oxopropyl}carbamate

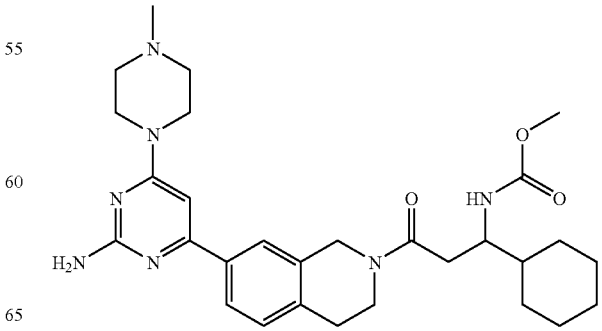

187

Step 1:
3-cyclohexyl-3-[(methoxycarbonyl)amino]propanoic acid

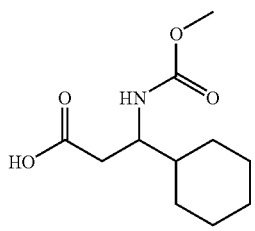 [SMILES: COC(=O)NC(CC(=O)O)C1CCCCC1]

Methyl chloroformate (54 uL, 0.70 mmol) was added to a mixture of 3-amino-3-cyclohexylpropanoic acid (100.0 mg, 0.5840 mmol) (Key Organics/Bionet, Cat. #7T-0112) and potassium carbonate (160 mg, 1.2 mmol) in water (2.0 mL, 110 mmol) and tetrahydrofuran (2.0 mL, 25 mmol). After stirring at r.t. for 10 min, the mixture was extracted with ether to remove impurity. The aqueous layer was adjusted to pH=2 with HCl, and extracted with ethyl acetate (3×10 mL). The combined organic layers were dried over MgSO$_4$, filtered and concentrated under reduced pressure to afford the desired product (130 mg, 97%). Analytic LCMS (M+H)$^+$: m/z=230.1.

Step 2: methyl{3-[7-[2-amino-6-(4-methylpiperazin-1-yl)pyrimidin-4-yl]-3,4-dihydroisoquinolin-2(1H)-yl]-1-cyclohexyl-3-oxopropyl}carbamate This compound was prepared by using procedures analogous to those described for the synthesis of Example 41 starting from 3-cyclohexyl-[(methoxycarbonyl)amino]propanoic acid and 4-(4-methylpiperazin-1-yl)-6-(1,2,3,4-tetrahydroisoquinolin-7-yl)pyrimidin-2-amine HCl salt. Analytic LCMS (M+H)$^+$: m/z=536.2.

Example 115

1-(Methoxycarbonyl)piperidin-4-yl 7-[2-amino-6-(4-methylpiperazin-1-yl)pyrimidin-4-yl]-3,4-dihydroisoquinoline-2(1H)-carboxylate

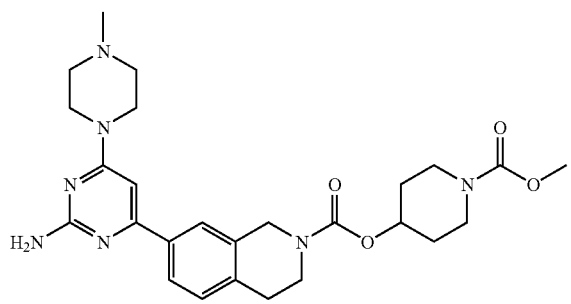 [SMILES: COC(=O)N1CCC(OC(=O)N2CCc3ccc(-c4cc(N5CCN(C)CC5)nc(N)n4)cc3C2)CC1]

This compound was prepared by using procedures analogous to those described for the synthesis of Example 67, Step 4 starting from methyl chloroformate and piperidin-4-yl 7-[2-amino-6-(4-methylpiperazin-1-yl)pyrimidin-4-yl]-3,4-dihydroisoquinoline-2(1H)-carboxylate HCl salt. Analytic LCMS (M+H)$^+$: m/z=510.2.

188

Example 116

1-(Ethoxycarbonyl)piperidin-4-yl 7-[2-amino-6-(4-methylpiperazin-1-yl)pyrimidin-4-yl]-3,4-dihydroisoquinoline-2(1H)-carboxylate

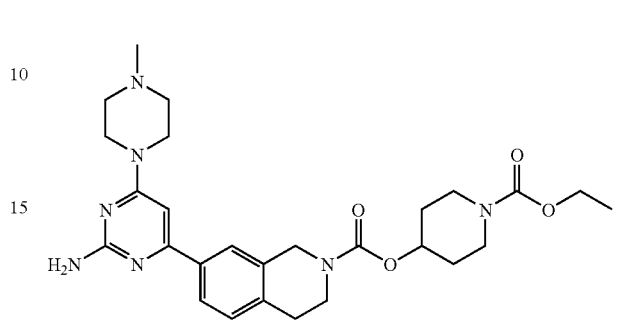

This compound was prepared by using procedures analogous to those described for the synthesis of Example 67, Step 4 starting from ethyl chloroformate and piperidin-4-yl 7-[2-amino-6-(4-methylpiperazin-1-yl)pyrimidin-4-yl]-3,4-dihydroisoquinoline-2(1H)-carboxylate HCl salt. Analytic LCMS (M+H)$^+$: m/z=524.3.

Example 117

7-[2-amino-6-(4-methylpiperazin-1-yl)pyrimidin-4-yl]-N-[1-(trifluoromethyl)cyclopropyl]-3,4-dihydroisoquinoline-2(1H)-carboxamide

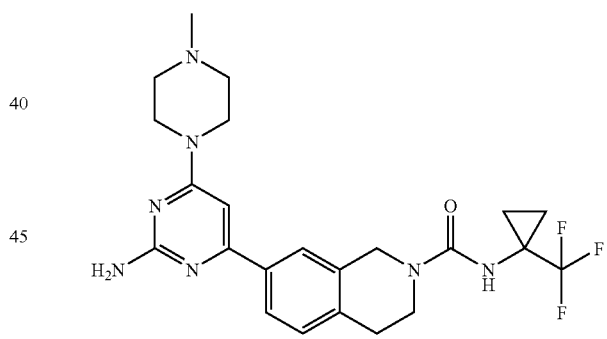

Step 1:
1-isocyanato-1-(trifluoromethyl)cyclopropane

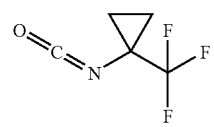

A mixture of 1-(trifluoromethyl)cyclopropanecarboxylic acid (13 mg, 0.084 mmol) (Oakwood, Cat. #013181), diphenylphosphonic azide (36 uL, 0.17 mmol) and triethylamine (18 uL, 0.13 mmol) in toluene (0.5 mL) was refluxed overnight. The mixture was concentrated under reduced pressure to afford the crude product which was used directly for next step without further purification.

Step 2: 7-[2-amino-6-(4-methylpiperazin-1-yl)pyrimidin-4-yl]-N-[1-(trifluoromethyl)cyclopropyl]-3,4-dihydroisoquinoline-2(1H)-carboxamide This compound was prepared by using procedures analogous to those described for the synthesis of Example 5 starting from 1-isocyanato-1-(trifluoromethyl)cyclopropane, and 4-(4-methylpiperazin-1-yl)-6-(1,2,3,4-tetrahydroisoquinolin-7-yl)pyrimidin-2-amine HCl salt. Analytic LCMS (M+H)⁺: m/z=476.2.

Example 118

Methyl 3-{2-[7-[2-amino-6-(4-methylpiperazin-1-yl)pyrimidin-4-yl]-3,4-dihydroisoquinolin-2(1H)-yl]-2-oxoethyl}pyrrolidine-1-carboxylate

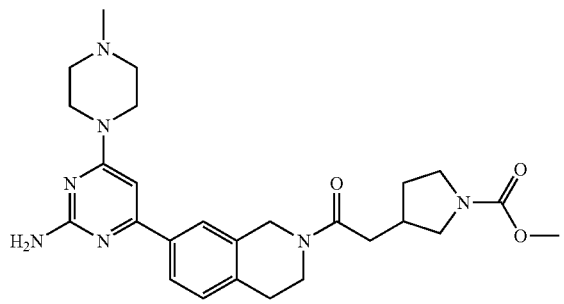 [SMILES: COC(=O)N1CCC(CC(=O)N2CCc3ccc(-c4cc(N5CCN(C)CC5)nc(N)n4)cc3C2)C1]

Step 1: tert-butyl 3-{2-[7-[2-amino-6-(4-methylpiperazin-1-yl)pyrimidin-4-yl]-3,4-dihydroisoquinolin-2(1H)-2(1H)-yl]-2-oxoethyl}pyrrolidine-1-carboxylate

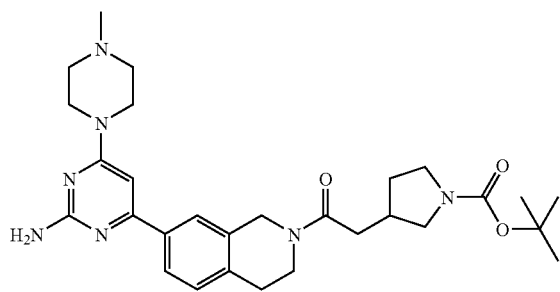 [SMILES: CN1CCN(c2cc(-c3ccc4c(c3)CN(C(=O)CC3CCN(C(=O)OC(C)(C)C)C3)CC4)nc(N)n2)CC1]

Triethylamine (0.16 mL, 1.2 mmol) was added to a mixture of 4-(4-methylpiperazin-1-yl)-6-(1,2,3,4-tetrahydroisoquinolin-7-yl)pyrimidin-2-amine HCl salt (0.10 g, 0.23 mmol), [1-(tert-butoxycarbonyl)pyrrolidin-3-yl]acetic acid (0.063 g, 0.28 mmol) (Ennova Medch, Cat. #AR01849), and benzotriazol-1-yloxytris(dimethylamino)phosphonium hexafluorophosphate (0.11 g, 0.25 mmol) in N,N-dimethylformamide (2 mL). After 1 h., the mixture was diluted with water, and extracted with ethyl acetate (3×10 mL). The combined organic layers were dried over MgSO₄, filtered and concentrated under reduced pressure. The residue was purified by flash chromatography on a silica gel column with MeOH in dicloromethane (0-10%) to afford the desired product (0.12 g, 97%). Analytic LCMS (M+H)⁺: m/z=536.3.

Step 2: 4-(4-methylpiperazin-1-yl)-6-[2-(pyrrolidin-3-ylacetyl)-1,2,3,4-tetrahydroisoquinolin-7-yl]pyrimidin-2-amine

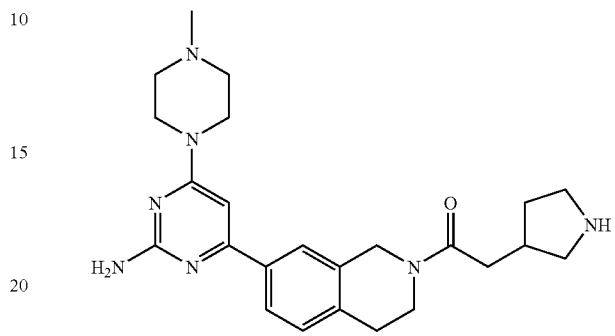

4 mL of 4 N HCl in 1,4-dioxane was added to a solution of tert-butyl 3-{2-[7-[2-amino-6-(4-methylpiperazin-1-yl)pyrimidin-4-yl]-3,4-dihydroisoquinolin-2(1H)-yl]-2-oxoethyl}pyrrolidine-1-carboxylate (0.12 g, 0.22 mmol) in methanol (1.0 mL). The reaction mixture was stirred at r.t. for 2 h. The mixture was concentrated under reduced pressure to afford the crude product as an HCl salt. Analytic LCMS (M+H)⁺: m/z=436.2.

Step 3: methyl 3-{2-[7-[2-amino-6-(4-methylpiperazin-1-yl)pyrimidin-4-yl]-3,4-dihydroisoquinolin-2(1H)-yl]-2-oxoethyl}pyrrolidine-1-carboxylate Methyl chloroformate (2.1 uL, 0.028 mmol) was added to a mixture of 4-(4-methylpiperazin-1-yl)-6-[2-(pyrrolidin-3-ylacetyl)-1,2,3,4-tetrahydroisoquinolin-7-yl]pyrimidin-2-amine HCl salt (10 mg, 0.02 mmol) and triethylamine (0.013 mL, 0.092 mmol) in acetonitrile (0.5 mL). The reaction mixture was stirred at r.t. for 30 min The mixture was purified by RP-LCMS (pH=10) to afford the desired product. Analytic LCMS (M+H)⁺: m/z=494.3.

Example 119

Isopropyl 3-{2-[7-[2-amino-6-(4-methylpiperazin-1-yl)pyrimidin-4-yl]-3,4-dihydroisoquinolin-2(1H)-yl]-2-oxoethyl}pyrrolidine-1-carboxylate

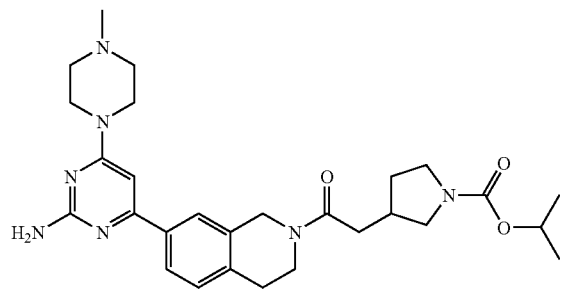 [SMILES: CC(C)OC(=O)N1CCC(CC(=O)N2CCc3ccc(-c4cc(N5CCN(C)CC5)nc(N)n4)cc3C2)C1]

This compound was prepared by using procedures analogous to those described for the synthesis of Example 118, Step 3 starting from isopropyl chloroformate and 4-(4-methylpiperazin-1-yl)-6-[2-(pyrrolidin-3-ylacetyl)-1,2,3,4-tetrahydroisoquinolin-7-yl]pyrimidin-2-amine HCl salt. Analytic LCMS (M+H)+: m/z=522.2.

Example 120

1-{2-[7-[2-Amino-6-(4-methylpiperazin-1-yl)pyrimidin-4-yl]-3,4-dihydroisoquinolin-2(1)-yl]-2-oxoethyl}cyclobutanecarbonitrile

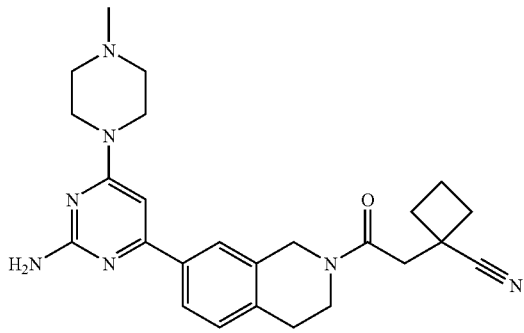 [SMILES: CN1CCN(c2cc(-c3ccc4c(c3)CN(C(=O)CC3(C#N)CCC3)CC4)nc(N)n2)CC1]

Step 1: 5-cyclobutylidene-2,2-dimethyl-1,3-dioxane-4,6-dione

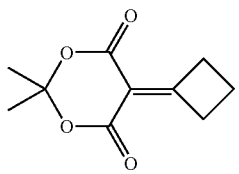

Cyclobutanone (0.50 g, 7.1 mmol) (Aldrich, Cat. #C96001) was added to a mixture of ammonium acetate (1.1 g, 14 mmol) and 2,2-dimethyl-1,3-dioxane-4,6-dione (1.0 g, 7.1 mmol) (Acros Organics, Cat. #19845) in toluene (10 mL), followed by acetic acid (1.0 mL). The reaction mixture was stirred at 50° C. for 4 h. After cooled to r.t., the mixture was diluted with water, and extracted with ethyl acetate (3×20 mL). The combined organic layers were washed with brine, dried over MgSO₄, filtered and concentrated under reduced pressure. The residue was purified by flash chromatography on a silica gel column with ethyl acetate in hexanes (0-30%) to afford the desired product (0.68, 48%).

Step 2: 1-(2,2-dimethyl-4,6-dioxo-1,3-dioxan-5-yl)cyclobutanecarbonitrile

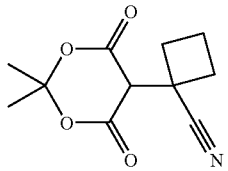 [SMILES: CC1(C)OC(=O)C(C2(C#N)CCC2)C(=O)O1]

Potassium cyanide (0.12 g, 1.8 mmol) was added to a mixture of 5-cyclobutylidene-2,2-dimethyl-1,3-dioxane-4,6-dione (0.30 g, 1.5 mmol) and tetra-N-butylammonium bromide (0.049 g, 0.15 mmol) (Sigma-Aldrich, Cat. #193119) in ethanol (5.0 mL). The reaction mixture was stirred at 80° C. for 2 h. After cooled to r.t., the mixture was adjusted to pH=2 with aqueous HCl. The mixture was extracted with ethyl acetate (3×20 mL). The combined organic layers were washed with brine, dried over MgSO₄, filtered and concentrated under reduced pressure. The residue was purified by flash chromatography on a silica gel column with ethyl acetate in dichloromethane (0-80%) to afford the desired product (0.32 g, 94%).

Step 3: (1-cyanocyclobutyl)acetic acid

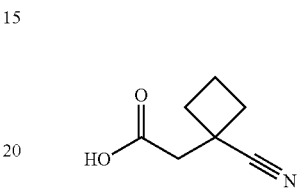

The reaction mixture of 1-(2,2-dimethyl-4,6-dioxo-1,3-dioxan-5-yl)cyclobutanecarbonitrile (0.32 g, 1.4 mmol) in N,N-dimethylformate (4.0 mL) and water (0.40 mL) was stirred at 100° C. for 2 h. After cooled to r.t., the mixture was diluted with water, adjusted to pH=2 with aqueous HCl, and extracted with ethyl acetate (3×20 mL). The combined organic layers were washed with brine, dried over MgSO₄, filtered and concentrated under reduced pressure to afford the crude product which was directly used in next step reaction without further purification.

Step 4: 1-{2-[7-[2-amino-6-(4-methylpiperazin-1-yl)pyrimidin-4-yl]-3,4-dihydroisoquinolin-2(1H)-yl]-2-oxoethyl}cyclobutanecarbonitrile Triethylamine (24 uL, 0.17 mmol) was added to a mixture of 4-(4-methylpiperazin-1-yl)-6-(1,2,3,4-tetrahydroisoquinolin-7-yl)pyrimidin-2-amine HCl salt (15 mg, 0.034 mmol), (1-cyanocyclobutyl)acetic acid (5.3 mg, 0.038 mmol), and benzotriazol-1-yloxytris(dimethylamino)phosphonium hexafluorophosphate (17 mg, 0.038 mmol) in N,N-dimethylformate (0.5 mL). The mixture was stirred at r.t. for 30 min., and purified by RP-LCMS (pH=10) to afford the desired product. Analytic LCMS (M+H)+: m/z=446.1.

Example 121

4-[7-[2-Amino-6-(4-methylpiperazin-1-yl)pyrimidin-4-yl]-3,4-dihydroisoquinolin-2(1H)-yl]-2,2-dimethyl-4-oxobutanenitrile

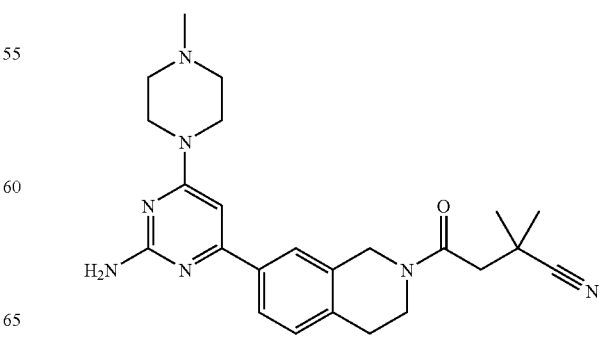

Step 1: 2,2-dimethyl-5-(1-methylethylidene)-1,3-dioxane-4,6-dione

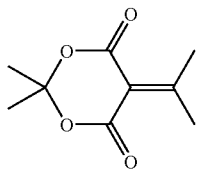

This compound was prepared by using procedures analogous to those described for the synthesis of Example 120, Step 1 starting from acetone and 2,2-dimethyl-1,3-dioxane-4,6-dione.

Step 2: 2-(2,2-dimethyl-4,6-dioxo-1,3-dioxan-5-yl)-2-methylpropanenitrile

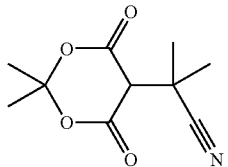

This compound was prepared by using procedures analogous to those described for the synthesis of Example 120, Step 2 starting from 2,2-dimethyl-5-(1-methylethylidene)-1,3-dioxane-4,6-dione and potassium cyanide.

Step 3: 3-cyano-3-methylbutanoic acid

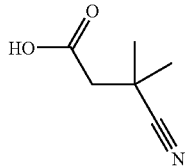

This compound was prepared by using procedures analogous to those described for the synthesis of Example 120, Step 3 starting from 2-(2,2-dimethyl-4,6-dioxo-1,3-dioxan-5-yl)-2-methylpropanenitrile.

Step 4: 4-[7-[2-amino-6-(4-methylpiperazin-1-yl)pyrimidin-4-yl]-3,4-dihydroisoquinolin-2(1)-yl]-2,2-dimethyl-4-oxobutanenitrile This compound was prepared by using procedures analogous to those described for the synthesis of Example 120, Step 4 starting from 3-cyano-3-methylbutanoic acid and piperidin-4-yl 7-[2-amino-6-(4-methylpiperazin-1-yl)pyrimidin-4-yl]-3,4-dihydroisoquinoline-2(1H)-carboxylate HCl salt. Analytic LCMS (M+H)$^+$: m/z=434.1.

Example 122

1-{2-[7-[2-Amino-6-(4-methylpiperazin-1-yl)pyrimidin-4-yl]-3,4-dihydroisoquinolin-2(1H)-yl]-2-oxoethyl}cyclopentanecarbonitrile

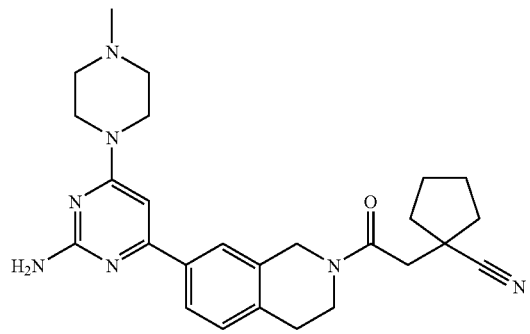 [SMILES: CN1CCN(c2cc(-c3ccc4c(c3)CN(C(=O)CC3(C#N)CCCC3)CC4)nc(N)n2)CC1]

Step 1: 5-cyclopentylidene-2,2-dimethyl-1,3-dioxane-4,6-dione

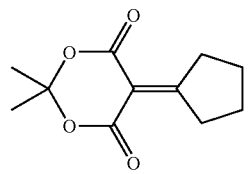

This compound was prepared by using procedures analogous to those described for the synthesis of Example 120, Step 1 starting from cyclopentanone and 2,2-dimethyl-1,3-dioxane-4,6-dione.

Step 2: 1-(2,2-dimethyl-4,6-dioxo-1,3-dioxan-5-yl)cyclopentanecarbonitrile

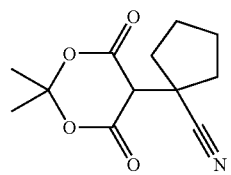 [SMILES: CC1(C)OC(=O)C(C2(C#N)CCCC2)C(=O)O1]

This compound was prepared by using procedures analogous to those described for the synthesis of Example 120, Step 2 starting from 5-cyclopentylidene-2,2-dimethyl-1,3-dioxane-4,6-dione and potassium cyanide.

Step 3: (1-cyanocyclopentyl)acetic acid

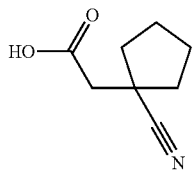 [SMILES: N#CC1(CC(=O)O)CCCC1]

This compound was prepared by using procedures analogous to those described for the synthesis of Example 120, Step 3 starting from 1-(2,2-dimethyl-4,6-dioxo-1,3-dioxan-5-yl)cyclopentanecarbonitrile.

Step 4: 4-[7-[2-amino-6-(4-methylpiperazin-1-yl)pyrimidin-4-yl]-3,4-dihydroisoquinolin-2(1)-yl]-2,2-dimethyl-4-oxobutanenitrile This compound was prepared by using procedures analogous to those described for the synthesis of Example 120, Step 4 starting from 3-cyano-3-methylbutanoic acid and piperidin-4-yl 7-[2-amino-6-(4-methylpiperazin-1-yl)pyrimidin-4-yl]-3,4-dihydroisoquinoline-2(1H)-carboxylate HCl salt. Analytic LCMS (M+H)+: m/z=460.1.

Example 123

4-[7-[2-Amino-6-(4-methylpiperazin-1-yl)pyrimidin-4-yl]-3,4-dihydroisoquinolin-2(1H)-yl]-2-cyclopropyl-2-methyl-4-oxobutanenitrile

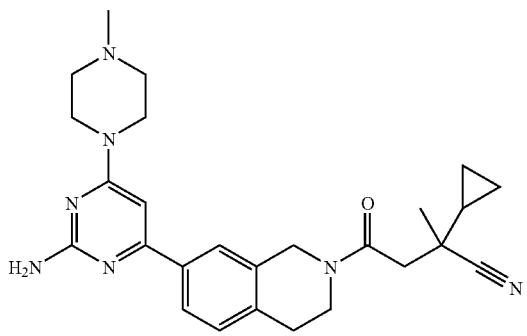 [SMILES: CN1CCN(c2cc(-c3ccc4c(c3)CN(C(=O)CC(C)(C#N)C3CC3)CC4)nc(N)n2)CC1]

Step 1: 5-(1-cyclopropylethylidene)-2,2-dimethyl-1,3-dioxane-4,6-dione

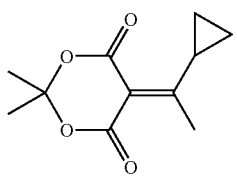

This compound was prepared by using procedures analogous to those described for the synthesis of Example 120, Step 1 starting from 1-cyclopropylethanone (Alfa Aesar, Cat. #A13540) and 2,2-dimethyl-1,3-dioxane-4,6-dione.

Step 2: 2-cyclopropyl-2-(2,2-dimethyl-4,6-dioxo-1,3-dioxan-5-yl)propanenitrile

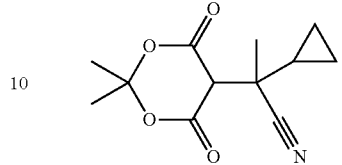

This compound was prepared by using procedures analogous to those described for the synthesis of Example 120, Step 2 starting from 5-(1-cyclopropylethylidene)-2,2-dimethyl-1,3-dioxane-4,6-dione and potassium cyanide.

Step 3: 3-cyano-3-cyclopropylbutanoic acid

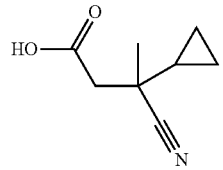

This compound was prepared by using procedures analogous to those described for the synthesis of Example 120, Step 3 starting from 2-cyclopropyl-2-(2,2-dimethyl-4,6-dioxo-1,3-dioxan-5-yl)propanenitrile.

Step 4: 4-[7-[2-Amino-6-(4-methylpiperazin-1-yl)pyrimidin-4-yl]-3,4-dihydroisoquinolin-2(1H)-yl]-2-cyclopropyl-2-methyl-4-oxobutanenitrile This compound was prepared by using procedures analogous to those described for the synthesis of Example 120, Step 4 starting from 3-cyano-3-cyclopropylbutanoic acid and piperidin-4-yl 7-[2-amino-6-(4-methylpiperazin-1-yl)pyrimidin-4-yl]-3,4-dihydroisoquinoline-2(1H)-carboxylate HCl salt. Analytic LCMS (M+H)+: m/z=460.1.

Example 124

4-[7-[2-Amino-6-(4-methylpiperazin-1-yl)pyrimidin-4-yl]-3,4-dihydroisoquinolin-2(1H)-yl]-4-oxo-2-phenylbutanenitrile

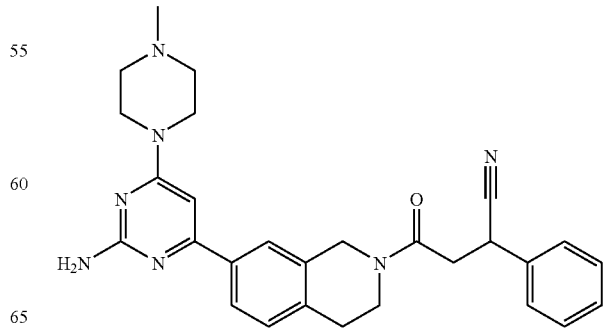

Step 1:
5-benzylidene-2,2-dimethyl-1,3-dioxane-4,6-dione

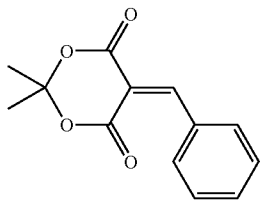 [SMILES: CC1(C)OC(=O)C(=Cc2ccccc2)C(=O)O1]

This compound was prepared by using procedures analogous to those described for the synthesis of Example 120, Step 1 starting from benzaldehyde and 2,2-dimethyl-1,3-dioxane-4,6-dione.

Step 2: 2-(2,2-dimethyl-4,6-dioxo-1,3-dioxan-5-yl)-2-phenylacetonitrile

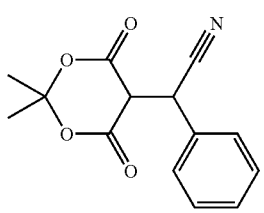 [SMILES: CC1(C)OC(=O)C(C(C#N)c2ccccc2)C(=O)O1]

This compound was prepared by using procedures analogous to those described for the synthesis of Example 120, Step 2 starting from 5-benzylidene-2,2-dimethyl-1,3-dioxane-4,6-dione and potassium cyanide.

Step 3: 3-cyano-3-phenylpropanoic acid

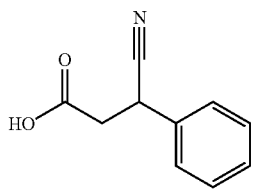 [SMILES: N#CC(CC(=O)O)c1ccccc1]

This compound was prepared by using procedures analogous to those described for the synthesis of Example 120, Step 3 starting from 2-(2,2-dimethyl-4,6-dioxo-1,3-dioxan-5-yl)-2-phenylacetonitrile.

Step 4: 4-[7-[2-amino-6-(4-methylpiperazin-1-yl)pyrimidin-4-yl]-3,4-dihydroisoquinolin-2(1H)-yl]-4-oxo-2-phenylbutanenitrile This compound was prepared by using procedures analogous to those described for the synthesis of Example 120, Step 4 starting from 3-cyano-3-phenylpropanoic acid and piperidin-4-yl 7-[2-amino-6-(4-methylpiperazin-1-yl)pyrimidin-4-yl]-3,4-dihydroisoquinoline-2(1H)-carboxylate HCl salt. Analytic LCMS (M+H)$^+$: m/z=482.1.

Example 125

5-{2-[7-[2-Amino-6-(4-methylpiperazin-1-yl)pyrimidin-4-yl]-3,4-dihydroisoquinolin-2(1H)-yl]-2-oxoethyl}nicotinonitrile

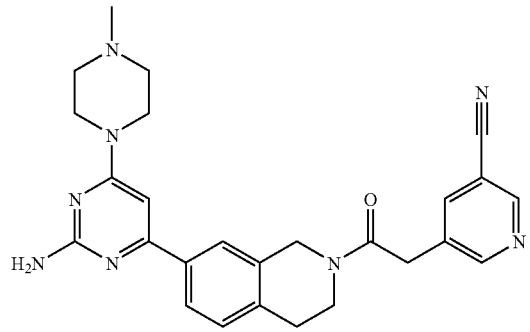 [SMILES: CN1CCN(c2cc(-c3ccc4c(c3)CN(C(=O)Cc3cncc(C#N)c3)CC4)nc(N)n2)CC1]

Step 1: 4-{2-[(5-bromopyridin-3-yl)acetyl]-1,2,3,4-tetrahydroisoquinolin-7-yl}-6-(4-methylpiperazin-1-yl)pyrimidin-2-amine

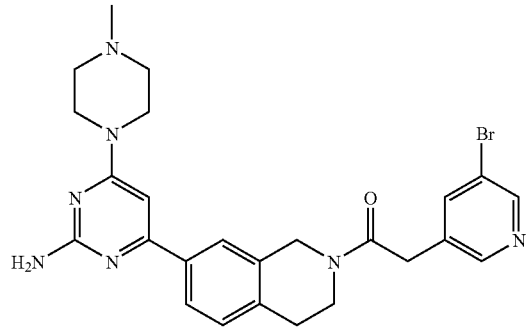 [SMILES: CN1CCN(c2cc(-c3ccc4c(c3)CN(C(=O)Cc3cncc(Br)c3)CC4)nc(N)n2)CC1]

Triethylamine (16 uL, 0.12 mmol) was added to a mixture of 4-(4-methylpiperazin-1-yl)-6-(1,2,3,4-tetrahydroisoquinolin-7-yl)pyrimidin-2-amine trihydrochloride (50 mg, 0.1 mmol), (5-bromopyridin-3-yl)acetic acid (30.0 mg, 0.14 mmol) (Lancaster, Cat. #L13579), and benzotriazol-1-yloxytris(dimethylamino)phosphonium hexafluorophosphate (56 mg, 0.13 mmol) in N,N-dimethylformate (1.5 mL). The reaction mixture was stirred at r.t. overnight. The mixture was diluted with water, and extracted with ethyl acetate (3×10 mL). The combined organic layers were dried over MgSO$_4$, filtered and concentrated under reduced pressure. The residue was purified by flash chromatography on a silica gel column with MeOH in dichloromethane (0-10%) to afford the desired product. Analytic LCMS (M+H)$^+$: m/z=521.95/523.95.

Step 2: 5-{2-[7-[2-amino-6-(4-methylpiperazin-1-yl)pyrimidin-4-yl]-3,4-dihydroisoquinolin-2(1H)-yl]-2-oxoethyl}nicotinonitrile A degassed mixture of 4-{2-[(5-bromopyridin-3-yl)acetyl]-1,2,3,4-tetrahydroisoquinolin-7-yl}-6-(4-methylpiperazin-1-yl)pyrimidin-2-amine (20 mg, 0.04 mmol), zinc cyanide (7 mg, 0.06 mmol), bis(tri-t-butylphosphine)palladium (1 mg, 0.002 mmol) and zinc (0.4 mg, 0.006 mmol) powder in anhydrous N-methylpyrrolidinone (0.1 mL, 1 mmol) was heated at 135° C. for 18 h. The mixture was adjusted to pH=10 with aqueous NH$_3$, filtered, washed with MeOH, and purified by RP-LCMS (pH=10) to afford the desire product. Analytic LCMS (M+H)⁺: m/z=469.1.

Example 126

7-[2-Amino-6-(4-methylpiperazin-1-yl)pyrimidin-4-yl]-N-(1-pyridin-3-ylethyl)-3,4-dihydroisoquinoline-2(1H)-carboxamide

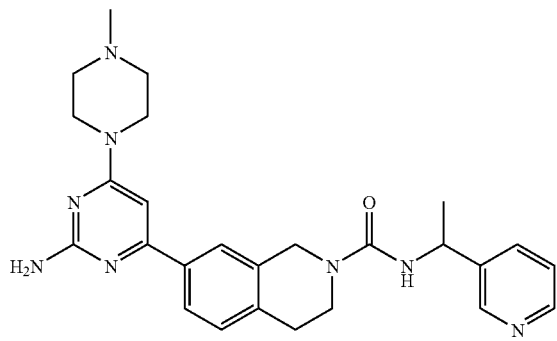 [SMILES: CC(NC(=O)N1CCc2ccc(-c3cc(N4CCN(C)CC4)nc(N)n3)cc2C1)c1cccnc1]

This compound was prepared by using procedures analogous to those described for the synthesis of Example 40 starting from 1-pyridin-3-ylethanamine (Enamine, Cat. #EN300-12752), phosgene and 4-(4-methylpiperazin-1-yl)-6-(1,2,3,4-tetrahydroisoquinolin-7-yl)pyrimidin-2-amine HCl salt. Analytic LCMS (M+H)⁺: m/z=473.1.

Example 127

7-[2-Amino-6-(4-methylpiperazin-1-yl)pyrimidin-4-yl]-N-[1-(1-methyl-1H-pyrazol-3-yl)ethyl]-3,4-dihydroisoquinoline-2(1H)-carboxamide

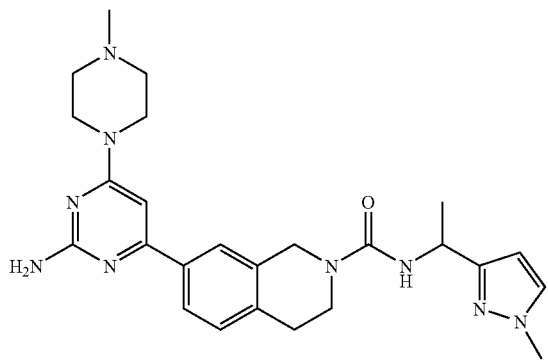 [SMILES: CC(NC(=O)N1CCc2ccc(-c3cc(N4CCN(C)CC4)nc(N)n3)cc2C1)c1ccn(C)n1]

This compound was prepared by using procedures analogous to those described for the synthesis of Example 40 starting from 1-(1-methyl-1H-pyrazol-3-yl)ethanamine (Ryan Scientific, Cat. #B019558), phosgene and 4-(4-methylpiperazin-1-yl)-6-(1,2,3,4-tetrahydroisoquinolin-7-yl)pyrimidin-2-amine HCl salt. Analytic LCMS (M+H)⁺: m/z=476.1.

Example 128

4-(4-Methylpiperazin-1-yl)-6-{2-[(6-pyrrolidin-1-ylpyridin-3-yl)acetyl]-1,2,3,4-tetrahydroisoquinolin-7-yl}pyrimidin-2-amine

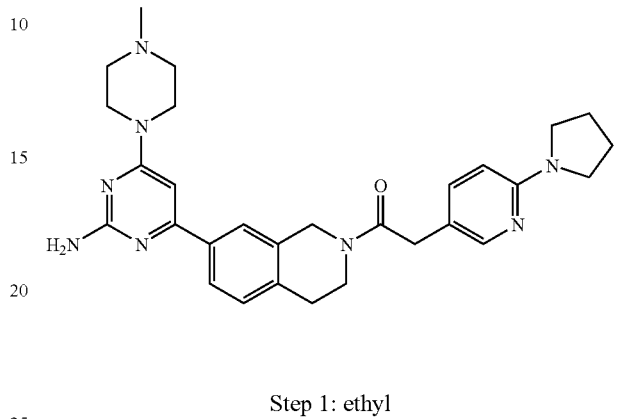

Step 1: ethyl 2-(6-(pyrrolidin-1-yl)pyridin-3-yl)acetate

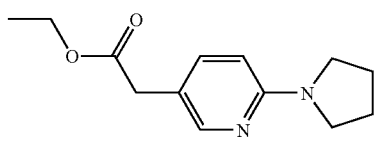

A reaction mixture of ethyl (6-chloropyridin-3-yl)acetate (0.30 g, 1.5 mmol) (Asymchem, Cat. #110112), pyrrolidine (0.14 mL, 1.6 mmol and 1,8-diazabicyclo[5.4.0]undec-7-ene (0.25 mL, 1.6 mmol) in dimethyl sulfoxide (2.0 mL) was stirred at 150° C. overnight. The mixture was diluted with water, and extracted with ethyl acetate (3×10 mL). The combined organic layers were dried over MgSO₄, filtered and concentrated under reduced pressure. The residue was purified by flash chromatography on a silica gel column with ethyl acetate in hexanes (0-40%) to afford the desired product (0.10 g, 28.4%). Analytic LCMS (M+H)⁺: m/z=235.2.

Step 2: 2-(6-(pyrrolidin-1-yl)pyridin-3-yl)acetic acid

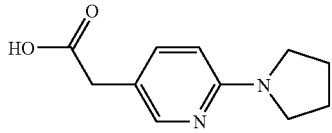 [SMILES: O=C(O)Cc1ccc(N2CCCC2)nc1]

Lithium hydroxide monohydrate (36 mg, 0.85 mmol) was added to a solution of ethyl (6-pyrrolidin-1-ylpyridin-3-yl) acetate (100 mg, 0.4 mmol) in methanol (3.0 mL) and water (1.0 mL). The reaction mixture was stirred at r.t. overnight. The mixture was adjusted to pH=4 with aqueous HCl, and concentrated to afford the crude product which was directly used for next step without further purification. Analytic LCMS (M+H)⁺: m/z=207.1.

Step 3: 4-(4-methylpiperazin-1-yl)-6-{2-[(6-pyrrolidin-1-ylpyridin-3-yl)acetyl]-1,2,3,4-tetrahydroisoquinolin-7-yl}pyrimidin-2-amine 4-(4-methylpiperazin-1-yl)-6-(1,2,3,4-tetrahydroisoquinolin-7-yl)pyrimidin-2-amine trihydrochloride (180 mg, 0.43 mmol), benzotriazol-1-yloxytris(dimethylamino)phosphonium hexafluorophosphate (190 mg, 0.43 mmol) and triethylamine (0.30 mL, 2.1 mmol) were added to 2-(6-(pyrrolidin-1-yl)pyridin-3-yl)acetic acid (0.4 mmol, from the above step) in N,N-dimethylformate (5 mL). The reaction mixture was stirred at r.t. for 2 h. The mixture was purified by Prep-LCMS (pH=10) to afford the desired product. Analytic LCMS (M+H)⁺: m/z=513.2.

Example 129

2-Amino-N-[cyano(phenyl)methyl]-4-(4-methylpiperazin-1-yl)quinazoline-7-carboxamide

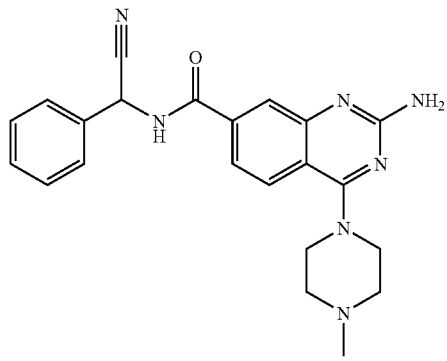 [SMILES: CN1CCN(c2nc(N)nc3cc(C(=O)NC(C#N)c4ccccc4)ccc23)CC1]

This compound was prepared using procedures analogous to those for Example 21, but using 2-amino-2-phenylacetonitrile (Aldrich Cat. #P25558) in Step 5. The crude compound was purified by RP-HPLC (pH=10) to afford the desired compound (0.011 g, 20%) as an amorphous white solid. Analytical LCMS (M+H)⁺: m/z=402.2.

Example 130

Ethyl (2S)-2-({[2-amino-4-(4-methylpiperazin-1-yl)quinazolin-7yl]carbonyl}amino)-4-phenylbutanoate

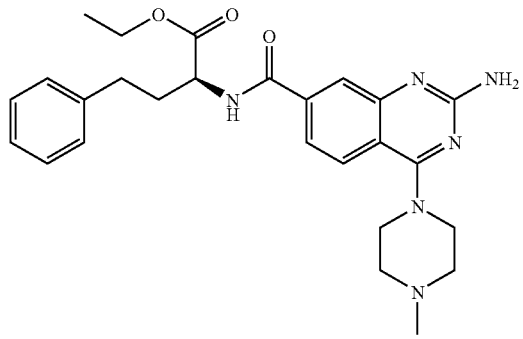 [SMILES: CCOC(=O)[C@H](CCc1ccccc1)NC(=O)c1ccc2c(N3CCN(C)CC3)nc(N)nc2c1]

This compound was prepared using procedures analogous to those for Example 21, but using (S)-ethyl 2-amino-4-phenylbutanoate (Aldrich Cat. #532916) in Step 5. The crude compound was purified by RP-HPLC (pH=10) to afford the desired compound (0.003 g, 24%) as an amorphous white solid. Analytical LCMS (M+H)⁺: m/z=477.1.

Example 131

2-Amino-N-(3,4-dichlorobenzyl)-4-(4-methylpiperazin-1-yl)quinazoline-7-carboxamide

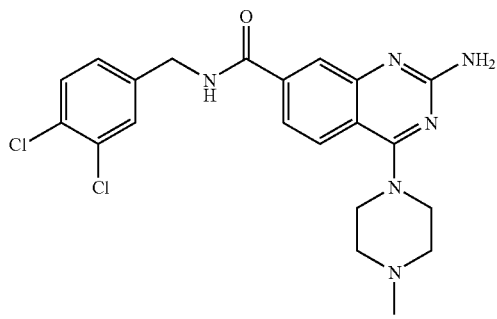 [SMILES: CN1CCN(c2nc(N)nc3cc(C(=O)NCc4ccc(Cl)c(Cl)c4)ccc23)CC1]

This compound was prepared using procedures analogous to those for Example 21, but using (3,4-dichlorophenyl)methanamine (Aldrich Cat. #D58600) in Step 5. The crude compound was purified by RP-HPLC (pH=2) to afford the desired compound (0.005 g, 20%) as an amorphous white solid TFA salt. Analytical LCMS (M+H)⁺: m/z=445.0/447.0.

Example 132

Benzyl({[2-amino-4-(4-methylpiperazin-1-yl)quinazolin-7yl]carbonyl}amino)acetate

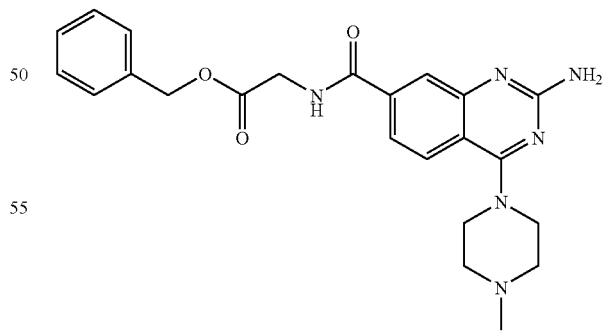

This compound was prepared using procedures analogous to those for Example 21, but using benzyl 2-aminoacetate (BaChem Cat. #E2970) in Step 5. The crude compound was purified by RP-HPLC (pH=2) to afford the desired compound (0.002 g, 7%) as an amorphous white solid TFA salt. Analytical LCMS (M+H)⁺: m/z=435.0.

Example 134

Methyl (2S)-2-({[2-amino-4-(4-methylpiperazin-1-yl)quinazolin-7-yl]carbonyl}amino)-3-(4-isopropoxyphenyl)propanoate

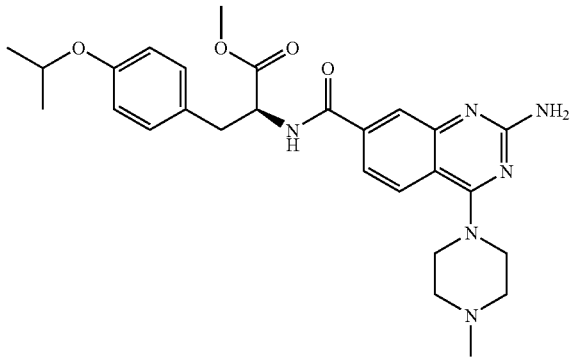 [SMILES: COC(=O)[C@H](Cc1ccc(OC(C)C)cc1)NC(=O)c1ccc2c(N3CCN(C)CC3)nc(N)nc2c1]

Step 1: (S)-methyl 2-(tert-butoxycarbonylamino)-3-(4-isopropoxyphenyl)propanoate

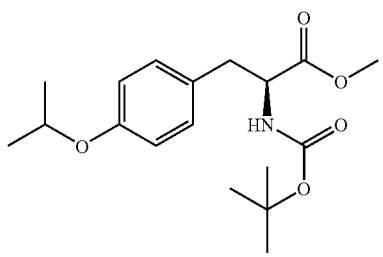 [SMILES: COC(=O)[C@H](Cc1ccc(OC(C)C)cc1)NC(=O)OC(C)(C)C]

Isopropyl iodide (30 uL, 0.3 mmol) was added to a mixture of methyl (2S)-2-[(tert-butoxycarbonyl)amino]-3-(4-hydroxyphenyl)propanoate (50 mg, 0.2 mmol) (Aldrich, Cat. #469106) and potassium carbonate (35 mg, 0.25 mmol) in acetonitrile (2 mL). The reaction was heated at 60° C. overnight. The reaction was partitioned between water and ethyl acetate. The organic phase was washed with saturated brine, dried over magnesium sulfate, filtered and concentrated under reduced pressure to give the crude product (S)-methyl 2-(tert-butoxycarbonylamino)-3-(4-isopropoxyphenyl)propanoate (50 mg, 90%) as a white solid. Analytical LCMS (M+H-Boc)$^+$: m/z=238.0.

Step 2: methyl (2S)-2-amino-3-(4-isopropoxyphenyl)propanoate

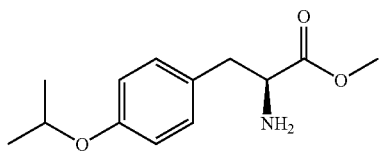 [SMILES: COC(=O)[C@@H](N)Cc1ccc(OC(C)C)cc1]

Trifluoroacetic acid (0.5 mL, 6 mmol) was added to the (S)-methyl 2-(tert-butoxycarbonylamino)-3-(4-isopropoxyphenyl)propanoate in methylene chloride (2 mL). The reaction was stirred for 1 h., and was concentrated under reduced pressure to give a crude product, methyl (2S)-2-amino-3-(4-isopropoxyphenyl)propanoate (40 mg, 100%) as colorless oil. Analytical LCMS (M+H)$^+$: m/z=238.0.

Step 3: methyl (2S)-2-({[2-amino-4-(4-methylpiperazin-1-yl)quinazolin-7-yl]carbonyl}amino)-isopropoxyphenyl)propanoate N,N,N',N'-Tetramethyl-O-(7-azabenzotriazol-1-yl)uronium hexafluorophosphate (20 mg, 0.052 mmol) was added to a solution of 2-amino-4-(4-methylpiperazin-1-yl)quinazoline-7-carboxylic acid (10 mg, 0.03 mmol) in N,N-dimethylformamide (2 mL) and N,N-diisopropylethylamine (12 uL, 0.070 mmol). The reaction was stirred for 10 min, and the methyl (2S)-2-amino-3-(4-isopropoxyphenyl)propanoate (16 mg, 0.070 mmol) was added. The reaction mixture was stirred for 2 h. at r.t. and was purified by RP-HPLC (pH=2) to afford the desired product (6 mg, 30%) as a white solid TFA salt. Analytical LCMS (M+H)$^+$: m/z=507.0.

Example 135

(S)-Methyl 2-(2-amino-4-(4-methylpiperazin-1-yl)quinazoline-7-carboxamido)-3-(4-(isopropylcarbamoyloxy)phenyl)propanoate

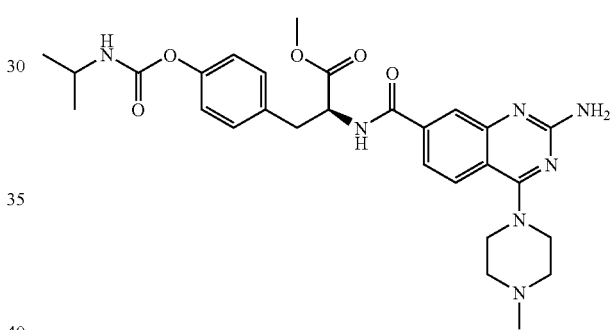

Step 1: (S)-methyl 2-(tert-butoxycarbonylamino)-3-(4(isopropylcarbamoyloxy)phenyl)propanoate

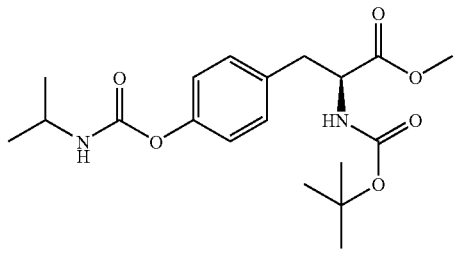 [SMILES: COC(=O)[C@H](Cc1ccc(OC(=O)NC(C)C)cc1)NC(=O)OC(C)(C)C]

2-Isocyanatopropane (Aldrich, Cat. #141070) (22 mg, 0.25 mmol) was added to a solution of methyl (2S)-2-[(tert-butoxycarbonyl)amino]-3-(4-hydroxyphenyl)propanoate (50 mg, 0.2 mmol) and triethylamine (26 mg, 0.25 mmol) in methylene chloride (2 mL). The reaction was stirred for 1 h. The reaction was partitioned between water and ethyl acetate. The organic phase was washed with saturated brine, dried over magnesium sulfate, filtered and concentrated under reduced pressure to give crude product, (S)-methyl 2-(tert-butoxycarbonylamino)-3-(4-(isopropylcarbamoyloxy)phe- Step 2: methyl (2S)-2-amino-3-(4-{[(isopropy-lamino)carbonyl]oxy}phenyl)propanoate

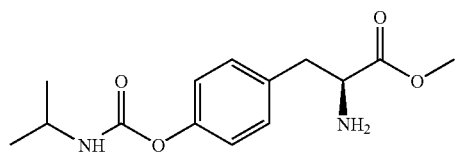 [SMILES: COC(=O)[C@@H](N)Cc1ccc(OC(=O)NC(C)C)cc1]

Trifluoroacetic acid (0.5 mL, 6 mmol) was added to (S)-methyl 2-(tert-butoxycarbonylamino)-3-(4-(isopropylcarbamoyloxy)phenyl)propanoate in methylene chloride (2 mL). The reaction was stirred for 1 h, and was concentrated under reduced pressure to give crude product, methyl (2S)-2-amino-3-(4-{[(isopropylamino)carbonyl]oxy}phenyl)propanoate (50 mg, 100%). Analytical LCMS (M+H)$^+$: m/z=281.0.

Step 3: (S)-methyl 2-(2-amino-4-(4-methylpiperazin-1-yl)quinazoline-7-carboxamido)-3-(4-(isopropylcarbamoyloxy)phenyl)

N,N,N',N'-Tetramethyl-O-(7-azabenzotriazol-1-yl)uronium hexafluorophosphate (26 mg, 0.070 mmol) was added to a solution of 2-amino-4-(4-methylpiperazin-1-yl)quinazoline-7-carboxylic acid (10 mg, 0.03 mmol) in N,N-dimethylformamide (1 mL) and N,N-diisopropylethylamine (12 uL, 0.070 mmol). The reaction was stirred for 10 min, and the methyl (2S)-2-amino-3-(4-{[(methylamino)carbonyl]oxy}phenyl)propanoate (18 mg, 0.070 mmol) was added. The reaction mixture was stirred for 1 h. at r.t., and was purified by RP-HPLC (pH=2), to obtain the desired product (5 mg, 30%) as a white solid TFA salt. Analytical LCMS (M+H)$^+$: m/z=550.0.

Example 136

(S)-2-Amino-N-(1-(dimethylamino)-3-(4-isopropoxyphenyl)-1-oxopropan-2-yl)-4-(4-methylpiperazin-1-yl)quinazoline-7-carboxamide

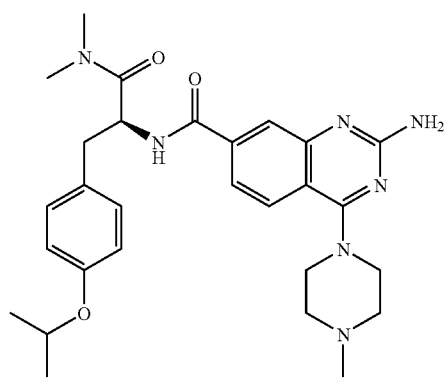 [SMILES: CC(C)Oc1ccc(C[C@H](NC(=O)c2ccc3c(N4CCN(C)CC4)nc(N)nc3c2)C(=O)N(C)C)cc1]

Step 1: (S)-methyl 2-(tert-butoxycarbonylamino)-3-(4-isopropoxyphenyl)propanoate

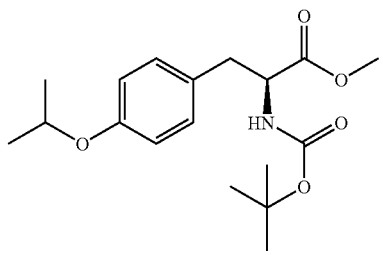 [SMILES: COC(=O)[C@H](Cc1ccc(OC(C)C)cc1)NC(=O)OC(C)(C)C]

Isopropyl iodide (680 uL, 6.8 mmol) was added to a mixture of methyl (2S)-2-[(tert-butoxycarbonyl)amino]-3-(4-hydroxyphenyl)propanoate (1 g, 3 mmol) (Step 1) and potassium carbonate (940 mg, 6.8 mmol) in acetonitrile (20 mL). The reaction was heated at 60° C. overnight. The reaction was partitioned between water and ethyl acetate. The organic phase was washed with saturated brine, dried over magnesium sulfate, filtered and concentrated under reduced pressure to give the crude product, (S)-methyl 2-(tert-butoxycarbonylamino)-3-(4-isopropoxyphenyl)propanoate (1 g, 90%) as a white solid. Analytical LCMS (M+H-Boc)$^+$: m/z=237.9.

Step 2: (2S)-2-[(tert-butoxycarbonyl)amino]-3-(4-isopropoxyphenyl)propanoic acid

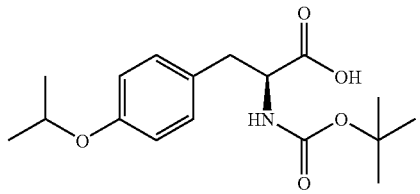 [SMILES: CC(C)Oc1ccc(C[C@H](NC(=O)OC(C)(C)C)C(=O)O)cc1]

Lithium hydroxide (160 mg, 6.8 mmol) in water (10 mL) was added to a solution of (S)-methyl 2-(tert-butoxycarbonylamino)-3-(4-isopropoxyphenyl)propanoate in methanol (30 mL). The reaction was stirred for 24 h., and was concentrated under reduced pressure to remove the methanol. The remaining water layer was adjusted to pH=3 using 1 N HCl aqueous solution, and was extracted with ethyl acetate. The organic phase was washed with saturated brine, dried over magnesium sulfate, filtered and concentrated under reduced pressure to give the crude product (2S)-2-[(tert-butoxycarbonyl)amino]-3-(4-isopropoxyphenyl)propanoic acid (1 g, 90%). Analytical LCMS (M+H-Boc)$^+$: m/z=223.9.

Step 3: (5)-tert-butyl 1-(dimethylamino)-3-(4-isopropoxyphenyl)-1-oxopropan-2-ylcarbamate

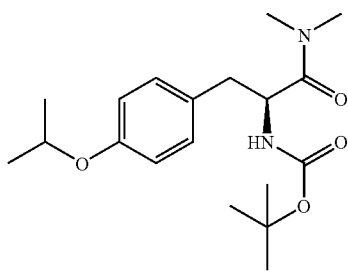 [SMILES: CC(C)Oc1ccc(C[C@H](NC(=O)OC(C)(C)C)C(=O)N(C)C)cc1]

N,N,N',N'-Tetramethyl-O-(7-azabenzotriazol-1-yl)uronium hexafluorophosphate (88 mg, 0.23 mmol) was added to a solution of (2S)-2-[(tert-butoxycarbonyl)amino]-3-(4-isopropoxyphenyl)propanoic acid (50 mg, 0.2 mmol) in N,N-dimethylformamide (5 mL) and N,N-diisopropylethylamine (54 uL, 0.31 mmol). The reaction was stirred for 10 min, and the 2.00 M of dimethylamine in tetrahydrofuran (0.4 mL, 0.6 mmol) was added. The reaction was stirred for 2 h. at r.t. and was partitioned between water and ethyl acetate. The organic phase was washed with saturated brine, dried over magnesium sulfate, filtered and concentrated under reduced pressure to give the crude product, (S)-tert-butyl 1-(dimethylamino)-3-(4-isopropoxyphenyl)-1-oxopropan-2-ylcarbamate (50 mg, 90%). Analytical LCMS (M+H-Boc)$^+$: m/z=251.0.

Step 4: (2S)-2-amino-3-(4-isopropoxyphenyl)-N,N-dimethylpropanamide

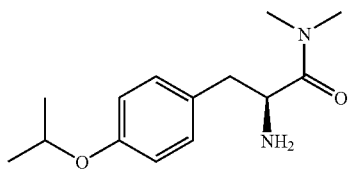 [SMILES: CC(C)Oc1ccc(C[C@H](N)C(=O)N(C)C)cc1]

Trifluoroacetic acid (1 mL, 10 mmol) was added to (S)-tert-butyl 1-(dimethylamino)-3-(4-isopropoxyphenyl)-1-oxopropan-2-ylcarbamate in methylene chloride (2 mL). After stirring for 1 h., the reaction was concentrated under reduced pressure to give the crude product, (2S)-2-amino-3-(4-isopropoxyphenyl)-N,N-dimethylpropanamide (40 mg, 100%). Analytical LCMS (M+H)$^+$: m/z=251.0.

Step 5: (S)-2-amino-N-(1-(dimethylamino)-3-(4-isopropoxyphenyl)-1-oxopropan-2-yl)-4-(4-methylpiperazin-1-yl)quinazoline-7-carboxamide N,N,N',N'-Tetramethyl-O-(7-azabenzotriazol-1-yl)uronium hexafluorophosphate (42 mg, 0.11 mmol) was added to a solution of 2-amino-4-(4-methylpiperazin-1-yl)quinazoline-7-carboxylic acid (20 mg, 0.07 mmol) in N,N-dimethylformamide (2 mL) and N,N-diisopropylethylamine (24 uL, 0.14 mmol). The reaction was stirred for 10 min, and the (2S)-2-amino-3-(4-isopropoxyphenyl)-N,N-dimethylpropanamide (35 mg, 0.14 mmol) was added. The reaction was stirred for 2 h. at r.t., and was purified by RP-HPLC (pH=2) to afford the desired product (7 mg, 20%) as a white solid TFA salt. Analytical LCMS (M+H)$^+$: m/z=520.0.

Example 137

2-Amino-N-[(1S)-1-cyano-2-(4-isopropoxyphenyp-ethyl]-4-(4-methylpiperazin-1-yl)quinazoline-7-carboxamide

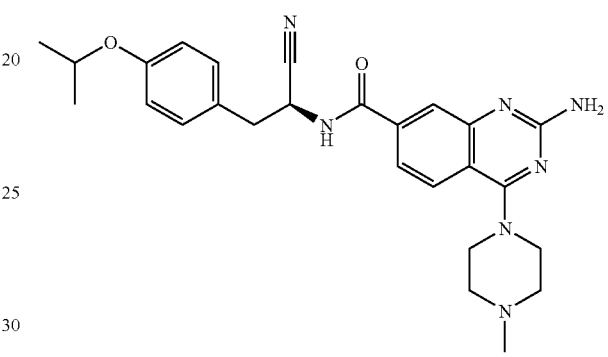

Step 1: (5)-tert-butyl1-amino-3-(4-isopropoxyphenyl)-1-oxopropan-2-ylcarbamate

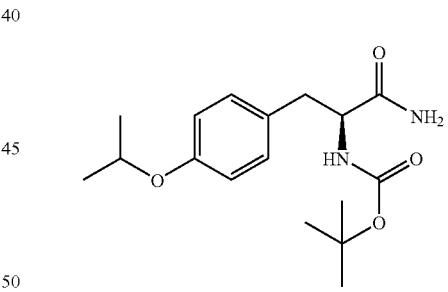

N,N,N',N'-Tetramethyl-O-(7-azabenzotriazol-1-yl)uronium hexafluorophosphate (180 mg, 0.46 mmol) was added to a solution of (2S)-2-[(tert-butoxycarbonyl)amino]-3-(4-isopropoxyphenyl)propanoic acid (100 mg, 0.3 mmol) (Example 136, step 2) in N,N-dimethylformamide (5 mL) and N,N-diisopropylethylamine (110 uL, 0.62 mmol). The reaction was stirred for 10 min., and 0.5 M ammonia in 1,4-dioxane (1.2 mL, 0.62 mmol) was added. The reaction was stirred for 1 h. at r.t., and was partitioned between water and ethyl acetate. The organic phase was washed with saturated brine, dried over magnesium sulfate, filtered and concentrated under reduced pressure to give the crude product, (S)-tert-butyl 1-amino-3-(4-isopropoxyphenyl)-1-oxopropan-2-ylcarbamate (90 mg, 90%). Analytical LCMS (M+H-Boc)$^+$: m/z=222.9.

Step 2: (S)-tert-butyl 1-cyano-2-(4-isopropoxyphenyl)ethylcarbamate

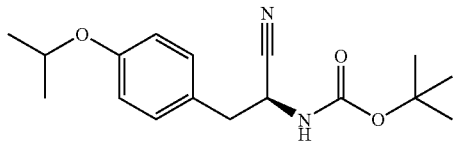 [SMILES: CC(C)Oc1ccc(C[C@@H](C#N)NC(=O)OC(C)(C)C)cc1]

Trichloroacetic acid anhydride (120 mg, 0.39 mmol) was added slowly to a solution of (S)-tert-butyl 1-amino-3-(4-isopropoxyphenyl)-1-oxopropan-2-ylcarbamate (50 mg, 0.2 mmol) in methylene chloride (3 mL) and triethylamine (86 uL, 0.62 mmol) at 0° C. The reaction was stirred for 1 h. at 0° C. The reaction was quenched with saturated NaHCO$_3$ and was extracted with ethyl acetate. The organic phase was washed with water, saturated brine, dried over magnesium sulfate, filtered and concentrated under reduced pressure to give the crude product, which was purified by Flash chromatography on a silica gel column (EtOAc:Hexane, 1:3 to 1:1) to obtain the (S)-tert-butyl 1-cyano-2-(4-isopropoxyphenyl) ethylcarbamate (40 mg, 80%) as clear oil. Analytical LCMS (M+Na)$^+$: m/z=327.0.

Step 3: (2S)-2-amino-3-(4-isopropoxyphenyl)propanenitrile

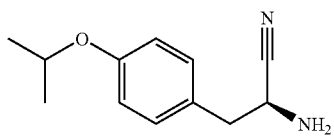

Trifluoroacetic acid (1 mL, 10 mmol) was added to a solution of the (S)-tert-butyl 1-cyano-2-(4-isopropoxyphenyl) ethylcarbamate (40 mg) in methylene chloride (2 mL). After stirring for 1 h., the reaction was concentrated under reduced pressure to give the crude product (2S)-2-amino-3-(4-isopropoxyphenyl)propanenitrile (30 mg, 90%).

Step 4: 2-amino-N-[(1S)-1-cyano-2-(4-isopropoxyphenyl)ethyl]-4-(4-methylpiperazin-1-yl)quinazoline-7-carboxamide N,N,N',N'-Tetramethyl-O-(7-azabenzotriazol-1-yl)uronium hexafluorophosphate (42 mg, 0.11 mmol) was added to a solution of 2-amino-4-(4-methylpiperazin-1-yl)quinazoline-7-carboxylic acid (20 mg, 0.07 mmol) in N,N-dimethylformamide (2 mL, 20 mmol) and N,N-diisopropylethylamine (24 uL, 0.14 mmol). The reaction was stirred for 10 min., and the (2S)-2-amino-3-(4-isopropoxyphenyl)propanenitrile (28 mg, 0.14 mmol) was added. The reaction was stirred for 1 h. at r.t., and was purified by RP-HPLC (pH=2) to afford the desired product (4 mg, 10%) as a white solid TFA salt. Analytical LCMS (M+H)$^+$: m/z=474.1.

Example 138

Methyl (2S)-2-({[2-amino-4-(4-methylpiperazin-1-yl)quinazolin-7-yl]carbonyl}amino)-3-biphenyl-4-ylpropanoate

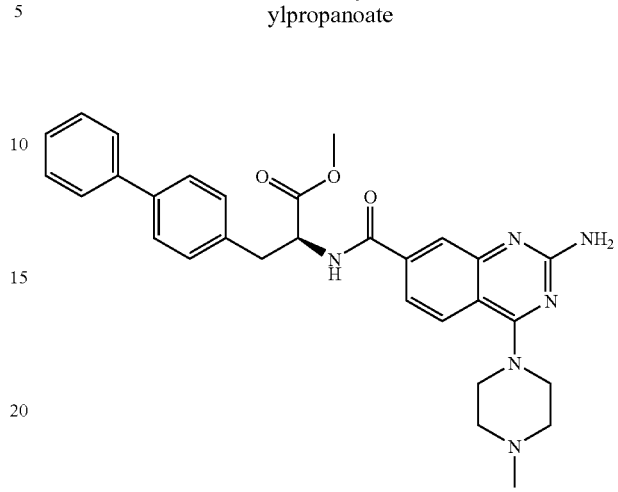

Step 1: (S)-2-tert-butoxycarbonylamino-3-(4-trifluoromethanesulfonyloxy-phenyl)-propionic acid methyl ester

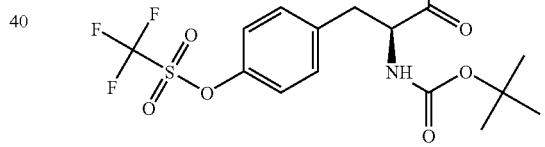

Trifluoromethanesulfonic anhydride (0.85 mL, 5.1 mmol) was added to a solution of methyl (2S)-2-[(tert-butoxycarbonyl)amino]-3-(4-hydroxyphenyl)propanoate (1 g, 3 mmol) (Aldrich, Cat 469106) and triethylamine (1 mL, 10 mmol) in methylene chloride (30 mL) at −78° C. The reaction was stirred for 1 h. at −78° C. Saturated NaHCO$_3$ was added and the reaction was extracted with dichloromethane. The organic phase was washed with saturated brine, dried over magnesium sulfate, filtered and concentrated under reduced pressure. The crude product was purified by Flash chromatography on a silica gel column (EtOAc:Hexane, 1:3 to 1:1) to obtain (S)-2-tert-butoxycarbonylamino-3-(4-trifluoromethanesulfonyloxy-phenyl)-propionic acid methyl ester (1.2 g, 80%) as light yellow oil. Analytical LCMS (M+H-Boc)$^+$: m/z=327.9.

Step 2: (S)-methyl 3-(biphenyl-4-yl)-2-(tert-butoxycarbonylamino)propanoate

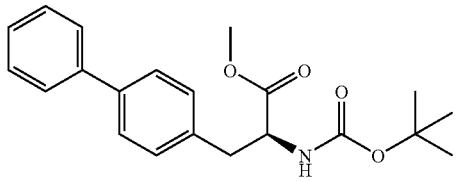 [SMILES: COC(=O)[C@H](Cc1ccc(-c2ccccc2)cc1)NC(=O)OC(C)(C)C]

Potassium carbonate (50 mg, 0.4 mmol) in water (0.2 mL) was added to a solution of (S)-2-tert-butoxycarbonylamino-3-(4-trifluoromethanesulfonyloxy-phenyl)-propionic acid methyl ester (50 mg, 0.1 mmol), and phenylboronic acid (Aldrich, Cat P20009) (21 mg, 0.18 mmol) in 1,4-dioxane (3.0 mL). The reaction was degassed by $N_2$ for 5 min Tetrakis(triphenylphosphine)palladium(0) (8 mg, 0.007 mmol) was added, and the reaction was degassed for another 5 min The reaction vial was sealed and stirred for 5 h. at 80° C. The reaction was partitioned between water and ethyl acetate. The organic phase was washed with saturated brine, dried over magnesium sulfate, filtered and concentrated under reduced pressure. The crude product was purified by Flash chromatography on a silica gel column (EtOAC:Hexanes, 1:3 to 1:1) to give the (S)-methyl 3-(biphenyl-4-yl)-2-(tert-butoxycarbonylamino)propanoate (30 mg, 70%). Analytical LCMS $(M+H-Boc)^+$: m/z=256.1.

Step 3: methyl (2S)-2-amino-3-biphenyl-4-ylpropanoate

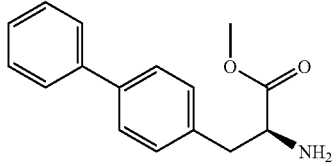 [SMILES: COC(=O)[C@@H](N)Cc1ccc(-c2ccccc2)cc1]

Trifluoroacetic acid (1 mL, 10 mmol) was added to a solution of (S)-methyl 3-(biphenyl-4-yl)-2-(tert-butoxycarbonylamino)propanoate (30 mg) in methylene chloride (2 mL). The reaction was stirred for 1 h, and was concentrated under reduced pressure to give the crude product methyl (2S)-2-amino-3-biphenyl-4-ylpropanoate (30 mg, 100%). Analytical LCMS $(M+H)^+$: m/z=256.1.

Step 4: methyl (2S)-2-({[2-amino-4-(4-methylpiperazin-1-yl)quinazolin-7-yl}carbonyl]amino)-3-biphenyl-4-ylpropanoate N,N,N',N'-Tetramethyl-O-(7-azabenzotriazol-1-yl)uronium hexafluorophosphate (42 mg, 0.11 mmol) was added to a solution of 2-amino-4-(4-methylpiperazin-1-yl)quinazoline-7-carboxylic acid (20 mg, 0.07 mmol) in N,N-dimethylformamide (2 mL) and N,N-diisopropylethylamine (24 uL, 0.14 mmol). The methyl (2S)-2-amino-3-biphenyl-4-ylpropanoate (36 mg, 0.14 mmol) was added. The reaction was stirred for 2 h. at r.t., and was purified by RP-HPLC (pH=2) to afford the desired product (5 mg, 10%) as a white solid TFA salt. Analytical LCMS $(M+H)^+$: m/z=525.1.

Example 139

2-Amino-N-[(1S)-1-(biphenyl-4-ylmethyl)-2-(dimethylamino)-2-oxoethyl]-4-(4-methylpiperazin-1-yl)quinazoline-7-carboxamide

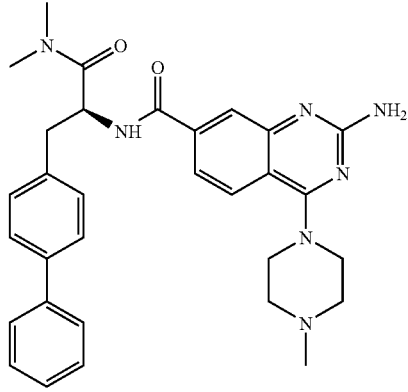 [SMILES: CN1CCN(c2nc(N)nc3cc(C(=O)N[C@@H](Cc4ccc(-c5ccccc5)cc4)C(=O)N(C)C)ccc23)CC1]

Step 1: N-(tert-butoxycarbonyl)-4-(dihydroxyboryl)-1-phenylalanine

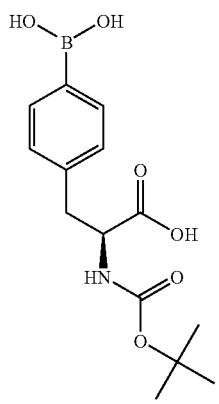 [SMILES: CC(C)(C)OC(=O)N[C@@H](Cc1ccc(B(O)O)cc1)C(=O)O]

Di-tert-Butyldicarbonate (0.5 g, 2 mmol) was added to a mixture of (2S)-2-amino-3-[4-(dihydroxyboryl)phenyl]propanoic acid (0.5 g, 2 mmol) (Fluka Cat. #17755) in tetrahydrofuran (20 mL) and water (5 uL) at 0° C. The reaction mixture was stirred at r.t. overnight, and was partitioned between water and ethyl acetate. The water layer was concentrated under reduced pressure to dryness to give the crude product N-(tert-butoxycarbonyl)-4-(dihydroxyboryl)-1-phenylalanine (0.7 g, 90%) as a white solid. Analytical LCMS $(M+H-Boc)^+$: m/z=209.9.

Step 2: {4-[(2S)-2-[(tert-butoxycarbonyl)amino]-3-(dimethylamino)-3-oxopropyl]phenyl}boronic acid

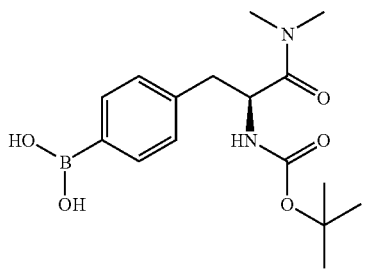 [SMILES: CN(C)C(=O)[C@H](Cc1ccc(B(O)O)cc1)NC(=O)OC(C)(C)C]

N,N,N',N'-Tetramethyl-O-(7-azabenzotriazol-1-yl)uronium hexafluorophosphate (920 mg, 2.4 mmol) was added to a solution of N-(tert-butoxycarbonyl)-4-(dihydroxyboryl)-1-phenylalanine (500 mg, 2 mmol), N,N-dimethylformamide (20 mL) and N,N-diisopropylethylamine (560 uL, 3.2 mmol). The reaction was stirred for 10 min., and the 2 M dimethylamine in tetrahydrofuran (3.2 mL, 6.4 mmol) was added. The reaction was stirred for 1 h at r.t., and was partitioned between water and ethyl acetate. The organic phase was washed with saturated brine, dried over magnesium sulfate, filtered and concentrated under reduced pressure to give the crude product {4-[(2S)-2-[(tert-butoxycarbonyl)amino]-3-(dimethylamino)-3-oxopropyl]phenyl}boronic acid (400 mg, 70%). Analytical LCMS (M+H-Boc)$^+$: m/z=235.9.

Step 3: tert-butyl [(1S)-1-(biphenyl-4-ylmethyl)-2-(dimethylamino)-2-oxoethyl]carbamate

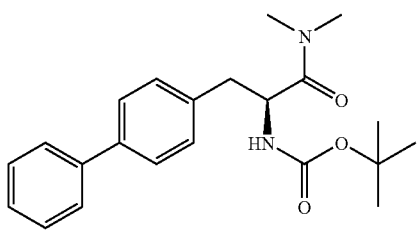 [SMILES: CN(C)C(=O)[C@H](Cc1ccc(-c2ccccc2)cc1)NC(=O)OC(C)(C)C]

Potassium carbonate (120 mg, 0.89 mmol) in water (0.5 mL) was added to a solution of product {4-[(2S)-2-[(tert-butoxycarbonyl)amino]-3-(dimethylamino)-3-oxopropyl]phenyl}boronic acid (100 mg, 0.3 mmol) and bromobenzene (53 mg, 0.34 mmol) in 1,4-dioxane (2 mL). The reaction was degassed by N$_2$ for 10 min The tetrakis(triphenylphosphine)palladium(0) (17 mg, 0.015 mmol) was added, and the reaction mixture was degassed for another 10 minutes. The reaction vial was sealed and the reaction was stirred for 5 h. at 80° C. The reaction was partitioned between water and ethyl acetate. The organic phase was washed with saturated brine, dried over magnesium sulfate, filtered and concentrated under reduced pressure to give the crude product which was purified by Flash chromatography on a silica gel column (EtOAc:Hexanes, 1:3 to 2:1) gave tert-butyl [1S)-1-(biphenyl-4-ylmethyl)-2-(dimethylamino)-2-oxoethyl]carbamate (70 mg, 60%). Analytical LCMS (M+H-Boc)$^+$: m/z=269.0.

Step 4. (2S)-2-amino-3-biphenyl-4-yl-N,N-dimethyl-propanamide

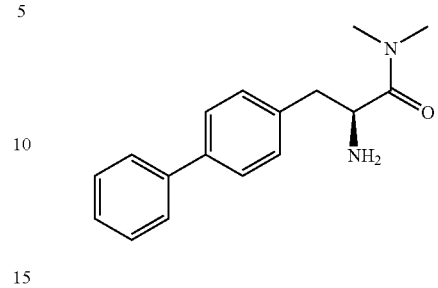

Trifluoroacetic acid (1 mL, 10 mmol) was added to a solution of tert-butyl[(1S)-1-(biphenyl-4-ylmethyl)-2-(dimethylamino)-2-oxoethyl]carbamate (50 mg, 0.1 mmol) in methylene chloride (2 mL). The reaction was stirred for 2 h., and was concentrated under reduced pressure to give the crude product (2S)-2-amino-3-biphenyl-4-yl-N,N-dimethylpropanamide (35 mg, 97%). Analytical LCMS (M+H)$^+$: m/z=269.0.

Step 5: 2-amino-N-[(1S)-1-(biphenyl-4-ylmethyl)-2-(dimethylamino)-2-oxoethyl]-4-(4-methylpiperazin-1-yl)quinazoline-7-carboxamide N,N,N',N'-Tetramethyl-O-(7-azabenzotriazol-1-yl)uronium hexafluorophosphate (26 mg, 0.070 mmol) was added to a solution of 2-amino-4-(4-methylpiperazin-1-yl)quinazoline-7-carboxylic acid (10 mg, 0.03 mmol) in N,N-dimethylformamide (1 mL) and N,N-diisopropylethylamine (12 uL, 0.070 mmol). The reaction was stirred for 10 min., and the (2S)-2-amino-3-biphenyl-4-yl-N,N-dimethylpropanamide (19 mg, 0.070 mmol) was added. The reaction was stirred for 2 h. at r.t., and was purified by RP-HPLC (pH=10) to afford the desired product (3 mg, 20%) as a white solid. Analytical LCMS (M+H)$^+$: m/z=538.0.

Example 140

Methyl (2S)-2-({[2-amino-4-(4-methylpiperazin-1-yl)quinazolin-7yl]carbonyl}amino)-3-[4-(1-methyl-1H-pyrazol-4-yl)phenyl]propanoate

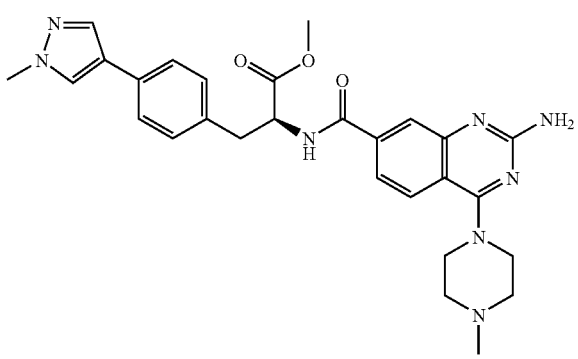 [SMILES: COC(=O)[C@H](Cc1ccc(-c2cnn(C)c2)cc1)NC(=O)c1ccc2c(N3CCN(C)CC3)nc(N)nc2c1]

This compound was prepared using procedures analogous to those for Example 138 but using 1-methyl-1H-pyrazol-4-ylboronic acid pinacol ester (Aldrich Cat. #595314) in Step 2. The crude compound was purified by RP-HPLC (pH=2) to afford the desired compound (0.005 g, 10%) as an amorphous white solid TFA salt. Analytical LCMS (M+H)+: m/z=529.0.

Example 141

2-Amino-N-[2-(1-benzofuran-2-yl)-1-methylethyl]-4-(4-methylpiperazin-1-yl)quinazoline-7-carboxamide

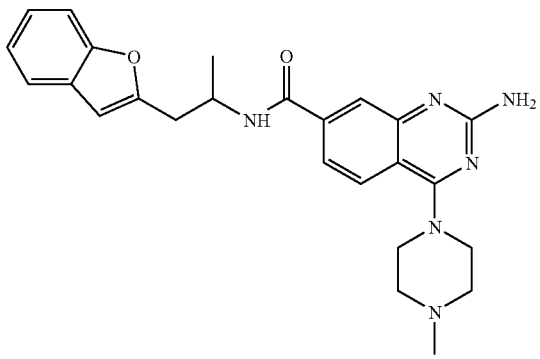 [SMILES: CC(Cc1cc2ccccc2o1)NC(=O)c1ccc2c(N3CCN(C)CC3)nc(N)nc2c1]

Step 1: 2-[(1E & Z)-2-nitroprop-1-en-1-yl]-1-benzofuran

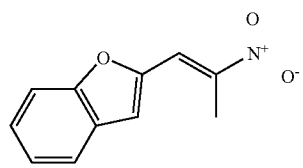

1-Benzofuran-2-carbaldehyde (Aldrich, Cat 493449) (0.10 g, 0.68 mmol) and nitroethane (0.15 mL, 2.0 mmol) were combined in acetic acid (0.53 mL) with cyclohexanamine (0.078 mL, 0.68 mmol) and heated in a sealed tube to 100° C. in the microwave for 15 min This was allowed to cool to r.t., taken up in ethyl acetate, washed with 1 N HCl, brine, dried over magnesium sulfate and concentrated under reduced pressure to give the crude product as an oil. The product was purified by Flash chromatography on a silica gel column eluting hexane:ethyl acetate gradient to give a mixture of cis- and trans-2-(2-nitroprop-1-en-1-yl)-1-benzofuran (0.080 g, 57% yield) as an oil. Analytical LCMS (M+H)+: m/z=204.1.

Step 2. 1-(1-benzofuran-2-yl)propan-2-amine

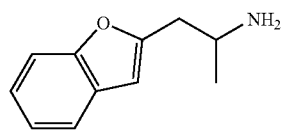

A mixture of cis- and trans-2-(2-nitroprop-1-en-1-yl)-1-benzofuran (0.08 g, 0.39 mmol) (from Step 1) was dissolved in tetrahydrofuran (3.0 mL) under nitrogen and 1.0 M of lithium tetrahydroaluminate in ether (0.79 mL, 0.79 mmol) was added slowly. This was stirred for 1 h. at r.t. and then heated to 75° C. After heating for 2.h. the reaction was complete. This was allowed to cool to 0° C. and quenched with methanol. The reaction was taken up in ethyl acetate, washed with sodium bicarbonate, brine, dried over magnesium sulfate and concentrated under reduced pressure to give 1-(1-benzofuran-2-yl)propan-2-amine as a dark oil. This was used as crude in the following reaction. Analytical LCMS (M+H)+: m/z=176.1.

Step 3: 2-amino-N-[2-(1-benzofuran-2-yl)-1-methylethyl]-4-(4-methylpiperazin-1-yl)quinazoline-7-carboxamide A solution of 2-amino-4-(4-methylpiperazin-1-yl)quinazoline-7-carboxylic acid (15 mg, 52.2 µmol), 1-(1-benzofuran-2-yl)propan-2-amine (18.3 mg, 104 µmol), N,N,N',N'-tetramethyl-o-(7-azabenzotriazol-1-yl)uronium hexafluorophosphate (31.8 mg, 83.5 p mol), N,N-dimethylformamide (1.50 ml) and N,N-diisopropylethylamine (18.2 µl, 104 µmol) was stirred at 25° C. for 60 min The reaction was purified without work up on a RP-HPLC (pH=2) to afford TFA salt of this compound (15 mg, 25%) as a white amorphous solid. Analytical LCMS (M+H)+: m/z=445.2.

Example 142

2-Amino-N-[1-methyl-2-(4-phenoxyphenyl)ethyl]-4-(4-methylpiperazin-1-yl)quinazoline-7-carboxamide

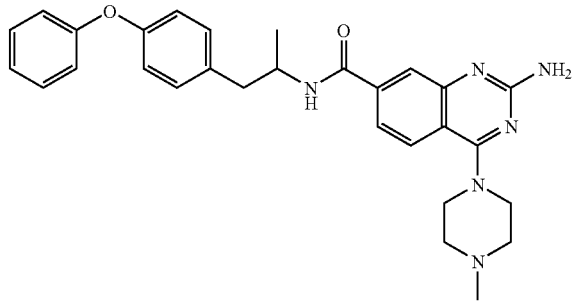 [SMILES: CC(Cc1ccc(Oc2ccccc2)cc1)NC(=O)c1ccc2c(N3CCN(C)CC3)nc(N)nc2c1]

This compound was prepared using procedures analogous to those for Example 141 but using in 4-phenoxybenzaldehyde (Aldrich, Cat. #211265) in Step 1. The crude compound was purified by RP-HPLC (pH=2) to afford the desired compound (0.005 g, 10%) as an amorphous white solid TFA salt. Analytical LCMS (M+H)+: m/z=497.0.

Example 143

2-Amino-N-{2-[4-(cyclopentyloxy)phenyl]-1-methylethyl}-4-(4-methylpiperazin-1-yl)quinazoline-7-carboxamide

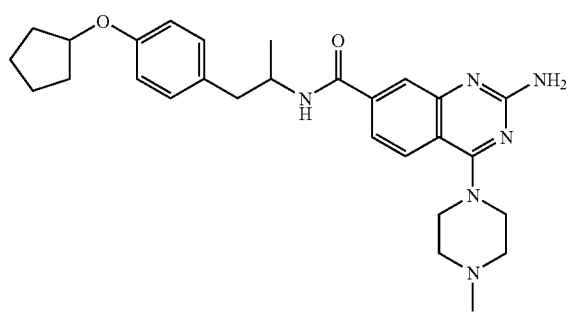 [SMILES: CC(Cc1ccc(OC2CCCC2)cc1)NC(=O)c1ccc2c(N3CCN(C)CC3)nc(N)nc2c1]

Step 1: 4-(cyclopentyloxy)benzaldehyde

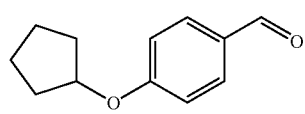

A solution of 4-hydroxybenzaldehyde (100 mg, 0.819 mmol), cyclopentyl bromide (176 µl, 1.64 mmol), potassium carbonate (340 mg, 2.46 mmol), acetonitrile (4 mL) and potassium iodide (136 mg, 819 µmol) was stirred at 60° C. for 18 h. The reaction was diluted with water and extracted with ethyl acetate. The organic layer was washed with brine, dried over magnesium sulfate, filtered, and concentrated under reduced pressure to give crude product 4-(cyclopentyloxy) benzaldehyde. This was used as crude in the following Step. Analytical LCMS (M+H)$^+$: m/z=191.1.

Step 2: 2-amino-N-{2-[4-(cyclopentyloxy)phenyl]-1-methylethyl}-4-(4-methylpiperazin-1-yl)quinazoline-7-carboxamide This compound was prepared using procedures analogous to those for Example 141 but using 4-(cyclopentyloxy)benzaldehyde in Step 1, above. The crude compound was purified by RP-HPLC (pH=2) to afford the desired compound (0.003 g, 10%) as an amorphous white solid TFA salt. Analytical LCMS (M+H)$^+$: m/z=489.0.

Example 144

2-Amino-N-[1-(1,3-benzothiazol-2-ylmethyl)-2-(dimethylamino)-2-oxoethyl]-4-(4-methylpiperazin-1-yl)quinazoline-7-carboxamide

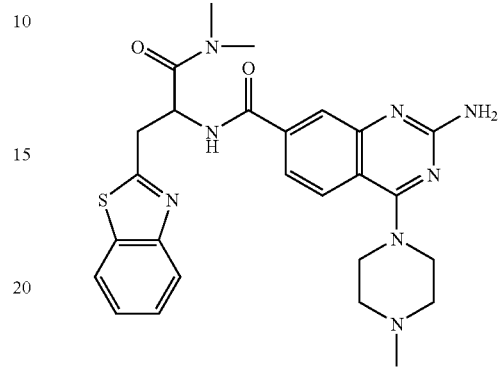

Step 1: methyl 3-(benzo[d]thiazol-2-yl)-2-(tert-butoxycarbonylamino)acrylate

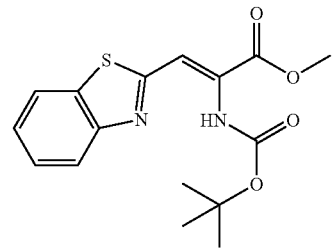 [SMILES: COC(=O)/C(=C/c1nc2ccccc2s1)NC(=O)OC(C)(C)C]

A solution of methyl [(tert-butoxycarbonyl)amino] (dimethoxyphosphoryl)acetate (Fluka, Cat. #09659) (194 mg, 651 µmol), benzo[d]thiazole-2-carbaldehyde (VWR, Cat. #100605-032) (80 mg, 543 µmol), methylene chloride (2.26 ml, 35.2 mmol) and 1,8-diazabicyclo[5.4.0]undec-7-ene (97.4 µl, 651 µmol) was stirred at 25° C. for 2 h. The reaction was taken up in ethyl acetate, washed with 1 N HCl, brine, dried over magnesium sulfate and concentrated under reduced pressure to give the crude product as an oil. The product was purified by Flash chromatography on a silica gel column eluting hexane: ethyl acetate gradient to give a mixture of methyl 3-(benzo[d]thiazol-2-yl)-2-(tert-butoxycarbonylamino)acrylate (0.18 g, 98%) as a clear oil. Analytical LCMS (M+H)$^+$: m/z=334.9.

Step 2: methyl 3-(benzo[d]thiazol-2-yl)-2-(tert-butoxycarbonylamino)propanoate

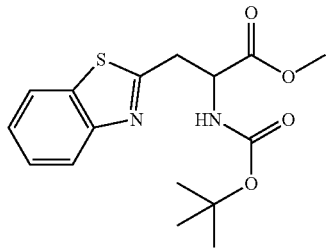 [SMILES: COC(=O)C(Cc1nc2ccccc2s1)NC(=O)OC(C)(C)C]

The mixture of methyl 3-(benzo[d]thiazol-2-yl)-2-(tert-butoxycarbonylamino)acrylate (0.18 g, 0.539 mmol) was taken up in methanol (10 mL) in a Parr Shaker bottle, this was degassed with nitrogen and the 10% Pd/C (0.05 g) was added. The reaction was charged with hydrogen to 55 PSI and shaken. After 2 h. the reaction was complete. This was filtered to remove the catalyst and concentrated under reduced pressure to give methyl 3-(benzo[d]thiazol-2-yl)-2-(tert-butoxycarbonylamino)propanoate (0.18 g, 100%). Analytical LCMS (M+H)$^+$: m/z=336.9.

Step 3: 3-(benzo[d]thiazol-2-yl)-2-(tert-butoxycarbonylamino)propanoic acid

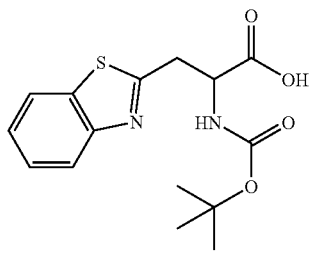 [SMILES: CC(C)(C)OC(=O)NC(Cc1nc2ccccc2s1)C(=O)O]

The methyl 3-(benzokilthiazol-2-yl)-2-(tert-butoxycarbonylamino)propanoate (0.18 g, 0.539 mmol) was taken up in methanol (5.0 ml) at r.t. To this, lithium hydroxide monhydrate (3 eq) dissolved in water (1.5 mL) was added. The reaction was stirred for 3 h, and the methanol was removed under reduced pressure and the resulting aqueous residue was partitioned between ethyl acetate and 1 N HCl. The organic layer was washed with brine, dried over magnesium sulfate and concentrated under reduced pressure to give 3-(benzo[d]thiazol-2-yl)-2-(tert-butoxycarbonylamino)propanoic acid (0.15 g, 86%) as a solid. Analytical LCMS (M+H)$^+$: m/z=322.9.

Step 4: tert-butyl 3-(benzo[d]thiazol-2-yl)-1-(dimethylamino)-1-oxopropan-2-ylcarbamate

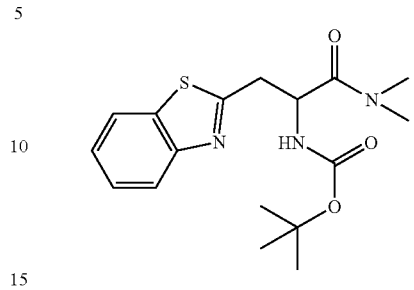

The 3-(benzo[d]thiazol-2-yl)-2-(tert-butoxycarbonylamino)propanoic acid (0.15 g, 0.465 mmol) was combined with N,N,N',N'-tetramethyl-o-(7-azabenzotriazol-1-yl)uronium hexafluorophosphate (0.21 g, 0.558 mmol), N,N-dimethylformamide (3.0 mL), N,N-diisopropylethylamine (120 µl, 0.92 mmol) and the 2 M dimethylamine in THF (1.0 mL). The reaction was stirred for 2 h., partitioned between ethyl acetate and 1 N HCl. The organic layer was washed with brine, dried over magnesium sulfate and concentrated under reduced pressure to give the crude product as a semisolid. The product was purified by Flash chromatography on a silica gel column eluting hexane:ethyl acetate gradient to give tert-butyl 3-(benzo[d]thiazol-2-yl)-1-(dimethylamino)-1-oxopropan-2-ylcarbamate (0.13 g, 80%). Analytical LCMS (M+H)$^+$: m/z=350.1.

Step 5: 2-amino-3-(benzo[d]thiazol-2-yl)-N,N-dimethylpropanamide

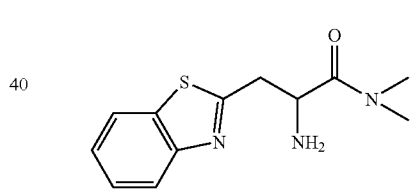

The tert-butyl 3-(benzo[d]thiazol-2-yl)-1-(dimethylamino)-1-oxopropan-2-ylcarbamate (0.13 g, 0.37 mmol) was taken up in a 4 M HCl dioxane solution (3 mL) at r.t. After stirring for 1 h. the reaction was concentrated under reduced pressure to give a residue. This was taken up in anhydrous acetonitrile and re-concentrated under reduced pressure 2 times, to finally 2-amino-3-(benzo[d]thiazol-2-yl)-N,N-dimethylpropanamide HCl salt (0.14 g, 100%) as a semisolid residue. Analytical LCMS (M+H)$^+$: m/z=250.1.

Step 6: 2-amino-N-[1-(1,3-benzothiazol-2-ylmethyl)-2-(dimethylamino)-2-oxoethyl]-4-(4-methylpiperazin-1-yl)quinazoline-7-carboxamide A solution of 2-amino-3-(benzo[d]thiazol-2-yl)-N,N-dimethylpropanamide (12.1 mg, 52.2 µmol), 2-amino-4-(4-methylpiperazin-1-yl)quinazoline-7-carboxylic acid (10 mg, 34.8 µmol) from Example 21 Step 4, N,N,N',N'-tetramethyl-o-(7-azabenzotriazol-1-yl)uronium hexafluorophosphate (21.2 mg, 55.7 µmol), N,N-dimethylformamide (2 mL) and N,N-diisopropylethylamine (12.1 µl, 69.6 µmol) was stirred at 25° C. for 60 min The reaction was purified by prep RP- HPLC (pH=10) to afford the desired compound (0.009 g, 49%) as an amorphous white solid. Analytical LCMS (M+H)+: m/z=519.0.

Example 145

2-Amino-N-[1-[(2,2-difluoro-1,3-benzodioxol-5-yl)methyl]-2-(dimethylamino)-2-oxoethyl]-4-(4-methylpiperazin-1-yl)quinazoline-7-carboxamide

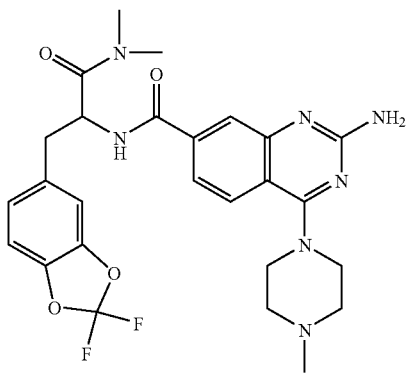 [SMILES: CN1CCN(c2nc(N)nc3cc(C(=O)NC(Cc4ccc5c(c4)OC(F)(F)O5)C(=O)N(C)C)ccc23)CC1]

This compound was prepared using procedures analogous to those for Example 144 but using 2,2-difluorobenzo[d][1,3]dioxole-5-carbaldehyde (Aldrich, Cat. #594423) in Step 1. The final product was purified by prep RP-HPLC (pH=10) to afford the desired compound (0.009 g, 40%) as an amorphous white solid. Analytical LCMS (M+H)+: m/z=542.0.

Example 145A (Enantiomer #1) and Example 145B (Enatiomer #2)

(2-Amino-N-(3-(2,2-difluorobenzo[d][1,3]dioxol-5-yl)-1-(dimethylamino)-1-oxopropan-2-yl)-4-(4-methylpiperazin-1-yl)quinazoline-7-carboxamide, Enatiomer #1 (Example 145A)

2-Amino-N-(3-(2,2-difluorobenzo[d][1,3]dioxol-5-yl)-1-(dimethylamino)-1-oxopropan-2-yl)-4-(4-methylpiperazin-1-yl)quinazoline-7-carboxamide, Enatiomer #2 (Example 145B)

These compounds were prepared using procedures analogous to those for Example 144 but using 2,2-difluorobenzo[d][1,3]dioxole-5-carbaldehyde in Step 1 and separating the two enantiomers in Step 4 by following conditions. Chiral column HPLC on a Cellulose-1 column 21.2 mm×250 mm, 5 µm (Phenomenex, Cat. 00G-4459-PO-AX) eluting with 10% ethanol:90% hexanes, flow rate 15 mL/Min: two separated enantiomers: Enatiomer #1 (Rt=6.7 Min.) and Enatiomer #2 (Rt=8.3 Min.). Analytical LCMS (M+H-Boc)+:: m/z=272.9. Each of these isomers were carried on separately through the remaining steps of Example 144 to afford its corresponding enantiomers of Example 145. The final products were purified by prep RP-HPLC on a C-18 column eluting with a water:acetonitrile gradient buffered to pH=10 to afford the desired compounds (0.010 g, 40%, 0.012 g 45%) as an amorphous white solid. Analytical LCMS (M+H)+: m/z=542.0.

Example 146

2-Amino-N-[2-(dimethylamino)-2-oxo-1-(3-phenoxybenzyl)ethyl]-4-(4-methylpiperazin-1-yl)quinazoline-7-carboxamide

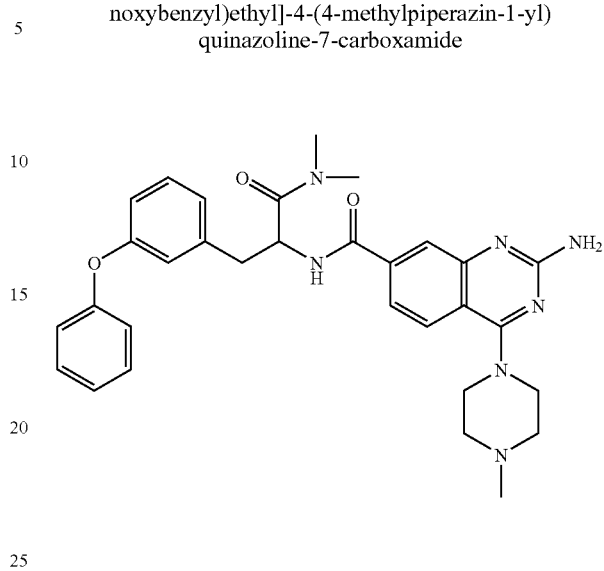

This compound was prepared using procedures analogous to those for Example 144 but using 3-phenoxybenzaldehyde (Aldrich, Cat. #191752) in Step 1. The final product was purified by prep RP-HPLC (pH=10) to afford the desired compound (0.003 g, 10%) as an amorphous white solid. Analytical LCMS (M+H)+: m/z=554.2.

Example 147

2-Amino-N-{2-(dimethylamino)-2-oxo-1-[(5-phenyl-2-thienyl)methyl]ethyl}-4-(4-methylpiperazin-1-yl)quinazoline-7-carboxamide

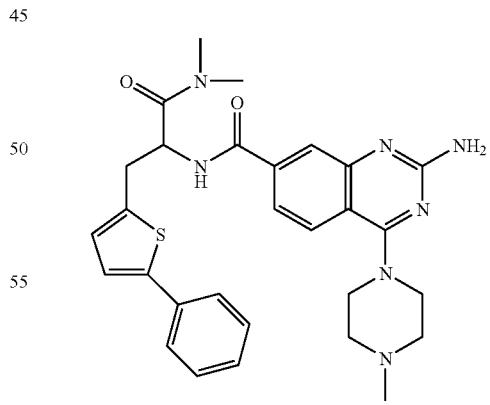

This compound was prepared using procedures analogous to those for Example 144 but using 5-phenylthiophene-2-carbaldehyde (Aldrich, Cat. #565938) in Step 1. The final product was purified by prep RP-HPLC (pH=10) to afford the desired compound (0.005 g, 15%) as an amorphous white solid. Analytical LCMS (M+H)+: m/z=544.0.

Example 148

2-Amino-N-{(1S)-2-(dimethylamino)-2-oxo-1-[4-(2-thienyl)benzyl]ethyl}-4-(4-methylpiperazin-1-yl)quinazoline-7-carboxamide

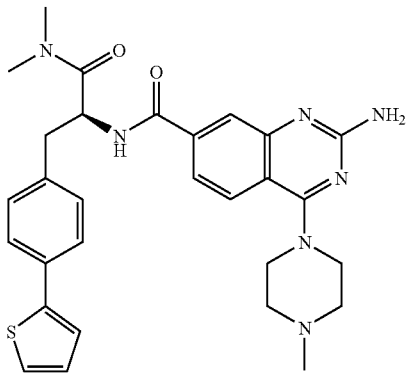 [SMILES: CN1CCN(c2nc(N)nc3cc(C(=O)N[C@@H](Cc4ccc(-c5cccs5)cc4)C(=O)N(C)C)ccc23)CC1]

This compound was prepared using procedures analogous to those for Example 139 but using 2-bromothiophene (Aldrich, Cat. #124168) in Step 3. The final product was purified by prep RP-HPLC (pH=10) to afford the desired compound (0.005 g, 12%) as an amorphous white solid. Analytical LCMS (M+H)$^+$: m/z=544.0.

Example 149

2-Amino-N-[2-(dimethylamino)-1-(4-isopropylbenzyl)-2-oxoethyl]-4-(4-methylpiperazin-1-yl)quinazoline-7-carboxamide

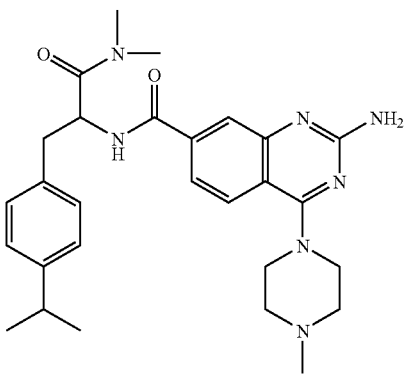 [SMILES: CC(C)c1ccc(CC(NC(=O)c2ccc3c(N4CCN(C)CC4)nc(N)nc3c2)C(=O)N(C)C)cc1]

This compound was prepared using procedures analogous to those for Example 144 but using 4-isopropylbenzaldehyde (Aldrich, Cat. #135178) in Step 1. The final product was purified by prep RP-HPLC (pH=10) to afford the desired compound (0.05 g, 15%) as an amorphous white solid. Analytical LCMS (M+H)$^+$: m/z=504.3.

Example 150

2-Amino-N-{2-(dimethylamino)-2-oxo-1-[4-(trifluoromethyl)benzyl]ethyl}-4-(4-methylpiperazin-1-yl)quinazoline-7-carboxamide

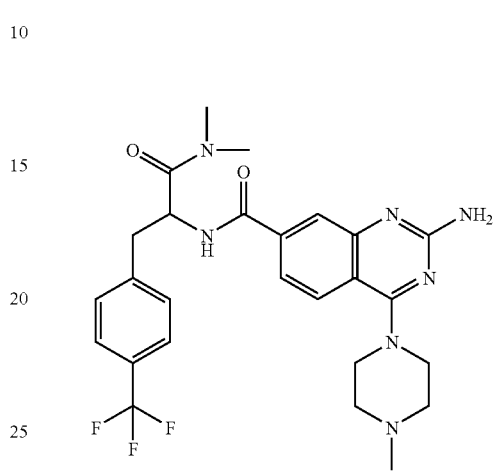

This compound was prepared using procedures analogous to those for Example 144 but using 4-(trifluoromethyl)benzaldehyde (Lancaster, Cat. #L20275) in Step 1. The final product was purified by prep RP-HPLC (pH=10) to afford the desired compound (0.006 g, 20%) as an amorphous white solid. Analytical LCMS (M+H)$^+$: m/z=530.7.

Example 151

2-amino-N-[2-biphenyl-4-yl-1-(1,3-thiazol-2-yl)ethyl]-4-(4-methylpiperazin-1-yl)quinazoline-7-carboxamide

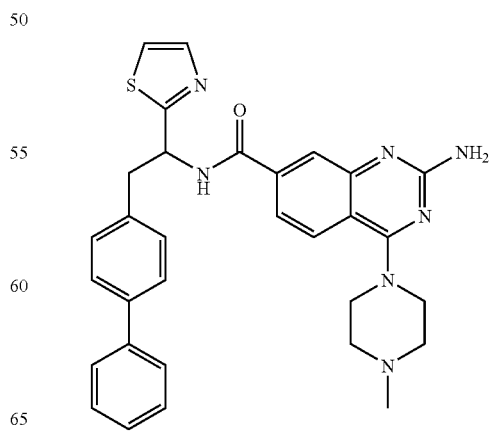

Step 1: 2-biphenyl-4-yl-N-methoxy-N-methylacetamide

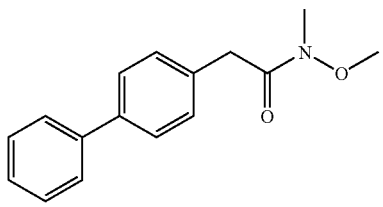 [SMILES: CON(C)C(=O)Cc1ccc(-c2ccccc2)cc1]

N,O-Dimethylhydroxylamine hydrochloride (550 mg, 5.6 mmol) was added to a mixture of biphenyl-4-ylacetic acid (Aldrich, Cat. #196487) (1 g, 5 mmol), benzotriazol-1-yloxy-tris(dimethylamino)phosphonium hexafluorophosphate (2.5 g, 5.6 mmol), and N,N-diisopropylethylamine (1.6 mL, 9.4 mmol) in N,N-dimethylformamide (20 mL). The reaction was stirred for 3 h. at r.t., and was partitioned between water and ethyl acetate. The organic phase was washed with saturated brine, dried over magnesium sulfate, filtered and concentrated under reduced pressure to give the crude product, which was purified by Flash chromatography on a silica gel column (EtOAc:Hexane, 1:3 to 1:1) gave 2-biphenyl-4-yl-N-methoxy-N-methylacetamide (0.9 g, 70%) as a white solid. Analytical LCMS (M+H)$^+$: m/z=255.9.

Step 2: 2-biphenyl-4-yl-1-(1,3-thiazol-2-yl)ethanone

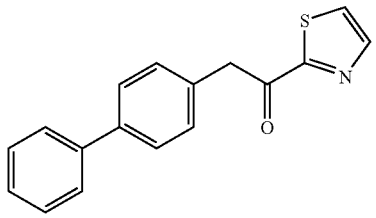 [SMILES: O=C(Cc1ccc(-c2ccccc2)cc1)c1nccs1]

2.0 M of Isopropylmagnesium chloride in tetrahydrofuran (0.24 mL) was added to a solution of 1,3-thiazole (40 mg, 0.47 mmol) in tetrahydrofuran (6 mL) at −78° C. The reaction was stirred for 1 h. as it was warmed to −10° C. 2-Biphenyl-4-yl-N-methoxy-N-methylacetamide (100 mg, 0.4 mmol) in Tetrahydrofuran (2 mL) was added dropwise at −10° C. The reaction was stirred for 2 h. while the reaction was warmed to r.t. gradually. The reaction was quenched with saturated NH$_4$Cl, and was extracted with ethyl acetate. The organic phase was washed with saturated brine, dried over magnesium sulfate, filtered and concentrated under reduced pressure to give the crude product, which was purified by Flash chromatography on a silica gel column (EtOAc:Hexane, 1:3 to 1:1) gave the 2-biphenyl-4-yl-1-(1,3-thiazol-2-yl)ethanone (70 mg, 60%) as a white solid. Analytical LCMS (M+H)$^+$: m/z=279.9.

Step 3: 2-biphenyl-4-yl-1-(1,3-thiazol-2-yl)ethanone oxime

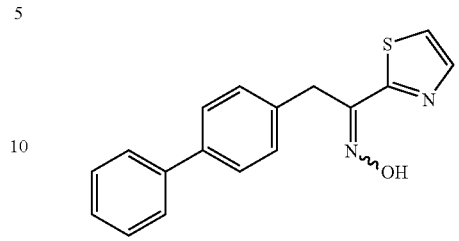

Hydroxylamine hydrochloride (30 mg, 0.4 mmol) and sodium acetate (30 mg, 0.4 mmol) were added sequentially to a solution of 2-biphenyl-4-yl-1-(1,3-thiazol-2-yl)ethanone (50 mg, 0.2 mm ethanol (2 mL). The reaction was refluxed for 2 h., and was concentrated under reduced pressure to remove the ethanol. The reaction was partitioned between water and ethyl acetate. The organic phase was washed with saturated brine, dried over magnesium sulfate, filtered and concentrated under reduced pressure to obtain a mixture of 2-biphenyl-4-yl-1-(1,3-thiazol-2-yl)ethanone oxime (60 mg, 100%) as a white solid. Analytical LCMS (M+H)$^+$: m/z=294.9.

Step 4: 2-biphenyl-4-yl-1-(1,3-thiazol-2-yl)ethanamine

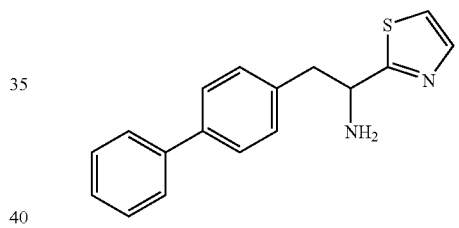

Zinc (60 mg, 0.9 mmol) was added to a solution of a mixture of 2-biphenyl-4-yl-1-(1,3-thiazol-2-yl)ethanone oxime (60 mg) in acetic acid (1 mL). The reaction was stirred for 3 h., was filtered and concentrated under reduced pressure. The crude was made basic with saturated NaHCO$_3$, and was extracted with ethyl acetate. The organic layer was washed with saturated brine, dried over magnesium sulfate, filtered and concentrated under reduced pressure to give 2-biphenyl-4-yl-1-(1,3-thiazol-2-yl)ethanamine (40 mg, 80%) as a white solid. Analytical LCMS (M+H)$^+$: m/z=280.9.

Step 5: 2-amino-N-[2-biphenyl-4-yl-1-(1,3-thiazol-2-yl)ethyl]-4-(4-methylpiperazin-1-yl)quinazoline-7-carboxamide N,N,N',N'-Tetramethyl-O-(7-azabenzotriazol-1-yl)uronium hexafluorophosphate (26 mg, 0.070 mmol) was added to a solution of 2-amino-4-(4-methylpiperazin-1-yl)quinazoline-7-carboxylic acid (10 mg, 0.03 mmol) in N,N-Dimethylformamide (1 mL) and N,N-Diisopropylethylamine (12 uL, 0.070 mmol). The reaction was stirred for 10 min., and the 2-biphenyl-4-yl-1-(1,3-thiazol-2-yl)ethanamine (20 mg, 0.070 mmol) was added. The reaction was stirred for 1 h. at r.t. The final product was purified by prep RP-HPLC (pH=10) to afford the desired compound (0.003 g, 20%) as an amorphous white solid. Analytical LCMS (M+H)$^+$: m/z=550.0.

Example 152

2-Amino-N-{(1S)-2-(dimethylamino)-1-[(2'-methoxybiphenyl-4-yl)methyl]-2-oxoethyl}-4-(4-methylpiperazin-1-yl)quinazoline-7-carboxamide

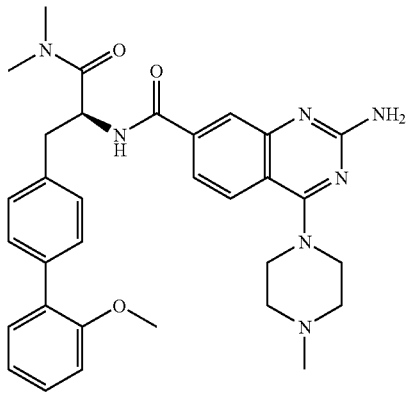 [SMILES: COc1ccccc1-c1ccc(C[C@H](NC(=O)c2ccc3c(N4CCN(C)CC4)nc(N)nc3c2)C(=O)N(C)C)cc1]

This compound was prepared using procedures analogous to those for Example 139 but using 1-bromo-2-methoxybenzene (Aldrich, Cat. #159239) in Step 3. The final product was purified by prep RP-HPLC (pH=10) to afford the desired compound (0.003 g, 20%) as an amorphous white solid. $^1$H NMR (400 MHz, DMSO): δ 8.92 (d, 1H), 7.73 (d, 1H), 7.67 (d, 1H), 7.35 (m, 1H), 7.31 (s, 4H), 7.24 (m, 1H), 7.18 (m1H), 7.01 (d, 1H), 6.93 (m, 1H), 6.40 (bs, 2H), 4.99 (M, 1H), 3.65 (s, 3H), 3.48 (bs, 4H), 3.27 (s, 4H), 2.99 (s, 3H), 2.97 (m, 2H), 2.78 (s, 3H), 2.17 (s, 3H). Analytical LCMS (M+H)$^+$: m/z=568.1.

Example 153

2-Amino-N-{(1S)-2-(dimethylamino)-1-[4-(6-methoxypyridin-2-yl)benzyl]-2-oxoethyl}-4-(4-methylpiperazin-1-yl)quinazoline-7-carboxamide

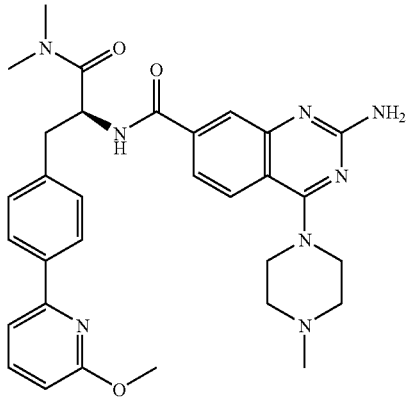 [SMILES: COc1cccc(-c2ccc(C[C@H](NC(=O)c3ccc4c(N5CCN(C)CC5)nc(N)nc4c3)C(=O)N(C)C)cc2)n1]

This compound was prepared using procedures analogous to those for Example 139 but using 2-bromo-6-methoxypyridine (Aldrich, Cat. #520535) in Step 3. The final product was purified by prep RP-HPLC HPLC (pH=2) to afford the desired compound (0.003 g, 20%) as an amorphous white solid TFA salt. Analytical LCMS (M+H)$^+$: m/z=569.0.

Example 154

2-Amino-N-[(1S)-1-[(3'-cyanobiphenyl-4-yl)methyl]-2-(dimethylamino)-2-oxoethyl]-4-(4-methylpiperazin-1-yl)quinazoline-7-carboxamide

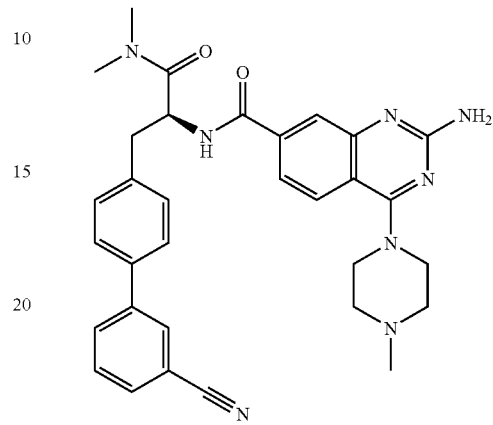

This compound was prepared using procedures analogous to those for Example 139 but using 3-bromo-benzonitrile (Aldrich, Cat. #B58282) in Step 3. The final product was purified by prep RP-HPLC (pH=2) to afford the desired compound (0.004 g, 25%) as an amorphous white solid TFA salt. Analytical LCMS (M+H)$^+$: m/z=563.3.

Example 155

2-Amino-N-[(1S)-1-[4-(5-cyanopyridin-2-yl)benzyl]-2-(dimethylamino)-2-oxoethyl]-4-(4-methylpiperazin-1-yl)quinazoline-7-carboxamide

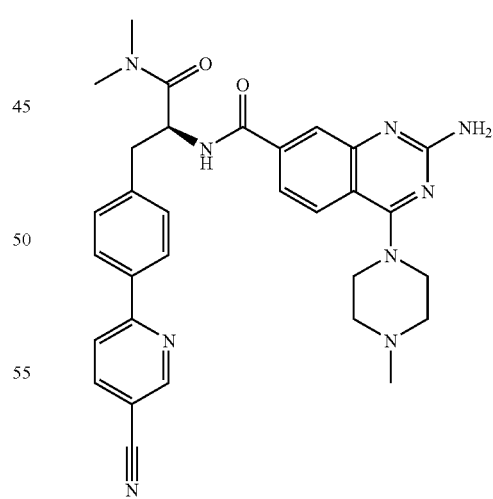

This compound was prepared using procedures analogous to those for Example 139 but using 6-bromonicotinonitrile (VWR, Cat. #101383-912) in Step 3. The final product was purified by prep RP-HPLC HPLC (pH=2) to afford the desired compound (0.004 g, 20%) as an amorphous white solid TFA salt. Analytical LCMS (M+H)$^+$: m/z=564.1.

Example 156

2-Amino-N-[(1S)-1-[4-(5-cyanopyridin-3-yl)benzyl]-2-(dimethylamino)-2-oxoethyl]-4-(4-methylpiperazin-1-yl)quinazoline-7-carboxamide

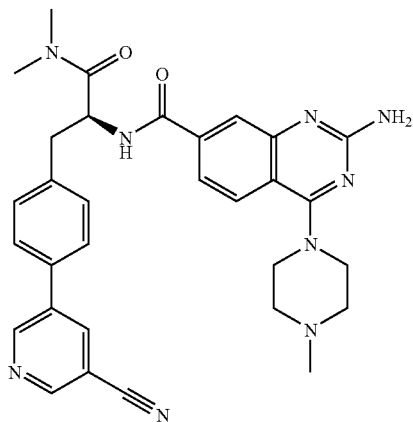 [SMILES: CN1CCN(c2nc(N)nc3cc(C(=O)N[C@@H](Cc4ccc(-c5cncc(C#N)c5)cc4)C(=O)N(C)C)ccc23)CC1]

This compound was prepared using procedures analogous to those for Example 139 but using 5-bromonicotinonitrile (Aldrich, Cat. #574422) in Step 3. The final product was purified by prep RP-HPLC (pH=2) to afford the desired compound (0.003 g, 20%) as an amorphous white solid TFA salt. Analytical LCMS (M+H)$^+$: m/z=564.1.

Example 157

2-Amino-N-[(1S)-1-{4-[3-cyano-6-(trifluoromethyl)pyridin-2-yl]benzyl}-2-(dimethylamino)-2-oxoethyl]-4-(4-methylpiperazin-1-yl)quinazoline-7-carboxamide

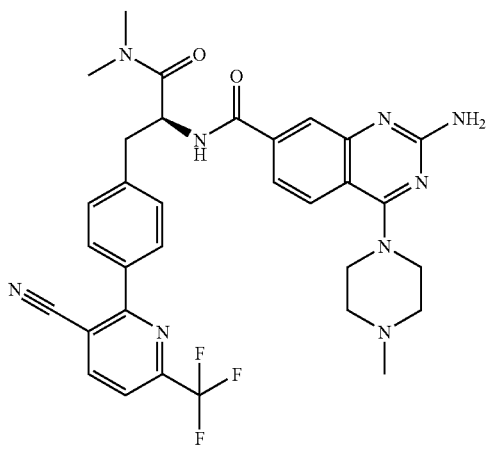 [SMILES: CN1CCN(c2nc(N)nc3cc(C(=O)N[C@@H](Cc4ccc(-c5nc(C(F)(F)F)ccc5C#N)cc4)C(=O)N(C)C)ccc23)CC1]

This compound was prepared using procedures analogous to those for Example 139 but using 2-chloro-6-(trifluoromethyl)nicotinonitrile (Oakwood, Cat. #009103) in Step 3. The final product was purified by prep RP-HPLC (pH=2) to afford the desired compound (0.004 g, 22%) as an amorphous white solid TFA salt. Analytical LCMS (M+H)$^+$: m/z=632.0.

Example 158

Methyl 4'-[(2S)-2-({[2-amino-4-(4-methylpiperazin-1-yl)quinazolin-7-yl]carbonyl}amino)-3-(dimethylamino)-3-oxopropyl]biphenyl-3-carboxylate

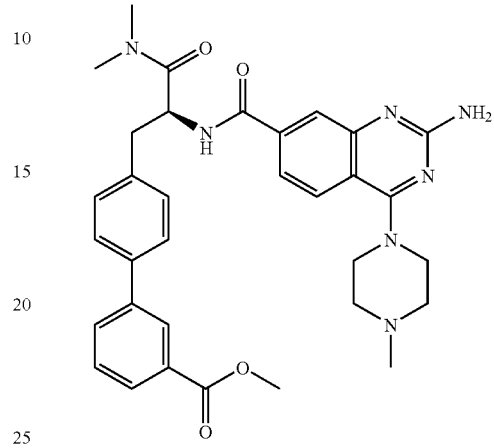

This compound was prepared using procedures analogous to those for Example 139 but using methyl 3-bromobenzoate (Aldrich, Cat. #499625) in Step 3. The final product was purified by prep RP-HPLC (pH=2) to afford the desired compound (0.006 g, 30%) as an amorphous white solid TFA salt. $^1$H NMR (400 MHz, DMSO): δ 9.24 (d, 1H), 8.13 (t, 1H), 8.05 (d, 1H), 7.91 (d, 2H), 7.85 (m, 1H), 7.74 (d, 1H), 7.62 (d, 2H), 7.58 (d, 1H), 7.46 (d, 2H), 5.12 (m, 1H), 4.57 (m, 2H), 3.86 (s, 3H), 3.67 (m, 2H), 3.57 (m, 2H), 3.22 (m, 2H), 3.08 (m, 2H), 3.05 (s, 3H), 2.85 (bs, 6H). Analytical LCMS (M+H)$^+$: m/z=596.0.

Example 159

2-Amino-N-((1S)-2-(dimethylamino)-1-{[4'-fluoro-3'-(trifluoromethyl)biphenyl-4-yl]methyl}-2-oxoethyl)-4-(4-methylpiperazin-1-yl)quinazoline-7-carboxamide

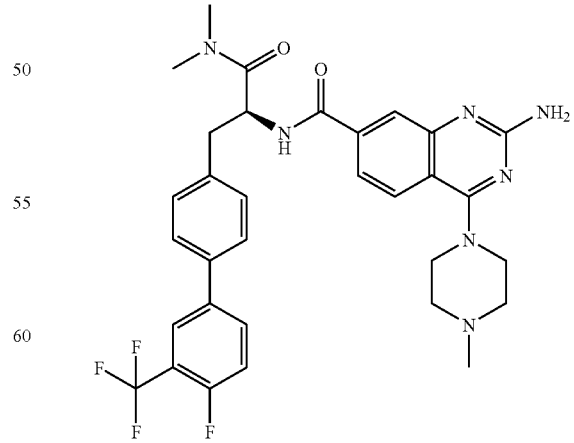

This compound was prepared using procedures analogous to those for Example 139 but using 4-bromo-1-fluoro-2-(trifluoromethyl)benzene (Aldrich, Cat. #549096) in Step 3. The final product was purified by prep RP-HPLC (pH=10) to afford the desired compound (0.003 g, 10%) as an amorphous white solid. $^1$H NMR (400 MHz, DMSO): δ 8.9 (d, 1H), 7.95 (m, 1H), 7.89 (m, 1H), 7.73 (d, 1H), 7.67 (d, 1H), 7.59 (d, 2H), 7.51 m, 1H), 7.41 (d, 2H), 7.37 (m, 1H), 6.40 (bs, 2H), 5.01 (m, 1H), 3.49 (bm, 4H), 3.27 (s, 4H), 3.01 (m, 2H), 3.01 (s, 3H), 2.78 (s, 3H), 2.17 (s, 3H). Analytical LCMS (M+H)$^+$: m/z=624.0.

Example 160

2-Amino-N-[(1S)-2-(dimethylamino)-2-oxo-1-(4-pyridin-2-ylbenzyl)ethyl]-4-(4-methylpiperazin-1-yl)quinazoline-7-carboxamide

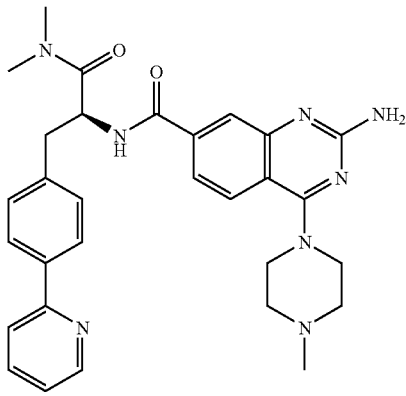 [SMILES: CN1CCN(c2nc(N)nc3cc(C(=O)N[C@@H](Cc4ccc(-c5ccccn5)cc4)C(=O)N(C)C)ccc23)CC1]

This compound was prepared using procedures analogous to those for Example 139 but using 2-bromopyridine 2) to afford the desired compound (0.003 g, 10%) as an amorphous white solid TFA salt. Analytical LCMS (M+H)$^+$: m/z=539.0.

Example 161

2-Amino-N-((1S)-2-(dimethylamino)-2-oxo-1-{4-[5-(trifluoromethyl)pyridin-3-yl]benzyl}ethyl)-4-(4-methylpiperazin-1-yl)quinazoline-7-carboxamide

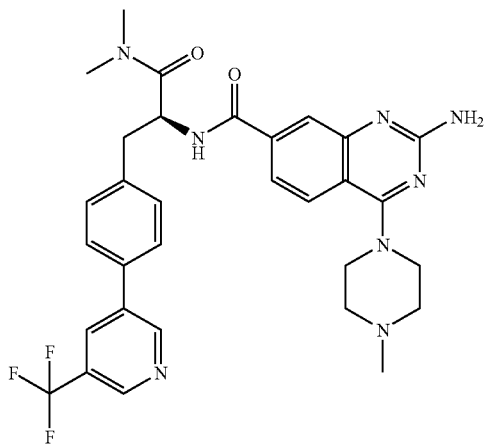 [SMILES: CN1CCN(c2nc(N)nc3cc(C(=O)N[C@@H](Cc4ccc(-c5cncc(C(F)(F)F)c5)cc4)C(=O)N(C)C)ccc23)CC1]

This compound was prepared using procedures analogous to those for Example 139 but using 3-bromo-5-(trifluorom-ethyl)pyridine (Aldrich, Cat. #661112) in Step 3. The final product was purified by prep RP-HPLC (pH=10) to afford the desired compound (0.005 g, 15%) as an amorphous white solid. Analytical LCMS (M+H)$^+$: m/z=607.0.

Example 162

2-Amino-N-[(1S)-1-[(2',3'-dichlorobiphenyl-4-yl)methyl]-2-(dimethylamino)-2-oxoethyl]-4-(4-methylpiperazin-1-yl)quinazoline-7-carboxamide

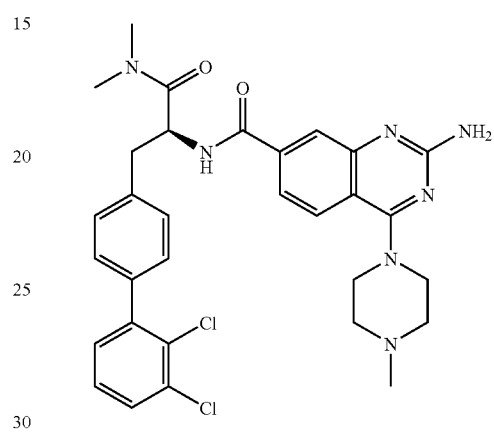

This compound was prepared using procedures analogous to those for Example 139 but using 1-bromo-2,3-dichlorobenzene (Aldrich, Cat. #280089) in Step 3. The final product was purified by prep RP-HPLC (pH=10) to afford the desired compound (0.003 g, 10%) as an amorphous white solid. Analytical LCMS (M+H)$^+$: m/z=606.0, 608.0.

Example 163

2-Amino-N-[1-{[6-(2,3-difluorophenyl)pyridin-3-yl]methyl}-2-(dimethylamino)-2-oxoethyl]-4-(4-methylpiperazin-1-yl)quinazoline-7-carboxamide

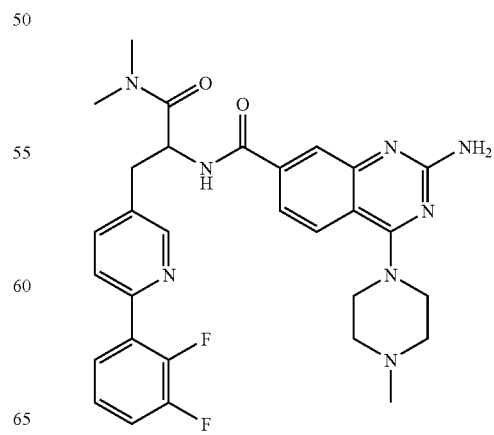

Step 1: methyl 3-(6-bromopyridin-3-yl)-2-[(tert-butoxycarbonyl)amino]acrylate

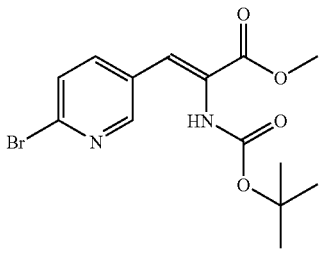 [SMILES: COC(=O)/C(=C/c1ccc(Br)nc1)NC(=O)OC(C)(C)C]

1,8-Diazabicyclo[5.4.0]undec-7-ene (480 uL, 3.2 mmol) was added to a mixture of 6-bromo-pyridine-3-carbaldehyde (Aldrich, Cat. #596280) (500 mg, 3 mmol) and methyl [(tert-butoxycarbonyl)amino](dimethoxyphosphoryl)acetate (Fluka, Cat. #09659) (960 mg, 3.2 mmol) in methylene chloride (5 mL) at r.t. under $N_2$. The reaction was stirred for 2 h. The reaction was partitioned between EtOAc and 1 N HCl. The organic layer was washed with brine, dried over $MgSO_4$, filtered and concentrated under reduced pressure to give crude methyl 3-(6-bromopyridin-3-yl)-2-[(tert-butoxycarbonyl)amino]acrylate (0.9 g, 93%) as an off white solid. Analytical LCMS $(M+H)^+$: m/z=356.8, 358.9.

Step 2: methyl 2-[(tert-butoxycarbonyl)amino]-3-[6-(2,3-difluorophenyl)pyridin-3-yl]acrylate

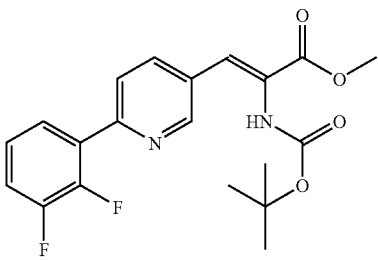 [SMILES: COC(=O)/C(=C/c1ccc(-c2cccc(F)c2F)nc1)NC(=O)OC(C)(C)C]

Potassium carbonate (97 mg, 0.70 mmol) in water (1 mL) was added to a solution of methyl (2E&Z)-3-(6-bromopyridin-3-yl)-2-[(tert-butoxycarbonyl)amino]acrylate (80 mg, 0.2 mmol) and difluorophenyl)boronic acid (Aldrich, Cat. #514039) (0.055 g, 0.35 mmol) in 1,4-dioxane (2 mL). The reaction was degassed by $N_2$ for 5 min. Then tetrakis(triphenylphosphine)palladium(0) (14 mg, 0.012 mmol) was added and degassed for another 4 min. The reaction was stirred at 80° C. in a sealed tube for 5 h. The reaction was allowed to cool to r.t. and was partitioned between water and EtOAc. The organic layer was washed with brine, dried over $MgSO_4$, filtered and concentrated under reduced pressure to give the crude material. The product was purified by Flash chromatography on a silica gel column eluting with (EtOAc:Hexanes, 1:3 to 1:1) to give a mixture of methyl 2-[(tert-butoxycarbonyl)amino]-3-[6-(2,3-difluorophenyl)pyridin-3-yl]acrylate (0.070 g, 80%) as a white solid. Analytical LCMS $(M+H)^+$: m/z=390.9.

Step 3: methyl 2-(tert-butoxycarbonylamino)-3-(6-(2,3-difluorophenyl)pyridin-3-yl)propanoate

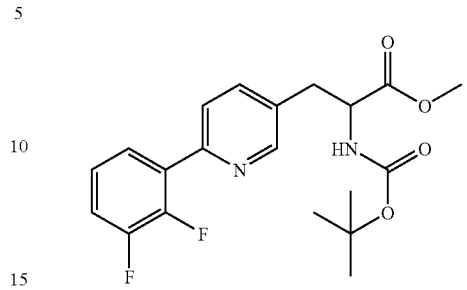

10% Palladium on carbon (10 mg) was added to a mixture of methyl 2-[(tert-butoxycarbonyl)amino]-3-[6-(2,3-difluorophenyl)pyridin-3-yl]acrylate (70 mg, 0.2 mmol) in methanol (3 mL) and acetic acid (0.5 mL, 9 mmol). The reaction was shaken in parr shaker under $H_2$ at 60 Psi for 5 h. The reaction was complete by LC-MS, this was filtered and concentrated under reduced pressure to give crude methyl 2-(tert-butoxycarbonylamino)-3-(6-(2,3-difluorophenyl)pyridin-3-yl)propanoate (0.07 g, 100%) as an oil. Analytical LCMS $(M+H)^+$: m/z=393.0.

Step 4: 2-[(tert-butoxycarbonyl)amino]-3-[6-(2,3-difluorophenyl)pyridin-3-yl]propanoic acid

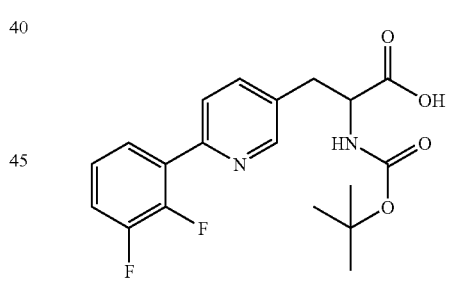

Lithium hydroxide (10 mg, 0.5 mmol) in water (1 mL) was added to a solution of methyl 2-[(tert-butoxycarbonyl)amino]-3-[6-(2,3-difluorophenyl)pyridin-3-yl]propanoate (70 mg, 0.2 mmol) in methanol (3 mL). The reaction was stirred at rt for 3 h. The reaction was concentrated under reduced pressure to remove methanol and was partitioned between EtOAc and ammonium chloride water. The organic was washed with brine, dried over $MgSO_4$, filtered and concentrated under reduced pressure to give crude 2-[(tert-butoxycarbonyl)amino]-3-[6-(2,3-difluorophenyl)pyridin-3-yl]propanoic acid (0.07 g, 100%) as a semisolid residue. Analytical LCMS $(M+H)^+$: m/z=378.9.

Step 5: tert-butyl 3-(6-(2,3-difluorophenyl)pyridin-3-yl)-1-(dimethylamino)-1-oxopropan-2-ylcarbamate

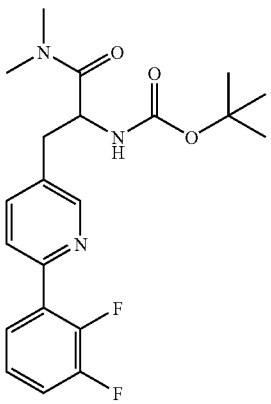 [SMILES: CN(C)C(=O)C(Cc1ccc(-c2cccc(F)c2F)nc1)NC(=O)OC(C)(C)C]

N,N,N',N'-Tetramethyl-O-(7-azabenzotriazol-1-yl)uronium hexafluorophosphate (120 mg, 0.32 mmol) and N,N-diisopropylethylamine (92 uL, 0.53 mmol) were added to a solution of 2-[(tert-butoxycarbonyl)amino]-3-[6-(2,3-difluorophenyl)pyridin-3-yl]propanoic acid (100 mg, 0.3 mmol) in N,N-dimethylformamide (5 mL). The reaction was stirred at r.t. for 10 min, and 2 M of dimethylamine in tetrahydrofuran (0.26 mL, 0.53 mmol) was added and stirred for 1 h. The reaction mixture was partitioned between water and EtOAc. The organic layer was washed with brine, dried over MgSO$_4$, filtered and concentrated under reduced pressure to give crude tert-butyl 3-(6-(2,3-difluorophenyl)pyridin-3-yl)-1-(dimethylamino)-1-oxopropan-2-ylcarbamate (0.06 g, 60%) as an oil. Analytical LCMS (M+H)$^+$: m/z=406.0.

Step 6: 2-amino-3-[6-(2,3-difluorophenyl)pyridin-3-yl]-N,N-dimethylpropanamide

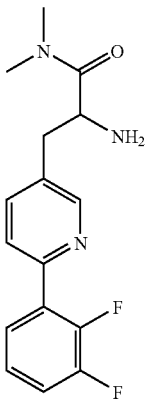

tert-Butyl [1-{[6-(2,3-difluorophenyl)pyridin-3-yl]methyl}-2-(dimethylamino)-2-oxoethyl]carbamate (60 mg, 0.10 mmol) was dissolved in 4 M of hydrogen chloride in 1,4-dioxane (2 mL, 8 mmol) at r.t. The reaction was stirred for 1 h., and concentrated under reduced pressure to give crude 2-amino-3-[6-(2,3-difluorophenyl)pyridin-3yl]-N,N-dimethylpropanamide HCl salt (0.040 g, 50%) as colorless oil. Analytical LCMS (M+H)$^+$: m/z=306.0.

Step 7: 2-amino-N-[1-{[6-(2,3-difluorophenyl)pyridin-3-yl]methyl}-2-(dimethylamino)-2-oxoethyl]-4-(4-methylpiperazin-1-yl)quinazoline-7-carboxamide N,N,N',N'-Tetramethyl-O-(7-azabenzotriazol-1-yl)uronium hexafluorophosphate (20 mg, 0.05 mmol) and N,N-diisopropylethylamine (10 uL, 0.07 mmol) were added to a solution of 2-amino-4-(4-methylpiperazin-1-yl)quinazoline-7-carboxylic acid (10 mg, 0.03 mmol) and 2-amino-3-[6-(2,3-difluorophenyl)pyridin-3yl]-N,N-dimethylpropanamide (20 mg, 0.07 mmol) in N,N-dimethylformamide (1 mL) at r.t. The reaction was stirred for 2 h. and the product was purified with out workup by RP-HPLC (pH=2) to afford the desired compound (0.003 g, 10%) as an amorphous white solid TFA salt. Analytical LCMS (M+H)$^+$: m/z=575.0.

Example 164

2-Amino-N-(-2-(dimethylamino)-1-{[6-(4-methoxyphenyl)pyridin-3-yl]methyl}-2-oxoethyl)-4-(4-methylpiperazin-1-yl)quinazoline-7-carboxamide

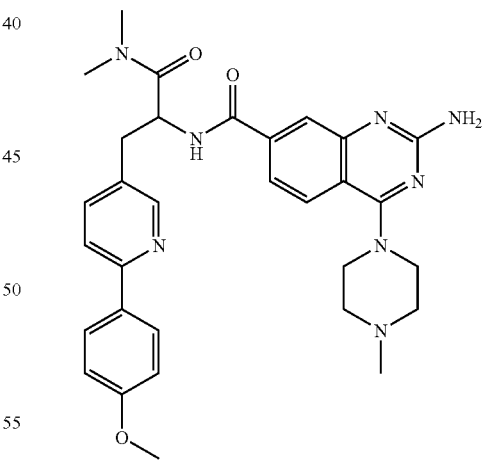

This compound was prepared using procedures analogous to those for Example 163 but using 4-methoxyphenylboronic acid (Aldrich, Cat. #417599) in Step 2. The final product was purified by prep RP-HPLC (pH=2) to afford the desired compound (0.005 g, 15%) as an amorphous white solid TFA salt. Analytical LCMS (M+H)$^+$: m/z=569.1.

Example 165

4-[(2S)-2-({[2-Amino-4-(4-methylpiperazin-1-yl)quinazolin-7-yl]carbonyl}amino)-3-(dimethylamino)-3-oxopropyl]phenyl (3-chlorophenyl)carbamate

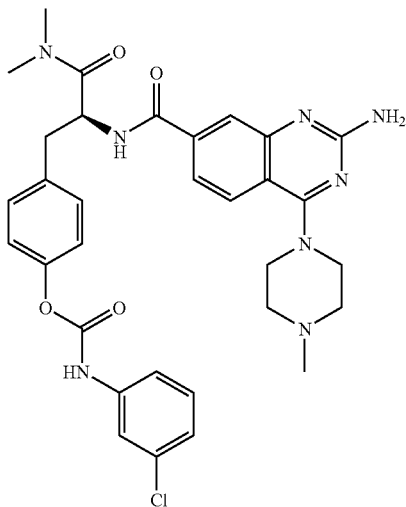 [SMILES: CN1CCN(c2nc(N)nc3cc(C(=O)N[C@@H](Cc4ccc(OC(=O)Nc5cccc(Cl)c5)cc4)C(=O)N(C)C)ccc23)CC1]

This compound was prepared using procedures analogous to those for Example 135 but using 1-chloro-3-isocyanatobenzene (Aldrich, Cat. #245682) in Step 1. The final product was purified by prep RP-HPLC (pH=2) to afford the desired compound (0.005 g, 15%) as an amorphous white solid TFA salt. Analytical LCMS (M+H)$^+$: m/z=631.0.

Example 166

2-Amino-N-{2-(dimethylamino)-1-[3-(4-methoxyphenoxy)benzyl]-2-oxoethyl}-4-(4-methylpiperazin-1-yl)quinazoline-7-carboxamide

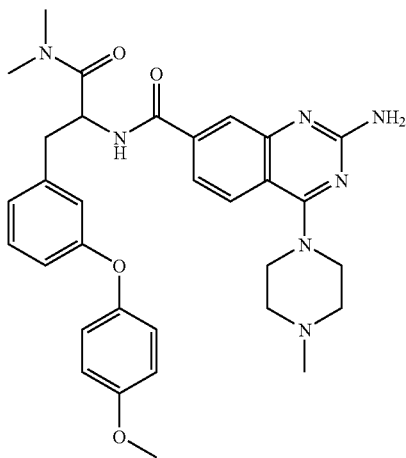 [SMILES: COc1ccc(Oc2cccc(CC(NC(=O)c3ccc4c(N5CCN(C)CC5)nc(N)nc4c3)C(=O)N(C)C)c2)cc1]

This compound was prepared using procedures analogous to those for Example 144 but using 3-(4-methoxyphenoxy)benzaldehyde (Aldrich, Cat. #195898) in Step 1. The final product was purified by prep RP-HPLC (pH=10) to afford the desired compound (0.008 g, 15%) as an amorphous white solid. $^1$H NMR (400 MHz, DMSO): δ 8.82 (d, 1H), 7.69 (s, 1H), 7.66 (d, 1H), 7.32 (d, 1H), 7.16 (t, 1H), 6.98 (d, 1H), 6.86 (s, 1H), 6.79 (m, 4H), 6.66 (d, 1H), 6.39 (s, 2H), 4.96 (m, 1H), 3.61 (s, 3H), 3.49 (bs, 4H), 3.27 (s, 4H), 2.95 (s, 3H), 2.92 (m, 2H), 2.75 (s, 3H), 2.17 (s, 3H). Analytical LCMS (M+H)$^+$: m/z=584.1.

Example 167

2-Amino-N-[1-[3-(3,5-dichlorophenoxy)benzyl]-2-(dimethylamino)-2-oxoethyl]-4-(4-methylpiperazin-1-yl)quinazoline-7-carboxamide

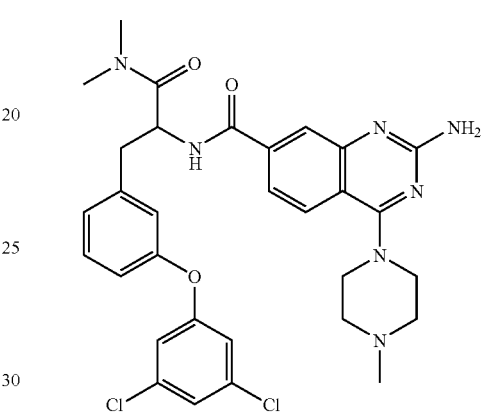

This compound was prepared using procedures analogous to those for Example 144 but using 3-(3,5-dichlorophenoxy)benzaldehyde (Aldrich, Cat. #197742) in Step 1. The final product was purified by prep RP-HPLC (pH=10) to afford the desired compound (0.010 g, 16%) as an amorphous white solid. Analytical LCMS (M+H)$^+$: m/z=621.9, 623.9.

Example 168

2-Amino-N-[1-{3-[(4-chloro-1,2,5-thiadiazol-3-yl)oxy]benzyl}-2-(dimethylamino)-2-oxoethyl]-4-(4-methylpiperazin-1-yl)quinazoline-7-carboxamide

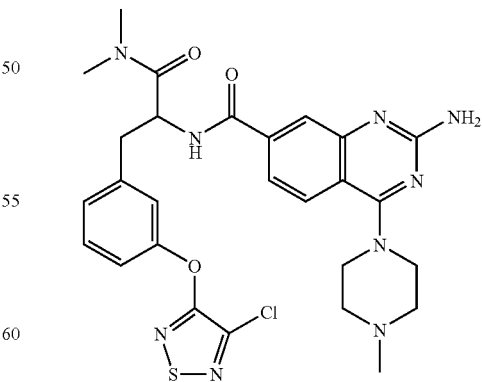

This compound was prepared using procedures analogous to those for Example 169 but using 3,4-dichloro-1,2,5-thiadiazole (Aldrich, Cat. #258903) in Step 5. The final product was purified by prep RP-HPLC (pH=10) to afford the desired compound (0.012 g, 20%) as an amorphous white solid. Analytical LCMS (M+H)⁺: m/z=596.0.

Example 169

Methyl 4-{3-[2-({[2-amino-4-(4-methylpiperazin-1-yl)quinazolin-7-yl]carbonyl}amino)-3-(dimethylamino)-3-oxopropyl]phenoxy}benzoate

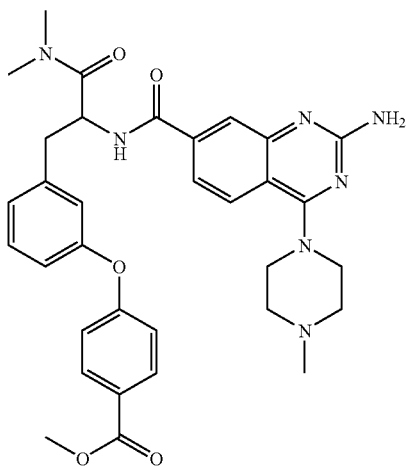 [SMILES: COC(=O)c1ccc(Oc2cccc(CC(NC(=O)c3ccc4c(N5CCN(C)CC5)nc(N)nc4c3)C(=O)N(C)C)c2)cc1]

Step 1: methyl 2-(tert-butoxycarbonylamino)-3-(3-hydroxyphenyl)acrylate

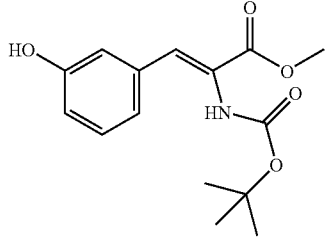 [SMILES: COC(=O)/C(=C/c1cccc(O)c1)NC(=O)OC(C)(C)C]

Methyl [(tert-butoxycarbonyl)amino](dimethoxyphosphoryl)acetate (Fluka, Cat. #09659) (0.97 g, 3.3 mmol) and 3-hydroxybenzaldehyde (0.400 g, 3.28 mmol) were combined in methylene chloride (14 mL) at r.t. under nitrogen. To this DBU (0.68 mL, 3.9 mmol) was added and the reaction was stirred at r.t. for 2 h. The reaction was taken up in ethyl acetate, washed with 1 N HCl, brine, dried over magnesium sulfate and concentrated under reduced pressure to give the crude product as an oil. The product was purified by Flash chromatography on a silica gel column eluting hexane: ethyl acetate gradient to give methyl 2-(tert-butoxycarbonylamino)-3-(3-hydroxyphenyl)acrylate (0.92 g, 96%) as a clear oil Analytical LCMS (M+H-Boc)⁺: m/z=193.9.

Step 2: methyl 2-(tert-butoxycarbonylamino)-3-(3-hydroxyphenyl)propanoate

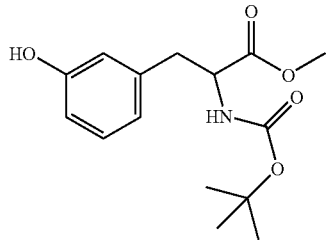 [SMILES: COC(=O)C(Cc1cccc(O)c1)NC(=O)OC(C)(C)C]

The methyl 2-(tert-butoxycarbonylamino)-3-(3-hydroxyphenyl)acrylate (0.92 g, 3.1 mmol) was dissolved in methanol (30 ml) in a Parr shaker bottle. This was degassed with nitrogen and the 10% Pd/C catalyst was added. The reaction was charged with hyrodgen to 55 Psi, and shaken for 3 h. The reaction was complete, the catalyst filtered off and the methanol removed under reduced pressure to give methyl 2-(tert-butoxycarbonylamino)-3-(3-hydroxyphenyl)propanoate (0.92 g, 100%) as a oil. Analytical LCMS (M+H-Boc)⁺: m/z=195.9.

Step 3: 2-(tert-butoxycarbonylamino)-3-(3-hydroxyphenyl)propanoic acid

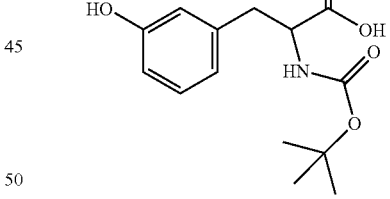

Methyl 2-(tert-butoxycarbonylamino)-3-(3-hydroxyphenyl)propanoate (0.91 g, 3.1 mmol) was taken up in methanol (30 mL) at rt and the lithium hydroxide monohydrate (0.51 g, 12.3 mmol) in water (10 mL) was added. The reaction was complete after stirring for 2 h. The methanol was removed under reduced pressure to give an aqueous layer which was partitioned between ethyl acetate and 1 N HCl. The organic layer was washed with brine, dried over magnesium sulfate and concentrated under reduced pressure to give 2-(tert-butoxycarbonylamino)-3-(3-hydroxyphenyl)propanoic acid (0.89 g, 100%). Analytical LCMS (M+H-Boc)⁺: m/z=181.9.

Step 4. tert-butyl 1-(dimethylamino)-3-(3-hydroxyphenyl)-1-oxopropan-2-ylcarbamate

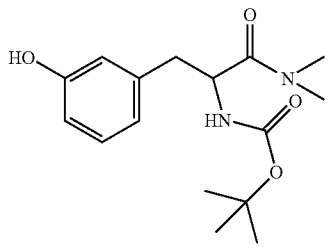 [SMILES: CN(C)C(=O)C(Cc1cccc(O)c1)NC(=O)OC(C)(C)C]

The 2-(tert-butoxycarbonylamino)-3-(3-hydroxyphenyl) propanoic acid (0.89 g, 3.1 mol) was treated with N,N,N',N'-tetramethyl-O-(7-azabenzotriazol-1-yl)uronium hexafluorophosphate (1.8 g, 4.6 mmol), N,N-diisopropylethylamine (1.6 mL, 9.3 mmol) and 2 M dimethylamine in THF (3.0 mL, 6.0 mmol), in N,N-dimethylformamide (20 mL) at r.t. The reaction was complete after stirring for 2 h. This was taken up in ethyl acetate and washed with 1 N HCl, brine, dried over magnesium sulfate and concentrated under reduced pressure to give the crude product as an oily residue. The product was purified by flash chromatography on a silica gel column eluting hexane: ethyl acetate gradient to give tert-butyl 1-(dimethylamino)-3-(3-hydroxyphenyl)-1-oxopropan-2-ylcarbamate (0.75 g, 78%) as an off white solid. Analytical LCMS (M+H-Boc)+: m/z=208.9.

Step 5: methyl 4-(3-(2-(tert-butoxycarbonylamino)-3-(dimethylamino)-3-oxopropyl)phenoxy)benzoate

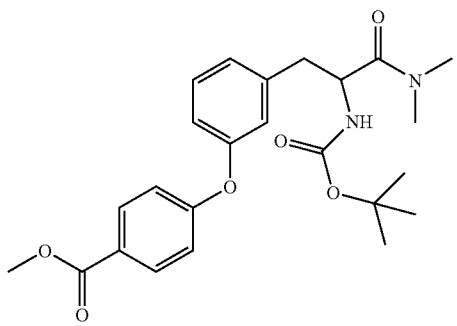

tert-Butyl 1-(dimethylamino)-3-(3-hydroxyphenyl)-1-oxopropan-2-ylcarbamate (0.025 g, 0.081 mmol) and methyl 4-fluorobenzoate (Aldrich, Cat. #120707) (0.025 g, 0.16 mmol) were combined in acetonitrile (1.0 mL) with cesium carbonate (0.053 g, 0.16 mmol) in a sealed tube and heated to 100° C. After 4 h., the reaction was allowed to cool, diluted with ethyl acetate and washed with water, brine, dried over magnesium sulfate and concentrated under reduced pressure to give crude methyl 4-(3-(2-(tert-butoxycarbonylamino)-3-(dimethylamino)-3-oxopropyl)phenoxy)benzoate as a semi-solid. Analytical LCMS (M+H-Boc)+: m/z=342.9.

Step 6: methyl 4-{3-[2-amino-3-(dimethylamino)-3-oxopropyl]phenoxy}benzoate

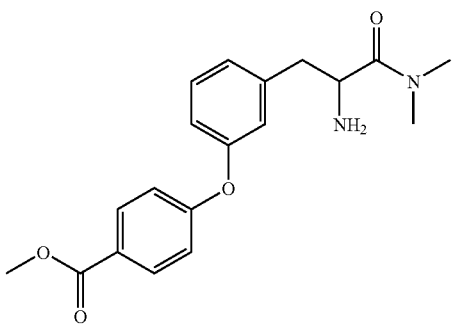

4-(3-(2-(tert-Butoxycarbonylamino)-3-(dimethylamino)-3-oxopropyl)phenoxy)benzoate, crude (0.045 g) was taken up in 4 M HCl in dioxane (2 mL) and stirred for 1 h. The reaction was concentrated under reduced pressure to give semi-solid. The residue was taken up in anhydrous acetonitrile and re-concentrated under reduced pressure for two times to give methyl 4-{3-[2-amino-3-(dimethylamino)-3-oxopropyl]phenoxy}benzoate HCl salt (0.045 g) as a semi-solid. Analytical LCMS (M+H)+: m/z=343.0

Step 7: methyl 4-{3-[2-({[2-amino-4-(4-methylpiperazin-1-yl)quinazolin-7-yl]carbonyl}amino)-3-(dimethylamino)-3-oxopropyl]phenoxy}benzoate N,N,N',N'-Tetramethyl-O-(7-azabenzotriazol-1-yl)uronium hexafluorophosphate (0.030 g, 0.078 mmol) was added to a solution of methyl 4-{3-[2-amino-3-(dimethylamino)-3-oxopropyl]phenoxy}benzoate HCl salt (0.045 g) and 2-amino-4-(4-methylpiperazin-1-yl)quinazoline-7-carboxylic acid (0.015 g, 0.052 mmol) in N,N-dimethylformamide (1.0 mL) with N,N-diisopropylethylamine (0.027 mL, 0.16 mmol) at r.t. The reaction was stirred for 1 h. The product was purified with out workup by HPLC (pH=10) to give the desired(0.012 g, 37%) as a white amorphous solid. 1H NMR (400 MHz, DMSO): δ 8.82 (d, 1H), 7.71 (d, 2H), 7.68 (d, 1H), 7.61 (d, 1H), 7.29 (m, 2H), 7.17 (d, 1H), 7.06 (s, 1H), 6.88 (d, 1H), 6.82 (d, 2H), 6.38 (s, 1H), 5.02 (m, 1H), 3.72 (s, 3H), 3.46 (bs, 4H), 3.27 (s, 4H), 2.98 (bs, 5H), 2.77 (s, 3H), 2.17 (s, 3H). Analytical LCMS (M+H)+: m/z=612.0.

Example 170

2-Amino-N-[1-[3-(2-cyano-5-methoxyphenoxy)benzyl]-2-(dimethylamino)-2-oxoethyl]-4-(4-methylpiperazin-1-yl)quinazoline-7-carboxamide

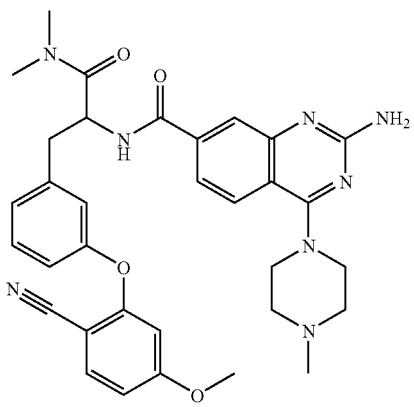 [SMILES: COc1ccc(C#N)c(Oc2cccc(CC(NC(=O)c3ccc4c(N5CCN(C)CC5)nc(N)nc4c3)C(=O)N(C)C)c2)c1]

This compound was prepared using procedures analogous to those for Example 169 but using 2-fluoro-4-methoxybenzonitrile (3B Medical Systems, Cat. #3B-3234) in Step 5. The final product was purified by prep RP-HPLC (pH=10) to afford the desired compound (0.010 g, 18%) as an amorphous white solid. Analytical LCMS (M+H)$^+$: m/z=609.0.

Example 171

2-Amino-N-[1-{3-[5-cyano-2-(trifluoromethyl)phenoxy]benzyl}-2-(dimethylamino)-2-oxoethyl]-4-(4-methylpiperazin-1-yl)quinazoline-7-carboxamide

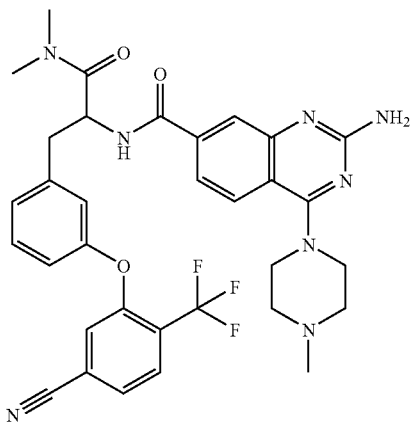 [SMILES: CN1CCN(c2nc(N)nc3cc(C(=O)NC(Cc4cccc(Oc5cc(C#N)ccc5C(F)(F)F)c4)C(=O)N(C)C)ccc23)CC1]

This compound was prepared using procedures analogous to those for Example 169 but using 3-fluoro-4-(trifluoromethyl)benzonitrile (Alfa Aeson, Cat. #L18934) in Step 5. The final product was purified by prep RP-HPLC (pH=10) to afford the desired compound (0.012 g, 21%) as an amorphous white solid. Analytical LCMS (M+H)$^+$: m/z=647.0.

Example 172

2-Amino-N-[1-[3-(4-chloro-2-cyanophenoxy)benzyl]-2-(dimethylamino)-2-oxoethyl]-4-(4-methylpiperazin-1-yl)quinazoline-7-carboxamide

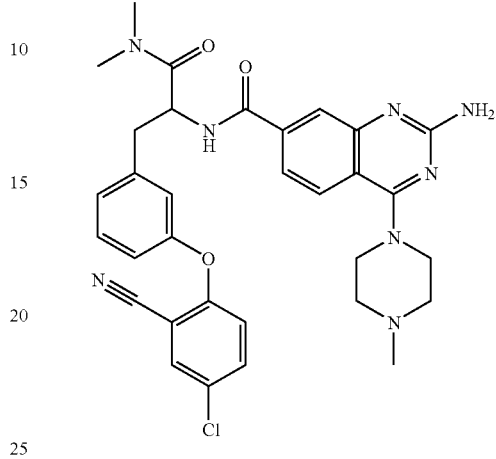

This compound was prepared using procedures analogous to those for Example 169 but using 5-chloro-2-fluorobenzonitrile (Aldrich, Cat. #548693) in Step 5. The final product was purified by prep RP-HPLC (pH=10) to afford the desired compound (0.008 g, 10%) as an amorphous white solid. Analytical LCMS (M+H)$^+$: m/z=613.0.

Example 173

2-Amino-N-[1-{3-[(3-cyano-6-methylpyridin-2-yl)oxy]benzyl}-2-(dimethylamino)-2-oxoethyl]-4-(4-methylpiperazin-1-yl)quinazoline-7-carboxamide

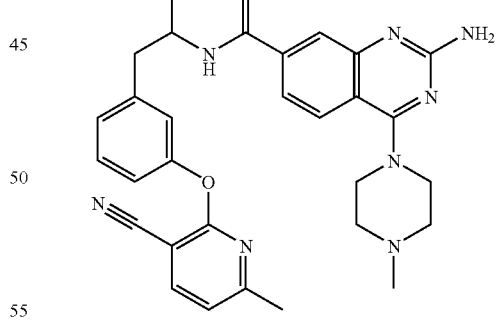

This compound was prepared using procedures analogous to those for Example 169 but using 2-chloro-6-methylnicotinonitrile (Alfa Aeson, Cat. #A15648) in Step 5. The final product was purified by prep RP-HPLC (pH=10) to afford the desired compound (0.013 g, 20%) as an amorphous white solid. $^1$H NMR (400 MHz, DMSO): δ 8.86 (d, 1H), 8.18 (d, 1H), 7.69 (s, 1H), 7.64 (d, 1H), 7.33 (m, 1H), 7.27 (d, 1H), 7.15 (m, 2H), 7.05 (d, 1H), 6.99 (d, 1H), 6.38 (bs, 2H), 4.99 (m, 1H), 3.48 (bs, 4H), 3.27 (s, 4H), 2.99 (d, 2H), 2.93 (s, 3H), 2.74 (s, 3H), 2.17 (s, 3H), 2.16 (s, 3 h).Analytical LCMS (M+H)$^+$: m/z=594.0.

Example 174

2-Amino-N-(3-(3-(3-cyanophenoxy)phenyl)-1-(dimethylamino)-1-oxopropan-2-yl)-4-(4-methylpiperazin-1-yl)quinazoline-7-carboxamide

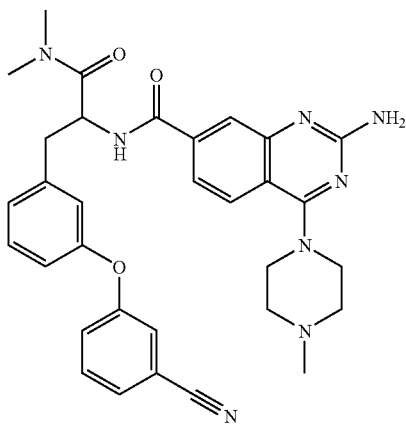 [SMILES: CN1CCN(c2nc(N)nc3cc(C(=O)NC(Cc4cccc(Oc5cccc(C#N)c5)c4)C(=O)N(C)C)ccc23)CC1]

Step 1: tert-butyl 3-(3-(3-cyanophenoxy)phenyl)-1-(dimethylamino)-1-oxopropan-2-ylcarbamate

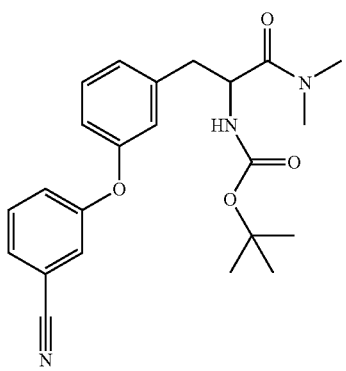 [SMILES: CN(C)C(=O)C(Cc1cccc(Oc2cccc(C#N)c2)c1)NC(=O)OC(C)(C)C]

The tert-butyl [2-(dimethylamino)-1-(3-hydroxybenzyl)-2-oxoethyl]carbamate (0.025 g, 0.081 mmol) from Example 169, step 4, was combined with (3-cyanophenyl)boronic acid (Aldich, Cat. #513016) (0.024 g, 0.16 mmol) and triethylamine (0.022 mL, 0.16 mmol), and copper(II)diacetate (0.015 g, 0.081 mmol) in methylene chloride (1.0 mL) at r.t. The reaction was vigorously stirred exposed to the atmosphere. After stirring for 48 h. this was taken up in ethyl acetate, washed with 1N HCl, brine, dried over magnesium sulfate and concentrated under reduced pressure to give crude tert-butyl 3-(3-(3-cyanophenoxy)phenyl)-1-(dimethylamino)-1-oxopropan-2-ylcarbamate (0.045 g) as a semisolid residue. Analytical LCMS (M+H-Boc)$^+$: m/z=310.0.

Step 2: 2-amino-3-[3-(3-cyanophenoxy)phenyl]-N,N-dimethylpropanamide

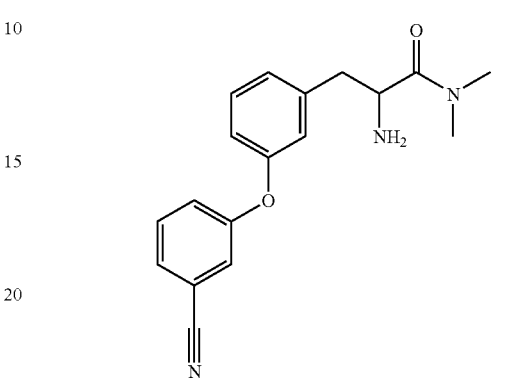

tert-Butyl 3-(3-(3-cyanophenoxy)phenyl)-1-(dimethylamino)-1-oxopropan-2-ylcarbamate (0.045 g crude) was taken up in 4 M HCl in dioxane 2 ml and stirred at r.t. for 2 h. The reaction was complete, concentrated under reduced pressure in vacuo. The residue was taken up in acetonitrile and reconcentrated under reduced pressure two times to give crude 2-amino-3-[3-(3-cyanophenoxy)phenyl]-N,N-dimethylpropanamide-HCl salt (0.045 g) as a semisolid residue which was directly used in next step reaction without further purification. Analytical LCMS (M+H)$^+$: m/z=310.0

Step 3: 2-amino-N-(3-(3-(3-cyanophenoxy)phenyl)-1-(dimethylamino)-1-oxopropan-2-yl)-4-(4-methylpiperazin-1-yl)quinazoline-7-carboxamide N,N,N',N'-Tetramethyl-O-(7-azabenzotriazol-1-yl)uronium hexafluorophosphate (0.030 g, 0.078 mmol) was added to a solution of 2-amino-3-[3-(3-cyanophenoxy)phenyl]-N,N-dimethylpropanamide HCl salt (0.045 g) and 2-amino-4-(4-methylpiperazin-1-yl)quinazoline-7-carboxylic acid (0.015 g, 0.052 mmol) in N,N-dimethylformamide (1.0 mL) with N,N-diisopropylethylamine (0.027 mL, 0.16 mmol) at r.t. The reaction was stirred for 1 h. The product was purified without workup by RP-HPLC (pH=2) to give the desired compound (0.004 g, 10%) as a white amorphous solid TFA salt. $^1$H NMR (400 MHz, DMSO): δ 7.98 (d, 1H), 7.79 (s, 1H), 7.68 (d, 1H), 7.45 (m, 2H), 7.25 (m, 2H), 7.14 (m, 2 h), 7.03 (s, 1H), 6.86 (d, 1H), 5.08 (m, 1H), 4.56 (m, 2H), 3.65 (m, 2H), 3.55 (m, 2H), 3.22 (m, 2H) 2.99 (m, 5H), 2.82 (s, 3H), 2.78 (s, 3H); Analytical LCMS (M+H)$^+$: m/z=579.2.

Example 175

2-Amino-N-[1-{3-[(3-cyanobenzyl)oxy]benzyl}-2-(dimethylamino)-2-oxoethyl]-4-(4-methylpiperazin-1-yl)quinazoline-7-carboxamide

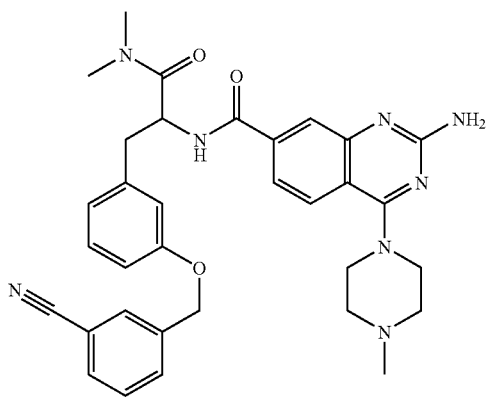 [SMILES: CN1CCN(c2nc(N)nc3cc(C(=O)NC(Cc4cccc(OCc5cccc(C#N)c5)c4)C(=O)N(C)C)ccc23)CC1]

This compound was prepared using procedures analogous to those for Example 169 but using 3-(bromomethyl)benzonitrile (Aldrich, Cat. #145610) in Step 5. The final product was purified by prep RP-HPLC (pH=10) to afford the desired compound (0.016 g, 28%) as an amorphous white solid. $^1$H NMR (400 MHz, DMSO): δ 8.84 (d, 1H), 7.81 (s, 1H), 7.72 (m, 2H), 7.67 (m, 2H), 7.51 (m, 1H), 7.33 (d, 1H), 7.12 (m, 1H), 6.94 (s, 1H), 6.87 (d, 1H), 6.78 (d, 1H), 6.39 (bs, 2H), 5.03 (s, 2H), 4.95 (m, 1H), 3.47 (bs, 4H), 3.26 (bs, 4H), 2.94 (bs, 5H), 2.75 (s, 3H), 2.17 (s, 3H). Analytical LCMS (M+H)$^+$: m/z=593.0.

Example 176

2-Amino-N-[2-(dimethylamino)-2-oxo-1-(3-{1-[3-(trifluoromethyl)phenyl]ethoxy}benzyl)ethyl]-4-(4-methylpiperazin-1-yl)quinazoline-7-carboxamide

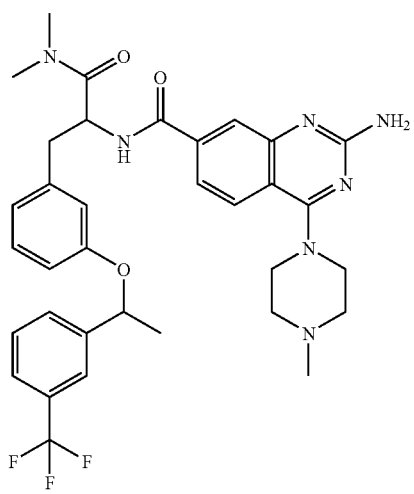 [SMILES: CC(Oc1cccc(CC(NC(=O)c2ccc3c(N4CCN(C)CC4)nc(N)nc3c2)C(=O)N(C)C)c1)c1cccc(C(F)(F)F)c1]

This compound was prepared using procedures analogous to those for Example 169 but using 1-(1-bromoethyl)-3-(trifluoromethyl)benzene (Matix Scientific, Cat. #002398) in Step 5. The final product was purified by prep RP-HPLC (pH=10) to afford the desired compound (0.012 g, 18%) as an amorphous white solid. Analytical LCMS (M+H)$^+$: m/z=650.1.

Example 177

2-Amino-N-[2-(dimethylamino)-2-oxo-1-(3-{[4-(trifluoromethoxy)benzyl]oxy}benzyl)ethyl]-4-(4-methylpiperazin-1-yl)quinazoline-7-carboxamide

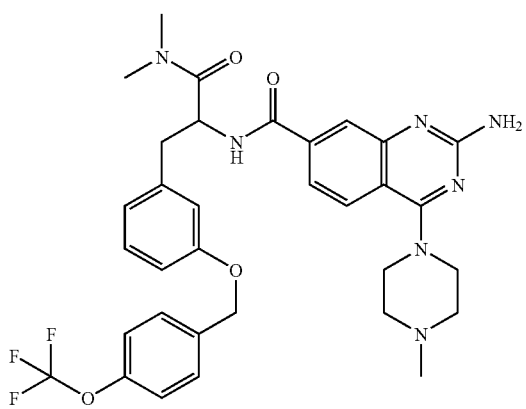 [SMILES: CN1CCN(c2nc(N)nc3cc(C(=O)NC(Cc4cccc(OCc5ccc(OC(F)(F)F)cc5)c4)C(=O)N(C)C)ccc23)CC1]

This compound was prepared using procedures analogous to those for Example 169 but using 1-(bromomethyl)-4-(trifluoromethoxy)benzene (Aldrich, Cat. #408891) in Step 5. The final product was purified by prep RP-HPLC (pH=10) to afford the desired compound (0.014 g, 22%) as an amorphous white solid. Analytical LCMS (M+H)$^+$: m/z=652.1.

Example 178

2-Amino-N-[3-(4-methoxyphenoxy)benzyl]-4-(4-methylpiperazin-1-yl)quinazoline-7-carboxamide

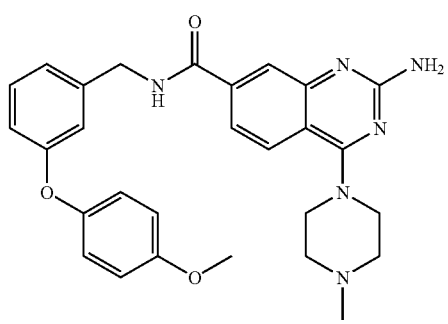 [SMILES: COc1ccc(Oc2cccc(CNC(=O)c3ccc4c(N5CCN(C)CC5)nc(N)nc4c3)c2)cc1]

249

Step 1: 3-(4-methoxyphenoxy)benzaldehyde oxime

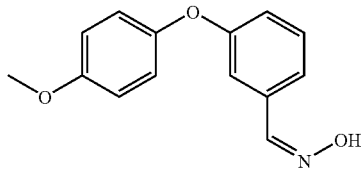 [SMILES: COc1ccc(Oc2cccc(/C=N\O)c2)cc1]

3-(4-Methoxyphenoxy)benzaldehyde (Aldrich, Cat. #195898) (0.10 g, 0.44 mmol) was dissolved in ethanol (2.1 mL, 37 mmol) and water (0.43 mL) at r.t., and the hydroxylamine hydrochloride (0.061 g, 0.88 mmol) and sodium acetate (0.072 g, 0.88 mmol) were added. The reaction was heated in a sealed tube to 85° C. for 2 h., and allowed to cool to r.t. The mixture was partitioned between ethyl acetate and water. The organic layer was washed with brine, dried over magnesium sulfate and concentrated under reduced pressure to give 3-(4-methoxyphenoxy)benzaldehyde oxime (0.11 g, 100%) as an oily residue.

Step 2: 1-[3-(4-methoxyphenoxy)phenyl]methanamine

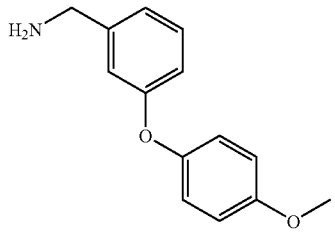 [SMILES: COc1ccc(Oc2cccc(CN)c2)cc1]

The 3-(4-methoxyphenoxy)benzaldehyde oxime (0.11 g, 0.44 mmol) was taken up in acetic acid (5.0 mL) at rt and the Zinc dust (0.14 g, 2.2 mmol) was added. The reaction was stirred at r.t. for 18 h. The reaction mixture was filtered and the filtrate was concentrated under reduced pressure to give crude 1-[3-(4-methoxyphenoxy)phenyl]methanamine as a dark oil. Analytical LCMS (M+H)$^+$: m/z=, 229.9

Step 3: 2-amino-N-[3-(4-methoxyphenoxy)benzyl]-4-(4-methylpiperazin-1-yl)quinazoline-7-carboxamide N,N,N',N'-Tetramethyl-O-(7-azabenzotriazol-1-yl)uronium hexafluorophosphate (0.030 g, 0.078 mmol) was added to a solution of crude 1-[3-(4-methoxyphenoxy)phenyl] methanamine (0.045 g) and 2-amino-4-(4-methylpiperazin-1-yl)quinazoline-7-carboxylic acid (0.015 g, 0.052 mmol) in N,N-dimethylformamide (2.0 mL) with N,N-diisopropylethylamine (0.027 mL, 0.16 mmol) at r.t. The reaction was stirred for 1 h. The product was purified without workup by RP-HPLC (pH=10) to give the desired product (0.014 g, 44%) as a white amorphous solid. Analytical LCMS (M+H)$^+$: m/z=499.0.

250

Example 179

Methyl 4-{3-[({[2-amino-4-(4-methylpiperazin-1-yl)quinazolin-7-yl]carbonyl}amino)methyl]phenoxy}benzoate

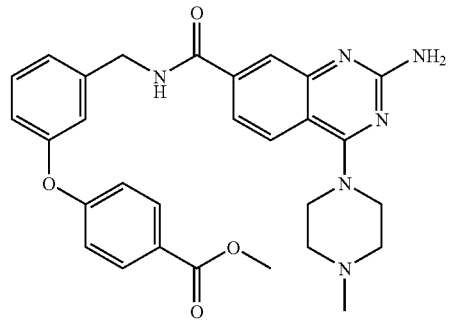 [SMILES: COC(=O)c1ccc(Oc2cccc(CNC(=O)c3ccc4c(N5CCN(C)CC5)nc(N)nc4c3)c2)cc1]

Step 1: tert-butyl 3-hydroxybenzylcarbamate

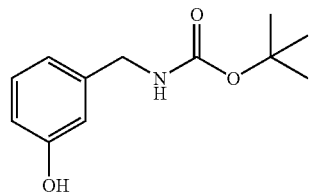 [SMILES: CC(C)(C)OC(=O)NCc1cccc(O)c1]

3-(Aminomethyl)phenol (Matix Scientific, Cat. #009265 (1.0 g, 8.2 mmol) was dissolved in 20 ml methylene chloride with N,N-diisopropylethylamine (2.1 mL, 12 mmol) and the di-tert-butyldicarbonate (2.1 g, 9.8 mmol) was added. The reaction was stirred at r.t. for 2 h. and was complete. The reaction was taken up in ethyl acetate, washed with 1 N HCl, brine, dried over magnesium sulfate and concentrated under reduced pressure to give tert-butyl 3-hydroxybenzylcarbamate (1.8 g, 100%) as an oil. Analytical LCMS (M+Na)$^+$: m/z=245.9.

Step 2: methyl 4-(3-((tert-butoxycarbonylamino)methyl)phenoxy)benzoate

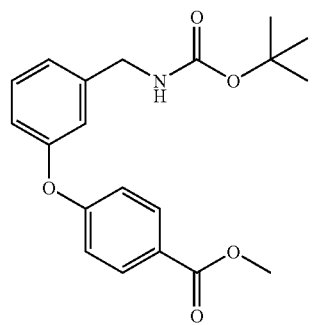 [SMILES: COC(=O)c1ccc(Oc2cccc(CNC(=O)OC(C)(C)C)c2)cc1]

tert-Butyl (3-hydroxybenzyl)carbamate (0.025 g, 0.11 mmol) was dissolved in acetonitrile (1.0 mL) with methyl 4-fluorobenzoate (Aldrich, Cat 120707) (0.034 g, 0.22 mmol) and cesium carbonate (0.073 g, 0.22 mmol) in a sealed tube. The reaction was heated to 100° C. for 2 h. and was complete. The reaction was taken up in ethyl acetate, filtered and concentrated under reduced pressure to give crude methyl 4-(3-((tert-butoxycarbonylamino)methyl)phenoxy)benzoate (0.040 g) as a clear oil.

Step 3: methyl 4-[3-(aminomethyl)phenoxy]benzoate

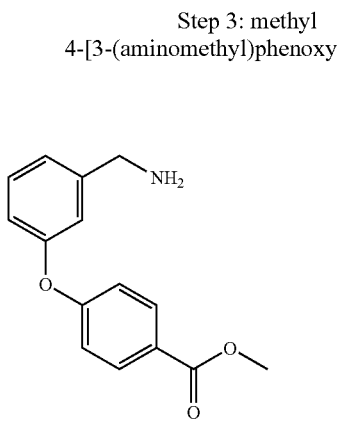

The methyl 4-(3-((tert-butoxycarbonylamino)methyl)phenoxy)benzoate (0.040 g) was taken up in 4 M HCl in dioxane (3 ml) at rt and was stirred for 2 h. The reaction was complete, was concentrated under reduced pressure, taken up in acetonitrile and re-concentrated under reduced pressure two times to give crude methyl 4-[3-(aminomethyl)phenoxy]benzoate-HCl (0.045 g) as a semisolid residue. Analytical LCMS (M+H)$^+$: m/z=258.0.

Step 4: methyl 4-{3-[({[2-amino-4-(4-methylpiperazin-1-yl)quinazolin-7-yl]carbonyl}amino)methyl]phenoxy}benzoate N,N,N',N'-Tetramethyl-O-(7-azabenzotriazol-1-yl)uronium hexafluorophosphate (0.030 g, 0.078 mmol) was added to a solution of methyl 4-[3-(aminomethyl)phenoxy]benzoate-HCl (0.045 g) and 2-amino-4-(4-methylpiperazin-1-yl)quinazoline-7-carboxylic acid (0.015 g, 0.052 mmol) in N,N-Dimethylformamide (1.0 mL) with N,N-diisopropylethylamine (0.027 mL, 0.16 mmol) at r.t. The reaction was stirred for 1 h. The product was purified without workup by RP-HPLC (pH=10) to give the desired product (0.020 g, 50%) as a white amorphous solid. $^1$H NMR (400 MHz, DMSO): δ 9.16 (m, 1H), 7.89 (d, 2H), 7.70 (m, 2H), 7.36 (m, 2H), 7.14 (d, 1H), 6.99 (d, 2H), 6.95 (m, 2H), 6.39 (bs, 2H), 4.44 (d, 2H), 3.75 (s, 3H), 3.50 (bs, 4H), 3.29 (s, 4H), 2.18 (s, 3H); Analytical LCMS (M+H)$^+$: m/z=527.0.

Example 180

2-Amino-N-[3-(2-cyano-5-methoxyphenoxy)benzyl]-4-(4-methylpiperazin-1-yl)quinazoline-7-carboxamide

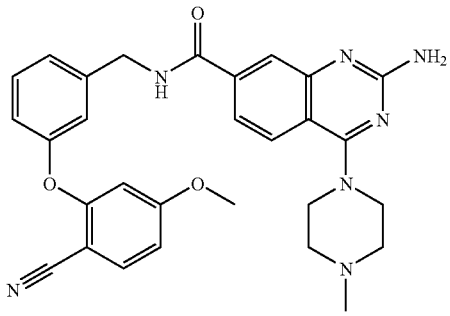 [SMILES: COc1ccc(C#N)c(Oc2cccc(CNC(=O)c3ccc4c(N5CCN(C)CC5)nc(N)nc4c3)c2)c1]

This compound was prepared using procedures analogous to those for Example 179 but using 2-fluoro-4-methoxybenzonitrile (Matrix Scientific, Cat. #020188) in Step 2. The final product was purified by prep RP-HPLC (pH=10) to afford the desired compound (0.014 g, 22%) as an amorphous white solid. Analytical LCMS (M+H)$^+$: m/z=524.0.

Example 181

2-Amino-N-[3-(isoquinolin-1-yloxy)benzyl]-4-(4-methylpiperazin-1-yl)quinazoline-7-carboxamide

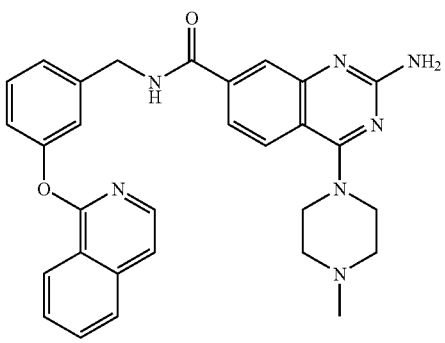 [SMILES: CN1CCN(c2nc(N)nc3cc(C(=O)NCc4cccc(Oc5nccc6ccccc56)c4)ccc23)CC1]

This compound was prepared using procedures analogous to those for Example 179 but using 1-chloroisoquinoline (Aldrich, Cat. #156744) in Step 2. The final product was purified by prep RP-HPLC (pH=10) to afford the desired compound (0.005 g, 10%) as an amorphous white solid. Analytical LCMS (M+H)$^+$: m/z=520.0.

Example 182

2-Amino-4-(4-methylpiperazin-1-yl)-N-{3-[(4-methylpyridin-2-yl)oxy]benzyl}quinazoline-7-carboxamide

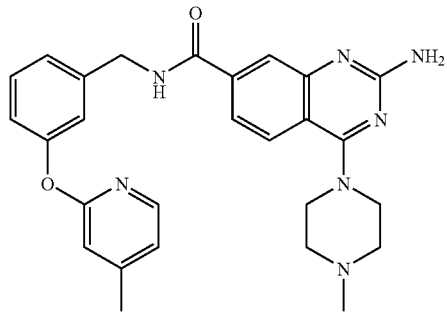 [SMILES: Cc1ccnc(Oc2cccc(CNC(=O)c3ccc4c(N5CCN(C)CC5)nc(N)nc4c3)c2)c1]

This compound was prepared using procedures analogous to those for Example 179 but using 2-bromo-4-methylpyridine (Aldrich, Cat. #349984) in Step 2. The final product was purified by prep RP-HPLC (pH=2) to afford the desired compound (0.015 g, 20%) as an amorphous white solid TFA salt. Analytical LCMS (M+H)+: m/z=484.0.

Example 183

2-Amino-N-{3-[(4-cyanopyridin-2-yl)oxy]benzyl}-4-(4-methylpiperazin-1-yl)quinazoline-7-carboxamide

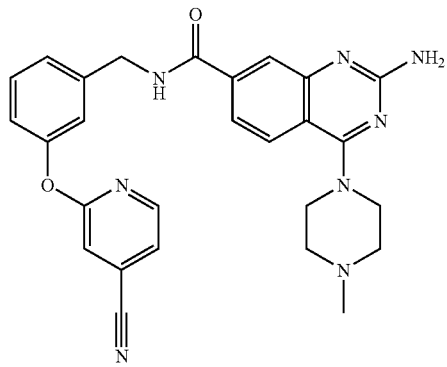 [SMILES: CN1CCN(c2nc(N)nc3cc(C(=O)NCc4cccc(Oc5cc(C#N)ccn5)c4)ccc23)CC1]

This compound was prepared using procedures analogous to those for Example 179 but using 2-chloroisonicotinonitrile (Aldrich, Cat. #548227) in Step 2. The final product was purified by prep RP-HPLC (pH=2) to afford the desired compound (0.009 g, 11%) as an amorphous white solid TFA salt. $^1$H NMR (400 MHz, DMSO): δ 9.45 (m, 1H), 8.34 (d, 1H), 8.05 (m, 1H), 7.93 (m, 1H), 7.76 (m, 1H), 7.63 (s, 1H), 7.56 (d, 1H), 7.39 (m, 1H), 7.20 (d, 1H), 7.10 (d, 1H), 7.06 (m, 1H), 4.57 (bm, 2H), 4.53 (d, 2H), 3.67 (bm, 2H), 3.55 (bm, 2H), 3.23 (bm, 2H), 2.83 (s, 3H). Analytical LCMS (M+H)+: m/z=495.0.

Example 184

Ethyl 2-{3-[({[2-amino-4-(4-methylpiperazin-1-yl)quinazolin-7-yl]carbonyl}amino)methyl]phenoxy}nicotinate

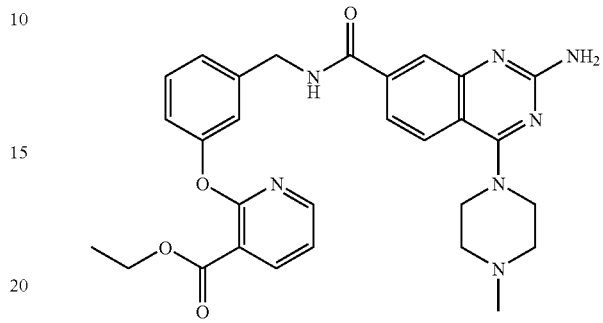

This compound was prepared using procedures analogous to those for Example 179 but using ethyl 2-chloronicotinate (Alfa Aeson, Cat. #B20359) in Step 2. The final product was purified by prep RP-HPLC (pH=2) to afford the desired compound (0.011 g, 15%) as an amorphous white solid TFA salt. $^1$H NMR (400 MHz, DMSO): δ 9.47 (m, 1H) 8.27 (m, 1H), 8.25 (m, 1H), 8.07 (d, 1H), 7.94 (m, 1H), 7.79 (d, 1H), 7.36 (m, 1H), 7.24 (m, 1H), 7.16 (dd, 1H), 7.05 (m, 1H), 6.99 (m, 1H), 4.60 (bm, 2H), 4.52 (d, 2H), 4.27 (q, 2H), 3.69 (bm, 2H), 3.56 (bm, 2H), 3.23 (bm, 2H), 2.84 (s, 3H), 1.26 (t, 3H). Analytical LCMS (M+H)+: m/z=542.3.

Example 185

Ethyl 2-{3-[({[2-amino-4-(4-methylpiperazin-1-yl)quinazolin-7-yl]carbonyl}amino)methyl]phenoxy}-4-methyl-1,3-thiazole-5-carboxylate

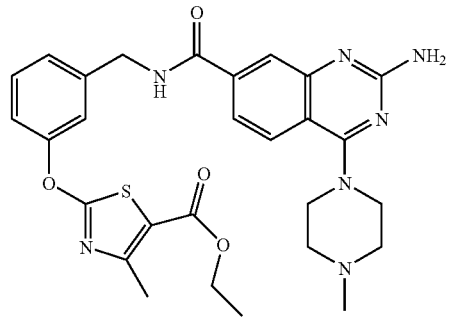 [SMILES: CCOC(=O)c1sc(Oc2cccc(CNC(=O)c3ccc4c(N5CCN(C)CC5)nc(N)nc4c3)c2)nc1C]

This compound was prepared using procedures analogous to those for Example 179 but using ethyl 2-bromo-4-methylthiazole-5-carboxylate (Aldrich, Cat. #645990) in Step 2. The final product was purified by prep RP-HPLC (pH=2) to afford the desired compound (0.005 g, 20%) as an amorphous white solid TFA salt. Analytical LCMS (M+H)+: m/z=562.3.

Example 186

Ethyl 2-{3-[({[2-amino-4-(4-methylpiperazin-1-yl)quinazolin-7-yl]carbonyl}amino)methyl]phenoxy}-3-cyano-6-methylisonicotinate

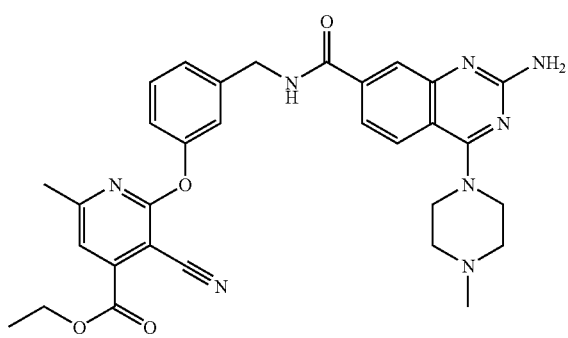 [SMILES: CCOC(=O)c1cc(C)nc(Oc2cccc(CNC(=O)c3ccc4c(N5CCN(C)CC5)nc(N)nc4c3)c2)c1C#N]

This compound was prepared using procedures analogous to those for Example 179 but using ethyl 2-chloro-3-cyano-6-methylisonicotinate (Aldrich, Cat. #S376787) in Step 2. The final product was purified by prep RP-HPLC (pH=2) to afford the desired compound (0.004 g, 20%) as an amorphous white solid TFA salt. Analytical LCMS (M+H)$^+$: m/z=580.9

Example 187

2-Amino-N-{3-[(3,6-dimethylpyrazin-2-yl)oxy]benzyl}-4-(4-methylpiperazin-1-yl)quinazoline-7-carboxamide

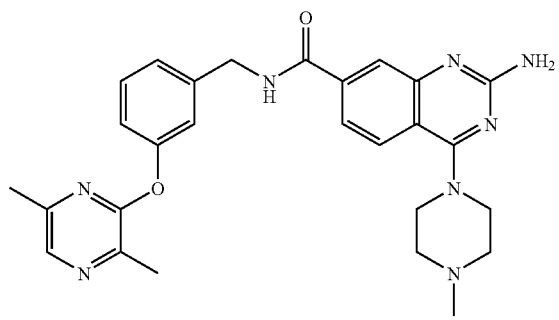 [SMILES: Cc1cnc(C)c(Oc2cccc(CNC(=O)c3ccc4c(N5CCN(C)CC5)nc(N)nc4c3)c2)n1]

This compound was prepared using procedures analogous to those for Example 179 but using 3-chloro-2,5-dimethylpyrazine (Aldrich, Cat. #C38400) in Step 2. The final product was purified by prep RP-HPLC (pH=2) to afford the desired compound (0.004 g, 20%) as an amorphous white solid TFA salt. $^1$H NMR (400 MHz, DMSO): δ 9.46 (m, 1H), 8.09 (s, 1H), 8.07 (d, 1H), 7.94 (m, 1H), 7.79 (d, 1H), 7.37 (m, 1H), 7.17 (d, 1H), 7.10 (m, 1H), 7.03 (dd, 1H), 4.58 (bm, 2H), 4.53 (d, 2H), 3.67 (bm, 2H), 3.58 (bm, 2H), 3.24 (bm, 2H), 2.84 (s, 3H), 2.46 (s, 3H), 2.20 (s, 3H). Analytical LCMS (M+H)$^+$: m/z=499.3

Example 188

2-Amino-4-(4-methylpiperazin-1-yl)-N-[3-(quinoxalin-2-yloxy)benzyl]quinazoline-7-carboxamide

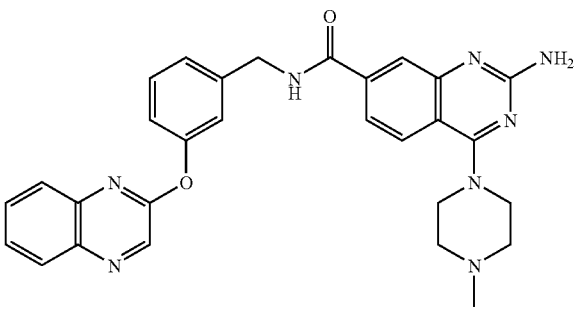 [SMILES: CN1CCN(c2nc(N)nc3cc(C(=O)NCc4cccc(Oc5cnc6ccccc6n5)c4)ccc23)CC1]

This compound was prepared using procedures analogous to those for Example 179 but using 2-chloroquinoxaline (Aldrich, Cat. #136301) in Step 2. The final product was purified by prep RP-HPLC (pH=2) to afford the desired compound (0.005 g, 30%) as an amorphous white solid TFA salt. Analytical LCMS (M+H)$^+$: m/z=521.3

Example 189

2-Amino-N-[3-(2-cyano-3-methylphenoxy)benzyl]-4-(4-methylpiperazin-1-yl)quinazoline-7-carboxamide

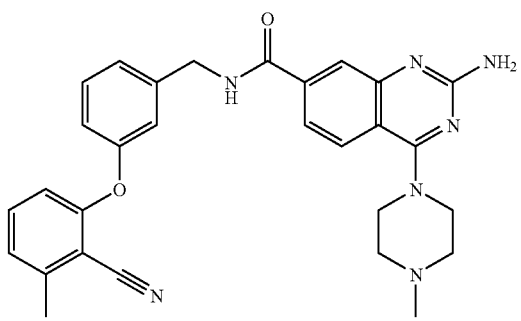 [SMILES: Cc1cccc(Oc2cccc(CNC(=O)c3ccc4c(N5CCN(C)CC5)nc(N)nc4c3)c2)c1C#N]

This compound was prepared using procedures analogous to those for Example 179 but using 2-fluoro-6-methylbenzonitrile (Apollo Scientific, Cat. #PC9287) in Step 2. The final product was purified by prep RP-HPLC (pH=2) to afford the desired compound (0.005 g, 30%) as an amorphous white solid TFA salt. $^1$H NMR (400 MHz, DMSO): δ 9.45 (m, 1H), 8.06 (d, 1H), 7.93 (d, 1H), 7.77 (d, 1H), 7.51 (m, 1H), 7.41 (m, 1H), 7.18 (m, 2H), 7.08 (d, 1H), 6.99 (dd, 1H), 6.74 (d, 1H), 4.58 (bm, 2H), 4.53 (d, 2H), 3.68 (bm, 2H), 3.55 (bm, 2H), 3.23 (bm, 2H), 2.83 (s, 3H), 2.48 (s, 3H). Analytical LCMS (M+H)$^+$: m/z=508.3.

Example 190

2-Amino-N-[3-(2-cyano-3-methoxyphenoxy)benzyl]-4-(4-methylpiperazin-1-yl)quinazoline-7-carboxamide

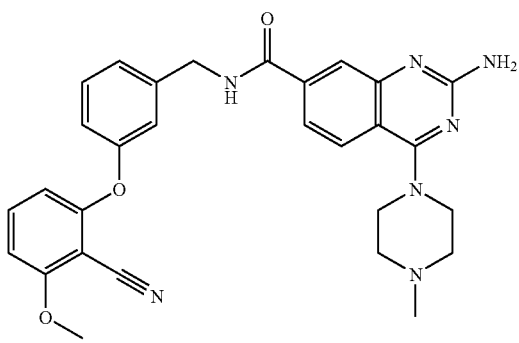 [SMILES: COc1cccc(Oc2cccc(CNC(=O)c3ccc4c(N5CCN(C)CC5)nc(N)nc4c3)c2)c1C#N]

This compound was prepared using procedures analogous to those for Example 179 but using 2-fluoro-6-methoxybenzonitrile (Aldrich, Cat. #406058) in Step 2. The final product was purified by prep RP-HPLC (pH=2) to afford the desired compound (0.004 g, 20%) as an amorphous white solid TFA salt. Analytical LCMS (M+H)$^+$: m/z=524.3.

Example 191

Methyl 2-{3-[({[2-amino-4-(4-methylpiperazin-1-yl)quinazolin-7-yl]carbonyl}amino)methyl]phenoxy}benzoate

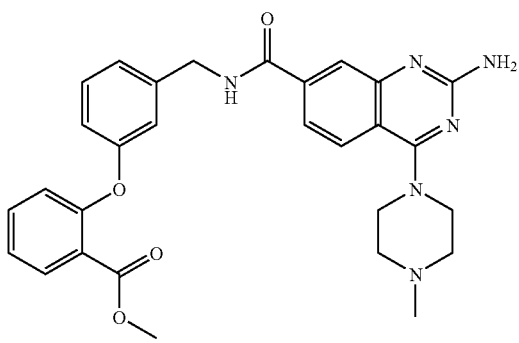 [SMILES: COC(=O)c1ccccc1Oc1cccc(CNC(=O)c2ccc3c(N4CCN(C)CC4)nc(N)nc3c2)c1]

This compound was prepared using procedures analogous to those for Example 179 but using methyl 2-fluorobenzoate (Aldrich, Cat. #528951) in Step 2. The final product was purified by prep RP-HPLC (pH=2) to afford the desired compound (0.005 g, 30%) as an amorphous white solid TFA salt. Analytical LCMS (M+H)$^+$: m/z=527.3.

Example 192

2-amino-N-(3-(3-cyanobenzyloxy)benzyl)-4-(4-methylpiperazin-1-yl)quinazoline-7-carboxamide

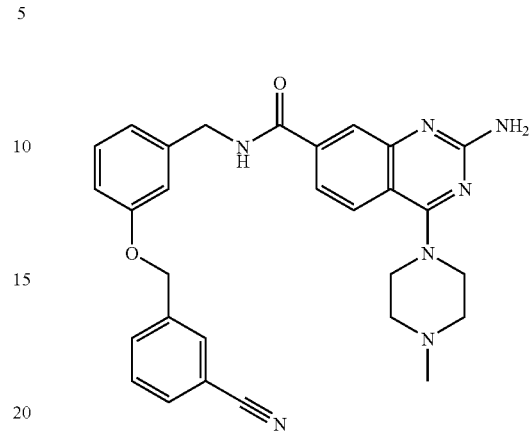

This compound was prepared using procedures analogous to those for Example 179 but using 3-(bromomethyl)benzonitrile (Aldrich, Cat. #145610) in Step 2. The final product was purified by prep RP-HPLC (pH=10) to afford the desired compound (0.012 g, 20%) as an amorphous white solid. $^1$H NMR (400 MHz, DMSO): δ 10.24 (m, 1H), 7.84 (s, 1H), 7.74 (d, 2H), 7.71 (m, 2H), 7.52 (t, 1H), 7.40 (d, 1H), 7.20 (m, 1H), 6.92 (s, 1H), 6.85 (m, 2H), 6.39 (s, 1H), 5.08 (s, 2H), 4.39 (m, 2H), 3.50 (bs, 4H), 3.28 (s, 4H), 2.18 (s, 3H). Analytical LCMS (M+H)$^+$: m/z=508.0.

Example 193

Methyl 4-({3-[({[2-amino-4-(4-methylpiperazin-1-yl)quinazolin-7-yl]carbonyl}amino)methyl]phenoxy}methyl)benzoate

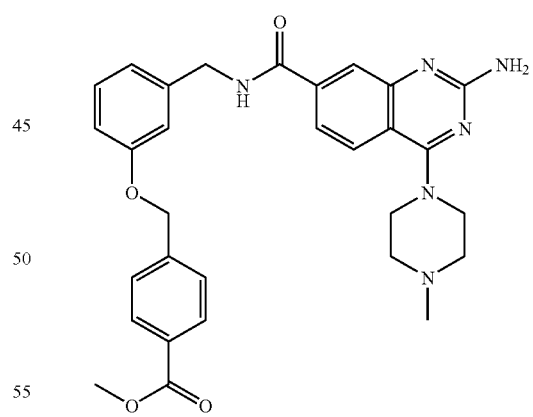

This compound was prepared using procedures analogous to those for Example 179 but using methyl 4-(bromomethyl)benzoate (Aldrich, Cat. #348155) in Step 2. The final product was purified by prep RP-HPLC (pH=10) to afford the desired compound (0.012 g, 15%) as an amorphous white solid. $^1$H NMR (400 MHz, DMSO): δ 9.11 (m, 1H), 7.87 (d, 2H), 7.74 (s, 1H), 7.70 (d, 1H), 7.50 (d, 2H), 7.40 (d, 1H), 7.18 (m, 1H), 6.91 (s, 1H), 6.83 (m, 2H), 6.40 (bs, 2H), 5.12 (s, 2H), 3.77 (s, 3H), 3.51 (bs, 4H), 3.29 (s, 4H), 2.7 (s, 3H). Analytical LCMS (M+H)$^+$: m/z=541.0.

Example 194

2-Amino-N-{3-[(3,5-dimethoxybenzyl)oxy]benzyl}-4-(4-methylpiperazin-1-yl)quinazoline-7-carboxamide

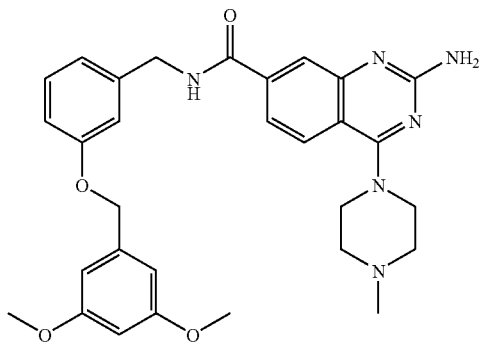 [SMILES: COc1cc(COc2cccc(CNC(=O)c3ccc4c(N5CCN(C)CC5)nc(N)nc4c3)c2)cc(OC)c1]

This compound was prepared using procedures analogous to those for Example 179 but using 1-(bromomethyl)-3,5-dimethoxybenzene (Aldrich, Cat. #480622) in Step 2. The final product was purified by prep RP-HPLC (pH=10) to afford the desired compound (0.011 g, 15%) as an amorphous white solid. Analytical LCMS (M+H)$^+$: m/z=543.0.

Example 195

2-Amino-N-[3-(2,1,3-benzothiadiazol-4-ylmethoxy)benzyl]-4-(4-methylpiperazin-1-yl)quinazoline-7-carboxamide

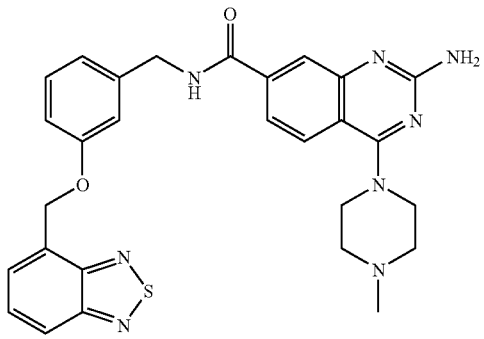 [SMILES: CN1CCN(c2nc(N)nc3cc(C(=O)NCc4cccc(OCc5cccc6nsnc56)c4)ccc23)CC1]

This compound was prepared using procedures analogous to those for Example 179 but using 4-(bromomethyl)benzo[c][1,2,5]thiadiazole (Maybridge, Cat. #CC09108) in Step 2. The final product was purified by prep RP-HPLC (pH=2) to afford the desired compound (0.005 g, 30%) as an amorphous white solid TFA salt. Analytical LCMS (M+H)$^+$: m/z=541.0.

Example 196

2-Amino-4-(4-methylpiperazin-1-yl)-N-(3-{1-[3-(trifluoromethyl)phenyl]ethoxy}benzyl)quinazoline-7-carboxamide

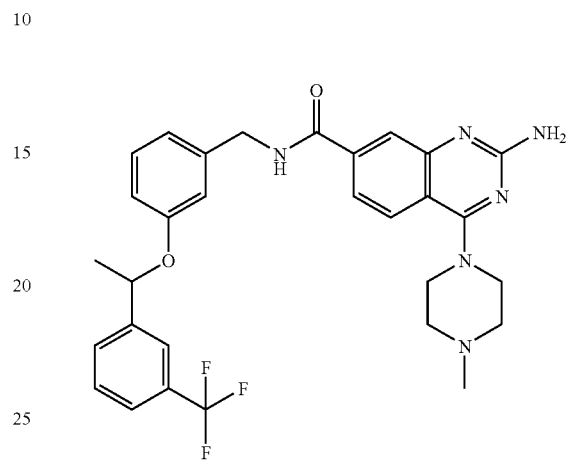

This compound was prepared using procedures analogous to those for Example 179 but using 1-(1-bromoethyl)-3-(trifluoromethyl)benzene (Matrix Scientific, Cat. #002398) in Step 2. The final product was purified by prep RP-HPLC (pH=2) to afford the desired compound (0.004 g, 20%) as an amorphous white solid TFA salt. Analytical LCMS (M+H)$^+$: m/z=565.0.

Example 197

2-Amino-N-{1-[3-(4-chloro-2-cyanophenoxy)phenyl]ethyl}-4-(4-methylpiperazin-1-yl)quinazoline-7-carboxamide

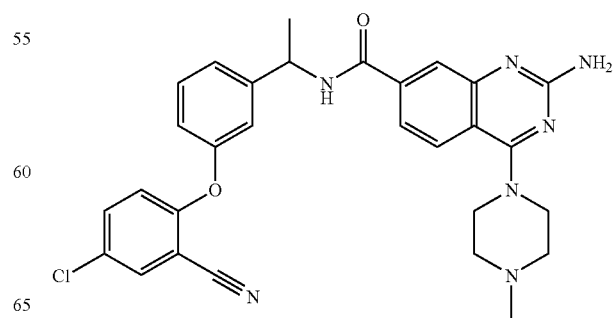

Step 1: 1-(3-hydroxyphenyl)ethanone oxime

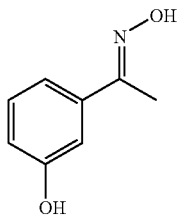

Hydroxylamine hydrochloride (1 g, 10 mmol) and sodium acetate (1 g, 10 mmol) were added to a solution of 1-(3-hydroxyphenyl)ethanone (Aldrich, Cat. #H18801) (1 g, 7 mmol) in ethanol (30 mL) and water (4 mL). The reaction was heated at 80° C. for 2 h. The reaction was allowed to cool to r.t. and taken up in ethyl acetate and washed with 1 N HCl. The organic layer was washed with brine, dried over MgSO$_4$, filtered and concentrated under reduced pressure to give crude 1-(3-hydroxyphenyl)ethanone oxime (1.2 g, 100%) as yellow oil. Analytical LCMS (M+H)$^+$: m/z=151.9.

Step 2: 3-(1-aminoethyl)phenol

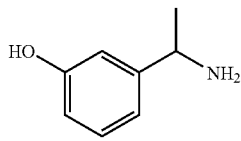

1-(3-Hydroxyphenyl)ethanone oxime (1.2 g; 7.9 mmol) was dissolved in methanol (20 mL), degassed with nitrogen. 10% Palladium on carbon (0.1 g) and conc. HCl (100 uL, 3 mmol) were added. The reaction was shaken under Parr shaker at 50 Psi for 5 h. The reaction was filtered and concentrated under reduced pressure to give crude 3-(1-aminoethyl)phenol (1.0 g, 100%) as a yellow oil. Analytical LCMS (M+H)$^+$: m/z=138.0.

Step 3: tert-butyl [1-(3-hydroxyphenyl)ethyl]carbamate

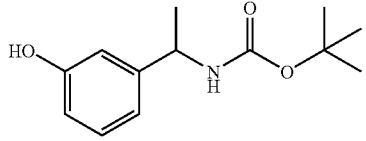 [SMILES: CC(NC(=O)OC(C)(C)C)c1cccc(O)c1]

To a solution of 3-(1-aminoethyl)phenol (1.2 g, 8.7 mmol) in methylene chloride (20 mL) and N,N-diisopropylethylamine (3.0 mL, 17 mmol), di-tert-butyldicarbonate (2.3 g, 10 mmol) was added at r.t. The reaction was stirred for 2 h. and was concentrated under reduced pressure to remove methylene chloride. The residuals were partitioned between EtOAc and water. The organic layer was washed with 1N HCl, brine, dried over MgSO$_4$, filtered and concentrated under reduced pressure to give crude product. The crude material was purified by flash chromatography on a silica gel column eluting with Ethyl acetate:Hexane, (1:5 to 1:3) to obtain desired product tert-butyl [1-(3-hydroxyphenyl)ethyl]carbamate (1.6 g, 77%) as light yellow color. Analytical LCMS (M+Na)$^+$: m/z=260.0.

Step 4: tert-butyl{1-[3-(4-chloro-2-cyanophenoxy)phenyl]ethyl}carbamate

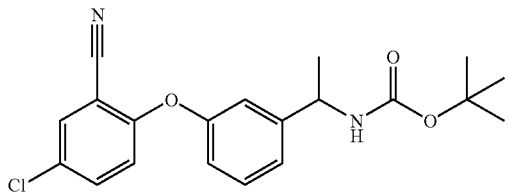 [SMILES: CC(NC(=O)OC(C)(C)C)c1cccc(Oc2ccc(Cl)cc2C#N)c1]

tert-Butyl [1-(3-hydroxyphenyl)ethyl]carbamate (0.025 g, 0.11 mmol) was dissolved in acetonitrile (1.0 mL) with 5-chloro-2-fluorobenzonitrile (Aldrich, Cat. #548693) (0.034 g, 0.22 mmol) and cesium carbonate (0.073 g, 0.22 mmol) in a sealed tube. The reaction was heated to 100° C. for 2 h. and was complete. The reaction was taken up in ethyl acetate, filtered and concentrated under reduced pressure to give crude tert-butyl{1-[3-(4-chloro-2-cyanophenoxy)phenyl]ethyl}carbamate (0.040 g) as a clear oil. Analytical LCMS (M+H-Boc)$^+$: m/z=272.9.

Step 5: 2-[3-(1-aminoethyl)phenoxy]-5-chlorobenzonitrile

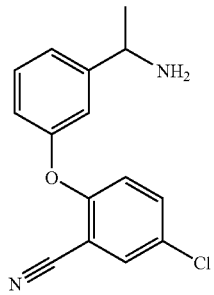 [SMILES: CC(N)c1cccc(Oc2ccc(Cl)cc2C#N)c1]

The tert-butyl{1-[3-(4-chloro-2-cyanophenoxy)phenyl]ethyl}carbamate (0.040 g) was taken up in 4 M HCl in dioxane (3 mL) at r.t. and was stirred for 2 h. The reaction was concentrated under reduced pressure, taken up in acetonitrile and re-concentrated under reduced pressure two times to give crude 2-[3-(1-aminoethyl)phenoxy]-5-chlorobenzonitrile as HCl salt (0.045 g) as a semisolid residue. Analytical LCMS (M+H)$^+$: m/z=272.9.

Step 6: 2-amino-N-{1-[3-(3-chloro-2-cyano-4-methylphenoxy)phenyl]ethyl}-4-(4-methylpiperazin-1-yl)quinazoline-7-carboxamide N,N,N',N'-Tetramethyl-O-(7-azabenzotriazol-1-yl)uronium hexafluorophosphate (0.030 g, 0.078 mmol) was added to a solution of 2-[3-(1-aminoethyl)phenoxy]-5-chlorobenzonitrile HCl salt (0.045 g) and 2-amino-4-(4-methylpiperazin-1-yl)quinazoline-7-carboxylic acid (0.015 g, 0.052 mmol) in N,N-dimethylformamide (1.0 mL) with N,N-diisopropylethylamine (0.027 mL, 0.16 mmol) at r.t. The reaction was stirred for 1 h. The product was purified without workup by RH-HPLC (pH=2) to give the desired product (0.005 g, 20%) as a white amorphous solid TFA salt. $^1$H NMR (400 MHz, DMSO): δ: 9.23 (d, 1H), 8.10 (d, 1H), 8.05 (d, 1H), 7.90 (d, 1H), 7.78 (d, 1H), 7.70, (dd, 1H), 7.43 (m, 1H), 7.30 (d, 1H), 7.21 (m, 1H), 7.04 (dd, 1H), 6.94 (d, 1H), 5.20 (m 1H), 4.58 (m, 2H), 4.10 (m, 2H), 3.70 (m, 2H), 3.05 (m, 2H), 2.83 (s, 3H), 1.49 (d, 3H). Analytical LCMS (M+H)$^+$: m/z=542.0.

Example 198

2-Amino-N-(1-{3-[(3-cyano-6-methylpyridin-2-yl)oxy]phenyl}ethyl)-4-(4-methylpiperazin-1-yl)quinazoline-7-carboxamide

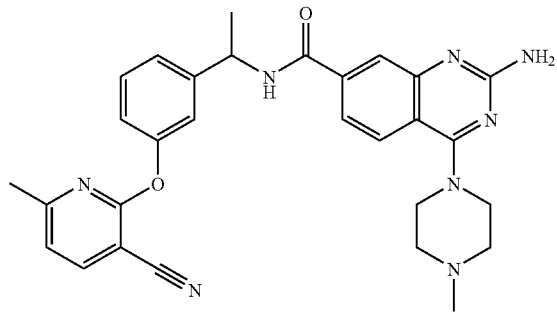 [SMILES: Cc1ccc(C#N)c(Oc2cccc(C(C)NC(=O)c3ccc4c(N5CCN(C)CC5)nc(N)nc4c3)c2)n1]

This compound was prepared using procedures analogous to those for Example 197 but using 2-chloro-6-methylnicotinonitrile (Alfa Aeson, Cat. #A15648) in Step 4. The final product was purified by prep RP-HPLC (pH=2) to afford the desired compound (0.007 g, 35%) as an amorphous white solid TFA salt. $^1$H NMR (400 MHz, DMSO): δ 9.24 (d, 1H), 8.26 (d, 1H), 8.06 (d, 1H), 7.92 (d, 1H), 7.81 (dd, 1H), 7.39 (m, 1H), 7.28 (d, 1H), 7.25 (m, 1H), 7.17 (d, 1H), 7.10 dd, 1H), 5.22 (m, 1H), 3.61 (m, 2H), 3.69 (m, 2H), 3.56 (m, 2H), 3.49 (m, 2H), 2.85 (s, 3H), 2.30 (s, 3H). Analytical LCMS (M+H)$^+$: m/z=523.0.

Example 199

2-Amino-N-(1-{3-[(3-cyanopyridin-2-yl)oxy]phenyl}ethyl)-4-(4-methylpiperazin-1-yl)quinazoline-7-carboxamide

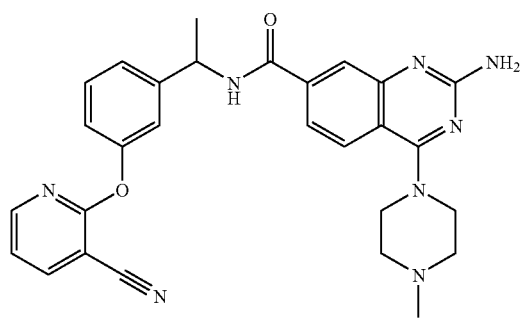 [SMILES: CC(NC(=O)c1ccc2c(N3CCN(C)CC3)nc(N)nc2c1)c1cccc(Oc2ncccc2C#N)c1]

This compound was prepared using procedures analogous to those for Example 197 but using 2-chloronicotinonitrile (Aldrich, Cat. #535338) in Step 4. The final product was purified by prep RP-HPLC (pH=2) to afford the desired compound (0.005 g, 30%) as an amorphous white solid TFA salt. Analytical LCMS (M+H)$^+$: m/z=509.0.

Example 200

Methyl 3-({3-[1-({[2-amino-4-(4-methylpiperazin-1-yl)quinazolin-7-yl]carbonyl}amino)ethyl]phenoxy}methyl)benzoate

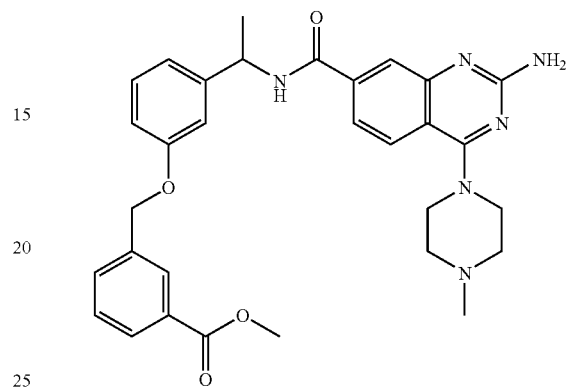

This compound was prepared using procedures analogous to those for Example 197 but using methyl 3-(bromomethyl)benzoate (Aldrich, Cat. #648116) in Step 4. The final product was purified by prep RP-HPLC (pH=2) to afford the desired compound as (0.007 g, 35%) as an amorphous white solid TFA salt. Analytical LCMS (M+H)$^+$: m/z=555.0.

Example 201

2-Amino-N-(1-{3-[(3-cyanobenzyl)oxy]phenyl}ethyl)-4-(4-methylpiperazin-1-yl)quinazoline-7-carboxamide

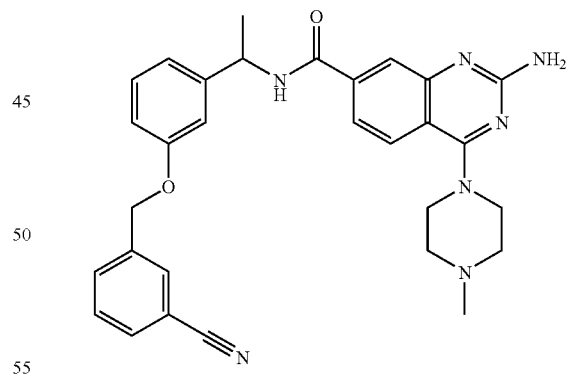

This compound was prepared using procedures analogous to those for Example 197 but using 3-(bromomethyl)benzonitrile (Aldrich, Cat. #145610) in Step 4. The final product was purified by prep RP-HPLC (pH=2) to afford the desired compound (0.006 g, 35%) as an amorphous white solid TFA salt. $^1$H NMR (400 MHz, DMSO): δ 9.19 (d, 1H), 8.05 (d, 1H), 7.89 (m, 2H), 7.78 (m, 3H), 7.58 (m, 1H), 7.25 (m, 1H), 7.04 (bs, 1H), 6.98 (dd, 1H), 6.89 (dd, 1H), 5.15 (m, 1H), 5.14 (s, 2H), 4.60 (m, 2H), 3.71)(m, 2H), 3.57 (m, 2H), 3.25 (m, 2H), 2.84 (s, 3H), 1.46 (d, 3H). Analytical LCMS (M+H)$^+$: m/z=522.0.

Example 202

2-Amino-N-(7-(3-cyanobenzyloxy)-1,2,3,4-tetrahydronaphthalen-1-yl)-4-(4-methylpiperazin-1-yl)quinazoline-7-carboxamide

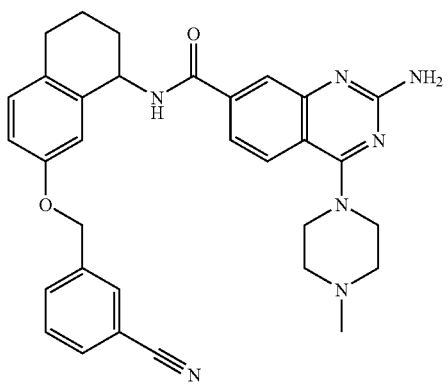 [SMILES: CN1CCN(c2nc(N)nc3cc(C(=O)NC4CCCc5ccc(OCc6cccc(C#N)c6)cc54)ccc23)CC1]

Step 1: 7-hydroxy-3,4-dihydronaphthalen-1(2H)-one

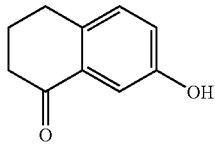 [SMILES: O=C1CCCc2ccc(O)cc21]

The 7-methoxy-1-tetralone (Aldrich, Cat. #163368) (0.75 g, 4.2 mmol) was dissolved in conc hydrobromic acid (3.0 ml) and was heated to 100° C. for 8 h. The reaction was allowed to cool to r.t. and partitioned between ethyl acetate and water. The organic layer was washed with brine, dried over magnesium sulfate and concentrated under reduced pressure to give crude 7-hydroxy-3,4-dihydronaphthalen-1(2H)-one (0.75 g, 100%) as a semisolid. Analytical LCMS (M+H)$^+$: m/z=163.0.

Step 2: 7-hydroxy-3,4-dihydronaphthalen-1(2H)-one oxime

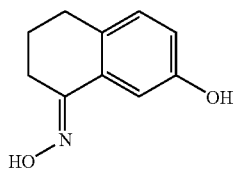 [SMILES: O/N=C1\CCCc2ccc(O)cc21]

7-Hydroxy-3,4-dihydronaphthalen-1(2H)-one (0.75 g, 4.2 mmol) was dissolved in ethanol (30 mL) and water (10 mL), then the hydroxylamine hydrochloride (0.59 g, 8.5 mmol) and sodium acetate (0.70 g, 8.5 mmol) were added. The reaction was heated to 80° C. for 2 h. The reaction was allowed to cool to r.t., concentrated under reduced pressure and the residue was partitioned between ethyl acetate and 1 N HCl. The organic layer was washed with brine, dried over magnesium sulfate and concentrated under reduced pressure to give the crude product as oil. The oil was purified by flash chromatography on a silica gel column eluting hexane: ethyl acetate gradient to give 7-hydroxy-3,4-dihydronaphthalen-1(2H)-one oxime (0.70 g, 95%) as a yellow green oil. Analytical LCMS (M+H)$^+$: m/z=178.1.

Step 3: 8-amino-5,6,7,8-tetrahydronaphthalen-2-ol

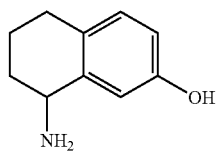 [SMILES: NC1CCCc2ccc(O)cc21]

7-hydroxy-3,4-dihydronaphthalen-1(2H)-one oxime (0.70 g, 3.2 mmol) was taken up in methanol (20.0 mL) and conc HCl (0.5 ml), degassed with nitrogen and the catalyst 10% Pd on Carbon was added. The reaction was charged with 55 Psi hydrogen in a Parr hydrogenation bottle. The reaction was shaken overnight, was filtered and concentrated under reduced pressure to give a semisolid residue. This was taken up in acetonitrile and concentrated under reduced pressure two times to give 8-amino-5,6,7,8-tetrahydronaphthalen-2-ol as HCl salt (0.70 g, 100%) as a solid residue.

Step 4: tert-butyl 7-hydroxy-1,2,3,4-tetrahydronaphthalen-1-ylcarbamate

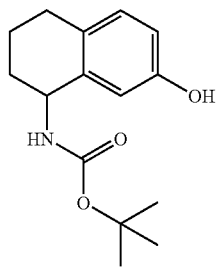 [SMILES: CC(C)(C)OC(=O)NC1CCCc2ccc(O)cc21]

8-Amino-5,6,7,8-tetrahydronaphthalen-2-ol-HCl salt (0.68 g, 3.2 mmol) was suspended in methylene chloride (25.0 mL) and N,N-diisopropylethylamine (2.96 mL, 17.0 mmol) at r.t. and the di-tert-butyldicarbonate (1.11 g, 5.11 mmol) was added portion wise over 10 min The reaction was stirred at r.t., slowly becoming an amber colored solution. This was taken up in ethyl acetate and washed with water, 1 N HCl, brine and dried over magnesium sulfate, concentrated under reduced pressure to give a crude viscous oil. The oil was purified by flash chromatography on a silica gel column eluting hexane:ethyl acetate gradient to give tert-butyl 7-hydroxy-1,2,3,4-tetrahydronaphthalen-1-ylcarbamate (0.64 g, 76%) as an oil. Analytical LCMS (M+Na)$^+$: m/z=286.1

Step 5: tert-butyl 7-(3-cyanobenzyloxy)-1,2,3,4-tetrahydronaphthalen-1-ylcarbamate

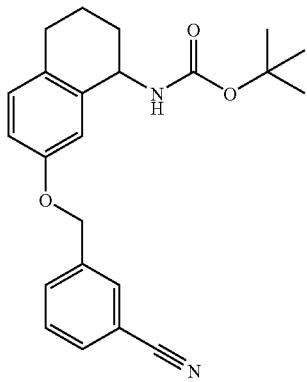 [SMILES: CC(C)(C)OC(=O)NC1CCCc2ccc(OCc3cccc(C#N)c3)cc21]

tert-Butyl (7-hydroxy-1,2,3,4-tetrahydronaphthalen-1-yl)carbamate (0.026 g, 0.10 mmol) was combined with m-cyanobenzyl bromide (Aldrich, Cat. #145610) (0.029 g, 0.15 mmol), acetonitrile (2.0 mL) and cesium carbonate (0.065 g, 0.20 mmol) and allowed to stir at r.t. overnight. This was diluted with ethyl acetate, filtered to remove the solids and concentrated under reduced pressure to give crude tert-butyl 7-(3-cyanobenzyloxy)-1,2,3,4-tetrahydronaphthalen-1-ylcarbamate (0.045 g) as a semisolid. Analytical LCMS (M+Na)$^+$: m/z=401.0.

Step 6: 3-{[(8-amino-5,6,7,8-tetrahydronaphthalen-2-yl)oxy]methyl}benzonitrile

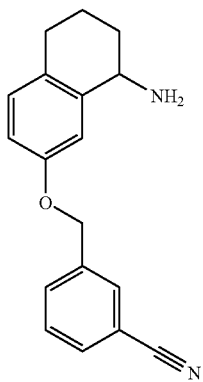 [SMILES: N#Cc1cccc(COc2ccc3c(c2)C(N)CCC3)c1]

The tert-butyl 7-(3-cyanobenzyloxy)-1,2,3,4-tetrahydronaphthalen-1-ylcarbamate (0.045 g) was taken up in 4 M HCl in dioxane (2 mL) at r.t. After stirring for 2 h. the reaction was concentrated under reduced pressure to give a residue. This residue was taken up in acetonitrile and reconcentrated under reduced pressure two times to give crude 3-{[(8-amino-5,6,7,8-tetrahydronaphthalen-2-yl)oxy]methyl}benzonitrile as HCl salt (0.035 g) as a solid residue.

Step 7: 2-amino-N-(7-(3-cyanobenzyloxy)-1,2,3,4-tetrahydronaphthalen-1-yl)-4-(4-methylpiperazin-1-yl)quinazoline-7-carboxamide N,N,N',N'-Tetramethyl-O-(7-azabenzotriazol-1-yl)uronium hexafluorophosphate (20 mg, 0.05 mmol) and N,N-diisopropylethylamine (10 uL, 0.07 mmol) were added to a solution of 2-amino-4-(4-methylpiperazin-1-yl)quinazoline-7-carboxylic acid (10 mg, 0.03 mmol) and 3-{[(8-amino-5,6,7,8-tetrahydronaphthalen-2-yl)oxy]methyl}benzonitrile HCl salt (30 mg, 0.07 mmol) in N,N-dimethylformamide (1 mL) at r.t. The reaction was stirred for 2 h. and the product was purified without workup by RP-HPLC (pH=10) to afford the desired compound (0.013 g, 30%) as an amorphous white solid. $^1$H NMR (400 MHz, DMSO): δ8.84 (d, 1H), 7.77-7.6 (m, 5H), 7.46 (dd, 1H), 7.42 (m, 1H), 6.99 (d, 1H), 6.80 (dd, 1H), 6.74 (m, 1H), 6.36 (bs, 2H), 5.12 (m, 1H), 5.02 (s, 2H), 3.51 (bs, 4H), 3.27 (s, 4H), 2.62 (m, 2H), 2.17 (s, 3H), 1.88 (m, 2H), 1.70 (m, 2H). Analytical LCMS (M+H)$^+$: m/z=548.1.

Example 203

2-Amino-N-(7-(3-methoxybenzyloxy)-1,2,3,4-tetrahydronaphthalen-1-yl)-4-(4-methylpiperazin-1-yl)quinazoline-7-carboxamide

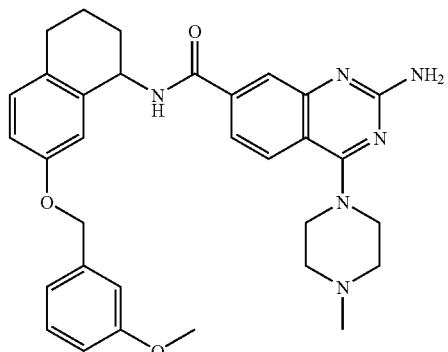

This compound was prepared using procedures analogous to those for Example 202 but using 1-(bromomethyl)-3-methoxybenzene (Aldrich, Cat. #429120) in Step 5. The final product was purified by prep RP-HPLC (pH=10) to afford the desired compound (0.015 g, 35%) as an amorphous white solid. Analytical LCMS (M+H)$^+$: m/z=553.1.

Example 204

Methyl 3-((8-(2-amino-4-(4-methylpiperazin-1-yl)quinazoline-7-carboxamido)-5,6,7,8-tetrahydronaphthalen-2-yloxy)methyl)benzoate

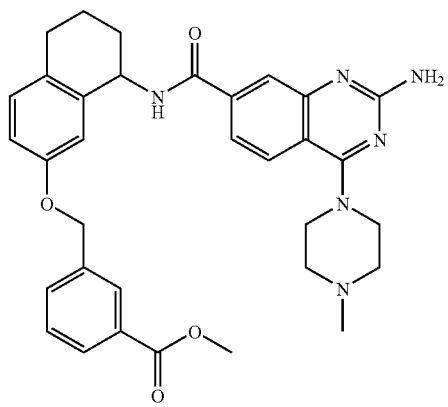 [SMILES: COC(=O)c1cccc(COc2ccc3c(c2)C(NC(=O)c2ccc4c(N5CCN(C)CC5)nc(N)nc4c2)CCC3)c1]

This compound was prepared using procedures analogous to those for Example 202 but using methyl 3-(bromomethyl)benzoate (Aldrich, Cat. #648116) in Step 5. The final product was purified by prep RP-HPLC (pH=10) to afford the desired compound (0.012 g, 30%) as an amorphous white solid. $^1$H NMR (400 MHz, DMSO): δ 8.84 (d, 1H), 7.90 (s, 1H), 7.70 (d, 1H), 7.73 (s, 1H), 7.68 (d, 1H), 7.58 (d, 1H), 7.39 (m, 2H), 6.98 (d, 1H), 6.79 (d, 1H), 6.74 (s, 1H), 6.36 (bs, 2H), 5.12 (m, 1H), 5.04 (s, 2H), 3.73 (s, 3H), 3.50 (bs, 4H), 3.26 (s, 4H), 2.62 (m, 2H), 2.18 (s, 3H), 1.89 (m, 2H), 1.74 (m, 1H). 1.67 (m, 1H). Analytical LCMS (M+H)$^+$: m/z=581.1.

Example 205

2-Amino-N-(7-(4-cyanobenzyloxy)-1,2,3,4-tetrahydronaphthalen-1-yl)-4-(4-methylpiperazin-1-yl)quinazoline-7-carboxamide

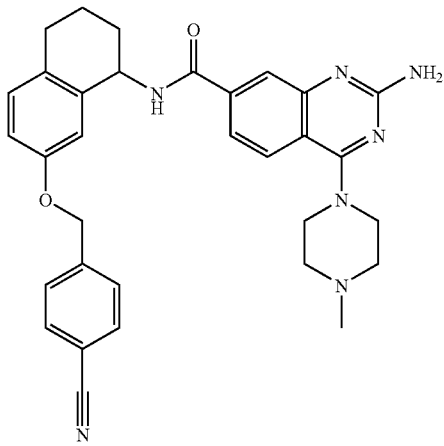 [SMILES: CN1CCN(c2nc(N)nc3cc(C(=O)NC4CCCc5ccc(OCc6ccc(C#N)cc6)cc54)ccc23)CC1]

This compound was prepared using procedures analogous to those for Example 202 but using 4-(bromomethyl)benzonitrile (Aldrich, Cat. #144061) in Step 5. The final product was purified by prep RP-HPLC (pH=10) to afford the desired compound (0.018 g, 38%) as an amorphous white solid. Analytical LCMS (M+H)$^+$: m/z=548.1.

Example 206

Methyl 4-((8-(2-amino-4-(4-methylpiperazin-1-yl)quinazoline-7-carboxamido)-5,6,7,8-tetrahydronaphthalen-2-yloxy)methyl)benzoate

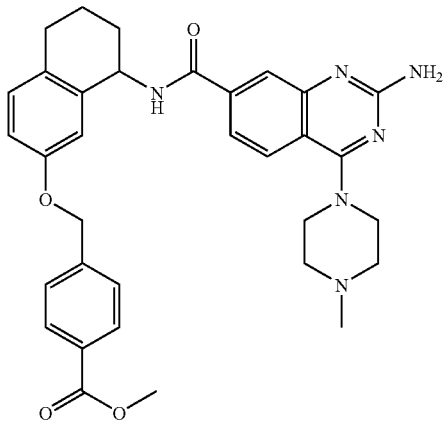 [SMILES: COC(=O)c1ccc(COc2ccc3c(c2)C(NC(=O)c2ccc4c(N5CCN(C)CC5)nc(N)nc4c2)CCC3)cc1]

This compound was prepared using procedures analogous to those for Example 202 but using methyl 4-(bromomethyl)benzoate (Aldrich, Cat. #348155) in Step 5. The final product was purified by prep RP-HPLC (pH=10) to afford the desired compound (0.010 g, 15%) as an amorphous white solid. Analytical LCMS (M+H)$^+$: m/z=581.2.

Example 207

3((2-(2-Amino-4-(4-methylpiperazin-1-yl)quinazoline-7-carbonyl)-1,2,3,4-tetrahydroisoquinolin-5-yloxy)methyl)benzonitrile

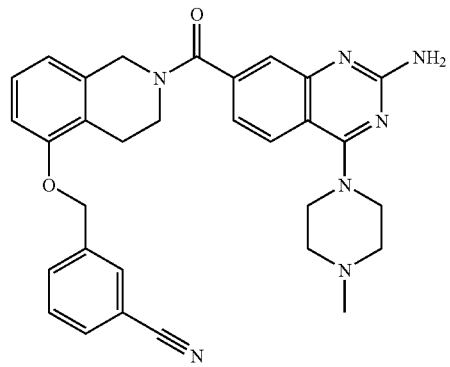 [SMILES: CN1CCN(c2nc(N)nc3cc(C(=O)N4CCc5c(cccc5OCc5cccc(C#N)c5)C4)ccc23)CC1]

Step 1: 1,2,3,4-tetrahydroisoquinolin-5-ol

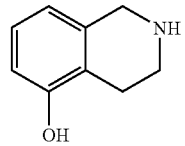 [SMILES: Oc1cccc2c1CCNC2]

Isoquinolin-5-ol (Aldrich, Cat. #H33207)(0.75 g, 5.2 mmol) was dissolved in acetic acid (20.0 mL) in a Parr shaker bottle. The reaction was degassed with nitrogen, and the platinum dioxide (0.050 g) was added. The reaction was charged to 55 Psi hydrogen and shaken. After shaking for 24 h. the reaction was complete. This was filtered to remove the catalyst and concentrated under reduced pressure give a dark amber 1,2,3,4-tetrahydroisoquinolin-5-ol (0.70 g, 90%) as an oil. Analytical LCMS (M+H)$^+$: m/z=150.1.

Step 2: tert-butyl 5-hydroxy-3,4-dihydroisoquinoline-2(1H)-carboxylate

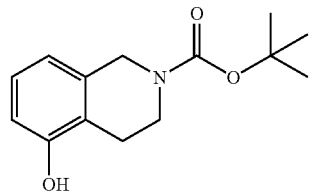 [SMILES: CC(C)(C)OC(=O)N1CCc2c(O)cccc2C1]

1,2,3,4-Tetrahydroisoquinolin-5-ol (0.70 g, 4.7 mmol) was taken up in methylene chloride (40.0 mL) and N,N-diisopropylethylamine (3.60 mL, 20.7 mmol) at r.t., and di-tert-butyl-dicarbonate (1.35 g, 6.20 mmol) in methylene chloride was added. The reaction was stirred for 2 h. The reaction was partitioned between ethyl acetate and water, the organic layer was washed with 1 N HCl, brine, dried over magnesium sulfate and concentrated under reduced pressure to give product as a semisolid. The product was purified by flash chromatography on a silica gel column eluting hexane: ethyl acetate gradient to give tert-butyl 5-hydroxy-3,4-dihydroisoquinoline-2(1H)-carboxylate (1.1 g, 85%) as a solid. Analytical LCMS (M+H-Boc)⁺: m/z=150.1.

Step 3: tert-butyl 5-(3-cyanobenzyloxy)-3,4-dihydroisoquinoline-2(1H)-carboxylate

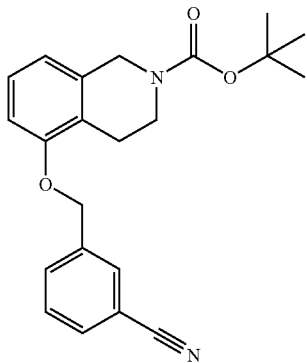 [SMILES: CC(C)(C)OC(=O)N1CCc2c(cccc2OCc2cccc(C#N)c2)C1]

tert-Butyl 5-hydroxy-3,4-dihydroisoquinoline-2(1H)-carboxylate (0.025 g, 0.10 mmol) was combined with 3-(bromomethyl)benzonitrile (Aldrich, 145610) (0.029 g, 0.15 mmol), acetonitrile (2.0 mL) and cesium carbonate (0.065 g, 0.20 mmol) and was stirred at r.t. overnight. This was diluted with ethyl acetate, filtered to remove the solids and concentrated under reduced pressure to give crude tert-butyl 5-(3-cyanobenzyloxy)-3,4-dihydroisoquinoline-2(1H)-carboxylate (0.040 g) as a semisolid. Analytical LCMS (M+Na)⁺: m/z=387.0.

Step 4: 3-[(1,2,3,4-tetrahydroisoquinolin-5-yloxy)methyl]benzonitrile

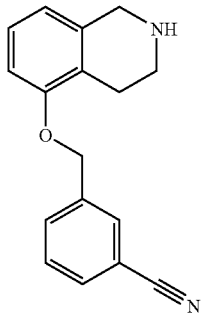 [SMILES: N#Cc1cccc(COc2cccc3c2CCNC3)c1]

tert-Butyl 5-(3-cyanobenzyloxy)-3,4-dihydroisoquinoline-2(1H)-carboxylate (0.040 g) was taken up in 4 M HCl in dioxane (2 mL) at r.t. After stirring for 2 h. the reaction was complete and this was concentrated under reduced pressure to give a residue. This was taken up in acetonitrile and reconcentrated under reduced pressure two times to give crude 3-[(1,2,3,4-tetrahydroisoquinolin-5-yloxy)methyl]benzonitrile HCl salt (0.040 g) as a solid residue. Analytical LCMS (M+H)⁺: m/z=265.0.

Step 6: 3-((2-(2-amino-4-(4-methylpiperazin-1-yl)quinazoline-7-carbonyl)-1,2,3,4-tetrahydroisoquinolin-5-yloxy)methyl)benzonitrile N,N,N',N'-Tetramethyl-O-(7-azabenzotriazol-1-yl)uronium hexafluorophosphate (20 mg, 0.05 mmol) and N,N-diisopropylethylamine (10 uL, 0.07 mmol) were added to a solution of 2-amino-4-(4-methylpiperazin-1-yl)quinazoline-7-carboxylic acid (10 mg, 0.03 mmol) and 3-[(1,2,3,4-tetrahydroisoquinolin-5-yloxy)methyl]benzonitrile HCl salt (30 mg, 0.07 mmol) in N,N-dimethylformamide (1 mL) at r.t. The reaction was stirred for 2 h. and the product was purified without workup by RP-HPLC (pH=10) to afford the desired compound (0.015 g, 33%) as an amorphous white solid. ¹H NMR (500 MHz, DMSO): δ 7.79 (s, 1H), 7.71 (m, 2H.), 7.67 (d, 1H), 7.52 (t, 1H), 7.20 (s, 1), 7.05 (t, 1H), 6.96 (d, 1H), 6.83 (d, 1H), 6.70 (bs, 1H.), 6.02 (s, 2H.), 5.10 (s, 2H), 4.61 (m, 2H), 3.54 (m, 4H), 2.96 (s, 4H), 2.74 (m, 2H.), 2.44 (m, 2H.), 2.18 (s, 3H). (NMR sample heated to 90 c); Analytical LCMS (M+H)⁺: m/z=534.1.

Example 208

(2-Amino-4-(4-methylpiperazin-1-yl)quinazolin-7-yl)(5-(3-methoxybenzyloxy)-3,4-dihydroisoquinolin-2(1H)-yl)methanone

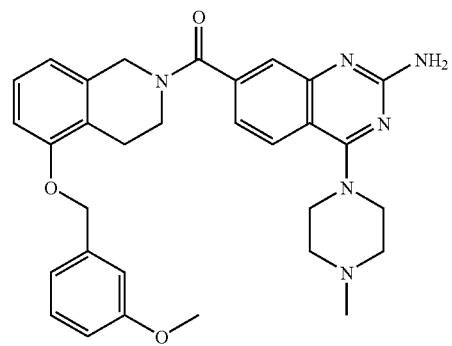 [SMILES: COc1cccc(COc2cccc3c2CCN(C(=O)c2ccc4c(N5CCN(C)CC5)nc(N)nc4c2)C3)c1]

This compound was prepared using procedures analogous to those for Example 207 but using 1-(bromomethyl)-3-methoxybenzene (Aldrich, Cat. #429120) in Step 3. The final product was purified by prep RP-HPLC (pH=10) to afford the desired compound (0.012 g, 15%) as an amorphous white solid. Analytical LCMS (M+H)⁺: m/z=539.0.

Example 209

Methyl 3-((2-(2-amino-4-(4-methylpiperazin-1-yl)quinazoline-7-carbonyl)-1,2,3,4-tetrahydroisoquinolin-5-yloxy)methyl)benzoate

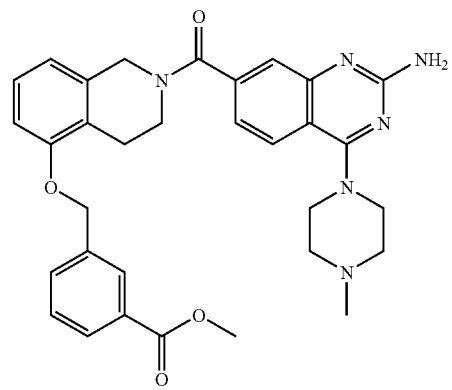 [SMILES: COC(=O)c1cccc(COc2cccc3c2CCN(C(=O)c2ccc4c(N5CCN(C)CC5)nc(N)nc4c2)C3)c1]

This compound was prepared using procedures analogous to those for Example 207 but using methyl 3-(bromomethyl)

benzoate (Aldrich, Cat. #648116) in Step 3. The final product was purified by prep RP-HPLC (pH=10) to afford the desired compound (0.018 g, 20%) as an amorphous white solid. $^1$H NMR (500 MHz, DMSO): δ 7.96 (s, 1H), 7.83 (d, 1H), 7.71 (d, 1H), 7.64 (d, 1H), 7.46 (t, 1H), 7.20 (s, 1H), 7.06 (t, 1H), 6.96 (d, 1H), 6.85 (d, 1H), 6.69 (bs, 2H.), 6.01 (s, 2H.), 5.12 (s, 2H.), 4.61 (m, 2H.), 3.78 (s, 3H), 3.54 (m, 4H), 2.95 (s, 4H), 2.72 (m, 2H.), 2.44 (m, 2H.), 2.18 (s, 3H) (NMR sample heated to 90 C); Analytical LCMS (M+H)$^+$: m/z=567.1.

Example 210

4-((2-(2-Amino-4-(4-methylpiperazin-1-yl)quinazoline-7-carbonyl)-1,2,3,4-tetrahydroisoquinolin-5-yloxy)methyl)benzonitrile

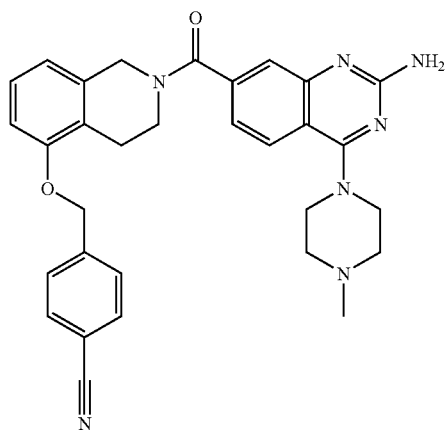 [SMILES: CN1CCN(c2nc(N)nc3cc(C(=O)N4CCc5c(cccc5OCc5ccc(C#N)cc5)C4)ccc23)CC1]

This compound was prepared using procedures analogous to those for Example 207 but using 4-(bromomethyl)benzonitrile (Aldrich, Cat. #144061) in Step 3. The final product was purified by prep RP-HPLC (pH=10) to afford the desired compound (0.010 g, 15%) as an amorphous white solid. Analytical LCMS (M+H)$^+$: m/z=534.0.

Example 211

Methyl 4-((2-(2-amino-4-(4-methylpiperazin-1-yl)quinazoline-7-carbonyl)-1,2,3,4-tetrahydroisoquinolin-5-yloxy)methyl)benzoate

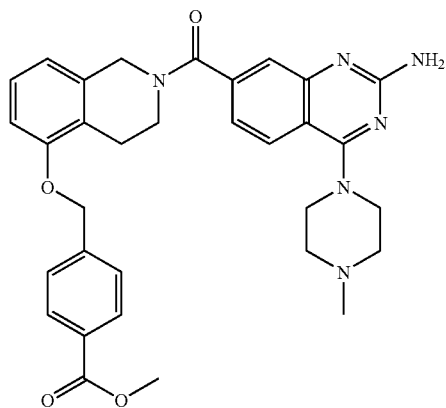 [SMILES: COC(=O)c1ccc(COc2cccc3c2CCN(C(=O)c2ccc4c(N5CCN(C)CC5)nc(N)nc4c2)C3)cc1]

This compound was prepared using procedures analogous to those for Example 207 but using methyl 4-(bromomethyl) benzoate (Aldrich, Cat. #348155) in Step 3. The final product was purified by prep RP-HPLC (pH=10) to afford the desired compound (0.011 g, 16%) as an amorphous white solid. Analytical LCMS (M+H)$^+$: m/z=567.1.

Example AA

H4 Membrane Binding Assay

Recombinant HEK293SFM cells expressing human H1, H2, H3, H4 or mouse H4 were harvested (Packard Filtermate Harvester) in ice-cold Tris-HCl, (50 mM, pH 7.5, Sigma) with protease inhibitors (Roche) and homogenized with a Polytron homogenizer. The homogenate was centrifuged for 5 minutes at 1000 g to remove nuclei and unbroken cells. The supernatant was centrifuged at 50000 g for 30 minutes, and the resulting pellet was re-suspended in ice-cold Tris-HCl (50 mM, pH 7.5). For binding displacement assays, the H1, H2, H3 and H4 membrane preparations (20-40 μg) were incubated in a total volume of 150 μL of Tris-HCl (50 mM, pH 7.5), with 2.5 nM $^3$H-Pyrilamine (Amersham), 2.5 nM $^3$H-Tiotidine (Perkin Elmer), 1 nM R(-)-α-Methy[$^3$H]histamine (Amersham) or 10 nM $^3$H-Histamine (Amersham) respectively, in the presence or absence of different amounts of test compounds for 1.5 hr at room temperature. Nonspecific binding was determined by inclusion of 1000× unlabeled ligands. The bound radioactivity was separated by filtration through polyethyleneimine-treated GF/B filters (Perkin Elmer). The filters were washed eight times with ice-cold Tris-HCl (50 mM, pH 7.5), and radioactivity retained on the filters was measured by liquid scintillation counting. The binding data were evaluated with Prism.

Example BB

Ca$^{2+}$Flux Assay

HEK-293 cells were transiently cotransfected in DMEM and 10% FCS with human H4 and G$_{α16}$ cDNAs using lipofectAMINE 2000 reagent. Twenty-four hours after transfection, the cells were harvested and reseeded at 5×10$^4$ cells/50 μL/well in DMEM and 10% FCS in poly(D-lysine)-treated, 384, clear-bottomed black plates. Forty eight hours after transfection, the cells were washed with Hank's balanced salt solution and loaded for 1 hr at 37° C. with Ca3 dye. Test compounds were then evaluated for their inhibitory activity against histamine-induced intracellular Ca$^{2+}$ mobilization using a florescence imaging plate reader. All experiments were performed in duplicate. The data (relative fluorescent unit change) was analyzed with Prizm.

Example CC

H4 Eosinophil Chemotaxis Assay

Human Whole Blood (Incyte Corp, Wilmington Del., or Biological Specialty, Colmar, Pa.) was obtained from normal, drug free donors. Polymorphnuclear leukocytes (PMNs) were isolated via density gradient centrifugation, using ficoll (Amersham Biologicals, Uppsala, Sweden) to make the gradient. Eosinophils are further isolated via MACS separation column (Miltenyi Biotec, Germany) and rested overnight at 4° C. 2e5 cells in 200 μL RPMI Media (Vitrogen/Gibco, Carlsbad, Calif.) with or without various concentrations of compound were loaded in the wells on top of an 8 micron polycarbonate filter in a 96 well modified Boyden chamber (Neuroprobe, Gaithersburg, Md.). Beneath the filter, 10 nM histamine (R&D Systems, Minneapolis, Minn.) with or without compound, or media was placed in a corresponding 96-well plate. The sealed chambers were incubated for 2 hours at 37° C., 5% $CO_2$. Filters were washed, Geimsa (Sigma, St Louis, Mo.) stained, and the number of eosinophils that migrated toward the histamine in the bottom chamber was counted by microscopy. The ability of the compound to antagonize H4-mediated chemotaxis was reported as the inhibitor concentration required for 50% inhibition ($IC_{50}$ values) of specific migration to histamine. Specific migration is defined as the total migration minus the background migration.

The $IC_{50}$ values for the example compounds of invention with respect histamine H4 receptor are provided in Table A1 as follows.

TABLE A1

| Compound Example Number | H4 Binding Assay: $IC_{50}$ (nM) |
|---|---|
| Example 1 | 198 |
| Example 2 | 172 |
| Example 3 | 170 |
| Example 4 | 267 |
| Example 5 | 20.8 |
| Example 6 | 37.8 |
| Example 7 | 43.3 |
| Example 8 | 13.2 |
| Example 9 | 301 |
| Example 10 | 53.4 |
| Example 11 | 43 |
| Example 12 | 23.4 |
| Example 13 | 57.2 |
| Example 14 | 23.1 |
| Example 15 | 39 |
| Example 16 | 48 |
| Example 17 | 199 |
| Example 18 | 34 |
| Example 19 | 508 |
| Example 20 | 19.6 |
| Example 21 | 105 |
| Example 22 | 128 |
| Example 23 | 384 |
| Example 24 | 565 |
| Example 25 | 579 |
| Example 26 | 495 |
| Example 27 | 896 |
| Example 28 | 171 |
| Example 29 | 157 |
| Example 30 | 492 |
| Example 31 | 355 |
| Example 32 | 334 |
| Example 33 | 190 |
| Example 34 | 106 |
| Example 35 | 287 |
| Example 36 | 126 |
| Example 37 | 129 |
| Example 38 | 106 |
| Example 39 | 186 |
| Example 40 | 16 |
| Example 41 | 28 |
| Example 42 | 103 |
| Example 43 | 58 |
| Example 44 | 118 |
| Example 45 | 60 |
| Example 46 | 70 |
| Example 47 | 27 |
| Example 48 | 99 |
| Example 49 | 47 |
| Example 50 | 58 |
| Example 51 | 63 |
| Example 52 | 130 |
| Example 53 | 107 |
| Example 54 | 439 |
| Example 55 | 120 |
| Example 56 | 210 |
| Example 57 | 93 |
| Example 58 | 165 |
| Example 59 | 19 |
| Example 60 | 497 |
| Example 61 | 70 |
| Example 62 | 24 |
| Example 63 | 37 |
| Example 64 | 43 |
| Example 65 | 25 |
| Example 66 | 44 |
| Example 67 | 110 |
| Example 68 | 38 |
| Example 69 | 33 |
| Example 70 | 361 |
| Example 71 | 66 |
| Example 72 | 419 |
| Example 73 | 357 |
| Example 74 | 123 |
| Example 75 | 44 |
| Example 76 | 77 |
| Example 77 | 95 |
| Example 78 | 250 |
| Example 79 | 364 |
| Example 80 | 232 |
| Example 81 | 163 |
| Example 82 | 67 |
| Example 83 | 38 |
| Example 84 | 744 |
| Example 85 | 57 |
| Example 86 | 49 |
| Example 87 | 218 |
| Example 88 | 135 |
| Example 89 | 77 |
| Example 90 | 143 |
| Example 91 | 63 |
| Example 92 | 50 |
| Example 93 | 43 |
| Example 94 | 149 |
| Example 95 | 24 |
| Example 96 | 52 |
| Example 97 | 73 |
| Example 98 | 61 |
| Example 99 | 31 |
| Example 100 | 45 |
| Example 101 | 99 |
| Example 102 | 83 |
| Example 103 | 84 |
| Example 104 | 259 |
| Example 105 | 81 |
| Example 106 | 69 |
| Example 107 | 34 |
| Example 108 | 33 |
| Example 109 | 9.6 |
| Example 110 | 86 |
| Example 111 | 9.5 |
| Example 112 | 337 |
| Example 113 | 147 |
| Example 114 | 109 |
| Example 115 | 33 |
| Example 116 | 38 |
| Example 117 | 183 |
| Example 118 | 178 |
| Example 119 | 70 |
| Example 120 | 34 |
| Example 121 | 39 |
| Example 122 | 22 |
| Example 123 | 105 |
| Example 124 | 36 |
| Example 125 | 92 |
| Example 126 | 569 |
| Example 127 | 253 |
| Example 128 | 45 |
| Example 129 | 156 |
| Example 130 | 71 |
| Example 131 | 17 |
| Example 132 | 139 |
| Example 134 | 29 |

TABLE A1-continued

| Compound Example Number | H4 Binding Assay: IC$_{50}$ (nM) |
|---|---|
| Example 135 | 70 |
| Example 136 | 59 |
| Example 137 | 42 |
| Example 138 | 23 |
| Example 139 | 25 |
| Example 140 | 42 |
| Example 141 | 71 |
| Example 142 | 34 |
| Example 143 | 37 |
| Example 144 | 190 |
| Example 145 | 34 |
| Example 145A | 519 |
| Example 145B | 26 |
| Example 146 | 65 |
| Example 147 | 71 |
| Example 148 | 18 |
| Example 149 | 40 |
| Example 150 | 44 |
| Example 151 | 69 |
| Example 152 | 10 |
| Example 153 | 19 |
| Example 154 | 14 |
| Example 155 | 55 |
| Example 156 | 41 |
| Example 157 | 22 |
| Example 158 | 6.6 |
| Example 159 | 26 |
| Example 160 | 52 |
| Example 161 | 31 |
| Example 162 | 10 |
| Example 163 | 66 |
| Example 164 | 57 |
| Example 165 | 16 |
| Example 166 | 31 |
| Example 167 | 15 |
| Example 168 | 9.6 |
| Example 169 | 23 |
| Example 170 | 23 |
| Example 171 | 13 |
| Example 172 | 26 |
| Example 173 | 67 |
| Example 174 | 23 |
| Example 175 | 18 |
| Example 176 | 51 |
| Example 177 | 56 |
| Example 178 | 7.5 |
| Example 179 | 46 |
| Example 180 | 25 |
| Example 181 | 16 |
| Example 182 | 56 |
| Example 183 | 65 |
| Example 184 | 43 |
| Example 185 | 8.4 |
| Example 186 | 7.9 |
| Example 187 | 41 |
| Example 188 | 13 |
| Example 189 | 6.6 |
| Example 190 | 11 |
| Example 191 | 20 |
| Example 192 | 6.3 |
| Example 193 | 7.2 |
| Example 194 | 8.7 |
| Example 195 | 3.4 |
| Example 196 | 4.4 |
| Example 197 | 7.1 |
| Example 198 | 34 |
| Example 199 | 63 |
| Example 200 | 7.1 |
| Example 201 | 14 |
| Example 202 | 9.2 |
| Example 203 | 17 |
| Example 204 | 9.3 |
| Example 205 | 11 |
| Example 206 | 24 |
| Example 207 | 36 |
| Example 208 | 24 |
| Example 209 | 36 |

TABLE A1-continued

| Compound Example Number | H4 Binding Assay: IC$_{50}$ (nM) |
|---|---|
| Example 210 | 41 |
| Example 211 | 63 |

Various modifications of the invention, in addition to those described herein, will be apparent to those skilled in the art from the foregoing description. Such modifications are also intended to fall within the scope of the appended claims. Each reference cited in the present application is herein incorporated by reference in its entirety.

What is claimed is:

1. A compound of Formula I:

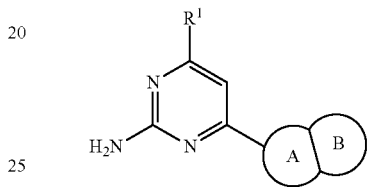

I or pharmaceutically acceptable salt thereof or N-oxide thereof or quaternary ammonium salt thereof, wherein:

the moiety of

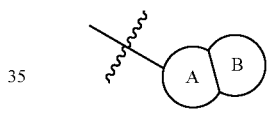

is a moiety of:

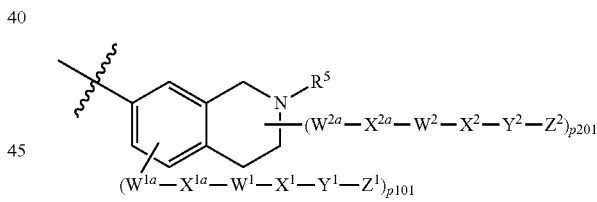

wherein:

p101 is 0, 1, or 2;
p201 is 0, 1, or 2;
$R^5$ is H or $-W^{2a}-X^{2a}-W^2-X^2-Y^2-Z^2$
  wherein $-W^{1a}-X^{1a}-W^1-X^1-Y^1-Z^1$ is other than H;
  wherein $-W^{2a}-X^{2a}-W^2-X^2-Y^2-Z^2$ is other than H;
$R^1$ is $NR^2R^3$, wherein $R^2$ and $R^3$ together with the N atom to which they are attached form a 4-10 membered heterocycloalkyl group wherein each of the ring-forming atoms of the 4-10 membered heterocycloalkyl group is independently selected from C, N, O, and S, and wherein the 4-10 membered heterocycloalkyl group is substituted with 0, 1, 2, 3, 4, 5, 6, 7, or 8 $R^4$;
each $R^4$ is independently selected from halo, CN, $C_{1-6}$ alkyl, $C_{1-6}$ haloalkyl, $C_{3-7}$ cycloalkyl, OH, oxo, $C_{1-6}$ alkoxy, $C_{1-6}$ haloalkoxy, $NH_2$, $NH(C_{1-4}$ alkyl), $NH(C_{3-7}$ cycloalkyl), and $N(C_{1-4}$ alkyl)$_2$, wherein each of the $C_{1-6}$ alkyl and $C_{3-7}$ cycloalkyl is substituted with 0, 1, 2, or 3 substituents each independently selected from halo, OH, CN, $NH_2$, $NH(C_{1-4}$ alkyl), and $N(C_{1-4}$ alkyl$)_2$;

$W^{1a}$, $W^{2a}$, $W^1$, and $W^2$ are each, independently, selected from absent, $C_{1-6}$ alkylenyl, $C_{2-6}$ alkenylenyl, $C_{2-6}$ alkynylenyl, $(CR^{11a}R^{11b})_{p1}O(CR^{11a}R^{11b})_{p2}$, $(CR^{11a}R^{11b})_{p1}S(CR^{11a}R^{11b})_{p2}$, $(CR^{11a}R^{11b})_{p1}NR^e(CR^{11a}R^{11b})_{p2}$, $(CR^{11a}R^{11b})_{p1}C(O)(CR^{11a}R^{11b})_{p2}$, $(CR^{11a}R^{11b})_{p1}C(S)(CR^{11a}R^{11b})_{p2}$, $(CR^{11a}R^{11b})_{p1}C(O)(CR^{11a}R^{11b})_{p2}$, $(CR^{11a}R^{11b})_{p1}C(O)NR^e(CR^{11a}R^{11b})_{p2}$, $(CR^{11a}R^{11b})_{p1}C(S)NR^e(CR^{11a}R^{11b})_{p2}$, $(CR^{11a}R^{11b})_{p1}S(O)(CR^{11a}R^{11b})_{p2}$, $(CR^{11a}R^{11b})_{p1}S(O)_2(CR^{11a}R^{11b})_{p2}$, $(CR^{11a}R^{11b})_{p1}S(O)NR^e(CR^{11a}R^{11b})_{p2}$, $(CR^{11a}R^{11b})_{p1}S(O)_2NR^e(CR^{11a}R^{11b})_{p2}$, $(CR^{11a}R^{11b})_{p1}C(=NR^g)NR^e(CR^{11a}R^{11b})_{p2}$, $O(CR^{11a}R^{11b})_{q1}C(O)$, $S(CR^{11a}R^{11b})_{q1}C(O)$, $NR^e(CR^{11a}R^{11b})_{q1}C(O)$, $C(O)(CR^{11a}R^{11b})_{q1}C(O)$, and $O(CR^{11a}R^{11b})_{q1}O$, wherein each of the $C_{1-6}$ alkylenyl, $C_{2-6}$ alkenylenyl and $C_{2-6}$ alkynylenyl is substituted with 0, 1, 2, 3, 4, 5, 6, 7, or 8 substituents each independently selected from halo, CN, $NO_2$, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cC(O)R^b$, $NR^cC(O)NR^cR^d$, $NR^cC(O)OR^a$, $C(=NR^g)NR^cR^d$, $NR^cC(=NR^g)NR^cR^d$, $NR^cS(O)_2NR^cR^d$, $S(O)R^b$, $S(O)NR^cR^d$, $S(O)_2R^b$, $NR^cS(O)_2R^b$, and $S(O)_2NR^cR^d$;

$X^{1a}$, $X^{2a}$, $X^1$, and $X^2$ are each, independently, selected from absent, $C_{1-6}$ alkylenyl, $C_{2-6}$ alkenylenyl, $C_{2-6}$ alkynylenyl, aryl, cycloalkyl, heteroaryl, heterocycloalkyl, arylalkyl, heteroarylalkyl, cycloalkylalkyl, and heterocycloalkylalkyl, wherein each of said $C_{1-6}$ alkylenyl, $C_{2-6}$ alkenylenyl, $C_{2-6}$ alkynylenyl, aryl, cycloalkyl, heteroaryl, heterocycloalkyl, arylalkyl, heteroarylalkyl, cycloalkylalkyl, and heterocycloalkylalkyl is substituted with 0, 1, 2, 3, 4, 5, 6, 7, or 8 substituents each independently selected from $R^{XX}$, halo, CN, $NO_2$, $OR^a$, $SR^a$, $SF_5$, $C(O)R^b$, $C(O)NR^cR^d$, $C(O)OR^a$, $OC(O)R^b$, $OC(O)NR^cR^d$, $NR^cR^d$, $NR^cC(O)R^b$, $NR^cC(O)NR^cR^d$, $NR^cC(O)OR^a$, $C(=NR^g)NR^cR^d$, $NR^cC(=NR^g)NR^cR^d$, $NR^cS(O)_2NR^cR^d$, $S(O)R^b$, $S(O)NR^cR^d$, $S(O)_2R^b$, $NR^cS(O)_2R^b$, and $S(O)_2NR^cR^d$;

$Y^1$ and $Y^2$ are each, independently, selected from absent, $C_{1-6}$ alkylenyl, $C_{2-6}$ alkenylenyl, $C_{2-6}$ alkynylenyl, $(CR^{12a}R^{12b})_{p3}O(CR^{12a}R^{12b})_{p4}$, $(CR^{12a}R^{12b})_{p3}S(CR^{12a}R^{12b})_{p4}$, $(CR^{12a}R^{12b})_{p3}NR^e(CR^{12a}R^{12b})_{p4}$, $(CR^{12a}R^{12b})_{p3}C(O)(CR^{12a}R^{12b})_{p4}$, $(CR^{12a}R^{12b})_{p3}C(S)(CR^{12a}R^{12b})_{p4}$, $(CR^{12a}R^{12b})_{p3}C(O)O(CR^{12a}R^{12b})_{p4}$, $(CR^{12a}R^{12b})_{p3}C(O)NR^e(CR^{12a}R^{12b})_{p4}$, $(CR^{12a}R^{12b})_{p3}C(S)NR^e(CR^{12a}R^{12b})_{p4}$, $(CR^{12a}R^{12b})_{p3}S(O)(CR^{12a}R^{12b})_{p4}$, $(CR^{12a}R^{12b})_{p3}S(O)_2(CR^{12a}R^{12b})_{p4}$, $(CR^{12a}R^{12b})_{p3}S(O)NR^e(CR^{12a}R^{12b})_{p4}$, $(CR^{12a}R^{12b})_{p3}S(O)_2NR^e(CR^{12a}R^{12b})_{p4}$, $(CR^{12a}R^{12b})_{p3}C(=NR^g)NR^e(CR^{12a}R^{12b})_{p4}$, $O(CR^{12a}R^{12b})_{q2}C(O)$, $S(CR^{12a}R^{12b})_{q2}C(O)$, $NR^e(CR^{12a}R^{12b})_{q2}C(O)$, and $O(CR^{12a}R^{12b})_{q2}O$, wherein each of the $C_{1-6}$ alkylenyl, $C_{2-6}$ alkenylenyl, and $C_{2-6}$ alkynylenyl is substituted with 0, 1, 2, 3, 4, 5, 6, 7, or 8 substituents independently selected from $C_{1-6}$ alkyl, $C_{1-6}$ haloalkyl, $C_{2-6}$ alkenyl, $C_{2-6}$ alkynyl, halo, CN, $NO_2$, $OR^a$, $SR^a$, $SF_5$, $C(O)R^b$, $C(O)NR^cR^d$, $C(O)OR^a$, $OC(O)R^b$, $OC(O)NR^cR^d$, $NR^cR^d$, $NR^cC(O)R^b$, $NR^cC(O)NR^cR^d$, $NR^cC(O)OR^a$, $C(=NR^g)NR^cR^d$, $NR^cC(=NR^g)NR^cR^d$, $NR^cS(O)_2NR^cR^d$, $S(O)R^b$, $S(O)NR^cR^d$, $S(O)_2R^b$, $NR^cS(O)_2R^b$, and $S(O)_2NR^cR^d$;

$Z^1$ and $Z^2$ are each, independently, selected from H, halo, CN, $NO_2$, $OR^a$, $SR^a$, $SF_5$, $C(O)R^b$, $C(O)NR^cR^d$, $C(O)OR^a$, $OC(O)R^b$, $OC(O)NR^cR^d$, $NR^cR^d$, $NR^cC(O)R^b$, $NR^cC(O)NR^cR^d$, $NR^cC(O)OR^a$, $C(=NR^g)NR^cR^d$, $NR^cC(=NR^g)NR^cR^d$, $NR^cS(O)_2NR^cR^d$, $S(O)R^b$, $S(O)NR^cR^d$, $S(O)_2R^b$, $NR^cS(O)_2R^b$, $S(O)_2NR^cR^d$, $C_{1-6}$ alkyl, $C_{1-6}$ haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl, and heterocycloalkylalkyl, wherein each of the $C_{1-6}$ alkyl, $C_{1-6}$ haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl, and heterocycloalkylalkyl is substituted with 0, 1, 2, 3, 4, 5, 6, 7, or 8 substituents each independently selected from $R^{ZZ}$, halo, CN, $NO_2$, $OR^a$, $SR^a$, $SF_5$, $C(O)R^b$, $C(O)NR^cR^d$, $C(O)OR^a$, $OC(O)R^b$, $OC(O)NR^cR^d$, $NR^cR^d$, $NR^cC(O)R^d$, $NR^cC(O)OR^a$, $NR^cS(O)_2R^b$, $NR^cS(O)_2NR^cR^d$; $S(O)R^b$, $S(O)NR^cR^d$, $S(O)_2R^b$, and $S(O)_2NR'R^d$;

$R^{11a}$, $R^{11b}$, $R^{12a}$, and a $R^{12b}$ are each, independently, selected from H, halo, $C_{1-6}$ alkyl, $C_{2-6}$ alkenyl, $C_{2-6}$ alkynyl, $C_{1-6}$ haloalkyl, cycloalkyl, heterocycloalkyl, aryl, heteroaryl, arylalkyl, heteroarylalkyl, cycloalkylalkyl, heterocycloalkylalkyl, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{b1}$, $NR^{c1}C(O)NR^{c1}R^{d1}$, $NR^{c1}C(O)OR^{a1}$, $C(=NR^{g1})NR^{c1}R^{d1}$, $NR^{c1}C(=NR^{g1})NR^{c1}R^{d1}$, $NR^{c1}S(O)_2NR^{c1}R^{d1}$, $S(O)R^{b1}$, $S(O)NR^{c1}R^{d1}$, $S(O)_2R^{b1}$, $NR^{c1}S(O)_2R^{b1}$, and $S(O)_2NR^{c1}R^{d1}$, wherein each of said $C_{1-6}$ alkyl, $C_{2-6}$ alkenyl, $C_{2-6}$ alkynyl, $C_{1-6}$ haloalkyl, cycloalkyl, heterocycloalkyl, aryl, heteroaryl, arylalkyl, heteroarylalkyl, cycloalkylalkyl, and heterocycloalkylalkyl is substituted with 0, 1, 2, 3, 4, or 5 substituents each independently selected from halo, $C_{1-6}$ alkyl, $C_{2-6}$ alkenyl, $C_{2-6}$ alkynyl, $C_{1-6}$ haloalkyl, cycloalkyl, heterocycloalkyl, aryl, heteroaryl, arylalkyl, heteroarylalkyl, cycloalkylalkyl, heterocycloalkylalkyl, CN, $NO_2$, $OR^{a1}$, $SR^{a1}$, $SF_5$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{b1}$, $NR^{c1}C(O)NR^{c1}R^{d1}$, $NR^{c1}C(O)OR^{a1}$, $C(=NR^g)NR^{c1}R^{d1}$, $NR^{c1}C(=NR^g)NR^{c1}R^{d1}$, $NR^{c1}S(O)_2NR^{c1}R^{d1}$, $S(O)R^{b1}$, $S(O)NR^{c1}R^{d1}$, $S(O)_2R^{b1}$, $NR^{c1}S(O)_2R^{b1}$, and $S(O)_2NR^{c1}R^{d1}$;

each $R^{XX}$ is independently selected from $C_{1-6}$ alkyl, $C_{1-6}$ haloalkyl, arylalkyl, heteroarylalkyl, cycloalkylalkyl, heterocycloalkylalkyl, $C_{2-6}$ alkenyl, $C_{2-6}$ alkynyl, aryl, cycloalkyl, heteroaryl, and heterocycloalkyl, each substituted with 0, 1, 2, 3, 4, or 5 substituents each independently selected from $C_{1-6}$ alkyl, $C_{1-6}$ haloalkyl, arylalkyl, heteroarylalkyl, cycloalkylalkyl, heterocycloalkylalkyl, $C_{2-6}$ alkenyl, $C_{2-6}$ alkynyl, aryl, cycloalkyl, heteroaryl, heterocycloalkyl, halo, CN, $NO_2$, $OR^{a2}$, $SR^{a2}$, $SF_5$, $C(O)R^{b2}$, $C(O)NR^{c2}R^{d2}$, $C(O)OR^{a2}$, $OC(O)R^{b2}$, $OC(O)NR^{c2}R^{d2}$, $NR^{c2}R^{d2}$, $NR^{c2}C(O)R^{b2}$, $NR^{c2}C(O)NR^{c2}R^{d2}$, $NR^{c2}C(O)OR^{a2}$, $C(=NR^{g2})NR^{c2}R^{d2}$, $NR^{c2}C(=NR^{g2})NR^{c2}R^{d2}$, $NR^{c2}S(O)_2NR^{c2}R^{d2}$, $S(O)R^{b2}$, $S(O)NR^{c2}R^{d2}$, $S(O)_2R^{b2}$, $NR^{c2}S(O)_2R^{b2}$, and $S(O)_2NR^{c2}R^{d2}$;

each $R^{ZZ}$ is independently selected from $C_{1-6}$ alkyl, $C_{1-6}$ haloalkyl, arylalkyl, heteroarylalkyl, cycloalkylalkyl, heterocycloalkylalkyl, $C_{2-6}$ alkenyl, $C_{2-6}$ alkynyl, aryl, cycloalkyl, heteroaryl, and heterocycloalkyl, each substituted with 0, 1, 2, 3, 4, or 5 substituents each independently selected from $C_{1-6}$ alkyl, $C_{1-6}$ haloalkyl, arylalkyl, heteroarylalkyl, cycloalkylalkyl, heterocycloalkylalkyl, $C_{2-6}$ alkenyl, $C_{2-6}$ alkynyl, aryl, cycloalkyl, heteroaryl, heterocycloalkyl, halo, CN, $NO_2$, $OR^{a3}$, $SR^{a3}$, $SF_5$, $C(O)R^{b3}$, $C(O)N^{c3}R^{d3}$, $C(O)OR^{a3}$, $OC(O)R^{b3}$, $OC(O)N^{c3}R^{d3}$, $N^{c3}R^{d3}$, $NR^{c3}C(O)R^{b3}$, $NR^{c3}(O)NR^{c3}R^{d3}$, $NR^{c3}C(O)OR^{a3}$, $C(=NR^{g3})NR^{c3}R^{d3}$, $NR^{c3}C(=NR^{g3})NR^{c3}R^{d3}$, $NR^{c3}S(O)_2$ $NR^{c3}R^{d3}$, $S(O)R^{b3}$, $S(O)NR^{c3}R^{d3}$, $S(O)_2R^{b3}$, $NR^{c3}S(O)_2R^{b3}$, and $S(O)_2NR^{c3}R^{d3}$;

$R^a$, $R^{a1}$, $R^{a2}$, and $R^{a3}$, are each, independently, selected from H, $C_{1-6}$ alkyl, $C_{1-6}$ haloalkyl, arylalkyl, heteroarylalkyl, cycloalkylalkyl, heterocycloalkylalkyl, $C_{2-6}$ alkenyl, $C_{2-6}$ alkynyl, aryl, cycloalkyl, heteroaryl and heterocycloalkyl, wherein each of the $C_{1-6}$ alkyl, $C_{1-6}$ haloalkyl, arylalkyl, heteroarylalkyl, cycloalkylalkyl, heterocycloalkylalkyl, $C_{2-6}$ alkenyl, $C_{2-6}$ alkynyl, aryl, cycloalkyl, heteroaryl and heterocycloalkyl is substituted with 0, 1, 2, 3, 4, or 5 substituents each independently selected from OH, CN, amino, $C_{1-6}$ alkylamino, $C_{2-8}$ dialkylamino, halo, $C_{1-6}$ alkyl, $C_{1-6}$ haloalkyl, $C_{1-6}$ hydroxylalkyl, $C_{1-6}$ cyanoalkyl, $C_{1-6}$ alkoxy, $C_{1-6}$ haloalkoxy, $C_{2-8}$ alkoxyalkoxy, aryl, arylalkyl, heteroaryl, heteroarylalkyl, cycloalkyl, and heterocycloalkyl;

$R^b$, $R^{b1}$, $R^{b2}$, and $R^{b3}$, are each, independently, selected from H, $C_{1-6}$ alkyl, $C_{1-6}$ haloalkyl, arylalkyl, heteroarylalkyl, cycloalkylalkyl, heterocycloalkylalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl and heterocycloalkylalkyl, wherein each of the $C_{1-6}$ alkyl, $C_{1-6}$ haloalkyl, arylalkyl, heteroarylalkyl, cycloalkylalkyl, heterocycloalkylalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl and heterocycloalkylalkyl is substituted with 0, 1, 2, 3, 4, or 5 substituents each independently selected from OH, CN, amino, $C_{1-6}$ alkylamino, $C_{2-8}$ dialkylamino, halo, $C_{1-6}$ alkyl, $C_{1-6}$ haloalkyl, $C_{1-6}$ hydroxylalkyl, $C_{1-6}$ cyanoalkyl, $C_{1-6}$ alkoxy, $C_{1-6}$ haloalkoxy, $C_{2-8}$ alkoxyalkoxy, aryl, arylalkyl, heteroaryl, heteroarylalkyl, cycloalkyl, and heterocycloalkyl;

$R^c$ and $R^d$ are independently selected from H, $C_{1-6}$ alkyl, $C_{1-6}$ haloalkyl, arylalkyl, heteroarylalkyl, cycloalkylalkyl, heterocycloalkylalkyl, $C_{2-6}$ alkenyl, $C_{2-6}$ alkynyl, aryl, heteroaryl, cycloalkyl, heterocycloalkyl, arylalkyl, heteroarylalkyl, cycloalkylalkyl and heterocycloalkylalkyl, wherein each of the $C_{1-6}$ alkyl, $C_{1-6}$ haloalkyl, arylalkyl, heteroarylalkyl, cycloalkylalkyl, heterocycloalkylalkyl, $C_{2-6}$ alkenyl, $C_{2-6}$ alkynyl, aryl, heteroaryl, cycloalkyl, heterocycloalkyl, arylalkyl, heteroarylalkyl, cycloalkylalkyl and heterocycloalkylalkyl is substituted with 0, 1, 2, 3, 4, or 5 substituents each independently selected from OH, amino, $C_{1-6}$ alkylamino, $C_{2-8}$ dialkylamino, halo, CN, $C_{1-6}$ alkyl, $C_{1-6}$ haloalkyl, $C_{1-6}$ hydroxylalkyl, $C_{1-6}$ cyanoalkyl, $C_{1-6}$ alkoxy, $C_{1-6}$ haloalkoxy, $C_{2-8}$ alkoxyalkoxy, aryl, arylalkyl, heteroaryl, heteroarylalkyl, cycloalkyl, and heterocycloalkyl;

or $R^c$ and $R^d$ together with the N atom to which they are attached form a 4-, 5-, 6- or 7-membered heterocycloalkyl group that is substituted with 0, 1, 2, 3, 4, or 5 substituents each independently selected from OH, amino, $C_{1-6}$ alkylamino, $C_{2-8}$ dialkylamino, halo, CN, $C_{1-6}$ alkyl, $C_{1-6}$ haloalkyl, $C_{1-6}$ hydroxylalkyl, $C_{1-6}$ cyanoalkyl, $C_{1-6}$ alkoxy, $C_{1-6}$ haloalkoxy, $C_{2-8}$ alkoxyalkoxy, aryl, arylalkyl, heteroaryl, heteroarylalkyl, cycloalkyl, and heterocycloalkyl;

$R^{c1}$ and $R^{d1}$ are independently selected from H, $C_{1-6}$ alkyl, $C_{1-6}$ haloalkyl, arylalkyl, heteroarylalkyl, cycloalkylalkyl, heterocycloalkylalkyl, $C_{2-6}$ alkenyl, $C_{2-6}$ alkynyl, aryl, heteroaryl, cycloalkyl, heterocycloalkyl, arylalkyl, heteroarylalkyl, cycloalkylalkyl and heterocycloalkylalkyl, wherein each of the $C_{1-6}$ alkyl, $C_{1-6}$ haloalkyl, arylalkyl, heteroarylalkyl, cycloalkylalkyl, heterocycloalkylalkyl, $C_{2-6}$ alkenyl, $C_{2-6}$ alkynyl, aryl, heteroaryl, cycloalkyl, heterocycloalkyl, arylalkyl, heteroarylalkyl, cycloalkylalkyl and heterocycloalkylalkyl is substituted with 0, 1, 2, 3, 4, or 5 substituents each independently selected from OH, amino, $C_{1-6}$ alkylamino, $C_{2-8}$ dialkylamino, halo, CN, $C_{1-6}$ alkyl, $C_{1-6}$ haloalkyl, $C_{1-6}$ hydroxylalkyl, $C_{1-6}$ cyanoalkyl, $C_{1-6}$ alkoxy, $C_{1-6}$ haloalkoxy, $C_{2-8}$ alkoxyalkoxy, aryl, arylalkyl, heteroaryl, heteroarylalkyl, cycloalkyl, and heterocycloalkyl;

or $R^{c1}$ and $R^{d1}$ together with the N atom to which they are attached form a 4-, 5-, 6- or 7-membered heterocycloalkyl group that is substituted with 0, 1, 2, 3, 4, or 5 substituents each independently selected from OH, amino, $C_{1-6}$ alkylamino, $C_{2-8}$ dialkylamino, halo, CN, $C_{1-6}$ alkyl, $C_{1-6}$ haloalkyl, $C_{1-6}$ hydroxylalkyl, $C_{1-6}$ cyanoalkyl, $C_{1-6}$ alkoxy, $C_{1-6}$ haloalkoxy, $C_{2-8}$ alkoxyalkoxy, aryl, arylalkyl, heteroaryl, heteroarylalkyl, cycloalkyl, and heterocycloalkyl;

$R^{c2}$ and $R^{d2}$ are independently selected from H, $C_{1-6}$ alkyl, $C_{1-6}$ haloalkyl, arylalkyl, heteroarylalkyl, cycloalkylalkyl, heterocycloalkylalkyl, $C_{2-6}$ alkenyl, $C_{2-6}$ alkynyl, aryl, heteroaryl, cycloalkyl, heterocycloalkyl, arylalkyl, heteroarylalkyl, cycloalkylalkyl and heterocycloalkylalkyl, wherein each of the $C_{1-6}$ alkyl, $C_{1-6}$ haloalkyl, arylalkyl, heteroarylalkyl, cycloalkylalkyl, heterocycloalkylalkyl, $C_{2-6}$ alkenyl, $C_{2-6}$ alkynyl, aryl, heteroaryl, cycloalkyl, heterocycloalkyl, arylalkyl, heteroarylalkyl, cycloalkylalkyl and heterocycloalkylalkyl is substituted with 0, 1, 2, 3, 4, or 5 substituents each independently selected from OH, amino, $C_{1-6}$ alkylamino, $C_{2-8}$ dialkylamino, halo, CN, $C_{1-6}$ alkyl, $C_{1-6}$ haloalkyl, $C_{1-6}$ hydroxylalkyl, $C_{1-6}$ cyanoalkyl, $C_{1-6}$ alkoxy, $C_{1-6}$ haloalkoxy, $C_{2-8}$ alkoxyalkoxy, aryl, arylalkyl, heteroaryl, heteroarylalkyl, cycloalkyl, and heterocycloalkyl;

or $R^{c2}$ and $R^{d2}$ together with the N atom to which they are attached form a 4-, 5-, 6- or 7-membered heterocycloalkyl group that is substituted with 0, 1, 2, 3, 4, or 5 substituents each independently selected from OH, amino, $C_{1-6}$ alkylamino, $C_{2-8}$ dialkylamino, halo, CN, $C_{1-6}$ alkyl, $C_{1-6}$ haloalkyl, $C_{1-6}$ hydroxylalkyl, $C_{1-6}$ cyanoalkyl, $C_{1-6}$ alkoxy, $C_{1-6}$ haloalkoxy, $C_{2-8}$ alkoxyalkoxy, aryl, arylalkyl, heteroaryl, heteroarylalkyl, cycloalkyl, and heterocycloalkyl;

$R^{c2}$ and $R^{d2}$ are independently selected from H, $C_{1-6}$ alkyl, $C_{1-6}$ haloalkyl, arylalkyl, heteroarylalkyl, cycloalkylalkyl, heterocycloalkylalkyl, $C_{2-6}$ alkenyl, $C_{2-6}$ alkynyl, aryl, heteroaryl, cycloalkyl, heterocycloalkyl, arylalkyl, heteroarylalkyl, cycloalkylalkyl and heterocycloalkylalkyl, wherein each of the $C_{1-6}$ alkyl, $C_{1-6}$ haloalkyl, arylalkyl, heteroarylalkyl, cycloalkylalkyl, heterocycloalkylalkyl, $C_{2-6}$ alkenyl, $C_{2-6}$ alkynyl, aryl, heteroaryl, cycloalkyl, heterocycloalkyl, arylalkyl, heteroarylalkyl, cycloalkylalkyl and heterocycloalkylalkyl is substituted with 0, 1, 2, 3, 4, or 5 substituents each independently selected from OH, amino, $C_{1-6}$ alkylamino, $C_{2-8}$ dialkylamino, halo, CN, $C_{1-6}$ alkyl, $C_{1-6}$ haloalkyl, $C_{1-6}$ hydroxylalkyl, $C_{1-6}$ cyanoalkyl, $C_{1-6}$ alkoxy, $C_{1-6}$ haloalkoxy, $C_{2-8}$ alkoxyalkoxy, aryl, arylalkyl, heteroaryl, heteroarylalkyl, cycloalkyl, and heterocycloalkyl;

or $R^{c2}$ and $R^{d2}$ together with the N atom to which they are attached form a 4-, 5-, 6- or 7-membered heterocycloalkyl group that is substituted with 0, 1, 2, 3, 4, or 5 substituents each independently selected from OH, amino, $C_{1-6}$ alkylamino, $C_{2-8}$ dialkylamino, halo, CN, $C_{1-6}$ alkyl, $C_{1-6}$ haloalkyl, $C_{1-6}$ hydroxylalkyl, $C_{1-6}$ cyanoalkyl, $C_{1-6}$ alkoxy, $C_{1-6}$ haloalkoxy, $C_{2-8}$ alkoxyalkoxy, aryl, arylalkyl, heteroaryl, heteroarylalkyl, cycloalkyl, and heterocycloalkyl;

$R^{c3}$ and $R^{d3}$ are independently selected from H, $C_{1-6}$ alkyl, $C_{1-6}$ haloalkyl, arylalkyl, heteroarylalkyl, cycloalkylalkyl, heterocycloalkylalkyl, $C_{2-6}$-alkenyl, $C_{2-6}$ alkynyl, aryl, heteroaryl, cycloalkyl, heterocycloalkyl, arylalkyl, heteroarylalkyl, cycloalkylalkyl and heterocycloalkylalkyl, wherein each of the $C_{1-6}$ alkyl, $C_{1-6}$ haloalkyl, arylalkyl, heteroarylalkyl, cycloalkylalkyl, heterocycloalkylalkyl, $C_{2-6}$ alkenyl, $C_{2-6}$ alkynyl, aryl, heteroaryl, cycloalkyl, heterocycloalkyl, arylalkyl, heteroarylalkyl, cycloalkylalkyl and heterocycloalkylalkyl is substituted with 0, 1, 2, 3, 4, or 5 substituents each independently selected from OH, amino, $C_{1-6}$ alkylamino, $C_{2-8}$ dialkylamino, halo, CN, $C_{1-6}$ alkyl, $C_{1-6}$ haloalkyl, $C_{1-6}$ hydroxylalkyl, $C_{1-6}$ cyanoalkyl, $C_{1-6}$ alkoxy, $C_{1-6}$ haloalkoxy, $C_{2-8}$ alkoxyalkoxy, aryl, arylalkyl, heteroaryl, heteroarylalkyl, cycloalkyl, and heterocycloalkyl;

or $R^{c3}$ and $R^{d3}$ together with the N atom to which they are attached form a 4, 5, 6 or 7-membered heterocycloalkyl group that is substituted with 0, 1, 2, 3, 4, or 5 substituents each independently selected from OH, amino, $C_{1-6}$ alkylamino, $C_{2-8}$ dialkylamino, halo, CN, $C_{1-6}$ alkyl, $C_{1-6}$ haloalkyl, $C_{1-6}$ hydroxylalkyl, $C_{1-6}$ cyanoalkyl, $C_{1-6}$ alkoxy, $C_{1-6}$ haloalkoxy, $C_{2-8}$ alkoxyalkoxy, aryl, arylalkyl, heteroaryl, heteroarylalkyl, cycloalkyl, and heterocycloalkyl;

$R^e$ is selected from H, $C_{1-6}$ alkyl, $C_{1-6}$ haloalkyl, arylalkyl, heteroarylalkyl, cycloalkylalkyl, heterocycloalkylalkyl, $C_{2-6}$ alkenyl, $C_{2-6}$ alkynyl, aryl, heteroaryl, cycloalkyl, heterocycloalkyl, arylalkyl, heteroarylalkyl, cycloalkylalkyl and heterocycloalkylalkyl, wherein each of the $C_{1-6}$ alkyl, $C_{1-6}$ haloalkyl, arylalkyl, heteroarylalkyl, cycloalkylalkyl, heterocycloalkylalkyl, $C_{2-6}$ alkenyl, $C_{2-6}$ alkynyl, aryl, heteroaryl, cycloalkyl, heterocycloalkyl, arylalkyl, heteroarylalkyl, cycloalkylalkyl and heterocycloalkylalkyl is substituted with 0, 1, 2, 3, 4, or 5 substituents each independently selected from OH, amino, $C_{1-6}$ alkylamino, $C_{2-8}$ dialkylamino, halo, CN, $C_{1-6}$ alkyl, $C_{1-6}$ haloalkyl, $C_{1-6}$ hydroxylalkyl, $C_{1-6}$ cyanoalkyl, $C_{1-6}$ alkoxy, $C_{1-6}$ haloalkoxy, $C_{2-8}$ alkoxyalkoxy, aryl, arylalkyl, heteroaryl, heteroarylalkyl, cycloalkyl, and heterocycloalkyl;

$R^g$, $R^{g1}$, $R^{g2}$, and $R^{g3}$ are each, independently, selected from H, CN, and $NO_2$;

each p1 is, independently, 0, 1, or 2;
each p2 is, independently, 0, 1, or 2;
each p3 is, independently, 0, 1, or 2;
each p4 is, independently, 0, 1, or 2;
each q1 is, independently, 1 or 2; and
each q2 is, independently, 1 or 2.

2. The compound of claim 1, or pharmaceutically acceptable salt or N-oxide or quaternary ammonium salt thereof, wherein the ring formed by $R^2$ and $R^3$ together with the N atom to which they are attached is a 5-7 membered heterocycloalkyl group substituted with 0, 1, 2, 3, 4, or 5 $R^4$, and wherein each of the ring-forming atoms of the 5-7 membered heterocycloalkyl group is C or N.

3. The compound of claim 1, or pharmaceutically acceptable salt or N-oxide or quaternary ammonium salt thereof, wherein the ring formed by $R^2$ and $R^3$ together with the N atom to which they are attached is a pyrrolidine ring or a piperazine ring, each substituted with 0, 1, 2, 3, 4, or 5 $R^4$.

4. The compound of claim 3, or pharmaceutically acceptable salt or N-oxide or quaternary ammonium salt thereof, wherein:
the ring formed by $R^2$ and $R^3$ together with the N atom to which they are attached is substituted with 0, 1, 2, or 3 $R^4$; and
each $R^4$ is independently selected from $C_{1-6}$ alkyl, $C_{3-7}$ cycloalkyl, $C_{1-6}$ haloalkyl, $NH_2$, $NH(C_{1-4}$ alkyl), $NH(C_{3-7}$ cycloalkyl), and $N(C_{1-4}$ alkyl$)_2$, wherein each of the $C_{1-6}$ alkyl, $C_{1-6}$ haloalkyl, and $C_{3-7}$ cycloalkyl is substituted with 0 or 1 substituent selected from halo, $NH_2$, $NH(C_{1-4}$ alkyl), and $N(C_{1-4}$ alkyl$)_2$.

5. The compound of claim 1, or pharmaceutically acceptable salt or N-oxide or quaternary ammonium salt thereof, wherein $R^1$ is selected from formula (A1), (B1), (C1), (D1), and (E1):

(A1)

(B1)

(C1)

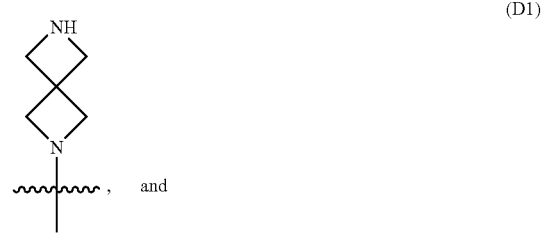
(D1), and

(E1)

6. The compound of claim 1, or pharmaceutically acceptable salt or N-oxide or quaternary ammonium salt thereof, wherein $R^1$ is 4-methyl-piperazin-1-yl.

7. The compound of Formula I of claim 1, or pharmaceutically acceptable salt or N-oxide or quaternary ammonium salt thereof, wherein ring A is phenyl substituted with 0, 1, or 2 $W^{1a}$—$X^{1a}$—$W^1$—$X^1$—$Y^1$—$Z^1$.

8. The compound of Formula I of claim 1, or pharmaceutically acceptable salt or N-oxide or quaternary ammonium salt thereof, wherein ring A is phenyl substituted with 0 or 1-$W^{1a}$—$X^{1a}$—$W^1$—$X^1$—$Y^1$—$Z^1$.

9. The compound of Formula I claim 1, or pharmaceutically acceptable salt or N-oxide or quaternary ammonium salt thereof, wherein each —$W^{1a}$—$X^{1a}$—$W^1$—$X^1$—$Y^1$—$Z^1$ is independently selected from halo, CN, $C_{1-4}$ alkyl, $C_{1-4}$ haloalkyl, $C_{1-4}$ hydroxylalkyl, $C_{1-4}$ cyanoalkyl, $C_{3-7}$ cycloalkyl, OH, $C_{1-4}$ alkoxy, and $C_{1-4}$ haloalkoxy.

10. The compound of Formula I of claim 1, or pharmaceutically acceptable salt or N-oxide or quaternary ammonium salt thereof, wherein the compound pharmaceutically acceptable salt or N-oxide or quaternary ammonium salt thereof is a compound of Formula III-1:

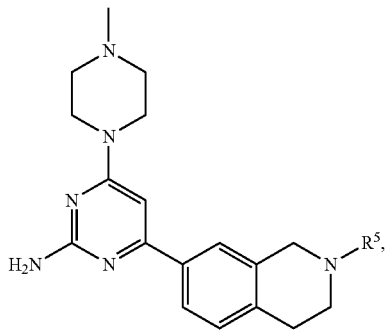

or pharmaceutically acceptable salt or N-oxide or quaternary ammonium salt thereof, wherein:
    each $R^5$ is independently H or —$W^{2a}$—$X^{2a}$—$W^2$—$X^2$—$Y^2$—$Z^2$.

11. The compound of Formula I of claim 1, or pharmaceutically acceptable salt or N-oxide or quaternary ammonium salt thereof, wherein the compound pharmaceutically acceptable salt or N-oxide or quaternary ammonium salt thereof is a compound of Formula III-0-a:

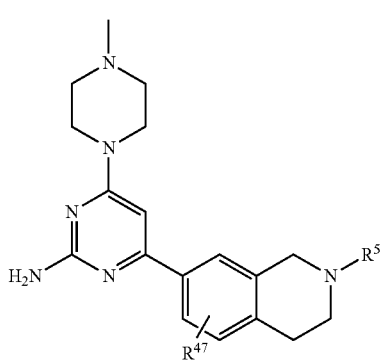

wherein $R^{47}$ is H, $C_{1-6}$ alkyl, $C_{1-6}$ haloalkyl, halo, $C_{1-6}$ alkoxy, $C_{1-6}$ haloalkoxy, or CN.

12. The compound of claim 11, or pharmaceutically acceptable salt or N-oxide or quaternary ammonium salt thereof, each $R^5$ is independently selected from H, $Z^2$, —C(O)$Z^2$, —C(S)$Z^2$, —C(O)NH$Z^2$, —C(O)N($C_{1-6}$ alkyl)$Z^2$, —C(S)NH$Z^2$, —C(S)N($C_{1-6}$ alkyl)$Z^2$, —C(O)O$Z^2$, —S(O)$Z^2$, —S(O)NH$Z^2$, —S(O)N($C_{1-6}$ alkyl)$Z^2$, —S(O)$_2$$Z^2$, —S(O)$_2$NH$Z^2$, and —S(O)$_2$N($C_{1-6}$ alkyl)$Z^2$; and each $Z^2$ is independently selected from $C_{1-6}$ alkyl, $C_{1-6}$ haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl, and heterocycloalkylalkyl, each substituted with 0, 1, 2 or 3 substituents each independently selected from $R^{zz}$, halo, CN, NO$_2$, OR$^a$, SR$^a$, SF$_5$, C(O)R$^b$, C(O)NR$^c$R$^d$, C(O)OR$^a$, OC(O)R$^b$, OC(O)NR$^c$R$^d$, NR$^c$R$^d$, NR$^c$C(O)R$^d$, NR$^c$C(O)OR$^a$, NR$^c$S(O)$_2$R$^b$, NR$^c$S(O)$_2$NR$^c$R$^d$; S(O)R$^b$, S(O)NR$^c$R$^d$, S(O)$_2$R$^b$, and S(O)$_2$NR$^c$R$^d$.

13. The compound of claim 11, or pharmaceutically acceptable salt or N-oxide or quaternary ammonium salt thereof, each $R^5$ is independently selected from:
    (1) H;
    (2) aryl substituted with 0, 1, 2, or 3 substituents each independently selected from $C_{1-6}$ alkyl, $C_{1-6}$ haloalkyl, halo, $C_{1-6}$ alkoxy, $C_{1-6}$ haloalkoxy, CN, C(O)OR$^a$, C(O)R$^b$, OR$^a$, C(O)NR$^c$R$^d$, NR$^c$C(O)R$^d$, NR$^c$C(O)OR$^a$, and S(O)$_2$R$^b$;
    (3) heteroaryl substituted with 0, 1, 2, or 3 substituents each independently selected from $C_{1-6}$ alkyl, $C_{1-6}$ haloalkyl, halo, $C_{1-6}$ alkoxy, $C_{1-6}$ haloalkoxy, Ar, CN, C(O)OR$^a$, C(O)R$^b$, OR$^a$, C(O)NR$^c$R$^d$, NR$^c$C(O)R$^d$, NR$^c$C(O)OR$^a$, and S(O)$_2$R$^b$;
    (4) —C(O)$Z^{21}$, wherein $Z^{21}$ is selected from $C_{1-6}$ alkyl, cycloalkyl, aryl, heterocycloalkyl, heteroaryl, arylalkyl, heteroarylalkyl, cycloalkylalkyl, and heterocycloalkylalkyl, each substituted with 0, 1, 2, 3, 4, or 5 substituents each independently selected from halo, $C_{1-6}$ alkyl, $C_{1-6}$ haloalkyl, $C_{2-8}$ alkoxyalkyl, CN, —OR$^a$, C(O)R$^b$, C(O)NR$^c$R$^d$, C(O)OR$^a$, S(O)$_2$R$^b$, NR$^c$R$^d$, NR$^c$C(O)R$^b$, and NR$^c$C(O)OR$^a$;
    (5) —S(O)$_2$$Z^{22}$, wherein $Z^{22}$ is selected from aryl and arylalkyl, each substituted with 0, 1, 2, 3, 4, or 5 substituents each independently selected from halo, $C_{1-6}$ alkyl, $C_{1-6}$ haloalkyl, $C_{2-8}$ alkoxyalkyl, CN, —O—Ar, C(O)R$^b$, C(O)NR$^c$R$^d$, C(O)OR$^a$, S(O)$_2$R$^b$, NR$^c$R$^d$, NR$^c$C(O)R$^b$, and NR$^c$C(O)OR$^a$;
    (6) —C(O)O$Z^{23}$; wherein $Z^{23}$ is selected from $C_{1-6}$ alkyl, cycloalkyl, aryl, heterocycloalkyl, heteroaryl, arylalkyl, heteroarylalkyl, cycloalkylalkyl, and heterocycloalkylalkyl, each substituted with 0, 1, 2, 3, 4, or 5 substituents each independently selected from halo, $C_{1-6}$ alkyl, $C_{1-6}$ haloalkyl, $C_{2-8}$ alkoxyalkyl, CN, —OR$^a$, C(O)R$^b$, C(O)NR$^c$R$^d$, C(O)OR$^a$, S(O)$_2$R$^b$, NR$^c$R$^d$, NR$^c$C(O)R$^b$, and NR$^c$C(O)OR$^a$;
    (7) —C(O)N$Z^{24}$$Z^{25}$ wherein $Z^{24}$ and $Z^{25}$ together with the N atom to which they are attached form a 4-10 membered heterocycloalkyl group wherein each of the ring-forming atoms of the 4-10 membered heterocycloalkyl group is independently selected from C, N, O, and S, and wherein the 4-10 membered heterocycloalkyl group is substituted with 0, 1, 2 or 3 substituents each independently selected from $C_{1-6}$ alkyl, $C_{1-6}$ haloalkyl, halo, Ar, HetAr; and
    (8) —C(O)N$Z^{26}$$Z^{27}$;
wherein:
    $Z^{26}$ is selected from H and $C_{1-6}$ alkyl;
    $Z^{27}$ is selected from $C_{1-6}$ alkyl, cycloalkyl, aryl, heterocycloalkyl, heteroaryl, arylalkyl, cycloalkylalkyl, and heterocycloalkylalkyl, each substituted with 0, 1, 2, 3, 4, or 5 substituents each independently selected from halo, $C_{1-6}$ alkyl, $C_{1-6}$ haloalkyl, $C_{2-8}$ alkoxyalkyl, CN, Ar, HetAr, —OR$^a$, C(O)R$^b$, C(O)NR$^c$R$^d$, C(O)OR$^a$, S(O)$_2$R$^b$, NR$^c$R$^d$, NR$^c$C(O)R$^b$, and NR$^c$C(O)OR$^a$;

each Ar is independently aryl substituted with 0, 1, 2, 3, 4, or 5 substituents each independently selected from halo, CN, $C_{1-6}$ alkyl, $C_{1-6}$ haloalkyl, $C_{2-8}$ alkoxyalkyl, $C_{1-6}$ alkoxy, $C_{1-6}$ haloalkoxy, and C(O)OR$^a$, and each HetAr is independently heteroaryl substituted with 0, 1, 2, 3, 4, or 5 substituents each independently selected from halo, CN, $C_{1-6}$ alkyl, $C_{1-6}$ haloalkyl, $C_{2-8}$ alkoxyalkyl, $C_{1-6}$ alkoxy, $C_{1-6}$ haloalkoxy, and C(O)OR$^a$.

14. The compound of claim 11, or pharmaceutically acceptable salt or N-oxide or quaternary ammonium salt thereof, each R$^5$ is independently selected from:

(1) H;

(2) phenyl or naphthyl, each substituted with 0, 1, 2, or 3 substituents each independently selected from $C_{1-6}$ alkyl, $C_{1-6}$ haloalkyl, halo, $C_{1-6}$ alkoxy, $C_{1-6}$ haloalkoxy, and CN;

(3) pyrdinyl, pyrazinyl, pyrazolyl, 1,3-thiazolyl, 1,3-benzothiazolyl, furanyl, benzofuranyl, thienyl, quinoxalinyl, and 2,1,3-benzothiadiazolyl, each substituted with 0, 1, 2, or 3 substituents each independently selected from $C_{1-6}$ alkyl, $C_{1-6}$ haloalkyl, halo, $C_{1-6}$ alkoxy, $C_{1-6}$ haloalkoxy, Ar, CN, and C(O)NR$^c$R$^d$;

(4) —C(O)Z$^{21}$, wherein Z$^{21}$ is selected from (a) $C_{1-6}$ alkyl substituted with 0, 1, 2, 3, or 4 substituents each independently selected from halo, CN, —OAr, and NR$^c$C(O)OR$^a$; (b) $C_{3-10}$ cycloalkyl substituted with 0, 1, 2, 3, or 4 substituents each independently selected from halo, CN, Ar, $C_{1-6}$ alkyl, and $C_{1-6}$ haloalkyl; (c) phenyl and naphthyl, each substituted with 0, 1, 2, 3, or 4 substituents each independently selected from $C_{1-6}$ alkyl, $C_{1-6}$ haloalkyl, halo, $C_{1-6}$ alkoxy, $C_{1-6}$ haloalkoxy, and CN; (d) arylakyl substituted with 0, 1, 2, 3, or 4 substituents each independently selected from $C_{1-6}$ alkyl, $C_{1-6}$ haloalkyl, $C_{1-6}$ alkoxy, $C_{1-6}$ haloalkoxy, halo, and CN; (e) cycloalkylalkyl substituted with 0, 1, 2, 3, or 4 substituents each independently selected from $C_{1-6}$ alkyl, $C_{1-6}$ haloalkyl, $C_{1-6}$ alkoxy, $C_{1-6}$ haloalkoxy, halo, NR$^c$C(O)OR$^a$, and CN; (f) heteroarylalkyl substituted with 0, 1, 2, 3, or 4 substituents each independently selected from $C_{1-6}$ alkyl, $C_{1-6}$ haloalkyl, $C_{1-6}$ alkoxy, $C_{1-6}$ haloalkoxy, NR$^c$C(O)OR$^a$, halo, NR$^c$R$^d$, and CN; and (g) heterocycloalkylalkyl substituted with 0, 1, 2, 3, or 4 substituents each independently selected from $C_{1-6}$ alkyl, $C_{1-6}$ haloalkyl, $C_{1-6}$ alkoxy, $C_{1-6}$ haloalkoxy, NR$^c$C(O)OR$^a$, halo, NR$^c$R$^d$, CN, C(O)R$^b$, C(O)OR$^a$, and S(O)$_2$R$^b$;

(5) —S(O)$_2$Z$^{22}$, wherein Z$^{22}$ is selected from phenyl, naphthyl, benzyl, phenylethyl, and phenylpropyl, each substituted with 0, 1, 2, 3, 4, or 5 substituents each independently selected from halo, $C_{1-6}$ alkyl, $C_{1-6}$ haloalkyl, $C_{2-8}$ alkoxyalkyl, CN, —O—Ar, C(O)R$^b$, C(O)NR$^c$R$^d$, C(O)OR$^a$, S(O)$_2$R$^b$, NR$^c$R$^d$, NR$^c$C(O)R$^b$, and NR$^c$C(O)OR$^a$;

(6) —C(O)OZ$^{23}$; wherein Z$^{23}$ is selected from (a) $C_{1-6}$ alkyl substituted with 0, 1, 2, 3, or 4 substituents each independently selected from halo, CN, —OAr, and NR$^c$-C(O)ORa; (b) $C_{3-10}$ cycloalkyl substituted with 0, 1, 2, 3, or 4 substituents each independently selected from halo, CN, Ar, $C_{1-6}$ alkyl, and $C_{1-6}$ haloalkyl; (c) phenyl and naphthyl, each substituted with 0, 1, 2, 3, or 4 substituents each independently selected from $C_{1-6}$ alkyl, $C_{1-6}$ haloalkyl, halo, $C_{1-6}$ alkoxy, $C_{1-6}$ haloalkoxy, and CN; (d) cycloalkylalkyl substituted with 0, 1, 2, 3, or 4 substituents each independently selected from $C_{1-6}$ alkyl, $C_{1-6}$ haloalkyl, $C_{1-6}$ alkoxy, $C_{1-6}$ haloalkoxy, halo, NR$^c$C(O)OR$^a$, and CN; and (e) heterocycloalkylalkyl substituted with 0, 1, 2, 3, or 4 substituents each independently selected from $C_{1-6}$ alkyl, $C_{1-6}$ haloalkyl, $C_{1-6}$ alkoxy, $C_{1-6}$ haloalkoxy, NR$^c$C(O)OR$^a$, halo, NR$^c$R$^d$, CN, C(O)NR$^c$R$^d$, C(O)R$^b$, C(O)OR$^a$, and S(O)$_2$R$^b$;

(7) —C(O)NZ$^{24}$Z$^{25}$ wherein Z$^{24}$ and Z$^{25}$ together with the N atom to which they are attached form a pyrrolidinyl or piperidinyl group, each substituted with 0, 1, 2 or 3 substituents each independently selected from $C_{1-6}$ alkyl, Ar, HetAr; and (8) —C(O)NZ$^{26}$Z$^{27}$;

wherein:

Z$^{26}$ is selected from H and $C_{1-3}$ alkyl;

Z$^{27}$ is selected from (a) $C_{1-6}$ alkyl substituted with 0, 1, 2, 3, or 4 substituents each independently selected from halo, and CN; (b) $C_{3-10}$ cycloalkyl substituted with 0, 1, 2, 3, or 4 substituents each independently selected from halo, CN, Ar, $C_{1-6}$ alkyl, $C_{1-6}$ haloalkyl, $C_{2-8}$ alkoxyalkyl, ORa, C(O)R$^b$, C(O)NR$^c$R$^d$, and C(O)OR$^a$; (c) phenyl and naphthyl, each substituted with 0, 1, 2, 3, or 4 substituents each independently selected from $C_{1-6}$ alkyl, $C_{1-6}$ haloalkyl, halo, ORa, HetAr, and CN; (d) arylakyl substituted with 0, 1, 2, 3, or 4 substituents each independently selected from $C_{1-6}$ alkyl, $C_{1-6}$ haloalkyl, $C_{1-6}$ alkoxy, $C_{1-6}$ haloalkoxy, C(O)NR$^c$R$^d$, halo, and CN; (e) heteroaryl substituted with 0, 1, 2, 3, or 4 substituents each independently selected from $C_{1-6}$ alkyl, $C_{1-6}$ haloalkyl, OR$^a$, C(O)OR$^a$, halo, NR$^c$R$^d$, Ar, and CN; and (f) heterocycloalkyl substituted with 0, 1, 2, 3, or 4 substituents each independently selected from $C_{1-6}$ alkyl, $C_{1-6}$ haloalkyl, halo, CN, C(O)R$^b$, C(O)OR$^a$, Ar, and HetAr;

each Ar is independently aryl substituted with 0, 1, 2, 3, 4, or 5 substituents each independently selected from halo, CN, $C_{1-6}$ alkyl, $C_{1-6}$ haloalkyl, $C_{2-8}$ alkoxyalkyl, $C_{1-6}$ alkoxy, $C_{1-6}$ haloalkoxy, and C(O)OR$^a$, and each HetAr is independently heteroaryl substituted with 0, 1, 2, 3, 4, or 5 substituents each independently selected from halo, CN, $C_{1-6}$ alkyl, $C_{1-6}$ haloalkyl, $C_{2-8}$ alkoxyalkyl, $C_{1-6}$ alkoxy, $C_{1-6}$ haloalkoxy, and C(O)OR$^a$.

15. The compound of any one of claim 11, or pharmaceutically acceptable salt or N-oxide or quaternary ammonium salt thereof, each R$^5$ is independently selected from:

(1) H;

(2) phenyl substituted with 0, 1, 2, or 3 substituents each independently selected from $C_{1-6}$ alkyl, $C_{1-6}$ haloalkyl, halo, $C_{1-6}$ alkoxy, $C_{1-6}$ haloalkoxy, and CN;

(3) pyrdinyl substituted with 0, 1, 2, or 3 substituents each independently selected from $C_{1-6}$ alkyl, $C_{1-6}$ haloalkyl, halo, $C_{1-6}$ alkoxy, $C_{1-6}$ haloalkoxy, Ar, CN, and C(O)NR$^c$R$^d$;

(4) —C(O)Z$^{21}$, wherein Z$^{21}$ is selected from (a) $C_{1-6}$ alkyl substituted with 0, 1, 2, 3, or 4 substituents each independently selected from halo, CN, —OAr, and NR$^c$C(O)OR$^a$; (b) $C_{3-10}$ cycloalkyl substituted with 0, 1, 2, 3, or 4 substituents each independently selected from halo, CN, Ar, $C_{1-6}$ alkyl, and $C_{1-6}$ haloalkyl; (c) phenyl substituted with 0, 1, 2, 3, or 4 substituents each independently selected from $C_{1-6}$ alkyl, $C_{1-6}$ haloalkyl, halo, $C_{1-6}$ alkoxy, $C_{1-6}$ haloalkoxy, and CN; (d) arylakyl substituted with 0, 1, 2, 3, or 4 substituents each independently selected from $C_{1-6}$ alkyl, $C_{1-6}$ haloalkyl, $C_{1-6}$ alkoxy, $C_{1-6}$ haloalkoxy, halo, and CN; (e) cycloalkylalkyl substituted with 0, 1, 2, 3, or 4 substituents each independently selected from $C_{1-6}$ alkyl, $C_{1-6}$ haloalkyl, $C_{1-6}$ alkoxy, $C_{1-6}$ haloalkoxy, halo, NR$^c$C(O)OR$^a$, and CN;

(f) heteroarylalkyl substituted with 0, 1, 2, 3, or 4 substituents each independently selected from $C_{1-6}$ alkyl, $C_{1-6}$ haloalkyl, $C_{1-6}$ alkoxy, $C_{1-6}$ haloalkoxy, $NR^cC(O)OR^a$, halo, $NR^cR^d$, and CN; and (g) heterocycloalkylalkyl substituted with 0, 1, 2, 3, or 4 substituents each independently selected from $C_{1-6}$ alkyl, $C_{1-6}$ haloalkyl, $C_{1-6}$ alkoxy, $C_{1-6}$ haloalkoxy, $NR^cC(O)OR^a$, halo, $NR^cR^d$, CN, $C(O)R^b$, $C(O)OR^a$, and $S(O)_2R^b$;

(5) —$S(O)_2Z^{22}$, wherein $Z^{22}$ is selected from phenyl and benzyl, each substituted with 0, 1, 2, 3, 4, or 5 substituents each independently selected from halo, $C_{1-6}$ alkyl, $C_{1-6}$ haloalkyl, $C_{2-8}$ alkoxyalkyl, CN, —O—Ar, $C(O)R^b$, $C(O)NR^cR^d$, $C(O)ORa$, $S(O)_2R^b$, $NR^cR^d$, $NR^cC(O)R^b$, and $NR^cC(O)OR^a$;

(6) —$C(O)OZ^{23}$; wherein $Z^{23}$ is selected from (a) $C_{1-6}$ alkyl substituted with 0, 1, 2, 3, or 4 substituents each independently selected from halo, CN, —OAr, and $NR^c$-$C(O)ORa$; (b) $C_{3-10}$ cycloalkyl substituted with 0, 1, 2, 3, or 4 substituents each independently selected from halo, CN, Ar, $C_{1-6}$ alkyl, and $C_{1-6}$ haloalkyl; (c) phenyl substituted with 0, 1, 2, 3, or 4 substituents each independently selected from $C_{1-6}$ alkyl, $C_{1-6}$ haloalkyl, halo, $C_{1-6}$ alkoxy, $C_{1-6}$ haloalkoxy, and CN; (d) cycloalkylalkyl substituted with 0, 1, 2, 3, or 4 substituents each independently selected from $C_{1-6}$ alkyl, $C_{1-6}$ haloalkyl, $C_{1-6}$ alkoxy, $C_{1-6}$ haloalkoxy, halo, $NR^cC(O)OR^a$, and CN; and (e) heterocycloalkylalkyl substituted with 0, 1, 2, 3, or 4 substituents each independently selected from $C_{1-6}$ alkyl, $C_{1-6}$ haloalkyl, $C_{1-6}$ alkoxy, $C_{1-6}$ haloalkoxy, $NR^cC(O)OR^a$, halo, $NR^cR^d$, CN, $C(O)NR^cR^d$, $C(O)R^b$, $C(O)OR^a$, and $S(O)_2R^b$;

(7) —$C(O)NZ^{24}Z^{25}$ wherein $Z^{24}$ and $Z^{25}$ together with the N atom to which they are attached form a pyrrolidinyl or piperidinyl group, each substituted with 0, 1, 2 or 3 substituents each independently selected from $C_{1-6}$ alkyl, Ar, HetAr; and (8) —$C(O)NZ^{26}Z^{27}$;

wherein:

$Z^{26}$ is selected from H and $C_{1-3}$ alkyl;

$Z^{27}$ is selected from (a) $C_{1-6}$ alkyl substituted with 0, 1, 2, 3, or 4 substituents each independently selected from halo, and CN; (b) $C_{3-10}$ cycloalkyl substituted with 0, 1, 2, 3, or 4 substituents each independently selected from halo, CN, Ar, $C_{1-6}$ alkyl, $C_{1-6}$ haloalkyl, $C_{2-8}$ alkoxyalkyl, $OR^a$, $C(O)R^b$, $C(O)NR^cR^d$, and $C(O)OR^a$; (c) phenyl substituted with 0, 1, 2, 3, or 4 substituents each independently selected from $C_{1-6}$ alkyl, $C_{1-6}$ haloalkyl, halo, $OR^a$, HetAr, and CN; (d) arylakyl substituted with 0, 1, 2, 3, or 4 substituents each independently selected from $C_{1-6}$ alkyl, $C_{1-6}$ haloalkyl, $C_{1-6}$ alkoxy, $C_{1-6}$ haloalkoxy, $C(O)NR^cR^d$, halo, and CN; (e) heteroaryl substituted with 0, 1, 2, 3, or 4 substituents each independently selected from $C_{1-6}$ alkyl, $C_{1-6}$ haloalkyl, $OR^a$, $C(O)OR^a$, halo, $NR^cR^d$, Ar, and CN; and (f) heterocycloalkyl substituted with 0, 1, 2, 3, or 4 substituents each independently selected from $C_{1-6}$ alkyl, $C_{1-6}$ haloalkyl, halo, CN, $C(O)R^b$, $C(O)OR^a$, Ar, and HetAr;

each Ar is independently aryl substituted with 0, 1, 2, 3, 4, or 5 substituents each independently selected from halo, CN, $C_{1-6}$ alkyl, $C_{1-6}$ haloalkyl, $C_{2-8}$ alkoxyalkyl, $C_{1-6}$ alkoxy, $C_{1-6}$ haloalkoxy, and $C(O)OR^a$, and each HetAr is independently heteroaryl substituted with 0, 1, 2, 3, 4, or 5 substituents each independently selected from halo, CN, $C_{1-6}$ alkyl, $C_{1-6}$ haloalkyl, $C_{2-8}$ alkoxyalkyl, $C_{1-6}$ alkoxy, $C_{1-6}$ haloalkoxy, and $C(O)OR^a$.

16. The compound of claim 5, or pharmaceutically acceptable salt or N-oxide or quaternary ammonium salt thereof, wherein:

each $W^{2a}$ is independently absent, $C(O)$, $S(O)_2$, $C(O)O$, or $C(O)NH$; and each $X^{2a}$ is independently $C_{1-6}$ alkylenyl, aryl, arylalkyl, cycloalkyl, heteroaryl, or heterocycloalkyl, each substituted with 0, 1, 2, 3, 4, 5, or 6 substituents each independently selected from $R^{XX}$, halo, CN, $NO_2$, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cC(O)R^b$, $NR^cC(O)NR^cR^d$, $NR^cC(O)OR^a$, $C(=NR^g)NR^cR^d$, $NR^cC(=NR^g)NR^cR^d$, $NR^cS(O)_2NR^cR^d$, $S(O)R^b$, $S(O)NR^cR^d$, $S(O)_2R^b$, $NR^cS(O)_2R^b$, and $S(O)_2NR^cR^d$.

17. The compound of claim 5, or pharmaceutically acceptable salt or N-oxide or quaternary ammonium salt thereof, wherein:

each $W^{2a}$ is independently absent, $C(O)$, $S(O)$, $S(O)_2$, $C(O)O$, $C(O)NH$, $S(O)_2NH$, $S(O)_2N(C_{1-6}$ alkyl$)$, or $C(O)N(C_{1-6}$ alkyl$)$; and each —$X^{2a}$—$W^2$—$X^2$—$Y^2$—$Z^2$ is independently $C_{1-6}$ alkyl, arylalkyl, heteroarylalkyl, cycloalkylalkyl, heterocycloalkylalkyl, aryl, cycloalkyl, heteroaryl, or heterocycloalkyl, each substituted with 0, 1, 2, 3, 4, 5, or 6 substituents each independently selected from $R^{XX}$, halo, CN, $C_{1-6}$ alkyl, $C_{1-6}$ haloalkyl, $C_{1-6}$ hydroxylalkyl, $C_{1-6}$ cyanoalkyl, $C_{3-6}$ cycloalkyl, —$C(O)$—$(C_{1-4}$ alkyl$)$, —$C(O)$—$NH(C_{1-4}$ alkyl$)$, —$C(O)$—$N(C_{1-4}$ alkyl$)_2$, OH, $C_{1-6}$ alkoxy, $C_{1-6}$ haloalkoxy, and $C_{2-8}$ alkoxyalkoxy.

18. The compound of claim 5, or pharmaceutically acceptable salt or N-oxide or quaternary ammonium salt thereof, wherein:

each $W^{2a}$ is independently absent, $C(O)$, $S(O)_2$, $C(O)O$, or $C(O)NH$; and each —$X^{2a}$—$W^2$—$X^2$—$Y^2$—$Z^2$ is independently $C_{1-6}$ alkyl, arylalkyl, heteroarylalkyl, cycloalkylalkyl, heterocycloalkylalkyl, aryl, cycloalkyl, heteroaryl, or heterocycloalkyl, each substituted with 0, 1, 2, 3, 4, 5, or 6 substituents each independently selected from $R^{XX}$, halo, CN, $C_{1-6}$ alkyl, $C_{1-6}$ haloalkyl, $C_{1-6}$ hydroxylalkyl, $C_{1-6}$ cyanoalkyl, $C_{3-6}$ cycloalkyl, —$C(O)$—$(C_{1-4}$ alkyl$)$, —$C(O)$—$NH(C_{1-4}$ alkyl$)$, —$C(O)$—$N(C_{1-4}$ alkyl$)_2$, OH, $C_{1-6}$ alkoxy, $C_{1-6}$ haloalkoxy, and $C_{2-8}$ alkoxyalkoxy.

19. The compound of claim 5, or pharmaceutically acceptable salt or N-oxide or quaternary ammonium salt thereof, wherein:

each $W^{2a}$ is independently absent, $C(O)$, $S(O)$, $S(O)_2$, $C(O)O$, $C(O)NH$, $S(O)_2NH$, $S(O)_2N(C_{1-6}$ alkyl$)$, or $C(O)N(C_{1-6}$ alkyl$)$; and each —$X^{2a}$—$W^2$—$X^2$—$Y^2$—$Z^2$ is independently $C_{1-6}$ alkyl, arylalkyl, heteroarylalkyl, cycloalkylalkyl, heterocycloalkylalkyl, aryl, cycloalkyl, heteroaryl, or heterocycloalkyl, each substituted with 0, 1, 2, 3, 4, 5, or 6 substituents each independently selected from $R^{XX}$, halo, CN, $C_{1-6}$ alkyl, $C_{1-6}$ haloalkyl, $C_{1-6}$ hydroxylalkyl, $C_{1-6}$ cyanoalkyl, $C_{3-6}$ cycloalkyl, —$C(O)$—$(C_{1-4}$ alkyl$)$, —$C(O)$—$NH(C_{1-4}$ alkyl$)$, —$C(O)$—$N(C_{1-4}$ alkyl$)_2$, OH, $C_{1-6}$ alkoxy, $C_{1-6}$ haloalkoxy, and $C_{2-8}$ alkoxyalkoxy; and each $R^{XX}$ is independently selected from arylalkyl, heteroarylalkyl, cycloalkylalkyl, heterocycloalkylalkyl, $C_{2-6}$ alkenyl, $C_{2-6}$ alkynyl, aryl, cycloalkyl, heteroaryl, and heterocycloalkyl, each substituted with 0, 1, 2, 3, 4, or 5 substituents each independently selected from halo, CN, $C_{1-6}$ alkyl, $C_{1-6}$ haloalkyl, $C_{1-6}$ hydroxylalkyl, $C_{1-6}$ cyanoalkyl, $C_{3-6}$ cycloalkyl, —C(O)—($C_{1-4}$ alkyl), —C(O)—NH($C_{1-4}$ alkyl), —C(O)—N($C_{1-4}$ alkyl)$_2$, OH, $C_{1-6}$ alkoxy, $C_{1-6}$ haloalkoxy, and $C_{2-8}$ alkoxyalkoxy.

20. The compound of claim 5, or pharmaceutically acceptable salt or N-oxide or quaternary ammonium salt thereof, wherein:

each $W^{2a}$ is independently absent, C(O), S(O)$_2$, C(O)O, or C(O)NH; and each —$X^{2a}$—$W^2$—$X^2$—$Y^2$—$Z^2$ is independently $C_{1-6}$ alkyl, arylalkyl, heteroarylalkyl, cycloalkylalkyl, heterocycloalkylalkyl, aryl, cycloalkyl, heteroaryl, or heterocycloalkyl, each substituted with 0, 1, 2, 3, 4, 5, or 6 substituents each independently selected from $R^{xx}$, halo, CN, $C_{1-6}$ alkyl, $C_{1-6}$ haloalkyl, $C_{1-6}$ hydroxylalkyl, $C_{1-6}$ cyanoalkyl, $C_{3-6}$ cycloalkyl, —C(O)—($C_{1-4}$ alkyl), —C(O)—NH($C_{1-4}$ alkyl), —C(O)—N($C_{1-4}$ alkyl)$_2$, OH, $C_{1-6}$ alkoxy, $C_{1-6}$ haloalkoxy, and $C_{2-8}$ alkoxyalkoxy; and each $R^{xx}$ is independently selected from arylalkyl, heteroarylalkyl, cycloalkylalkyl, heterocycloalkylalkyl, $C_{2-6}$ alkenyl, $C_{2-6}$ alkynyl, aryl, cycloalkyl, heteroaryl, and heterocycloalkyl, each substituted with 0, 1, 2, 3, 4, or 5 substituents each independently selected from halo, CN, $C_{1-6}$ alkyl, $C_{1-6}$ haloalkyl, $C_{1-6}$ hydroxylalkyl, $C_{1-6}$ cyanoalkyl, $C_{3-6}$ cycloalkyl, —C(O)—($C_{1-4}$ alkyl), —C(O)—NH($C_{1-4}$ alkyl), —C(O)—N($C_{1-4}$ alkyl)$_2$, OH, $C_{1-6}$ alkoxy, $C_{1-6}$ haloalkoxy, and $C_{2-8}$ alkoxyalkoxy.

21. A compound selected from:
4-(4-Methylpiperazin-1-yl)-6-(1,2,3,4-tetrahydroisoquinolin-7-yl)pyrimidin-2-amine;
4-[2-(4-Chlorobenzoyl)-1,2,3,4-tetrahydroisoquinolin-7-yl]-6-(4-methylpiperazin-1-yl)pyrimidin-2-amine;
4-[2-(Cyclobutylcarbonyl)-1,2,3,4-tetrahydroisoquinolin-7-yl]-6-(4-methylpiperazin-1-yl)pyrimidin-2-amine;
4-(4-Methylpiperazin-1-yl)-6-[2-(phenylsulfonyl)-1,2,3,4-tetrahydroisoquinolin-7-yl]pyrimidin-2-amine;
7-[2-Amino-6-(4-methylpiperazin-1-yl)pyrimidin-4-yl]-N-cyclopentyl-3,4-dihydroisoquinoline-2(1H)-carboxamide;
4-(4-Methylpiperazin-1-yl)-6-[2-(phenylacetyl)-1,2,3,4-tetrahydroisoquinolin-7-yl]pyrimidin-2-amine;
Cyclopentyl 7-[2-amino-6-(4-methylpiperazin-1-yl)pyrimidin-4-yl]-3,4-dihydroisoquinoline-2(1H)-carboxylate;
7-[2-Amino-6-(4-methylpiperazin-1-yl)pyrimidin-4-yl]-N-(4-chlorophenyl)-3,4-dihydroisoquinoline-2(1H)-carboxamide;
4-(4-Methylpiperazin-1-yl)-6-[2-(pyrrolidin-1-ylcarbonyl)-1,2,3,4-tetrahydroisoquinolin-7-yl]pyrimidin-2-amine;
Isobutyl 7-[2-amino-6-(4-methylpiperazin-1-yl)pyrimidin-4-yl]-3,4-dihydroisoquinoline-2(1H)-carboxylate;
Isopropyl 7-[2-amino-6-(4-methylpiperazin-1-yl)pyrimidin-4-yl]-3,4-dihydroisoquinoline-2(1H)-carboxylate;
7-[2-Amino-6-(4-methylpiperazin-1-yl)pyrimidin-4-yl]-N-phenyl-3,4-dihydroisoquinoline-2(1H)-carboxamide;
7-[2-Amino-6-(4-methylpiperazin-1-yl)pyrimidin-4-yl]-N-isopropyl-3,4-dihydroisoquinoline-2(1H)-carboxamide;
4-{7-[2-Amino-6-(4-methylpiperazin-1-yl)pyrimidin-4-yl]-3,4-dihydroisoquinolin-2(1H)-yl}benzonitrile;
4-{7-[2-Amino-6-(4-methylpiperazin-1-yl)pyrimidin-4-yl]-3,4-dihydroisoquinolin-2(1H)-yl}-2-fluorobenzonitrile;
6-{7-[2-Amino-6-(4-methylpiperazin-1-yl)pyrimidin-4-yl]-3,4-dihydroisoquinolin-2(1H)-yl}nicotinonitrile;
5-{7-[2-Amino-6-(4-methylpiperazin-1-yl)pyrimidin-4-yl]-3,4-dihydroisoquinolin-2(1H)-yl}-N-methylpyridine-2-carboxamide;
4-{6-[7-[2-Amino-6-(4-methylpiperazin-1-yl)pyrimidin-4-yl]-3,4-dihydroisoquinolin-2(1H)-yl]pyridin-3-yl}benzonitrile;
4-{6-[7-[2-Amino-6-(4-methylpiperazin-1-yl)pyrimidin-4-yl]-3,4-dihydroisoquinolin-2(1H)-yl]pyridin-3-yl}-N-methylbenzamide;
7-[2-Amino-6-(4-methylpiperazin-1-yl)pyrimidin-4-yl]-N-(3-chlorophenyl)-3,4-dihydroisoquinoline-2(1H)-carboxamide;
4-[2-(3-Chlorobenzoyl)-1,2,3,4-tetrahydroisoquinolin-7-yl]-6-(4-methylpiperazin-1-yl)pyrimidin-2-amine;
7-[2-Amino-6-(4-methylpiperazin-1-yl)pyrimidin-4-yl]-N-(3-chloro-2-fluorophenyl)-3,4-dihydroisoquinoline-2(1H)-carboxamide;
4-[2-(Cyclopentylacetyl)-1,2,3,4-tetrahydroisoquinolin-7-yl]-6-(4-methylpiperazin-1-yl)pyrimidin-2-amine;
7-[2-Amino-6-(4-methylpiperazin-1-yl)pyrimidin-4-yl]-N-[1-(3-methylpyridin-2-yl)piperidin-4-yl]-3,4-dihydroisoquinoline-2(1H)-carboxamide;
7-[2-Amino-6-(4-methylpiperazin-1-yl)pyrimidin-4-yl]-N-(5-cyanopyridin-2-yl)-3,4-dihydroisoquinoline-2(1H)-carboxamide;
7-[2-Amino-6-(4-methylpiperazin-1-yl)pyrimidin-4-yl]-N-(6-cyanopyridin-3-yl)-3,4-dihydroisoquinoline-2(1H)-carboxamide;
Methyl 6-({[7-[2-amino-6-(4-methylpiperazin-1-yl)pyrimidin-4-yl]-3,4-dihydroisoquinolin-2(1H)-yl]carbonyl}amino)nicotinate;
7-[2-Amino-6-(4-methylpiperazin-1-yl)pyrimidin-4-yl]-N-(6-methoxypyridin-3-yl)-3,4-dihydroisoquinoline-2(1H)-carboxamide;
7-[2-Amino-6-(4-methylpiperazin-1-yl)pyrimidin-4-yl]-N-(1-methylcyclohexyl)-3,4-dihydroisoquinoline-2(1H)-carboxamide;
7-[2-Amino-6-(4-methylpiperazin-1-yl)pyrimidin-4-yl]-N [4-(4-chlorophenyl)-1,3-thiazol-2-yl]-3,4-dihydroisoquinoline-2(1H)-carboxamide;
7-[2-Amino-6-(4-methylpiperazin-1-yl)pyrimidin-4-yl]-N-(trans-2-phenylcyclopropyl)-3,4-dihydroisoquinoline-2(1H)-carboxamide;
7-[2-Amino-6-(4-methylpiperazin-1-yl)pyrimidin-4-yl]-N-[4-(trifluoromethyl)-1,3-thiazol-2-yl]-3,4-dihydroisoquinoline-2(1H)-carboxamide;
7-[2-Amino-6-(4-methylpiperazin-1-yl)pyrimidin-4-yl]-N-(1-phenylethyl)-3,4-dihydroisoquinoline-2(1H)-carboxamide;
Ethyl 4-({[7-[2-amino-6-(4-methylpiperazin-1-yl)pyrimidin-4-yl]-3,4-dihydroisoquinolin-2(1H)-yl]carbonyl}amino)piperidine-1-carboxylate;
Ethyl cis-2-({[7-[2-amino-6-(4-methylpiperazin-1-yl)pyrimidin-4-yl]-3,4-dihydroisoquinolin-2(1H)-yl]carbonyl}amino)cyclohexanecarboxylate;
7-[2-Amino-6-(4-methylpiperazin-1-yl)pyrimidin-4-yl]-N-{4-[(dimethylamino)carbonyl]cyclohexyl}-3,4-dihydroisoquinoline-2(1H)-carboxamide;
7-[2-Amino-6-(4-methylpiperazin-1-yl)pyrimidin-4-yl]-N-(cis-2-methoxycyclohexyl)-3,4-dihydroisoquinoline-2(1H)-carboxamide;
7-[2-Amino-6-(4-methylpiperazin-1-yl)pyrimidin-4-yl]-N-(trans-4-methoxycyclohexyl)-3,4-dihydroisoquinoline-2(1H)-carboxamide;

7-[2-Amino-6-(4-methylpiperazin-1-yl)pyrimidin-4-yl]-N-[(1S,2R)-2-methoxy-2,3-dihydro-1H-inden-1-yl]-3,4-dihydroisoquinoline-2(1H)-carboxamide;

7-[2-Amino-6-(4-methylpiperazin-1-yl)pyrimidin-4-yl]-N-[(1R,2S)-2-methoxy-2,3-dihydro-1H-inden-1-yl]-3,4-dihydroisoquinoline-2(1H)-carboxamide;

N-1-Adamantyl-7-[2-amino-6-(4-methylpiperazin-1-yl)pyrimidin-4-yl]-3,4-dihydroisoquinoline-2(1H)-carboxamide;

7-[2-Amino-6-(4-methylpiperazin-1-yl)pyrimidin-4-yl]-N-[(1R)-1-benzyl-2-(dimethylamino)-2-oxoethyl]-3,4-dihydroisoquinoline-2(1H)-carboxamide;

4-{2-[Difluoro(phenyl)acetyl]-1,2,3,4-tetrahydroisoquinolin-7-yl}-6-(4-methylpiperazin-1-yl)pyrimidin-2-amine;

4-(4-Methylpiperazin-1-yl)-6-[2-(4,4,4-trifluoro-3-methylbutanoyl)-1,2,3,4-tetrahydroisoquinolin-7-yl]pyrimidin-2-amine;

7-[2-Amino-6-(4-methylpiperazin-1-yl)pyrimidin-4-yl]-N-(4,4-difluorocyclohexyl)-3,4-dihydroisoquinoline-2(1H)-carboxamide;

7-[2-Amino-6-(4-methylpiperazin-1-yl)pyrimidin-4-yl]-N-[4-(trifluoromethyl)cyclohexyl]-3,4-dihydroisoquinoline-2(1H)-carboxamide;

4-{2-[(4-Fluorophenyl)acetyl]-1,2,3,4-tetrahydroisoquinolin-7-yl}-6-(4-methylpiperazin-1-yl)pyrimidin-2-amine;

4-{2-[(3-Chlorophenoxy)acetyl]-1,2,3,4-tetrahydroisoquinolin-7-yl}-6-(4-methylpiperazin-1-yl)pyrimidin-2-amine;

1-(Cyclopentylcarbonyl)piperidin-4-yl 7-[2-amino-6-(4-methylpiperazin-1-yl)pyrimidin-4-yl]-3,4-dihydroisoquinoline-2(1H)-carboxylate;

1-(Isopropoxycarbonyl)piperidin-4-yl 7-[2-amino-6-(4-methylpiperazin-1-yl)pyrimidin-4-yl]-3,4-dihydroisoquinoline-2(1H)-carboxylate;

1-[(Cyclopentyloxy)carbonyl]piperidin-4-yl 7-[2-amino-6-(4-methylpiperazin-1-yl)pyrimidin-4-yl]-3,4-dihydroisoquinoline-2(1H)-carboxylate;

1-[(Cyclopentylamino)carbonyl]piperidin-4-yl 7-[2-amino-6-(4-methylpiperazin-1-yl)pyrimidin-4-yl]-3,4-dihydroisoquinoline-2(1H)-carboxylate;

Isopropyl 4-{2-[7-[2-amino-6-(4-methylpiperazin-1-yl)pyrimidin-4-yl]-3,4-dihydroisoquinolin-2(1H)-yl]-2-oxoethyl}piperidine-1-carboxylate;

4-(2-{1-(Cyclopropylcarbonyl)piperidin-4-yl]acetyl}-1,2,3,4-tetrahydroisoquinolin-7-yl)-6-(4-methylpiperazin-1-yl)pyrimidin-2-amine;

4-{2-[(1-Benzoylpiperidin-4-yl)acetyl]-1,2,3,4-tetrahydroisoquinolin-7-yl}-6-(4-methylpiperazin-1-yl)pyrimidin-2-amine;

4-(2-{[1-(Ethylsulfonyl)piperidin-4-yl]acetyl}-1,2,3,4-tetrahydroisoquinolin-7-yl)-6-(4-methylpiperazin-1-yl)pyrimidin-2-amine;

7-[2-Amino-6-(4-methylpiperazin-1-yl)pyrimidin-4-yl]-N-(4-chlorophenyl)-6-fluoro-3,4-dihydroisoquinoline-2(1H)-carboxamide;

7-[2-Amino-6-(4-methylpiperazin-1-yl)pyrimidin-4-yl]-N-cyclohexyl-6-fluoro-3,4-dihydroisoquinoline-2(1H)-carboxamide;

7-[2-Amino-6-(4-methylpiperazin-1-yl)pyrimidin-4-yl]-N-(4-chlorophenyl)-6-methyl-3,4-dihydroisoquinoline-2(1H)-carboxamide;

7-[2-Amino-6-(4-methylpiperazin-1-yl)pyrimidin-4-yl]-N-cyclohexyl-6-methyl-3,4-dihydroisoquinoline-2(1H)-carboxamide;

Tetrahydrofuran-3-yl 7-[2-amino-6-(4-methylpiperazin-1-yl)pyrimidin-4-yl]-3,4-dihydroisoquinoline-2(1H)-carboxylate;

7-[2-Amino-6-(4-methylpiperazin-1-yl)pyrimidin-4-yl]-N-benzyl-3,4-dihydroisoquinoline-2(1H)-carboxamide;

7-[2-Amino-6-(4-methylpiperazin-1-yl)pyrimidin-4-yl]-N-cyclohexyl-N-methyl-3,4-dihydroisoquinoline-2(1H)-carboxamide;

7-[2-Amino-6-(4-methylpiperazin-1-yl)pyrimidin-4-yl]-N-(2,3-dihydro-1H-inden-1-yl)-3,4-dihydroisoquinoline-2(1H)-carboxamide;

7-[2-Amino-6-(4-methylpiperazin-1-yl)pyrimidin-4-yl]-N-(1,2,3,4-tetrahydronaphthalen-1-yl)-3,4-dihydroisoquinoline-2(1H)-carboxamide;

7-[2-Amino-6-(4-methylpiperazin-1-yl)pyrimidin-4-yl]-N [(3R)-tetrahydrofuran-3-yl]-3,4-dihydroisoquinoline-2(1H)-carboxamide;

7-[2-Amino-6-(4-methylpiperazin-1-yl)pyrimidin-4-yl]-N-[(cis)-2-ethoxycyclohexyl]-3,4-dihydroisoquinoline-2(1H)-carboxamide;

7-[2-Amino-6-(4-methylpiperazin-1-yl)pyrimidin-4-yl]-N-[(cis)-2-(cyclopropylmethoxy)cyclohexyl]-3,4-dihydroisoquinoline-2(1H)-carboxamide;

7-[2-Amino-6-(4-methylpiperazin-1-yl)pyrimidin-4-yl]-N-[(1R,2S)-2-hydroxy-2,3-dihydro-1H-inden-1-yl]-3,4-dihydroisoquinoline-2(1H)-carboxamide;

7-[2-Amino-6-(4-methylpiperazin-1-yl)pyrimidin-4-yl]-N-1,3-thiazol-2-yl-3,4-dihydroisoquinoline-2(1H)-carboxamide;

1-(Cyclopentylsulfonyl)piperidin-4-yl 7-[2-amino-6-(4-methylpiperazin-1-yl)pyrimidin-4-yl]-3,4-dihydroisoquinoline-2(1H)-carboxylate;

7-[2-Amino-6-(4-methylpiperazin-1-yl)pyrimidin-4-yl]-N-1,3-benzothiazol-2-yl-3,4-dihydroisoquinoline-2(1H)-carboxamide;

7-[2-Amino-6-(4-methylpiperazin-1-yl)pyrimidin-4-yl]-N-(5-phenylpyridin-2-yl)-3,4-dihydroisoquinoline-2(1H)-carboxamide;

7-[2-Amino-6-(4-methylpiperazin-1-yl)pyrimidin-4-yl]-N-(4-isopropoxyphenyl)-3,4-dihydroisoquinoline-2(1H)-carboxamide;

7-[2-Amino-6-(4-methylpiperazin-1-yl)pyrimidin-4-yl]-N-[4-(1H-pyrazol-1-yl)phenyl]-3,4-dihydroisoquinoline-2(1H)-carboxamide;

7-[2-Amino-6-(4-methylpiperazin-1-yl)pyrimidin-4-yl]-N [1-(methoxymethyl)cyclopentyl]-3,4-dihydroisoquinoline-2(1H)-carboxamide;

7-[2-Amino-6-(4-methylpiperazin-1-yl)pyrimidin-4-yl]-N-cyclohexyl-3,4-dihydroisoquinoline-2(1H)-carboxamide;

7-[2-Amino-6-(4-methylpiperazin-1-yl)pyrimidin-4-yl]-N-(4-phenoxyphenyl)-3,4-dihydroisoquinoline-2(1H)-carboxamide;

7-[2-Amino-6-(4-methylpiperazin-1-yl)pyrimidin-4-yl]-N-[(1S)-1,2-dimethylpropyl]-3,4-dihydroisoquinoline-2(1H)-carboxamide;

7-[2-Amino-6-(4-methylpiperazin-1-yl)pyrimidin-4-yl]-N-[(1R)-1,2-dimethylpropyl]-3,4-dihydroisoquinoline-2(1H)-carboxamide;

7-[2-Amino-6-(4-methylpiperazin-1-yl)pyrimidin-4-yl]-N-(2-fluorophenyl)-3,4-dihydroisoquinoline-2(1H)-carboxamide;

4-[2-(3-Methylbutanoyl)-1,2,3,4-tetrahydroisoquinolin-7-yl]-6-(4-methylpiperazin-1-yl)pyrimidin-2-amine;

4-(4-Methylpiperazin-1-yl)-6-[2-(3-phenylpropanoyl)-1,2,3,4-tetrahydroisoquinolin-7-yl]pyrimidin-2-amine;

4-[2-(2-Cyclohexylpropanoyl)-1,2,3,4-tetrahydroiso-
quinolin-7-yl]-6-(4-methylpiperazin-1-yl)pyrimidin-2-
amine;
4-(4-Methylpiperazin-1-yl)-6-{2-[(4-phenylpiperidin-1-
yl)carbonyl]-1,2,3,4-tetrahydroisoquinolin-7-
yl}pyrimidin-2-amine;
4-{2-[(4,4-Difluoropiperidin-1-yl)carbonyl]-1,2,3,4-tet-
rahydroisoquinolin-7-yl}-6-(4-methylpiperazin-1-yl)
pyrimidin-2-amine;
4-[2-(Cyclohexylcarbonyl)-1,2,3,4-tetrahydroisoquino-
lin-7-yl]-6-(4-methylpiperazin-1-yl)pyrimidin-2-
amine;
4-[2-(Cyclopropylacetyl)-1,2,3,4-tetrahydroisoquinolin-
7-yl]-6-(4-methylpiperazin-1-yl)pyrimidin-2-amine;
4-{2-[7-[2-Amino-6-(4-methylpiperazin-1-yl)pyrimidin-
4-yl]-3,4-dihydroisoquinolin-2(1H)-yl]-2-
oxoethyl}benzonitrile;
4-{2-[(6-Chloropyridin-3-yl)acetyl]-1,2,3,4-tetrahy-
droisoquinolin-7-yl}-6-(4-methylpiperazin-1-yl)pyri-
midin-2-amine;
4-[2-(Cyclobutylacetyl)-1,2,3,4-tetrahydroisoquinolin-7-
yl]-6-(4-methylpiperazin-1-yl)pyrimidin-2-amine;
4-(4-Methylpiperazin-1-yl)-6-[2-(tetrahydro-2H-pyran-4-
ylacetyl)-1,2,3,4-tetrahydroisoquinolin-7-yl]pyrimi-
din-2-amine;
4-[2-(3-Methylpentanoyl)-1,2,3,4-tetrahydroisoquinolin-
7-yl]-6-(4-methylpiperazin-1-yl)pyrimidin-2-amine;
4-(4-Methylpiperazin-1-yl)-6-[2-(1H-pyrazol-1-
ylacetyl)-1,2,3,4-tetrahydroisoquinolin-7-yl]pyrimi-
din-2-amine;
Methyl{3-[7-[2-amino-6-(4-methylpiperazin-1-yl)pyri-
midin-4-yl]-3,4-dihydroisoquinolin-2(1H)-yl]-1-me-
thyl-3-oxopropyl}carbamate;
Methyl{3-[7-[2-amino-6-(4-methylpiperazin-1-yl)pyri-
midin-4-yl]-3,4-dihydroisoquinolin-2(1H)-yl]-1-cyclo-
hexyl-3-oxopropyl}carbamate;
1-(Methoxycarbonyl)piperidin-4-yl 7-[2-amino-6-(4-me-
thylpiperazin-1-yl)pyrimidin-4-yl]-3,4-dihydroiso-
quinoline-2(1H)-carboxylate;
1-(Ethoxycarbonyl)piperidin-4-yl 7-[2-amino-6-(4-meth-
ylpiperazin-1-yl)pyrimidin-4-yl]-3,4-dihydroisoquino-
line-2(1H)-carboxylate;
7-[2-amino-6-(4-methylpiperazin-1-yl)pyrimidin-4-yl]-
N-[1-(trifluoromethyl)cyclopropyl]-3,4-dihydroiso-
quinoline-2(1H)-carboxamide;
Methyl 3-{2-[7-[2-amino-6-(4-methylpiperazin-1-yl)py-
rimidin-4-yl]-3,4-dihydroisoquinolin-2(1H)-yl]-2-
oxoethyl}pyrrolidine-1-carboxylate;
Isopropyl 3-{2-[7-[2-amino-6-(4-methylpiperazin-1-yl)
pyrimidin-4-yl]-3,4-dihydroisoquinolin-2(1H)-yl]-2-
oxoethyl}pyrrolidine-1-carboxylate;
1-{2-[7-[2-Amino-6-(4-methylpiperazin-1-yl)pyrimidin-
4-yl]-3,4-dihydroisoquinolin-2(1H)-yl]-2-
oxoethyl}cyclobutanecarbonitrile;
4-[7-[2-Amino-6-(4-methylpiperazin-1-yl)pyrimidin-4-
yl]-3,4-dihydroisoquinolin-2(1H)-yl]-2,2-dimethyl-4-
oxobutanenitrile;
1-{2-[7-[2-Amino-6-(4-methylpiperazin-1-yl)pyrimidin-
4-yl]-3,4-dihydroisoquinolin-2(1H)-yl]-2-
oxoethyl}cyclopentanecarbonitrile;
4-[7-[2-Amino-6-(4-methylpiperazin-1-yl)pyrimidin-4-
yl]-3,4-dihydroisoquinolin-2(1H)-yl]-2-cyclopropyl-2-
methyl-4-oxobutanenitrile;
4-[7-[2-Amino-6-(4-methylpiperazin-1-yl)pyrimidin-4-
yl]-3,4-dihydroisoquinolin-2(1H)-yl]-4-oxo-2-phe-
nylbutanenitrile;
5-{2-[7-[2-Amino-6-(4-methylpiperazin-1-yl)pyrimidin-
4-yl]-3,4-dihydroisoquinolin-2(1H)-yl]-2-
oxoethyl}nicotinonitrile;
7-[2-Amino-6-(4-methylpiperazin-1-yl)pyrimidin-4-yl]-
N-(1-pyridin-3-ylethyl)-3,4-dihydroisoquinoline-2
(1H)-carboxamide;
7-[2-Amino-6-(4-methylpiperazin-1-yl)pyrimidin-4-yl]-
N-[1-(1-methyl-1H-pyrazol-3-yl)ethyl]-3,4-dihy-
droisoquinoline-2(1H)-carboxamide; and
4-(4-Methylpiperazin-1-yl)-6-{2-[(6-pyrrolidin-1-ylpyri-
din-3-yl)acetyl]-1,2,3,4-tetrahydroisoquinolin-7-
yl}pyrimidin-2-amine;
or pharmaceutically acceptable salt or N-oxide or quater-
nary ammonium salt thereof.

22. The compound of Formula I of claim 1, or pharmaceutically acceptable salt or N-oxide or quaternary ammonium salt thereof, wherein the compound is of Formula III-0-b:

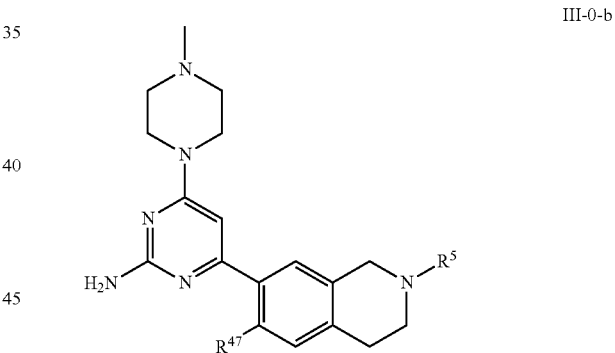

III-0-b wherein $R^{47}$ is H, $C_{1-6}$ alkyl, $C_{1-6}$ haloalkyl, halo, $C_{1-6}$ alkoxy, $C_{1-6}$ haloalkoxy, or CN.

* * * * *